US006673910B1

(12) United States Patent
Breton

(10) Patent No.: US 6,673,910 B1
(45) Date of Patent: Jan. 6, 2004

(54) **NUCLEIC ACID AND AMINO ACID SEQUENCES RELATING TO *M. CATARRHALIS* FOR DIAGNOSTICS AND THERAPEUTICS**

(75) Inventor: Gary L. Breton, Marlboro, MA (US)

(73) Assignee: Genome Therapeutics Corporation, Waltham, MA (US)

( * ) Notice: Subject to any disclaimer, the term of this patent is extended or adjusted under 35 U.S.C. 154(b) by 0 days.

(21) Appl. No.: 09/540,236

(22) Filed: Apr. 4, 2000

Related U.S. Application Data

(60) Provisional application No. 60/128,416, filed on Apr. 8, 1999.

(51) Int. Cl.[7] ............... C07H 21/04; C12Q 1/68; C12N 15/63; C12N 15/85
(52) U.S. Cl. ............... 536/23.1; 536/24.1; 435/6; 435/320.1; 435/325
(58) Field of Search ............... 435/6, 252.3, 320.1, 435/325; 536/23.1, 24.1

(56) References Cited

U.S. PATENT DOCUMENTS

| | | | |
|---|---|---|---|
| 5,030,556 A | 7/1991 | Beaulieu et al. | 435/6 |
| 5,556,755 A | 9/1996 | Murphy | 435/6 |
| 5,607,846 A | 3/1997 | Murphy et al. | 435/69.3 |
| 5,712,118 A | 1/1998 | Murphy | 435/69.3 |
| 5,721,097 A | 2/1998 | Roussau et al. | 435/6 |
| 5,725,862 A | 3/1998 | Murphy | 424/251.1 |
| 5,808,024 A | 9/1998 | Sasaki et al. | 536/23.1 |
| 5,948,412 A | 9/1999 | Murphy | 424/251.1 |
| 5,972,657 A | 10/1999 | Murphy et al. | 435/69.3 |
| 5,981,213 A | 11/1999 | Hansen et al. | 435/69.1 |
| 6,001,564 A | 12/1999 | Bergeron et al. | 435/6 |
| 6,004,562 A | 12/1999 | Campagnari | 424/251.1 |
| 6,090,576 A | 7/2000 | Myers et al. | 435/69.1 |
| 6,184,371 B1 | 2/2001 | Loosmore et al. | 536/23.7 |
| 6,214,981 B1 | 4/2001 | Tucker et al. | 536/23.1 |

OTHER PUBLICATIONS

Ullrich, GenBank Accession: X70766, Aug. 3, 1994.*
Celnicker et al., GenBank Acc. No :AC005286, Jul. 15, 1998.*

Murphy, T.F., et al., "The major heat–modifiable outer membrane protein CD is highly conserved among strains of *Branhamella catarrhalis*," *Mol. Microbiol.*, 10 (1) :89–97 (1993).

Hsiao, C.B., et al., "Outer membrane protein CD of *Branhamella catarrhalis*: sequence conservation in strains recovered from the human respiratory tract," *Microb. Pathog.*, 19:215–25 (1995).

Bhushan, R., et al., "Molecular cloning and characterization of outer membrane protein E of *Moraxella (Branhamella) catarrhalis*," *J. Bacteriol.*, 176(21):6636–43 (1994).

Bootsma, H.J., "Molecular characterization of the BRO β–lactamase of *Moraxella (Branhamella) catarrhalis*," *Antimicrob Agents Chemother.*, 40(4):966–72 (1996).

Aebi, C., et al., "Mapping of a protective epitope of the CopB outer membrane protein of *Moraxella catarrhalis*," *Infect. & Immun.*, 66(2):540–8 (1998).

Myers, L.E., et al., "The transferring binding protein B of *Moraxella catarrhalis* elicits bactericidal antibodies and is a potential vaccine antigen," *Infect. & Immun.*, 66(9):4183–92 (1998).

Du, R.P., et al., "Cloning and expression of the *Moraxella catarrhalis* lactoferrin receptor genes," *Infec. & Immun.*, 66(8):3656–65 (1998).

Helminen, M.E., et al., "A Major Outer Membrane Protein of *Moraxella catarrhalis* Is a Target for Antibodies That Enhance Pulmonary Clearance of the Pathogen in an Animal Model," *Infec. & Immun.*, 61(5):2003–10 (1993).

* cited by examiner

Primary Examiner—Michael P. Woodward
Assistant Examiner—Shubo Zhou
(74) Attorney, Agent, or Firm—Genome Therapeutics Corporation

(57) ABSTRACT

The invention provides isolated polypeptide and nucleic acid sequences derived from *Moracella catarrhalis* that are useful in diagnosis and therapy of pathological conditions; antibodies against the polypeptides; and methods for the production of the polypeptides. The invention also provides methods for the detection, prevention and treatment of pathological conditions resulting from bacterial infection.

14 Claims, No Drawings

NUCLEIC ACID AND AMINO ACID SEQUENCES RELATING TO *M. CATARRHALIS* FOR DIAGNOSTICS AND THERAPEUTICS

RELATED APPLICATIONS

This application claims the benefit of U.S. Provisional Application Ser. No. 60/128,416, filed Apr. 8, 1999, the entire teachings of which are incorporated herein by reference.

BACKGROUND OF THE INVENTION

The genus Moraxella is a member of the family Neisseriaceae. The 10 species of this genus, are separated into 2 subgenera, Moraxella (rods) and Branhamella (cocci). Moraxella are gram-negative, aerobic, oxidase-positive, and usually catalase-postive. (Bovre, K. 1984. Genus II. Moraxella Lwoff .1939, 173 emend. Henriksen and Bovre 1968, 391, 105. Krieg and Holt (editors) In Bergey's Manual of Systematic Bacteriology, 1:296–303.). *Moraxella catarrhalis*, a member of the subgenera Branhamella, was previously called *Branhamella catarrhalis* and *Neisseria catarrhalis*.

*Moraxella catarrhalis* is frequently isolated from the nasal cavity of humans, and until recently, was considered a nonpathogenic commensal of the upper respiratory tract. Currently it is most important lower respiratory pathogen after *S.pneumoniae* and *H. influenzae* (Doren, G., et al, 1986. Diagn. Microbiol. Infect. Dis. 4:191–201.). It is a common cause of otitis media in children, acute bronchitis or pneumonia in adults, and sinusitis (Wood, G., et al, 1996. Clin. Infect. Dis. 22:632–636.). Bacteremia, meningitis, skeletal infections and endocarditis due to *M. catarrhalis* are rare, but are observed in immunocompromised individuals (Aebi, C., et al, 1998. Infect. Immun. 66:540–548.). Concern for *M. catarrhalis* infections of cystic fibrosis (CF) patients is growing. Damage to the respiratory tract by *M. catarrhalis* could promote invasion by other pathogens such as *P. aeruginosa* in CF patients. (Deneuville, E., et al, 1995. ACTA Paediatr. 84:1212.). *M. catarrhalis* is also associated with acute laryngitis. In one study, 50% of patients with acute laryngitis were colonized with *M. catarrhalis* (Hol, C., et al, 1996. Journal of Infectious Diseases. 174:636–638.), while isolates from healthy adults occur at the rate of 6% –11%. The colonization rates of children can be much higher, with average rates of 30%–35% (Sehgal, SC. et al, 1994. Infection 22:193–196.). In some hospitals, *M. catarrhalis* accounts for half of all the respiratory infections (Bluesone, C., et al, 1992. Pediatr. Infect. Dis. J. 11:S7–S11.).

Increasing levels of antibiotic resistance have been observed in clinical isolates of *M. catarrhalis* recently. Before 1980, less than 10% of *M. catarrhalis* isolates were β-lactamase-positive. Currently, most clinical isolates produce β-lactamase, making them resistant to β-lactam antibiotics such as penicillin. (Doern, G., et al, 1996. Antimicob. Agents Chemother. 40:2884–2886.). *M. catarrhalis* is intrinsically resistant to a small group of drugs that include vancomycin and trimethoprim (Wallace, R J. 1990. Am. J. Med. 88:46S–50S), and is becoming increasingly resistant to sulfamethoxazole, oral cephalosporins, and macrolides (Hoppe, H L. 1998. Am.J. Health. Syst. Pharm. 55:1881–97).

Although, *M. catarrhalis* was once considered only as part of the nonpathogenic flora of the upper respiratory tract, it is emerging as an important respiratory pathogen. Currently, it is the third leading cause of lower respiratory tract infections and otitis media. Sequencing and further analysis of this genome will aid in identification of essential genes for development of drug targets, and reduce the health threat this organism poses.

SUMMARY OF THE INVENTION

The present invention fulfills the need for diagnostic tools and therapeutics by providing bacterial-specific compositions and methods for detecting. Moraxella species including *M. catarrhalis*, as well as compositions and methods useful for treating and preventing Moraxella infection, in particular, *M. catarrhalis* infection, in vertebrates including mammals.

The present invention encompasses isolated nucleic acids and polypeptides derived from *M. catarrhalis* that are useful as reagents for diagnosis of bacterial disease, components of effective antibacterial vaccines, and/or as targets for antibacterial drugs including anti-*M. catarrhalis* drugs. They can also be used to detect the presence of *M. catarrhalis* and other Moraxella species in a sample; and in screening compounds for the ability to interfere with the *M. catarrhalis* life cycle or to inhibit *M. catarrhalis* infection. They also have use as biocontrol agents for plants.

In one aspect, the invention features compositions of nucleic acids corresponding to entire coding sequences of *M. catarrhalis* proteins (SEQ ID NO: 1–SEQ ID NO: 1920), including surface or secreted proteins or parts thereof, nucleic acids capable of binding mRNA from *M. catarrhalis* proteins to block protein translation, and methods for producing *M. catarrhalis* proteins or parts thereof using peptide synthesis and recombinant DNA techniques. This invention also features antibodies and nucleic acids useful as probes to detect *M. catarrhalis* infection. In addition, vaccine compositions and methods for the protection or treatment of infection by *M. catarrhalis* are within the scope of this invention.

The nucleotide sequences provided in SEQ ID NO: 1–SEQ ID NO: 1920, a fragment thereof, or a nucleotide sequence at least about 99.5% identical to a sequence contained within SEQ ID NO: 1–SEQ ID NO: 1920 may be "provided" in a variety of medias to facilitate use thereof. As used herein, "provided" refers to a manufacture, other than an isolated nucleic acid molecule, which contains a nucleotide sequence of the present invention, i.e., the nucleotide sequence provided in SEQ ID NO: 1–SEQ ID NO: 1920, a fragment thereof, or a nucleotide sequence at least about 99.5% identical to a sequence contained within SEQ ID NO: 1–SEQ ID NO: 1920. Uses for and methods for providing nucleotide sequences in a variety of media is well known in the art (see e.g., EPO Publication No. EP 0 756 006).

In one application of this embodiment, a nucleotide sequence of the present invention can be recorded on computer readable media. As used herein, "computer readable media" refers to any media which can be read and accessed directly by a computer. Such media include, but are not limited to: magnetic storage media, such as floppy discs, hard disc storage media, and magnetic tape; optical storage media such as CD-ROM; electrical storage media such as RAM and ROM; and hybrids of these categories such as magnetic/optical storage media. A person skilled in the art can readily appreciate how any of the presently known computer readable media can be used to create a manufacture comprising computer readable media having recorded thereon a nucleotide sequence of the present invention.

As used herein, "recorded" refers to a process for storing information on computer readable media. A person skilled in the art can readily adopt any of the presently known methods for recording information on computer readable media to generate manufactures comprising the nucleotide sequence information of the present invention.

A variety of data storage structures are available to a person skilled in the art for creating a computer readable media having recorded thereon a nucleotide sequence of the present invention. The choice of the data storage structure will generally be based on the means chosen to access the stored information. In addition, a variety of data processor programs and formats can be used to store the nucleotide sequence information of the present invention on computer readable media. The sequence information can be represented in a word processing text file, formatted in commercially-available software such as WordPerfect and Microsoft Word, or represented in the form of an ASCII file, stored in a database application, such as DB2,Sybase, Oracle, or the like. A person skilled in the art can readily adapt any number of data processor structuring formats (e.g. text file or database) in order to obtain computer readable media having recorded thereon the nucleotide sequence information of the present invention.

By providing the nucleotide sequence of SEQ ID NO: 1–SEQ ID NO: 1920, a fragment thereof, or a nucleotide sequence at least about 99.5% identical to SEQ ID NO: 1–SEQ ID NO: 1920 in computer readable form, a person skilled in the art can routinely access the coding sequence information for a variety of purposes. Computer software is publicly available which allows a person skilled in the art to access sequence information provided in a computer readable media. Examples of such computer software include programs of the "Staden Package", "DNA Star", "MacVector", GCG "Wisconsin Package" (Genetics Computer Group, Madison, Wis.) and "NCBI Toolbox" (National Center For Biotechnology Information). Suitable programs are described, for example, in Martin J. Bishop, ed., *Guide to Human Genome Computing,* 2d Edition, Academic Press, San Diego, Calif. (1998); and Leonard F. Peruski, Jr., and Anne Harwood Peruski, *The Internet and the New Biology: Tools for Genomic and Molecular Research,* American Society for Microbiology, Washington, D.C. (1997).

Computer algorithms enable the identification of *M. catarrhalis* open reading frames (ORFs) within SEQ ID NO: 1–SEQ ID NO: 1920 which contain homology to ORFs or proteins from other organisms. Examples of such similarity-search algorithms include the BLAST [Altschul et al., J. Mol. Biol. 215:403–410 (1990)] and Smith-Waterman [Smith and Waterman (1981) Advances in Applied Mathematics, 2:482–489] search algorithms. Suitable search algorithms are described, for example, in Martin J. Bishop, ed., *Guide to Human Genome Computing,* 2d Edition, Academic Press, San Diego, Calif. (1998); and Leonard F. Peruski, Jr., and Anne Harwood Peruski, *The Internet and the New Biology: Tools for Genomic and Molecular Research,* American Society for Microbiology, Washington, D.C. (1997). Such algorithms are utilized on computer systems as exemplified below. The ORFs so identified represent protein encoding fragments within the *M. catarrhalis* genome and *M. catarrhalis* plasmidsand are useful in producing commercially important proteins such as enzymes used in fermentation reactions and in the production of commercially useful metabolites.

The present invention further provides systems, particularly computer-based systems, which contain the sequence information described herein. Such systems are designed to identify commercially important fragments of the *M. catarrhalis* genome and plasmids. As used herein, "a computer-based system" refers to the hardware means, software means, and data storage means used to analyze the nucleotide sequence information of the present invention. The minimum hardware means of the computer-based systems of the present invention comprises a central processing unit (CPU), input means, output means, and data storage means. A person skilled in the art can readily appreciate that any one of the currently a available computer-based systems is suitable for use in the present invention. The computer-based systems of the present invention comprise a data storage means having stored therein a nucleotide sequence of the present invention and the necessary hardware means and software means for supporting and implementing a search means. As used herein, "data storage means" refers to memory which can store nucleotide sequence information of the present invention, or a memory access means which can access manufactures having recorded thereon the nucleotide sequence information of the present invention.

As used herein, "search means" refers to one or more programs which are implemented on the computer-based system to compare a target sequence or target structural motif with the sequence information stored within the data storage means. Search means are used to identify fragments or regions of the *M. catarrhalis* genome and plasmids which are similar to, or "match", a particular target sequence or target motif. A variety of known algorithms are known in the art and have been disclosed publicly, and a variety of commercially available software for conducting homology-based similarity searches are available and can be used in the computer-based systems of the present invention. Examples of such software includes, but is not limited to, FASTA (GCG Wisconsin Package), Bic_SW (Compugen Bioccelerator), BLASTN2, BLASTP2, BLASTX2 (NCBI) and Motifs (GCG). Suitable software programs are described, for example, in Martin J. Bishop, ed., *Guide to Human Genome Computing,* 2d Edition, Academic Press, San Diego, Calif. (1998); and Leonard F. Peruski, Jr., and Anne Harwood Peruski, *The Internet and the New Biology: Tools for Genomic and Molecular Research,* American Society for Microbiology, Washington, D.C. (1997). A person skilled in the art can readily recognize that any one of the available algorithms or implementing software packages for conducting homology searches can be adapted for use in the present computer-based systems.

As used herein, a "target sequence" can be any DNA or amino acid sequence of six or more nucleotides or two or more amino acids. A person skilled in the art can readily recognize that the longer a target sequence is, the less likely a target sequence will be present as a random occurrence in the database. The most preferred sequence length of a target sequence is from about 10 to 100 amino acids or from about 30 to 300 nucleotide residues. However, it is well recognized that many genes are longer than 500 amino acids, or 1.5 kb in length, and that commercially important fragments of the *M. catarrhalis* genome and plasmids from *M. catarrhalis,* such as sequence fragments involved in gene expression and protein processing, will often be shorter than 30 nucleotides.

As used herein, "a target structural motif," or "target motif," refers to any rationally selected sequence or combination of sequences in which the sequence(s) are chosen based on a specific functional domain or three-dimensional configuration which is formed upon the folding of the target polypeptide. There are a variety of target motifs known in the art. Protein target motifs include, but are not limited to, enzymatic active sites, membrane-spanning regions, and signal sequences. Nucleic acid target motifs include, but are not limited to, promoter sequences, hairpin structures and inducible expression elements (protein binding sequences).

A variety of structural formats for the input and output means can be used to input and output the information in the computer-based systems of the present invention. A preferred format for an output means ranks fragments of the *M. catarrhalis* genome and plasmids possessing varying degrees of homology to the target sequence or target motif. Such presentation provides a person skilled in the art with a ranking of sequences which contain various amounts of the target sequence or target motif and identifies the degree of homology contained in the identified fragment.

A variety of comparing means can be used to compare a target sequence or target motif with the data storage means to identify sequence fragments of the *M. catarrhalis* genome and plasmids. In the present examples, implementing software which implement the BLASTP2 and bic_SW algorithms (Altschul et al., J Mol. Biol. 215:403–410 (1990); Compugen Biocellerator) was used to identify open reading frames within the *M. catarrhalis* genome and plasmids. A person skilled in the art can readily recognize that any one of the publicly available homology search programs can be used as the search means for the computer-based systems of the present invention. Suitable programs are described, for example, in Martin J. Bishop, ed., *Guide to Human Genome Computing*, 2d Edition, Academic Press, San Diego, Calif. (1998); and Leonard F. Peruski, Jr., and Anne Harwood Peruski, *The Internet and the New Biology: Tools for Genomic and Molecular Research*, American Society for Microbiology, Washington, D.C. (1997).

The invention features *M. catarrhalis* polypeptides, preferably a substantially pure preparation of an *M. catarrhalis* polypeptide, or a recombinant *M. catarrhalis* polypeptide. In preferred embodiments: the polypeptide has biological activity; the polypeptide has an amino acid sequence at least about 60%, 70%, 80%, 90%, 95%, 98%, or 99% identical to an amino acid sequence of the invention contained in the Sequence Listing, preferably it has about 65% sequence identity with an amino acid sequence of the invention contained in the Sequence Listing, and most preferably it has about 92% to about 99% sequence identity with, an amino acid sequence of the invention contained in the Sequence Listing; the polypeptide has an amino acid sequence essentially the same as an amino acid sequence of the invention contained in the Sequence Listing; the polypeptide is at least about 5, 10, 20, 50, 100, or 150 amino acid residues in length; the polypeptide includes at least about 5, preferably at least about 10, more preferably at least about 20, still more preferably at least about 50, 100, or 150 contiguous amino acid residues of the invention contained in the Sequence Listing. In yet another preferred embodiment, the amino acid sequence which differs in sequence identity by about 7% to about 8% from the *M. catarrhalis* amino acid sequences of the invention contained in the Sequence Listing is also encompassed by the invention.

In preferred embodiments: the *M. catarrhalis* polypeptide is encoded by a nucleic acid of the invention contained in the Sequence Listing, or by a nucleic acid having at least about 60%, 70%, 80%, 90%, 95%, 98%, or 99% sequence identify nucleic acid of the invention contained in the Sequence Listing.

In a preferred embodiment, the subject *M. catarrhalis* polypeptide differs in amino acid sequence at about 1, 2, 3, 5, 10 or more residues from a sequence of the invention contained in the Sequence Listing. The differences, however, are such that the *M. catarrhalis* polypeptide exhibits an *M. catarrhalis* biological activity, e.g., the *M. catarrhalis* polypeptide retains a biological activity of a naturally occurring *M. catarrhalis* enzyme.

In preferred embodiments, the polypeptide includes all or a fragment of an amino acid sequence of the invention contained in the Sequence Listing; fused, in reading frame, to additional amino acid residues, preferably to residues encoded by genomic DNA 5' or 3' to the genomic DNA which encodes a sequence of the invention contained in the Sequence Listing.

In yet other preferred embodiments, the *M. catarrhalis* polypeptide is a recombinant fusion protein having a first *M. catarrhalis* polypeptide portion and a second polypeptide portion, e.g., a second polypeptide portion having an amino acid sequence unrelated to *M. catarrhalis*. The second polypeptide portion can be, e.g., any of glutathione-S-transferase, a DNA binding domain, or a polymerase activating domain. In preferred embodiment the fusion protein can be used in a two-hybrid assay.

Polypeptides of the invention include those which arise as a result of alternative transcription events, alternative RNA splicing events, and alternative translational and posttranslational events.

In a preferred embodiment, the encoded *M. catarrhalis* polypeptide differs (e.g., by amino acid substitution, addition or deletion of at least one amino acid residue) in amino acid sequence at about 1, 2, 3, 5, 10 or more residues, from a sequence of the invention contained in the Sequence Listing. The differences, however, are such that: the *M. catarrhalis* encoded polypeptide exhibits an *M. catarrhalis* biological activity, e.g., the encoded *M. catarrhalis* enzyme retains a biological activity of a naturally occurring *M. catarrhalis*.

In preferred embodiments, the encoded polypeptide includes all or a fragment of an amino acid sequence of the invention contained in the Sequence Listing; fused, in reading frame, to additional amino acid residues, preferably to residues encoded by genomic DNA 5' or 3' to the genomic DNA which encodes a sequence of the invention contained in the Sequence Listing.

The *M. catarrhalis* strain, 98-4362, from which genomic sequences have been sequenced, has been deposited on Jul. 20, 1998, in the American Type Culture Collection and assigned the ATCC designation # 202156.

Included in the invention are: allelic variations; natural mutants; induced mutants; proteins encoded by DNA that hybridize under high or low stringency conditions to a nucleic acid which encodes a polypeptide of the invention contained in the Sequence Listing (for definitions of high and low stringency see Current Protocols in Molecular Biology, John Wiley & Sons, New York, 1989, 6.3.1–6.3.6, hereby incorporated by reference); and, polypeptides specifically bound by antisera to *M. catarrhalis* polypeptides, especially by antisera to an active site or binding domain of *M. catarrhalis* polypeptide. The invention also includes fragments, preferably biologically active fragments. These and other polypeptides are also referred to herein as *M. catarrhalis* polypeptide analogs or variants.

The invention further provides nucleic acids, e.g., RNA or DNA and their respective complements, encoding a polypeptide of the invention. This includes double stranded nucleic acids as well as coding and antisense single strands.

In preferred embodiments, the subject *M. catarrhalis* nucleic acid will include a transcriptional regulatory sequence, e.g., at least one of a transcriptional promoter or transcriptional enhancer sequence, operably linked to the *M. catarrhalis* gene sequence, e.g., to render the *M. catarrhalis* gene sequence suitable for expression in a recombinant host cell.

In yet a further preferred embodiment, the nucleic acid which encodes an *M. catarrhalis* polypeptide of the invention, hybridizes under stringent conditions to a nucleic acid probe corresponding to at least about 8 consecutive nucleotides of the invention contained in the Sequence Listing; more preferably to at least about 12 consecutive nucleotides of the invention contained in the Sequence Listing; still more preferably to at least about 20 consecutive nucleotides of the invention contained in the Sequence Listing; most preferably to at least about 40 consecutive nucleotides of the invention contained in the Sequence Listing.

In another aspect, the invention provides a substantially pure nucleic acid having a nucleotide sequence which encodes an *M. catarrhalis* polypeptide. In preferred embodiments: the encoded polypeptide has biological activity; the encoded polypeptide has an amino acid sequence at least about 60%, 70%, 80%, 90%, 95%, 98% or 99% homologous to an amino acid sequence of the invention contained in the Sequence Listing; the encoded polypeptide has an amino acid sequence essentially the same as an amino acid sequence of the invention contained in the Sequence Listing; the encoded polypeptide is at least about 5, 10, 20, 50, 100, or 150 amino acids in length; the encoded polypeptide comprises at least about 5, preferably at least about 10, more preferably at least about 20, still more preferably at least about 50, 100, or 150 contiguous amino acids of the invention contained in the Sequence Listing.

In another aspect, the invention encompasses: a vector including a nucleic acid which encodes an *M. catarrhalis* polypeptide or an *M. catarrhalis* polypeptide variant as described herein; a host cell transfected with the vector; and a method of producing a recombinant *M. catarrhalis* polypeptide or *M. catarrhalis* polypeptide variant; including culturing the cell, e.g., in a cell culture medium, and isolating an *M. catarrhalis* or *M. catarrhalis* polypeptide variant, e.g., from the cell or from the cell culture medium.

One embodiment of the invention is directed to substantially isolated nucleic acids. Nucleic acids of the invention include sequences comprising at least about 8 nucleotides in length, more preferably at least about 12 nucleotides in length, even more preferably at least about 15–20 nucleotides in length, that correspond to a subsequence of any one of SEQ ID NO: 1–SEQ ID NO: 1920 or complements thereof. Alternatively, the nucleic acids comprise sequences contained within any ORF (open reading frame), including a complete protein-coding sequence, of which any of SEQ ID NO: 1–SEQ ID NO: 1920 forms a part. The invention encompasses sequence-conservative variants and function-conservative variants of these sequences. The nucleic acids may be DNA, RNA, DNA/RNA duplexes, protein-nucleic acid (PNA), or derivatives thereof.

In another aspect, the invention features a purified recombinant nucleic acid having at least about 50%, 60%, 70%, 80%, 90%, 95%, 98%, or 99% homology with a sequence of the invention contained in the Sequence Listing The invention also encompasses recombinant DNA (including DNA cloning and expression vectors) comprising these *M. catarrhalis*—derived sequences; host cells comprising such DNA, including fungal, bacterial, yeast, plant, insect, and mammalian host cells; and methods for producing expression products comprising RNA and polypeptides encoded by the *M. catarrhalis* sequences. These methods are carried out by incubating a host cell comprising an *M. catarrhalis*—derived nucleic acid sequence under conditions in which the sequence is expressed. The host cell may be native or recombinant. The polypeptides can be obtained by (a) harvesting the incubated cells to produce a cell fraction and a medium fraction; and (b) recovering the *M. catarrhalis* polypeptide from the cell fraction, the medium fraction, or both. The polypeptides can also be made by in vitro translation.

In another aspect, the invention features nucleic acids capable of binding mRNA of *M. catarrhalis*. Such nucleic acid is capable of acting as antisense nucleic acid to control the translation of mRNA of *M. catarrhalis*. A further aspect features a nucleic acid which is capable of binding specifically to an *M. catarrhalis* nucleic acid. These nucleic acids are also referred to herein as complements and have utility as probes and as capture reagents.

In another aspect, the invention features an expression system comprising an open reading frame corresponding to *M. catarrhalis* nucleic acid. The nucleic acid further comprises a control sequence compatible with an intended host. The expression system is useful for making polypeptides corresponding to *M. catarrhalis* nucleic acid.

In another aspect, the invention encompasses: a vector including a nucleic acid which encodes an *M. catarrhalis* polypeptide or an *M. catarrhalis* polypeptide variant as described herein; a host cell transfected with the vector; and a method of producing a recombinant *M. catarrhalis* polypeptide or *M. catarrhalis* polypeptide variant; including culturing the cell, e.g., in a cell culture medium, and isolating the *M. catarrhalis* or *M. catarrhalis* polypeptide variant, e.g., from the cell or from the cell culture medium.

In yet another embodiment of the invention encompasses reagents for detecting bacterial infection, including *M. catarrhalis* infection, which comprise at least one *M. catarrhalis*—derived nucleic acid defined by any one of SEQ ID NO: 1–SEQ ID NO: 1920, or sequence-conservative or function-conservative variants thereof. Alternatively, the diagnostic reagents comprise nucleotide sequences that are contained within any open reading-frames (ORFs), including preferably complete protein-coding sequences, contained within any of SEQ ID NO: 1–SEQ ID NO: 1920, or polypeptide sequences contained within any of SEQ ID NO: 1921–SEQ ID NO: 3840, or polypeptides of which any of the above sequences forms a part, or antibodies directed against any of the above peptide sequences or function-conservative variants and/or fragments thereof.

The invention further provides antibodies, preferably monoclonal antibodies, which specifically bind to the polypeptides of the invention. Methods are also provided for producing antibodies in a host animal. The methods of the invention comprise immunizing an animal with at least one *M. catarrhalis*—derived immunogenic component, wherein the immunogenic component comprises one or more of the polypeptides encoded by any one of SEQ ID NO: 1–SEQ ID NO: 1920 or sequence-conservative or function-conservative variants thereof; or polypeptides that are contained within any ORFs, including complete protein-coding sequences, of which any of SEQ ID NO: 1–SEQ ID NO: 1920 forms a part; or polypeptide sequences contained within any of SEQ ID NO: 1921–SEQ ID NO: 3840; or polypeptides of which any of SEQ ID NO: 1921–SEQ ID NO: 3840 forms a part. Host animals include any warm blooded animal, including without limitation mammals and birds. Such antibodies have utility as reagents for immunoassays to evaluate the abundance and distribution of *M. catarrhalis*—specific antigens.

In yet another aspect, the invention provides diagnostic methods for detecting *M. catarrhalis* antigenic components or anti-*M. catarrhalis* antibodies in a sample. *M. catarrhalis* antigenic components may be detected by known processes, including but not limited to detection by a process comprising: (i) contacting a sample suspected to contain a bacterial antigenic component with a bacterial-specific antibody, under conditions in which a stable antigen-antibody complex can form between the antibody and bacterial antigenic components in the sample; and (ii) detecting any antigen-antibody complex formed in step (i), wherein detection of an antigen-antibody complex indicates the presence of at least one bacterial antigenic component in the sample. In different embodiments of this method, the antibodies used are directed against a sequence encoded by any of SEQ ID NO: 1–SEQ ID NO: 1920 or sequence-conservative or function-conservative variants thereof, or against a polypeptide sequence contained in any of SEQ ID NO: 1921–SEQ ID NO: 3840 or function-conservative variants thereof.

In yet another aspect, the invention provides a method for detecting antibacterial-specific antibodies in a sample, which comprises: (i) contacting a sample suspected to contain antibacterial-specific antibodies with an *M. catarrhalis* antigenic component, under conditions in which a stable antigen-antibody complex can form between the *M. catarrhalis* antigenic component and antibacterial antibodies in the sample; and (ii) detecting any antigen-antibody complex formed in step (i), wherein detection of an antigen-antibody complex indicates the presence of antibacterial antibodies in the sample. In different embodiments of this method, the antigenic component is encoded by a sequence contained in any of SEQ ID NO: 1–SEQ ID NO: 1920 or sequence-conservative and function-conservative variants thereof, or is a polypeptide sequence contained in any of SEQ ID NO: 1921–SEQ ID NO: 3840 or function-conservative variants thereof.

In another aspect, the invention features a method of generating vaccines for immunizing an individual against *M. catarrhalis*. The method includes: immunizing a subject with an *M. catarrhalis* polypeptide, e.g., a surface or secreted polypeptide, or a combination of such peptides or active portion(s) thereof, and a pharmaceutically acceptable carrier. Such vaccines have therapeutic and prophylactic utilities.

In another aspect, the invention features a method of evaluating a compound, e.g., a polypeptide, e.g., a fragment of a host cell polypeptide, for the ability to bind an *M. catarrhalis* polypeptide. The method includes contacting the compound to be evaluated with an *M. catarrhalis* polypeptide and determining if the compound binds or otherwise interacts with the *M. catarrhalis* polypeptide. Compounds which bind or otherwise interact with *M. catarrhalis* polypeptides are candidates as modulators, including activators and inhibitors, of the bacterial life cycle. These assays can be performed in vitro or in vivo.

In another aspect, the invention features a method of evaluating a compound, e.g., a polypeptide, e.g., a fragment of a host cell polypeptide, for the ability to bind an *M. catarrhalis* nucleic acid, e.g., DNA or RNA. The method includes contacting the compound to be evaluated with an *M. catarrhalis* nucleic acid and determining if the compound binds or otherwise interacts with the *M. catarrhalis* nucleic acid. Compounds which bind *M. catarrhalis* are candidates as modulators, including activators and inhibitors, of the bacterial life cycle. These assays can be performed in vitro or in vivo.

A particularly preferred embodiment of the invention is directed to a method of screening test compounds for anti-bacterial activity, which method comprises: selecting as a target a bacterial specific sequence, which sequence is essential to the viability of a bacterial species; contacting a test compound with said target sequence; and selecting those test compounds which bind to said target sequence as potential anti-bacterial candidates. In one embodiment, the target sequence selected is specific to a single species, or even a single strain, such as, for example, the strain *M. catarrhalis*98-4362. In a second embodiment, the target sequence is common to at least two species of bacteria. In a third embodiment, the target sequence is common to a family of bacteria. The target sequence may be a nucleic acid sequence or a polypeptide sequence. Methods employing sequences common to more than one species of microorganism may be used to screen candidates for broad spectrum anti-bacterial activity.

The invention also provides methods for preventing or treating disease caused by certain bacteria, including *M. catarrhalis*, which are carried out by administering to an animal in need of such treatment, in particular a warm-blooded vertebrate, including but not limited to birds and mammals, a compound that specifically inhibits or interferes with the function of a bacterial polypeptide or nucleic acid. In a particularly preferred embodiment, the mammal to be treated is human.

DETAILED DESCRIPTION OF THE INVENTION

The sequences of the present invention include the specific nucleic acid and amino acid sequences set forth in the Sequence Listing that forms a part of the present specification, and which are designated SEQ ID NO: 1–SEQ ID NO: 3840. Use of the terms "SEQ ID NO: 1–SEQ ID NO: 1920", "SEQ ID NO: 1921–SEQ ID NO: 3840, "the sequences depicted in Table 2", etc., is intended, for convenience, to refer to each individual SEQ ID NO individually, and is not intended to refer to the genus of these sequences unless such reference would be indicated. In other words, it is a shorthand for listing all of these sequences individually. The invention encompasses each sequence individually, as well as any combination thereof.

DEFINITIONS

"Nucleic acid" or "polynucleotide" as used herein refers to purine- and pyrimidine-containing polymers of any length, either polyribonucleotides or polydeoxyribonucleotides or mixed polyribo-polydeoxyribo nucleotides. This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases.

A nucleic acid or polypeptide sequence that is "derived from" a designated sequence refers to a sequence that corresponds to a region of the designated sequence. For nucleic acid sequences, this encompasses sequences that are homologous or complementary to the sequence, as well as "sequence-conservative variants" and "function-conservative variants." For polypeptide sequences, this encompasses "function-conservative variants." Sequence-conservative variants are those in which a change of one or more nucleotides in a given codon position results in no alteration in the amino acid encoded at that position. Function-conservative variants are those in which a given amino acid residue in a polypeptide has been changed without altering the overall conformation and function of the native polypeptide, including, but not limited to, replacement of an amino acid with one having similar physicochemical properties (such as, for example, acidic, basic, hydrophobic, and the like). "Function-conservative" variants also include any polypeptides that have the ability to elicit antibodies specific to a designated polypeptide.

An "*M. catarrhalis*—derived" nucleic acid or polypeptide sequence may or may not be present in other bacterial species, and may or may not be present in all *M. catarrhalis* strains. This term is intended to refer to the source from which the sequence was originally isolated. Thus, an *M. catarrhalis*—derived polypeptide, as used herein, may be used, e.g., as a target to screen for a broad spectrum antibacterial agent, to search for homologous proteins in other species of bacteria or in eukaryotic organisms such as bacteria humans, etc.

A purified or isolated polypeptide or a substantially pure preparation of a polypeptide are used interchangeably herein and, as used herein, mean a polypeptide that has been separated from other proteins, lipids, and nucleic acids with which it naturally occurs. Preferably, the polypeptide is also separated from substances, e.g., antibodies or gel matrix, e.g., polyacrylamide, which are used to purify it. Preferably, the polypeptide constitutes at least about 10, 20, 50 70, 80 or 95% dry weight of the purified preparation. Preferably, the preparation contains sufficient polypeptide to allow protein sequencing; at least about 1, 10, or preferably 100 mg of polypeptide.

A purified preparation of cells refers to, in the case of plant or animal cells, an in vitro preparation of cells and not an entire intact plant or animal. In the case of cultured cells or microbial cells, it consists of a preparation of at least about 10%, more preferably at least about 50%, of the subject cells.

A purified or isolated or a substantially pure nucleic acid, e.g., a substantially pure DNA, (are terms used interchangeably herein) is a nucleic acid which is one or both of the following: not immediately contiguous with both of the coding sequences with which it is immediately contiguous (i.e., one at the 5' end and one at the 3' end) in the naturally-occurring genome and plasmids of the organism from which the nucleic acid is derived; or which is substantially free of a nucleic acid with which it occurs in the organism from which the nucleic acid is derived. The term includes, for example, a recombinant DNA which is incorporated into a vector, e.g., into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other DNA sequences. Substantially pure DNA also includes a recombinant NA which is part of a hybrid gene encoding additional *M. catarrhalis* DNA sequence.

A "contig" as used herein is a nucleic acid representing a continuous stretch of genomic sequence of an organism.

An "open reading frame", also referred to herein as ORF, is a region of nucleic acid which encodes a polypeptide. This region may represent a portion of a coding sequence or a total sequence and can be determined from a stop to stop codon or from a start to stop codon.

As used herein, a "coding sequence" is a nucleic acid which is transcribed into messenger RNA and/or translated into a polypeptide when placed under the control of appropriate regulatory sequences. The boundaries of the coding sequence are determined by a translation start codon at the five prime terminus and a translation stop code at the three prime terminus. A coding sequence can include but is not limited to messenger RNA, synthetic DNA, and recombinant nucleic acid sequences.

A "complement" of a nucleic acid as used herein refers to an anti-parallel or antisense sequence that participates in Watson-Crick base-pairing with the original sequence.

A "gene product" is a protein or structural RNA which is specifically encoded by a gene.

As used herein, the term "probe" refers to a nucleic acid, peptide or other chemical entity which specifically binds to a molecule of interest. Probes are often associated with or capable of associating with a label. A label is a chemical moiety capable of detection. Typical labels comprise dyes, radioisotopes, luminescent and chemiluminescent moieties, fluorophores, enzymes, precipitating agents, amplification sequences, and the like. Similarly, a nucleic acid, peptide or other chemical entity which specifically binds to a molecule of interest and immobilizes such molecule is referred herein as a "capture ligand". Capture ligands are typically associated with or capable of associating with a support such as nitro-cellulose, glass, nylon membranes, beads, particles and the like. The specificity of hybridization is dependent on conditions such as the base pair composition of the nucleotides, and the temperature and salt concentration of the reaction. These conditions are readily discernable to one of ordinary skill in the art using routine experimentation.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared× 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

Nucleic acids are hybridizable to each other when at least one strand of a nucleic acid can anneal to the other nucleic acid under defined stringency conditions. Stringency of hybridization is determined by: (a) the temperature at which hybridization and/or washing is performed; and (b) the ionic strength and polarity of the hybridization and washing solutions. Hybridization requires that the two nucleic acids contain complementary sequences; depending on the stringency of hybridization, however, mismatches may be tolerated. Typically, hybridization of two sequences at high stringency (such as, for example, in a solution of 0.5×SSC, at 65° C.) requires that the sequences be essentially completely homologous. Conditions of intermediate stringency (such as, for example, 2×SSC at 65° C.) and low stringency (such. as, for example 2×SSC at 55° C.) require correspondingly less overall complementarity between the hybridizing sequences. (1×SSC is 0.15 M NaCl, 0.015 M Na citrate).

The terms peptides, proteins, and polypeptides are used interchangeably herein.

As used herein, the term "surface protein" refers to all surface accessible proteins, e.g. inner and outer membrane proteins, proteins adhering to the cell wall, and secreted proteins.

A polypeptide has *M. catarrhalis* biological activity if it has one, two or preferably more of the following properties:

(1) if when expressed in the course of an *M. catarrhalis* infection, it can promote, or mediate the attachment of *M. catarrhalis* to a cell; (2) it has an enzymatic activity, structural or regulatory function characteristic of an *M. catarrhalis* protein; (3) the gene which encodes it can rescue a lethal mutation in an *M. catarrhalis* gene. A polypeptide has biological activity if it is an antagonist, agonist, or super-agonist of a polypeptide having one of the above-listed properties.

A biologically active fragment or analog is one having an in vivo or in vitro activity which is characteristic of the *M. catarrhalis* polypeptides of the invention contained in the Sequence Listing, or of other naturally occurring *M. catarrhalis* polypeptides, e.g., one or more of the biological activities described herein. Especially preferred are fragments which exist in vivo, e.g., fragments which arise from post transcriptional processing or which arise from translation of alternatively spliced RNA's. Fragments include those expressed in native or endogenous cells as well as those made in expression systems, e.g., in CHO (Chinese Hamster Ovary) cells. Because peptides such as *M. catarrhalis* polypeptides often exhibit a range of physiological properties and because such properties may be attributable to different portions of the molecule, a useful *M. catarrhalis* fragment or *M. catarrhalis* analog is one which exhibits a biological activity in any biological assay for *M. catarrhalis* activity. The fragment or analog possesses about 10%, preferably about 40%, more preferably about 60%, 70%, 80% or 90% or greater of the activity of *M. catarrhalis*, in any in vivo or in vitro assay.

Analogs can differ from naturally occurring *M. catarrhalis* polypeptides in amino acid sequence or in ways that do not involve sequence, or both. Non-sequence modifications include changes in acetylation, methylation, phosphorylation, carboxylation, or glycosylation. Preferred analogs include: *M. catarrhalis* polypeptides (or biologically active fragments thereof) whose sequences differ from the wild-type sequence by one or more conservative amino acid substitutions or by one or more non-conservative amino acid substitutions, deletions, or insertions which do not substantially diminish the biological activity of the *M. catarrhalis* polypeptide. Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. Other conservative substitutions can be made in view of the table below.

TABLE 1

CONSERVATIVE AMINO ACID REPLACEMENTS

| For Amino Acid | Code | Replace with any of |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, β-Ala, Acp |
| Isoleucine | I | D-Ile, Val, D-Val, Leu, D-Leu, Met, D-Met |

TABLE 1-continued

CONSERVATIVE AMINO ACID REPLACEMENTS

| For Amino Acid | Code | Replace with any of |
|---|---|---|
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-I-thioazolidine-4-carboxylic acid, D-or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Other analogs within the invention are those with modifications which increase peptide stability; such analogs may contain, for example, one or more non-peptide bonds (which replace the peptide bonds) in the peptide sequence. Also included are: analogs that include residues other than naturally occurring L-amino acids, e.g., D-amino acids or non-naturally occurring or synthetic amino acids, e.g., β or γ amino acids; and cyclic analogs.

As used herein, the term "fragment", as applied to an *M. catarrhalis* analog, will ordinarily be at least about 20 residues, more typically at least about 40 residues, preferably at least about 60 residues in length. Fragments of *M. catarrhalis* polypeptides can be generated by methods known to those skilled in the art. The ability of an Moraxella fragment to exhibit a biological activity of *M. catarrhalis* polypeptide can be assessed by methods known to those skilled in the art as described herein. Also included are *M. catarrhalis* polypeptides containing residues that are not required for biological activity of the peptide or that result from alternative mRNA splicing or alternative protein processing events.

An "immunogenic component" as used herein is a moiety, such as an *M. catarrhalis* polypeptide, analog or fragment thereof, that is capable of eliciting a humoral and/or cellular immune response in a host animal.

An "antigenic component" as used herein is a moiety, such as an *M. catarrhalis* polypeptide, analog or fragment thereof, that is capable of binding to a specific antibody with sufficiently high affinity to form a detectable antigen-antibody complex.

The term "antibody" as used herein is intended to include fragments thereof which are specifically reactive with *M. catarrhalis* polypeptides.

As used herein, the term "cell-specific promoter" means a DNA sequence that serves as a promoter, i.e., regulates expression of a selected DNA sequence operably linked to the promoter, and which effects expression of the selected DNA sequence in specific cells of a tissue. The term also covers so-called "leaky" promoters, which regulate expression of a selected DNA primarily in one tissue, but cause expression in other tissues as well.

Misexpression, as used herein, refers to a non-wild type pattern of gene expression. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of increased expression (as compared with wild type) in a predetermined cell type or tissue type; a pattern of expression that differs from wild type in terms of the splicing size, amino acid sequence, post-translational modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

As used herein, "host cells" and other such terms denoting microorganisms or higher eukaryotic cell lines cultured as unicellular entities refers to cells which can become or have been used as recipients for a recombinant vector or other transfer DNA, and include the progeny of the original cell which has been transfected. It is understood by individuals skilled in the art that the progeny of a single parental cell may not necessarily be completely identical in genomic or total DNA compliment to the original parent, due to accident or deliberate mutation.

As used herein, the term "control sequence" refers to a nucleic acid having a base sequence which is recognized by the host organism to effect the expression of encoded sequences to which they are ligated. The nature of such control sequences differs depending upon the host organism; in prokaryotes, such control sequences generally include a promoter, ribosomal binding site, terminators, and in some cases operators; in eukaryotes, generally such control sequences include promoters, terminators and in some instances, enhancers. The term control sequence is intended to include at a minimum, all components whose presence is necessary for expression, and may also include additional components whose presence is advantageous, for example, leader sequences.

As used herein, the term "operably linked" refers to sequences joined or ligated to function in their intended manner. For example, a control sequence is operably linked to coding sequence by ligation in such a way that expression of the coding sequence is achieved under conditions compatible with the control sequence and host cell.

The "metabolism" of a substance, as used herein, means any aspect of the expression, function, action, or regulation of the substance. The metabolism of a substance includes modifications, e.g., covalent or non-covalent modifications of the substance. The metabolism of a substance includes modifications, e.g., covalent or non-covalent modification, the substance induces in other substances. The metabolism of a substance also includes changes in the distribution of the substance. The metabolism of a substance includes changes the substance induces in the distribution of other substances.

A "sample" as used herein refers to a biological sample, such as, for example, tissue or fluid isloated from an individual (including without limitation plasma, serum, cerebrospinal fluid, lymph, tears, saliva and tissue sections) or from in vitro cell culture constituents, as well as samples from the environment.

Technical and scientific terms used herein have the meanings commonly understood by one of ordinary skill in the art to which the present invention pertains, unless otherwise defined. Reference is made herein to various methodologies known to those of skill in the art. Publications and other materials setting forth such known methodologies to which reference is made are incorporated herein by reference in their entireties as though set forth in full. The practice of the invention will employ, unless otherwise indicated, conventional techniques of chemistry, molecular biology, microbiology, recombinant DNA, and immunology, which are within the skill of the art. Such techniques are explained fully in the literature. See e.g., Sambrook, Fritsch, and Maniatis, *Molecular Cloning; Laboratory Manual* 2nd ed. (1989); DNA Cloning, Volumes I and II (D. N Glover ed. 1985); *Oligonucleotide Synthesis* (M. J. Gait ed, 1984); *Nucleic Acid Hybridization* (B. D. Hames & S. J. Higgins eds. 1984); the series, *Methods in Enzymology* (Academic Press, Inc.), particularly Vol. 154 and Vol. 155 (Wu and Grossman, eds.); PCR-A *Practical Approach* (McPherson, Quirke, and Taylor, eds., 1991); *Immunology,* 2d Edition, 1989, Roitt et al., C. V. Mosby Company, and New York; *Advanced Immunology,* 2d Edition, 1991, Male et al., Grower Medical Publishing, New York.; *DNA Cloning: A Practical Approach,* Volumes I and II, 1985 (D. N. Glover ed.); *Oligonucleotide Synthesis,* 1984, (M. L. Gait ed); *Transcription and Translation,* 1984 (Hames and Higgins eds.); *Animal Cell Culture,* 1986 (R. I. Freshney ed.); *Immobilized Cells and Enzymes,* 1986 (IRL Press); Perbal, 1984, A *Practical Guide to Molecular Cloning; Gene Transfer Vectors for Mammalian Cells,* 1987 (J. H. Miller and M. P. Calos eds., Cold Spring Harbor Laboratory); Martin J. Bishop, ed., *Guide to Human Genome Computing,* 2d Edition, Academic Press, San Diego, Calif. (1998); and Leonard F. Peruski, Jr., and Anne Harwood Peruski, *The Internet and the New Biology: Tools for Genomic and Molecular Research,* American Society for Microbiology, Washington, D.C. (1997).

Any suitable materials and/or methods known to those of skill can be utilized in carrying out the present invention; however, preferred materials and/or methods are described. Materials, reagents and the like to which reference is made in the following description and examples are obtainable from commercial sources, unless otherwise noted.

*M. catarrhalis* Genomic Sequence

This invention provides nucleotide sequences of the genome of *M. catarrhalis* which thus comprises a DNA sequence library of *M. catarrhalis* genomic DNA. The detailed description that follows provides nucleotide sequences of *M. catarrhalis,* and also describes how the sequences were obtained and how ORFs and protein-coding sequences were identified. Also described are compositions and methods of using the disclosed *M. catarrhalis* sequences in methods including diagnostic and therapeutic applications. Furthermore, the library can be used as a database for identification and comparison of medically important sequences in this and other strains of *M. catarrhalis.*

To determine the genomic sequence of *M. catarrhalis,* DNA from strain 98-4362. of *M. catarrhalis* was isolated and a library of DNA fragments were transformed into DH5α cells. DNA sequencing was achieved using established ABI sequencing methods on ABI377 automated DNA sequencers. The cloning and sequencing procedures are described in more detail in the Exemplification.

Individual sequence reads were assembled using PHRAP (P. Green, Abstracts of DOE Human Genome Program Contractor-Grantee Workshop V, January 1996, p. 157). The average contig length was about 3–4 kb.

All subsequent steps were based on sequencing by ABI377 automated DNA sequencing methods. The cloning and sequencing procedures are described in more detail in the Exemplification.

A variety of approaches may be used to order the contigs so as to obtain a continuous sequence representing the entire

*M. catarrhalis* genome. Synthetic oligonucleotides are designed that are complementary to sequences at the end of each contig. These oligonucleotides may be hybridized, to libaries of *M. catarrhalis* genomic DNA in, for example, lambda phage vectors or plasmid vectors to identify clones that contain sequences corresponding to the junctional regions between individual contigs. Such clones are then used to isolate template DNA and the same oligonucleotides are used as primers in polymerase chain reaction (PCR) to amplify junctional fragments, the nucleotide sequence of which is then determined.

The *M. catarrhalis* sequences were analyzed for the presence of open reading frames (ORFs) comprising at least 180 nucleotides. As a result of the analysis of ORFs based on stop-to-stop codon reads, it should be understood that these ORFs may not correspond to the ORF of a naturally-occurring *M. catarrhalis* polypeptide. These ORFs may contain start codons which indicate the initiation of protein synthesis of a naturally-occuring *M. catarrhalis* polypeptide. Such start codons within the ORFs provided herein were identified by those of ordinary skill in the relevant art, and the resulting ORF and the encoded *M. catarrhalis* polypeptide is within the scope of this invention. For example, within the ORFs a codon such as AUG or GUG (encoding methionine or valine) which is part of the initiation signal for protein synthesis were identified and the portion of an ORF to corresponding to a naturally-occurring *M. catarrhalis* polypeptide was recognized. The predicted coding regions were defined by evaluating the coding potential of such sequences with the program GENEMARK™ (Borodovsky and McIninch, 1993, *Comp.* 17:123).

Each predicted ORF amino acid sequence was compared with all sequences found in current GENBANK, SWISS-PROT, and PIR databases using the BLAST algorithm. BLAST identifies local alignments occurring by chance between the ORF sequence and the sequence in the databank (Altschal et al., 1990, L Mol. Biol. 215:403–410). Homologous ORFs (probabilities less than $10^{-5}$ by chance) and ORF's that are probably non-homologous probabilities greater than $10^{-5}$ by chance) but have good codon usage were identified. Both homologous, sequences and non-homologous sequences with good codon usage, are likely to encode proteins and are encompassed by the invention.

*M. catarrhalis* Nucleic Acids

The present invention provides a library of *M. catarrhalis*—derived nucleic acid sequences. The libraries provide probes, primers, and markers which are used as markers in epidemiological studies. The present invention also provides a library of *M. catarrhalis*—derived nucleic acid sequences which comprise or encode targets for therapeutic drugs.

The nucleic acids of this invention may be obtained directly from the DNA of the above reference *M. catarrhalis* strain by using the polymerase chain reaction (PCR). See *"PCR, A Practical Approach"* (McPherson, Quirke, and Taylor, eds., IRL Press, Oxford, UK, 1991) for details about the PCR. High fidelity PCR is used to ensure a faithful DNA copy prior to expression. In addition, the authenticity of amplified products is verified by conventional sequencing methods. Clones carrying the desired sequences described in this invention may also be obtained by screening the libraries by means of the PCR or by hybridization of synthetic oligonucleotide probes to filter lifts of the library colonies or plaques as known in the art (see, e.g., Sambrook et al., *Molecular Cloning, A Laboratory Manual* 2nd edition, 1989, Cold Spring Harbor Press, N.Y.).

It is also possible to obtain nucleic acids encoding *M. catarrhalis* polypeptides from a cDNA library in accordance with protocols herein described. A cDNA encoding an *M. catarrhalis* polypeptide can be obtained by isolating total mRNA from an appropriate strain. Double stranded cDNAs can then be prepared from the total mRNA. Subsequently, the cDNAs can be inserted into a suitable plasmid or viral (e.g., bacteriophage) vector using any one of a number of known techniques. Genes encoding *M. catarrhalis* polypeptides can also be cloned using established polymerase chain reaction techniques in accordance with the nucleotide sequence information provided by the invention. The nucleic acids of the invention can be DNA or RNA. Preferred nucleic acids of the invention are contained in the Sequence Listing.

The nucleic acids of the invention can also be chemically synthesized using standard techniques. Various methods of chemically synthesizing polydeoxynucleotides are known, including solid-phase synthesis which, like peptide synthesis, has been fully automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071, incorporated by reference herein).

In another example, DNA can be chemically synthesized using, e.g., the phosphoramidite solid support method of Matteucci et al., 1981, *J. Am. Chem. Soc.* 103:3185, the method of Yoo et al., 1989, *J. Biol. Chem.* 764:17078, or other well known methods. This can be done by sequentially linking a series of oligonucleotide cassettes comprising pairs of synthetic oligonucleotides, as described below.

Nucleic acids isolated or synthesized in accordance with features of the present invention are useful, by way of example, without limitation, as probes, primers, capture ligands, antisense genes and for developing expression systems for the synthesis of proteins and peptides corresponding to such sequences. As probes, primers, capture ligands and antisense agents, the nucleic acid normally consists of all or part (approximately twenty or more nucleotides for specificity as well as the ability to form stable hybridization products) of the nucleic acids of the invention contained in the Sequence Listing. These uses are described in further detail below.

Probes

A nucleic acid isolated or synthesized in accordance with the sequence of the invention contained in the Sequence Listing can be used as a probe to specifically detect *M. catarrhalis*. With the sequence information set forth in the present application, sequences of twenty or more nucleotides are identified which provide the desired inclusivity and exclusivity with respect to *M. catarrhalis,* and extraneous nucleic acids likely to be encountered during hybridization conditions. More preferably, the sequence will comprise at least about twenty to thirty nucleotides to convey stability to the hybridization product formed between the probe and the intended target molecules.

Sequences larger than 1000 nucleotides in length are difficult to synthesize but can be generated by recombinant DNA techniques. Individuals skilled in the art will readily recognize that the nucleic acids, for use as probes, can be provided with a label to facilitate detection of a hybridization product.

Nucleic acid isolated and synthesized in accordance with the sequence of the invention contained in the Sequence Listing can also be useful as probes to detect homologous regions (especially homologous genes) of other Moraxella species using appropriate stringency hybridization conditions as described herein.

Capture Ligand

For use as a capture ligand, the nucleic acid selected in the manner described above with respect to probes, can be readily associated with a support. The manner in which nucleic acid is associated with supports is well known. Nucleic acid having twenty or more nucleotides in a sequence of the invention contained in the Sequence Listing have utility to separate M. catarrhalis nucleic acid from one strain from the nucleic acid of other another strain as well as from other organisms. Nucleic acid having twenty or more nucleotides in a sequence of the invention contained in the Sequence Listing can also have utility to separate other Moraxella species from each other and from other organisms. Preferably, the sequence will comprise at least about twenty nucleotides to convey stability to the hybridization product formed between the probe and the intended target molecules. Sequences larger than 1000 nucleotides in length are difficult to synthesize but can be generated by recombinant DNA techniques.

Primers

Nucleic acid isolated or synthesized in accordance with the sequences described herein have utility as primers for the amplification of M. catarrhalis nucleic acid. These nucleic acids may also have utility as primers for the amplification of nucleic acids in other Moraxella species. With respect to polymerase chain reaction (PCR) techniques, nucleic acid sequences of ≧10–15 nucleotides of the invention contained in the Sequence Listing have utility in conjunction with suitable enzymes and reagents to create copies of M. catarrhalis nucleic acid. More preferably, the sequence will comprise twenty or more nucleotides to convey stability to the hybridization product formed between the primer and the intended target molecules. Binding conditions of primers greater than 100 nucleotides are more difficult to control to obtain specificity. High fidelity PCR can be used to ensure a faithful DNA copy prior to expression. In addition, amplified products can be checked by conventional sequencing methods.

The copies can be used in diagnostic assays to detect specific sequences, including genes from M. catarrhalis and/or other Moraxella species. The copies can also be incorporated into cloning and expression vectors to generate polypeptides corresponding to the nucleic acid synthesized by PCR, as is described in greater detail herein.

The nucleic acids of the present invention find use as templates for the recombinant production of M. catarrhalis—derived peptides or polypeptides Antisense Nucleic acid or nucleic acid-hybridizing derivatives isolated or synthesized in accordance with the sequences described herein have utility as antisense agents to prevent the expression of M. catarrhalis genes. These sequences also have utility as antisense agents to prevent expression of genes of other Moraxella species.

In one embodiment, nucleic acid or derivatives corresponding to M. catarrhalis nucleic acids is loaded into a suitable carrier such as a liposome or bacteriophage for introduction into bacterial cells. For example, a nucleic acid having twenty or more nucleotides is capable of binding to bacteria nucleic acid or bacteria messenger RNA. Preferably, the antisense nucleic acid is comprised of 20 or more nucleotides to provide necessary stability of a hybridization product of non-naturally occurring nucleic acid and bacterial nucleic acid and/or bacterial messenger RNA. Nucleic acid having a sequence greater than 1000 nucleotides in length is difficult to synthesize but can be generated by recombinant DNA techniques. Methods for loading antisense nucleic acid in liposomes is known in the art as exemplified by U.S. Pat. No. 4,241,046 issued Dec. 23, 1980 to Papahadjopoulos et al.

The present invention encompasses isolated polypeptides and nucleic acids derived from M. catarrhalis that are useful as reagents for diagnosis of bacterial infection, components of effective anti-bacterial vaccines, and/or as targets for anti-bacterial drugs, including anti-M. catarrhalis drugs.

Expression of M. catarrhalis Nucleic Acids

Table 2, which is appended herewith and which forms part of the present specification, provides a list of open reading frames (ORFs) in both strands and a putative identification of the particular function of a polypeptide which is encoded by each ORF, based on the homology match (determined by the BLASTP2 algorithm) of the predicted polypeptide with known proteins encoded by ORFs in other organisms. An ORF is a region of nucleic acid which encodes a polypeptide. This region may represent a portion of a coding sequence or a total sequence and was determined from stop to stop codons. The first column contains a designation for the ORF ("ORF Name"). The second and third columns list the SEQ ID numbers for the nucleic acid ("NT ID") and amino acid ("AA ID") sequences corresponding to each ORF, respectively. The fourth and fifth columns list the length of the nucleic acid ORF ("NT Length") and the length of the amino acid ORF ("AA Length"), respectively. The nucleotide sequence corresponding to each ORF begins at the first nucleotide immediately following a stop codon and ends at the nucleotide immediately preceding the next downstream stop codon in the same reading frame. It will be recognized by one skilled in the art that the natural translation initiation sites will correspond to ATG, GTG, or TTG codons located within the ORFs. The natural initiation sites depend not only on the sequence of a start codon but also on the context of the DNA sequence adjacent to the start codon. Usually, a recognizable ribosome binding site is found within 20 nucleotides upstream from the initiation codon. In some cases where genes are translationally coupled and coordinately expressed together in "operons", ribosome binding sites are not present, but the initiation codon of a downstream gene may occur very close to, or overlap, the stop codon of the an upstream gene in the same operon. The correct start codons can be generally identified without undue experimentation because only a few codons need be tested. It is recognized that the translational machinery in bacteria initiates all polypeptide chains with the amino acid methionine, regardless of the sequence of the start codon. In some cases, polypeptides are post-translationally modified, resulting in an N-terminal amino acid other than methionine in vivo. The sixth and seventh columns provide metrics for assessing the likelihood of the homology match (determined by the BLASTP2 algorithm), as is known in the art, to the genes indicated in the description frame ("Description") defined further below. These genes in the Description were identified when the designated ORF was compared against a comprehensive non-redundant protein database. Specifically, the sixth column represents the Blast Score ("Score") for the match (a higher score is a better match), and the seventh column represents the probability ("Probability") for the match (the probability that such a match can have occurred by chance; the lower the value, the more likely the match is valid). If a BLASTP2 score of less than 100 was obtained, no value is reported in the table. The remaining fields below the columns contain additional information relating to the potential function of the sequence based on the BLASTP2 analysis. Where a match was discovered, the field "Protein name" list the protein's name identified from the match. In addition, one skilled in the art would be able to identify the match and elucidate its function using the "Locus name" and where available the accession number, "Acc#" from the database. Lastly, one skilled in the art would appreciate the "Description" field to further describe the potential function of the protein based on this analysis. This information allows one of ordinary skill in the art to determine a potential use for each identified coding sequence and, as a result, allows to use the polypeptides of the present invention for commercial and industrial purposes.

Using the information provided in SEQ ID NO: 1–SEQ ID NO: 1920, SEQ ID NO: 1921–SEQ ID NO: 3840 and in Table 2 together with routine cloning and sequencing methods, one of ordinary skill in the art will be able to clone and sequence all the nucleic acid fragments of interest including open reading frames (ORFs) encoding a large variety of proteins of *M. catarrhalis*.

Nucleic acid isolated or synthesized in accordance with the sequences described herein have utility to generate polypeptides. The nucleic acid of the invention exemplified in SEQ ID NO: 1–SEQ ID NO: 1920 and in Table 2 or fragments of said nucleic acid encoding active portions of *M. catarrhalis* polypeptides can be cloned into suitable vectors or used to isolate nucleic acid. The isolated nucleic acid is combined with suitable DNA linkers and cloned into a suitable vector.

The function of a specific gene or operon can be ascertained by expression in a bacterial strain under conditions where the activity of the gene product(s) specified by the gene or operon in question can be specifically measured. Alternatively, a gene product may be produced in large quantities in an expressing strain for use as an antigen, an industrial reagent, for structural studies, etc. This expression can be accomplished in a mutant strain which lacks the activity of the gene to be tested, or in a strain that does not produce the same gene product(s). This includes, but is not limited to, Eucaryotic species such as the yeast *Saccharomyces cerevisiae*, Methanobacterium strains or other Archaea, and Eubacteria such as *E. coli, B. Subtilis, S. Aureus, S. Pneumonia* or *Pseudomonas putida*. In some cases the expression host will utilize the natural *M. catarrhalis* promoter whereas in others, it will be necessary to drive the gene with a promoter sequence derived from the expressing organism (e.g., an *E. coli* beta-galactosidase promoter for expression in *E. coli*).

To express a gene product using the natural *M. catarrhalis* promoter, a procedure such as the following can be used. A restriction fragment containing the gene of interest, together with its associated natural promoter element and regulatory sequences (identified using the DNA sequence data) is cloned into an appropriate recombinant plasmid containing an origin of replication that functions in the host organism and an appropriate selectable marker. This can be accomplished by a number of procedures known to those skilled in the art. It is most preferably done by cutting the plasmid and the fragment to be cloned with the same restriction enzyme to produce compatible ends that can be ligated to join the two pieces together. The recombinant plasmid is introduced into the host organism by, for example, electroporation and cells containing the recombinant plasmid are identified by selection for the marker on the plasmid. Expression of the desired gene product is detected using an assay specific for that gene product.

In the case of a gene that requires a different promoter, the body of the gene (coding sequence) is specifically excised and cloned into an appropriate expression plasmid. This subcloning can be done by several methods, but is most easily accomplished by PCR amplification of a specific fragment and ligation into an expression plasmid after treating the PCR product with a restriction enzyme or exonuclease to create suitable ends for cloning.

A suitable host cell for expression of a gene can be any procaryotic or eucaryotic cell. Suitable methods for transforming host cells can be found in Sambrook et al. (*Molecular Cloning: A Laboratory Manual*, 2nd Edition, Cold Spring Harbor Laboratory Press (1989)), and other laboratory textbooks.

For example, a host cell transfected with a nucleic acid vector directing expression of a nucleotide sequence encoding an *M. catarrhalis* polypeptide can be cultured under appropriate conditions to allow expression of the polypeptide to occur. Suitable media for cell culture are well known in the art. Polypeptides of the invention can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such polypeptides. Additionally, in many situations, polypeptides can be produced by chemical cleavage of a native protein (e.g., tryptic digestion) and the cleavage products can then be purified by standard techniques.

In the case of membrane bound proteins, these can be isolated from a host cell by contacting a membrane-associated protein fraction with a detergent forming a solubilized complex, where the membrane-associated protein is no longer entirely embedded in the membrane fraction and is solubilized at least to an extent which allows it to be chromatographically isolated from the membrane fraction. Chromatographic techniques which can be used in the final purification step are known in the art and include hydrophobic interaction, lectin affinity, ion exchange, dye affinity and immunoaffinity.

One strategy to maximize recombinant *M. catarrhalis* peptide expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy would be to alter the nucleic acid encoding an *M. catarrhalis* peptide to be inserted into an expression vector so that the individual codons for each amino acid would be those preferentially utilized in highly expressed *E. coli* proteins (Wada et al., (1992) *Nuc. Acids Res.* 20:2111–2118). Such alteration of nucleic acids of the invention can be carried out by standard DNA synthesis techniques.

The nucleic acids of the invention can also be chemically synthesized using standard techniques. Various methods of chemically synthesizing polydeoxynucleotides are known, including solid-phase synthesis which, like peptide synthesis, has been fully automated in commercially available DNA synthesizers (See, e.g., Itakura et al. U.S. Pat. No. 4,598,049; Caruthers et al. U.S. Pat. No. 4,458,066; and Itakura U.S. Pat. Nos. 4,401,796 and 4,373,071, incorporated by reference herein).

The present invention provides a library of *M. catarrhalis*—derived nucleic acid sequences. The libraries provide probes, primers, and markers which can be used as markers in epidemiological studies. The present invention also provides a library of *M. catarrhalis* derived nucleic acid sequences which comprise or encode targets for therapeutic drugs.

Nucleic acids comprising any of the sequences disclosed herein or sub-sequences thereof can be prepared by standard methods using the nucleic acid sequence information provided in SEQ ID NO: 1–SEQ ID NO: 1920. For example, DNA can be chemically synthesized using, e.g., the phosphoramidite solid support method of Matteucci et al., 1981, *J. Am. Chem. Soc.* 103:3185, the method of Yoo et al., 1989, *J. Biol. Chem.* 764:17078, or other well known methods. This can be done by sequentially linking a series of oligonucleotide cassettes comprising pairs of synthetic oligonucleotides, as described below.

Of course, due to the degeneracy of the genetic code, many different nucleotide sequences can encode polypeptides having the amino acid sequences defined by SEQ ID NO: 1921–SEQ ID NO: 3840 or sub-sequences thereof. The codons can be selected for optimal expression in prokaryotic or eukaryotic systems. Such degenerate variants are also encompassed by this invention.

Insertion of nucleic acids (typically DNAs) encoding the polypeptides of the invention into a vector is easily accomplished when the termini of both the DNAs and the vector comprise compatible restriction sites. If this cannot be done, it may be necessary to modify the termini of the DNAs and/or vector by digesting back single-stranded DNA overhangs generated by restriction endonuclease cleavage to produce blunt ends, or to achieve the same result by filling in the single-stranded termini with an appropriate DNA polymerase.

Alternatively, any site desired may be produced, e.g., by ligating nucleotide sequences (linkers) onto the termini. Such linkers may comprise specific oligonucleotide sequences that define desired restriction sites. Restriction sites can also be generated by the use of the polymerase chain reaction (PCR). See, e.g., Saiki et al., 1988, *Science* 239:48. The cleaved vector and the DNA fragments may also be modified if required by homopolymeric tailing.

The nucleic acids of the invention may be isolated directly from cells. Alternatively, the polymerase chain reaction (PCR) method can be used to produce the nucleic acids of the invention, using either chemically synthesized strands or genomic material as templates. Primers used for PCR can be synthesized using the sequence information provided herein and can further be designed to introduce appropriate new restriction sites, if desirable, to facilitate incorporation into a given vector for recombinant expression.

The nucleic acids of the present invention may be flanked by natural *M. catarrhalis* regulatory sequences, or may be associated with heterologous sequences, including promoters, enhancers, response elements, signal sequences, polyadenylation sequences, introns, 5'- and 3'- noncoding regions, and the like. The nucleic acids may also be modified by many means known in the art. Non-limiting examples of such modifications include methylation, "caps", substitution of one or more of the naturally occurring nucleotides with an analog, internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Nucleic acids may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. PNAs are also included. The nucleic acid may be derivatized by formation of a methyl or ethyl phosphotriester or an alkyl phosphoramidate linkage. Furthermore, the nucleic acid sequences of the present invention may also be modified with a label capable of providing a detectable signal, either directly or indirectly. Exemplary labels include radioisotopes, fluorescent molecules, biotin, and the like.

The invention also provides nucleic acid vectors comprising the disclosed *M. catarrhalis*—derived sequences or derivatives or fragments thereof. A large number of vectors, including plasmid and bacterial vectors, have been described for replication and/or expression in a variety of eukaryotic and prokaryotic hosts, and may be used for cloning or protein expression.

The encoded *M. catarrhalis* polypeptides may be expressed by using many known vectors, such as pUC plasmids, pET plasmids (Novagen, Inc., Madison, Wis.), or pRSET or pREP (Invitrogen, San Diego, Calif.), and many appropriate host cells, using methods disclosed or cited herein or otherwise known to those skilled in the relevant art. The particular choice of vector/host is not critical to the practice of the invention.

Recombinant cloning vectors will often include one or more replication systems for cloning or expression, one or more markers for selection in the host, e.g. antibiotic resistance, and one or more expression cassettes. The inserted *M. catarrhalis* coding sequences may be synthesized by standard methods, isolated from natural sources, or prepared as hybrids, etc. Ligation of the *M. catarrhalis* coding sequences to transcriptional regulatory elements and/or to other amino acid coding sequences may be achieved by known methods. Suitable host cells may be transformed/transfected/infected as appropriate by any suitable method including electroporation, $CaCl_2$ mediated DNA uptake, bacterial infection, microinjection, microprojectile, or other established methods.

Appropriate host cells include bacteria, archebacteria, fungi, especially yeast, and plant and animal cells, especially mammalian cells. Of particular interest are *M. catarrhalis E. coli, B. Subtilis, Saccharomyces cerevisiae, Saccharomyces carlsbergensis, Schizosaccharomyces pombi,* SF9 cells, C129 cells, 293 cells, *Neurospora,* and CHO cells, COS cells, HeLa cells, and immortalized mammalian myeloid and lymphoid cell lines. Preferred replication systems include M13, ColE1, SV40, baculovirus, lambda, adenovirus, and the like. A large number of transcription initiation and termination regulatory regions have been isolated and shown to be effective in the transcription and translation of heterologous proteins in the various hosts. Examples of these regions, methods of isolation, manner of manipulation, etc. are known in the art. Under appropriate expression conditions, host cells can be used as a source of recombinantly produced *M. catarrhalis*—derived peptides and polypeptides.

Advantageously, vectors may also include a transcription regulatory element (i.e., a promoter) operably linked to the *M. catarrhalis* portion. The promoter may optionally contain operator portions and/or ribosome binding sites. Non-limiting examples of bacterial promoters compatible with *E. coli* include: b-lactamase (penicillinase) promoter; lactose promoter; tryptophan (trp) promoter; araBAD (arabinose) operon promoter; lambda-derived $P_1$ promoter and N gene ribosome binding site; and the hybrid tac promoter derived from sequences of the trp and lac UV5 promoters. Non-limiting examples of yeast promoters include 3-phosphoglycerate kinase promoter, glyceraldehyde-3-phosphate dehydrogenase (GAPDH) promoter, galactokinase (GAL1) promoter, galactoepimerase promoter, and alcohol dehydrogenase (ADH) promoter. Suitable promoters for mammalian cells include without limitation viral promoters such as that from Simian Virus 40 (SV40), Rous sarcoma virus (RSV), adenovirus (ADV), and bovine papilloma virus (BPV). Mammalian cells may also require terminator sequences, polyA addition sequences and enhancer sequences to increase expression. Sequences which cause amplification of the gene may also be desirable. Furthermore, sequences that facilitate secretion of the recombinant product from cells, including, but not limited to, bacteria, yeast, and animal cells, such as secretory signal sequences and/or prohormone pro region sequences, may also be included. These sequences are well described in the art.

Nucleic acids encoding wild-type or variant *M. catarrhalis*—derived polypeptides may also be introduced into cells by recombination events. For example, such a sequence can be introduced into a cell, and thereby effect homologous recombination at the site of an endogenous gene or a sequence with substantial identity to the gene. Other recombination-based methods such as nonhomologous recombinations or deletion of endogenous genes by homologous recombination may also be used.

The nucleic acids of the present invention find use as templates for the recombinant production of *M. catarrhalis*—derived peptides or polypeptides.

Identification and Use of *M. catarrhalis* Nucleic Acid Sequences

The disclosed *M. catarrhalis* polypeptide and nucleic acid sequences, or other sequences that are contained within ORFs, including complete protein-coding sequences, of which any of the disclosed *M. catarrhalis*—specific sequences forms a part, are useful as target components for diagnosis and/or treatment of *M. catarrhalis*—caused infection.

It will be understood that the sequence of an entire protein-coding sequence of which each disclosed nucleic acid sequence forms a part can be isolated and identified based on each disclosed sequence. This can be achieved, for example, by using an isolated nucleic acid encoding the disclosed sequence, or fragments thereof, to prime a sequencing reaction with genomic *M. catarrhalis* DNA as template; this is followed by sequencing the amplified product. The isolated nucleic acid encoding the disclosed sequence, or fragments thereof, can also be hybridized to *M. catarrhalis* genomic libraries to identify clones containing additional complete segments of the protein-coding sequence of which the shorter sequence forms a part. Then, the entire protein-coding sequence, or fragments thereof, or nucleic acids encoding all or part of the sequence, or sequence-conservative or function-conservative variants thereof, may be employed in practicing the present invention.

Preferred sequences are those that are useful in diagnostic and/or therapeutic applications. Diagnostic applications include without limitation nucleic-acid-based and antibody-based methods for detecting bacterial infection. Therapeutic applications include without limitation vaccines, passive immunotherapy, and drug treatments directed against gene products that are both unique to bacteria and essential for growth and/or replication of bacteria.

Identification of Nucleic Acids Encoding Vaccine Components and Targets for Agents Effective against *M. catarrhalis*

The disclosed *M. catarrhalis* genome sequence includes segments that direct the synthesis of ribonucleic acids and polypeptides, as well as origins of replication, promoters, other types of regulatory sequences, and intergenic nucleic acids. The invention encompasses nucleic acids encoding immunogenic components of vaccines and targets for agents effective against *M. catarrhalis*. Identification of said immunogenic components involved in the determination of the function of the disclosed sequences, which can be achieved using a variety of approaches. Non-limiting examples of these approaches are described briefly below.

Homology to Known Sequences

Computer-assisted comparison of the disclosed *M. catarrhalis* sequences with previously reported sequences present in publicly available databases is useful for identifying functional *M. catarrhalis* nucleic acid and polypeptide sequences. It will be understood that protein-coding sequences, for example, may be compared as a whole, and that a high degree of sequence homology between two proteins (such as, for example, >80–90%) at the amino acid level indicates that the two proteins also possess some degree of functional homology, such as, for example, among enzymes involved in metabolism, DNA synthesis, or cell wall synthesis, and proteins involved in transport, cell division, etc. In addition, many structural features of particular protein classes have been identified and correlate with specific consensus sequences, such as, for example, binding domains for nucleotides, DNA, metal ions, and other small molecules; sites for covalent modifications such as phosphorylation, acylation, and the like; sites of protein-:protein interactions, etc. These consensus sequences may be quite short and thus may represent only a fraction of the entire protein-coding sequence. Identification of such a feature in an *M. catarrhalis* sequence is therefore useful in determining the function of the encoded protein and identifying useful targets of antibacterial drugs.

Of particular relevance to the present invention are structural features that are common to secretory, transmembrane, and surface proteins, including secretion signal peptides and hydrophobic transmembrane domains. *M. catarrhalis* proteins identified as containing putative signal sequences and/or transmembrane domains are useful as immunogenic components of vaccines.

Targets for therapeutic drugs according to the invention include, but are not limited to, polypeptides of the invention, whether unique to *M. catarrhalis* or not, that are essential for growth and/or viability of *M. catarrhalis* under at least one growth condition. Polypeptides essential for growth and/or viability can be determined by examining the effect of deleting and/or disrupting the genes, i.e., by so-called gene "knockout". Alternatively, genetic footprinting can be used (Smith et al., 1995, *Proc. Natl. Acad. Sci. USA* 92:5479–6433; Published International Application WO 94/26933; U.S. Pat. No. 5,612,180). Still other methods for assessing essentiality includes the ability to isolate conditional lethal mutations in the specific gene (e.g., temperature sensitive mutations). Other useful targets for therapeutic drugs, which include polypeptides that are not essential for growth or viability per se but lead to loss of viability of the cell, can be used to target therapeutic agents to cells.

Strain-Specific Sequences

Because of the evolutionary relationship between different *M. catarrhalis* strains, it is believed that the presently disclosed *M. catarrhalis* sequences are useful for identifying, and/or discriminating between, previously known and new *M. catarrhalis* strains. It is believed that other *M. catarrhalis* strains will exhibit at least about 70% sequence homology with the presently disclosed sequence. Systematic and routine analyses of DNA sequences derived from samples containing *M. catarrhalis* strains, and comparison with the present sequence allows for the identification of sequences that can be used to discriminate between strains, as well as those that are common to all *M. catarrhalis* strains. In one embodiment, the invention provides nucleic acids, including probes, and peptide and polypeptide sequences that discriminate between different strains of *M. catarrhalis*. Strain-specific components can also be identified functionally by their ability to elicit or react with antibodies that selectively recognize one or more *M. catarrhalis* strains.

In another embodiment, the invention provides nucleic acids, including probes, and peptide and polypeptide sequences that are common to all *M. catarrhalis* strains but are not found in other bacterial species.

*M. catarrhalis* Polypeptides

This invention encompasses isolated *M. catarrhalis* polypeptides encoded by the disclosed *M. catarrhalis* genomic sequences, including the polypeptides of the invention contained in the Sequence Listing. Polypeptides of the invention are preferably at least about 5 amino acid residues in length. Using the DNA sequence information provided herein, the amino acid sequences of the polypeptides encompassed by the invention can be deduced using methods well-known in the art. It wilt be understood that the sequence of an entire nucleic acid encoding an *M. catarrhalis* polypeptide can be isolated and identified based on an ORF that encodes only a fragment of the cognate protein-coding region. This can be achieved, for example, by using the isolated nucleic acid encoding the ORF, or fragments thereof, to prime a polymerase chain reaction with genomic *M. catarrhalis* DNA as template; this is followed by sequencing the amplified product.

The polypeptides of the present invention, including function-conservative variants of the disclosed ORFs, may be isolated from wild-type or mutant *M. catarrhalis* cells, or from heterologous organisms or cells (including, but not limited to, bacteria, fungi, insect, plant, and mammalian cells) including *M. catarrhalis* into which an *M. catarrhalis*—derived protein-coding sequence has been introduced and expressed. Furthermore, the polypeptides may be part of recombinant fusion proteins.

*M. catarrhalis* polypeptides of the invention can be chemically synthesized using commercially automated procedures such as those referenced herein, including, without limitation, exclusive solid phase synthesis, partial solid phase methods, fragment condensation or classical solution synthesis. The polypeptides are preferably prepared by solid phase peptide synthesis as described by Merrifield, 1963, *J. Am. Chem. Soc.* 85:2149. The synthesis is carried out with amino acids that are protected at the alpha-amino terminus. Trifunctional amino acids with labile side-chains are also protected with suitable groups to prevent undesired chemical reactions from occurring during the assembly of the polypeptides. The alpha-amino protecting group is selectively removed to allow subsequent reaction to take place at the amino-terminus. The conditions for the removal of the alpha-amino protecting group do not remove the side-chain protecting groups.

Methods for polypeptide purification are well-known in the art, including, without limitation, preparative disc-gel electrophoresis, isoelectric focusing, HPLC, reversed-phase HPLC, gel filtration, ion exchange and partition chromatography, and countercurrent distribution. For some purposes, it is preferable to produce the polypeptide in a recombinant system in which the *M. catarrhalis* protein contains an additional sequence tag that facilitates purification, such as, but not limited to, a polyhistidine sequence. The polypeptide can then be purified from a crude lysate of the host cell by chromatography on an appropriate solid-phase matrix. Alternatively, antibodies produced against an *M. catarrhalis* protein or against peptides derived therefrom can be used as purification reagents. Other purification methods are possible.

The present invention also encompasses derivatives and homologues of *M. catarrhalis*—encoded polypeptides. For some purposes, nucleic acid sequences encoding the peptides may be altered by substitutions, additions, or deletions that provide for functionally equivalent molecules, i.e., function-conservative variants. For example, one or more amino acid residues within the sequence can be substituted by another amino acid of similar properties, such as, for example, positively charged amino acids (arginine, lysine, and histidine); negatively charged amino acids (aspartate and glutamate); polar neutral amino acids; and non-polar amino acids.

The isolated polypeptides may be modified by, for example, phosphorylation, sulfation, acylation, or other protein modifications. They may also be modified with a label capable of providing a detectable signal, either directly or indirectly, including, but not limited to, radioisotopes and fluorescent compounds.

To identify *M. catarrhalis*—derived polypeptides for use in the present invention, essentially the complete genomic sequence of a virulent, methicillin-resistant isolate of *M. catarrhalis* isolate was analyzed. While, in very rare instances, a nucleic acid sequencing error may be revealed, resolving a rare sequencing error is well within the art, and such an occurrence will not prevent one skilled in the art from practicing the invention.

Also encompassed are any *M. catarrhalis* polypeptide sequences that are contained within the open reading frames (ORFs), including complete protein-coding sequences, of which any of SEQ ID NO: 1–SEQ ID NO: 1920 forms a part. Table 2, which is appended herewith and which forms part of the present specification, provides a putative identification of the particular function of a polypeptide which is encoded by each ORF, based on the homology match (determined by the BLAST algorithm) of the predicted polypeptide with known proteins encoded by ORFs in other organisms. As a result, one skilled in the art can use the polypeptides of the present invention for commercial and industrial purposes consistent with the type of putative identification of the polypeptide.

The present invention provides a library of *M. catarrhalis*—derived polypeptide sequences, and a corresponding library of nucleic acid sequences encoding the polypeptides, wherein the polypeptides themselves, or polypeptides contained within ORFs of which they form a part, comprise sequences that are contemplated for use as components of vaccines. Non-limiting examples of such sequences are listed by SEQ ID NO in Table 2, which is appended herewith and which forms part of the present specification.

The present invention also provides a library of *M. catarrhalis*—derived polypeptide sequences, and a corresponding library of nucleic acid sequences encoding the polypeptides, wherein the polypeptides themselves, or polypeptides contained within ORFs of which they form a part, comprise sequences lacking homology to any known prokaryotic or eukaryotic sequences. Such libraries provide probes, primers, and markers which can be used to diagnose *M. catarrhalis* infection, including use as markers in epidemiological studies. Non-limiting examples of such sequences are listed by SEQ ID NO in Table 2, which is appended hereto and part hereof.

The present invention also provides a library of *M. catarrhalis*—derived polypeptide sequences, and a corresponding library of nucleic acid sequences encoding the polypeptides, wherein the polypeptides themselves, or polypeptides contained within ORFs of which they form a part, comprise targets for therapeutic drugs.

Specific Example: Determination of Moraxella Protein Antigens for Antibody and Vaccine Development The selection of Moraxella protein antigens for vaccine development can be derived from the nucleic acids encoding *M. catarrhalis* polypeptides. First, the ORF's can be analyzed for homology to other known exported or membrane proteins and analyzed using the discriminant analysis described by Klein, et al. (Klein, P., Kanehsia, M., and DeLisi, C. (1985) *Biochimica et Biophysica Acta* 815, 468–476) for predicting exported and membrane proteins.

Homology searches can be performed using the BLAST algorithm contained in the Wisconsin Sequence Analysis Package (Genetics Computer Group, University Research Park, 575 Science Drive, Madison, Wis. 53711) to compare each predicted ORF amino acid sequence with all sequences found in the current GenBank, SWISS-PROT and PIR databases. BLAST searches for local alignments between the ORF and the databank sequences and reports a probability score which indicates the probability of finding this sequence by chance in the database. ORF's with significant homology (e.g. probabilities lower than $1 \times 10^{-6}$ that the homology is only due to random chance) to membrane or exported proteins represent protein antigens for vaccine development. Possible functions can be provided to *M. catarrhalis* genes based on sequence homology to genes cloned in other organisms.

Discriminant analysis (Klein, et al. supra) can be used to examine the,ORF amino acid sequences. This algorithm uses the intrinsic information contained in the ORF amino acid sequence and compares it to information derived from the properties of known membrane and exported proteins. This comparison predicts which proteins will be exported, membrane associated or cytoplasmic. ORF amino acid sequences identified as exported or membrane associated by this algorithm are likely protein antigens for vaccine development.

Production of Fragments and Analogs of *M. catarrhalis* Nucleic Acids and Polypeptides Based on the discovery of the *M. catarrhalis* gene products of the invention provided in the Sequence Listing, one skilled in the art can alter the disclosed structure of *M. catarrhalis* genes, e.g., by producing fragments or analogs, and test the newly produced structures for activity. Examples of techniques known to those skilled in the relevant art which allow the production and testing of fragments and analogs are discussed below. These, or analogous methods can be used to make and screen libraries of polypeptides, e.g., libraries of random peptides or libraries of fragments or analogs of cellular proteins for the ability to bind *M. catarrhalis* polypeptides. Such screens are useful for the identification of inhibitors of *M. catarrhalis*.

Generation of Fragments

Fragments of a protein can be produced in several ways, e.g., recombinantly, by proteolytic digestion, or by chemical synthesis. Internal or terminal fragments of a polypeptide can be generated by removing one or more nucleotides from one end (for a terminal fragment) or both ends (for an internal fragment) of a nucleic acid which encodes the polypeptide. Expression of the mutagenized DNA produces polypeptide fragments. Digestion with "end-nibbling" endonucleases can thus generate DNAs which encode an array of fragments. DNAs which encode fragments of a protein can also be generated by random shearing, restriction digestion or a combination of the above-discussed methods.

Fragments can also be chemically synthesized using techniques known in the art such as conventional Merrifield solid phase f-Moc or t-Boc chemistry. For example, peptides of the present invention may be arbitrarily divided into fragments of desired length with no overlap of the fragments, or divided into overlapping fragments of a desired length.

Alteration of Nucleic Acids and Polypeptides: Random Methods

Amino acid sequence variants of a protein can be prepared by random mutagenesis of DNA which encodes a protein or a particular domain or region of a protein. Useful methods include PCR mutagenesis and saturation mutagenesis. A library of random amino acid sequence variants can also be generated by the synthesis of a set of degenerate oligonucleotide sequences. (Methods for screening proteins in a library of variants are elsewhere herein).

PCR Mutagenesis

In PCR mutagenesis, reduced Taq polymerase fidelity is used to introduce random mutations into a cloned fragment of DNA (Leung et al., 1989, Technique 1:11–15). The DNA region to be mutagenized is amplified using the polymerase chain reaction (PCR) under conditions that reduce the fidelity of DNA synthesis by Taq DNA polymerase, e.g., by using a dGTP/dATP ratio of five and adding $Mn^{2+}$ to the PCR reaction. The pool of amplified DNA fragments are inserted into appropriate cloning vectors to provide random mutant libraries.

Saturation Mutagenesis

Saturation mutagenesis allows for the rapid introduction of a large number of single base substitutions into cloned DNA fragments (Mayers et al., 1985, *Science* 229:242). This technique includes generation of mutations, e.g., by chemical treatment or irradiation of single-stranded DNA in vitro, and synthesis of a complimentary DNA strand. The mutation frequency can be modulated by modulating the severity of the treatment, and essentially all possible base substitutions can be obtained. Because this procedure does not involve a genetic selection for mutant fragments both neutral substitutions, as well as those that alter function, are obtained. The distribution of point mutations is not biased toward conserved sequence elements.

Degenerate Oligonucleotides

A library of homologs can also be generated from a set of degenerate oligonucleotide sequences. Chemical synthesis of a degenerate sequences can be carried out in an automatic DNA synthesizer, and the synthetic genes then ligated into an appropriate expression vector. The synthesis of degenerate oligonucleotides is known in the art (see for example, Narang, SA (1983) *Tetrahedron* 39:3; Itakura et al. (1981) *Recombinant DNA, Proc 3rd Cleveland Sympos. Macromolecules,* ed. A G Walton, Amsterdam: Elsevier pp273–289; Itakura et al. (1984) *Annu. Rev. Biochem.* 53:323; Itakura et al. (1984) *Science* 198:1056; Ike et al. (1983) *Nucleic Acid Res.* 11:477.Such techniques have been employed in the directed evolution of other proteins (see, for example, Scott et al. (1990) *Science* 249:386–390; Roberts et al. (1992) PNAS. 89:2429–2433; Devlin et al. (1990) *Science* 249: 404406; Cwirla et al. (1990) PNAS 87: 6378–6382; as well as U.S. Pat. Nos. 5,223,409, 5,198,346, and 5,096,815).

Alteration of Nucleic Acids and Polypeptides: Methods for Directed Mutagenesis

Non-random or directed, mutagenesis techniques can be used to provide specific sequences or mutations in specific regions. These techniques can be used to create variants which include, e.g., deletions, insertions, or substitutions, of residues of the known amino acid sequence of a protein. The sites for mutation can be modified individually or in series, e.g., by (1) substituting first with conserved amino acids and then with more radical choices depending upon results achieved, (2) deleting the target residue, or (3) inserting residues of the same or a different class adjacent to the located site, or combinations of options 1–3.

Alanine Scanning Mutagenesis

Alanine scanning mutagenesis is a useful method for identification of certain residues or regions of the desired protein that are preferred locations or domains for mutagenesis, Cunningham and Wells (*Science* 244:1081–1085, 1989). In alanine scanning, a residue or group of target residues are identified (e.g., charged residues such as Arg, Asp, His, Lys, and Glu) and replaced by a neutral or negatively charged amino acid (most preferably alanine or polyalanine). Replacement of an amino acid can affect the interaction of the amino acids with the surrounding aqueous environment in or outside the cell. Those domains demonstrating functional sensitivity to the substitutions are then refined by introducing further or other variants at or for the sites of substitution. Thus, while the site for introducing an amino acid sequence variation is predetermined, the nature of the mutation per se need not be predetermined. For example, to optimize the performance of a mutation at a given site, alanine scanning or random mutagenesis may be conducted at the target codon or region and the expressed desired protein subunit variants are screened for the optimal combination of desired activity.

Oligonucleotide-Mediated Mutagenesis

Oligonucleotide-mediated mutagenesis is a useful method for preparing substitution, deletion, and insertion variants of DNA, see, e.g., Adelman et al., (*DNA* 2:183, 1983). Briefly, the desired DNA is altered by hybridizing an oligonucleotide encoding a mutation to a DNA template, where the template is the single-stranded form of a plasmid or bacteriophage containing the unaltered or native DNA sequence of the desired protein. After hybridization, a DNA polymerase is used to synthesize an entire second complementary strand of the template that will thus incorporate the oligonucleotide primer, and will code for the selected alteration in the desired protein DNA. Generally, oligonucleotides of at least about 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art. such as that described by Crea et al. (*Proc. Natl. Acad. Sci. USA*, 75: 5765[1978]).

Cassette Mutagenesis

Another method for preparing variants, cassette mutagenesis, is based on the technique described by Wells et al. (*Gene,* 34:315[1985]). The starting material is a plasmid (or other vector) which includes the protein subunit DNA to be mutated. The codon(s) in the protein subunit DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the desired protein subunit DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are comparable with the ends of the linearized plasmid, such that it can be directly ligated to the plasmid. This plasmid now contains the mutated desired protein subunit DNA sequence.

Combinatorial Mutagenesis

Combinatorial mutagenesis can also be used to generate mutants (Ladner et al., WO 88/06630). In this method, the amino acid sequences for a group of homologs or other related proteins are aligned, preferably to promote the highest homology possible. All of the amino acids which appear at a given position of the aligned sequences can be selected to create a degenerate set of combinatorial sequences. The variegated library of variants is generated by combinatorial mutagenesis at the nucleic acid level, and is encoded by a variegated gene library. For example, a mixture of synthetic oligonucleotides can be enzymatically ligated into gene sequences such that the degenerate set of potential sequences are expressible as individual peptides, or alternatively, as a set of larger fusion proteins containing the set of degenerate sequences.

Other Modifications of *M. catarrhalis* Nucleic Acids and Polypeptides

It is possible to modify the structure of an *M. catarrhalis* polypeptide for such purposes as increasing solubility, enhancing stability (e.g., shelf life ex vivo and resistance to proteolytic degradation in vivo). A modified *M. catarrhalis* protein or peptide can be produced in which the amino acid sequence has been altered, such as by amino acid substitution, deletion, or addition as described herein.

An *M. catarrhalis* peptide can also be modified by substitution of cysteine residues preferably with alanine, serine, threonine, leucine or glutamic acid residues to minimize dimerization via disulfide linkages. In addition, amino acid side chains of fragments of the protein of the invention can be chemically modified. Another modification is cyclization of the peptide.

In order to enhance stability and/or reactivity, an *M. catarrhalis* polypeptide can be modified to incorporate one or more polymorphisms in the amino acid sequence of the protein resulting from any natural allelic variation. Additionally, D-amino acids, non-natural amino acids, or non-amino acid analogs can be substituted or added to produce a modified protein within the scope of this invention. Furthermore, an *M. catarrhalis* polypeptide can be modified using polyethylene glycol (PEG) according to the method of A. Sehon and co-workers (Wie et al., supra) to produce a protein conjugated with PEG. In addition, PEG can be added during chemical synthesis of the protein. Other modifications of *M. catarrhalis* proteins include reduction/alkylation (Tarr, *Methods of Protein Microcharacterization,* J. E. Silver ed., Humana Press, Clifton N.J. 155–194 (1986)); acylation (Tarr, supra); chemical coupling to an appropriate carrier (Mishell and Shiigi, eds, *Selected Methods in Cellular Immunology,* WH Freeman, San Francisco, Calif. (1980), U.S. Pat. No. 4,939,239; or mild formalin treatment (Marsh, (1971) *Int. Arch. of Allergy and Appl. Immunol.,* 41: 199–215).

To facilitate purification and potentially increase solubility of an *M. catarrhalis* protein or peptide, it is possible to add an amino acid fusion moiety to the peptide backbone. For example, hexa-histidine can be added to the protein for purification by immobilized metal ion affinity chromatography (Hochuli, E. et al., (1988) *Bio/Technology,* 6: 1321–1325). In addition, to facilitate isolation of peptides free of irrelevant sequences, specific endoprotease cleavage sites can be introduced between the sequences of the fusion moiety and the peptide.

To potentially aid proper antigen processing of epitopes within an *M. catarrhalis* polypeptide, canonical protease sensitive sites can be engineered between regions, each comprising at least one epitope via recombinant or synthetic methods. For example, charged amino acid pairs, such as KK or RR, can be introduced between regions within a protein or fragment during recombinant construction thereof. The resulting peptide can be rendered sensitive to cleavage by cathepsin and/or other trypsin-like enzymes which would generate portions of the protein containing one or more epitopes. In addition, such charged amino acid residues can result in an increase in the solubility of the peptide.

Primary Methods for Screening Polypeptides and Analogs

Various techniques are known in the art for screening generated mutant gene products. Techniques for screening large gene libraries often include cloning the gene library into replicable expression vectors, transforming appropriate cells with the resulting library of vectors, and expressing the genes under conditions in which detection of a desired activity, e.g., in this case, binding to *M. catarrhalis* polypeptide or an interacting protein, facilitates relatively easy isolation of the vector encoding the gene whose product was detected. Each of the techniques described below is amenable to high through-put analysis for screening large numbers of sequences created, e.g., by random mutagenesis techniques.

Two Hybrid Systems

Two hybrid assays such as the system described below (as with the other screening methods described herein), can be. used to identify polypeptides, e.g., fragments or analogs of a naturally-occurring *M. catarrhalis* polypeptide, e.g., of cellular proteins, or of randomly generated polypeptides which bind to an *M. catarrhalis* protein. (The *M. catarrhalis* domain is used as the bait protein and the library of variants are expressed as prey fusion proteins.) In an analogous fashion, a two hybrid assay (as with the other screening methods described herein), can be used to find polypeptides which bind an *M. catarrhalis* polypeptide.

Display Libraries

In one approach to screening assays, the Moraxella peptides are displayed on the surface of a cell or viral particle, and the ability of particular cells or viral particles to bind an appropriate receptor protein via the displayed product is detected in a "panning assay". For example, the gene library can be cloned into the gene for a surface membrane protein of a bacterial cell, and the resulting fusion protein detected by panning (Ladner et al., WO 88/06630; Fuchs et al. (1991) *Bio/Technology* 9:1370–1371; and Goward et al. (1992) *TIBS* 18:136–140). In a similar fashion, a detectably labeled ligand can be used to score for potentially functional peptide homologs. Fluorescently labeled ligands, e.g., receptors, can be used to detect homologs which retain ligand-binding activity. The use of fluorescently labeled ligands, allows cells to be visually inspected and separated under a fluorescence microscope, or, where the morphology of the cell permits, to be separated by a fluorescence-activated cell sorter.

A gene library can be expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at concentrations well over $10^{13}$ phage per milliliter, a large number of phage can be screened at one time. Second, since each infectious phage displays a gene product on its surface, if a particular phage is recovered from an affinity matrix in low yield, the phage can be amplified by another round of infection. The group of almost identical *E. coli* filamentous phages, M13, fd., and fl, are most often used in phage display libraries. Either of the phage gIII or gVIII coat proteins can be used to generate fusion proteins without disrupting the ultimate packaging of the viral particle. Foreign epitopes can be expressed at the $NH_2$-terminal end of pIII and phage bearing such epitopes recovered from a large excess of phage lacking this epitope (Ladner et al. PCT publication WO 90/02909; Garrard et al., PCT publication WO 92/09690; Marks et al. (1992) *J. Biol. Chem.* 267:16007–16010; Griffiths et al. (1993) *EMBO J* 12:725–734; Clackson et al. (1991) *Nature* 352:624–628; and Barbas et al. (1992) PNAS 89:4457–4461).

A common approach uses the maltose receptor of *E. coli* (the outer membrane protein, LamB) as a peptide fusion partner (Charbit et al. (1986) *EMBO* 5, 3029–3037). Oligonucleotides have been inserted into plasmids encoding the LamB gene to produce peptides fused into one of the extracellular loops of the protein. These peptides are available for binding to ligands, e.g., to antibodies, and can elicit an immune response when the cells are administered to animals. Other cell surface proteins, e.g., OmpA (Schorr et al. (1991) *Vaccines* 91, pp. 387–392), PhoE (Agterberg, et al. (1990) *Gene* 88, 37–45), and PAL (Fuchs et al. (1991) *Bio/Tech* 9, 1369–1372), as well as large bacterial surface structures have served as vehicles for peptide display. Peptides can be fused to pilin, a protein which polymerizes to form the pilus-a conduit for interbacterial exchange of genetic information (Thiry et al. (1989) *Appl. Environ. Microbiol.* 55, 984–993). Because of its role in interacting with other cells, the pilus provides a useful support for the presentation of peptides to the extracellular environment. Another large surface structure used for peptide display is the bacterial motive organ, the flagellum. Fusion of peptides to the subunit protein flagellin offers a dense array of many peptide copies on the host cells (Kuwajima et al. (1988) *Bio/Tech.* 6, 1080–1083). Surface proteins of other bacterial species have also served as peptide fusion partners. Examples include the Moraxella protein A and the outer membrane IgA protease of Neisseria (Hansson et al. (1992) *J. Bacteriol.* 174, 4239–4245 and Klauser et al. (1990) *EMBO J.* 9, 1991–1999).

In the filamentous phage systems and the LamB system described above, the physical link between the peptide and its encoding DNA occurs by the containment of the DNA within a particle (cell or phage) that carries the peptide on its surface. Capturing the peptide captures the particle and the DNA within. An alternative scheme uses the DNA-binding protein LacI to form a link between peptide and DNA (Cull et al. (1992) *PNAS USA,* 89:1865–1869). This system uses a plasmid containing the LacI gene with an oligonucleotide cloning site at its 3'-end. Under the controlled induction by arabinose, a LacI-peptide fusion protein is produced. This fusion retains the natural ability of LacI to bind to a short DNA sequence known as LacO operator (LacO). By installing two copies of LacO on the expression plasmid, the LacI-peptide fusion binds tightly to the plasmid that encoded it. Because the plasmids in each cell contain only a single oligonucleotide sequence and each cell expresses only a single peptide sequence, the peptides become specifically and stablely associated with the DNA sequence that directed its synthesis. The cells of the library are gently lysed and the peptide-DNA complexes are exposed to a matrix of immobilized receptor to recover the complexes containing active peptides. The associated plasmid DNA is then reintroduced into cells for amplification and DNA sequencing to determine the identity of the peptide ligands. As a demonstration of the practical utility of the method, a large random library of dodecapeptides was made and selected on a monoclonal antibody raised against the opioid peptide dynorphin B. A cohort of peptides was recovered, all related by a consensus sequence corresponding to a six-residue portion of dynorphin B. (Cull et al. (1992) *Proc. Natl. Acad. Sci. U.S.A.* 89–1869).

This scheme, sometimes referred to as peptides-on-plasmids, differs in two important ways from the phage display methods. First, the peptides are attached to the C-terminus of the fusion protein, resulting in the display of the library members as peptides having free carboxy termini. Both of the filamentous phage coat proteins, pIII and pVIII, are anchored to the phage through their C-termini, and the guest peptides are placed into the outward-extending N-terminal domains. In some designs, the phage-displayed peptides are presented right at the amino terminus of the fusion protein. (Cwirla, et al. (1990) *Proc. Natl. Acad. Sci. U.S.A.* 87, 6378–6382) A second difference is the set of biological biases affecting the population of peptides actually present in the libraries. The LacI fusion molecules are confined to the cytoplasm of the host cells. The phage coat fusions are exposed briefly to the cytoplasm during translation but are rapidly secreted through the inner membrane into the periplasmic compartment, remaining anchored in the membrane by their C-terminal hydrophobic domains, with the N-termini, containing the peptides, protruding into the periplasm while awaiting assembly into phage particles. The peptides in the LacI and phage libraries may differ significantly as a result of their exposure to different proteolytic activities. The phage coat proteins require transport across the inner membrane and signal peptidase processing as a prelude to incorporation into phage. Certain peptides exert a deleterious effect on these processes and are under-represented in the libraries (Gallop et al. (1994) *J. Med. Chem.* 37 (9):1233–1251). These particular biases are not a factor in display system.

The number of small peptides available in recombinant random libraries is enormous. Libraries of $10^7$–$10^9$ independent clones are routinely prepared. Libraries as large as $10^{11}$ recombinants have been created, but this size approaches the practical limit for clone libraries. This limitation in library size occurs at the step of transforming the DNA containing randomized segments into the host bacterial cells. To circumvent this limitation, an in vitro system based on the display of nascent peptides in polysome complexes has recently been developed. This display library method has the potential of producing libraries 3–6 orders of magnitude larger than the currently available phage/phagemid or plasmid libraries. Furthermore, the construction of the libraries, expression of the peptides, and screening, is done in an entirely cell-free format.

In one application of this method (Gallop et al. (1994) *J. Med. Chem.* 37 (9):1233–1251), a molecular DNA library encoding 10 decapeptides was constructed and the library expressed in an *E. coli* S30 in vitro coupled transcription/translation system. Conditions were chosen to stall the ribosomes on the mRNA, causing the accumulation of a substantial. proportion of the RNA in polysomes and yielding complexes containing nascent peptides still linked to their encoding RNA. The polysomes are sufficiently robust to be affinity purified on immobilized receptors in much the same way as the more conventional recombinant peptide display libraries are screened. RNA from the bound complexes is recovered, converted to cDNA, and amplified by PCR to produce a template for the next round of synthesis and screening. The polysome display method can be coupled to the phage display system. Following several rounds of screening, cDNA from the enriched pool of polysomes was cloned into a phagemid vector. This vector serves as both a peptide expression vector, displaying peptides fused to the coat proteins, and as a DNA sequencing vector for peptide identification. By expressing the polysome-derived peptides on phage, one can either continue the affinity selection procedure in this format or assay the peptides on individual clones for binding activity in a phage ELISA, or for binding specificity in a completion phage ELISA (Barret, et al. (1992) *Anal. Biochem* 204,357–364). To identify the sequences of the active peptides one sequences the DNA produced by the phagemid host.

Secondary Screening of Polypeptides and Analogs

The high through-put assays described above can be followed by secondary screens in order to identify further biological activities which will, e.g., allow one skilled in the art to differentiate agonists from antagonists. The type of a secondary screen used will depend on the desired activity that needs to be tested. For example, an assay can be developed in which the ability to inhibit an interaction between a protein of interest and its respective ligand can be used to identify antagonists from a group of peptide fragments isolated though one of the primary screens described above.

Therefore, methods for generating fragments and analogs and testing them for activity are known in the art. Once the core sequence of interest is identified, it is routine for one skilled in the art to obtain analogs and fragments.

Peptide Mimetics of *M. catarrhalis* Polypeptides

The invention also provides for reduction of the protein binding domains of the subject *M. catarrhalis* polypeptides to generate mimetics, e.g. peptide or non-peptide agents. The peptide mimetics are able to disrupt binding of a polypeptide to its counter ligand, e.g., in the case of an *M. catarrhalis* polypeptide binding to a naturally occurring ligand. The critical residues of a subject *M. catarrhalis* polypeptide which are involved in molecular recognition of a polypeptide can be determined and used to generate *M. catarrhalis*—derived peptidomimetics which competitively or noncompetitively inhibit binding of the *M. catarrhalis* polypeptide with an interacting polypeptide (see, for example, European patent applications EP-412,762A and EP-B31,080A).

For example, scanning mutagenesis can be used to map the amino acid residues of a particular *M. catarrhalis* polypeptide involved in binding an interacting polypeptide, peptidomimetic compounds (e.g. diazepine or isoquinoline derivatives) can be generated which mimic those residues in binding to an interacting polypeptide, and which therefore can inhibit binding of an *M. catarrhalis* polypeptide to an interacting polypeptide and thereby interfere with the function of *M. catarrhalis* polypeptide. For instance, non-hydrolyzable peptide analogs of such residues can be generated using benzodiazepine (e.g., see Freidinger et al. in *Peptides: Chemistry and Biology,* G. R. Marshall ed., ESCOM Publisher: Leiden, Netherlands, 1988), azepine (e.g., see Huffman et al. in *Peptides: Chemistry and Biology,* G. R. Marshall ed., ESCOM Publisher: Leiden, Netherlands, 1988), substituted gama lactam rings (Garvey et al. in *Peptides: Chemistry and Biology,* G. R. Marshall ed., ESCOM Publisher: Leiden, Netherlands, 1988), keto-methylene pseudopeptides (Ewenson et al. (1986) *J Med Chem* 29:295; and Ewenson et al. in *Peptides: Structure and Function* (Proceedings of the 9th American Peptide Symposium) Pierce Chemical Co. Rockland, Ill., 1985), b-turn dipeptide cores (Nagai et al. (1985) *Tetrahedron Lett* 26:647; and Sato et al. (1986) *J Chem Soc Perkin Trans* 1:1231), and b-aminoalcohols (Gordon et al. (1985) *Biochem Biophys Res Commun* 126:419; and et al. (1986) *Biochem Biophys Res Commun* 134:71).

Vaccine Formulations for *M. catarrhalis* Nucleic Acids and Polypeptides

This invention also features vaccine compositions for protection against infection by *M. catarrhalis* or for treatment of *M. catarrhalis* infection. In one embodiment, the vaccine compositions contain one or more immunogenic components such as a surface protein from *M. catarrhalis*, or portion thereof, and a pharmaceutically acceptable carrier. Nucleic acids within the scope of the invention are exemplified by the nucleic acids of the invention contained in the Sequence Listing which encode *M. catarrhalis* surface proteins. Any nucleic acid encoding an immunogenic *M. catarrhalis* protein, or portion thereof, which is capable of expression inca cell, can be used in the present invention. These vaccines have therapeutic and prophylactic utilities.

One aspect of the invention provides a vaccine composition for protection against infection by *M. catarrhalis* which contains at least one immunogenic fragment of an *M. catarrhalis* protein and a pharmaceutically acceptable carrier. Preferred fragments include peptides of at least about 10 amino acid residues in length, preferably about 10–20 amino acid residues in length, and more preferably about 12–16 amino acid residues in length.

Immunogenic components of the invention can be obtained, for example, by. screening polypeptides recombinantly produced from the corresponding fragment of the nucleic acid encoding the full-length *M. catarrhalis* protein. In addition, fragments can be chemically synthesized using techniques known in the art such as conventional Merrifield solid phase f-Moc or t-Boc chemistry.

In one embodiment, immunogenic components are identified by the ability of the peptide to stimulate T cells. Peptides which stimulate T cells, as determined by, for example, T cell proliferation or cytokine secretion are defined herein as comprising at least one T cell epitope. T cell epitopes are believed to be involved in initiation and perpetuation of the immune response to the protein allergen which is responsible for the clinical symptoms of allergy. These T cell epitopes are thought to trigger early events at the level of the T helper cell by binding to an appropriate HLA molecule on the surface of an antigen presenting cell, thereby stimulating the T cell subpopulation with the relevant T cell receptor for the epitope. These events lead to T cell proliferation, lymphokine secretion, local inflammatory reactions, recruitment of additional immune cells to the site of antigen/T cell interaction, and activation of the B cell cascade, leading to the production of antibodies. A T cell epitope is the basic element, or smallest unit of recognition by a T cell receptor, where the epitope comprises amino acids essential to receptor recognition (e.g., approximately 6 or 7 amino acid residues). Amino acid sequences which mimic those of the T cell epitopes are within the scope of this invention.

Screening immunogenic components can be accomplished using one or more of several different assays. For example, in vitro, peptide T cell stimulatory activity is assayed by contacting a peptide known or suspected of being immunogenic with an antigen presenting cell which presents appropriate MHC molecules in a T cell culture. Presentation of an immunogenic *M. catarrhalis* peptide in association with appropriate MHC molecules to T cells in conjunction with the necessary co-stimulation has the effect of transmitting a signal to the T cell that induces the production of increased levels of cytokines, particularly of interleukin-2 and interleukin4. The culture supernatant can be obtained and assayed for interleukin-2 or other known cytokines. For example, any one of several conventional assays for interleukin-2 can be employed, such as the assay described in *Proc. Natl. Acad. Sci USA,* 86: 1333 (1989) the pertinent portions of which are incorporated herein by reference. A kit for an assay for the production of interferon is also available from Genzyme Corporation (Cambridge, Mass.).

Alternatively, a common assay for T cell proliferation entails measuring tritiated thymidine incorporation. The proliferation of T cells can be measured in vitro by determining the amount of $^3$H-labeled thymidine incorporated into the replicating DNA of cultured cells. Therefore, the rate of DNA synthesis and, in turn, the rate of cell division can be quantified.

Vaccine compositions of the invention containing immunogenic components (e.g., *M. catarrhalis* polypeptide or fragment thereof or nucleic acid encoding an *M. catarrhalis* polypeptide or fragment thereof) preferably include a pharmaceutically acceptable carrier. The term "pharmaceutically acceptable carrier" refers to a carrier that does not cause an allergic reaction or other untoward effect in patients to whom it is administered. Suitable pharmaceutically acceptable carriers include, for example, one or more of water, saline, phosphate buffered saline, dextrose, glycerol, ethanol and the like, as well as combinations thereof. Pharmaceutically acceptable carriers may further comprise minor amounts of auxiliary substances such as wetting or emulsifying agents, preservatives or buffers, which enhance the shelf life or effectiveness of the antibody. For vaccines of the invention containing *M. catarrhalis* polypeptides, the polypeptide is co-administered with a suitable adjuvant.

It will be apparent to those of skill in the art that the therapeutically effective amount of DNA or protein of this invention will depend, inter alia, upon the administration schedule, the unit dose of antibody administered, whether the protein or DNA is administered in combination with other therapeutic agents, the immune status and health of the patient, and the therapeutic activity of the particular protein or DNA.

Vaccine compositions are conventionally administered parenterally, e.g., by injection, either subcutaneously or intramuscularly. Methods for intramuscular immunization are described by Wolff et al. (1990) *Science* 247: 1465–1468 and by Sedegah et al. (1994) *Immunology* 91: 9866–9870. Other modes of administration include oral and pulmonary formulations, suppositories, and transdermal applications. Oral immunization is preferred over parenteral methods for inducing protection against infection by *M. catarrhalis*. Cain et. al. (1993) *Vaccine* 11: 637–642. Oral formulations include such normally employed excipients as, for example, pharmaceutical grades of mannitol, lactose, starch, magnesium stearate, sodium saccharine, cellulose, magnesium carbonate, and the like.

The vaccine compositions of the invention can include an adjuvant, including, but not limited to aluminum hydroxide; N-acetyl-muramyl-L-threonyl-D-isoglutamine (thr-MDP); N-acetyl-nor-muramyl-L-alanyl-D-isoglutamine (CGP 11637, referred to as nor-MDP); N-acetylmuramyl-L-alanyl-D-isoglutaminyl-L-alanine-2-(1'-2'-dipalmitoyl-sn-glycero-3-hydroxyphos-phoryloxy)-ethylamine (CGP 19835 A, referred to a MTP-PE); RIBI, which contains three components from bacteria; monophosphoryl lipid A; trehalose dimycoloate; cell wall skeleton (MPL+TDM+CWS) in a 2% squalene/Tween 80 emulsion; and cholera toxin.

Others which may be used are non-toxic derivatives of cholera toxin, including its B subunit, and/or conjugates or genetically engineered fusions of the *M. catarrhalis* polypeptide with cholera toxin or its B subunit, procholeragenoid, fungal polysaccharides, including schizophyllan, muramyl dipeptide, muramyl dipeptide derivatives, phorbol esters, labile toxin of *E. coli,* non-*M. catarrhalis* bacterial lysates, block polymers or saponins.

Other suitable delivery methods include biodegradable microcapsules or immuno-stimulating complexes (ISCOMs), cochleates, or liposomes, genetically engineered attenuated live vectors such as viruses or bacteria, and recombinant (chimeric) virus-like particles, e.g., bluetongue. The amount of adjuvant employed will depend on the type of adjuvant used. For example, when the mucosal adjuvant is cholera toxin, it is suitably used in an amount of 5 mg to 50 mg, for example 10 mg to 35 mg. When used in the form of microcapsules, the amount used will depend on the amount employed in the matrix of the microcapsule to achieve the desired dosage. The determination of this amount is within the skill of a person of ordinary skill in the art.

Carrier systems in humans may include enteric release capsules protecting the antigen from the acidic environment of the stomach, and including *M. catarrhalis* polypeptide in an insoluble form as fusion proteins. Suitable carriers for the vaccines of the invention are enteric coated capsules and polylactide-glycolide microspheres. Suitable diluents are 0.2 N $NaHCO_3$ and/or saline.

Vaccines of the invention can be administered as a primary prophylactic agent in adults or in children, as a secondary prevention, after successful eradication of *M. catarrhalis* in an infected host, or as a therapeutic agent in the aim to induce an immune response in a susceptible host to prevent infection by *M. catarrhalis.* The vaccines of the invention are administered in amounts readily determined by persons of ordinary skill in the art. Thus, for adults a suitable dosage will be in the range of 10 mg to 10 g, preferably 10 mg to 100 mg. A suitable dosage for adults will also be in the range of 5 mg to 500 mg. Similar dosage ranges will be applicable for children. Those skilled in the art will recognize that the optimal dose may be more or less depending upon the patient's body weight, disease, the route of administration, and other factors. Those skilled in the art will also recognize that appropriate dosage levels can be obtained based on results with known oral vaccines such as, for example, a vaccine based on an *E. coli* lysate (6 mg dose daily up to total of 540 mg) and with an enterotoxigenic *E. coli* purified antigen (4 doses of 1 mg) (Schulman et al., *J. Urol.* 150:917–921 (1993); Boedeker et al., *American Gastroenterological Assoc.* 999:A-222 (1993)). The number of doses will depend upon the disease, the formulation, and efficacy data from clinical trials. Without intending any limitation as to the course of treatment, the treatment can be administered over 3 to 8 doses for a primary immunization schedule over 1 month (Boedeker, *American Gastroenterological Assoc.* 888:A-222 (1993)).

In a preferred embodiment, a vaccine composition of the invention can be based on a killed whole *E. coli* preparation with an immunogenic fragment of an *M. catarrhalis* protein of the invention expressed on its surface or it can be based on an *E. coli* lysate, wherein the killed *E. coli* acts as a carrier or an adjuvant.

It will be apparent to those skilled in the art that some of the vaccine compositions of the invention are useful only for preventing *M. catarrhalis* infection, some are useful only for treating *M. catarrhalis* infection, and some are useful for both preventing and treating *M. catarrhalis* infection. In a preferred embodiment, the vaccine composition of the invention provides protection against *M. catarrhalis* infection by stimulating humoral and/or cell-mediated immunity against *M. catarrhalis*. It should be understood that amelioration of any of the symptoms of *M. catarrhalis* infection is a desirable clinical goal, including a lessening of the dosage of medication used to treat *M. catarrhalis*—caused disease, or an increase in the production of antibodies in the serum or mucous of patients.

Antibodies Reactive with *M. catarrhalis* Polypeptides

The invention also includes antibodies specifically reactive with the subject *M. catarrhalis* polypeptide. Antiprotein/anti-peptide antisera or monoclonal antibodies can be made by standard protocols (See, for example, *Antibodies: A Laboratory Manual* ed. by Harlow and Lane (Cold Spring Harbor Press: 1988)). A mammal such as a mouse, a hamster or rabbit can be immunized with an immunogenic form of the peptide. Techniques for conferring immunogenicity on a protein or peptide include conjugation to carriers or other techniques well known in the art. An immunogenic portion of the subject *M. catarrhalis* polypeptide can be administered in the presence of adjuvant. The progress of immunization can be monitored by detection of antibody titers in plasma or serum. Standard ELISA or other immunoassays can be used with the immunogen as antigen to assess the levels of antibodies.

In a preferred embodiment, the subject antibodies are immunospecific for antigenic determinants of the *M. catarrhalis* polypeptides of the invention, e.g. antigenic determinants of a polypeptide of the invention contained in the Sequence Listing, or a closely related human or non-human mammalian homolog (e.g., 90% homologous, more preferably at least about 95% homologous). In yet a further preferred embodiment of the invention, the anti-*M. catarrhalis* antibodies do not substantially cross react (i.e., react specifically) with a protein which is for example, less than 80% percent homologous to a sequence of the invention contained in the Sequence Listing. By "not substantially cross react", it is meant that the antibody has a binding affinity for a non-homologous protein which is less than 10 percent, more preferably less than 5 percent, and even more preferably less than 1 percent, of the binding affinity for a protein of the invention contained in the Sequence Listing. In a most preferred embodiment, there is no cross-reactivity between bacterial and mammalian antigens.

The term antibody as used herein is intended to include fragments thereof which are also specifically reactive with *M. catarrhalis* polypeptides. Antibodies can be fragmented using conventional techniques and the fragments screened for utility in the same manner as described above for whole antibodies. For example, $F(ab')_2$ fragments can be generated by treating antibody with pepsin. The resulting $F(ab')_2$ fragment can be treated to reduce disulfide bridges to produce Fab' fragments. The antibody of the invention is further intended to include bispecific and chimeric molecules having an anti-*M. catarrhalis* portion.

Both monoclonal and polyclonal antibodies (Ab) directed against *M. catarrhalis* polypeptides or *M. catarrhalis* polypeptide variants, and antibody fragments such as Fab' and $F(ab')_2$, can be used to block the action of *M. catarrhalis* polypeptide and allow the study of the role of a particular *M. catarrhalis* polypeptide of the invention in aberrant or unwanted intracellular signaling, as well as the normal cellular function of the *M. catarrhalis* and by microinjection of anti-*M. catarrhalis* polypeptide antibodies of the present invention.

Antibodies which specifically bind *M. catarrhalis* epitopes can also be used in immunohistochemical staining of tissue samples in order to evaluate the abundance and pattern of expression of *M. catarrhalis* antigens. Anti-*M. catarrhalis* polypeptide antibodies can be used diagnostically in immuno-precipitation and immuno-blotting to detect and evaluate *M. catarrhalis* levels in tissue or bodily fluid as part of a clinical testing procedure. Likewise, the ability to monitor *M. catarrhalis* polypeptide levels in an individual can allow determination of the efficacy of a given treatment regimen for an individual afflicted with such a disorder. The level of an *M. catarrhalis* polypeptide can be measured in cells found in bodily fluid, such as in urine samples or can be measured in tissue, such as produced by gastric biopsy. Diagnostic assays using anti-*M. catarrhalis* antibodies can include, for example, immunoassays designed to aid in early diagnosis of *M. catarrhalis* infections. The present invention can also be used as a method of detecting antibodies contained in samples from individuals infected by this bacterium using specific *M. catarrhalis* antigens.

Another application of anti-*M. catarrhalis* polypeptide antibodies of the invention is in the immunological screening of cDNA libraries constructed in expression vectors such as λgt11, λgt18–23, λZAP, and λORF8. Messenger libraries of this type, having coding sequences inserted in the correct reading frame and orientation, can produce fusion proteins. For instance, λgt11 will produce fusion proteins whose amino termini consist of β-galactosidase amino acid sequences and whose carboxy termini consist of a foreign polypeptide. Antigenic epitopes of a subject *M. catarrhalis* polypeptide can then be detected with antibodies, as, for example, reacting nitrocellulose filters lifted from infected plates with anti-*M. catarrhalis* polypeptide antibodies. Phage, scored by this assay, can then be isolated from the infected plate. Thus, the presence of *M. catarrhalis* gene homologs can be detected and cloned from other species, and alternate isoforms (including splicing variants) can be detected and cloned.

Kits Containing Nucleic Acids, Polypeptides or Antibodies of the Invention

The nucleic acid, polypeptides and antibodies of the invention can be combined with other reagents and articles to form kits. Kits for diagnostic purposes typically comprise the nucleic acid, polypeptides or antibodies in vials or other suitable vessels. Kits typically comprise other reagents for performing hybridization reactions, polymerase chain reactions (PCR), or for reconstitution of lyophilized components, such as aqueous media, salts, buffers, and the like. Kits may also comprise reagents for sample processing such as detergents, chaotropic salts and the like. Kits may also comprise immobilization means such as particles, supports, wells, dipsticks and the like. Kits may also comprise labeling means such as dyes, developing reagents, radioisotopes, fluorescent agents, luminescent or chemiluminescent agents, enzymes, intercalating agents and the like. With the nucleic acid and amino acid sequence information provided herein, individuals skilled in art can readily assemble kits to serve their particular purpose. Kits further can include instructions for use.

Bio Chip Technology

The nucleic acid sequence of the present invention may be used to detect *M. catarrhalis* or other species of Moraxella acid sequence using bio chip technology. Bio chips containing arrays of nucleic acid sequence can also be used to measure expression of genes of *M. catarrhalis* or other species of Moraxella. For example, to diagnose a patient with a *M. catarrhalis* or other Moraxella infection, a sample from a human or animal can be used as a probe on a bio chip containing an array of nucleic acid sequence from the present invention. In addition, a sample from a disease state can be compared to a sample from a non-disease state which would help identify a gene that is up-regulated or expressed in the disease state. This would provide valuable insight as to the mechanism by which the disease manifests. Changes in gene expression can also be used to identify critical pathways involved in drug transport or metabolism, and may enable the identification of novel targets involved in virulence or host cell interactions involved in maintenance of an infection. Procedures using such techniques have been described by Brown et al., 1995, *Science* 270: 467–470.

Bio chips can also be used to monitor the genetic changes of potential therapeutic compounds including, deletions, insertions or mismatches. Once the therapeutic is added to the patient, changes to the genetic sequence can be evaluated for its efficacy. In addition, the nucleic acid sequence of the present invention can be used to determine essential genes in cell cycling. As described in Iyer et al., 1999 (*Science*, 283:83–87) genes essential in the cell cycle can be identified using bio chips. Furthermore, the present invention provides nucleic acid sequence which can be used with bio chip technology to understand regulatory networks in bacteria, measure the response to environmental signals or drugs as in drug screening, and study virulence induction. (Mons et al., 1998, *Nature Biotechnology*, 16: 45–48. Patents teaching this technology include U.S. Pat. Nos. 5,445,934, 5,744,305, and 5,800,992.

Drug Screening Assays Using *M. catarrhalis* Polypeptides

By making available purified and recombinant *M. catarrhalis* polypeptides, the present invention provides assays which can be used to screen for drugs which are either agonists or antagonists of the normal cellular function, in this case, of the subject *M. catarrhalis* polypeptides, or of their role in intracellular signaling. Such inhibitors or potentiators may be useful as new therapeutic agents to combat *M. catarrhalis* infections in humans. A variety of assay formats will suffice and, in light of the present inventions, will be comprehended by the person skilled in the art.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with other proteins or change in enzymatic properties of the molecular target. Accordingly, in an exemplary screening assay of the present invention, the compound of interest is contacted with an isolated and purified *M. catarrhalis* polypeptide.

Screening assays can be constructed in vitro with a purified *M. catarrhalis* polypeptide or fragment thereof, such as an *M. catarrhalis* polypeptide having enzymatic activity, such that the activity of the polypeptide produces a detectable reaction product. The efficacy of the compound can be assessed by generating dose response curves from data obtained using various concentrations of the test compound. Moreover, a control assay can also be performed to provide a baseline for comparison. Suitable products include those with distinctive absorption, fluorescence, or chemiluminescence properties, for example, because detection may be easily automated. A variety of synthetic or naturally occurring compounds can be tested in the assay to. identify those which inhibit or potentiate the activity of the *M. catarrhalis* polypeptide. Some of these active compounds may directly, or with chemical alterations to promote membrane permeability or solubility, also inhibit or potentiate the same activity (e.g., enzymatic activity) in whole, live *M. catarrhalis* cells.

Overexpression Assays

Overexpression assays are based on the premise that overproduction of a protein would lead to a higher level of resistance to compounds that selectively interfere with the function of that protein. Overexpression assays may be used to identify compounds that interfere with the function of virtually any type of protein, including without limitation enzymes, receptors, DNA- or RNA-binding proteins, or any proteins that are directly or indirectly involved in regulating cell growth.

Typically, two bacterial strains are constructed. One contains a single copy of the gene of interest, and a second contains several copies of the same gene. Identification of useful inhibitory compounds of this type of assay is based on a comparison of the activity of a test compound in inhibiting growth and/or viability of the two strains. The method involves constructing a nucleic acid vector that directs high level expression of a particular target nucleic acid. The vectors are then transformed into host cells in single or multiple copies to produce strains that express low to moderate and high levels of protein encoding by the target sequence (strain A and B, respectively). Nucleic acid comprising sequences encoding the target gene can, of course, be directly integrated into the host cell.

Large numbers of compounds (or crude substances which may contain active compounds) are screened for their effect on the growth of the two strains. Agents which interfere with an unrelated target equally inhibit the growth of both strains. Agents which interfere with the function of the target at high concentration should inhibit the growth of both strains. It should be possible, however, to titrate out the inhibitory effect of the compound in the overexpressing strain. That is, if the compound is affecting the particular target that is being tested, it should be possible to inhibit the growth of strain A at a concentration of the compound that allows strain B to grow.

Alternatively, a bacterial strain is constructed that contains the gene of interest under the control of an inducible promoter. Identification of useful inhibitory agents using this type of assay is based on a comparison of the activity of a test compound in inhibiting growth and/or viability of this strain under both inducing and non-inducing conditions. The method involves constructing a nucleic acid vector that directs high-level expression of a particular target nucleic acid. The vector is then transformed into host cells that are grown under both non-inducing and inducing conditions (conditions A and B, respectively).

Large numbers of compounds (or crude substances which may contain active compounds) are screened for their effect on growth under these two conditions. Agents that interfere with the function of the target should inhibit growth under both conditions. It should be possible, however, to titrate out the inhibitory effect of the compound in the overexpressing strain. That is, if the compound is affecting the particular target that is being tested, it should be possible to inhibit growth under condition A at a concentration that allows the strain to grow under condition B.

Ligand-Binding Assays

Many of the targets according to the invention have functions that have not yet been identified. Ligand-binding assays are useful to identify inhibitor compounds that interfere with the function of a particular target, even when that function is unknown. These assays are designed to detect binding of test compounds to particular targets. The detection may involve direct measurement of binding. Alternatively, indirect indications of binding may involve stabilization of protein structure or disruption of a biological function. Non-limiting examples of useful ligand-binding assays are detailed below.

A useful method for the detection and isolation of binding proteins is the Biomolecular Interaction Assay (BIAcore) system developed by Pharmacia Biosensor and described in the manufacturer's protocol (LKB Pharmacia, Sweden). The BIAcore system uses an affinity purified anti-GST antibody to immobilize GST-fusion proteins onto a sensor chip. The sensor utilizes surface plasmon resonance which is an optical phenomenon that detects changes in refractive indices. In accordance with the practice of the invention, a protein of interest is coated onto a chip and test compounds are passed over the chip. Binding is detected by a change in the refractive index (surface plasmon resonance).

A different type of ligand-binding assay involves scintillation proximity assays (SPA, described in U.S. Pat. No. 4,568,649).

Another type of ligand binding assay, also undergoing development, is based on the fact that proteins containing mitochondrial targeting signals are imported into isolated mitochondria in vitro (Hurt et al., 1985, *Embo J.* 4:2061–2068; Eilers and Schatz, *Nature,* 1986, 322:228–231). In a mitochondrial import assay, expression vectors are constructed in which nucleic acids encoding particular target proteins are inserted downstream of sequences encoding mitochondrial import signals. The chimeric proteins are synthesized and tested for their ability to be imported into isolated mitochondria in the absence and presence of test compounds. A test compound that binds to the target protein should inhibit its uptake into isolated mitochondria in vitro.

Another ligand-binding assay is the yeast two-hybrid system (Fields and Song, 1989, *Nature* 340:245–246). The yeast two-hybrid system takes advantage of the properties of the GAL4 protein of the yeast *Saccharomyces cerevisiae.* The GAL4 protein is a transcriptional activator required for the expression of genes encoding enzymes of galactose utilization. This protein consists of two separable and functionally essential domains: an N-terminal domain which binds to specific DNA sequences ($UAS_G$); and a C-terminal domain containing acidic regions, which is necessary to activate transcription. The native GAL4 protein, containing both domains, is a potent activator of transcription when yeast are grown on galactose media. The N-terminal domain binds to DNA in a sequence-specific manner but is unable to activate transcription. The C-terminal domain contains the activating regions but cannot activate transcription because it fails to be localized to $UAS_G$. In the two-hybrid system, a system of two hybrid proteins containing parts of GAL4: (1) a GAL4 DNA-binding domain fused to a protein 'X' and (2) a GAL4 activation region fused to a protein 'Y'. If X and Y can form a protein-protein complex and reconstitute proximity of the GAL4 domains, transcription of a gene regulated by $UAS_G$ occurs. Creation of two hybrid proteins, each containing one of the interacting proteins X and Y, allows the activation region of $UAS_G$ to be brought to its normal site of action.

The binding assay described in Fodor et al., 1991, *Science* 251:767–773, which involves testing the binding affinity of test compounds for a plurality of defined polymers synthesized on a solid substrate, may also be useful.

Compounds which bind to the polypeptides of the invention are potentially useful as antibacterial agents for use in therapeutic compositions.

Pharmaceutical formulations suitable for antibacterial therapy comprise the antibacterial agent in conjunction with one or more biologically acceptable carriers. Suitable biologically acceptable carriers include, but are not limited to, phosphate-buffered saline, saline, deionized water, or the like. Preferred biologically acceptable carriers are physiologically or pharmaceutically acceptable carriers.

The antibacterial compositions include an antibacterial effective amount of active agent. Antibacterial effective amounts are those quantities of the antibacterial agents of the present invention that afford prophylactic protection against bacterial infections or which result in amelioration or cure of an existing bacterial infection. This antibacterial effective amount will depend upon the agent, the location and nature of the infection, and the particular host. The amount can be determined by experimentation known in the art, such as by establishing a matrix of dosages and frequencies and comparing a group of experimental units or subjects to each point in the matrix.

The antibacterial active agents or compositions can be formed into dosage unit forms, such as for example, creams, ointments, lotions, powders, liquids, tablets, capsules, suppositories, sprays, aerosols or the like. If the antibacterial composition is formulated into a dosage unit form, the dosage unit form may contain an antibacterial effective amount of active agent. Alternatively, the dosage unit form may include less than such an amount if multiple dosage unit forms or multiple dosages are to be used to administer a total dosage of the active agent. Dosage unit forms can include, in addition, one or more excipient(s), diluent(s), disintegrant (s), lubricant(s), plasticizer(s), colorant(s), dosage vehicle (s), absorption enhancer(s), stabilizer(s), bactericide(s), or the like.

For general information concerning formulations, see, e.g., Gilman et al. (eds.), 1990, Goodman and Gilman's: *The Pharmacological Basis of Therapeutics,* 8th ed., Pergamon Press; and *Remington's Pharmaceutical Sciences,* 17th ed., 1990, Mack Publishing Co., Easton, Pa.; Avis et al. (eds.), 1993, *Pharmaceutical Dosage Forms: Parenteral Medications,* Dekker, New York; Lieberman et al (eds.), 1990, *Pharmaceutical Dosage Forms: Disperse Systems,* Dekker, New York.

The antibacterial agents and compositions of the present invention are useful for preventing or treating *M. catarrhalis* infections. Infection prevention methods incorporate a prophylactically effective amount of an antibacterial agent or composition. A prophylactically effective amount is an amount effective to prevent *M. catarrhalis* infection and will depend upon the specific bacterial strain, the agent, and the host. These amounts can be determined experimentally by methods known in the art and as described above.

*M. catarrhalis* infection treatment methods incorporate a therapeutically effective amount of an antibacterial agent or composition. A therapeutically effective amount is an amount sufficient to ameliorate or eliminate the infection. The prophylactically and/or therapeutically effective amounts can be administered in one administration or over repeated administrations. Therapeutic administration can be followed by prophylactic administration, once the initial bacterial infection has been resolved.

The antibacterial agents and compositions can be administered topically or systemically. Topical application is typically achieved by administration of creams, ointments, lotions, or sprays-as described above. Systemic administration includes both oral and parental routes. Parental routes include, without limitation, subcutaneous, intramuscular, intraperitoneal, intravenous, transdermal, inhalation and intranasal administration.

EXEMPLIFICATION

Cloning and Sequencing *M. catarrhalis* Genomic Sequence

This invention provides nucleotide sequences of the genome of *M. catarrhalis* which thus comprises a DNA sequence library of *M. catarrhalis* genomic DNA. The invention also provides nucleotide sequences of two naturally occurring plasmids in *M. catarrhalis*. The detailed description that follows provides nucleotide sequences of *M. catarrhalis,* and also describes how the sequences were obtained and how ORFs (Open Reading Frames) and protein-coding sequences can be identified. Also described are methods of using the disclosed *M. catarrhalis* sequences in methods including diagnostic and therapeutic applications. Furthermore, the library can be used as a database for identification and comparison of medically important sequences in this and other strains of *M. catarrhalis* as well as other species of Moraxella.

Chromosomal DNA from strain 98-4362. of *M. catarrhalis,* was isolated using a protocol described by Storrs, et al.(*J. Bacteriol.* 173: 4347–4352 (1991). The only exception to this protocol was that lysostaphin (120 U/ml) was used instead of lysozyme. The genomic DNA prep involved a lysozyme:lysostaphin digestion, sodium dodecyl sulfate lysis, Proteinase K and RNase treatment, phenol:chloroform extraction, and sodium acetate precipitation, followed by the CsCl gradient to remove the plasmid.

In the construction of both libraries, genomic *M. catarrhalis* DNA was hydrodynamically sheared in an HPLC and then separated on a standard 1% agarose gel. A fraction corresponding to 2000–3000 bp in length was excised from the gel and purifed by the GeneClean procedure (Bio101, Inc.).

The purified DNA fragments were then blunt-ended using T4 DNA polymerase. The healed DNA was then ligated to unique BstXI-linker adapters (5'-GTCTTCACCACGGGG-3' and 5'-GTGGTGAAGAC-3' in 100–1000 fold molar excess). These linkers are complimentary to the BstXI-cut pGTC vector, while the overhang is not self-complimentary. Therefore, the linkers will not concatermerize nor will the cut-vector religate itself easily. The linker-adapted inserts were separated from the unincorporated linkers on a 1% agarose gel and purified using GeneClean. The linker-adapted inserts were then ligated to BstXI-cut vector to construct a "shotgun" sublclone libraries.

Only major modifications to the protocols are highlighted. Briefly, the library was then transformed into DH5á competent cells (Gibco/BRL, DH5α transformation protocol). It was assessed by plating onto antibiotic plates containing ampicillin and IPTG/Xgal. The plates were incubated overnight at 37° C. Transformants were then used for plating of clones and picking for sequencing. The cultures were grown overnight at 37° C. DNA was purified using a silica bead DNA preparation (Engelstein, 1996) method. In this manner, 25 µg of DNA was obtained per clone.

These purified DNA samples were then sequenced using primarily ABI dye-terminator chemistry. All subsequent steps were based on sequencing by ABI377 automated DNA sequencing methods. The ABI dye terminator sequence reads were run on ABI377 machines and the data was transferred to UNIX machines following lane tracking of the gels. Base calls and quality scores were determined using the program PHRED (Ewing et al., 1998, Genome Res. 8: 175–185; Ewing and Green, 1998, Genome Res. 8: 685–734). Reads were assembled using PHRAP:(P. Green, Abstracts of DOE Human Genome Program Contractor-Grantee Workshop V, January 1996, p.157) with default program parameters and quality scores.

Finishing followed the initial assembly. Missing mates (sequences from clones that only gave reads from one end of the Moraxella DNA inserted in the plasmid) were identified and sequenced with ABI technology to allow the identification of additional overlapping contigs.

End-sequencing of randomly picked genomic lambda was also performed. Sequencing of both sides was done for all lambda sequences. The lambda library backbone helped to verify the integrity of the assembly and allowed closure of some of the physical gaps. Primers for walking off the ends of contigs would be selected using pick_primer (a GTC program) near the ends of the clones to facilitate gap closure. These walks can be sequenced using the selected clones and primers. These data are then reassembled with PHRAP. Additional sequencing using PCR-generated templates and screened and/or unscreened lambda templates can be done in addition.

Additional templates for the physical gaps were obtained through PCR using primers designed from the ends of the contigs. These templates were then used in sequencing reactions to close the gaps.

Contigs were ordered by aligning identified *M. catarrhalis* genes to the published physical maps. Order was confirmed by PCR. The final chromosomal assembly included 119 contigs.

To identify *M. catarrhalis* polypeptides the complete genomic sequence of *M. catarrhalis* were analyzed essentially as follows: First, all possible stop-to-stop open reading frames (ORFs) greater than 180 nucleotides in all six reading frames were translated into amino acid sequences. Second, the identified ORFs were analyzed for homology to known (archeabacter, prokaryotic and eukaryotic) protein sequences. Third, the coding potential of non-homologous sequences were evaluated with the program GENEMARK™ (Borodovsky and McIninch, 1993, Comp. Chem. 17:123)

Identification, Cloning and Expression of *M. catarrhalis* Nucleic Acids

Expression and purification of the *M. catarrhalis* polypeptides of the invention can be performed essentially as outlined below.

To facilitate the cloning, expression and purification of membrane and secreted proteins from *M. catarrhalis,* a gene expression system, such as the pET System (Novagen), for cloning and expression of recombinant proteins in *E. coli,* is selected. Also, a DNA sequence encoding a peptide tag, the His-Tag, is fused to the 3' end of DNA sequences of interest in order to facilitate purification of the recombinant protein products. The 3' end is selected for fusion in order to avoid alteration of any 5' terminal signal sequence.

PCR Amplificaiton and Cloning of Nucleic Acids Containing ORF's Encoding Enzymes Nucleic acids chosen (for example, from the nucleic acids set forth in SEQ ID NO: 1 SEQ ID NO: 2501 for cloning from the 98-4362. strain of *M. catarrhalis* and plasmids are prepared for amplification cloning by polymerase chain reaction (PCR). Synthetic oligonucleotide primers specific for the 5' and 3' ends of open reading frames (ORFs) are designed and purchased from GibcoBRL Life Technologies (Gaithersburg, Md., USA). All forward primers (specific for the 5' end of the sequence) are designed to include an NcoI cloning site at the extreme 5' terminus. These primers are designed to permit initiation of protein translation at a methionine residue followed by a valine residue and the coding sequence for the remainder of the native *M. catarrhalis* DNA sequence. All reverse primers (specific for the 3' end of any *M. catarrhalis* ORF) include a EcoRI site at the extreme 5' terminus to permit cloning of each *M. catarrhalis* sequence into the reading frame of the pET-28 b. The pET-28 b vector provides sequence encoding an additional 20 carboxy-terminal amino acids including six histidine residues (at the extreme C-terminus), which comprise the His-Tag.

Genomic DNA or plasmid DNA prepared from the 98-4362. strain of *M. catarrhalis* is used as the source of template DNA for PCR amplification reactions (Current Protocols in Molecular Biology, John Wiley and Sons, Inc., F. Ausubel et al., eds., 1994). To amplify a DNA sequence containing an *M. catarrhalis* ORF, genomic DNA (50 nanograms) is introduced into a reaction vial containing 2 mM $MgCl_2$, 1 micromolar synthetic oligonucleotide primers (forward and reverse primers) complementary to and flanking a defined *M. catarrhalis* ORF, 0.2 mM of each deoxynucleotide triphosphate; dATP, dGTP, dCTP, dTTP and 2.5 units of heat stable DNA polymerase (Amplitaq, Roche Molecular Systems, Inc., Branchburg, N.J., USA) in a final volume of 100 microliters.

Upon completion of thermal cycling reactions, each sample of amplified DNA is washed and purified using the Qiaquick Spin PCR purification kit (Qiagen, Gaithersburg, Md., USA). All amplified DNA samples are subjected to digestion with the restriction endonucleases, e.g., NcoI and EcoRI (New England BioLabs, Beverly, Mass., USA) (Current Protocols in Molecular Biology, John Wiley and Sons, Inc., F. Ausubel et al., eds., 1994). DNA samples are then subjected to electrophoresis on 1.0% NuSeive (FMC BioProducts, Rockland, Me. USA) agarose gels. DNA is visualized by exposure to ethidium bromide and long wave uv irradiation. DNA contained in slices isolated from the agarose gel is purified using the Bio 101 GeneClean Kit protocol (Bio 101 Vista, Calif., USA).

Cloning of *M. catarrhalis* Nucleic Acids into an Expression Vector

The pET-28b vector is prepared for cloning by digestion with restriction endonucleases, e.g., NcoI and EcoRI (Current Protocols in Molecular Biology, John Wiley and Sons, Inc., F. Ausubel et al., eds., 1994). The pET-28 a vector, which encodes a His-Tag that can be fused to the 5 end of an inserted gene, is prepared by digestion with appropriate restriction endonucleases.

Following digestion, DNA inserts are cloned (Current Protocols in Molecular Biology, John Wiley and Sons, Inc., F. Ausubel et al., eds., 1994) into the previously digested pET-28b expression vector. Products of the ligation reaction are then used to transform the BL21 strain of *E. coli* (Current Protocols in Molecular Biology, John Wiley and Sons, Inc., F. Ausubel et al., eds., 1994) as described below.

Transformation of Competent Bacteria with Recombinant Plasmids

Competent bacteria, *E coli* strain BL21 or *E. coli* strain BL21 (DE3), are transformed with recombinant pET expression plasmids carrying the cloned *M. catarrhalis* sequences according to standard methods (Current Protocols in Molecular Biology, John Wiley and Sons, Inc., F. Ausubel et al., eds., 1994). Briefly, 1 microliter of ligation reaction is mixed with 50 microliters of electrocompetent cells and subjected to a high voltage pulse, after which, samples are incubated in 0.45 milliliters SOC medium (0.5% yeast extract, 2.0% tryptone, 10 mM NaCl, 2.5 mM KCl, 10 mM MgCl12, 10 mM MgSO4 and 20, mM glucose) at 37° C. with shaking for 1 hour. Samples are then spread on LB agar plates containing 25 microgram/ml kanamycin sulfate for growth overnight. Transformed colonies of BL21 are then picked and analyzed to evaluate cloned inserts as described below.

Identification of Recombinant Expression Vectors with *M. Catarrhalis* Nucleic Acids Individual BL21 clones transformed with recombinant pET-28 b *M. catarrhalis* ORFs are analyzed by PCR amplification of the cloned inserts using the same forward and reverse primers, specific for each *M. catarrhalis* sequence, that were used in the original PCR amplification cloning reactions. Successful amplification verifies the integration of the *M. catarrhalis* sequences in the expression vector (Current Protocols in Molecular Biology, John Wiley and Sons, Inc., F. Ausubel et al., eds., 1994).

Isolation and Preparation of Nucleic Acids from Transformants

Individual clones of recombinant pET-28b vectors carrying properly cloned *M. catarrhalis* ORFs are picked and incubated in 5 mls of LB broth plus 25 microgram/ml kanamycin sulfate overnight. The following day plasmid DNA is isolated and purified using the Qiagen plasmid purification protocol (Qiagen Inc., Chatsworth, Calif., USA).

Expression of Recombinant *M. catarrhalis* Sequences in *E. coli*

The pET vector can be propagated in any *E. coli* K-12 strain e.g. HMS174, HB101, JM109, DH5, etc. for the purpose of cloning or plasmid preparation. Hosts for expression include E. coli strains containing a chromosomal copy of the gene for T7 RNA polymerase. These hosts are lysogens of bacteriophage DE3, a lambda derivative that carries the lacd gene, the lacUV5 promoter and the gene for T7 RNA polymerase. T7 RNA polymerase is induced by addition of isopropyl-B-D-thiogalactoside (IPTG), and the T7 RNA polymerase transcribes any target plasmid, such as pET-28b, carrying its gene of interest. Strains used include: BL21 (DE3) (Studier, F. W., Rosenberg, A. H., Dunn, J. J., and Dubendorff, J. W. (1990) Meth. Enzymol. 185, 60–89).

To express recombinant *M. catarrhalis* sequences, 50 nanograms of plasmid DNA isolated as described above is used to transform competent BL21 (DE3) bacteria as described above (provided by Novagen as part of the pET expression system kit). The lacZ gene (beta-galactosidase) is expressed in the pET-System as described for the *M. catarrhalis* recombinant constructions. Transformed cells are cultured in SOC medium for 1 hour, and the culture is then plated on LB plates containing 25 micrograms/ml kanamycin sulfate. The following day, bacterial colonies are pooled and grown in LB medium containing kanamycin sulfate (25 micrograms/ml) to an optical density at 600 nM of 0.5 to 1.0 O.D. units, at which point, 1 millimolar IPTG was added to the culture for 3 hours to induce gene expression of the *M. catarrhalis* recombinant DNA constructions After induction of gene expression with IPTG, bacteria are pelleted by centrifugation in a Sorvall RC-3B centrifuge at 3500×g for 15 minutes at 4° C. Pellets are resuspended in 50 milliliters of cold 10 mM Tris-HCl, pH 8.0, 0.1 M NaCl and 0.1 mM EDTA (STE buffer). Cells are then centrifuged at 2000×g for 20 min at 4° C. Wet pellets are weighed and frozen at −80° C. until ready for protein purification.

A variety of methodologies known in the art can be utilized to purify the isolated proteins. (Current Protocols in Protein Science, John Wiley and Sons, Inc., J. E. Coligan et al., eds., 1995). For example, the frozen cells may be thawed, resuspended in buffer and ruptured by several passages through a small volume microfluidizer (Model M-110S, Microfluidics International Corporation, Newton, Mass.). The resultant homogenate may be centrifuged to yield a clear supernatant (crude extract) and following filtration the crude extract may be fractionated over columns. Fractions may be monitored by absorbance at $OD_{280}$ nm. and peak fractions may analyzed by SDS-PAGE.

The concentrations of purified protein preparations may be quantified spectrophotometrically using absorbance coefficients calculated from amino acid content (Perkins, S. J. 1986 Eur. J. Biochem. 157, 169–180). Protein concentrations are also measured by the method of Bradford, M. M. (1976) Anal. Biochem. 72, 248–254, and Lowry, O. H., Rosebrough, N., Farr, A. L. & Randall, R. J. (1951) J. Biol. Chem. 193, pages 265–275, using bovine serum albumin as a standard.

SDS-polyacrylamide gels of various concentrations may be purchased from BioRad (Hercules, Calif., USA), and stained with Coomassie blue. Molecular weight markers may include rabbit skeletal muscle myosin (200 kDa), *E. coli* (-galactosidase (116 kDa), rabbit muscle phosphorylase B (97.4 kDa), bovine serum albumin (66.2 kDa), ovalbumin (45 kDa), bovine carbonic anhydrase (31 kDa), soybean trypsin inhibitor (21.5 kDa), egg white lysozyme (14.4 kDa) and bovine aprotinin (6.5 kDa).

EQUIVALENTS

Those skilled in the art will recognize, or be able to ascertain using no more than routine experimentation, many equivalents to the specific embodiments and methods described herein. The specific embodiments described herein are offered by way of example only, and the invention is to limited only by the terms of the appended claims, along with the full scope of equivalents to which such claims are entitled.

TABLE 2

| ORF Name | NTID | AAID | NT Length | AA Length | Score | Probability |
|---|---|---|---|---|---|---|
| 2538928_c3_3 | 1 | 1921 | 84 | 255 | 306 | 3.3e-27 |

| Protein name | | | | Locus Name | | Acc# |
|---|---|---|---|---|---|---|
| | | | | sp:ETFA_HUMAN | | P13804 |

Description

ELECTRON TRANSFER FLAVOPROTEIN ALPHA-SUBUNIT PRECURSOR (ALPHA-ETF)

| ORF Name | NTID | AAID | NT Length | AA Length | Score | Probability |
|---|---|---|---|---|---|---|
| 24035192_f2_1 | 2 | 1922 | 502 | 1509 | 138 | 1.5e-05 |

| Protein name | | | | Locus Name | | Acc# |
|---|---|---|---|---|---|---|
| icmF protein | | | | pir:T18341 | | T18341 |

Description

| ORF Name | NTID | AAID | NT Length | AA Length | Score | Probability |
|---|---|---|---|---|---|---|
| 10547151_c1_2 | 3 | 1923 | 62 | 189 | | |

| Protein name | | | | Locus Name | | Acc# |
|---|---|---|---|---|---|---|

Description

NO-HIT

| ORF Name | NTID | AAID | NT Length | AA Length | Score | Probability |
|---|---|---|---|---|---|---|
| 24317313_c2_2 | 4 | 1924 | 201 | 606 | 316 | 3.2e-27 |

| Protein name | | | | Locus Name | | Acc# |
|---|---|---|---|---|---|---|
| | | | | sp:SYFB_HAEIN | | P43820 |

Description

TRNA LIGASE BETA CHAIN) (PHERS)

| ORF Name | NTID | AAID | NT Length | AA Length | Score | Probability |
|---|---|---|---|---|---|---|
| 11911687_c2_42 | 5 | 1925 | 284 | 855 | 709 | 6.5e-70 |

| Protein name | | | | Locus Name | | Acc# |
|---|---|---|---|---|---|---|
| 3-methyl-2-oxobutanoate | | | | gp:PFL130846 | | AJ130846 |

Description

Pseudomonas fluorescens folK (partial), panB and panC (partial) genes.

| ORF Name | NTID | AAID | NT Length | AA Length | Score | Probability |
|---|---|---|---|---|---|---|
| 14334452_c2_44 | 6 | 1926 | 221 | 666 | 339 | 2.9e-35 |

| Protein name | | | | Locus Name | | Acc# |
|---|---|---|---|---|---|---|
| | | | | gp:ECHSDMSR | | X13145 |

Description

Escherichia Coli plasmid R124/3 hsdM, hsdS and hsdR genes for EcoR124/3 type I restriction and modification enzyme.

| ORF Name | NTID | AAID | NT Length | AA Length | Score | Probability |
|---|---|---|---|---|---|---|
| 16619747_c3_48 | 7 | 1927 | 73 | 222 | 158 | 1.6e-11 |

| Protein name | | | | Locus Name | | Acc# |
|---|---|---|---|---|---|---|
| | | | | sp:YBAV_HAEIN | | Q57134 |

Description

HYPOTHETICAL PROTEIN HI1008

| ORF Name | NTID | AAID | NT Length | AA Length | Score | Probability |
|---|---|---|---|---|---|---|
| 21657635_f3_22 | 8 | 1928 | 221 | 666 | 381 | 3.7e-35 |

| Protein name | | | | Locus Name | | Acc# |
|---|---|---|---|---|---|---|
| | | | | sp:DSBA_PSEAE | | P95460 |

Description

THIOL:DISULFIDE INTERCHANGE PROTEIN DSBA PRECURSOR

| ORF Name | NTID | AAID | NT Length | AA Length | Score | Probability |
|---|---|---|---|---|---|---|
| 23476431_c3_54 | 9 | 1929 | 181 | 546 | 123 | 3.8e-07 |

| Protein name | | | | Locus Name | | Acc# |
|---|---|---|---|---|---|---|
| | | | | sp:YJGA_HAEIN | | P45076 |

Description

HYPOTHETICAL PROTEIN HI1151

| ORF Name | NTID | AAID | NT Length | AA Length | Score | Probability |
|---|---|---|---|---|---|---|
| 23945165_c3_49 | 10 | 1930 | 170 | 513 | 334 | 3.6e-30 |

| Protein name | Locus Name | Acc# |
|---|---|---|
| 2-amino-4-hydroxy-6-hydroxymethyldihydropteridine | pir:C64046 | C64046 |

Description

| ORF Name | NTID | AAID | NT Length | AA Length | Score | Probability |
|---|---|---|---|---|---|---|
| 24351555_c2_38 | 11 | 1931 | 130 | 393 | 135 | 1.0e-08 |

| Protein name | Locus Name | Acc# |
|---|---|---|
|  | sp:MAZG_HAEIN | P44723 |

Description

MAZG PROTEIN HOMOLOG

| ORF Name | NTID | AAID | NT Length | AA Length | Score | Probability |
|---|---|---|---|---|---|---|
| 2835152_f2_14 | 12 | 1932 | 82 | 249 |  |  |

| Protein name | Locus Name | Acc# |
|---|---|---|

Description

NO-HIT

| ORF Name | NTID | AAID | NT Length | AA Length | Score | Probability |
|---|---|---|---|---|---|---|
| 34178802_c2_45 | 13 | 1933 | 132 | 399 | 184 | 3.3e-14 |

| Protein name | Locus Name | Acc# |
|---|---|---|
| conserved hypothetical secreted protein HP1098 | pir:B64657 | B64657 |

Description

| ORF Name | NTID | AAID | NT Length | AA Length | Score | Probability |
|---|---|---|---|---|---|---|
| 35819090_c1_31 | 14 | 1934 | 623 | 1872 | 689 | 8.5e-68 |

| Protein name | Locus Name | Acc# |
|---|---|---|
| polynucleotide adenylyltransferase | gp:PPY18131 | Y18131 |

Description

Pseudomonas putida pcnB gene and partial folK gene.

| ORF_Name | NTID | AAID | NT Length | AA Length | Score | Probability |
|---|---|---|---|---|---|---|
| 4468761_f2_18 | 15 | 1935 | 61 | 186 | | |

| Protein name | | | | | Locus Name | Acc# |
|---|---|---|---|---|---|---|

Description

NO-HIT

| ORF_Name | NTID | AAID | NT Length | AA Length | Score | Probability |
|---|---|---|---|---|---|---|
| 4492138_c2_43 | 16 | 1936 | 283 | 852 | 660 | 1.0e-64 |

| Protein name | | | | | Locus Name | Acc# |
|---|---|---|---|---|---|---|
| | | | | | sp:PANC_SCHPO | Q09673 |

Description (SYNTHETASE) (PANTOATE ACTIVATING ENZYME)

| ORF_Name | NTID | AAID | NT Length | AA Length | Score | Probability |
|---|---|---|---|---|---|---|
| 48796812_c3_47 | 17 | 1937 | 84 | 255 | 138 | 1.8e-08 |

| Protein name | | | | | Locus Name | Acc# |
|---|---|---|---|---|---|---|
| | | | | | sp:CBF5_YEAST | P33322 |

Description 5) (NUCLEOLAR PROTEIN CBF5) (P64')

| ORF_Name | NTID | AAID | NT Length | AA Length | Score | Probability |
|---|---|---|---|---|---|---|
| 5110943_c1_32 | 18 | 1938 | 298 | 897 | 604 | 8.7e-59 |

| Protein name | | | | | Locus Name | Acc# |
|---|---|---|---|---|---|---|
| | | | | | gp:AB033988 | AB033988 |

Description

Shewanella violacea gene for RpoN(sigma54), nitrogen reguratory IIAprotein, phosphocarrier protein NPR, hypothetical proteins, partialand complete cds.

| ORF_Name | NTID | AAID | NT Length | AA Length | Score | Probability |
|---|---|---|---|---|---|---|
| 5112807_c3_52 | 19 | 1939 | 92 | 279 | | |

| Protein name | | | | | Locus Name | Acc# |
|---|---|---|---|---|---|---|

Description

NO-HIT

| ORF_Name | NTID | AAID | NT Length | AA Length | Score | Probability |
|---|---|---|---|---|---|---|
| 26285938_f1_1 | 20 | 1940 | 207 | 624 | 541 | 4.1e-52 |

| Protein name | | | | Locus_Name | | Acc# |
|---|---|---|---|---|---|---|
| | | | | sp:YCEG_HAEIN | | P44720 |

Description

HYPOTHETICAL PROTEIN HI0457

| ORF_Name | NTID | AAID | NT Length | AA Length | Score | Probability |
|---|---|---|---|---|---|---|
| 30658587_f1_2 | 21 | 1941 | 73 | 219 | 126 | 4.8e-08 |

| Protein name | | | | Locus_Name | | Acc# |
|---|---|---|---|---|---|---|
| | | | | sp:KTHY_BACSU | | P37537 |

Description

THYMIDYLATE KINASE, (DTMP KINASE)

| ORF_Name | NTID | AAID | NT Length | AA Length | Score | Probability |
|---|---|---|---|---|---|---|
| 2767080_f1_2 | 22 | 1942 | 373 | 1122 | 1522 | 4.6e-156 |

| Protein name | | | | Locus_Name | | Acc# |
|---|---|---|---|---|---|---|
| | | | | sp:EFTU_SHEPU | | P33169 |

Description

ELONGATION FACTOR TU (EF-TU)

| ORF_Name | NTID | AAID | NT Length | AA Length | Score | Probability |
|---|---|---|---|---|---|---|
| 32110007_c2_8 | 23 | 1943 | 88 | 267 | 114 | 7.3e-07 |

| Protein name | | | | Locus_Name | | Acc# |
|---|---|---|---|---|---|---|
| hypothetical protein PH1485 | | | | pir:H71023 | | H71023 |

Description

| ORF_Name | NTID | AAID | NT Length | AA Length | Score | Probability |
|---|---|---|---|---|---|---|
| 36329582_c1_5 | 24 | 1944 | 60 | 183 | 144 | 5.5e-09 |

| Protein name | | | | Locus_Name | | Acc# |
|---|---|---|---|---|---|---|
| | | | | sp:YHA2_EIKCO | | P35649 |

Description

HYPOTHETICAL 66.3 KD PROTEIN IN HAG2 5'REGION

| ORF Name | NTID | AAID | NT Length | AA Length | Score | Probability |
|---|---|---|---|---|---|---|
| 971016_f1_1 | 25 | 1945 | 198 | 597 | 643 | 6.4e-63 |

| Protein name | | | | Locus Name | | Acc# |
|---|---|---|---|---|---|---|
| | | | | sp:EFG_HELPY | | P56002 |

Description

ELONGATION FACTOR G (EF-G)

| ORF Name | NTID | AAID | NT Length | AA Length | Score | Probability |
|---|---|---|---|---|---|---|
| 2225312_f3_18 | 26 | 1946 | 427 | 1284 | 416 | 1.9e-64 |

| Protein name | | | | Locus Name | | Acc# |
|---|---|---|---|---|---|---|
| glycerophosphoryl diester phosphodiesterase | | | | pir:D75630 | | D75630 |

Description

| ORF Name | NTID | AAID | NT Length | AA Length | Score | Probability |
|---|---|---|---|---|---|---|
| 23457692_f1_1 | 27 | 1947 | 392 | 1179 | 360 | 1.9e-42 |

| Protein name | | | | Locus Name | | Acc# |
|---|---|---|---|---|---|---|
| | | | | sp:RECF_PSEPU | | P13456 |

Description

RECF PROTEIN

| ORF Name | NTID | AAID | NT Length | AA Length | Score | Probability |
|---|---|---|---|---|---|---|
| 26042927_f3_19 | 28 | 1948 | 84 | 255 | | |

| Protein name | | | | Locus Name | | Acc# |
|---|---|---|---|---|---|---|

Description

NO-HIT

| ORF Name | NTID | AAID | NT Length | AA Length | Score | Probability |
|---|---|---|---|---|---|---|
| 26750837_f1_4 | 29 | 1949 | 111 | 336 | 202 | 4.9e-16 |

| Protein name | | | | Locus Name | | Acc# |
|---|---|---|---|---|---|---|
| hypothetical protein | | | | pir:S76551 | | S76551 |

Description

| ORF Name | NTID | AAID | NT Length | AA Length | Score | Probability |
|---|---|---|---|---|---|---|
| 36144675_f1_2 | 30 | 1950 | 525 | 1578 | 1851 | 6.3e-191 |

| Protein name | | | | Locus Name | | Acc# |
|---|---|---|---|---|---|---|
| | | | | sp:GUAA_HAEIN | | P44335 |

Description

AMIDOTRANSFERASE) (GMP SYNTHETASE)

| ORF Name | NTID | AAID | NT Length | AA Length | Score | Probability |
|---|---|---|---|---|---|---|
| 4298443_f2_8 | 31 | 1951 | 822 | 2469 | 2597 | 5.6e-270 |

| Protein name | | | | Locus Name | | Acc# |
|---|---|---|---|---|---|---|
| | | | | sp:GYRB_ECOLI | | |

Description

DNA GYRASE SUBUNIT B,

| ORF Name | NTID | AAID | NT Length | AA Length | Score | Probability |
|---|---|---|---|---|---|---|
| 12617627_c1_1 | 32 | 1952 | 128 | 387 | 650 | 1.2e-63 |

| Protein name | | | | Locus Name | | Acc# |
|---|---|---|---|---|---|---|
| transposase | | | | pir:I67760 | | I67760 |

Description

| ORF Name | NTID | AAID | NT Length | AA Length | Score | Probability |
|---|---|---|---|---|---|---|
| 34175180_c2_2 | 33 | 1953 | 90 | 273 | 137 | 1.7e-08 |

| Protein name | | | | Locus Name | | Acc# |
|---|---|---|---|---|---|---|
| transposase | | | | gp:AB026428 | | AB026428 |

Description

Methylomonas aminofaciens ribulose monophosphate pathway genes(rmpD, rmpA, IS10-R rmpI, rmpB), complete cds.

| ORF Name | NTID | AAID | NT Length | AA Length | Score | Probability |
|---|---|---|---|---|---|---|
| 16690875_f1_2 | 34 | 1954 | 82 | 249 | 90 | 0.00026 |

| Protein name | | | | Locus Name | | Acc# |
|---|---|---|---|---|---|---|
| TolR protein | | | | gp:PPPAL1 | | X74218 |

Description

Pseudomonas putida ruvB, tolQ, tolR, tolA, tolB and oprL genes.

| ORF Name | NTID | AAID | NT Length | AA Length | Score | Probability |
|---|---|---|---|---|---|---|
| 1953953_c2_15 | 35 | 1955 | 534 | 1605 | 1387 | 9.3e-142 |

| Protein name | | | | | Locus Name | Acc# |
|---|---|---|---|---|---|---|
| | | | | | sp:ANIA_NEIGO | Q02219 |

Description

MAJOR OUTER MEMBRANE PROTEIN PAN 1 PRECURSOR

| ORF Name | NTID | AAID | NT Length | AA Length | Score | Probability |
|---|---|---|---|---|---|---|
| 22667557_f2_6 | 36 | 1956 | 177 | 534 | 260 | 4.5e-31 |

| Protein name | | | | | Locus Name | Acc# |
|---|---|---|---|---|---|---|
| | | | | | sp:YHDE_BACSU | O07573 |

Description

HYPOTHETICAL 16.6 KD PROTEIN IN GLPD-SPOVR INTERGENIC REGION

| ORF Name | NTID | AAID | NT Length | AA Length | Score | Probability |
|---|---|---|---|---|---|---|
| 30644217_f2_8 | 37 | 1957 | 83 | 252 | | |

| Protein name | | | | | Locus Name | Acc# |
|---|---|---|---|---|---|---|

Description

NO-HIT

| ORF Name | NTID | AAID | NT Length | AA Length | Score | Probability |
|---|---|---|---|---|---|---|
| 4881533_f2_7 | 38 | 1958 | 62 | 189 | | |

| Protein name | | | | | Locus Name | Acc# |
|---|---|---|---|---|---|---|

Description

NO-HIT

| ORF Name | NTID | AAID | NT Length | AA Length | Score | Probability |
|---|---|---|---|---|---|---|
| 6651712_f2_2 | 39 | 1959 | 271 | 816 | 611 | 1.6e-59 |

| Protein name | | | | | Locus Name | Acc# |
|---|---|---|---|---|---|---|
| isocitrate lyase | | | | | gp:AB004651 | AB004651 |

Description

Hyphomicrobium methylovorum gene for isocitrate lyase,inorganicphosphate transporter,methionine synthase,complete and partial cds.

| ORF_Name | NTID | AAID | NT Length | AA Length | Score | Probability |
|---|---|---|---|---|---|---|
| 14647952_f1_1 | 40 | 1960 | 912 | 2739 | 2108 | 3.7e-218 |

| Protein name | Locus Name | Acc# |
|---|---|---|
| initiation factor IF2-alpha | gp:PVAJ2737 | AJ002737 |

Description

Proteus vulgaris infB gene and partial nusA and rbfA genes.

| ORF_Name | NTID | AAID | NT Length | AA Length | Score | Probability |
|---|---|---|---|---|---|---|
| 15032818_c1_15 | 41 | 1961 | 172 | 519 | 112 | 4.1e-05 |

| Protein name | Locus Name | Acc# |
|---|---|---|
| hypothetical protein | pir:G75410 | G75410 |

Description

| ORF_Name | NTID | AAID | NT Length | AA Length | Score | Probability |
|---|---|---|---|---|---|---|
| 21644075_c1_14 | 42 | 1962 | 199 | 600 | 381 | 3.7e-35 |

| Protein name | Locus Name | Acc# |
|---|---|---|
| conserved hypothetical protein | pir:F75410 | F75410 |

Description

| ORF_Name | NTID | AAID | NT Length | AA Length | Score | Probability |
|---|---|---|---|---|---|---|
| 24650277_f1_3 | 43 | 1963 | 312 | 939 | 543 | 2.5e-52 |

| Protein name | Locus Name | Acc# |
|---|---|---|
|  | sp:TRUB_HAEIN | P45142 |

Description (HYDROLYASE)

| ORF_Name | NTID | AAID | NT Length | AA Length | Score | Probability |
|---|---|---|---|---|---|---|
| 3332760_f2_11 | 44 | 1964 | 61 | 186 |  |  |

| Protein name | Locus Name | Acc# |
|---|---|---|

Description

NO-HIT

| ORF Name | NTID | AAID | NT Length | AA Length | Score | Probability |
|---|---|---|---|---|---|---|
| 3407812_f2_9 | 45 | 1965 | 168 | 507 | 215 | 1.4e-17 |

| Protein name | | | | Locus Name | | Acc# |
|---|---|---|---|---|---|---|
| | | | | sp:RBFA_ECOLI | | P09170 |

Description

RIBOSOME-BINDING FACTOR A (P15B PROTEIN)

| ORF Name | NTID | AAID | NT Length | AA Length | Score | Probability |
|---|---|---|---|---|---|---|
| 4573462_c2_24 | 46 | 1966 | 103 | 312 | 171 | 2.0e-12 |

| Protein name | | | | Locus Name | | Acc# |
|---|---|---|---|---|---|---|
| conserved hypothetical protein | | | | pir:F75410 | | F75410 |

Description

| ORF Name | NTID | AAID | NT Length | AA Length | Score | Probability |
|---|---|---|---|---|---|---|
| 4968825_f2_5 | 47 | 1967 | 217 | 654 | 466 | 3.7e-44 |

| Protein name | | | | Locus Name | | Acc# |
|---|---|---|---|---|---|---|
| | | | | sp:NUSA_ECOLI | | P03003 |

Description

N UTILIZATION SUBSTANCE PROTEIN A (NUSA PROTEIN) (L FACTOR)

| ORF Name | NTID | AAID | NT Length | AA Length | Score | Probability |
|---|---|---|---|---|---|---|
| 7070265_f1_4 | 48 | 1968 | 62 | 189 | | |

| Protein name | | | | Locus Name | | Acc# |
|---|---|---|---|---|---|---|

Description

NO-HIT

| ORF Name | NTID | AAID | NT Length | AA Length | Score | Probability |
|---|---|---|---|---|---|---|
| 4143942_f3_1 | 49 | 1969 | 319 | 957 | 164 | 1.1e-11 |

| Protein name | | | | Locus Name | | Acc# |
|---|---|---|---|---|---|---|
| hypothetical protein b1759 | | | | pir:G64935 | | G64935 |

Description

| ORF_Name | NTID | AAID | NT Length | AA Length | Score | Probability |
|---|---|---|---|---|---|---|
| 1072952_f3_19 | 50 | 1970 | 331 | 996 | 281 | 2.5e-24 |

| Protein name | | | | Locus Name | | Acc# |
|---|---|---|---|---|---|---|
| | | | | sp:SUG2_YEAST | | |

Description

PROBABLE 26S PROTEASE SUBUNIT SUG2 (PROTEASOMAL CAP SUBUNIT)

| ORF_Name | NTID | AAID | NT Length | AA Length | Score | Probability |
|---|---|---|---|---|---|---|
| 112880_f1_4 | 51 | 1971 | 99 | 300 | 120 | 1.7e-07 |

| Protein name | | | | Locus Name | | Acc# |
|---|---|---|---|---|---|---|
| hypothetical protein APE2554 | | | | pir:C72489 | | C72489 |

Description

| ORF_Name | NTID | AAID | NT Length | AA Length | Score | Probability |
|---|---|---|---|---|---|---|
| 14633260_f2_12 | 52 | 1972 | 167 | 504 | | |

| Protein name | | | | Locus Name | | Acc# |
|---|---|---|---|---|---|---|

Description

NO-HIT

| ORF_Name | NTID | AAID | NT Length | AA Length | Score | Probability |
|---|---|---|---|---|---|---|
| 19532782_c2_33 | 53 | 1973 | 513 | 1542 | 1454 | 7.4e-149 |

| Protein name | | | | Locus Name | | Acc# |
|---|---|---|---|---|---|---|
| | | | | sp:TRPE_ACICA | | P23315 |

Description

ANTHRANILATE SYNTHASE COMPONENT I,

| ORF_Name | NTID | AAID | NT Length | AA Length | Score | Probability |
|---|---|---|---|---|---|---|
| 20939567_f1_1 | 54 | 1974 | 138 | 417 | | |

| Protein name | | | | Locus Name | | Acc# |
|---|---|---|---|---|---|---|

Description

NO-HIT

| ORF Name | NTID | AAID | NT Length | AA Length | Score | Probability |
|---|---|---|---|---|---|---|
| 22070965_f2_11 | 55 | 1975 | 123 | 372 | 88 | 0.018 |

Protein name: alanine--tRNA ligase, alaS:alanyl-tRNA synthetase:alanyl-tRNA synthetase Locus Name: pir:D70127  Acc#: D70127

Description:

| ORF Name | NTID | AAID | NT Length | AA Length | Score | Probability |
|---|---|---|---|---|---|---|
| 23839667_c1_25 | 56 | 1976 | 318 | 957 | 732 | 2.4e-72 |

Protein name:

Locus Name: sp:DAPA_HAEIN  Acc#: P43797

Description: DIHYDRODIPICOLINATE SYNTHASE, (DHDPS)

| ORF Name | NTID | AAID | NT Length | AA Length | Score | Probability |
|---|---|---|---|---|---|---|
| 26281300_c3_35 | 57 | 1977 | 119 | 360 | 257 | 5.1e-22 |

Protein name:

Locus Name: sp:Y01B_MYCTU  Acc#: Q10514

Description: HYPOTHETICAL 39.6 KD PROTEIN CY427.11C

| ORF Name | NTID | AAID | NT Length | AA Length | Score | Probability |
|---|---|---|---|---|---|---|
| 30507291_f3_20 | 58 | 1978 | 174 | 525 | | |

Protein name:

Locus Name:  Acc#:

Description: NO-HIT

| ORF Name | NTID | AAID | NT Length | AA Length | Score | Probability |
|---|---|---|---|---|---|---|
| 4792250_c1_26 | 59 | 1979 | 114 | 345 | | |

Protein name:

Locus Name:  Acc#:

Description: NO-HIT

| ORF Name | NTID | AAID | NT Length | AA Length | Score | Probability |
|---|---|---|---|---|---|---|
| 5282805_c3_34 | 60 | 1980 | 241 | 726 | 786 | 4.5e-78 |

| Protein name | Locus Name | Acc# |
|---|---|---|
| | sp:PUR7_ECOLI | P21155 |

Description (SAICAR SYNTHETASE)

| ORF Name | NTID | AAID | NT Length | AA Length | Score | Probability |
|---|---|---|---|---|---|---|
| 24020430_f2_1 | 61 | 1981 | 127 | 381 | 649 | 1.5e-63 |

| Protein name | Locus Name | Acc# |
|---|---|---|
| transposase | pir:I67760 | I67760 |

Description

| ORF Name | NTID | AAID | NT Length | AA Length | Score | Probability |
|---|---|---|---|---|---|---|
| 129813_f2_1 | 62 | 1982 | 126 | 381 | | |

| Protein name | Locus Name | Acc# |
|---|---|---|

Description

NO-HIT

| ORF Name | NTID | AAID | NT Length | AA Length | Score | Probability |
|---|---|---|---|---|---|---|
| 4391518_f2_4 | 63 | 1983 | 64 | 195 | 108 | 3.2e-06 |

| Protein name | Locus Name | Acc# |
|---|---|---|
| | sp:THIX_HAEIN | P43787 |

Description

THIOREDOXIN-LIKE PROTEIN HI1115

| ORF Name | NTID | AAID | NT Length | AA Length | Score | Probability |
|---|---|---|---|---|---|---|
| 4495268_f2_2 | 64 | 1984 | 110 | 333 | 512 | 4.9e-49 |

| Protein name | Locus Name | Acc# |
|---|---|---|
| ferredoxin [3Fe-4S | pir:FEAV | |

Description

| ORF Name | NTID | AAID | NT Length | AA Length | Score | Probability |
|---|---|---|---|---|---|---|
| 4860875_f3_6 | 65 | 1985 | 159 | 480 | 204 | 2.1e-16 |

Protein name: hypothetical protein APE2447
Locus Name: pir:F72475
Acc#: F72475

Description:

| ORF Name | NTID | AAID | NT Length | AA Length | Score | Probability |
|---|---|---|---|---|---|---|
| 15677200_f2_2 | 66 | 1986 | 158 | 477 | 428 | 3.9e-40 |

Protein name:
Locus Name: sp:CYSW_ECOLI
Acc#:

Description: SULFATE TRANSPORT SYSTEM PERMEASE PROTEIN CYSW

| ORF Name | NTID | AAID | NT Length | AA Length | Score | Probability |
|---|---|---|---|---|---|---|
| 4490678_f1_1 | 67 | 1987 | 247 | 741 | 643 | 6.4e-63 |

Protein name:
Locus Name: sp:CYSA_ECOLI
Acc#:

Description: SULFATE TRANSPORT ATP-BINDING PROTEIN CYSA

| ORF Name | NTID | AAID | NT Length | AA Length | Score | Probability |
|---|---|---|---|---|---|---|
| 16054077_f3_20 | 68 | 1988 | 520 | 1563 | | |

Protein name:
Locus Name:
Acc#:

Description: NO-HIT

| ORF Name | NTID | AAID | NT Length | AA Length | Score | Probability |
|---|---|---|---|---|---|---|
| 16495465_f1_1 | 69 | 1989 | 77 | 234 | 72 | 0.020 |

Protein name:
Locus Name: sp:YDIE_ECOLI
Acc#: P40721

Description: HYPOTHETICAL 7.1 KD PROTEIN IN AROH-NLPC INTERGENIC REGION

| ORF Name | NTID | AAID | NT Length | AA Length | Score | Probability |
|---|---|---|---|---|---|---|
| 23485750_c3_36 | 70 | 1990 | 68 | 207 | | |

Protein name | | | | | Locus Name | Acc#

Description

NO-HIT

| ORF Name | NTID | AAID | NT Length | AA Length | Score | Probability |
|---|---|---|---|---|---|---|
| 23730017_c1_24 | 71 | 1991 | 947 | 2844 | 278 | 2.2e-36 |

Protein name | | | | | Locus Name | Acc#
| | | | | | sp:YTFM_HAEIN | P44038

Description

HYPOTHETICAL PROTEIN HI0698 PRECURSOR

| ORF Name | NTID | AAID | NT Length | AA Length | Score | Probability |
|---|---|---|---|---|---|---|
| 23859387_f2_14 | 72 | 1992 | 296 | 891 | 93 | 0.048 |

Protein name | | | | | Locus Name | Acc#
conserved hypothetical protein yrrB | | | | | pir:H69978 | H69978

Description

| ORF Name | NTID | AAID | NT Length | AA Length | Score | Probability |
|---|---|---|---|---|---|---|
| 34119002_f3_18 | 73 | 1993 | 444 | 1335 | 714 | 1.1e-69 |

Protein name | | | | | Locus Name | Acc#
2-acylglycerophosphoethanolamine acyltransferase (aas) RP620 | | | | | pir:E71667 | E71667

Description

| ORF Name | NTID | AAID | NT Length | AA Length | Score | Probability |
|---|---|---|---|---|---|---|
| 4480217_c3_35 | 74 | 1994 | 1675 | 5028 | 678 | 1.5e-79 |

Protein name | | | | | Locus Name | Acc#
| | | | | | sp:YTFN_HAEIN | Q57523

Description

HYPOTHETICAL PROTEIN HI0696

| ORF Name | NTID | AAID | NT Length | AA Length | Score | Probability |
|---|---|---|---|---|---|---|
| 12378407_c2_32 | 75 | 1995 | 278 | 834 | 626 | 4.1e-61 |

| Protein name | | | | Locus Name | | Acc# |
|---|---|---|---|---|---|---|
| | | | | sp:PDXJ_ECOLI | | P24223 |

Description

PYRIDOXAL PHOSPHATE BIOSYNTHETIC PROTEIN PDXJ

| ORF Name | NTID | AAID | NT Length | AA Length | Score | Probability |
|---|---|---|---|---|---|---|
| 14487952_f1_7 | 76 | 1996 | 72 | 219 | | |

| Protein name | | | | Locus Name | | Acc# |
|---|---|---|---|---|---|---|

Description

NO-HIT

| ORF Name | NTID | AAID | NT Length | AA Length | Score | Probability |
|---|---|---|---|---|---|---|
| 161402_c2_29 | 77 | 1997 | 61 | 186 | 59 | 0.018 |

| Protein name | | | | Locus Name | | Acc# |
|---|---|---|---|---|---|---|
| envelope glycoprotein | | | | gp:HIVU90070 | | U90070 |

Description

HIV-1 strain VN16 from Vietnam, envelope glycoprotein V3 region(env) gene, partial cds.

| ORF Name | NTID | AAID | NT Length | AA Length | Score | Probability |
|---|---|---|---|---|---|---|
| 16171905_c2_28 | 78 | 1998 | 67 | 204 | | |

| Protein name | | | | Locus Name | | Acc# |
|---|---|---|---|---|---|---|

Description

NO-HIT

| ORF Name | NTID | AAID | NT Length | AA Length | Score | Probability |
|---|---|---|---|---|---|---|
| 22324331_f2_16 | 79 | 1999 | 77 | 234 | | |

| Protein name | | | | Locus Name | | Acc# |
|---|---|---|---|---|---|---|

Description

NO-HIT

| ORF Name | NTID | AAID | NT Length | AA Length | Score | Probability |
|---|---|---|---|---|---|---|
| 22463311_f3_22 | 80 | 2000 | 103 | 312 | | |

| Protein name | | | | Locus Name | | Acc# |
|---|---|---|---|---|---|---|

Description

NO-HIT

| ORF Name | NTID | AAID | NT Length | AA Length | Score | Probability |
|---|---|---|---|---|---|---|
| 23442503_c2_31 | 81 | 2001 | 346 | 1041 | 831 | 7.7e-83 |

| Protein name | | | | Locus Name | | Acc# |
|---|---|---|---|---|---|---|
| Era | | | | gp:AF123492 | | AF123492 |

Description

Pseudomonas aeruginosa rnc-era-recO operon, complete sequence.

| ORF Name | NTID | AAID | NT Length | AA Length | Score | Probability |
|---|---|---|---|---|---|---|
| 24412781_c3_34 | 82 | 2002 | 101 | 306 | | |

| Protein name | | | | Locus Name | | Acc# |
|---|---|---|---|---|---|---|

Description

NO-HIT

| ORF Name | NTID | AAID | NT Length | AA Length | Score | Probability |
|---|---|---|---|---|---|---|
| 26570925_c2_30 | 83 | 2003 | 268 | 807 | 500 | 9.1e-48 |

| Protein name | | | | Locus Name | | Acc# |
|---|---|---|---|---|---|---|
| | | | | sp:RNC_ECOLI | | |

Description

RIBONUCLEASE III, (RNASE III)

| ORF Name | NTID | AAID | NT Length | AA Length | Score | Probability |
|---|---|---|---|---|---|---|
| 26678567_c1_24 | 84 | 2004 | 63 | 192 | 88 | 0.00042 |

| Protein name | | | | Locus Name | | Acc# |
|---|---|---|---|---|---|---|
| hypothetical protein 29.1 | | | | pir:S59084 | | S59084 |

Description

| ORF Name | NTID | AAID | NT Length | AA Length | Score | Probability |
|---|---|---|---|---|---|---|
| 35161562_c1_27 | 85 | 2005 | 212 | 639 | 103 | 0.0015 |

Protein name: RecO
Locus Name: gp:AF123492
Acc#: AF123492

Description: Pseudomonas aeruginosa rnc-era-recO operon, complete sequence.

| ORF Name | NTID | AAID | NT Length | AA Length | Score | Probability |
|---|---|---|---|---|---|---|
| 4063308_c3_35 | 86 | 2006 | 607 | 1824 | 2257 | 5.9e-234 |

Protein name:
Locus Name: sp:LEPA_HAEIN
Acc#: P43729

Description: GTP-BINDING PROTEIN LEPA

| ORF Name | NTID | AAID | NT Length | AA Length | Score | Probability |
|---|---|---|---|---|---|---|
| 4100003_f3_20 | 87 | 2007 | 159 | 480 | 624 | 6.6e-61 |

Protein name:
Locus Name: sp:Y882_HAEIN
Acc#: P44068

Description: HYPOTHETICAL PROTEIN HI0882

| ORF Name | NTID | AAID | NT Length | AA Length | Score | Probability |
|---|---|---|---|---|---|---|
| 7032838_c3_36 | 88 | 2008 | 367 | 1104 | 276 | 2.0e-44 |

Protein name: signal peptidase I
Locus Name: gp:ECOK12RIII
Acc#: D64044

Description: Escherichia coli ribonuclease III and other genes, complete cds.

| ORF Name | NTID | AAID | NT Length | AA Length | Score | Probability |
|---|---|---|---|---|---|---|
| 9869702_f3_21 | 89 | 2009 | 60 | 183 | | |

Protein name:
Locus Name:
Acc#:

Description: NO-HIT

| ORF Name | NTID | AAID | NT Length | AA Length | Score | Probability |
|---|---|---|---|---|---|---|
| 10802330_f3_20 | 90 | 2010 | 64 | 195 | | |

Protein name: 
Locus Name: 
Acc#:

Description: NO-HIT

| ORF Name | NTID | AAID | NT Length | AA Length | Score | Probability |
|---|---|---|---|---|---|---|
| 12714056_c1_22 | 91 | 2011 | 377 | 1134 | 1472 | 9.1e-151 |

Protein name: putative formaldehyde dehydrogenase
Locus Name: gp:PSP243941
Acc#: AJ243941

Description: Pseudomonas sp. strain HR199 partial vanB, fdh, gcs, ehyA and ehyBgenes.

| ORF Name | NTID | AAID | NT Length | AA Length | Score | Probability |
|---|---|---|---|---|---|---|
| 14844626_c2_34 | 92 | 2012 | 202 | 609 | 93 | 0.028 |

Protein name: transcription regulator, TetR family
Locus Name: pir:F75482
Acc#: F75482

Description:

| ORF Name | NTID | AAID | NT Length | AA Length | Score | Probability |
|---|---|---|---|---|---|---|
| 15705056_c1_24 | 93 | 2013 | 72 | 219 | | |

Protein name:
Locus Name:
Acc#:

Description: NO-HIT

| ORF Name | NTID | AAID | NT Length | AA Length | Score | Probability |
|---|---|---|---|---|---|---|
| 159667_c2_31 | 94 | 2014 | 67 | 204 | | |

Protein name:
Locus Name:
Acc#:

Description: NO-HIT

| ORF Name | NTID | AAID | NT Length | AA Length | Score | Probability |
|---|---|---|---|---|---|---|
| 30079512_f3_17 | 95 | 2015 | 76 | 231 | 87 | 0.00053 |

Protein name | Locus Name | Acc#
sp:FIXS_RHIME | P18399

Description

NITROGEN FIXATION PROTEIN FIXS

| ORF Name | NTID | AAID | NT Length | AA Length | Score | Probability |
|---|---|---|---|---|---|---|
| 35578402_f2_7 | 96 | 2016 | 441 | 1326 | 1116 | 4.8e-113 |

Protein name | Locus Name | Acc#
sp:YEEF_ECOLI | P33016

Description

HYPOTHETICAL 49.8 KD TRANSPORT PROTEIN IN SBCB-HISL INTERGENIC REGION

| ORF Name | NTID | AAID | NT Length | AA Length | Score | Probability |
|---|---|---|---|---|---|---|
| 3910876_f3_16 | 97 | 2017 | 501 | 1506 | 742 | 2.1e-73 |

Protein name | Locus Name | Acc#
sp:YDIU_ECOLI |

Description

HYPOTHETICAL 54.4 KD PROTEIN IN AROH-NLPC INTERGENIC REGION

| ORF Name | NTID | AAID | NT Length | AA Length | Score | Probability |
|---|---|---|---|---|---|---|
| 5097812_c2_30 | 98 | 2018 | 120 | 363 | 280 | 1.9e-24 |

Protein name | Locus Name | Acc#
sp:YAIM_ECOLI |

Description

HYPOTHETICAL 31.4 KD PROTEIN IN MHPT-ADHC INTERGENIC REGION

| ORF Name | NTID | AAID | NT Length | AA Length | Score | Probability |
|---|---|---|---|---|---|---|
| 5210318_f2_10 | 99 | 2019 | 289 | 870 | 196 | 1.5e-15 |

Protein name | Locus Name | Acc#
hypothetical protein HP0861 | pir:E64627 | E64627

Description

| ORF Name | NTID | AAID | NT Length | AA Length | Score | Probability |
|---|---|---|---|---|---|---|
| 6740877_f3_15 | 100 | 2020 | 406 | 1221 | 639 | 1.7e-62 |

| Protein name | | | | Locus Name | | Acc# |
|---|---|---|---|---|---|---|
| stearoyl-CoA desaturase | | | | gp:AF026401 | | AF026401 |

Description

Mucor rouxii stearoyl-CoA desaturase (Ole1) gene, complete cds.

| ORF Name | NTID | AAID | NT Length | AA Length | Score | Probability |
|---|---|---|---|---|---|---|
| 994001_c1_23 | 101 | 2021 | 176 | 531 | 573 | 1.7e-55 |

| Protein name | | | | Locus Name | | Acc# |
|---|---|---|---|---|---|---|
| | | | | sp:YEIG_ECOLI | | P33018 |

Description

HYPOTHETICAL 31.3 KD PROTEIN IN FOLE-CIRA INTERGENIC REGION

| ORF Name | NTID | AAID | NT Length | AA Length | Score | Probability |
|---|---|---|---|---|---|---|
| 1048137_c3_65 | 102 | 2022 | 67 | 204 | | |

| Protein name | | | | Locus Name | | Acc# |
|---|---|---|---|---|---|---|

Description

NO-HIT

| ORF Name | NTID | AAID | NT Length | AA Length | Score | Probability |
|---|---|---|---|---|---|---|
| 10585925_f1_2 | 103 | 2023 | 73 | 222 | | |

| Protein name | | | | Locus Name | | Acc# |
|---|---|---|---|---|---|---|

Description

NO-HIT

| ORF Name | NTID | AAID | NT Length | AA Length | Score | Probability |
|---|---|---|---|---|---|---|
| 14885910_c2_51 | 104 | 2024 | 86 | 258 | 71 | 0.026 |

| Protein name | | | | Locus Name | | Acc# |
|---|---|---|---|---|---|---|
| PagK | | | | gp:AF013775 | | AF013775 |

Description

Salmonella typhimurium PagK (pagK), PagM (pagM), and PagO (pagO) genes, complete cds.

| ORF Name | NTID | AAID | NT Length | AA Length | Score | Probability |
|---|---|---|---|---|---|---|
| 22554587_c3_57 | 105 | 2025 | 159 | 480 | 480 | 1.2e-45 |

| Protein name | Locus Name | Acc# |
|---|---|---|
| | sp:SMPB_ECOLI | |

Description

SMALL PROTEIN B (18.3 KD PROTEIN)

| ORF Name | NTID | AAID | NT Length | AA Length | Score | Probability |
|---|---|---|---|---|---|---|
| 23437838_f3_28 | 106 | 2026 | 725 | 2178 | 1684 | 3.1e-173 |

| Protein name | Locus Name | Acc# |
|---|---|---|
| | sp:DNLJ_HAEIN | P43813 |

Description

)

| ORF Name | NTID | AAID | NT Length | AA Length | Score | Probability |
|---|---|---|---|---|---|---|
| 23468813_f3_22 | 107 | 2027 | 309 | 930 | 294 | 6.2e-26 |

| Protein name | Locus Name | Acc# |
|---|---|---|
| putative permease BitE | gp:SHU75349 | U75349 |

Description

Serpulina hyodysenteriae bit operon, complete sequence.

| ORF Name | NTID | AAID | NT Length | AA Length | Score | Probability |
|---|---|---|---|---|---|---|
| 234807_f1_11 | 108 | 2028 | 175 | 528 | 456 | 4.2e-43 |

| Protein name | Locus Name | Acc# |
|---|---|---|
| lipopolysaccharide core biosynthesis protein kdtB homolog | pir:S72166 | S72166 |

Description

| ORF Name | NTID | AAID | NT Length | AA Length | Score | Probability |
|---|---|---|---|---|---|---|
| 23705040_f2_16 | 109 | 2029 | 360 | 1083 | 670 | 8.8e-66 |

| Protein name | Locus Name | Acc# |
|---|---|---|
| | sp:POTA_HAEIN | P45171 |

Description

SPERMIDINE/PUTRESCINE TRANSPORT ATP-BINDING PROTEIN POTA

| ORF Name | NTID | AAID | NT Length | AA Length | Score | Probability |
|---|---|---|---|---|---|---|
| 23726687_f2_17 | 110 | 2030 | 335 | 1008 | 745 | 9.9e-74 |

Protein name: conserved hypothetical protein yddN
Locus Name: pir:F69776
Acc#: F69776

Description

| ORF Name | NTID | AAID | NT Length | AA Length | Score | Probability |
|---|---|---|---|---|---|---|
| 23884387_c1_37 | 111 | 2031 | 219 | 660 | | |

Protein name
Locus Name
Acc#

Description

NO-HIT

| ORF Name | NTID | AAID | NT Length | AA Length | Score | Probability |
|---|---|---|---|---|---|---|
| 24252305_f2_19 | 112 | 2032 | 298 | 897 | 155 | 8.2e-09 |

Protein name
Locus Name: sp:YDFC_BACSU
Acc#: P96680

Description

HYPOTHETICAL 33.6 KD PROTEIN IN CSPC-NAP INTERGENIC REGION

| ORF Name | NTID | AAID | NT Length | AA Length | Score | Probability |
|---|---|---|---|---|---|---|
| 24797312_f1_4 | 113 | 2033 | 275 | 828 | 132 | 5.0e-06 |

Protein name: hypothetical protein PH1114
Locus Name: pir:C71052
Acc#: C71052

Description

| ORF Name | NTID | AAID | NT Length | AA Length | Score | Probability |
|---|---|---|---|---|---|---|
| 25901467_c3_54 | 114 | 2034 | 88 | 267 | | |

Protein name
Locus Name
Acc#

Description

NO-HIT

| ORF Name | NTID | AAID | NT Length | AA Length | Score | Probability |
|---|---|---|---|---|---|---|
| 30272051_f3_24 | 115 | 2035 | 248 | 747 | 169 | 2.2e-11 |

| Protein name | Locus Name | Acc# |
|---|---|---|
| probable morphological differentiation-associated protein | pir:T36679 | T36679 |

Description

| ORF Name | NTID | AAID | NT Length | AA Length | Score | Probability |
|---|---|---|---|---|---|---|
| 3323802_f3_23 | 116 | 2036 | 286 | 861 | 232 | 2.3e-19 |

| Protein name | Locus Name | Acc# |
|---|---|---|
| permease protein | gp:CJAJ750 | AJ000750 |

Description

Campylobacter jejuni malF gene, partial.

| ORF Name | NTID | AAID | NT Length | AA Length | Score | Probability |
|---|---|---|---|---|---|---|
| 35976510_f3_30 | 117 | 2037 | 89 | 270 | 343 | 4.0e-31 |

| Protein name | Locus Name | Acc# |
|---|---|---|
|  | pir:FEKRV |  |

Description

| ORF Name | NTID | AAID | NT Length | AA Length | Score | Probability |
|---|---|---|---|---|---|---|
| 36383542_f1_13 | 118 | 2038 | 107 | 321 | 96 | 5.9e-05 |

| Protein name | Locus Name | Acc# |
|---|---|---|
| KH type splicing regulatory protein | gp:HSKHSRP3 | AF093747 |

Description

Homo sapiens KH type splicing regulatory protein (KHSRP) gene, exon2 and partial cds.

| ORF Name | NTID | AAID | NT Length | AA Length | Score | Probability |
|---|---|---|---|---|---|---|
| 3923288_c1_39 | 119 | 2039 | 343 | 1032 | 254 | 1.1e-21 |

| Protein name | Locus Name | Acc# |
|---|---|---|
| probable regulatory protein (pfoS/R) | pir:E71373 | E71373 |

Description

| ORF Name | NTID | AAID | NT Length | AA Length | Score | Probability |
|---|---|---|---|---|---|---|
| 3938393_c3_64 | 120 | 2040 | 218 | 657 | 726 | 1.0e-71 |
| Protein name | | | | Locus Name | | Acc# |
| uracil phosphoribosyltransferase, upp | | | | pir:A65026 | | |

Description

| ORF Name | NTID | AAID | NT Length | AA Length | Score | Probability |
|---|---|---|---|---|---|---|
| 4064638_f1_3 | 121 | 2041 | 371 | 1116 | 152 | 4.7e-08 |
| Protein name | | | | Locus Name | | Acc# |
| | | | | sp:Y131_HAEIN | | P43951 |

Description

HYPOTHETICAL PROTEIN HI0131 PRECURSOR

| ORF Name | NTID | AAID | NT Length | AA Length | Score | Probability |
|---|---|---|---|---|---|---|
| 4101568_f3_29 | 122 | 2042 | 263 | 792 | 512 | 4.9e-49 |
| Protein name | | | | Locus Name | | Acc# |
| | | | | sp:FRP_VIBHA | | Q56691 |

Description (NADPH-FMN OXIDOREDUCTASE)

| ORF Name | NTID | AAID | NT Length | AA Length | Score | Probability |
|---|---|---|---|---|---|---|
| 682641_c1_33 | 123 | 2043 | 86 | 261 | 100 | 2.2e-05 |
| Protein name | | | | Locus Name | | Acc# |
| hypothetical protein PH0217 | | | | pir:G71244 | | G71244 |

Description

| ORF Name | NTID | AAID | NT Length | AA Length | Score | Probability |
|---|---|---|---|---|---|---|
| 10790_f3_68 | 124 | 2044 | 731 | 2196 | 594 | 9.0e-86 |
| Protein name | | | | Locus Name | | Acc# |
| | | | | sp:PRIM_HAEIN | | Q08346 |

Description

DNA PRIMASE,

| ORF Name | NTID | AAID | NT Length | AA Length | Score | Probability |
|---|---|---|---|---|---|---|
| 119012_c3_118 | 125 | 2045 | 438 | 1317 | 1830 | 1.1e-188 |

| Protein name | | | | Locus Name | | Acc# |
|---|---|---|---|---|---|---|
| | | | | sp:YJCD_HAEIN | | P44530 |

Description

HYPOTHETICAL PROTEIN HI0125

| ORF Name | NTID | AAID | NT Length | AA Length | Score | Probability |
|---|---|---|---|---|---|---|
| 12214386_c3_117 | 126 | 2046 | 125 | 378 | | |

| Protein name | | | | Locus Name | | Acc# |
|---|---|---|---|---|---|---|

Description

NO-HIT

| ORF Name | NTID | AAID | NT Length | AA Length | Score | Probability |
|---|---|---|---|---|---|---|
| 12540957_c3_121 | 127 | 2047 | 280 | 843 | 227 | 7.7e-19 |

| Protein name | | | | Locus Name | | Acc# |
|---|---|---|---|---|---|---|
| probable yfiH protein | | | | pir:A70579 | | A70579 |

Description

| ORF Name | NTID | AAID | NT Length | AA Length | Score | Probability |
|---|---|---|---|---|---|---|
| 12593961_f2_35 | 128 | 2048 | 68 | 207 | | |

| Protein name | | | | Locus Name | | Acc# |
|---|---|---|---|---|---|---|

Description

NO-HIT

| ORF Name | NTID | AAID | NT Length | AA Length | Score | Probability |
|---|---|---|---|---|---|---|
| 19532813_f3_73 | 129 | 2049 | 134 | 405 | 252 | 1.7e-21 |

| Protein name | | | | Locus Name | | Acc# |
|---|---|---|---|---|---|---|
| RpsT protein | | | | gp:VCNHAR | | AJ002395 |

Description

Vibrio cholerae nhaR, hlyU, mviN, and rpsT genes.

| ORF Name | NTID | AAID | NT Length | AA Length | Score | Probability |
|---|---|---|---|---|---|---|
| 209375_c1_95 | 130 | 2050 | 750 | 2250 | 1867 | 1.3e-192 |

Protein name | Locus Name | Acc#
sp:CLPA_ECOLI

Description
ATP-DEPENDENT CLP PROTEASE ATP-BINDING SUBUNIT CLPA

| ORF Name | NTID | AAID | NT Length | AA Length | Score | Probability |
|---|---|---|---|---|---|---|
| 21641077_f2_49 | 131 | 2051 | 199 | 600 | 132 | 4.3e-08 |

Protein name | Locus Name | Acc#
hypothetical protein | gp:SYCSLLE

Description
Synechocystis sp. PCC6803 complete genome, 22/27, 2755703-2868766.

| ORF Name | NTID | AAID | NT Length | AA Length | Score | Probability |
|---|---|---|---|---|---|---|
| 22143827_c1_89 | 132 | 2052 | 250 | 753 | 246 | 7.5e-21 |

Protein name | Locus Name | Acc#
 | sp:YIV8_YEAST | P40582

Description
HYPOTHETICAL 26.8 KD PROTEIN IN HYR1 3'REGION

| ORF Name | NTID | AAID | NT Length | AA Length | Score | Probability |
|---|---|---|---|---|---|---|
| 22453453_c2_104 | 133 | 2053 | 426 | 1281 | 492 | 6.4e-47 |

Protein name | Locus Name | Acc#
carboxyl-terminal proteinase | pir:F70369 | F70369

Description

| ORF Name | NTID | AAID | NT Length | AA Length | Score | Probability |
|---|---|---|---|---|---|---|
| 22831262_c1_94 | 134 | 2054 | 128 | 387 | 185 | 2.2e-14 |

Protein name | Locus Name | Acc#
 | sp:YLJA_ECOLI | P75832

Description
12.2 KD PROTEIN IN CSPD-CLPA INTERGENIC REGION

| ORF Name | NTID | AAID | NT Length | AA Length | Score | Probability |
|---|---|---|---|---|---|---|
| 23632215_f2_59 | 135 | 2055 | 64 | 195 | | |
| Protein name | | | | Locus Name | | Acc# |
| | | | | | | |

Description

NO-HIT

| ORF Name | NTID | AAID | NT Length | AA Length | Score | Probability |
|---|---|---|---|---|---|---|
| 23645875_c1_84 | 136 | 2056 | 605 | 1818 | 723 | 2.1e-71 |
| Protein name | | | | Locus Name | | Acc# |
| | | | | sp:CYDD_ECOLI | | |

Description

TRANSPORT ATP-BINDING PROTEIN CYDD

| ORF Name | NTID | AAID | NT Length | AA Length | Score | Probability |
|---|---|---|---|---|---|---|
| 23875303_c2_109 | 137 | 2057 | 72 | 219 | | |
| Protein name | | | | Locus Name | | Acc# |

Description

NO-HIT

| ORF Name | NTID | AAID | NT Length | AA Length | Score | Probability |
|---|---|---|---|---|---|---|
| 24236642_c1_91 | 138 | 2058 | 350 | 1053 | 695 | 2.0e-68 |
| Protein name | | | | Locus Name | | Acc# |
| | | | | sp:RLUD_ECOLI | | |

Description (PSEUDOURIDYLATE SYNTHASE) (URACIL HYDROLYASE)

| ORF Name | NTID | AAID | NT Length | AA Length | Score | Probability |
|---|---|---|---|---|---|---|
| 24317757_f3_67 | 139 | 2059 | 368 | 1107 | 352 | 4.4e-32 |
| Protein name | | | | Locus Name | | Acc# |
| | | | | sp:YPIY_PSEAE | | P33641 |

Description

HYPOTHETICAL 38.5 KD LIPOPROTEIN IN PILS 5'REGION PRECURSOR (ORFY)

| ORF Name | NTID | AAID | NT Length | AA Length | Score | Probability |
|---|---|---|---|---|---|---|
| 24318805_f2_60 | 140 | 2060 | 205 | 618 | 229 | 4.8e-19 |

| Protein name | Locus Name | Acc# |
|---|---|---|
| hypothetical protein | gp:ASA224767 | AJ224767 |

Description

Acinetobacter sp. ADP1 lon gene and ORFs.

| ORF Name | NTID | AAID | NT Length | AA Length | Score | Probability |
|---|---|---|---|---|---|---|
| 24417012_f2_52 | 141 | 2061 | 232 | 699 | 101 | 0.011 |

| Protein name | Locus Name | Acc# |
|---|---|---|
| LpsB | gp:AF193023 | AF193023 |

Description

Sinorhizobium meliloti GreA (greA), LpsB (lpsB), LpsE (lpsE), LpsD(lpsD), LpsC (lpsC), and Lrp (lrp) genes, complete cds.

| ORF Name | NTID | AAID | NT Length | AA Length | Score | Probability |
|---|---|---|---|---|---|---|
| 24650062_c3_119 | 142 | 2062 | 234 | 705 | 148 | 3.1e-09 |

| Protein name | Locus Name | Acc# |
|---|---|---|
| hypothetical protein C33F10.3 | pir:T15745 | T15745 |

Description

| ORF Name | NTID | AAID | NT Length | AA Length | Score | Probability |
|---|---|---|---|---|---|---|
| 2468950_c3_123 | 143 | 2063 | 67 | 204 | 123 | 1.4e-06 |

| Protein name | Locus Name | Acc# |
|---|---|---|
|  | sp:COPA_HELFE | O32619 |

Description

COPPER-TRANSPORTING ATPASE,

| ORF Name | NTID | AAID | NT Length | AA Length | Score | Probability |
|---|---|---|---|---|---|---|
| 25391941_c2_116 | 144 | 2064 | 298 | 897 |  |  |

| Protein name | Locus Name | Acc# |
|---|---|---|

Description

NO-HIT

| ORF_Name | NTID | AAID | NT Length | AA Length | Score | Probability |
|---|---|---|---|---|---|---|
| 261635_f1_16 | 145 | 2065 | 217 | 654 | 603 | 1.1e-58 |

| Protein name | Locus_Name | Acc# |
|---|---|---|
| response regulator GacA | gp:AF115381 | AF115381 |

Description

Pseudomonas aureofaciens 30-84 response regulator GacA (gacA) gene, complete cds.

| ORF_Name | NTID | AAID | NT Length | AA Length | Score | Probability |
|---|---|---|---|---|---|---|
| 31431512_f1_22 | 146 | 2066 | 182 | 549 | 295 | 4.8e-26 |

| Protein name | Locus_Name | Acc# |
|---|---|---|
| bacterioferritin comigratory protein | pir:F71971 | F71971 |

Description

| ORF_Name | NTID | AAID | NT Length | AA Length | Score | Probability |
|---|---|---|---|---|---|---|
| 31832188_c2_114 | 147 | 2067 | 440 | 1323 | 1025 | 2.1e-103 |

| Protein name | Locus_Name | Acc# |
|---|---|---|
|  | sp:Y290_HAEIN | P77868 |

Description

PROBABLE CATION-TRANSPORTING ATPASE HI0290,

| ORF_Name | NTID | AAID | NT Length | AA Length | Score | Probability |
|---|---|---|---|---|---|---|
| 33845302_c2_115 | 148 | 2068 | 288 | 867 | 653 | 5.6e-64 |

| Protein name | Locus_Name | Acc# |
|---|---|---|
|  | sp:Y290_HAEIN | P77868 |

Description

PROBABLE CATION-TRANSPORTING ATPASE HI0290,

| ORF_Name | NTID | AAID | NT Length | AA Length | Score | Probability |
|---|---|---|---|---|---|---|
| 35974750_f2_38 | 149 | 2069 | 261 | 786 | 603 | 1.1e-58 |

| Protein name | Locus_Name | Acc# |
|---|---|---|
|  | sp:YBGI_HAEIN |  |

Description

HYPOTHETICAL PROTEIN HI0105

| ORF Name | NTID | AAID | NT Length | AA Length | Score | Probability |
|---|---|---|---|---|---|---|
| 4806512_c2_96 | 150 | 2070 | 463 | 1392 | 1501 | 7.7e-154 |

| Protein name | Locus Name | Acc# |
|---|---|---|
| hypothetical protein 7 | pir:T00129 | T00129 |

Description

| ORF Name | NTID | AAID | NT Length | AA Length | Score | Probability |
|---|---|---|---|---|---|---|
| 5109843_c2_99 | 151 | 2071 | 579 | 1740 | 291 | 4.3e-45 |

| Protein name | Locus Name | Acc# |
|---|---|---|
|  | sp:CYDC_ECOLI | P23886 |

Description

TRANSPORT ATP-BINDING PROTEIN CYDC

| ORF Name | NTID | AAID | NT Length | AA Length | Score | Probability |
|---|---|---|---|---|---|---|
| 6718_c2_103 | 152 | 2072 | 531 | 1596 | 1457 | 3.5e-149 |

| Protein name | Locus Name | Acc# |
|---|---|---|
|  | sp:PMGI_ECOLI | P37689 |

Description (EC 5.4.2.1) (PHOSPHOGLYCEROMUTASE) (BPG-INDEPENDENT PGAM)

| ORF Name | NTID | AAID | NT Length | AA Length | Score | Probability |
|---|---|---|---|---|---|---|
| 6837753_f1_23 | 153 | 2073 | 224 | 675 | 147 | 3.2e-08 |

| Protein name | Locus Name | Acc# |
|---|---|---|
| capm protein (capM1) RP344 | pir:B71691 | B71691 |

Description

| ORF Name | NTID | AAID | NT Length | AA Length | Score | Probability |
|---|---|---|---|---|---|---|
| 789811_c1_88 | 154 | 2074 | 892 | 2679 | 2203 | 2.3e-256 |

| Protein name | Locus Name | Acc# |
|---|---|---|
|  | sp:GYRA_ECOLI | P09097 |

Description

DNA GYRASE SUBUNIT A,

| ORF Name | NTID | AAID | NT Length | AA Length | Score | Probability |
|---|---|---|---|---|---|---|
| 986638_c3_5 | 155 | 2075 | 262 | 789 | 1149 | 1.5e-116 |

Protein name: multidrug transporter homolog
Locus Name: pir:G69005
Acc#: G69005

Description

| ORF Name | NTID | AAID | NT Length | AA Length | Score | Probability |
|---|---|---|---|---|---|---|
| 12985037_c2_42 | 156 | 2076 | 158 | 477 | 354 | 1.9e-31 |

Protein name:
Locus Name: sp:PILQ_PSEAE
Acc#: P34750

Description: FIMBRIAL ASSEMBLY PROTEIN PILQ PRECURSOR

| ORF Name | NTID | AAID | NT Length | AA Length | Score | Probability |
|---|---|---|---|---|---|---|
| 14301467_c3_49 | 157 | 2077 | 231 | 696 | 316 | 2.9e-28 |

Protein name: carbonic anhydrase
Locus Name: pir:D75298
Acc#: D75298

Description

| ORF Name | NTID | AAID | NT Length | AA Length | Score | Probability |
|---|---|---|---|---|---|---|
| 1557_c1_31 | 158 | 2078 | 501 | 1506 | 1393 | 2.1e-142 |

Protein name:
Locus Name: sp:YLEA_HAEIN
Acc#: Q57163

Description: HYPOTHETICAL PROTEIN HI0019

| ORF Name | NTID | AAID | NT Length | AA Length | Score | Probability |
|---|---|---|---|---|---|---|
| 19615687_f1_6 | 159 | 2079 | 87 | 264 | | |

Protein name:
Locus Name:
Acc#:

Description: NO-HIT

| ORF Name | NTID | AAID | NT Length | AA Length | Score | Probability |
|---|---|---|---|---|---|---|
| 23445308_f2_18 | 160 | 2080 | 224 | 672 | | |

Protein name | | | | Locus Name | | Acc#

Description

NO-HIT

| ORF Name | NTID | AAID | NT Length | AA Length | Score | Probability |
|---|---|---|---|---|---|---|
| 23859562_c1_32 | 161 | 2081 | 233 | 702 | 140 | 1.7e-09 |

Protein name: pilus expression protein | Locus Name: gp:PSEPONA | Acc#: L28837

Description

Pseudomonas syringae penicillin binding protein (ponA), membraneproteins (pilN, pilO), pilus expression proteins (pilM, pilP) genes, complete cds and pilus expression protein (pilQ) gene, partial cds.

| ORF Name | NTID | AAID | NT Length | AA Length | Score | Probability |
|---|---|---|---|---|---|---|
| 24040911_c1_33 | 162 | 2082 | 327 | 984 | 220 | 6.3e-30 |

Protein name | | | | Locus Name: sp:PILQ_PSEAE | | Acc#: P34750

Description

FIMBRIAL ASSEMBLY PROTEIN PILQ PRECURSOR

| ORF Name | NTID | AAID | NT Length | AA Length | Score | Probability |
|---|---|---|---|---|---|---|
| 34510950_c2_39 | 163 | 2083 | 645 | 1938 | 201 | 4.9e-15 |

Protein name: membrane protein | Locus Name: gp:PSEPONA | Acc#: L28837

Description

Pseudomonas syringae penicillin binding protein (ponA), membraneproteins (pilN, pilO), pilus expression proteins (pilM, pilP) genes, complete cds and pilus expression protein (pilQ) gene, partial cds.

| ORF_Name | NTID | AAID | NT Length | AA Length | Score | Probability |
|---|---|---|---|---|---|---|
| 34589061_c1_36 | 164 | 2084 | 183 | 552 | 365 | 1.8e-33 |

Protein name: lactoylglutathione lyase,:glyoxalase I
Locus Name: pir:A46714
Acc#:

Description

| ORF_Name | NTID | AAID | NT Length | AA Length | Score | Probability |
|---|---|---|---|---|---|---|
| 4304693_c1_34 | 165 | 2085 | 375 | 1128 | 883 | 2.4e-88 |

Protein name:
Locus Name: sp:AROB_NEIGO
Acc#: O50468

Description: 3-DEHYDROQUINATE SYNTHASE,

| ORF_Name | NTID | AAID | NT Length | AA Length | Score | Probability |
|---|---|---|---|---|---|---|
| 4877328_c1_35 | 166 | 2086 | 318 | 957 | | |

Protein name:
Locus Name:
Acc#:

Description: NO-HIT

| ORF_Name | NTID | AAID | NT Length | AA Length | Score | Probability |
|---|---|---|---|---|---|---|
| 7042153_c2_43 | 167 | 2087 | 231 | 696 | 452 | 1.1e-42 |

Protein name:
Locus Name: sp:AROK_HAEIN
Acc#: P43880

Description: SHIKIMATE KINASE, (SK)

| ORF_Name | NTID | AAID | NT Length | AA Length | Score | Probability |
|---|---|---|---|---|---|---|
| 7083457_c3_46 | 168 | 2088 | 216 | 651 | 154 | 4.2e-11 |

Protein name: fimbrial assembly protein pilO
Locus Name: pir:S77728
Acc#: S77728

Description

| ORF Name | NTID | AAID | NT Length | AA Length | Score | Probability |
|---|---|---|---|---|---|---|
| 23703142_c1_3 | 169 | 2089 | 300 | 900 | 635 | 4.5e-62 |

| Protein name | | | | Locus Name | | Acc# |
|---|---|---|---|---|---|---|
| | | | | sp:YJEK_ECOLI | | P39280 |

Description

HYPOTHETICAL 38.7 KD PROTEIN IN MOPA-EFP INTERGENIC REGION

| ORF Name | NTID | AAID | NT Length | AA Length | Score | Probability |
|---|---|---|---|---|---|---|
| 34119052_f1_1 | 170 | 2090 | 204 | 612 | 663 | 4.9e-65 |

| Protein name | | | | Locus Name | | Acc# |
|---|---|---|---|---|---|---|
| translation elongation factor EF-P | | | | pir:S34443 | | |

Description

| ORF Name | NTID | AAID | NT Length | AA Length | Score | Probability |
|---|---|---|---|---|---|---|
| 32712915_c2_17 | 171 | 2091 | 77 | 234 | | |

| Protein name | | | | Locus Name | | Acc# |
|---|---|---|---|---|---|---|

Description

NO-HIT

| ORF Name | NTID | AAID | NT Length | AA Length | Score | Probability |
|---|---|---|---|---|---|---|
| 33984701_f3_10 | 172 | 2092 | 579 | 1740 | 1233 | 1.9e-125 |

| Protein name | | | | Locus Name | | Acc# |
|---|---|---|---|---|---|---|
| | | | | sp:PMSR_NEIGO | | P14930 |

Description

PEPTIDE METHIONINE SULFOXIDE REDUCTASE (PEPTIDE MET(O) REDUCTASE)

| ORF Name | NTID | AAID | NT Length | AA Length | Score | Probability |
|---|---|---|---|---|---|---|
| 36131500_c3_21 | 173 | 2093 | 308 | 927 | 655 | 3.4e-64 |

| Protein name | | | | Locus Name | | Acc# |
|---|---|---|---|---|---|---|
| | | | | sp:HTPX_ECOLI | | P23894 |

Description

PROBABLE PROTEASE HTPX, (HEAT SHOCK PROTEIN HTPX)

| ORF_Name | NTID | AAID | NT Length | AA Length | Score | Probability |
|---|---|---|---|---|---|---|
| 3907578_c1_15 | 174 | 2094 | 299 | 900 | 572 | 2.1e-55 |

| Protein name | | | | Locus Name | | Acc# |
|---|---|---|---|---|---|---|
| | | | | sp:DHPS_ECOLI | | |

Description

PYROPHOSPHORYLASE)

| ORF_Name | NTID | AAID | NT Length | AA Length | Score | Probability |
|---|---|---|---|---|---|---|
| 4100312_f3_13 | 175 | 2095 | 106 | 321 | | |

| Protein name | | | | Locus Name | | Acc# |
|---|---|---|---|---|---|---|

Description

NO-HIT

| ORF_Name | NTID | AAID | NT Length | AA Length | Score | Probability |
|---|---|---|---|---|---|---|
| 48828062_c2_16 | 176 | 2096 | 115 | 348 | 223 | 1.2e-16 |

| Protein name | | | | Locus Name | | Acc# |
|---|---|---|---|---|---|---|
| probable transglycosylase | | | | pir:T12796 | | |

Description

| ORF_Name | NTID | AAID | NT Length | AA Length | Score | Probability |
|---|---|---|---|---|---|---|
| 831318_f2_7 | 177 | 2097 | 472 | 1419 | 1225 | 1.4e-124 |

| Protein name | | | | Locus Name | | Acc# |
|---|---|---|---|---|---|---|
| | | | | sp:HFLX_ECOLI | | P25519 |

Description

GTP-BINDING PROTEIN HFLX

| ORF_Name | NTID | AAID | NT Length | AA Length | Score | Probability |
|---|---|---|---|---|---|---|
| 870250_f2_6 | 178 | 2098 | 255 | 768 | 394 | 1.6e-36 |

| Protein name | | | | Locus Name | | Acc# |
|---|---|---|---|---|---|---|
| hypothetical protein in endA-gshB intergenic region | | | | pir:A65080 | | A65080 |

Description

115

| ORF Name | NTID | AAID | NT Length | AA Length | Score | Probability |
|---|---|---|---|---|---|---|
| 10548386_f2_19 | 179 | 2099 | 647 | 1944 | | |

Protein name | Locus Name | Acc#

Description

NO-HIT

| ORF Name | NTID | AAID | NT Length | AA Length | Score | Probability |
|---|---|---|---|---|---|---|
| 10626558_c2_94 | 180 | 2100 | 182 | 549 | 73 | 0.039 |

Protein name | Locus Name | Acc#
| | sp:TEGP_HSV11 | P06481

Description

TEGUMENT PHOSPHOPROTEIN US9 (10 KD PROTEIN)

| ORF Name | NTID | AAID | NT Length | AA Length | Score | Probability |
|---|---|---|---|---|---|---|
| 1178127_f1_10 | 181 | 2101 | 445 | 1338 | 1319 | 1.5e-134 |

Protein name | Locus Name | Acc#
| | sp:SYS_HAEIN | P43833

Description

SERYL-TRNA SYNTHETASE, (SERINE--TRNA LIGASE) (SERRS)

| ORF Name | NTID | AAID | NT Length | AA Length | Score | Probability |
|---|---|---|---|---|---|---|
| 12109686_c1_63 | 182 | 2102 | 66 | 201 | | |

Protein name | Locus Name | Acc#

Description

NO-HIT

| ORF Name | NTID | AAID | NT Length | AA Length | Score | Probability |
|---|---|---|---|---|---|---|
| 12892086_f2_26 | 183 | 2103 | 81 | 246 | | |

Protein name | Locus Name | Acc#

Description

NO-HIT

| ORF Name | NTID | AAID | NT Length | AA Length | Score | Probability |
|---|---|---|---|---|---|---|
| 1369428_c2_97 | 184 | 2104 | 78 | 237 | | |

Protein name | Locus Name | Acc#

Description

NO-HIT

| ORF Name | NTID | AAID | NT Length | AA Length | Score | Probability |
|---|---|---|---|---|---|---|
| 13710925_f3_46 | 185 | 2105 | 148 | 447 | 652 | 7.1e-64 |

Protein name | Locus Name: sp:MT1C_MORBO | Acc# P34721

Description

METHYLTRANSFERASE MBOI C) (M.MBOI C)

| ORF Name | NTID | AAID | NT Length | AA Length | Score | Probability |
|---|---|---|---|---|---|---|
| 1412642_c1_65 | 186 | 2106 | 147 | 444 | 88 | 0.00042 |

Protein name | Locus Name: sp:YRKI_BACSU | Acc# P54436

Description

HYPOTHETICAL 8.2 KD PROTEIN IN BLTR-SPOIIIC INTERGENIC REGION

| ORF Name | NTID | AAID | NT Length | AA Length | Score | Probability |
|---|---|---|---|---|---|---|
| 14250312_c2_100 | 187 | 2107 | 246 | 741 | | |

Protein name | Locus Name | Acc#

Description

NO-HIT

| ORF Name | NTID | AAID | NT Length | AA Length | Score | Probability |
|---|---|---|---|---|---|---|
| 1433466_c2_111 | 188 | 2108 | 85 | 258 | 141 | 9.6e-09 |

Protein name | Locus Name: sp:MVIN_ECOLI | Acc# P75932

Description

VIRULENCE FACTOR MVIN HOMOLOG

| ORF Name | NTID | AAID | NT Length | AA Length | Score | Probability |
|---|---|---|---|---|---|---|
| 14875390_f3_51 | 189 | 2109 | 134 | 405 | 302 | 1.0e-26 |

Protein name | | | | Locus Name | Acc# |
| | | | sp:YAEL_ECOLI | P37764 |

Description

HYPOTHETICAL 49.1 KD PROTEIN IN CDSA-HLPA INTERGENIC REGION

| ORF Name | NTID | AAID | NT Length | AA Length | Score | Probability |
|---|---|---|---|---|---|---|
| 15020887_c1_83 | 190 | 2110 | 189 | 570 | | |

Protein name | | | | Locus Name | Acc# |

Description

NO-HIT

| ORF Name | NTID | AAID | NT Length | AA Length | Score | Probability |
|---|---|---|---|---|---|---|
| 15885450_c3_142 | 191 | 2111 | 342 | 1029 | 624 | 6.6e-61 |

Protein name | | | | Locus Name | Acc# |
| | | | sp:MVIN_HAEIN | P44958 |

Description

VIRULENCE FACTOR MVIN HOMOLOG

| ORF Name | NTID | AAID | NT Length | AA Length | Score | Probability |
|---|---|---|---|---|---|---|
| 166043_f1_8 | 192 | 2112 | 259 | 780 | 416 | 7.3e-39 |

Protein name | | | | Locus Name | Acc# |
cytochrome c maturation protein B | | | | gp:AF044582 | AF044582 |

Description

Shewanella putrefaciens NrfG homolog gene, partial cds; andmono-heme c-type cytochrome ScyA (scyA), cytochrome c maturationprotein A (ccmA), cytochrome c maturation protein B (ccmB),cytochrome c maturation protein C (ccmC), cytochrome c maturationprotein D (ccmD), and cytochrome c maturation protein E (ccmE)genes, complete cds.

| ORF_Name | NTID | AAID | NT Length | AA Length | Score | Probability |
|---|---|---|---|---|---|---|
| 17069628_f1_4 | 193 | 2113 | 116 | 351 | | |

Protein name | | | | Locus_Name | | Acc#

Description

NO-HIT

| ORF_Name | NTID | AAID | NT Length | AA Length | Score | Probability |
|---|---|---|---|---|---|---|
| 187703_f2_21 | 194 | 2114 | 113 | 342 | 90 | 0.00026 |

Protein name | | | | Locus_Name | | Acc#
| | | | | sp:Y4AR_RHISN | | P55365

Description

HYPOTHETICAL 12.1 KD PROTEIN Y4AR

| ORF_Name | NTID | AAID | NT Length | AA Length | Score | Probability |
|---|---|---|---|---|---|---|
| 22462757_c1_67 | 195 | 2115 | 67 | 204 | 89 | 0.00033 |

Protein name | | | | Locus_Name | | Acc#
hypothetical protein SC6E10.02 | | | | pir:T35489 | | T35489

Description

| ORF_Name | NTID | AAID | NT Length | AA Length | Score | Probability |
|---|---|---|---|---|---|---|
| 23470003_c1_81 | 196 | 2116 | 155 | 468 | 346 | 2.3e-31 |

Protein name | | | | Locus_Name | | Acc#
| | | | | sp:MVIN_ECOLI | | P75932

Description

VIRULENCE FACTOR MVIN HOMOLOG

| ORF_Name | NTID | AAID | NT Length | AA Length | Score | Probability |
|---|---|---|---|---|---|---|
| 23914017_c2_104 | 197 | 2117 | 88 | 267 | 134 | 5.5e-09 |

Protein name | | | | Locus_Name | | Acc#
hypothetical protein ydaT | | | | pir:C69770 | | C69770

Description

| ORF Name | NTID | AAID | NT Length | AA Length | Score | Probability |
|---|---|---|---|---|---|---|
| 24219792_f2_34 | 198 | 2118 | 296 | 891 | 440 | 2.1e-41 |

| Protein name | | | | Locus Name | | Acc# |
|---|---|---|---|---|---|---|
| | | | | sp:CDSA_PSEAE | | Q59640 |

Description

SYNTHASE)

| ORF Name | NTID | AAID | NT Length | AA Length | Score | Probability |
|---|---|---|---|---|---|---|
| 24244033_c1_70 | 199 | 2119 | 302 | 909 | 620 | 1.8e-60 |

| Protein name | | | | Locus Name | | Acc# |
|---|---|---|---|---|---|---|
| | | | | sp:YGLA_SYNP2 | | P28606 |

Description

HYPOTHETICAL 34.1 KD PROTEIN IN GLNA 3'REGION

| ORF Name | NTID | AAID | NT Length | AA Length | Score | Probability |
|---|---|---|---|---|---|---|
| 24252302_c2_106 | 200 | 2120 | 493 | 1482 | 1229 | 5.1e-125 |

| Protein name | | | | Locus Name | | Acc# |
|---|---|---|---|---|---|---|
| 2-oxoglutarate/malate translocator homolog yfIS | | | | pir:F69811 | | F69811 |

Description

| ORF Name | NTID | AAID | NT Length | AA Length | Score | Probability |
|---|---|---|---|---|---|---|
| 24330005_c3_122 | 201 | 2121 | 314 | 945 | 413 | 1.5e-38 |

| Protein name | | | | Locus Name | | Acc# |
|---|---|---|---|---|---|---|
| | | | | gp:AB017194 | | AB017194 |

Description

Plectonema boryanum ORF270, proline iminopeptidase, ferredoxin andamidase enhancer genes, complete and partial cds.

| ORF_Name | NTID | AAID | NT Length | AA Length | Score | Probability |
|---|---|---|---|---|---|---|
| 24650962_f3_45 | 202 | 2122 | 261 | 786 | 806 | 3.4e-80 |

| Protein name | | Locus Name | Acc# |
|---|---|---|---|
| | | sp:T2D1_STRPN | P09356 |

Description (R.DPNI)

| ORF_Name | NTID | AAID | NT Length | AA Length | Score | Probability |
|---|---|---|---|---|---|---|
| 24735875_f2_16 | 203 | 2123 | 73 | 222 | 54 | 0.017 |

| Protein name | | Locus Name | Acc# |
|---|---|---|---|
| | | sp:YMT0_YEAST | Q04210 |

Description

HYPOTHETICAL 19.2 KD PROTEIN IN SUB1-ARGR1 INTERGENIC REGION

| ORF_Name | NTID | AAID | NT Length | AA Length | Score | Probability |
|---|---|---|---|---|---|---|
| 25391007_c2_110 | 204 | 2124 | 216 | 651 | 443 | 1.0e-41 |

| Protein name | Locus Name | Acc# |
|---|---|---|
| N-acetyl-anhydromuramyl-L-alanine amidase | gp:AF082575 | AF082575 |

Description

Pseudomonas aeruginosa N-acetyl-anhydromuramyl-L-alanine amidase(ampD) and transmembrane protein AmpE (ampE) genes, complete cds.

| ORF_Name | NTID | AAID | NT Length | AA Length | Score | Probability |
|---|---|---|---|---|---|---|
| 25662782_f2_24 | 205 | 2125 | 258 | 777 | 288 | 2.7e-25 |

| Protein name | | Locus Name | Acc# |
|---|---|---|---|
| | | sp:CCMA_RHOCA | P29959 |

Description

PROTEIN HELA)

| ORF_Name | NTID | AAID | NT Length | AA Length | Score | Probability |
|---|---|---|---|---|---|---|
| 289052_c1_66 | 206 | 2126 | 154 | 465 | 220 | 4.3e-18 |

| Protein name | Locus Name | Acc# |
|---|---|---|
| conserved hypothetical protein | pir:B75344 | B75344 |

Description

| ORF_Name | NTID | AAID | NT Length | AA Length | Score | Probability |
|---|---|---|---|---|---|---|
| 29301457_f3_44 | 207 | 2127 | 93 | 282 | | |

Protein name | | | | Locus_Name | | Acc# |

Description

NO-HIT

| ORF_Name | NTID | AAID | NT Length | AA Length | Score | Probability |
|---|---|---|---|---|---|---|
| 29507800_c2_95 | 208 | 2128 | 397 | 1194 | 883 | 2.4e-88 |

Protein name | | | | Locus_Name | | Acc# |
| | | | | sp:RP32_PSEAE | | P42378 |

Description

RNA POLYMERASE SIGMA-32 FACTOR

| ORF_Name | NTID | AAID | NT Length | AA Length | Score | Probability |
|---|---|---|---|---|---|---|
| 34569707_c3_131 | 209 | 2129 | 95 | 288 | 74 | 0.023 |

Protein name | | | | Locus_Name | | Acc# |
F22C12.13 | | | | gp:AC007764 | | AC007764 |

Description

Genomic sequence for Arabidopsis thaliana BAC F22C12 from chromosome I, complete sequence.

| ORF_Name | NTID | AAID | NT Length | AA Length | Score | Probability |
|---|---|---|---|---|---|---|
| 36335200_f1_13 | 210 | 2130 | 347 | 1044 | 506 | 2.1e-48 |

Protein name | | | | Locus_Name | | Acc# |
| | | | | sp:YAEL_ECOLI | | P37764 |

Description

HYPOTHETICAL 49.1 KD PROTEIN IN CDSA-HLPA INTERGENIC REGION

| ORF Name | NTID | AAID | NT Length | AA Length | Score | Probability |
|---|---|---|---|---|---|---|
| 36520625_f2_31 | 211 | 2131 | 256 | 771 | 723 | 2.1e-71 |

| Protein name | Locus Name | Acc# |
|---|---|---|
| UMP kinase | gp:AB010087 | AB010087 |

Description

Pseudomonas aeruginosa rpsB, tsf, pyrH, frr genes for ribosomalprotein S2, elongation factor Ts, UMP kinase, ribosome recyclingfactor, complete cds.

| ORF Name | NTID | AAID | NT Length | AA Length | Score | Probability |
|---|---|---|---|---|---|---|
| 3907818_f2_32 | 212 | 2132 | 187 | 564 | 614 | 7.6e-60 |

| Protein name | Locus Name | Acc# |
|---|---|---|
| ribosome recycling factor | gp:AB010087 | AB010087 |

Description

Pseudomonas aeruginosa rpsB, tsf, pyrH, frr genes for ribosomalprotein S2, elongation factor Ts, UMP kinase, ribosome recyclingfactor, complete cds.

| ORF Name | NTID | AAID | NT Length | AA Length | Score | Probability |
|---|---|---|---|---|---|---|
| 391068_f2_33 | 213 | 2133 | 272 | 819 | 534 | 2.3e-51 |

| Protein name | Locus Name | Acc# |
|---|---|---|
|  | sp:UPPS_ECOLI |  |

Description (DI-TRANS-POLY-CIS-DECAPRENYLCISTRANSFERASE)

| ORF Name | NTID | AAID | NT Length | AA Length | Score | Probability |
|---|---|---|---|---|---|---|
| 3915930_f3_50 | 214 | 2134 | 204 | 615 | 592 | 1.6e-57 |

| Protein name | Locus Name | Acc# |
|---|---|---|
|  | sp:TKT1_ECOLI | P27302 |

Description

TRANSKETOLASE 1, (TK 1)

| ORF Name | NTID | AAID | NT Length | AA Length | Score | Probability |
|---|---|---|---|---|---|---|
| 3947932_f3_41 | 215 | 2135 | 299 | 900 | 125 | 2.0e-05 |

| Protein name | | | | Locus Name | | Acc# |
|---|---|---|---|---|---|---|
| | | | | sp:YEEZ_ECOLI | | P76370 |

Description

HYPOTHETICAL 29.7 KD PROTEIN IN SBCB-HISL INTERGENIC REGION PRECURSOR

| ORF Name | NTID | AAID | NT Length | AA Length | Score | Probability |
|---|---|---|---|---|---|---|
| 4110687_f2_30 | 216 | 2136 | 497 | 1494 | 1775 | 7.1e-183 |

| Protein name | | | | Locus Name | | Acc# |
|---|---|---|---|---|---|---|
| | | | | sp:TKT1_ECOLI | | P27302 |

Description

TRANSKETOLASE 1, (TK 1)

| ORF Name | NTID | AAID | NT Length | AA Length | Score | Probability |
|---|---|---|---|---|---|---|
| 4345300_f2_20 | 217 | 2137 | 989 | 2970 | 2958 | 0.0 |

| Protein name | | | | Locus Name | | Acc# |
|---|---|---|---|---|---|---|
| | | | | sp:SYV_HAEIN | | P43834 |

Description

VALYL-TRNA SYNTHETASE, (VALINE--TRNA LIGASE) (VALRS)

| ORF Name | NTID | AAID | NT Length | AA Length | Score | Probability |
|---|---|---|---|---|---|---|
| 4495268_c1_84 | 218 | 2138 | 110 | 333 | 512 | 4.9e-49 |

| Protein name | | | | Locus Name | | Acc# |
|---|---|---|---|---|---|---|
| ferredoxin [3Fe-4S] | | | | pir:FEAV | | |

Description

| ORF Name | NTID | AAID | NT Length | AA Length | Score | Probability |
|---|---|---|---|---|---|---|
| 4693768_f1_11 | 219 | 2139 | 435 | 1308 | 854 | 2.8e-85 |

| Protein name | | | | Locus Name | | Acc# |
|---|---|---|---|---|---|---|
| | | | | sp:DXR_ECOLI | | |

Description

REDUCTOISOMERASE)

| ORF_Name | NTID | AAID | NT Length | AA Length | Score | Probability |
|---|---|---|---|---|---|---|
| 4772325_c1_69 | 220 | 2140 | 93 | 282 | 77 | 0.0071 |

| Protein name | | | | Locus Name | | Acc# |
|---|---|---|---|---|---|---|
| cytochrome b | | | | gp:ASA228475 | | AJ228475 |

Description

Andricus solitarius cytb gene.

| ORF_Name | NTID | AAID | NT Length | AA Length | Score | Probability |
|---|---|---|---|---|---|---|
| 5109626_f1_6 | 221 | 2141 | 81 | 246 | 355 | 2.1e-32 |

| Protein name | | | | Locus Name | | Acc# |
|---|---|---|---|---|---|---|
| | | | | sp:MT1A_MORBO | | P34720 |

Description

METHYLTRANSFERASE MBOI A) (M.MBOI A)

| ORF_Name | NTID | AAID | NT Length | AA Length | Score | Probability |
|---|---|---|---|---|---|---|
| 5350281_c3_139 | 222 | 2142 | 76 | 231 | | |

| Protein name | | | | Locus Name | | Acc# |
|---|---|---|---|---|---|---|

Description

NO-HIT

| ORF_Name | NTID | AAID | NT Length | AA Length | Score | Probability |
|---|---|---|---|---|---|---|
| 6823912_f3_37 | 223 | 2143 | 63 | 192 | | |

| Protein name | | | | Locus Name | | Acc# |
|---|---|---|---|---|---|---|

Description

NO-HIT

| ORF_Name | NTID | AAID | NT Length | AA Length | Score | Probability |
|---|---|---|---|---|---|---|
| 103187_f2_5 | 224 | 2144 | 98 | 297 | | |

| Protein name | | | | Locus Name | | Acc# |
|---|---|---|---|---|---|---|

Description

NO-HIT

| ORF Name | NTID | AAID | NT Length | AA Length | Score | Probability |
|---|---|---|---|---|---|---|
| 16917_f2_4 | 225 | 2145 | 164 | 495 | 307 | 2.6e-27 |

| Protein name | | | | Locus Name | | Acc# |
|---|---|---|---|---|---|---|
| | | | | sp:CYST_ECOLI | | P16701 |

Description

SULFATE TRANSPORT SYSTEM PERMEASE PROTEIN CYST

| ORF Name | NTID | AAID | NT Length | AA Length | Score | Probability |
|---|---|---|---|---|---|---|
| 20163930_c1_9 | 226 | 2146 | 271 | 813 | 502 | 5.6e-48 |

| Protein name | | | | Locus Name | | Acc# |
|---|---|---|---|---|---|---|
| | | | | sp:RHLB_HAEIN | | P44922 |

Description

ATP-DEPENDENT RNA HELICASE RHLB HOMOLOG

| ORF Name | NTID | AAID | NT Length | AA Length | Score | Probability |
|---|---|---|---|---|---|---|
| 24257755_c1_8 | 227 | 2147 | 155 | 468 | | |

| Protein name | | | | Locus Name | | Acc# |

Description

NO-HIT

| ORF Name | NTID | AAID | NT Length | AA Length | Score | Probability |
|---|---|---|---|---|---|---|
| 16594167_f1_5 | 228 | 2148 | 510 | 1533 | | |

| Protein name | | | | Locus Name | | Acc# |

Description

NO-HIT

| ORF Name | NTID | AAID | NT Length | AA Length | Score | Probability |
|---|---|---|---|---|---|---|
| 22897255_f2_6 | 229 | 2149 | 269 | 810 | 305 | 4.2e-27 |

| Protein name | | | | Locus Name | | Acc# |
|---|---|---|---|---|---|---|
| putative acyltransferase | | | | gp:SCM10 | | AL133469 |

Description

Streptomyces coelicolor cosmid M10.

| ORF Name | NTID | AAID | NT Length | AA Length | Score | Probability |
|---|---|---|---|---|---|---|
| 24485937_f3_13 | 230 | 2150 | 62 | 189 | 147 | 1.7e-09 |

| Protein name | Locus Name | Acc# |
|---|---|---|
| glutamate dehydrogenase | gp:UAN010746 | AJ010746 |

Description

Antarctic bacterium TAD1, dhe gene.

| ORF Name | NTID | AAID | NT Length | AA Length | Score | Probability |
|---|---|---|---|---|---|---|
| 2501562_f3_9 | 231 | 2151 | 288 | 867 | 547 | 9.5e-53 |

| Protein name | Locus Name | Acc# |
|---|---|---|
| | sp:FTSH_ECOLI | P28691 |

Description

CELL DIVISION PROTEIN FTSH,

| ORF Name | NTID | AAID | NT Length | AA Length | Score | Probability |
|---|---|---|---|---|---|---|
| 25415636_f1_4 | 232 | 2152 | 679 | 2040 | 1148 | 7.4e-181 |

| Protein name | Locus Name | Acc# |
|---|---|---|
| | sp:HTPG_ECOLI | P10413 |

Description

PROTEIN C62.5)

| ORF Name | NTID | AAID | NT Length | AA Length | Score | Probability |
|---|---|---|---|---|---|---|
| 26366686_c2_24 | 233 | 2153 | 791 | 2376 | 1520 | 7.5e-156 |

| Protein name | Locus Name | Acc# |
|---|---|---|
| penicillin-binding protein 1A | gp:PAU73780 | U73780 |

Description

Pseudomonas aeruginosa penicillin-binding protein 1A (ponA) gene, complete cds, and malic enzyme gene, partial cds.

| ORF Name | NTID | AAID | NT Length | AA Length | Score | Probability |
|---|---|---|---|---|---|---|
| 12304661_f2_18 | 234 | 2154 | 584 | 1755 | 763 | 1.2e-75 |

Protein name | | | | Locus Name | | Acc# |
| | | | | sp:RECN_ECOLI | | |

Description

DNA REPAIR PROTEIN RECN (RECOMBINATION PROTEIN N)

| ORF Name | NTID | AAID | NT Length | AA Length | Score | Probability |
|---|---|---|---|---|---|---|
| 16578133_c3_57 | 235 | 2155 | 65 | 198 | 74 | 0.013 |

Protein name | | | | Locus Name | | Acc# |
| | | | | sp:PSBR_TOBAC | | Q40519 |

Description

PHOTOSYSTEM II 10 KD POLYPEPTIDE PRECURSOR (PII10)

| ORF Name | NTID | AAID | NT Length | AA Length | Score | Probability |
|---|---|---|---|---|---|---|
| 19564510_f2_17 | 236 | 2156 | 194 | 585 | 444 | 7.8e-42 |

Protein name | | | | Locus Name | | Acc# |
| N-formylmethionylaminoacyl-tRNA deformylase, | | | | pir:S23107 | | |

Description

| ORF Name | NTID | AAID | NT Length | AA Length | Score | Probability |
|---|---|---|---|---|---|---|
| 23554638_f3_29 | 237 | 2157 | 285 | 858 | 531 | 4.7e-51 |

Protein name | | | | Locus Name | | Acc# |
| beta-ketoacyl-acyl carrier protein synthase II | | | | gp:AF188707 | | AF188707 |

Description

Photobacterium profundum acyl carrier protein (acpP) gene, partialcds; beta-ketoacyl-acyl carrier protein synthase II (fabF) gene,complete cds; and aminodeoxychorismate lyase (pabC) gene, partialcds.

| ORF_Name | NTID | AAID | NT Length | AA Length | Score | Probability |
|---|---|---|---|---|---|---|
| 23912502_f1_9 | 238 | 2158 | 90 | 273 | 200 | 5.6e-16 |

| Protein name | | | | Locus Name | | Acc# |
|---|---|---|---|---|---|---|
| | | | | sp:YHHP_ECOLI | | P37618 |

Description

HYPOTHETICAL 9.1 KD PROTEIN IN FTSY-NIKA INTERGENIC REGION

| ORF_Name | NTID | AAID | NT Length | AA Length | Score | Probability |
|---|---|---|---|---|---|---|
| 23985753_f3_27 | 239 | 2159 | 167 | 504 | 273 | 1.0e-23 |

| Protein name | | | | Locus Name | | Acc# |
|---|---|---|---|---|---|---|
| | | | | gp:ECU28377 | | U28377 |

Description

Escherichia coli K-12 genome; approximately 65 to 68 minutes.

| ORF_Name | NTID | AAID | NT Length | AA Length | Score | Probability |
|---|---|---|---|---|---|---|
| 24302263_f1_6 | 240 | 2160 | 193 | 582 | 340 | 8.2e-31 |

| Protein name | | | | Locus Name | | Acc# |
|---|---|---|---|---|---|---|
| hypothetical protein b2948 | | | | pir:C65080 | | C65080 |

Description

| ORF_Name | NTID | AAID | NT Length | AA Length | Score | Probability |
|---|---|---|---|---|---|---|
| 24353458_f2_20 | 241 | 2161 | 308 | 927 | 671 | 6.9e-66 |

| Protein name | | | | Locus Name | | Acc# |
|---|---|---|---|---|---|---|
| site-specific recombinase | | | | gp:AF033497 | | AF033497 |

Description

Proteus mirabilis site-specific recombinase (xerD) gene, completecds.

| ORF_Name | NTID | AAID | NT Length | AA Length | Score | Probability |
|---|---|---|---|---|---|---|
| 24642562_f2_13 | 242 | 2162 | 102 | 309 | | |

| Protein name | | | | Locus Name | | Acc# |
|---|---|---|---|---|---|---|

Description

NO-HIT

| ORF_Name | NTID | AAID | NT Length | AA Length | Score | Probability |
|---|---|---|---|---|---|---|
| 3007832_f2_19 | 243 | 2163 | 169 | 510 | | |

| Protein name | | | | | Locus_Name | Acc# |
|---|---|---|---|---|---|---|
| | | | | | | |

Description

NO-HIT

| ORF_Name | NTID | AAID | NT Length | AA Length | Score | Probability |
|---|---|---|---|---|---|---|
| 36205013_f3_23 | 244 | 2164 | 361 | 1086 | 291 | 1.3e-25 |

| Protein name | | | | | Locus_Name | Acc# |
|---|---|---|---|---|---|---|
| hypothetical protein | | | | | pir:G75388 | G75388 |

Description

| ORF_Name | NTID | AAID | NT Length | AA Length | Score | Probability |
|---|---|---|---|---|---|---|
| 3953593_c1_39 | 245 | 2165 | 211 | 636 | 386 | 1.1e-35 |

| Protein name | | | | | Locus_Name | Acc# |
|---|---|---|---|---|---|---|
| imidazoleglycerol-phosphate synthase | | | | | pir:D69070 | D69070 |

Description

| ORF_Name | NTID | AAID | NT Length | AA Length | Score | Probability |
|---|---|---|---|---|---|---|
| 4883425_f1_2 | 246 | 2166 | 206 | 621 | 234 | 1.4e-19 |

| Protein name | | | | | Locus_Name | Acc# |
|---|---|---|---|---|---|---|
| | | | | | sp:YQIA_ECOLI | P36653 |

Description

HYPOTHETICAL 21.6 KD PROTEIN IN PARE-ICC INTERGENIC REGION (F193)

| ORF_Name | NTID | AAID | NT Length | AA Length | Score | Probability |
|---|---|---|---|---|---|---|
| 6506_f1_3 | 247 | 2167 | 637 | 1914 | 2041 | 4.6e-211 |

| Protein name | | | | | Locus_Name | Acc# |
|---|---|---|---|---|---|---|
| topoisomerase IV subunit | | | | | gp:AB003429 | AB003429 |

Description

Pseudomonas aeruginosa DNA for topoisomerase IV subunit, completecds.

| ORF Name | NTID | AAID | NT Length | AA Length | Score | Probability |
|---|---|---|---|---|---|---|
| 805180_c1_38 | 248 | 2168 | 222 | 669 | 554 | 1.7e-53 |

| Protein name | | | | Locus Name | | Acc# |
|---|---|---|---|---|---|---|
| | | | | sp:HIS7_PEA | | Q43072 |

Description

IMIDAZOLEGLYCEROL-PHOSPHATE DEHYDRATASE, (IGPD)

| ORF Name | NTID | AAID | NT Length | AA Length | Score | Probability |
|---|---|---|---|---|---|---|
| 823381_f3_24 | 249 | 2169 | 134 | 405 | | |

| Protein name | Locus Name | Acc# |
|---|---|---|

Description

NO-HIT

| ORF Name | NTID | AAID | NT Length | AA Length | Score | Probability |
|---|---|---|---|---|---|---|
| 862761_c1_43 | 250 | 2170 | 72 | 219 | | |

| Protein name | Locus Name | Acc# |
|---|---|---|

Description

NO-HIT

| ORF Name | NTID | AAID | NT Length | AA Length | Score | Probability |
|---|---|---|---|---|---|---|
| 12281888_c1_40 | 251 | 2171 | 78 | 237 | | |

| Protein name | Locus Name | Acc# |
|---|---|---|

Description

NO-HIT

| ORF Name | NTID | AAID | NT Length | AA Length | Score | Probability |
|---|---|---|---|---|---|---|
| 1367177_f2_15 | 252 | 2172 | 304 | 915 | 674 | 3.3e-66 |

| Protein name | | | | Locus Name | | Acc# |
|---|---|---|---|---|---|---|
| | | | | sp:GALU_ECOLI | | P25520 |

Description

URIDYLYLTRANSFERASE) (URIDINE DIPHOSPHOGLUCOSE PYROPHOSPHORYLASE)

| ORF Name | NTID | AAID | NT Length | AA Length | Score | Probability |
|---|---|---|---|---|---|---|
| 14463877_f3_23 | 253 | 2173 | 330 | 993 | 273 | 1.0e-23 |

Protein name | | | | Locus Name | | Acc#
sp:YJGQ_ECOLI — P39341

Description

HYPOTHETICAL 39.8 KD PROTEIN IN PEPA-GNTV INTERGENIC REGION (O361)

| ORF Name | NTID | AAID | NT Length | AA Length | Score | Probability |
|---|---|---|---|---|---|---|
| 156515_f2_20 | 254 | 2174 | 178 | 537 | | |

Protein name | | | | Locus Name | | Acc#

Description

NO-HIT

| ORF Name | NTID | AAID | NT Length | AA Length | Score | Probability |
|---|---|---|---|---|---|---|
| 16040927_c2_50 | 255 | 2175 | 112 | 339 | | |

Protein name | | | | Locus Name | | Acc#

Description

NO-HIT

| ORF Name | NTID | AAID | NT Length | AA Length | Score | Probability |
|---|---|---|---|---|---|---|
| 16610183_c2_54 | 256 | 2176 | 310 | 933 | 569 | 4.4e-55 |

Protein name | | | | Locus Name | | Acc#
sp:TESB_ECOLI — P23911

Description

ACYL-COA THIOESTERASE II,

| ORF Name | NTID | AAID | NT Length | AA Length | Score | Probability |
|---|---|---|---|---|---|---|
| 16819827_f1_6 | 257 | 2177 | 137 | 414 | | |

Protein name | | | | Locus Name | | Acc#

Description

NO-HIT

| ORF Name | NTID | AAID | NT Length | AA Length | Score | Probability |
|---|---|---|---|---|---|---|
| 19531885_c3_57 | 258 | 2178 | 60 | 183 | | |

Protein name | | | | Locus Name | | Acc# |

Description

NO-HIT

| ORF Name | NTID | AAID | NT Length | AA Length | Score | Probability |
|---|---|---|---|---|---|---|
| 19538388_f2_14 | 259 | 2179 | 75 | 228 | 73 | 0.016 |

Protein name | | | | Locus Name | | Acc# |
| | | | | gp:SMI240618 | | AJ240618 |

Description

Streptococcus mitis xpt gene, strain 12261.

| ORF Name | NTID | AAID | NT Length | AA Length | Score | Probability |
|---|---|---|---|---|---|---|
| 20942936_f3_27 | 260 | 2180 | 376 | 1131 | 1060 | 4.1e-107 |

Protein name | | | | Locus Name | | Acc# |
| | | | | sp:GALE_BACSU | | P55180 |

Description

GALACTOSE 4-EPIMERASE)

| ORF Name | NTID | AAID | NT Length | AA Length | Score | Probability |
|---|---|---|---|---|---|---|
| 21675051_f3_28 | 261 | 2181 | 321 | 966 | 447 | 3.8e-42 |

Protein name | | | | Locus Name | | Acc# |
| | | | | sp:YRFI_ECOLI | | P45803 |

Description

HYPOTHETICAL 32.5 KD PROTEIN IN MRCA-PCKA INTERGENIC REGION

| ORF Name | NTID | AAID | NT Length | AA Length | Score | Probability |
|---|---|---|---|---|---|---|
| 23557930_c3_61 | 262 | 2182 | 619 | 1860 | 1768 | 3.9e-182 |

| Protein name | Locus Name | Acc# |
|---|---|---|
| glucosamine synthase | gp:AF032884 | |

Description

Thiobacillus ferrooxidans N-acetylglucosamine-1-phosphateuridyltransferase (glmU) gene, partial cds; glucosamine synthase(glmS) and RecG (recG) genes, complete cds; and transposon Tn5468,complete sequence.

| ORF Name | NTID | AAID | NT Length | AA Length | Score | Probability |
|---|---|---|---|---|---|---|
| 23634680_f2_18 | 263 | 2183 | 423 | 1272 | 383 | 2.3e-35 |

| Protein name | Locus Name | Acc# |
|---|---|---|
| putative UDP-glucose dehydrogenase | gp:ALW243431 | AJ243431 |

Description

Acinetobacter lwoffii wzc, wzb, wza, weeA, weeB, wceC, wzx, wzy,weeD, weeE, weeF, weeG, weeH, weeI, weeJ, weeK, galU, ugd, pgi,galE, pgm (partial) and mip (partial) genes (emulsan biosyntheticgene cluster), strain RAG-1.

| ORF Name | NTID | AAID | NT Length | AA Length | Score | Probability |
|---|---|---|---|---|---|---|
| 24400250_f3_24 | 264 | 2184 | 860 | 2583 | 1162 | 6.4e-118 |

| Protein name | Locus Name | Acc# |
|---|---|---|
| | sp:PLSB_HAEIN | P44857 |

Description

GLYCEROL-3-PHOSPHATE ACYLTRANSFERASE, (GPAT)

| ORF Name | NTID | AAID | NT Length | AA Length | Score | Probability |
|---|---|---|---|---|---|---|
| 24493801_f3_30 | 265 | 2185 | 375 | 1128 | 489 | 1.3e-46 |

| Protein name | Locus Name | Acc# |
|---|---|---|
| FauI DNA methyltransferase | gp:AF029070 | AF029070 |

Description

Flavobacterium aquatile FauI DNA methyltransferase (fauIM) gene,complete cds.

| ORF_Name | NTID | AAID | NT Length | AA Length | Score | Probability |
|---|---|---|---|---|---|---|
| 26797302_c2_55 | 266 | 2186 | 393 | 1182 | 515 | 2.3e-49 |

| Protein name | Locus Name | Acc# |
|---|---|---|
| | sp:YAIW_ECOLI | P77562 |

Description

HYPOTHETICAL 40.4 KD PROTEIN IN SBMA-DDLA INTERGENIC REGION

| ORF_Name | NTID | AAID | NT Length | AA Length | Score | Probability |
|---|---|---|---|---|---|---|
| 3317260_f1_5 | 267 | 2187 | 573 | 1722 | 1505 | 2.9e-154 |

| Protein name | Locus Name | Acc# |
|---|---|---|
| putative phosphoglucose isomerase | gp:ALW243431 | AJ243431 |

Description

Acinetobacter lwoffii wzc, wzb, wza, weeA, weeB, wceC, wzx, wzy, weeD, weeE, weeF, weeG, weeH, weeI, weeJ, weeK, galU, ugd, pgi, galE, pgm (partial) and mip (partial) genes (emulsan biosyntheticgene cluster), strain RAG-1.

| ORF_Name | NTID | AAID | NT Length | AA Length | Score | Probability |
|---|---|---|---|---|---|---|
| 3938762_f2_22 | 268 | 2188 | 71 | 216 | 71 | 0.026 |

| Protein name | Locus Name | Acc# |
|---|---|---|
| transcription regulator homolog yozG | pir:C69931 | C69931 |

Description

| ORF_Name | NTID | AAID | NT Length | AA Length | Score | Probability |
|---|---|---|---|---|---|---|
| 6729635_c2_46 | 269 | 2189 | 171 | 516 | 94 | 0.0062 |

| Protein name | Locus Name | Acc# |
|---|---|---|
| hypothetical protein C45H4.14 | pir:T32722 | T32722 |

Description

| ORF_Name | NTID | AAID | NT Length | AA Length | Score | Probability |
|---|---|---|---|---|---|---|
| 976387_f2_19 | 270 | 2190 | 88 | 267 | 74 | 0.0025 |

| Protein name | Locus Name | Acc# |
|---|---|---|
| hypothetical protein T16L4.170 | pir:T09929 | T09929 |

Description

| ORF Name | NTID | AAID | NT Length | AA Length | Score | Probability |
|---|---|---|---|---|---|---|
| 10823462_cl_13 | 271 | 2191 | 67 | 204 | | |

| Protein name | Locus Name | Acc# |
|---|---|---|
| | | |

Description

NO-HIT

| ORF Name | NTID | AAID | NT Length | AA Length | Score | Probability |
|---|---|---|---|---|---|---|
| 12376535_f2_5 | 272 | 2192 | 214 | 645 | 74 | 0.0011 |

| Protein name | Locus Name | Acc# |
|---|---|---|
| | gp:VCU39068 | U39068 |

Description

Vibrio cholerae pathogenicity island, partial and complete cds.

| ORF Name | NTID | AAID | NT Length | AA Length | Score | Probability |
|---|---|---|---|---|---|---|
| 22065635_f2_9 | 273 | 2193 | 521 | 1566 | 1440 | 2.2e-147 |

| Protein name | Locus Name | Acc# |
|---|---|---|
| sodium/proline symporter opuE:proline transporter opuE | pir:H69670 | H69670 |

Description

| ORF Name | NTID | AAID | NT Length | AA Length | Score | Probability |
|---|---|---|---|---|---|---|
| 24228400_cl_20 | 274 | 2194 | 479 | 1440 | 1110 | 2.1e-112 |

| Protein name | Locus Name | Acc# |
|---|---|---|
| | sp:HEMN_ECOLI | |

Description (COPROPORPHYRINOGENASE) (COPROGEN OXIDASE)

| ORF Name | NTID | AAID | NT Length | AA Length | Score | Probability |
|---|---|---|---|---|---|---|
| 29328457_cl_14 | 275 | 2195 | 98 | 297 | 95 | 7.5e-05 |

| Protein name | Locus Name | Acc# |
|---|---|---|
| | sp:MINE_ECOLI | P18198 |

Description

CELL DIVISION TOPOLOGICAL SPECIFICITY FACTOR

| ORF Name | NTID | AAID | NT Length | AA Length | Score | Probability |
|---|---|---|---|---|---|---|
| 4880303_c1_19 | 276 | 2196 | 193 | 582 | 514 | 3.0e-49 |

| Protein name | | | | Locus Name | | Acc# |
|---|---|---|---|---|---|---|
| | | | | sp:PTH_HAEIN | | P44682 |

Description

PEPTIDYL-TRNA HYDROLASE, (PTH)

| ORF Name | NTID | AAID | NT Length | AA Length | Score | Probability |
|---|---|---|---|---|---|---|
| 6835875_f2_4 | 277 | 2197 | 60 | 183 | | |

| Protein name | | | | Locus Name | | Acc# |
|---|---|---|---|---|---|---|

Description

NO-HIT

| ORF Name | NTID | AAID | NT Length | AA Length | Score | Probability |
|---|---|---|---|---|---|---|
| 900011_c3_28 | 278 | 2198 | 234 | 705 | 269 | 2.7e-23 |

| Protein name | | | | Locus Name | | Acc# |
|---|---|---|---|---|---|---|
| probable ribosomal protein L25 | | | | pir:H71665 | | H71665 |

Description

| ORF Name | NTID | AAID | NT Length | AA Length | Score | Probability |
|---|---|---|---|---|---|---|
| 9869006_f1_2 | 279 | 2199 | 72 | 219 | 271 | 1.7e-23 |

| Protein name | | | | Locus Name | | Acc# |
|---|---|---|---|---|---|---|
| 30S subunit ribosomal protein S21 | | | | gp:AF014397 | | AF014397 |

Description

Pseudomonas putida macromolecular synthesis operon: 30S subunit ribosomal protein S21 (rpsU), DNA primase (dnaG), and sigma-70(rpoD) genes, complete cds.

| ORF Name | NTID | AAID | NT Length | AA Length | Score | Probability |
|---|---|---|---|---|---|---|
| 11885875_c3_76 | 280 | 2200 | 455 | 1368 | 1218 | 7.5e-124 |

| Protein name | | | | Locus Name | | Acc# |
|---|---|---|---|---|---|---|
| | | | | sp:Y164_HAEIN | | |

Description

HYPOTHETICAL PROTEIN HI0164/165

| ORF Name | NTID | AAID | NT Length | AA Length | Score | Probability |
|---|---|---|---|---|---|---|
| 12687781_c3_70 | 281 | 2201 | 174 | 525 | 512 | 4.9e-49 |

| Protein name | Locus Name | Acc# |
|---|---|---|
| | sp:IF3_HAEIN | P43814 |

Description

TRANSLATION INITIATION FACTOR IF-3

| ORF Name | NTID | AAID | NT Length | AA Length | Score | Probability |
|---|---|---|---|---|---|---|
| 14093967_c1_49 | 282 | 2202 | 211 | 636 | 741 | 2.6e-73 |

| Protein name | Locus Name | Acc# |
|---|---|---|
| NqrE | gp:AF165980 | AF165980 |

Description

Vibrio harveyi Na+-translocating NADH-quinone oxidoreductase complex operon, complete sequence.

| ORF Name | NTID | AAID | NT Length | AA Length | Score | Probability |
|---|---|---|---|---|---|---|
| 14540908_c3_77 | 283 | 2203 | 270 | 813 | 474 | 5.2e-45 |

| Protein name | Locus Name | Acc# |
|---|---|---|
| NqrC | gp:AF117331 | AF117331 |

Description

Vibrio cholerae N16961 Na+-translocating NADH-ubiquinone oxidoreductase enzyme complex, complete sequence.

| ORF Name | NTID | AAID | NT Length | AA Length | Score | Probability |
|---|---|---|---|---|---|---|
| 15865712_f2_21 | 284 | 2204 | 189 | 570 | 162 | 6.0e-12 |

| Protein name | Locus Name | Acc# |
|---|---|---|
| | gp:ECOUW93 | U14003 |

Description

Escherichia coli K-12 chromosomal region from 92.8 to 00.1 minutes.

| ORF Name | NTID | AAID | NT Length | AA Length | Score | Probability |
|---|---|---|---|---|---|---|
| 16460432_c2_65 | 285 | 2205 | 78 | 237 | | |

Protein name | Locus Name | Acc#

Description

NO-HIT

| ORF Name | NTID | AAID | NT Length | AA Length | Score | Probability |
|---|---|---|---|---|---|---|
| 22038177_f3_27 | 286 | 2206 | 557 | 1674 | 1801 | 1.2e-185 |

Protein name: putative efflux pump component MtrF
Locus Name: gp:AF176821
Acc#: AF176821

Description

Neisseria gonorrhoeae strain EU75 putative efflux pump componentMtrF (mtrF) gene, complete cds.

| ORF Name | NTID | AAID | NT Length | AA Length | Score | Probability |
|---|---|---|---|---|---|---|
| 24423260_c1_42 | 287 | 2207 | 437 | 1314 | 121 | 2.5e-05 |

Protein name: pr2
Locus Name: gp:MHU19289
Acc#: U19289

Description

Mycoplasma hyopneumoniae J ATCC 27219 multidrug resistance proteinhomologs pr1 and pr2 genes, complete cds, and 23S rRNA gene, partial sequence.

| ORF Name | NTID | AAID | NT Length | AA Length | Score | Probability |
|---|---|---|---|---|---|---|
| 25392778_f1_1 | 288 | 2208 | 201 | 606 | 387 | 8.6e-36 |

Protein name: 4-hydroxyphenylacetate 3-monooxygenase (EC
Locus Name: gp:D90737
Acc#:

Description

Escherichia coli genomic DNA. (22.8 - 23.1 min).

| ORF Name | NTID | AAID | NT Length | AA Length | Score | Probability |
|---|---|---|---|---|---|---|
| 31268837_f3_28 | 289 | 2209 | 412 | 1239 | 1836 | 2.4e-189 |

| Protein name | | | | Locus Name | | Acc# |
|---|---|---|---|---|---|---|
| | | | | sp:CATA_HAEIN | | P44390 |

Description

CATALASE,

| ORF Name | NTID | AAID | NT Length | AA Length | Score | Probability |
|---|---|---|---|---|---|---|
| 33223291_f2_19 | 290 | 2210 | 71 | 216 | | |

| Protein name | | | | Locus Name | | Acc# |
|---|---|---|---|---|---|---|

Description

NO-HIT

| ORF Name | NTID | AAID | NT Length | AA Length | Score | Probability |
|---|---|---|---|---|---|---|
| 33235937_c2_59 | 291 | 2211 | 782 | 2349 | 1415 | 1.0e-144 |

| Protein name | | | | Locus Name | | Acc# |
|---|---|---|---|---|---|---|
| | | | | sp:VACB_ECOLI | | |

Description

VACB PROTEIN

| ORF Name | NTID | AAID | NT Length | AA Length | Score | Probability |
|---|---|---|---|---|---|---|
| 33867132_f1_12 | 292 | 2212 | 225 | 678 | | |

| Protein name | | | | Locus Name | | Acc# |
|---|---|---|---|---|---|---|

Description

NO-HIT

| ORF Name | NTID | AAID | NT Length | AA Length | Score | Probability |
|---|---|---|---|---|---|---|
| 3399183_c2_61 | 293 | 2213 | 415 | 1248 | 1268 | 3.8e-129 |

| Protein name | | | | Locus Name | | Acc# |
|---|---|---|---|---|---|---|
| NqrB | | | | gp:AF117331 | | AF117331 |

Description

Vibrio cholerae N16961 Na+-translocating NADH-ubiquinoneoxidoreductase enzyme complex, complete sequence.

| ORF_Name | NTID | AAID | NT Length | AA Length | Score | Probability |
|---|---|---|---|---|---|---|
| 34000785_c3_73 | 294 | 2214 | 61 | 186 | | |

| Protein name | | | | | Locus Name | Acc# |
|---|---|---|---|---|---|---|
| | | | | | | |

Description

NO-HIT

| ORF_Name | NTID | AAID | NT Length | AA Length | Score | Probability |
|---|---|---|---|---|---|---|
| 34196052_c2_63 | 295 | 2215 | 416 | 1251 | 1650 | 1.2e-169 |

| Protein name | | | | | Locus Name | Acc# |
|---|---|---|---|---|---|---|
| NqrF | | | | | gp:AF117331 | AF117331 |

Description

Vibrio cholerae N16961 Na+-translocating NADH-ubiquinoneoxidoreductase enzyme complex, complete sequence.

| ORF_Name | NTID | AAID | NT Length | AA Length | Score | Probability |
|---|---|---|---|---|---|---|
| 3939043_c2_58 | 296 | 2216 | 642 | 1929 | 2200 | 6.5e-228 |

| Protein name | | | | | Locus Name | Acc# |
|---|---|---|---|---|---|---|
| | | | | | sp:SYT_HAEIN | P43014 |

Description (THRRS)

| ORF_Name | NTID | AAID | NT Length | AA Length | Score | Probability |
|---|---|---|---|---|---|---|
| 4720967_c2_62 | 297 | 2217 | 227 | 684 | 679 | 9.8e-67 |

| Protein name | | | | | Locus Name | Acc# |
|---|---|---|---|---|---|---|
| | | | | | sp:Y168_HAEIN | |

Description

HYPOTHETICAL PROTEIN HI0168/169

| ORF_Name | NTID | AAID | NT Length | AA Length | Score | Probability |
|---|---|---|---|---|---|---|
| 473137_c1_41 | 298 | 2218 | 76 | 231 | | |

| Protein name | | | | | Locus Name | Acc# |
|---|---|---|---|---|---|---|
| | | | | | | |

Description

NO-HIT

| ORF Name | NTID | AAID | NT Length | AA Length | Score | Probability |
|---|---|---|---|---|---|---|
| 4801625_f2_20 | 299 | 2219 | 252 | 759 | 622 | 1.1e-60 |

Protein name | | | | Locus Name | | Acc#
| | | | | sp:HIS4_RHOSH | | P50936

Description

ISOMERASE,

| ORF Name | NTID | AAID | NT Length | AA Length | Score | Probability |
|---|---|---|---|---|---|---|
| 5882211_f2_14 | 300 | 2220 | 118 | 357 | 153 | 2.7e-10 |

Protein name | | | | Locus Name | | Acc#
hypothetical protein 1 | | | | pir:S47051 | | S47051

Description

| ORF Name | NTID | AAID | NT Length | AA Length | Score | Probability |
|---|---|---|---|---|---|---|
| 682641_c2_55 | 301 | 2221 | 86 | 261 | 100 | 2.2e-05 |

Protein name | | | | Locus Name | | Acc#
hypothetical protein PH0217 | | | | pir:G71244 | | G71244

Description

| ORF Name | NTID | AAID | NT Length | AA Length | Score | Probability |
|---|---|---|---|---|---|---|
| 14103377_f2_9 | 302 | 2222 | 166 | 501 | 434 | 9.0e-41 |

Protein name | | | | Locus Name | | Acc#
| | | | | sp:MTGA_ACICA | | O24849

Description (EC 2.4.2.-) (MONOFUNCTIONAL TGASE)

| ORF Name | NTID | AAID | NT Length | AA Length | Score | Probability |
|---|---|---|---|---|---|---|
| 16973437_c3_30 | 303 | 2223 | 79 | 240 | | |

Protein name | | | | Locus Name | | Acc#

Description

NO-HIT

| ORF Name | NTID | AAID | NT Length | AA Length | Score | Probability |
|---|---|---|---|---|---|---|
| 19745308_f1_3 | 304 | 2224 | 66 | 201 | | |

| Protein name | | | | | Locus Name | Acc# |
|---|---|---|---|---|---|---|
| | | | | | | |

Description

NO-HIT

| ORF Name | NTID | AAID | NT Length | AA Length | Score | Probability |
|---|---|---|---|---|---|---|
| 24261257_f3_14 | 305 | 2225 | 123 | 372 | 140 | 8.0e-09 |

| Protein name | | | | | Locus Name | Acc# |
|---|---|---|---|---|---|---|
| | | | | | sp:PNCB_SALTY | P22253 |

Description

NICOTINATE PHOSPHORIBOSYLTRANSFERASE, (NAPRTASE)

| ORF Name | NTID | AAID | NT Length | AA Length | Score | Probability |
|---|---|---|---|---|---|---|
| 25600925_f1_2 | 306 | 2226 | 91 | 276 | 98 | 9.9e-05 |

| Protein name | | | | | Locus Name | Acc# |
|---|---|---|---|---|---|---|
| | | | | | sp:MTGA_ACICA | O24849 |

Description (EC 2.4.2.-) (MONOFUNCTIONAL TGASE)

| ORF Name | NTID | AAID | NT Length | AA Length | Score | Probability |
|---|---|---|---|---|---|---|
| 30659433_c2_21 | 307 | 2227 | 68 | 207 | | |

| Protein name | | | | | Locus Name | Acc# |
|---|---|---|---|---|---|---|
| | | | | | | |

Description

NO-HIT

| ORF Name | NTID | AAID | NT Length | AA Length | Score | Probability |
|---|---|---|---|---|---|---|
| 3303178_f1_1 | 308 | 2228 | 179 | 540 | 430 | 2.4e-40 |

| Protein name | | | | | Locus Name | Acc# |
|---|---|---|---|---|---|---|
| solanesyl diphosphate synthase | | | | | gp:AB001997 | AB001997 |

Description

Rhodobacter capsulatus DNA for solanesyl diphosphate synthase, complete cds.

| ORF Name | NTID | AAID | NT Length | AA Length | Score | Probability |
|---|---|---|---|---|---|---|
| 35182887_c2_23 | 309 | 2229 | 191 | 576 | 684 | 2.9e-67 |

Protein name | Locus Name | Acc#
sp:IPYR_HAEIN | P44529

Description

PHOSPHO-HYDROLASE) (PPASE)

| ORF Name | NTID | AAID | NT Length | AA Length | Score | Probability |
|---|---|---|---|---|---|---|
| 36126655_f1_4 | 310 | 2230 | 374 | 1125 | 1283 | 9.7e-131 |

Protein name | Locus Name | Acc#
sp:AROC_HAEIN | P43875

Description

PHOSPHOLYASE)

| ORF Name | NTID | AAID | NT Length | AA Length | Score | Probability |
|---|---|---|---|---|---|---|
| 6834702_f2_11 | 311 | 2231 | 162 | 489 | 371 | 4.3e-34 |

Protein name | Locus Name | Acc#
sp:YCHJ_HAEIN | P44609

Description

HYPOTHETICAL PROTEIN HI0277

| ORF Name | NTID | AAID | NT Length | AA Length | Score | Probability |
|---|---|---|---|---|---|---|
| 882636_c1_15 | 312 | 2232 | 258 | 777 | 417 | 5.7e-39 |

Protein name | Locus Name | Acc#
lipoate biosynthesis protein B | gp:AF147448 | AF147448

Description

Pseudomonas aeruginosa strain PAO1 penicillin-binding protein 2(pbpA), rod-shape-determining protein (rodA), membrane-bound lytictransglycosylase (mltB), rare lipoprotein A (rlpA),penicillin-binding protein 5 (dacA), and lipoate biosynthesisprotein B (lipB) genes, complete cds; and unknown gene.

| ORF Name | NTID | AAID | NT Length | AA Length | Score | Probability |
|---|---|---|---|---|---|---|
| 973756_c3_34 | 313 | 2233 | 138 | 417 | | |

Protein name | Locus Name | Acc#

Description

NO-HIT

| ORF Name | NTID | AAID | NT Length | AA Length | Score | Probability |
|---|---|---|---|---|---|---|
| 975055_f2_10 | 314 | 2234 | 745 | 2238 | 2349 | 1.1e-243 |

Protein name: polyphosphate kinase | Locus Name: gp:ACRBDOXN | Acc# Z46863

Description

Acinetobacter sp. cysD, cobQ, sodM, lysS, rubA, rubB, estB, oxyR, ppk, mtgA, ORF2 and ORF3 genes.

| ORF Name | NTID | AAID | NT Length | AA Length | Score | Probability |
|---|---|---|---|---|---|---|
| 10673587_f1_4 | 315 | 2235 | 402 | 1209 | 1210 | 5.3e-123 |

Protein name | Locus Name: sp:TYRB_ECOLI | Acc# P04693

Description

AROMATIC-AMINO-ACID AMINOTRANSFERASE, (AROAT) (ARAT)

| ORF Name | NTID | AAID | NT Length | AA Length | Score | Probability |
|---|---|---|---|---|---|---|
| 14572162_f1_1 | 316 | 2236 | 260 | 783 | 586 | 7.0e-57 |

Protein name | Locus Name: sp:YCIK_ECOLI | Acc#

Description (EC 1.-.-.-)

| ORF Name | NTID | AAID | NT Length | AA Length | Score | Probability |
|---|---|---|---|---|---|---|
| 20126386_f2_8 | 317 | 2237 | 198 | 597 | 325 | 3.2e-29 |

Protein name | Locus Name: sp:YTFL_ECOLI | Acc# P39319

Description

HYPOTHETICAL 49.8 KD PROTEIN IN CYSQ-MSRA INTERGENIC REGION

| ORF Name | NTID | AAID | NT Length | AA Length | Score | Probability |
|---|---|---|---|---|---|---|
| 2609375_c2_26 | 318 | 2238 | 92 | 279 | | |

Protein name | Locus Name | Acc#

Description

NO-HIT

| ORF Name | NTID | AAID | NT Length | AA Length | Score | Probability |
|---|---|---|---|---|---|---|
| 26808317_f2_6 | 319 | 2239 | 232 | 699 | 576 | 8.1e-56 |

Protein name | Locus Name | Acc#
| | sp:UBIG_ECOLI | |

Description

METHYLTRANSFERASE)

| ORF Name | NTID | AAID | NT Length | AA Length | Score | Probability |
|---|---|---|---|---|---|---|
| 34394050_f3_15 | 320 | 2240 | 308 | 927 | 889 | 5.5e-89 |

Protein name | Locus Name | Acc#
| | sp:YTFL_ECOLI | P39319 |

Description

HYPOTHETICAL 49.8 KD PROTEIN IN CYSQ-MSRA INTERGENIC REGION

| ORF Name | NTID | AAID | NT Length | AA Length | Score | Probability |
|---|---|---|---|---|---|---|
| 3911568_f2_7 | 321 | 2241 | 233 | 702 | 267 | 4.5e-23 |

Protein name | Locus Name | Acc#
| | sp:GPHC_ALCEU | P40852 |

Description

PHOSPHOGLYCOLATE PHOSPHATASE, CHROMOSOMAL, (PGP)

| ORF Name | NTID | AAID | NT Length | AA Length | Score | Probability |
|---|---|---|---|---|---|---|
| 4117193_c2_25 | 322 | 2242 | 506 | 1521 | 963 | 7.9e-97 |

Protein name | Locus Name | Acc#
leucine aminopeptidase | gp:PPU010261 | AJ010261

Description

Pseudomonas putida pepA gene.

146

| ORF_Name | NTID | AAID | NT Length | AA Length | Score | Probability |
|---|---|---|---|---|---|---|
| 4144818_f3_16 | 323 | 2243 | 362 | 1089 | 766 | 5.9e-76 |

Protein name: probable ionictransporter
Locus Name: pir:F70819
Acc#: F70819

Description

| ORF_Name | NTID | AAID | NT Length | AA Length | Score | Probability |
|---|---|---|---|---|---|---|
| 4976550_f1_3 | 324 | 2244 | 312 | 939 | 399 | 4.6e-37 |

Protein name:
Locus Name: sp:YBHD_ECOLI
Acc#:

Description: HYPOTHETICAL TRANSCRIPTIONAL REGULATOR IN MODC-BIOA INTERGENIC REGION

| ORF_Name | NTID | AAID | NT Length | AA Length | Score | Probability |
|---|---|---|---|---|---|---|
| 1441017_c1_38 | 325 | 2245 | 98 | 297 | 124 | 1.2e-07 |

Protein name: opacity protein opa51
Locus Name: pir:S36329
Acc#:

Description

| ORF_Name | NTID | AAID | NT Length | AA Length | Score | Probability |
|---|---|---|---|---|---|---|
| 14462827_c3_53 | 326 | 2246 | 89 | 270 | 292 | 1.0e-25 |

Protein name: ribosomal protein S15
Locus Name: pir:S38882
Acc#: S38882

Description

| ORF_Name | NTID | AAID | NT Length | AA Length | Score | Probability |
|---|---|---|---|---|---|---|
| 14494026_c2_50 | 327 | 2247 | 219 | 660 | 500 | 9.1e-48 |

Protein name:
Locus Name: sp:HIS1_BACSU
Acc#: O34520

Description: ATP PHOSPHORIBOSYLTRANSFERASE,

| ORF_Name | NTID | AAID | NT Length | AA Length | Score | Probability |
|---|---|---|---|---|---|---|
| 14509682_c2_45 | 328 | 2248 | 165 | 498 | 230 | 3.7e-19 |

Protein name

Locus Name: gp:VCU39068  Acc#: U39068

Description

Vibrio cholerae pathogenicity island, partial and complete cds.

| ORF_Name | NTID | AAID | NT Length | AA Length | Score | Probability |
|---|---|---|---|---|---|---|
| 157765_c2_48 | 329 | 2249 | 96 | 291 | 182 | 4.5e-14 |

Protein name

Locus Name: sp:YRPM_ACICA  Acc#: P33989

Description

HYPOTHETICAL 9.2 KD PROTEIN IN RPON-MURA INTERGENIC REGION (ORF3)

| ORF_Name | NTID | AAID | NT Length | AA Length | Score | Probability |
|---|---|---|---|---|---|---|
| 16510933_c2_52 | 330 | 2250 | 525 | 1578 | 545 | 1.6e-52 |

Protein name

Locus Name: sp:FUMB_ECOLI  Acc#:

Description

FUMARATE HYDRATASE CLASS I, ANAEROBIC, (FUMARASE)

| ORF_Name | NTID | AAID | NT Length | AA Length | Score | Probability |
|---|---|---|---|---|---|---|
| 23445931_c2_51 | 331 | 2251 | 454 | 1365 | 942 | 1.3e-94 |

Protein name: histidinol dehydrogenase

Locus Name: pir:E70368  Acc#: E70368

Description

| ORF_Name | NTID | AAID | NT Length | AA Length | Score | Probability |
|---|---|---|---|---|---|---|
| 23650253_c2_49 | 332 | 2252 | 421 | 1266 | 1337 | 1.8e-136 |

Protein name

Locus Name: sp:MURA_ACICA  Acc#: P33986

Description

TRANSFERASE) (EPT)

| ORF Name | NTID | AAID | NT Length | AA Length | Score | Probability |
|---|---|---|---|---|---|---|
| 2381950_c3_58 | 333 | 2253 | 61 | 186 | | |

Protein name | Locus Name | Acc#

Description

NO-HIT

| ORF Name | NTID | AAID | NT Length | AA Length | Score | Probability |
|---|---|---|---|---|---|---|
| 23867127_c1_41 | 334 | 2254 | 275 | 828 | 147 | 5.2e-10 |

Protein name | Locus Name: sp:YRAP_ECOLI | Acc# P45467

Description (O191)

| ORF Name | NTID | AAID | NT Length | AA Length | Score | Probability |
|---|---|---|---|---|---|---|
| 24395637_c1_40 | 335 | 2255 | 149 | 450 | 143 | 6.2e-10 |

Protein name | Locus Name: sp:YRAN_ECOLI | Acc# P45465

Description

HYPOTHETICAL 14.8 KD PROTEIN IN AGAI-MTR INTERGENIC REGION (O131)

| ORF Name | NTID | AAID | NT Length | AA Length | Score | Probability |
|---|---|---|---|---|---|---|
| 34010260_f1_1 | 336 | 2256 | 119 | 360 | 204 | 2.1e-16 |

Protein name: general stress protein homolog ykzA | Locus Name: pir:F69870 | Acc# F69870

Description

| ORF Name | NTID | AAID | NT Length | AA Length | Score | Probability |
|---|---|---|---|---|---|---|
| 5079188_f3_35 | 337 | 2257 | 163 | 492 | 461 | 1.2e-43 |

Protein name: hypothetical protein | Locus Name: gp:ASA224767 | Acc# AJ224767

Description

Acinetobacter sp. ADP1 lon gene and ORFs.

| ORF Name | NTID | AAID | NT Length | AA Length | Score | Probability |
|---|---|---|---|---|---|---|
| 5330087_c3_61 | 338 | 2258 | 370 | 1113 | 922 | 1.7e-92 |

Protein name:

Locus Name: sp:HIS8_ACEXY

Acc#: P45358

Description: PHOSPHATE TRANSAMINASE)

| ORF Name | NTID | AAID | NT Length | AA Length | Score | Probability |
|---|---|---|---|---|---|---|
| 954837_c2_44 | 339 | 2259 | 699 | 2100 | 2198 | 1.1e-227 |

Protein name: polyribonucleotide nucleotidyltransferase

Locus Name: gp:PPY18132

Acc#: Y18132

Description: Pseudomonas putida rps0 and pnp genes.

| ORF Name | NTID | AAID | NT Length | AA Length | Score | Probability |
|---|---|---|---|---|---|---|
| 969392_f1_13 | 340 | 2260 | 73 | 222 | | |

Protein name:

Locus Name:

Acc#:

Description: NO-HIT

| ORF Name | NTID | AAID | NT Length | AA Length | Score | Probability |
|---|---|---|---|---|---|---|
| 1070165_c3_42 | 341 | 2261 | 72 | 219 | | |

Protein name:

Locus Name:

Acc#:

Description: NO-HIT

| ORF Name | NTID | AAID | NT Length | AA Length | Score | Probability |
|---|---|---|---|---|---|---|
| 10993750_f1_2 | 342 | 2262 | 137 | 414 | | |

Protein name:

Locus Name:

Acc#:

Description: NO-HIT

| ORF Name | NTID | AAID | NT Length | AA Length | Score | Probability |
|---|---|---|---|---|---|---|
| 20884677_c3_43 | 343 | 2263 | 560 | 1683 | 1389 | 5.7e-142 |

Protein name: probable acyl-CoA dehydrogenase
Locus Name: pir:B75282
Acc#: B75282

Description

| ORF Name | NTID | AAID | NT Length | AA Length | Score | Probability |
|---|---|---|---|---|---|---|
| 24395191_c1_31 | 344 | 2264 | 97 | 294 | 71 | 0.011 |

Protein name: conserved hypothetical protein aq_1236
Locus Name: pir:F70406
Acc#: F70406

Description

| ORF Name | NTID | AAID | NT Length | AA Length | Score | Probability |
|---|---|---|---|---|---|---|
| 33804680_c2_35 | 345 | 2265 | 796 | 2391 | 709 | 4.4e-72 |

Protein name: site-specific recombinase
Locus Name: gp:NGU82253
Acc#: U82253

Description: Neisseria gonorrhoeae site-specific recombinase (gcr) gene, complete cds.

| ORF Name | NTID | AAID | NT Length | AA Length | Score | Probability |
|---|---|---|---|---|---|---|
| 34085165_f3_20 | 346 | 2266 | 496 | 1491 | 1327 | 2.1e-135 |

Protein name
Locus Name: sp:RPSD_PSEAE
Acc#: P26480

Description: RNA POLYMERASE SIGMA FACTOR RPOD (SIGMA-70)

| ORF Name | NTID | AAID | NT Length | AA Length | Score | Probability |
|---|---|---|---|---|---|---|
| 35823506_c2_32 | 347 | 2267 | 514 | 1545 | 1343 | 4.3e-137 |

Protein name: Butyryl-CoA:Acetate Coenzyme A transferase
Locus Name: gp:CTACTAGEN
Acc#: Z69031

Description: C.thermosaccharolyticum actA gene.

| ORF_Name | NTID | AAID | NT Length | AA Length | Score | Probability |
|---|---|---|---|---|---|---|
| 35939753_c2_34 | 348 | 2268 | 73 | 222 | 106 | 7.2e-05 |

| Protein name | Locus Name | Acc# |
|---|---|---|
| probable acyl-CoA dehydrogenase | pir:B75282 | B75282 |

Description

| ORF_Name | NTID | AAID | NT Length | AA Length | Score | Probability |
|---|---|---|---|---|---|---|
| 3917193_c2_33 | 349 | 2269 | 95 | 288 | 147 | 2.9e-09 |

| Protein name | Locus Name | Acc# |
|---|---|---|
| probable acyl-CoA dehydrogenase | pir:B75282 | B75282 |

Description

| ORF_Name | NTID | AAID | NT Length | AA Length | Score | Probability |
|---|---|---|---|---|---|---|
| 3954817_c1_27 | 350 | 2270 | 159 | 480 | 386 | 2.9e-35 |

| Protein name | Locus Name | Acc# |
|---|---|---|
| probable acyl-CoA dehydrogenase | pir:B75282 | B75282 |

Description

| ORF_Name | NTID | AAID | NT Length | AA Length | Score | Probability |
|---|---|---|---|---|---|---|
| 5167157_c2_39 | 351 | 2271 | 161 | 486 | 104 | 8.4e-06 |

| Protein name | Locus Name | Acc# |
|---|---|---|
| hypothetical protein PH1801 | pir:A71191 | A71191 |

Description

| ORF_Name | NTID | AAID | NT Length | AA Length | Score | Probability |
|---|---|---|---|---|---|---|
| 9923125_c2_40 | 352 | 2272 | 73 | 222 | | |

| Protein name | Locus Name | Acc# |
|---|---|---|
| | | |

Description

NO-HIT

| ORF_Name | NTID | AAID | NT Length | AA Length | Score | Probability |
|---|---|---|---|---|---|---|
| 10355437_f2_5 | 353 | 2273 | 147 | 444 | 159 | 2.0e-11 |

Protein name | | | | Locus Name | | Acc# |
| | | | | sp:THID_HAEIN | | P44697 |

Description (HMP-P KINASE)

| ORF_Name | NTID | AAID | NT Length | AA Length | Score | Probability |
|---|---|---|---|---|---|---|
| 23912827_c3_10 | 354 | 2274 | 79 | 240 | | |

Protein name | | | | Locus Name | | Acc# |

Description

NO-HIT

| ORF_Name | NTID | AAID | NT Length | AA Length | Score | Probability |
|---|---|---|---|---|---|---|
| 35267912_c3_11 | 355 | 2275 | 306 | 921 | 483 | 5.8e-46 |

Protein name | | | | Locus Name | | Acc# |
| | | | | sp:PROC_HAEIN | | P43869 |

Description

PYRROLINE-5-CARBOXYLATE REDUCTASE, (P5CR) (P5C REDUCTASE)

| ORF_Name | NTID | AAID | NT Length | AA Length | Score | Probability |
|---|---|---|---|---|---|---|
| 4062840_c2_9 | 356 | 2276 | 191 | 576 | 206 | 1.3e-16 |

Protein name | | | | Locus Name | | Acc# |
| | | | | sp:YGGT_HAEIN | | P44097 |

Description

HYPOTHETICAL PROTEIN HI1036

| ORF_Name | NTID | AAID | NT Length | AA Length | Score | Probability |
|---|---|---|---|---|---|---|
| 10164063_c2_87 | 357 | 2277 | 242 | 729 | 425 | 8.1e-40 |

Protein name | | | | Locus Name | | Acc# |
| | | | | sp:YAEB_ECOLI | | P28634 |

Description

HYPOTHETICAL 26.4 KD PROTEIN IN PROS-RCSF INTERGENIC REGION (ORF3)

| ORF Name | NTID | AAID | NT Length | AA Length | Score | Probability |
|---|---|---|---|---|---|---|
| 14568812_c3_97 | 358 | 2278 | 426 | 1281 | 287 | 5.5e-37 |

| Protein name | Locus Name | Acc# |
|---|---|---|
| probable lipD protein | pir:G70634 | G70634 |

Description

---

| ORF Name | NTID | AAID | NT Length | AA Length | Score | Probability |
|---|---|---|---|---|---|---|
| 14901512_c3_103 | 359 | 2279 | 156 | 471 | 210 | 4.9e-17 |

| Protein name | Locus Name | Acc# |
|---|---|---|
| | sp:HIT_BACSU | O07513 |

Description

HIT PROTEIN

---

| ORF Name | NTID | AAID | NT Length | AA Length | Score | Probability |
|---|---|---|---|---|---|---|
| 164813_f3_52 | 360 | 2280 | 431 | 1296 | 1416 | 7.8e-145 |

| Protein name | Locus Name | Acc# |
|---|---|---|
| | gp:AB025342 | AB025342 |

Description

Moritella marina genes, complete cds, similar to eicosapentaenoicacid synthesis gene cluster.

---

| ORF Name | NTID | AAID | NT Length | AA Length | Score | Probability |
|---|---|---|---|---|---|---|
| 17068763_f1_16 | 361 | 2281 | 337 | 1014 | 1048 | 7.8e-106 |

| Protein name | Locus Name | Acc# |
|---|---|---|
| | sp:HEM2_PSEAE | Q59643 |

Description

SYNTHASE) (ALAD) (ALADH)

---

| ORF Name | NTID | AAID | NT Length | AA Length | Score | Probability |
|---|---|---|---|---|---|---|
| 23444400_c3_92 | 362 | 2282 | 336 | 1011 | 1151 | 9.4e-117 |

| Protein name | Locus Name | Acc# |
|---|---|---|
| | sp:RUVB_ECOLI | P08577 |

Description

HOLLIDAY JUNCTION DNA HELICASE RUVB

| ORF_Name | NTID | AAID | NT Length | AA Length | Score | Probability |
|---|---|---|---|---|---|---|
| 23526552_c2_83 | 363 | 2283 | 422 | 1269 | 316 | 2.9e-28 |

| Protein name | | Locus Name | Acc# |
|---|---|---|---|
| conserved hypothetical protein yueF | | pir:G70007 | G70007 |

Description

| ORF_Name | NTID | AAID | NT Length | AA Length | Score | Probability |
|---|---|---|---|---|---|---|
| 23595281_f1_17 | 364 | 2284 | 783 | 2352 | 2265 | 8.4e-235 |

| Protein name | | Locus Name | Acc# |
|---|---|---|---|
| hypothetical protein b2463 | | pir:F65021 | F65021 |

Description

| ORF_Name | NTID | AAID | NT Length | AA Length | Score | Probability |
|---|---|---|---|---|---|---|
| 23828428_f3_57 | 365 | 2285 | 272 | 819 | 250 | 1.6e-40 |

| Protein name | | Locus Name | Acc# |
|---|---|---|---|
| aldoketoreductase | | gp:AF001865 | AF001865 |

Description

Leishmania mexicana amazonensis aldoketoreductase (PTR-1) gene, complete cds.

| ORF_Name | NTID | AAID | NT Length | AA Length | Score | Probability |
|---|---|---|---|---|---|---|
| 24250012_c1_66 | 366 | 2286 | 576 | 1731 | 1104 | 9.0e-112 |

| Protein name | | Locus Name | Acc# |
|---|---|---|---|
| glycine betaine transporter BetL | | gp:AF102174 | AF102174 |

Description

Listeria monocytogenes glycine betaine transporter BetL (betL) gene, complete cds.

| ORF_Name | NTID | AAID | NT Length | AA Length | Score | Probability |
|---|---|---|---|---|---|---|
| 24313512_f2_37 | 367 | 2287 | 121 | 366 | | |

| Protein name | | Locus Name | Acc# |
|---|---|---|---|
| | | | |

Description

NO-HIT

| ORF Name | NTID | AAID | NT Length | AA Length | Score | Probability |
|---|---|---|---|---|---|---|
| 24317157_f3_55 | 368 | 2288 | 179 | 540 | | |

Protein name | Locus Name | Acc#

Description

NO-HIT

| ORF Name | NTID | AAID | NT Length | AA Length | Score | Probability |
|---|---|---|---|---|---|---|
| 2517175_f1_18 | 369 | 2289 | 78 | 237 | | |

Protein name | Locus Name | Acc#

Description

NO-HIT

| ORF Name | NTID | AAID | NT Length | AA Length | Score | Probability |
|---|---|---|---|---|---|---|
| 29376681_f1_1 | 370 | 2290 | 84 | 255 | | |

Protein name | Locus Name | Acc#

Description

NO-HIT

| ORF Name | NTID | AAID | NT Length | AA Length | Score | Probability |
|---|---|---|---|---|---|---|
| 30360452_f1_6 | 371 | 2291 | 80 | 243 | | |

Protein name | Locus Name | Acc#

Description

NO-HIT

| ORF Name | NTID | AAID | NT Length | AA Length | Score | Probability |
|---|---|---|---|---|---|---|
| 30662517_c3_106 | 372 | 2292 | 479 | 1440 | 514 | 3.0e-49 |

Protein name | Locus Name | Acc#
| | sp:ACRE_ECOLI | P24180

Description

ACRIFLAVIN RESISTANCE PROTEIN E PRECURSOR (ENVC PROTEIN)

| ORF Name | NTID | AAID | NT Length | AA Length | Score | Probability |
|---|---|---|---|---|---|---|
| 31423292_c2_80 | 373 | 2293 | 308 | 927 | 327 | 2.0e-29 |

| Protein name | | | | Locus Name | | Acc# |
|---|---|---|---|---|---|---|
| hypothetical protein Rv0241c | | | | pir:E70938 | | E70938 |

Description

| ORF Name | NTID | AAID | NT Length | AA Length | Score | Probability |
|---|---|---|---|---|---|---|
| 31466_f3_54 | 374 | 2294 | 71 | 216 | | |

| Protein name | | | | Locus Name | | Acc# |
|---|---|---|---|---|---|---|
| | | | | | | |

Description

NO-HIT

| ORF Name | NTID | AAID | NT Length | AA Length | Score | Probability |
|---|---|---|---|---|---|---|
| 34110436_f2_30 | 375 | 2295 | 116 | 351 | 83 | 0.030 |

| Protein name | | | | Locus Name | | Acc# |
|---|---|---|---|---|---|---|
| microfilarial sheath protein SHP3 | | | | gp:LSU54556 | | U54556 |

Description

Litomosoides sigmodontis microfilarial sheath protein SHP3a (shp3a) and microfilarial sheath protein SHP3 (shp3) genes, complete cds.

| ORF Name | NTID | AAID | NT Length | AA Length | Score | Probability |
|---|---|---|---|---|---|---|
| 4147193_f2_29 | 376 | 2296 | 635 | 1908 | 1651 | 3.4e-242 |

| Protein name | | | | Locus Name | | Acc# |
|---|---|---|---|---|---|---|
| dihydroxy-acid dehydratase, | | | | pir:DWECDA | | |

Description

| ORF Name | NTID | AAID | NT Length | AA Length | Score | Probability |
|---|---|---|---|---|---|---|
| 4350088_c3_96 | 377 | 2297 | 458 | 1377 | 863 | 3.1e-86 |

| Protein name | | | | Locus Name | | Acc# |
|---|---|---|---|---|---|---|
| | | | | gp:MLCB1883 | | AL022486 |

Description

Mycobacterium leprae cosmid B1883.

| ORF Name | NTID | AAID | NT Length | AA Length | Score | Probability |
|---|---|---|---|---|---|---|
| 4381318_f3_56 | 378 | 2298 | 250 | 753 | 585 | 9.0e-57 |

| Protein name | | | | | Locus Name | Acc# |
|---|---|---|---|---|---|---|
| | | | | | sp:CCA_ECOLI | P06961 |

Description (TRNA CCA-PYROPHOSPHORYLASE) (CCA-ADDING ENZYME)

| ORF Name | NTID | AAID | NT Length | AA Length | Score | Probability |
|---|---|---|---|---|---|---|
| 4712537_c1_60 | 379 | 2299 | 117 | 354 | | |

| Protein name | | | | | Locus Name | Acc# |
|---|---|---|---|---|---|---|

Description

NO-HIT

| ORF Name | NTID | AAID | NT Length | AA Length | Score | Probability |
|---|---|---|---|---|---|---|
| 4769050_c2_79 | 380 | 2300 | 99 | 300 | 117 | 3.5e-07 |

| Protein name | | | | | Locus Name | Acc# |
|---|---|---|---|---|---|---|
| hypothetical protein APE0395 | | | | | pir:B72732 | B72732 |

Description

| ORF Name | NTID | AAID | NT Length | AA Length | Score | Probability |
|---|---|---|---|---|---|---|
| 5266540_f1_8 | 381 | 2301 | 219 | 660 | | |

| Protein name | | | | | Locus Name | Acc# |
|---|---|---|---|---|---|---|

Description

NO-HIT

| ORF Name | NTID | AAID | NT Length | AA Length | Score | Probability |
|---|---|---|---|---|---|---|
| 6250012_f1_7 | 382 | 2302 | 313 | 942 | 952 | 1.2e-95 |

| Protein name | | | | | Locus Name | Acc# |
|---|---|---|---|---|---|---|
| ferredoxin--NADP+ reductase, | | | | | pir:A57432 | |

Description

| ORF Name | NTID | AAID | NT Length | AA Length | Score | Probability |
|---|---|---|---|---|---|---|
| 6697266_c1_62 | 383 | 2303 | 78 | 237 | | |

Protein name | Locus Name | Acc#

Description

NO-HIT

| ORF Name | NTID | AAID | NT Length | AA Length | Score | Probability |
|---|---|---|---|---|---|---|
| 6817191_c2_89 | 384 | 2304 | 975 | 2925 | 2816 | 3.5e-293 |

Protein name | Locus Name | Acc#
| sp:YHIV_ECOLI | P37637

Description

HYPOTHETICAL 111.5 KD PROTEIN IN HDED-GADA INTERGENIC REGION

| ORF Name | NTID | AAID | NT Length | AA Length | Score | Probability |
|---|---|---|---|---|---|---|
| 781302_c3_98 | 385 | 2305 | 185 | 558 | 541 | 4.1e-52 |

Protein name | Locus Name | Acc#
| sp:HPRT_ECOLI | P36766

Description

HYPOXANTHINE PHOSPHORIBOSYLTRANSFERASE, (HPRT)

| ORF Name | NTID | AAID | NT Length | AA Length | Score | Probability |
|---|---|---|---|---|---|---|
| 100305_c3_168 | 386 | 2306 | 251 | 756 | 528 | 9.8e-51 |

Protein name | Locus Name | Acc#
| sp:YHHW_ECOLI | P46852

Description

HYPOTHETICAL 26.3 KD PROTEIN IN GNTR-GGT INTERGENIC REGION (F231)

| ORF Name | NTID | AAID | NT Length | AA Length | Score | Probability |
|---|---|---|---|---|---|---|
| 10604658_f2_36 | 387 | 2307 | 488 | 1467 | 705 | 1.7e-69 |

Protein name | Locus Name | Acc#
| RdxB | gp:RSU67862 | U67862

Description

Rhodobacter sphaeroides rdxB and rdxH genes, complete cds, and ccoP and rdxI genes, partial cds.

| ORF Name | NTID | AAID | NT Length | AA Length | Score | Probability |
|---|---|---|---|---|---|---|
| 12509836_f2_57 | 388 | 2308 | 137 | 414 | 178 | 1.2e-13 |

Protein name: hypothetical protein R186.1
Locus Name: pir:T24235
Acc#: T24235

Description

| ORF Name | NTID | AAID | NT Length | AA Length | Score | Probability |
|---|---|---|---|---|---|---|
| 1272201_c3_158 | 389 | 2309 | 168 | 507 | 109 | 8.2e-05 |

Protein name: hypothetical protein SPAC869.06c
Locus Name: pir:T39117
Acc#: T39117

Description

| ORF Name | NTID | AAID | NT Length | AA Length | Score | Probability |
|---|---|---|---|---|---|---|
| 13080050_f1_26 | 390 | 2310 | 66 | 201 | 74 | 0.021 |

Protein name: PilT
Locus Name: gp:STAF000001
Acc#:

Description: Salmonella typhi topoisomerase B (topB), single strand bindingprotein (ssb), Ytl2 homolog (ytl2) genes, complete cds; pil operon, complete sequence; Rci (rci) gene, complete cds.

| ORF Name | NTID | AAID | NT Length | AA Length | Score | Probability |
|---|---|---|---|---|---|---|
| 13723751_c3_176 | 391 | 2311 | 423 | 1272 | 1357 | 1.4e-138 |

Protein name: FixNd
Locus Name: gp:RLFIXND
Acc#: Z80339

Description: R.leguminosarum fixNd and fixOd genes.

| ORF Name | NTID | AAID | NT Length | AA Length | Score | Probability |
|---|---|---|---|---|---|---|
| 140_f1_11 | 392 | 2312 | 144 | 435 | | |

Protein name:
Locus Name:
Acc#:

Description

NO-HIT

| ORF Name | NTID | AAID | NT Length | AA Length | Score | Probability |
|---|---|---|---|---|---|---|
| 14650251_c1_125 | 393 | 2313 | 243 | 732 | 385 | 1.4e-35 |
| Protein name | | | | Locus Name | | Acc# |
| | | | | sp:YGBP_HAEIN | | O05029 |

Description

HYPOTHETICAL PROTEIN HI0672

| ORF Name | NTID | AAID | NT Length | AA Length | Score | Probability |
|---|---|---|---|---|---|---|
| 156261_f2_53 | 394 | 2314 | 158 | 477 | 522 | 4.3e-50 |
| Protein name | | | | Locus Name | | Acc# |
| | | | | sp:RL13_HAEIN | | P44387 |

Description

50S RIBOSOMAL PROTEIN L13

| ORF Name | NTID | AAID | NT Length | AA Length | Score | Probability |
|---|---|---|---|---|---|---|
| 15859456_f3_74 | 395 | 2315 | 96 | 291 | 105 | 6.6e-06 |
| Protein name | | | | Locus Name | | Acc# |
| hypothetical protein PH0639 | | | | pir:H71108 | | H71108 |

Description

| ORF Name | NTID | AAID | NT Length | AA Length | Score | Probability |
|---|---|---|---|---|---|---|
| 16803811_f1_13 | 396 | 2316 | 216 | 651 | 87 | 0.040 |
| Protein name | | | | Locus Name | | Acc# |
| somatostatin sst2B receptor | | | | gp:RNSST2B | | X98234 |

Description

R.norvegicus mRNA for somatostatin receptor.

| ORF Name | NTID | AAID | NT Length | AA Length | Score | Probability |
|---|---|---|---|---|---|---|
| 16853590_c3_164 | 397 | 2317 | 233 | 702 | 265 | 7.3e-23 |
| Protein name | | | | Locus Name | | Acc# |
| | | | | sp:YEAZ_ECOLI | | |

Description

HYPOTHETICAL 25.2 KD PROTEIN IN FADD-PABB INTERGENIC REGION

| ORF Name | NTID | AAID | NT Length | AA Length | Score | Probability |
|---|---|---|---|---|---|---|
| 19563312_c2_137 | 398 | 2318 | 96 | 291 | 71 | 0.038 |

| Protein name | | | | | Locus Name | Acc# |
|---|---|---|---|---|---|---|
| | | | | | sp:YYAB_BACSU | P37523 |

Description

HYPOTHETICAL 17.0 KD PROTEIN IN SPO0J-GIDB INTERGENIC REGION

| ORF Name | NTID | AAID | NT Length | AA Length | Score | Probability |
|---|---|---|---|---|---|---|
| 19632661_f3_91 | 399 | 2319 | 134 | 405 | | |

| Protein name | | | | | Locus Name | Acc# |
|---|---|---|---|---|---|---|

Description

NO-HIT

| ORF Name | NTID | AAID | NT Length | AA Length | Score | Probability |
|---|---|---|---|---|---|---|
| 203577_c1_95 | 400 | 2320 | 751 | 2256 | 2566 | 1.1e-266 |

| Protein name | | | | | Locus Name | Acc# |
|---|---|---|---|---|---|---|
| | | | | | sp:CLPB_HAEIN | P44403 |

Description

CLPB PROTEIN

| ORF Name | NTID | AAID | NT Length | AA Length | Score | Probability |
|---|---|---|---|---|---|---|
| 21988931_f3_88 | 401 | 2321 | 211 | 636 | 563 | 1.9e-54 |

| Protein name | | | | | Locus Name | Acc# |
|---|---|---|---|---|---|---|
| | | | | | sp:UCRI_CHRVI | O31214 |

Description (RIESKE IRON-SULFUR PROTEIN) (RISP)

| ORF Name | NTID | AAID | NT Length | AA Length | Score | Probability |
|---|---|---|---|---|---|---|
| 22066661_f2_40 | 402 | 2322 | 191 | 576 | 364 | 2.4e-33 |

| Protein name | | | | | Locus Name | Acc# |
|---|---|---|---|---|---|---|
| | | | | | sp:YAJQ_HAEIN | P44096 |

Description

HYPOTHETICAL PROTEIN HI1034

| ORF Name | NTID | AAID | NT Length | AA Length | Score | Probability |
|---|---|---|---|---|---|---|
| 23525307_c2_146 | 403 | 2323 | 213 | 642 | 554 | 3.5e-58 |

Protein name: cytochrome-c oxidase, type cbb3 chain fixO
Locus Name: pir:S77596
Acc#: S77596

Description:

| ORF Name | NTID | AAID | NT Length | AA Length | Score | Probability |
|---|---|---|---|---|---|---|
| 23720002_c2_140 | 404 | 2324 | 61 | 186 | | |

Protein name:
Locus Name:
Acc#:

Description: NO-HIT

| ORF Name | NTID | AAID | NT Length | AA Length | Score | Probability |
|---|---|---|---|---|---|---|
| 23860681_f2_39 | 405 | 2325 | 455 | 1368 | 1917 | 6.4e-198 |

Protein name:
Locus Name: sp:ASSY_HAEIN
Acc#: P44315

Description: LIGASE)

| ORF Name | NTID | AAID | NT Length | AA Length | Score | Probability |
|---|---|---|---|---|---|---|
| 23864180_f1_18 | 406 | 2326 | 271 | 816 | 254 | 1.1e-21 |

Protein name: CorE
Locus Name: gp:AF130857
Acc#: AF130857

Description: Salmonella typhimurium cobalt resistance locus, partial sequence.

| ORF Name | NTID | AAID | NT Length | AA Length | Score | Probability |
|---|---|---|---|---|---|---|
| 23947151_f1_19 | 407 | 2327 | 102 | 309 | 119 | 2.2e-07 |

| Protein name | Locus Name | Acc# |
|---|---|---|
| unknown | gp:AF147448 | AF147448 |

Description

Pseudomonas aeruginosa strain PAO1 penicillin-binding protein 2(pbpA), rod-shape-determining protein (rodA), membrane-bound lytictransglycosylase (mltB), rare lipoprotein A (rlpA), penicillin-binding protein 5 (dacA), and lipoate biosynthesisprotein B (lipB) genes, complete cds; and unknown gene.

| ORF Name | NTID | AAID | NT Length | AA Length | Score | Probability |
|---|---|---|---|---|---|---|
| 24083208_f3_82 | 408 | 2328 | 71 | 216 | | |

| Protein name | Locus Name | Acc# |
|---|---|---|
| | | |

Description

NO-HIT

| ORF Name | NTID | AAID | NT Length | AA Length | Score | Probability |
|---|---|---|---|---|---|---|
| 24271875_c1_122 | 409 | 2329 | 558 | 1677 | 1857 | 1.5e-191 |

| Protein name | Locus Name | Acc# |
|---|---|---|
| | sp:PYRG_HAEIN | P44341 |

Description

CTP SYNTHASE, (UTP--AMMONIA LIGASE) (CTP SYNTHETASE)

| ORF Name | NTID | AAID | NT Length | AA Length | Score | Probability |
|---|---|---|---|---|---|---|
| 24337827_f1_15 | 410 | 2330 | 355 | 1068 | 1038 | 8.9e-105 |

| Protein name | Locus Name | Acc# |
|---|---|---|
| dihydroorotase, | pir:T10453 | T10453 |

Description

| ORF Name | NTID | AAID | NT Length | AA Length | Score | Probability |
|---|---|---|---|---|---|---|
| 24344138_f3_68 | 411 | 2331 | 70 | 213 | | |

| Protein name | Locus Name | Acc# |
|---|---|---|
| | | |

Description

NO-HIT

| ORF Name | NTID | AAID | NT Length | AA Length | Score | Probability |
|---|---|---|---|---|---|---|
| 24417875_c1_124 | 412 | 2332 | 141 | 426 | 135 | 4.3e-09 |
| Protein name | | | | Locus Name | | Acc# |
| | | | | sp:YGBQ_HAEIN | | P44035 |

Description

HYPOTHETICAL PROTEIN HI0673

| ORF Name | NTID | AAID | NT Length | AA Length | Score | Probability |
|---|---|---|---|---|---|---|
| 24500286_c3_163 | 413 | 2333 | 519 | 1560 | 1458 | 2.6e-152 |
| Protein name | | | | Locus Name | | Acc# |
| | | | | sp:SR54_ECOLI | | P07019 |

Description

SIGNAL RECOGNITION PARTICLE PROTEIN (FIFTY-FOUR HOMOLOG) (P48)

| ORF Name | NTID | AAID | NT Length | AA Length | Score | Probability |
|---|---|---|---|---|---|---|
| 24648402_f1_22 | 414 | 2334 | 1298 | 3897 | 386 | 5.4e-59 |
| Protein name | | | | Locus Name | | Acc# |
| probable exonuclease, | | | | pir:T03465 | | T03465 |

Description

| ORF Name | NTID | AAID | NT Length | AA Length | Score | Probability |
|---|---|---|---|---|---|---|
| 24844562_c3_167 | 415 | 2335 | 548 | 1647 | 1470 | 1.5e-150 |
| Protein name | | | | Locus Name | | Acc# |
| probable pitB protein | | | | pir:E70731 | | E70731 |

Description

| ORF Name | NTID | AAID | NT Length | AA Length | Score | Probability |
|---|---|---|---|---|---|---|
| 29880042_f3_83 | 416 | 2336 | 485 | 1458 | 527 | 3.1e-61 |
| Protein name | | | | Locus Name | | Acc# |
| | | | | sp:SBCD_ECOLI | | P13457 |

Description

EXONUCLEASE SBCD

| ORF_Name | NTID | AAID | NT Length | AA Length | Score | Probability |
|---|---|---|---|---|---|---|
| 3166026_f3_87 | 417 | 2337 | 67 | 204 | | |
| Protein name | | | | Locus Name | | Acc# |
| | | | | | | |

Description

NO-HIT

| ORF_Name | NTID | AAID | NT Length | AA Length | Score | Probability |
|---|---|---|---|---|---|---|
| 33204808_c1_101 | 418 | 2338 | 350 | 1053 | 231 | 2.8e-18 |
| Protein name | | | | Locus Name | | Acc# |
| hypothetical protein RP372 | | | | pir:E71694 | | E71694 |

Description

| ORF_Name | NTID | AAID | NT Length | AA Length | Score | Probability |
|---|---|---|---|---|---|---|
| 3367635_f2_55 | 419 | 2339 | 421 | 1266 | 1355 | 2.3e-138 |
| Protein name | | | | Locus Name | | Acc# |
| | | | | sp:CYB_CHRVI | | O31215 |

Description

CYTOCHROME B

| ORF_Name | NTID | AAID | NT Length | AA Length | Score | Probability |
|---|---|---|---|---|---|---|
| 33707182_f1_27 | 420 | 2340 | 252 | 759 | 364 | 2.7e-46 |
| Protein name | | | | Locus Name | | Acc# |
| | | | | sp:CY1_CHRVI | | O31216 |

Description

CYTOCHROME C1 PRECURSOR

| ORF_Name | NTID | AAID | NT Length | AA Length | Score | Probability |
|---|---|---|---|---|---|---|
| 33875885_c3_157 | 421 | 2341 | 68 | 207 | | |
| Protein name | | | | Locus Name | | Acc# |
| | | | | | | |

Description

NO-HIT

| ORF Name | NTID | AAID | NT Length | AA Length | Score | Probability |
|---|---|---|---|---|---|---|
| 34064681_c1_119 | 422 | 2342 | 87 | 264 | 71 | 0.026 |

| Protein name | Locus Name | Acc# |
|---|---|---|
| cb-type cytochrome c oxidase CcoQ subunit | gp:AB024290 | AB024290 |

Description

Magnetospirillum magnetotacticum ccoN, ccoO, ccoQ, ccoP gene forcb-type cytochrome c oxidase, complete cds.

| ORF Name | NTID | AAID | NT Length | AA Length | Score | Probability |
|---|---|---|---|---|---|---|
| 34120251_c1_105 | 423 | 2343 | 322 | 969 | 647 | 2.4e-63 |

| Protein name | Locus Name | Acc# |
|---|---|---|
|  | sp:UBIA_ECOLI | P26601 |

Description

POLYPRENYLTRANSFERASE)

| ORF Name | NTID | AAID | NT Length | AA Length | Score | Probability |
|---|---|---|---|---|---|---|
| 36379680_c2_127 | 424 | 2344 | 60 | 183 |  |  |

| Protein name | Locus Name | Acc# |
|---|---|---|

Description

NO-HIT

| ORF Name | NTID | AAID | NT Length | AA Length | Score | Probability |
|---|---|---|---|---|---|---|
| 3906686_c3_155 | 425 | 2345 | 653 | 1962 | 2231 | 3.4e-231 |

| Protein name | Locus Name | Acc# |
|---|---|---|
|  | sp:GIDA_PSEPU | P25756 |

Description

GLUCOSE INHIBITED DIVISION PROTEIN A

| ORF Name | NTID | AAID | NT Length | AA Length | Score | Probability |
|---|---|---|---|---|---|---|
| 3932753_c2_149 | 426 | 2346 | 767 | 2304 | 235 | 1.3e-16 |

| Protein name | Locus Name | Acc# |
|---|---|---|
|  | sp:REC2_HAEIN | P44408 |

Description

RECOMBINATION PROTEIN 2

| ORF_Name | NTID | AAID | NT Length | AA Length | Score | Probability |
|---|---|---|---|---|---|---|
| 3942318_f2_54 | 427 | 2347 | 131 | 396 | 507 | 1.7e-48 |

| Protein name | | | | Locus_Name | | Acc# |
|---|---|---|---|---|---|---|
| | | | | sp:RS9_HAESO | | P31782 |

Description

30S RIBOSOMAL PROTEIN S9

| ORF_Name | NTID | AAID | NT Length | AA Length | Score | Probability |
|---|---|---|---|---|---|---|
| 3947193_f2_56 | 428 | 2348 | 132 | 399 | 311 | 9.7e-28 |

| Protein name | | | | Locus_Name | | Acc# |
|---|---|---|---|---|---|---|
| | | | | sp:SSPB_HAEIN | | P45206 |

Description

STRINGENT STARVATION PROTEIN B HOMOLOG

| ORF_Name | NTID | AAID | NT Length | AA Length | Score | Probability |
|---|---|---|---|---|---|---|
| 4119075_c1_103 | 429 | 2349 | 281 | 846 | 464 | 6.0e-44 |

| Protein name | | | | Locus_Name | | Acc# |
|---|---|---|---|---|---|---|
| | | | | sp:BACA_ECOLI | | |

Description (EC 2.7.1.66)

| ORF_Name | NTID | AAID | NT Length | AA Length | Score | Probability |
|---|---|---|---|---|---|---|
| 4334463_c3_172 | 430 | 2350 | 169 | 510 | 78 | 2.8e-05 |

| Protein name | | | | Locus_Name | | Acc# |
|---|---|---|---|---|---|---|
| unknown | | | | gp:AF083916 | | AF083916 |

Description

Rhizobium etli Fnr-type transcriptional regulator FnrNc (fnrNc)gene, complete cds; and unknown genes.

| ORF Name | NTID | AAID | NT Length | AA Length | Score | Probability |
|---|---|---|---|---|---|---|
| 4798193_c3_178 | 431 | 2351 | 358 | 1077 | 368 | 5.6e-48 |

Protein name cytochrome-c oxidase, fixP chain:cb-type cytochrome-c oxidase 32K chain:cytochrome b410:fixP protein

Locus Name: pir:D47468   Acc#: D47468

Description

---

| ORF Name | NTID | AAID | NT Length | AA Length | Score | Probability |
|---|---|---|---|---|---|---|
| 500017_f3_73 | 432 | 2352 | 241 | 726 | 550 | 4.6e-53 |

Protein name

Locus Name: sp:RNT_VIBPA   Acc#: P46232

Description

RIBONUCLEASE T, (EXORIBONUCLEASE T) (RNASE T)

---

| ORF Name | NTID | AAID | NT Length | AA Length | Score | Probability |
|---|---|---|---|---|---|---|
| 520003_c1_126 | 433 | 2353 | 67 | 204 | | |

Protein name

Locus Name:   Acc#:

Description

NO-HIT

---

| ORF Name | NTID | AAID | NT Length | AA Length | Score | Probability |
|---|---|---|---|---|---|---|
| 5203453_c3_181 | 434 | 2354 | 445 | 1338 | 1467 | 3.1e-150 |

Protein name

Locus Name: sp:ENO_ECOLI   Acc#: P08324

Description

(GLYCERATE HYDRO-LYASE)

---

| ORF Name | NTID | AAID | NT Length | AA Length | Score | Probability |
|---|---|---|---|---|---|---|
| 5281318_c3_180 | 435 | 2355 | 290 | 873 | 1037 | 1.1e-104 |

Protein name

2-dehydro-3-deoxyphosphooctonate aldolase

Locus Name: gp:AF098791   Acc#: AF098791

Description

Pseudomonas aeruginosa 2-dehydro-3-deoxyphosphooctonate aldolase(kdsA) gene, complete cds.

| ORF Name | NTID | AAID | NT Length | AA Length | Score | Probability |
|---|---|---|---|---|---|---|
| 5901067_cl_104 | 436 | 2356 | 274 | 825 | 202 | 3.5e-16 |

| Protein name | Locus Name | Acc# |
|---|---|---|
| | sp:YHIQ_HAEIN | P44901 |

Description

HYPOTHETICAL PROTEIN HI0849

| ORF Name | NTID | AAID | NT Length | AA Length | Score | Probability |
|---|---|---|---|---|---|---|
| 7054650_cl_118 | 437 | 2357 | 62 | 189 | 53 | 0.015 |

| Protein name | Locus Name | Acc# |
|---|---|---|
| ORF-D | gp:ECO10KLS | D11109 |

Description

E. coli gene for 10K-L and 10K-S protein.

| ORF Name | NTID | AAID | NT Length | AA Length | Score | Probability |
|---|---|---|---|---|---|---|
| 957705_cl_113 | 438 | 2358 | 335 | 1008 | 407 | 6.5e-38 |

| Protein name | Locus Name | Acc# |
|---|---|---|
| putative regulatory protein | gp:AF087482 | AF087482 |

Description

Pseudomonas aeruginosa clcC and ohbH genes, Lys-R type regulatoryprotein (clcR), chlorocatechol-1,2-dioxygenase (clcA),chloromuconate cycloisomerase (clcB), dienelactone hydrolase(clcD), maleylacetate reductase (clcE), transposase (tnpA),ATP-binding protein (tnpB), putative regulatory protein (ohbR),o-halobenzoate dioxygenase reductase (ohbA), o-halobenzoatedioxygenase alpha subunit (ohbB), o-halobenzoate dioxygenase betasubunit (ohbC),

| ORF Name | NTID | AAID | NT Length | AA Length | Score | Probability |
|---|---|---|---|---|---|---|
| 9960917_f3_90 | 439 | 2359 | 223 | 672 | 354 | 2.7e-32 |

| Protein name | Locus Name | Acc# |
|---|---|---|
| | sp:SSPA_ECOLI | P05838 |

Description

STRINGENT STARVATION PROTEIN A

| ORF Name | NTID | AAID | NT Length | AA Length | Score | Probability |
|---|---|---|---|---|---|---|
| 10632090_f1_17 | 440 | 2360 | 506 | 1521 | 981 | 9.8e-99 |

| Protein name | | | | Locus Name | | Acc# |
|---|---|---|---|---|---|---|
| | | | | sp:NUON_ECOLI | | |

Description

OXIDOREDUCTASE CHAIN 14) (NUO14)

| ORF Name | NTID | AAID | NT Length | AA Length | Score | Probability |
|---|---|---|---|---|---|---|
| 1069465_c1_85 | 441 | 2361 | 75 | 228 | | |

| Protein name | | | | Locus Name | | Acc# |
|---|---|---|---|---|---|---|

Description

NO-HIT

| ORF Name | NTID | AAID | NT Length | AA Length | Score | Probability |
|---|---|---|---|---|---|---|
| 10734830_c1_89 | 442 | 2362 | 60 | 183 | | |

| Protein name | | | | Locus Name | | Acc# |
|---|---|---|---|---|---|---|

Description

NO-HIT

| ORF Name | NTID | AAID | NT Length | AA Length | Score | Probability |
|---|---|---|---|---|---|---|
| 1385390_f3_54 | 443 | 2363 | 216 | 651 | 409 | 4.0e-38 |

| Protein name | | | | Locus Name | | Acc# |
|---|---|---|---|---|---|---|
| | | | | sp:NUOJ_ECOLI | | |

Description

OXIDOREDUCTASE CHAIN 10) (NUO10)

| ORF Name | NTID | AAID | NT Length | AA Length | Score | Probability |
|---|---|---|---|---|---|---|
| 13863425_f2_23 | 444 | 2364 | 276 | 831 | 480 | 1.2e-45 |

| Protein name | | | | Locus Name | | Acc# |
|---|---|---|---|---|---|---|
| hypothetical protein RP682 | | | | pir:E71674 | | E71674 |

Description

| ORF Name | NTID | AAID | NT Length | AA Length | Score | Probability |
|---|---|---|---|---|---|---|
| 14454827_f2_28 | 445 | 2365 | 211 | 636 | 561 | 3.1e-54 |

| Protein name | Locus Name | Acc# |
|---|---|---|
| pyridoxamine 5-phosphate oxidase | pir:B75513 | B75513 |

Description

| ORF Name | NTID | AAID | NT Length | AA Length | Score | Probability |
|---|---|---|---|---|---|---|
| 14475702_c1_90 | 446 | 2366 | 259 | 780 | 91 | 0.00081 |

| Protein name | Locus Name | Acc# |
|---|---|---|
| ORF8 | gp:D78257 | D78257 |

Description

Enterococcus faecalis plasmid pYI17 genes for BacA, BacB, ORF3, ORF4, ORF5, ORF6, ORF7, ORF8, ORF9, ORF10, ORF11, partial cds.

| ORF Name | NTID | AAID | NT Length | AA Length | Score | Probability |
|---|---|---|---|---|---|---|
| 14578202_f1_12 | 447 | 2367 | 182 | 549 | 763 | 1.2e-75 |

| Protein name | Locus Name | Acc# |
|---|---|---|
| | sp:NUOI_ECOLI | |

Description

OXIDOREDUCTASE CHAIN 9) (NUO9)

| ORF Name | NTID | AAID | NT Length | AA Length | Score | Probability |
|---|---|---|---|---|---|---|
| 15625443_c1_84 | 448 | 2368 | 61 | 186 | | |

| Protein name | Locus Name | Acc# |
|---|---|---|
| | | |

Description

NO-HIT

| ORF_Name | NTID | AAID | NT Length | AA Length | Score | Probability |
|---|---|---|---|---|---|---|
| 175760_f3_46 | 449 | 2369 | 215 | 648 | 352 | 4.4e-32 |

Protein name: NADH dehydrogenase chain A
Locus Name: gp:AF057063
Acc#: AF057063

Description:
Erwinia carotovora subsp. carotovora aspartate aminotransferase(aat) gene, partial cds; HexA (hexA), NADH dehydrogenase chain A(nuoA), and NADH dehydrogenase chain B (nuoB) genes, complete cds;and NADH dehydrogenase chain C (nuoC) gene, partial cds.

| ORF_Name | NTID | AAID | NT Length | AA Length | Score | Probability |
|---|---|---|---|---|---|---|
| 19806577_f2_27 | 450 | 2370 | 452 | 1359 | 1177 | 1.7e-119 |

Protein name:
Locus Name: sp:MRSA_HAEIN
Acc#: P45164

Description:
MRSA PROTEIN HOMOLOG

| ORF_Name | NTID | AAID | NT Length | AA Length | Score | Probability |
|---|---|---|---|---|---|---|
| 2110657_f1_3 | 451 | 2371 | 328 | 987 | 760 | 2.6e-75 |

Protein name:
Locus Name: sp:Y926_SYNY3
Acc#: P72872

Description:
HYPOTHETICAL 37.9 KD PROTEIN SLL0926

| ORF_Name | NTID | AAID | NT Length | AA Length | Score | Probability |
|---|---|---|---|---|---|---|
| 22402252_f2_25 | 452 | 2372 | 63 | 192 | | |

Protein name:
Locus Name:
Acc#:

Description:
NO-HIT

| ORF Name | NTID | AAID | NT Length | AA Length | Score | Probability |
|---|---|---|---|---|---|---|
| 23683215_f2_38 | 453 | 2373 | 579 | 1740 | 1583 | 1.6e-162 |

Protein name — Locus Name: sp:NUOM_ECOLI — Acc#

Description: OXIDOREDUCTASE CHAIN 13) (NUO13)

| ORF Name | NTID | AAID | NT Length | AA Length | Score | Probability |
|---|---|---|---|---|---|---|
| 24225213_f3_50 | 454 | 2374 | 266 | 801 | 1183 | 3.8e-120 |

Protein name: Tou2 — Locus Name: gp:AF058689 — Acc#: AF058689

Description: Neisseria meningitidis strain Z2491, genomic sequence.

| ORF Name | NTID | AAID | NT Length | AA Length | Score | Probability |
|---|---|---|---|---|---|---|
| 24226502_c3_132 | 455 | 2375 | 270 | 813 | 888 | 7.0e-89 |

Protein name — Locus Name: sp:Y572_HAEIN — Acc#: P44758

Description: HYPOTHETICAL PROTEIN HI0572

| ORF Name | NTID | AAID | NT Length | AA Length | Score | Probability |
|---|---|---|---|---|---|---|
| 24391557_f1_10 | 456 | 2376 | 1046 | 3141 | 1655 | 8.6e-252 |

Protein name: NADH dehydrogenase (ubiquinone), I chain G:nuoK protein — Locus Name: pir:A65000 — Acc#

Description:

| ORF Name | NTID | AAID | NT Length | AA Length | Score | Probability |
|---|---|---|---|---|---|---|
| 24642893_f1_15 | 457 | 2377 | 619 | 1860 | 1809 | 1.8e-186 |

Protein name — Locus Name: sp:NUOL_ECOLI — Acc#

Description: OXIDOREDUCTASE CHAIN 12) (NUO12)

| ORF Name | NTID | AAID | NT Length | AA Length | Score | Probability |
|---|---|---|---|---|---|---|
| 2507286_f2_22 | 458 | 2378 | 213 | 642 | 770 | 2.2e-76 |

Protein name: outer membrane protein B1
Locus Name: gp:AF045251
Acc#: AF045251

Description: Moraxella catarrhalis outer membrane protein B1 gene, complete cds.

| ORF Name | NTID | AAID | NT Length | AA Length | Score | Probability |
|---|---|---|---|---|---|---|
| 25392135_f2_26 | 459 | 2379 | 61 | 186 | | |

Protein name:
Locus Name:
Acc#:

Description: NO-HIT

| ORF Name | NTID | AAID | NT Length | AA Length | Score | Probability |
|---|---|---|---|---|---|---|
| 25579763_f3_61 | 460 | 2380 | 281 | 846 | 374 | 2.3e-39 |

Protein name:
Locus Name: sp:FENR_ECOLI
Acc#:

Description: (FLXR) (FLDR) (METHYL VIOLOGEN RESISTANCE PROTEIN A) (DA1)

| ORF Name | NTID | AAID | NT Length | AA Length | Score | Probability |
|---|---|---|---|---|---|---|
| 26228401_c2_105 | 461 | 2381 | 156 | 471 | 123 | 8.1e-08 |

Protein name: hypothetical protein APE1413
Locus Name: pir:D72619
Acc#: D72619

Description:

| ORF Name | NTID | AAID | NT Length | AA Length | Score | Probability |
|---|---|---|---|---|---|---|
| 29688176_f1_1 | 462 | 2382 | 70 | 213 | 304 | 4.8e-26 |

Protein name: transferrin-binding protein 2 precursor
Locus Name: gp:AF105251
Acc#: AF105251

Description: Moraxella catarrhalis transferrin-binding protein 2 precursor(ompB1) gene, partial cds.

| ORF Name | NTID | AAID | NT Length | AA Length | Score | Probability |
|---|---|---|---|---|---|---|
| 30082693_f3_51 | 463 | 2383 | 491 | 1476 | 1378 | 8.3e-141 |

Protein name | Locus Name | Acc#
sp:NUOF_ECOLI

Description

OXIDOREDUCTASE CHAIN 6) (NUO6)

| ORF Name | NTID | AAID | NT Length | AA Length | Score | Probability |
|---|---|---|---|---|---|---|
| 30252036_c2_98 | 464 | 2384 | 63 | 192 | | |

Protein name | Locus Name | Acc#

Description

NO-HIT

| ORF Name | NTID | AAID | NT Length | AA Length | Score | Probability |
|---|---|---|---|---|---|---|
| 31283452_f1_11 | 465 | 2385 | 342 | 1029 | 1126 | 4.2e-114 |

Protein name | Locus Name | Acc#
sp:NUOH_ECOLI

Description

OXIDOREDUCTASE CHAIN 8) (NUO8)

| ORF Name | NTID | AAID | NT Length | AA Length | Score | Probability |
|---|---|---|---|---|---|---|
| 3182067_c3_131 | 466 | 2386 | 516 | 1551 | 1966 | 4.1e-203 |

Protein name | Locus Name | Acc#
sp:SYR_HAEIN | P43832

Description

ARGINYL-TRNA SYNTHETASE, (ARGININE--TRNA LIGASE) (ARGRS)

| ORF Name | NTID | AAID | NT Length | AA Length | Score | Probability |
|---|---|---|---|---|---|---|
| 33723387_f1_6 | 467 | 2387 | 235 | 708 | 799 | 1.9e-79 |

Protein name | Locus Name | Acc#
sp:NUOB_ECOLI

Description

OXIDOREDUCTASE CHAIN 2) (NUO2)

| ORF Name | NTID | AAID | NT Length | AA Length | Score | Probability |
|---|---|---|---|---|---|---|
| 33772186_f3_41 | 468 | 2388 | 416 | 1251 | 1601 | 1.9e-164 |

| Protein name | Locus Name | Acc# |
|---|---|---|
| transferrin binding protein B | gp:AF039313 | AF039313 |

Description

Moraxella catarrhalis strain LES-1 transferrin binding protein B (tbpB) gene, complete cds.

| ORF Name | NTID | AAID | NT Length | AA Length | Score | Probability |
|---|---|---|---|---|---|---|
| 34176950_f3_42 | 469 | 2389 | 548 | 1647 | 331 | 2.2e-29 |

| Protein name | Locus Name | Acc# |
|---|---|---|
|  | sp:Y170_METJA | Q57634 |

Description

HYPOTHETICAL PROTEIN MJ0170

| ORF Name | NTID | AAID | NT Length | AA Length | Score | Probability |
|---|---|---|---|---|---|---|
| 34414552_f3_47 | 470 | 2390 | 584 | 1755 | 2190 | 7.5e-227 |

| Protein name | Locus Name | Acc# |
|---|---|---|
| NADH dehydrogenase (ubiquinone), I, chain C-D | pir:D65000 |  |

Description

| ORF Name | NTID | AAID | NT Length | AA Length | Score | Probability |
|---|---|---|---|---|---|---|
| 35166075_f1_4 | 471 | 2391 | 294 | 885 | 315 | 3.7e-28 |

| Protein name | Locus Name | Acc# |
|---|---|---|
| periplasmic chaperone protein | gp:AF095845 | AF095845 |

Description

Pseudomonas syringae cell division/stress response protein (ftsK) and periplasmic chaperone protein (lolA) genes, complete cds.

| ORF Name | NTID | AAID | NT Length | AA Length | Score | Probability |
|---|---|---|---|---|---|---|
| 36144687_f3_49 | 472 | 2392 | 62 | 189 | 240 | 3.2e-20 |

| Protein name | | | | Locus Name | | Acc# |
|---|---|---|---|---|---|---|
| | | | | sp:NUOD_SALTY | | P33902 |

Description

OXIDOREDUCTASE CHAIN 4) (NUO4) (FRAGMENT)

| ORF Name | NTID | AAID | NT Length | AA Length | Score | Probability |
|---|---|---|---|---|---|---|
| 3915693_c1_80 | 473 | 2393 | 416 | 1251 | 211 | 1.7e-14 |

| Protein name | | | | Locus Name | | Acc# |
|---|---|---|---|---|---|---|
| | | | | gp:ECPMC7A | | X57583 |

Description

E.coli Plasmid pMccC7 mccA,B,C,D,E,F genes.

| ORF Name | NTID | AAID | NT Length | AA Length | Score | Probability |
|---|---|---|---|---|---|---|
| 4740902_c2_127 | 474 | 2394 | 313 | 942 | 114 | 0.00043 |

| Protein name | | | | Locus Name | | Acc# |
|---|---|---|---|---|---|---|
| | | | | sp:PRXH_BPMD2 | | O64252 |

Description

PUTATIVE NON-HEME HALOPEROXIDASE,

| ORF Name | NTID | AAID | NT Length | AA Length | Score | Probability |
|---|---|---|---|---|---|---|
| 4796875_f1_5 | 475 | 2395 | 78 | 237 | 144 | 4.8e-10 |

| Protein name | | | | Locus Name | | Acc# |
|---|---|---|---|---|---|---|
| conserved hypothetical protein | | | | pir:H75273 | | H75273 |

Description

| ORF Name | NTID | AAID | NT Length | AA Length | Score | Probability |
|---|---|---|---|---|---|---|
| 5097886_f1_14 | 476 | 2396 | 145 | 438 | 320 | 1.1e-28 |

| Protein name | | | | Locus Name | | Acc# |
|---|---|---|---|---|---|---|
| | | | | sp:NUOK_ECOLI | | |

Description

OXIDOREDUCTASE CHAIN 11) (NUO11)

| ORF_Name | NTID | AAID | NT Length | AA Length | Score | Probability |
|---|---|---|---|---|---|---|
| 7226452_f1_9 | 477 | 2397 | 174 | 525 | 470 | 1.4e-44 |

| Protein name | | | | Locus Name | | Acc# |
|---|---|---|---|---|---|---|
| | | | | sp:NUOE_SALTY | | P33903 |

Description

OXIDOREDUCTASE CHAIN 5) (NUO5)

| ORF_Name | NTID | AAID | NT Length | AA Length | Score | Probability |
|---|---|---|---|---|---|---|
| 10181576_f2_42 | 478 | 2398 | 101 | 306 | | |

| Protein name | Locus Name | Acc# |
|---|---|---|

Description

NO-HIT

| ORF_Name | NTID | AAID | NT Length | AA Length | Score | Probability |
|---|---|---|---|---|---|---|
| 10751312_f1_7 | 479 | 2399 | 939 | 2820 | 710 | 2.9e-114 |

| Protein name | | | | Locus Name | | Acc# |
|---|---|---|---|---|---|---|
| | | | | sp:YCBY_HAEIN | | |

Description

HYPOTHETICAL PROTEIN HI0116/115

| ORF_Name | NTID | AAID | NT Length | AA Length | Score | Probability |
|---|---|---|---|---|---|---|
| 10975302_c1_93 | 480 | 2400 | 293 | 882 | 185 | 2.5e-13 |

| Protein name | | | | Locus Name | | Acc# |
|---|---|---|---|---|---|---|
| probable D,D-carboxypeptidase | | | | pir:B71353 | | B71353 |

Description

| ORF_Name | NTID | AAID | NT Length | AA Length | Score | Probability |
|---|---|---|---|---|---|---|
| 19587762_c1_77 | 481 | 2401 | 89 | 270 | | |

| Protein name | Locus Name | Acc# |
|---|---|---|

Description

NO-HIT

| ORF_Name | NTID | AAID | NT Length | AA Length | Score | Probability |
|---|---|---|---|---|---|---|
| 19735877_f2_34 | 482 | 2402 | 63 | 192 | | |

| Protein name | | | | Locus_Name | | Acc# |
|---|---|---|---|---|---|---|
| | | | | | | |

Description

NO-HIT

| ORF_Name | NTID | AAID | NT Length | AA Length | Score | Probability |
|---|---|---|---|---|---|---|
| 21491075_c3_127 | 483 | 2403 | 517 | 1554 | 309 | 1.4e-41 |

| Protein name | | | | Locus_Name | | Acc# |
|---|---|---|---|---|---|---|
| CjaB protein | | | | gp:CJE17971 | | Y17971 |

Description

Campylobacter jejuni cjaB gene.

| ORF_Name | NTID | AAID | NT Length | AA Length | Score | Probability |
|---|---|---|---|---|---|---|
| 21520276_c3_136 | 484 | 2404 | 275 | 828 | | |

| Protein name | | | | Locus_Name | | Acc# |
|---|---|---|---|---|---|---|
| | | | | | | |

Description

NO-HIT

| ORF_Name | NTID | AAID | NT Length | AA Length | Score | Probability |
|---|---|---|---|---|---|---|
| 21603403_c3_126 | 485 | 2405 | 543 | 1632 | 857 | 1.3e-85 |

| Protein name | | | | Locus_Name | | Acc# |
|---|---|---|---|---|---|---|
| | | | | sp:YMDC_ECOLI | | P75919 |

Description

HYPOTHETICAL 55.9 KD PROTEIN IN CSGC-MDOG INTERGENIC REGION

| ORF_Name | NTID | AAID | NT Length | AA Length | Score | Probability |
|---|---|---|---|---|---|---|
| 21679677_f3_58 | 486 | 2406 | 476 | 1431 | 1649 | 1.6e-169 |

| Protein name | | | | Locus_Name | | Acc# |
|---|---|---|---|---|---|---|
| | | | | sp:GLNA_AZOVI | | P22248 |

Description

GLUTAMINE SYNTHETASE, (GLUTAMATE--AMMONIA LIGASE)

| ORF Name | NTID | AAID | NT Length | AA Length | Score | Probability |
|---|---|---|---|---|---|---|
| 22306532_c3_134 | 487 | 2407 | 255 | 768 | 426 | 6.3e-40 |

| Protein name | | | | Locus Name | | Acc# |
|---|---|---|---|---|---|---|
| | | | | sp:LPSA_PASHA | | Q05770 |

Description

LPSA PROTEIN

| ORF Name | NTID | AAID | NT Length | AA Length | Score | Probability |
|---|---|---|---|---|---|---|
| 22442010_f1_1 | 488 | 2408 | 354 | 1065 | 450 | 1.8e-42 |

| Protein name | | | | Locus Name | | Acc# |
|---|---|---|---|---|---|---|
| unknown | | | | gp:AF116284 | | AF116284 |

Description

Pseudomonas aeruginosa DnaJ-like protein gene, complete cds; and unknown genes.

| ORF Name | NTID | AAID | NT Length | AA Length | Score | Probability |
|---|---|---|---|---|---|---|
| 2375337_f3_49 | 489 | 2409 | 60 | 183 | | |

| Protein name | | | | Locus Name | | Acc# |
|---|---|---|---|---|---|---|

Description

NO-HIT

| ORF Name | NTID | AAID | NT Length | AA Length | Score | Probability |
|---|---|---|---|---|---|---|
| 23944431_c2_116 | 490 | 2410 | 80 | 243 | 106 | 5.1e-06 |

| Protein name | | | | Locus Name | | Acc# |
|---|---|---|---|---|---|---|
| hypothetical protein APE0029 | | | | pir:H72754 | | H72754 |

Description

| ORF Name | NTID | AAID | NT Length | AA Length | Score | Probability |
|---|---|---|---|---|---|---|
| 23945931_f3_55 | 491 | 2411 | 346 | 1041 | 136 | 1.2e-06 |

| Protein name | | | | Locus Name | | Acc# |
|---|---|---|---|---|---|---|
| hypothetical protein slr1166 | | | | pir:S75877 | | S75877 |

Description

| ORF Name | NTID | AAID | NT Length | AA Length | Score | Probability |
|---|---|---|---|---|---|---|
| 23954511_f1_6 | 492 | 2412 | 811 | 2436 | 2745 | 1.2e-285 |

| Protein name | | | | Locus Name | | Acc# |
|---|---|---|---|---|---|---|
| | | | | sp:PPSA_ECOLI | | P23538 |

Description (PEP SYNTHASE)

| ORF Name | NTID | AAID | NT Length | AA Length | Score | Probability |
|---|---|---|---|---|---|---|
| 23989752_c1_84 | 493 | 2413 | 166 | 501 | 288 | 1.0e-42 |

| Protein name | | | | Locus Name | | Acc# |
|---|---|---|---|---|---|---|
| | | | | sp:3DHQ_NEUCR | | P05195 |

Description (DEHYDRATASE)

| ORF Name | NTID | AAID | NT Length | AA Length | Score | Probability |
|---|---|---|---|---|---|---|
| 24306512_c2_99 | 494 | 2414 | 202 | 609 | 509 | 1.0e-48 |

| Protein name | | | | Locus Name | | Acc# |
|---|---|---|---|---|---|---|
| | | | | sp:GCH1_OSTOS | | O61573 |

Description

GTP CYCLOHYDROLASE I, (GTP-CH-I)

| ORF Name | NTID | AAID | NT Length | AA Length | Score | Probability |
|---|---|---|---|---|---|---|
| 24337752_f2_32 | 495 | 2415 | 378 | 1137 | 884 | 1.9e-88 |

| Protein name | | | | Locus Name | | Acc# |
|---|---|---|---|---|---|---|
| | | | | sp:YDAO_ECOLI | | |

Description

HYPOTHETICAL 35.6 KD PROTEIN IN DBPA-INTR INTERGENIC REGION

| ORF Name | NTID | AAID | NT Length | AA Length | Score | Probability |
|---|---|---|---|---|---|---|
| 24646887_f1_16 | 496 | 2416 | 169 | 510 | | |

| Protein name | | | | Locus Name | | Acc# |
|---|---|---|---|---|---|---|

Description

NO-HIT

| ORF Name | NTID | AAID | NT Length | AA Length | Score | Probability |
|---|---|---|---|---|---|---|
| 24881717_f2_39 | 497 | 2417 | 107 | 324 | | |

Protein name | Locus Name | Acc#

Description

NO-HIT

| ORF Name | NTID | AAID | NT Length | AA Length | Score | Probability |
|---|---|---|---|---|---|---|
| 25595262_f3_68 | 498 | 2418 | 168 | 507 | | |

Protein name | Locus Name | Acc#

Description

NO-HIT

| ORF Name | NTID | AAID | NT Length | AA Length | Score | Probability |
|---|---|---|---|---|---|---|
| 26354750_f3_50 | 499 | 2419 | 60 | 183 | | |

Protein name | Locus Name | Acc#

Description

NO-HIT

| ORF Name | NTID | AAID | NT Length | AA Length | Score | Probability |
|---|---|---|---|---|---|---|
| 29332503_f3_66 | 500 | 2420 | 301 | 906 | 797 | 3.1e-79 |

Protein name: enoyl-(acyl-carrier protein) reductase | Locus Name: gp:AF104262 | Acc#: AF104262

Description

Pseudomonas aeruginosa enoyl-(acyl-carrier protein) reductase(fabI) gene, complete cds.

| ORF Name | NTID | AAID | NT Length | AA Length | Score | Probability |
|---|---|---|---|---|---|---|
| 29335786_f3_46 | 501 | 2421 | 249 | 750 | 428 | 3.9e-40 |

Protein name: unknown | Locus Name: gp:AF116284 | Acc#: AF116284

Description

Pseudomonas aeruginosa DnaJ-like protein gene, complete cds; andunknown genes.

| ORF Name | NTID | AAID | NT Length | AA Length | Score | Probability |
|---|---|---|---|---|---|---|
| 29382075_f1_4 | 502 | 2422 | 312 | 939 | 429 | 3.0e-40 |

| Protein name | Locus Name | Acc# |
|---|---|---|
| probable membrane protein b1520 | pir:C64906 | C64906 |

Description

| ORF Name | NTID | AAID | NT Length | AA Length | Score | Probability |
|---|---|---|---|---|---|---|
| 31425825_f1_22 | 503 | 2423 | 220 | 663 | 771 | 1.7e-76 |

| Protein name | Locus Name | Acc# |
|---|---|---|
| | sp:RPE_HAEIN | P44756 |

Description

EPIMERASE) (PPE) (R5P3E)

| ORF Name | NTID | AAID | NT Length | AA Length | Score | Probability |
|---|---|---|---|---|---|---|
| 32177_c3_133 | 504 | 2424 | 64 | 195 | | |

| Protein name | Locus Name | Acc# |
|---|---|---|
| | | |

Description

NO-HIT

| ORF Name | NTID | AAID | NT Length | AA Length | Score | Probability |
|---|---|---|---|---|---|---|
| 3316436_f1_19 | 505 | 2425 | 462 | 1389 | 331 | 7.4e-30 |

| Protein name | Locus Name | Acc# |
|---|---|---|
| | sp:VISC_ECOLI | P25535 |

Description

VISC PROTEIN,

| ORF Name | NTID | AAID | NT Length | AA Length | Score | Probability |
|---|---|---|---|---|---|---|
| 33632828_f3_62 | 506 | 2426 | 249 | 750 | 559 | 5.1e-54 |

| Protein name | Locus Name | Acc# |
|---|---|---|
| ribose-5-phosphate isomerase | gp:AF037440 | AF037440 |

Description

Edwardsiella ictaluri D-3-phosphoglycerate dehydrogenase (serA)gene, partial cds; ribose-5-phosphate isomerase (rpiA), inhibitorof chromosome initiation (iciA), putative 26 kDa protein (yggE),putative 30.6 kDa protein (yggB), and fructose 1,6-bisphosphatealdolase (fda) genes, complete cds; and phosphoglycerate kinase(pgk) gene, partial cds.

| ORF Name | NTID | AAID | NT Length | AA Length | Score | Probability |
|---|---|---|---|---|---|---|
| 33863431_f3_53 | 507 | 2427 | 430 | 1293 | 456 | 4.2e-43 |

| Protein name | Locus Name | Acc# |
|---|---|---|
| conserved hypothetical protein | pir:F75546 | F75546 |

Description

| ORF Name | NTID | AAID | NT Length | AA Length | Score | Probability |
|---|---|---|---|---|---|---|
| 35163902_c2_109 | 508 | 2428 | 627 | 1884 | 960 | 8.9e-103 |

| Protein name | Locus Name | Acc# |
|---|---|---|
|  | sp:MSBA_ECOLI | P27299 |

Description

PROBABLE TRANSPORT ATP-BINDING PROTEIN MSBA

| ORF Name | NTID | AAID | NT Length | AA Length | Score | Probability |
|---|---|---|---|---|---|---|
| 35350061_c2_98 | 509 | 2429 | 64 | 195 |  |  |

| Protein name | Locus Name | Acc# |
|---|---|---|

Description

NO-HIT

| ORF Name | NTID | AAID | NT Length | AA Length | Score | Probability |
|---|---|---|---|---|---|---|
| 36128378_f3_67 | 510 | 2430 | 124 | 375 | | |

| Protein name | | | Locus Name | | | Acc# |
|---|---|---|---|---|---|---|

Description

NO-HIT

| ORF Name | NTID | AAID | NT Length | AA Length | Score | Probability |
|---|---|---|---|---|---|---|
| 3912568_c1_92 | 511 | 2431 | 525 | 1578 | 1470 | 1.5e-150 |

| Protein name | | | Locus Name | | | Acc# |
|---|---|---|---|---|---|---|
| soluble pyridine nucleotide transhydrogenase | | | gp:AF159108 | | | AF159108 |

Description

Azotobacter vinelandii soluble pyridine nucleotide transhydrogenase(sth) gene, complete cds.

| ORF Name | NTID | AAID | NT Length | AA Length | Score | Probability |
|---|---|---|---|---|---|---|
| 4111008_f2_33 | 512 | 2432 | 94 | 285 | 240 | 3.2e-20 |

| Protein name | | | Locus Name | | | Acc# |
|---|---|---|---|---|---|---|
| | | | sp:CSPA_PSEAE | | | P95459 |

Description

MAJOR COLD SHOCK PROTEIN CSPA

| ORF Name | NTID | AAID | NT Length | AA Length | Score | Probability |
|---|---|---|---|---|---|---|
| 4500892_c1_91 | 513 | 2433 | 291 | 876 | 599 | 2.9e-58 |

| Protein name | | | Locus Name | | | Acc# |
|---|---|---|---|---|---|---|
| | | | sp:YDIA_ECOLI | | | |

Description

HYPOTHETICAL 31.2 KD PROTEIN IN PPSA-AROH INTERGENIC REGION

| ORF Name | NTID | AAID | NT Length | AA Length | Score | Probability |
|---|---|---|---|---|---|---|
| 5132667_f1_12 | 514 | 2434 | 368 | 1107 | 124 | 6.4e-05 |

| Protein name | Locus Name | Acc# |
|---|---|---|
| mannosyltransferase-like protein | gp:YPS251712 | AJ251712 |

Description

Yersinia pseudotuberculosis serotype O:1b hemH gene (partial) andO-antigen gene cluster for ddhD gene, ddhA gene, ddhB gene, ddhCgene, prt gene, wbyH gene, wzx gene, wbyI gene, wbyJ gene, wzygene, wbyK gene, gmd gene, fcl gene, manC gene, wbyL gene, manBgene and wzz gene.

| ORF Name | NTID | AAID | NT Length | AA Length | Score | Probability |
|---|---|---|---|---|---|---|
| 5859762_c2_120 | 515 | 2435 | 115 | 348 | | |

| Protein name | Locus Name | Acc# |
|---|---|---|
| | | |

Description

NO-HIT

| ORF Name | NTID | AAID | NT Length | AA Length | Score | Probability |
|---|---|---|---|---|---|---|
| 5894501_c1_82 | 516 | 2436 | 551 | 1656 | 564 | 1.5e-54 |

| Protein name | Locus Name | Acc# |
|---|---|---|
| | sp:Y653_HAEIN | P44029 |

Description

HYPOTHETICAL PROTEIN HI0653

| ORF Name | NTID | AAID | NT Length | AA Length | Score | Probability |
|---|---|---|---|---|---|---|
| 5993768_c2_122 | 517 | 2437 | 514 | 1542 | 305 | 4.6e-24 |

| Protein name | Locus Name | Acc# |
|---|---|---|
| | sp:OSTA_HAEIN | P44846 |

Description

ORGANIC SOLVENT TOLERANCE PROTEIN HOMOLOG PRECURSOR

| ORF Name | NTID | AAID | NT Length | AA Length | Score | Probability |
|---|---|---|---|---|---|---|
| 7150051_c3_131 | 518 | 2438 | 70 | 213 | 131 | 1.2e-08 |

| Protein name | | | | Locus Name | | Acc# |
|---|---|---|---|---|---|---|
| hypothetical protein APE2143 | | | | pir:B72521 | | B72521 |

Description

| ORF Name | NTID | AAID | NT Length | AA Length | Score | Probability |
|---|---|---|---|---|---|---|
| 977055_c3_129 | 519 | 2439 | 327 | 984 | 505 | 2.7e-48 |

| Protein name | | | | Locus Name | | Acc# |
|---|---|---|---|---|---|---|
| | | | | sp:YBJE_ECOLI | | P75826 |

Description

HYPOTHETICAL 34.4 KD PROTEIN IN POXB-AQPZ INTERGENIC REGION

| ORF Name | NTID | AAID | NT Length | AA Length | Score | Probability |
|---|---|---|---|---|---|---|
| 9882793_c3_128 | 520 | 2440 | 65 | 198 | 109 | 2.5e-06 |

| Protein name | | | | Locus Name | | Acc# |
|---|---|---|---|---|---|---|
| hypothetical protein APE0666 | | | | pir:F72654 | | F72654 |

Description

| ORF Name | NTID | AAID | NT Length | AA Length | Score | Probability |
|---|---|---|---|---|---|---|
| 23615951_c1_12 | 521 | 2441 | 125 | 378 | 182 | 4.5e-14 |

| Protein name | | | | Locus Name | | Acc# |
|---|---|---|---|---|---|---|
| adhesin complex 25K protein precursor:LecA protein | | | | pir:JC5327 | | |

Description

| ORF Name | NTID | AAID | NT Length | AA Length | Score | Probability |
|---|---|---|---|---|---|---|
| 24259425_c3_15 | 522 | 2442 | 165 | 498 | 194 | 2.4e-15 |

| Protein name | | | | Locus Name | | Acc# |
|---|---|---|---|---|---|---|
| adhesin complex 25K protein precursor:LecA protein | | | | pir:JC5327 | | |

Description

| ORF Name | NTID | AAID | NT Length | AA Length | Score | Probability |
|---|---|---|---|---|---|---|
| 33986343_f3_10 | 523 | 2443 | 699 | 2100 | 2411 | 2.9e-250 |

| Protein name | Locus Name | Acc# |
|---|---|---|
| oligopeptidepermease | gp:SPOPPDACA | X89237 |

Description

S.pyogenes DNA for oppA, oppB, oppC, oppD, oppF, and dacA genes.

| ORF Name | NTID | AAID | NT Length | AA Length | Score | Probability |
|---|---|---|---|---|---|---|
| 4727338_f3_9 | 524 | 2444 | 325 | 978 | 1264 | 1.0e-128 |

| Protein name | Locus Name | Acc# |
|---|---|---|
| oligopeptidepermease | gp:SPOPPDACA | X89237 |

Description

S.pyogenes DNA for oppA, oppB, oppC, oppD, oppF, and dacA genes.

| ORF Name | NTID | AAID | NT Length | AA Length | Score | Probability |
|---|---|---|---|---|---|---|
| 4788508_f3_11 | 525 | 2445 | 63 | 192 | | |

| Protein name | Locus Name | Acc# |
|---|---|---|
| | | |

Description

NO-HIT

| ORF Name | NTID | AAID | NT Length | AA Length | Score | Probability |
|---|---|---|---|---|---|---|
| 6053212_f3_8 | 526 | 2446 | 340 | 1023 | 1398 | 6.3e-143 |

| Protein name | Locus Name | Acc# |
|---|---|---|
| oligopeptidepermease | gp:SPOPPDACA | X89237 |

Description

S.pyogenes DNA for oppA, oppB, oppC, oppD, oppF, and dacA genes.

| ORF Name | NTID | AAID | NT Length | AA Length | Score | Probability |
|---|---|---|---|---|---|---|
| 12265658_c2_101 | 527 | 2447 | 221 | 666 | 753 | 1.4e-74 |

| Protein name | Locus Name | Acc# |
|---|---|---|
| | sp:DP3X_HAEIN | P43746 |

Description

DNA POLYMERASE III SUBUNIT GAMMA/TAU,

| ORF Name | NTID | AAID | NT Length | AA Length | Score | Probability |
|---|---|---|---|---|---|---|
| 12501562_c2_109 | 528 | 2448 | 214 | 645 | 254 | 3.5e-21 |

| Protein name | Locus Name | Acc# |
|---|---|---|
| hemolysin-related protein | pir:F72326 | F72326 |

Description

---

| ORF Name | NTID | AAID | NT Length | AA Length | Score | Probability |
|---|---|---|---|---|---|---|
| 12605253_c1_85 | 529 | 2449 | 967 | 2904 | 563 | 1.3e-65 |

| Protein name | Locus Name | Acc# |
|---|---|---|
| | sp:MLTD_ECOLI | |

Description (MUREIN HYDROLASE D) (REGULATORY PROTEIN DNIR)

---

| ORF Name | NTID | AAID | NT Length | AA Length | Score | Probability |
|---|---|---|---|---|---|---|
| 12891082_f3_51 | 530 | 2450 | 237 | 714 | 234 | 1.4e-19 |

| Protein name | Locus Name | Acc# |
|---|---|---|
| | sp:YBHD_ECOLI | |

Description

HYPOTHETICAL TRANSCRIPTIONAL REGULATOR IN MODC-BIOA INTERGENIC REGION

---

| ORF Name | NTID | AAID | NT Length | AA Length | Score | Probability |
|---|---|---|---|---|---|---|
| 13876010_f1_11 | 531 | 2451 | 135 | 408 | 156 | 7.0e-11 |

| Protein name | Locus Name | Acc# |
|---|---|---|
| | sp:RBCR_CHRVI | P25544 |

Description

RUBISCO OPERON TRANSCRIPTIONAL REGULATOR

---

| ORF Name | NTID | AAID | NT Length | AA Length | Score | Probability |
|---|---|---|---|---|---|---|
| 15870706_c1_68 | 532 | 2452 | 344 | 1035 | 1009 | 1.1e-101 |

| Protein name | Locus Name | Acc# |
|---|---|---|
| | sp:LEU2_ECOLI | |

Description (ISOPROPYLMALATE ISOMERASE) (ALPHA-IPM ISOMERASE) (IPMI)

| ORF Name | NTID | AAID | NT Length | AA Length | Score | Probability |
|---|---|---|---|---|---|---|
| 175062_c1_79 | 533 | 2453 | 219 | 660 | 740 | 3.4e-73 |

| Protein name | | | | Locus Name | | Acc# |
|---|---|---|---|---|---|---|
| | | | | sp:HPPD_PSESP | | P80064 |

Description

4-HYDROXYPHENYLPYRUVATE DIOXYGENASE, (4HPPD) (HPD)

| ORF Name | NTID | AAID | NT Length | AA Length | Score | Probability |
|---|---|---|---|---|---|---|
| 19769052_c1_74 | 534 | 2454 | 131 | 396 | 294 | 2.0e-25 |

| Protein name | | | | Locus Name | | Acc# |
|---|---|---|---|---|---|---|
| | | | | sp:SYK_ACICA | | Q43990 |

Description

LYSYL-TRNA SYNTHETASE, (LYSINE--TRNA LIGASE) (LYSRS)

| ORF Name | NTID | AAID | NT Length | AA Length | Score | Probability |
|---|---|---|---|---|---|---|
| 20178438_c1_80 | 535 | 2455 | 173 | 522 | 629 | 1.9e-61 |

| Protein name | | | | Locus Name | | Acc# |
|---|---|---|---|---|---|---|
| | | | | sp:HPPD_PSESP | | P80064 |

Description

4-HYDROXYPHENYLPYRUVATE DIOXYGENASE, (4HPPD) (HPD)

| ORF Name | NTID | AAID | NT Length | AA Length | Score | Probability |
|---|---|---|---|---|---|---|
| 21729513_c3_129 | 536 | 2456 | 61 | 186 | | |

| Protein name | | | | Locus Name | | Acc# |
|---|---|---|---|---|---|---|

Description

NO-HIT

| ORF Name | NTID | AAID | NT Length | AA Length | Score | Probability |
|---|---|---|---|---|---|---|
| 21738306_f2_30 | 537 | 2457 | 100 | 303 | 185 | 4.9e-14 |

| Protein name | | | | Locus Name | | Acc# |
|---|---|---|---|---|---|---|
| | | | | sp:SECF_HAEIN | | P44590 |

Description

PROTEIN-EXPORT MEMBRANE PROTEIN SECF

| ORF_Name | NTID | AAID | NT Length | AA Length | Score | Probability |
|---|---|---|---|---|---|---|
| 22443750_c3_128 | 538 | 2458 | 201 | 606 | 166 | 8.1e-12 |

| Protein name | | | | Locus Name | | Acc# |
|---|---|---|---|---|---|---|
| | | | | sp:YC54_SYNY3 | | P74078 |

Description

HYPOTHETICAL 38.3 KD PROTEIN SLL1254

| ORF_Name | NTID | AAID | NT Length | AA Length | Score | Probability |
|---|---|---|---|---|---|---|
| 23572128_c1_92 | 539 | 2459 | 103 | 312 | 179 | 6.0e-13 |

| Protein name | | | | Locus Name | | Acc# |
|---|---|---|---|---|---|---|
| | | | | sp:RADA_PSEAE | | P96963 |

Description

DNA REPAIR PROTEIN RADA HOMOLOG (DNA REPAIR PROTEIN SMS HOMOLOG)

| ORF_Name | NTID | AAID | NT Length | AA Length | Score | Probability |
|---|---|---|---|---|---|---|
| 23614376_c3_119 | 540 | 2460 | 312 | 939 | 742 | 2.1e-73 |

| Protein name | | | | Locus Name | | Acc# |
|---|---|---|---|---|---|---|
| | | | | sp:EX3_HAEIN | | P44318 |

Description

EXODEOXYRIBONUCLEASE III, (EXONUCLEASE III) (EXO III)

| ORF_Name | NTID | AAID | NT Length | AA Length | Score | Probability |
|---|---|---|---|---|---|---|
| 23994182_f1_17 | 541 | 2461 | 171 | 516 | 175 | 2.5e-13 |

| Protein name | | | | Locus Name | | Acc# |
|---|---|---|---|---|---|---|
| orf1 | | | | gp:PAU39558 | | U39558 |

Description

Pseudomonas aeruginosa orf1, TolQ (tolQ), TolR (tolR), TolA (tolA),and TolB (tolB) genes, complete cds.

| ORF Name | NTID | AAID | NT Length | AA Length | Score | Probability |
|---|---|---|---|---|---|---|
| 24276625_c3_122 | 542 | 2462 | 293 | 882 | 337 | 1.7e-30 |

Protein name | | | | Locus Name | | Acc# |
| | | | | sp:YGIP_ECOLI | | P45463 |

Description

HYPOTHETICAL TRANSCRIPTIONAL REGULATOR IN BACA-TTDA INTERGENIC REGION

| ORF Name | NTID | AAID | NT Length | AA Length | Score | Probability |
|---|---|---|---|---|---|---|
| 24406575_c1_69 | 543 | 2463 | 227 | 684 | 780 | 1.9e-77 |

Protein name | | | | Locus Name | | Acc# |
| | | | | sp:LEUD_AZOVI | | P96196 |

Description (ISOPROPYLMALATE ISOMERASE) (ALPHA-IPM ISOMERASE)

| ORF Name | NTID | AAID | NT Length | AA Length | Score | Probability |
|---|---|---|---|---|---|---|
| 24415911_c3_115 | 544 | 2464 | 97 | 294 | 97 | 4.6e-05 |

Protein name: outer membrane protein H.8 precursor | Locus Name: pir:S04157 | Acc#: S04157

Description

| ORF Name | NTID | AAID | NT Length | AA Length | Score | Probability |
|---|---|---|---|---|---|---|
| 24417077_c3_121 | 545 | 2465 | 555 | 1668 | 229 | 9.9e-16 |

Protein name | | | | Locus Name | | Acc# |
| | | | | sp:DP3X_HAEIN | | P43746 |

Description

DNA POLYMERASE III SUBUNIT GAMMA/TAU,

| ORF Name | NTID | AAID | NT Length | AA Length | Score | Probability |
|---|---|---|---|---|---|---|
| 25584501_c2_110 | 546 | 2466 | 230 | 693 | | |

Protein name | | | | Locus Name | | Acc# |

Description

NO-HIT

| ORF Name | NTID | AAID | NT Length | AA Length | Score | Probability |
|---|---|---|---|---|---|---|
| 30198405_c2_100 | 547 | 2467 | 417 | 1254 | 1913 | 1.7e-197 |

| Protein name | | | | Locus Name | Acc# |
|---|---|---|---|---|---|
| | | | | sp:SYK_ACICA | Q43990 |

Description

LYSYL-TRNA SYNTHETASE, (LYSINE--TRNA LIGASE) (LYSRS)

| ORF Name | NTID | AAID | NT Length | AA Length | Score | Probability |
|---|---|---|---|---|---|---|
| 34406268_c1_70 | 548 | 2468 | 169 | 510 | | |

| Protein name | | | | Locus Name | Acc# |
|---|---|---|---|---|---|

Description

NO-HIT

| ORF Name | NTID | AAID | NT Length | AA Length | Score | Probability |
|---|---|---|---|---|---|---|
| 3912568_c2_105 | 549 | 2469 | 467 | 1404 | 819 | 1.4e-81 |

| Protein name | | | | Locus Name | Acc# |
|---|---|---|---|---|---|
| | | | | sp:NHAC_BACFI | P27611 |

Description

NA(+)/H(+) ANTIPORTER

| ORF Name | NTID | AAID | NT Length | AA Length | Score | Probability |
|---|---|---|---|---|---|---|
| 3953377_c3_117 | 550 | 2470 | 218 | 657 | 534 | 3.1e-51 |

| Protein name | | | | Locus Name | Acc# |
|---|---|---|---|---|---|
| | | | | sp:LEU2_CANMA | Q00464 |

Description

ISOMERASE) (ALPHA-IPM ISOMERASE) (IPMI)

| ORF Name | NTID | AAID | NT Length | AA Length | Score | Probability |
|---|---|---|---|---|---|---|
| 3988813_f1_4 | 551 | 2471 | 628 | 1887 | 1391 | 3.5e-142 |

| Protein name | Locus Name | Acc# |
|---|---|---|
| general protein secretion pathway subunit SecD | gp:AF179925 | AF179925 |

Description

Citrobacter freundii general protein secretion pathway subunit SecDgene, complete cds.

| ORF Name | NTID | AAID | NT Length | AA Length | Score | Probability |
|---|---|---|---|---|---|---|
| 4314068_c3_118 | 552 | 2472 | 359 | 1080 | 1356 | 1.8e-138 |

| Protein name | Locus Name | Acc# |
|---|---|---|
|  | sp:LEU3_NEILA | P50180 |

Description (IMDH) (3-IPM-DH) (FRAGMENT)

| ORF Name | NTID | AAID | NT Length | AA Length | Score | Probability |
|---|---|---|---|---|---|---|
| 4335328_c2_98 | 553 | 2473 | 62 | 189 | | |

| Protein name | Locus Name | Acc# |
|---|---|---|

Description

NO-HIT

| ORF Name | NTID | AAID | NT Length | AA Length | Score | Probability |
|---|---|---|---|---|---|---|
| 4487638_f1_1 | 554 | 2474 | 613 | 1842 | 1886 | 1.2e-194 |

| Protein name | Locus Name | Acc# |
|---|---|---|
|  | sp:PPCK_CHLLI | Q08262 |

Description (PHOSPHOENOLPYRUVATE CARBOXYLASE) (PEPCK)

| ORF Name | NTID | AAID | NT Length | AA Length | Score | Probability |
|---|---|---|---|---|---|---|
| 4771925_c2_94 | 555 | 2475 | 207 | 624 | 331 | 7.4e-30 |

| Protein name | | | | Locus Name | | Acc# |
|---|---|---|---|---|---|---|
| | | | | sp:RUVA_PSEAE | | Q51425 |

Description

HOLLIDAY JUNCTION DNA HELICASE RUVA

| ORF Name | NTID | AAID | NT Length | AA Length | Score | Probability |
|---|---|---|---|---|---|---|
| 4866427_f3_61 | 556 | 2476 | 289 | 870 | 247 | 5.9e-21 |

| Protein name | | | | Locus Name | | Acc# |
|---|---|---|---|---|---|---|
| hypothetical protein | | | | pir:S75235 | | S75235 |

Description

| ORF Name | NTID | AAID | NT Length | AA Length | Score | Probability |
|---|---|---|---|---|---|---|
| 4881338_f1_5 | 557 | 2477 | 287 | 864 | 420 | 2.7e-39 |

| Protein name | | | | Locus Name | | Acc# |
|---|---|---|---|---|---|---|
| | | | | sp:SECF_HAEIN | | P44590 |

Description

PROTEIN-EXPORT MEMBRANE PROTEIN SECF

| ORF Name | NTID | AAID | NT Length | AA Length | Score | Probability |
|---|---|---|---|---|---|---|
| 5084463_f2_28 | 558 | 2478 | 114 | 345 | 240 | 3.2e-20 |

| Protein name | | | | Locus Name | | Acc# |
|---|---|---|---|---|---|---|
| | | | | sp:YAJC_ECOLI | | P19677 |

Description

HYPOTHETICAL 11.9 KD PROTEIN IN TGT-SECD INTERGENIC REGION (ORF12)

| ORF Name | NTID | AAID | NT Length | AA Length | Score | Probability |
|---|---|---|---|---|---|---|
| 5111588_c3_116 | 559 | 2479 | 348 | 1047 | 1466 | 3.9e-150 |

| Protein name | | | | Locus Name | | Acc# |
|---|---|---|---|---|---|---|
| fructose-1,6-bisphosphate aldolase | | | | gp:PST011927 | | AJ011927 |

Description

Pseudomonas stutzeri fda gene and gene encoding hypothetical protein.

| ORF Name | NTID | AAID | NT Length | AA Length | Score | Probability |
|---|---|---|---|---|---|---|
| 978400_c1_83 | 560 | 2480 | 387 | 1164 | 503 | 4.4e-48 |

| Protein name | Locus Name | Acc# |
|---|---|---|
| penicillin-binding protein 4 | gp:AF156692 | AF156692 |

Description

Neisseria gonorrhoeae penicillin-binding protein 4 (pbp4) gene, complete cds.

| ORF Name | NTID | AAID | NT Length | AA Length | Score | Probability |
|---|---|---|---|---|---|---|
| 1053753_f3_63 | 561 | 2481 | 588 | 1767 | 801 | 1.2e-79 |

| Protein name | Locus Name | Acc# |
|---|---|---|
| putative membrane protein | gp:AF150928 | AF150928 |

Description

Acinetobacter sp. ADP1 BenP (benP) and AreR (areR) genes, completecds; are operon, complete sequence; SalD (salD), and SalE (salE)genes, complete cds; SalR (salR), SalA (salA), putative membraneprotein, putative 2-component regulatory protein, putativehistidine kinase of 2-component regulatory system, and carbonicanhydrase homolog genes, complete cds; and dihydropyrimidinasehomolog gene, partial cds.

| ORF Name | NTID | AAID | NT Length | AA Length | Score | Probability |
|---|---|---|---|---|---|---|
| 1058425_c2_108 | 562 | 2482 | 80 | 243 | 310 | 1.2e-27 |

| Protein name | Locus Name | Acc# |
|---|---|---|
| ribosomal protein S18 | pir:E64076 | E64076 |

Description

| ORF Name | NTID | AAID | NT Length | AA Length | Score | Probability |
|---|---|---|---|---|---|---|
| 1203450_f1_5 | 563 | 2483 | 530 | 1593 | 1297 | 3.2e-132 |

| Protein name | Locus Name | Acc# |
|---|---|---|
| | sp:YB2X_HAEIN | O86233 |

Description

HYPOTHETICAL PROTEIN HI1126.1

| ORF Name | NTID | AAID | NT Length | AA Length | Score | Probability |
|---|---|---|---|---|---|---|
| 12271926_c1_71 | 564 | 2484 | 143 | 432 | 197 | 1.2e-15 |

Protein name | | | | Locus Name | | Acc# |
| | | | | sp:YFFB_HAEIN | | P44515 |

Description

HYPOTHETICAL PROTEIN HI0103

| ORF Name | NTID | AAID | NT Length | AA Length | Score | Probability |
|---|---|---|---|---|---|---|
| 15635930_f3_61 | 565 | 2485 | 373 | 1122 | 842 | 5.2e-84 |

Protein name | | | | Locus Name | | Acc# |
| | | | | sp:QUEA_ECOLI | | P21516 |

Description (QUEUOSINE BIOSYNTHESIS PROTEIN QUEA)

| ORF Name | NTID | AAID | NT Length | AA Length | Score | Probability |
|---|---|---|---|---|---|---|
| 16134657_f2_24 | 566 | 2486 | 367 | 1104 | 895 | 1.3e-89 |

Protein name | | | | Locus Name | | Acc# |
| | | | | sp:GCST_ECOLI | | P27248 |

Description

PROTEIN)

| ORF Name | NTID | AAID | NT Length | AA Length | Score | Probability |
|---|---|---|---|---|---|---|
| 197211_c1_91 | 567 | 2487 | 240 | 723 | 304 | 5.4e-27 |

Protein name | | | | Locus Name | | Acc# |
| hypothetical protein | | | | gp:ACRBDOXN | | Z46863 |

Description

Acinetobacter sp. cysD, cobQ, sodM, lysS, rubA, rubB, estB, oxyR, ppk, mtgA, ORF2 and ORF3 genes.

| ORF Name | NTID | AAID | NT Length | AA Length | Score | Probability |
|---|---|---|---|---|---|---|
| 20890660_f3_56 | 568 | 2488 | 121 | 366 | | |

Protein name | | | | Locus Name | | Acc# |

Description

NO-HIT

| ORF Name | NTID | AAID | NT Length | AA Length | Score | Probability |
|---|---|---|---|---|---|---|
| 20915682_f1_1 | 569 | 2489 | 142 | 429 | 162 | 6.0e-12 |

| Protein name | Locus Name | Acc# |
|---|---|---|
| | sp:YIBN_ECOLI | P37688 |

Description

HYPOTHETICAL 15.6 KD PROTEIN IN SECB-TDH INTERGENIC REGION

| ORF Name | NTID | AAID | NT Length | AA Length | Score | Probability |
|---|---|---|---|---|---|---|
| 21759656_f1_8 | 570 | 2490 | 591 | 1776 | 630 | 1.6e-103 |

| Protein name | Locus Name | Acc# |
|---|---|---|
| Na(+):solute symporter (Ssf family) | pir:E70480 | E70480 |

Description

| ORF Name | NTID | AAID | NT Length | AA Length | Score | Probability |
|---|---|---|---|---|---|---|
| 22353380_f1_7 | 571 | 2491 | 89 | 270 | | |

| Protein name | Locus Name | Acc# |
|---|---|---|
| | | |

Description

NO-HIT

| ORF Name | NTID | AAID | NT Length | AA Length | Score | Probability |
|---|---|---|---|---|---|---|
| 23438426_f2_26 | 572 | 2492 | 961 | 2886 | 2873 | 3.1e-299 |

| Protein name | Locus Name | Acc# |
|---|---|---|
| | sp:GCSP_ECOLI | P33195 |

Description (DECARBOXYLASE) (GLYCINE CLEAVAGE SYSTEM P-PROTEIN)

| ORF Name | NTID | AAID | NT Length | AA Length | Score | Probability |
|---|---|---|---|---|---|---|
| 23444531_f2_25 | 573 | 2493 | 138 | 417 | 411 | 2.5e-38 |

| Protein name | Locus Name | Acc# |
|---|---|---|
| glycine cleavage system protein H:aminomethyl carrier protein:glycine decarboxylase complex protein H | pir:A56623 | |

Description

| ORF Name | NTID | AAID | NT Length | AA Length | Score | Probability |
|---|---|---|---|---|---|---|
| 24391340_f3_47 | 574 | 2494 | 82 | 249 | | |

| Protein name | | Locus Name | Acc# |
|---|---|---|---|
| | | | |

Description

NO-HIT

| ORF Name | NTID | AAID | NT Length | AA Length | Score | Probability |
|---|---|---|---|---|---|---|
| 24397200_f2_32 | 575 | 2495 | 410 | 1233 | 1330 | 1.0e-135 |

| Protein name | | Locus Name | Acc# |
|---|---|---|---|
| | | sp:TGT_HAEIN | P44594 |

Description

TRANSGLYCOSYLASE) (GUANINE INSERTION ENZYME)

| ORF Name | NTID | AAID | NT Length | AA Length | Score | Probability |
|---|---|---|---|---|---|---|
| 25400263_c3_117 | 576 | 2496 | 399 | 1200 | 725 | 1.3e-71 |

| Protein name | | Locus Name | Acc# |
|---|---|---|---|
| | | sp:YCAB_PSEFR | P72190 |

Description

HYPOTHETICAL 30.2 KD PROTEIN IN CAPB 3'REGION

| ORF Name | NTID | AAID | NT Length | AA Length | Score | Probability |
|---|---|---|---|---|---|---|
| 25562762_f2_18 | 577 | 2497 | 109 | 330 | 199 | 7.2e-16 |

| Protein name | | Locus Name | Acc# |
|---|---|---|---|
| glutaredoxin 3 (grxC1) RP204 | | pir:F71731 | F71731 |

Description

| ORF Name | NTID | AAID | NT Length | AA Length | Score | Probability |
|---|---|---|---|---|---|---|
| 25626452_c3_125 | 578 | 2498 | 106 | 321 | 129 | 1.9e-08 |

| Protein name | | Locus Name | Acc# |
|---|---|---|---|
| | | sp:YCGL_ECOLI | P76003 |

Description

HYPOTHETICAL 12.4 KD PROTEIN IN MINC-SHEA INTERGENIC REGION

| ORF_Name | NTID | AAID | NT Length | AA Length | Score | Probability |
|---|---|---|---|---|---|---|
| 282550_c3_110 | 579 | 2499 | 316 | 951 | 127 | 2.3e-05 |

| Protein name | Locus Name | Acc# |
|---|---|---|
| hypothetical protein | gp:SFR236923 | AJ236923 |

Description

Shewanella frigidimarina ifcA gene and ORF2 (partial) and ORF1.

| ORF_Name | NTID | AAID | NT Length | AA Length | Score | Probability |
|---|---|---|---|---|---|---|
| 29314057_c1_90 | 580 | 2500 | 289 | 870 | 705 | 1.7e-69 |

| Protein name | Locus Name | Acc# |
|---|---|---|
| probable ion transporter | pir:E75470 | E75470 |

Description

| ORF_Name | NTID | AAID | NT Length | AA Length | Score | Probability |
|---|---|---|---|---|---|---|
| 29333458_f2_39 | 581 | 2501 | 143 | 432 | 196 | 2.7e-14 |

| Protein name | Locus Name | Acc# |
|---|---|---|
|  | sp:SYL_SYNY3 | P73274 |

Description

LEUCYL-TRNA SYNTHETASE, (LEUCINE--TRNA LIGASE) (LEURS)

| ORF_Name | NTID | AAID | NT Length | AA Length | Score | Probability |
|---|---|---|---|---|---|---|
| 30100432_f3_66 | 582 | 2502 | 361 | 1086 | 128 | 2.3e-05 |

| Protein name | Locus Name | Acc# |
|---|---|---|
|  | sp:HOLA_ECOLI | P28630 |

Description

DNA POLYMERASE III, DELTA SUBUNIT,

| ORF_Name | NTID | AAID | NT Length | AA Length | Score | Probability |
|---|---|---|---|---|---|---|
| 3298257_f1_16 | 583 | 2503 | 178 | 537 |  |  |

| Protein name | Locus Name | Acc# |
|---|---|---|

Description

NO-HIT

| ORF_Name | NTID | AAID | NT Length | AA Length | Score | Probability |
|---|---|---|---|---|---|---|
| 35637_f2_30 | 584 | 2504 | 165 | 498 | 146 | 3.0e-10 |

Protein name: unknown
Locus Name: gp:AF064527
Acc#: AF064527

Description: Rhodocista centenaria PPH (pph) gene, complete cds; and unknown genes.

| ORF_Name | NTID | AAID | NT Length | AA Length | Score | Probability |
|---|---|---|---|---|---|---|
| 3907781_c3_126 | 585 | 2505 | 170 | 513 | | |

Protein name:
Locus Name:
Acc#:

Description: NO-HIT

| ORF_Name | NTID | AAID | NT Length | AA Length | Score | Probability |
|---|---|---|---|---|---|---|
| 3925443_c2_107 | 586 | 2506 | 136 | 411 | 369 | 6.9e-34 |

Protein name:
Locus Name: sp:RS6_ECOLI
Acc#: P02358

Description: 30S RIBOSOMAL PROTEIN S6

| ORF_Name | NTID | AAID | NT Length | AA Length | Score | Probability |
|---|---|---|---|---|---|---|
| 4003558_f1_2 | 587 | 2507 | 157 | 474 | 508 | 1.3e-48 |

Protein name:
Locus Name: sp:DUT_ECOLI
Acc#: P06968

Description: (DUTPASE) (DUTP PYROPHOSPHATASE)

| ORF_Name | NTID | AAID | NT Length | AA Length | Score | Probability |
|---|---|---|---|---|---|---|
| 4328443_f3_43 | 588 | 2508 | 151 | 456 | 393 | 2.0e-36 |

Protein name:
Locus Name: sp:SECB_ECOLI
Acc#: P15040

Description: PROTEIN-EXPORT PROTEIN SECB

| ORF Name | NTID | AAID | NT Length | AA Length | Score | Probability |
|---|---|---|---|---|---|---|
| 4860762_f3_64 | 589 | 2509 | 268 | 807 | | |

| Protein name | | | Locus Name | | Acc# |
|---|---|---|---|---|---|
| | | | | | |

Description

NO-HIT

| ORF Name | NTID | AAID | NT Length | AA Length | Score | Probability |
|---|---|---|---|---|---|---|
| 4860943_c1_89 | 590 | 2510 | 185 | 558 | 199 | 7.2e-16 |

| Protein name | | | Locus Name | | Acc# |
|---|---|---|---|---|---|
| NADPH:quinone oxidoreductase | | | gp:AF145234 | | AF145234 |

Description

Arabidopsis thaliana NADPH:quinone oxidoreductase (NQR) mRNA, complete cds.

| ORF Name | NTID | AAID | NT Length | AA Length | Score | Probability |
|---|---|---|---|---|---|---|
| 4897050_f3_44 | 591 | 2511 | 153 | 462 | 355 | 2.1e-32 |

| Protein name | | | Locus Name | | Acc# |
|---|---|---|---|---|---|
| acetylglutamate kinase | | | pir:D70477 | | D70477 |

Description

| ORF Name | NTID | AAID | NT Length | AA Length | Score | Probability |
|---|---|---|---|---|---|---|
| 50160_c1_75 | 592 | 2512 | 127 | 384 | 460 | 1.9e-42 |

| Protein name | | | Locus Name | | Acc# |
|---|---|---|---|---|---|
| haemoglobin-haptoglobin binding protein HhuA | | | gp:HIU43198 | | U43198 |

Description

Haemophilus influenzae haemoglobin-haptoglobin binding protein HhuA (hhuA) gene, complete cds.

| ORF Name | NTID | AAID | NT Length | AA Length | Score | Probability |
|---|---|---|---|---|---|---|
| 6650718_f2_40 | 593 | 2513 | 82 | 249 | | |

| Protein name | | | Locus Name | | Acc# |
|---|---|---|---|---|---|
| | | | | | |

Description

NO-HIT

| ORF_Name | NTID | AAID | NT Length | AA Length | Score | Probability |
|---|---|---|---|---|---|---|
| 6822152_c3_128 | 594 | 2514 | 160 | 483 | 438 | 3.4e-41 |

Protein name | Locus Name | Acc#
sp:RL9_ECOLI | P02418

Description
50S RIBOSOMAL PROTEIN L9

| ORF_Name | NTID | AAID | NT Length | AA Length | Score | Probability |
|---|---|---|---|---|---|---|
| 783426_f1_15 | 595 | 2515 | 766 | 2301 | 2022 | 4.8e-209 |

Protein name | Locus Name | Acc#
sp:SYL_ECOLI

Description
LEUCYL-TRNA SYNTHETASE, (LEUCINE--TRNA LIGASE) (LEURS)

| ORF_Name | NTID | AAID | NT Length | AA Length | Score | Probability |
|---|---|---|---|---|---|---|
| 860300_f2_29 | 596 | 2516 | 85 | 258 | | |

Protein name | Locus Name | Acc#

Description
NO-HIT

| ORF_Name | NTID | AAID | NT Length | AA Length | Score | Probability |
|---|---|---|---|---|---|---|
| 9803127_c1_88 | 597 | 2517 | 321 | 966 | 53 | 0.041 |

Protein name | Locus Name | Acc#
hypothetical protein (bpi 3' region) | pir:C37397 | C37397

Description

| ORF_Name | NTID | AAID | NT Length | AA Length | Score | Probability |
|---|---|---|---|---|---|---|
| 9898513_c2_101 | 598 | 2518 | 527 | 1584 | 600 | 1.3e-88 |

Protein name | Locus Name | Acc#
sp:YF67_HAEIN

Description
PROBABLE TONB-DEPENDENT RECEPTOR HI1567 PRECURSOR

| ORF Name | NTID | AAID | NT Length | AA Length | Score | Probability |
|---|---|---|---|---|---|---|
| 1040887_c1_72 | 599 | 2519 | 301 | 906 | 601 | 1.8e-58 |

| Protein name | | | | Locus Name | Acc# |
|---|---|---|---|---|---|
| | | | | gp:AB025342 | AB025342 |

Description

Moritella marina genes, complete cds, similar to eicosapentaenoicacid synthesis gene cluster.

| ORF Name | NTID | AAID | NT Length | AA Length | Score | Probability |
|---|---|---|---|---|---|---|
| 10648402_f3_46 | 600 | 2520 | 395 | 1188 | 953 | 9.0e-96 |

| Protein name | | | | Locus Name | Acc# |
|---|---|---|---|---|---|
| | | | | sp:AROF_ECOLI | P00888 |

Description

SYNTHETASE) (3-DEOXY-D-ARABINO-HEPTULOSONATE 7-PHOSPHATE SYNTHASE)

| ORF Name | NTID | AAID | NT Length | AA Length | Score | Probability |
|---|---|---|---|---|---|---|
| 10723543_f3_48 | 601 | 2521 | 73 | 222 | | |

| Protein name | | | | Locus Name | Acc# |
|---|---|---|---|---|---|

Description

NO-HIT

| ORF Name | NTID | AAID | NT Length | AA Length | Score | Probability |
|---|---|---|---|---|---|---|
| 10969087_f3_60 | 602 | 2522 | 1242 | 3729 | 2416 | 3.1e-286 |

| Protein name | | | | Locus Name | Acc# |
|---|---|---|---|---|---|
| DNA polymerase III | | | | gp:AF062919 | AF062919 |

Description

Pseudomonas fluorescens DNA polymerase III (dnaE) gene, completecds.

| ORF Name | NTID | AAID | NT Length | AA Length | Score | Probability |
|---|---|---|---|---|---|---|
| 19552252_c3_122 | 603 | 2523 | 111 | 336 | 238 | 5.3e-20 |

| Protein name | | | | Locus Name | Acc# |
|---|---|---|---|---|---|
| | | | | gp:D90863 | |

Description

E.coli genomic DNA, Kohara clone #407(52.4-52.8 min.).

205

| ORF Name | NTID | AAID | NT Length | AA Length | Score | Probability |
|---|---|---|---|---|---|---|
| 20180387_c2_104 | 604 | 2524 | 208 | 627 | 117 | 1.0e-05 |

Protein name | | | | Locus Name | | Acc#
sp:Y366_HAEIN — P43988

Description: HYPOTHETICAL PROTEIN HI0366 PRECURSOR

| ORF Name | NTID | AAID | NT Length | AA Length | Score | Probability |
|---|---|---|---|---|---|---|
| 20355003_f2_25 | 605 | 2525 | 173 | 522 | | |

Protein name | | | | Locus Name | | Acc#

Description: NO-HIT

| ORF Name | NTID | AAID | NT Length | AA Length | Score | Probability |
|---|---|---|---|---|---|---|
| 20486501_c3_115 | 606 | 2526 | 154 | 465 | 239 | 4.1e-20 |

Protein name: hypothetical protein PH0336 | Locus Name: pir:E71140 | Acc#: E71140

Description:

| ORF Name | NTID | AAID | NT Length | AA Length | Score | Probability |
|---|---|---|---|---|---|---|
| 2120263_c3_114 | 607 | 2527 | 200 | 603 | 217 | 8.9e-18 |

Protein name | | | | Locus Name: sp:YGGB_ECOLI | | Acc#: P11666

Description: (F286)

| ORF Name | NTID | AAID | NT Length | AA Length | Score | Probability |
|---|---|---|---|---|---|---|
| 22131925_c3_124 | 608 | 2528 | 387 | 1164 | 1176 | 2.1e-119 |

Protein name: AarC | Locus Name: gp:PSU67933 | Acc#: U67933

Description: Providencia stuartii AarC (aarC) gene, complete cds.

| ORF Name | NTID | AAID | NT Length | AA Length | Score | Probability |
|---|---|---|---|---|---|---|
| 24219200_f3_59 | 609 | 2529 | 413 | 1242 | 872 | 3.5e-87 |

Protein name | Locus Name | Acc#
sp:YCFD_HAEIN | P44683

Description: HYPOTHETICAL PROTEIN HI0396

| ORF Name | NTID | AAID | NT Length | AA Length | Score | Probability |
|---|---|---|---|---|---|---|
| 24412678_f2_27 | 610 | 2530 | 253 | 762 | 291 | 1.3e-25 |

Protein name | Locus Name | Acc#
sp:RNH2_VIBCH | P52021

Description: RIBONUCLEASE HII, (RNASE HII) (FRAGMENT)

| ORF Name | NTID | AAID | NT Length | AA Length | Score | Probability |
|---|---|---|---|---|---|---|
| 24423250_f3_53 | 611 | 2531 | 67 | 204 | | |

Protein name | Locus Name | Acc#

Description: NO-HIT

| ORF Name | NTID | AAID | NT Length | AA Length | Score | Probability |
|---|---|---|---|---|---|---|
| 25573802_f1_4 | 612 | 2532 | 446 | 1341 | 456 | 4.2e-43 |

Protein name: lipid-A-disaccharide synthase, | Locus Name: pir:E64180 | Acc#: E64180

Description:

| ORF Name | NTID | AAID | NT Length | AA Length | Score | Probability |
|---|---|---|---|---|---|---|
| 29407800_c1_80 | 613 | 2533 | 403 | 1212 | 1125 | 5.4e-114 |

Protein name | Locus Name | Acc#
sp:YFGB_PSEAE |

Description: HYPOTHETICAL 41.7 KD PROTEIN IN PILF-NDK INTERGENIC REGION (ORF1)

| ORF Name | NTID | AAID | NT Length | AA Length | Score | Probability |
|---|---|---|---|---|---|---|
| 3145438_c1_69 | 614 | 2534 | 485 | 1458 | 644 | 1.3e-66 |

| Protein name | | | | Locus Name | | Acc# |
|---|---|---|---|---|---|---|
| unknown | | | | gp:AF003741 | | AF003741 |

Description

Escherichia coli CFT073 pathogenicity island gene, complete cds.

| ORF Name | NTID | AAID | NT Length | AA Length | Score | Probability |
|---|---|---|---|---|---|---|
| 33882816_c1_79 | 615 | 2535 | 273 | 822 | 243 | 1.2e-41 |

| Protein name | | | | Locus Name | | Acc# |
|---|---|---|---|---|---|---|
| | | | | sp:YFCB_ECOLI | | |

Description (EC 2.1.1.72)

| ORF Name | NTID | AAID | NT Length | AA Length | Score | Probability |
|---|---|---|---|---|---|---|
| 3906293_f1_3 | 616 | 2536 | 110 | 333 | 146 | 3.0e-10 |

| Protein name | | | | Locus Name | | Acc# |
|---|---|---|---|---|---|---|
| | | | | sp:YDAL_ECOLI | | P76053 |

Description

HYPOTHETICAL 21.5 KD PROTEIN IN OGT-DBPA INTERGENIC REGION

| ORF Name | NTID | AAID | NT Length | AA Length | Score | Probability |
|---|---|---|---|---|---|---|
| 3907568_c2_105 | 617 | 2537 | 395 | 1188 | 386 | 1.1e-35 |

| Protein name | | | | Locus Name | | Acc# |
|---|---|---|---|---|---|---|
| | | | | sp:YFGL_ECOLI | | P77774 |

Description

HYPOTHETICAL 41.9 KD PROTEIN IN XSEA-HISS INTERGENIC REGION

| ORF Name | NTID | AAID | NT Length | AA Length | Score | Probability |
|---|---|---|---|---|---|---|
| 3912818_c3_125 | 618 | 2538 | 425 | 1278 | 1077 | 6.6e-109 |

Protein name:

Locus Name: sp:SYH_ECOLI

Acc#: P04804

Description: (HISRS)

| ORF Name | NTID | AAID | NT Length | AA Length | Score | Probability |
|---|---|---|---|---|---|---|
| 3945293_c3_113 | 619 | 2539 | 328 | 987 | 696 | 1.5e-68 |

Protein name:

Locus Name: sp:SOHB_HAEIN

Acc#: P45315

Description: POSSIBLE PROTEASE SOHB,

| ORF Name | NTID | AAID | NT Length | AA Length | Score | Probability |
|---|---|---|---|---|---|---|
| 3946892_c3_126 | 620 | 2540 | 280 | 843 | 164 | 6.3e-12 |

Protein name:

Locus Name: sp:Y370_HAEIN

Acc#: P43989

Description: HYPOTHETICAL PROTEIN HI0370

| ORF Name | NTID | AAID | NT Length | AA Length | Score | Probability |
|---|---|---|---|---|---|---|
| 3946917_f3_64 | 621 | 2541 | 205 | 618 | 508 | 1.3e-48 |

Protein name:

Locus Name: sp:3MGA_HAEIN

Acc#: P44321

Description: GLYCOSIDASE) (TAG)

| ORF Name | NTID | AAID | NT Length | AA Length | Score | Probability |
|---|---|---|---|---|---|---|
| 4148383_c1_83 | 622 | 2542 | 321 | 966 | 557 | 8.3e-54 |

Protein name: hypothetical protein HP0852

Locus Name: pir:D64626

Acc#: D64626

Description:

| ORF_Name | NTID | AAID | NT Length | AA Length | Score | Probability |
|---|---|---|---|---|---|---|
| 4181537_c1_88 | 623 | 2543 | 473 | 1422 | 952 | 2.2e-144 |

| Protein name | | | | Locus Name | | Acc# |
|---|---|---|---|---|---|---|
| | | | | sp:YFGK_ECOLI | | P77254 |

Description

HYPOTHETICAL GTP-BINDING PROTEIN IN XSEA-HISS INTERGENIC REGION

| ORF_Name | NTID | AAID | NT Length | AA Length | Score | Probability |
|---|---|---|---|---|---|---|
| 4460938_f2_37 | 624 | 2544 | 271 | 816 | 664 | 3.8e-65 |

| Protein name | | | | Locus Name | | Acc# |
|---|---|---|---|---|---|---|
| O-acetylserine synthase | | | | gp:AF010139 | | AF010139 |

Description

Azotobacter vinelandii iron-sulfur cluster assembly gene cluster, suhB, cysE2, iscS, iscU, iscA, hscB, hscA and fdx genes completecds; ndk gene, partial cds.

| ORF_Name | NTID | AAID | NT Length | AA Length | Score | Probability |
|---|---|---|---|---|---|---|
| 5114700_c1_86 | 625 | 2545 | 77 | 234 | | |

| Protein name | | | | Locus Name | | Acc# |
|---|---|---|---|---|---|---|

Description

NO-HIT

| ORF_Name | NTID | AAID | NT Length | AA Length | Score | Probability |
|---|---|---|---|---|---|---|
| 52138_c1_91 | 626 | 2546 | 109 | 330 | 199 | 1.2e-15 |

| Protein name | | | | Locus Name | | Acc# |
|---|---|---|---|---|---|---|
| solanesyl diphosphate synthase | | | | gp:AB001997 | | AB001997 |

Description

Rhodobacter capsulatus DNA for solanesyl diphosphate synthase, complete cds.

| ORF_Name | NTID | AAID | NT Length | AA Length | Score | Probability |
|---|---|---|---|---|---|---|
| 6140680_f2_36 | 627 | 2547 | 300 | 903 | 187 | 1.9e-29 |

| Protein name | | | | Locus Name | | Acc# |
|---|---|---|---|---|---|---|
| hypothetical protein b2532 | | | | pir:C65030 | | C65030 |

Description

| ORF Name | NTID | AAID | NT Length | AA Length | Score | Probability |
|---|---|---|---|---|---|---|
| 648425_c1_90 | 628 | 2548 | 87 | 264 | | |

| Protein name | | | | | Locus Name | Acc# |
|---|---|---|---|---|---|---|

Description

NO-HIT

| ORF Name | NTID | AAID | NT Length | AA Length | Score | Probability |
|---|---|---|---|---|---|---|
| 10378_c2_184 | 629 | 2549 | 85 | 258 | 251 | 2.2e-21 |

| Protein name | | | | | Locus Name | Acc# |
|---|---|---|---|---|---|---|
| cold shock protein, CSPA | | | | | gp:VCCSPA | Y11908 |

Description

V.cholerae cspA gene.

| ORF Name | NTID | AAID | NT Length | AA Length | Score | Probability |
|---|---|---|---|---|---|---|
| 1063510_c2_198 | 630 | 2550 | 175 | 528 | 208 | 1.5e-15 |

| Protein name | | | | | Locus Name | Acc# |
|---|---|---|---|---|---|---|
| uridylyl transferase | | | | | gp:AB024601 | AB024601 |

Description

Pseudomonas aeruginosa dapD gene for tetrahydrodipicolinateN-succinyletransferase, complete cds, strain PAO1.

| ORF Name | NTID | AAID | NT Length | AA Length | Score | Probability |
|---|---|---|---|---|---|---|
| 1175012_c1_174 | 631 | 2551 | 411 | 1236 | 929 | 3.2e-93 |

| Protein name | | | | | Locus Name | Acc# |
|---|---|---|---|---|---|---|
| acetate kinase | | | | | pir:B75254 | B75254 |

Description

| ORF Name | NTID | AAID | NT Length | AA Length | Score | Probability |
|---|---|---|---|---|---|---|
| 11988812_c1_171 | 632 | 2552 | 161 | 486 | | |

| Protein name | | | | | Locus Name | Acc# |
|---|---|---|---|---|---|---|

Description

NO-HIT

| ORF Name | NTID | AAID | NT Length | AA Length | Score | Probability |
|---|---|---|---|---|---|---|
| 12532562_c3_232 | 633 | 2553 | 299 | 900 | | |

Protein name | Locus Name | Acc#

Description

NO-HIT

| ORF Name | NTID | AAID | NT Length | AA Length | Score | Probability |
|---|---|---|---|---|---|---|
| 12542005_f3_130 | 634 | 2554 | 92 | 279 | | |

Protein name | Locus Name | Acc#

Description

NO-HIT

| ORF Name | NTID | AAID | NT Length | AA Length | Score | Probability |
|---|---|---|---|---|---|---|
| 13001052_f1_50 | 635 | 2555 | 62 | 189 | | |

Protein name | Locus Name | Acc#

Description

NO-HIT

| ORF Name | NTID | AAID | NT Length | AA Length | Score | Probability |
|---|---|---|---|---|---|---|
| 13852337_c2_202 | 636 | 2556 | 351 | 1056 | 515 | 2.3e-49 |

Protein name | Locus Name | Acc#
 | sp:APBE_HAEIN | P44550

Description

THIAMINE BIOSYNTHESIS LIPOPROTEIN APBE PRECURSOR

| ORF Name | NTID | AAID | NT Length | AA Length | Score | Probability |
|---|---|---|---|---|---|---|
| 14225300_c3_224 | 637 | 2557 | 123 | 372 | 440 | 2.1e-41 |

Protein name | Locus Name | Acc#
PII-protein | gp:AVU91902 | U91902

Description

Azotobacter vinelandii PII-protein (glnB) and methylammoniumtransport protein (amtB) genes, complete cds.

| ORF Name | NTID | AAID | NT Length | AA Length | Score | Probability |
|---|---|---|---|---|---|---|
| 15628127_f3_98 | 638 | 2558 | 72 | 219 | | |

Protein name     Locus Name     Acc#

Description

NO-HIT

| ORF Name | NTID | AAID | NT Length | AA Length | Score | Probability |
|---|---|---|---|---|---|---|
| 15630192_c3_217 | 639 | 2559 | 162 | 489 | 270 | 2.0e-25 |

Protein name     Locus Name: sp:UP04_ECOLI     Acc#

Description

UNKNOWN PROTEIN FROM 2D-PAGE (SPOT LM6)

| ORF Name | NTID | AAID | NT Length | AA Length | Score | Probability |
|---|---|---|---|---|---|---|
| 16597790_f3_131 | 640 | 2560 | 353 | 1062 | 232 | 2.6e-19 |

Protein name     Locus Name: sp:NUC1_CUNEE     Acc# P81203

Description

NUCLEASE C1,

| ORF Name | NTID | AAID | NT Length | AA Length | Score | Probability |
|---|---|---|---|---|---|---|
| 16603411_f2_85 | 641 | 2561 | 319 | 960 | 597 | 4.8e-58 |

Protein name     Locus Name: sp:YF56_HAEIN     Acc# P45250

Description

PUTATIVE 2-HYDROXYACID DEHYDROGENASE HI1556

| ORF Name | NTID | AAID | NT Length | AA Length | Score | Probability |
|---|---|---|---|---|---|---|
| 17036428_f3_138 | 642 | 2562 | 62 | 189 | | |

Protein name     Locus Name     Acc#

Description

NO-HIT

| ORF_Name | NTID | AAID | NT Length | AA Length | Score | Probability |
|---|---|---|---|---|---|---|
| 19564458_f2_55 | 643 | 2563 | 212 | 639 | 192 | 4.0e-15 |

Protein name: probable glpG protein
Locus Name: pir:D71258
Acc#: D71258

Description:

| ORF_Name | NTID | AAID | NT Length | AA Length | Score | Probability |
|---|---|---|---|---|---|---|
| 21766930_f3_100 | 644 | 2564 | 610 | 1833 | 554 | 1.7e-53 |

Protein name: hypothetical protein
Locus Name: pir:S75944
Acc#: S75944

Description:

| ORF_Name | NTID | AAID | NT Length | AA Length | Score | Probability |
|---|---|---|---|---|---|---|
| 22035932_c2_209 | 645 | 2565 | 416 | 1251 | 515 | 2.3e-49 |

Protein name: B1306.06c protein
Locus Name: gp:MLB1306
Acc#: Y13803

Description: Mycobacterium leprae cosmid B1306 DNA.

| ORF_Name | NTID | AAID | NT Length | AA Length | Score | Probability |
|---|---|---|---|---|---|---|
| 22775251_c1_144 | 646 | 2566 | 543 | 1632 | 1799 | 2.0e-185 |

Protein name: acetolactate synthase, III large chain:acetohydroxy-acid synthase III large chain
Locus Name: pir:YCEC3I
Acc#:

Description:

| ORF_Name | NTID | AAID | NT Length | AA Length | Score | Probability |
|---|---|---|---|---|---|---|
| 22890836_c2_214 | 647 | 2567 | 179 | 540 | 415 | 1.8e-41 |

Protein name:
Locus Name: gp:AHU56832
Acc#: U56832

Description: Aeromonas hydrophila FK506 binding protein (fkpA) gene, completecds in 3.9 kb fragment.

| ORF Name | NTID | AAID | NT Length | AA Length | Score | Probability |
|---|---|---|---|---|---|---|
| 23595787_c3_220 | 648 | 2568 | 150 | 453 | | |

Protein name | Locus Name | Acc#

Description

NO-HIT

| ORF Name | NTID | AAID | NT Length | AA Length | Score | Probability |
|---|---|---|---|---|---|---|
| 23718750_f2_93 | 649 | 2569 | 202 | 609 | 432 | 1.5e-40 |

Protein name | Locus Name | Acc#
| | sp:RUVC_HAEIN | P44633

Description

JUNCTION NUCLEASE RUVC) (HOLLIDAY JUCTION RESOLVASE RUVC)

| ORF Name | NTID | AAID | NT Length | AA Length | Score | Probability |
|---|---|---|---|---|---|---|
| 23727181_c2_215 | 650 | 2570 | 330 | 993 | | |

Protein name | Locus Name | Acc#

Description

NO-HIT

| ORF Name | NTID | AAID | NT Length | AA Length | Score | Probability |
|---|---|---|---|---|---|---|
| 23939008_c1_161 | 651 | 2571 | 123 | 372 | 141 | 1.0e-09 |

Protein name | Locus Name | Acc#
hypothetical protein | pir:T10511 | T10511

Description

| ORF Name | NTID | AAID | NT Length | AA Length | Score | Probability |
|---|---|---|---|---|---|---|
| 23942567_c2_212 | 652 | 2572 | 66 | 201 | | |

Protein name | Locus Name | Acc#

Description

NO-HIT

| ORF Name | NTID | AAID | NT Length | AA Length | Score | Probability |
|---|---|---|---|---|---|---|
| 23963325_f3_123 | 653 | 2573 | 403 | 1212 | 879 | 6.3e-88 |

Protein name | | | | Locus Name | | Acc# |
| | | | | sp:FADH_ECOLI | | P42593 |

Description

A REDUCTASE)

| ORF Name | NTID | AAID | NT Length | AA Length | Score | Probability |
|---|---|---|---|---|---|---|
| 24353427_c2_200 | 654 | 2574 | 546 | 1641 | 2074 | 1.5e-214 |

Protein name | | | | Locus Name | | Acc# |
| | | | | sp:CH60_YEREN | | P48219 |

Description 60) (CROSS-REACTING PROTEIN ANTIGEN)

| ORF Name | NTID | AAID | NT Length | AA Length | Score | Probability |
|---|---|---|---|---|---|---|
| 24612761_c3_246 | 655 | 2575 | 259 | 780 | 467 | 2.9e-44 |

Protein name | | | | Locus Name | | Acc# |
| | | | | sp:YMFC_HAEIN | | P44827 |

Description

HYPOTHETICAL PROTEIN HI0694

| ORF Name | NTID | AAID | NT Length | AA Length | Score | Probability |
|---|---|---|---|---|---|---|
| 24648387_c1_170 | 656 | 2576 | 282 | 849 | 926 | 6.6e-93 |

Protein name | | | | Locus Name | | Acc# |
thymidylate synthase | | | | gp:L78665 | | L78665 |

Description

Methylobacillus flagellatum aspartate aminotransferase (aat),membrane protein (orf-1), homoserine dehydrogenase (hom), andthreonine synthase (thrC) thymidylate sythase (thyA) genes,complete cds.

| ORF Name | NTID | AAID | NT Length | AA Length | Score | Probability |
|---|---|---|---|---|---|---|
| 24796885_c2_197 | 657 | 2577 | 268 | 807 | 801 | 1.2e-79 |

Protein name: | Locus Name | Acc# |
| sp:AMPM_ECOLI | P07906 |

Description: METHIONINE AMINOPEPTIDASE, (MAP) (PEPTIDASE M)

| ORF Name | NTID | AAID | NT Length | AA Length | Score | Probability |
|---|---|---|---|---|---|---|
| 25390711_c1_153 | 658 | 2578 | 414 | 1245 | 593 | 2.8e-60 |

Protein name: | Locus Name | Acc# |
| sp:MUTY_ECOLI | P17802 |

Description: A/G-SPECIFIC ADENINE GLYCOSYLASE,

| ORF Name | NTID | AAID | NT Length | AA Length | Score | Probability |
|---|---|---|---|---|---|---|
| 25412907_f1_37 | 659 | 2579 | 95 | 288 | 74 | 0.044 |

Protein name: hypothetical protein | Locus Name: gp:AP000363 | Acc#: AP000363

Description: Bacteriophage VT2-Sa, complete genome sequence.

| ORF Name | NTID | AAID | NT Length | AA Length | Score | Probability |
|---|---|---|---|---|---|---|
| 25566577_f1_23 | 660 | 2580 | 83 | 252 | | |

Protein name: | Locus Name | Acc# |

Description: NO-HIT

| ORF Name | NTID | AAID | NT Length | AA Length | Score | Probability |
|---|---|---|---|---|---|---|
| 25585263_f2_64 | 661 | 2581 | 311 | 936 | 790 | 1.7e-78 |

Protein name: diaminopimelate epimerase, | Locus Name: pir:S01913 | Acc# |

Description:

| ORF Name | NTID | AAID | NT Length | AA Length | Score | Probability |
|---|---|---|---|---|---|---|
| 26213386_c3_242 | 662 | 2582 | 404 | 1215 | 393 | 2.0e-36 |

Protein name | Locus Name | Acc#
sp:UBIH_ECOLI | P25534

Description
UBIH PROTEIN,

| ORF Name | NTID | AAID | NT Length | AA Length | Score | Probability |
|---|---|---|---|---|---|---|
| 26214428_c2_201 | 663 | 2583 | 296 | 891 | 719 | 5.7e-71 |

Protein name | Locus Name | Acc#
sp:LGT_SALTY | Q07293

Description
PROLIPOPROTEIN DIACYLGLYCERYL TRANSFERASE,

| ORF Name | NTID | AAID | NT Length | AA Length | Score | Probability |
|---|---|---|---|---|---|---|
| 29303578_f2_74 | 664 | 2584 | 69 | 210 | | |

Protein name | Locus Name | Acc#

Description
NO-HIT

| ORF Name | NTID | AAID | NT Length | AA Length | Score | Probability |
|---|---|---|---|---|---|---|
| 29380307_c2_199 | 665 | 2585 | 166 | 501 | | |

Protein name | Locus Name | Acc#

Description
NO-HIT

| ORF Name | NTID | AAID | NT Length | AA Length | Score | Probability |
|---|---|---|---|---|---|---|
| 30268885_c3_234 | 666 | 2586 | 63 | 192 | | |

Protein name | Locus Name | Acc#

Description
NO-HIT

| ORF Name | NTID | AAID | NT Length | AA Length | Score | Probability |
|---|---|---|---|---|---|---|
| 33626535_f1_51 | 667 | 2587 | 141 | 426 | | |

Protein name Locus Name Acc#

Description

NO-HIT

| ORF Name | NTID | AAID | NT Length | AA Length | Score | Probability |
|---|---|---|---|---|---|---|
| 34416075_c3_231 | 668 | 2588 | 803 | 2412 | 1247 | 6.3e-127 |

Protein name Locus Name Acc#
 sp:NFRX_AZOVI P36223

Description

TRANSFERASE) (URIDYLYL REMOVING ENZYME)

| ORF Name | NTID | AAID | NT Length | AA Length | Score | Probability |
|---|---|---|---|---|---|---|
| 35425918_c3_241 | 669 | 2589 | 176 | 531 | 302 | 8.7e-27 |

Protein name Locus Name Acc#
dihydrofolate reductase, pir:S52336 S52336

Description

| ORF Name | NTID | AAID | NT Length | AA Length | Score | Probability |
|---|---|---|---|---|---|---|
| 36051061_f2_78 | 670 | 2590 | 327 | 984 | 930 | 2.5e-93 |

Protein name Locus Name Acc#
probable 2 pir:G70875 G70875

Description

| ORF Name | NTID | AAID | NT Length | AA Length | Score | Probability |
|---|---|---|---|---|---|---|
| 3910943_c1_146 | 671 | 2591 | 343 | 1032 | 1278 | 3.3e-130 |

Protein name Locus Name Acc#
ketol-acid reductoisomerase gp:AF125563 AF125563

Description

Neisseria meningitidis NMB putative aconitate hydratase (acn), ornithine carbomyltransferase (argF), and ketol-acidreductoisomerase (ilvC) genes, complete cds.

| ORF Name | NTID | AAID | NT Length | AA Length | Score | Probability |
|---|---|---|---|---|---|---|
| 3914002_f3_114 | 672 | 2592 | 253 | 762 | | |

Protein name · Locus Name · Acc#

Description

NO-HIT

| ORF Name | NTID | AAID | NT Length | AA Length | Score | Probability |
|---|---|---|---|---|---|---|
| 3939063_f2_89 | 673 | 2593 | 469 | 1410 | 627 | 3.2e-61 |

Protein name · Locus Name: sp:MURD_ECOLI · Acc#: P14900

Description

ADDING ENZYME)

| ORF Name | NTID | AAID | NT Length | AA Length | Score | Probability |
|---|---|---|---|---|---|---|
| 3947713_f1_5 | 674 | 2594 | 260 | 783 | 594 | 1.0e-57 |

Protein name · Locus Name: sp:YAAA_HAEIN · Acc#: P43908

Description

HYPOTHETICAL PROTEIN HI0984

| ORF Name | NTID | AAID | NT Length | AA Length | Score | Probability |
|---|---|---|---|---|---|---|
| 3954638_f2_63 | 675 | 2595 | 438 | 1317 | 1067 | 7.5e-108 |

Protein name · Locus Name: sp:DCDA_PSEAE · Acc#: P19572

Description

DIAMINOPIMELATE DECARBOXYLASE, (DAP DECARBOXYLASE)

| ORF Name | NTID | AAID | NT Length | AA Length | Score | Probability |
|---|---|---|---|---|---|---|
| 3962885_c3_219 | 676 | 2596 | 181 | 546 | 486 | 2.8e-46 |

Protein name: acetolactate synthase, III small chain:acetohydroxy-acid synthase III small chain · Locus Name: pir:YCEC3H · Acc#

Description

| ORF_Name | NTID | AAID | NT Length | AA Length | Score | Probability |
|---|---|---|---|---|---|---|
| 3992035_c1_175 | 677 | 2597 | 500 | 1503 | 1163 | 4.6e-127 |

| Protein name | Locus Name | Acc# |
|---|---|---|
| | sp:PTA_HAEIN | P45107 |

Description

PHOSPHATE ACETYLTRANSFERASE, (PHOSPHOTRANSACETYLASE)

| ORF_Name | NTID | AAID | NT Length | AA Length | Score | Probability |
|---|---|---|---|---|---|---|
| 4140881_f1_40 | 678 | 2598 | 467 | 1404 | 710 | 5.1e-70 |

| Protein name | Locus Name | Acc# |
|---|---|---|
| NorM | gp:AB010463 | AB010463 |

Description

Vibrio parahaemolyticus gene for NorM, complete cds.

| ORF_Name | NTID | AAID | NT Length | AA Length | Score | Probability |
|---|---|---|---|---|---|---|
| 4147562_c1_159 | 679 | 2599 | 523 | 1572 | 1209 | 6.7e-123 |

| Protein name | Locus Name | Acc# |
|---|---|---|
| | sp:YIFB_HAEIN | P45049 |

Description

HYPOTHETICAL PROTEIN HI1117

| ORF_Name | NTID | AAID | NT Length | AA Length | Score | Probability |
|---|---|---|---|---|---|---|
| 4471887_f3_135 | 680 | 2600 | 415 | 1248 | 637 | 2.8e-62 |

| Protein name | Locus Name | Acc# |
|---|---|---|
| FtsW | gp:AF123260 | AF123260 |

Description

Coxiella burnetii FtsW (ftsW) gene, complete cds.

| ORF Name | NTID | AAID | NT Length | AA Length | Score | Probability |
|---|---|---|---|---|---|---|
| 4720313_c1_180 | 681 | 2601 | 149 | 450 | 161 | 1.2e-10 |

| Protein name | Locus Name | Acc# |
|---|---|---|
| | sp:METE_ECOLI | P25665 |

Description (COBALAMIN-INDEPENDENT METHIONINE SYNTHASE)

| ORF Name | NTID | AAID | NT Length | AA Length | Score | Probability |
|---|---|---|---|---|---|---|
| 4770887_f2_72 | 682 | 2602 | 176 | 531 | 130 | 2.7e-14 |

| Protein name | Locus Name | Acc# |
|---|---|---|
| hypothetical protein | gp:SSU18930 | Y18930 |

Description

Sulfolobus solfataricus 281 kb genomic DNA fragment, strain P2.

| ORF Name | NTID | AAID | NT Length | AA Length | Score | Probability |
|---|---|---|---|---|---|---|
| 5100010_f1_7 | 683 | 2603 | 333 | 1002 | 581 | 2.4e-56 |

| Protein name | Locus Name | Acc# |
|---|---|---|
| | sp:XERC_HAEIN | P44818 |

Description

INTEGRASE/RECOMBINASE XERC

| ORF Name | NTID | AAID | NT Length | AA Length | Score | Probability |
|---|---|---|---|---|---|---|
| 5275250_c3_235 | 684 | 2604 | 202 | 609 | 328 | 1.5e-29 |

| Protein name | Locus Name | Acc# |
|---|---|---|
| Trp repressor binding protein | gp:AF067083 | AF067083 |

Description

Vitreoscilla sp. outer membrane protein homolog gene, complete cds;Trp repressor binding protein gene, partial cds; and unknown genes.

| ORF Name | NTID | AAID | NT Length | AA Length | Score | Probability |
|---|---|---|---|---|---|---|
| 593802_f2_71 | 685 | 2605 | 506 | 1521 | 433 | 1.1e-40 |

| Protein name | Locus Name | Acc# |
|---|---|---|
| | sp:RBN_HAEIN | P44608 |

Description

RIBONUCLEASE BN, (RNASE BN)

| ORF Name | NTID | AAID | NT Length | AA Length | Score | Probability |
|---|---|---|---|---|---|---|
| 5970933_f1_15 | 686 | 2606 | 105 | 318 | 249 | 3.6e-21 |

| Protein name | Locus Name | Acc# |
|---|---|---|
| unknown protein | gp:MSGTCWPA | M15467 |

Description

M.tuberculosis 65 kDa antigen (cell wall protein a) gene.

| ORF Name | NTID | AAID | NT Length | AA Length | Score | Probability |
|---|---|---|---|---|---|---|
| 5988327_c3_227 | 687 | 2607 | 927 | 2784 | 1588 | 4.6e-163 |

| Protein name | Locus Name | Acc# |
|---|---|---|
| | sp:HEPA_ECOLI | |

Description

RNA POLYMERASE ASSOCIATED PROTEIN (ATP-DEPENDENT HELICASE HEPA)

| ORF Name | NTID | AAID | NT Length | AA Length | Score | Probability |
|---|---|---|---|---|---|---|
| 6488910_f2_94 | 688 | 2608 | 66 | 201 | 85 | 0.0050 |

| Protein name | Locus Name | Acc# |
|---|---|---|
| | sp:YIHR_ECOLI | P32139 |

Description

HYPOTHETICAL 34.0 KD PROTEIN IN GLNA-RBN INTERGENIC REGION

| ORF Name | NTID | AAID | NT Length | AA Length | Score | Probability |
|---|---|---|---|---|---|---|
| 6516885_c2_185 | 689 | 2609 | 213 | 642 | 140 | 3.5e-09 |

Protein name: putative membrane protein.
Locus Name: gp:SC6D7
Acc#: AL133213

Description: Streptomyces coelicolor cosmid 6D7.

| ORF Name | NTID | AAID | NT Length | AA Length | Score | Probability |
|---|---|---|---|---|---|---|
| 665876_c3_245 | 690 | 2610 | 552 | 1659 | 215 | 1.1e-16 |

Protein name:
Locus Name: sp:OMPA_BORAV
Acc#: Q05146

Description: OUTER MEMBRANE PROTEIN A PRECURSOR

| ORF Name | NTID | AAID | NT Length | AA Length | Score | Probability |
|---|---|---|---|---|---|---|
| 8575_c3_236 | 691 | 2611 | 140 | 423 | 343 | 4.0e-31 |

Protein name:
Locus Name: sp:CH10_PSEST
Acc#: O33499

Description: 10)

| ORF Name | NTID | AAID | NT Length | AA Length | Score | Probability |
|---|---|---|---|---|---|---|
| 859388_f2_86 | 692 | 2612 | 342 | 1029 | 537 | 1.1e-51 |

Protein name:
Locus Name: sp:ISPA_HAEIN
Acc#: P45204

Description: (FPP SYNTHASE)

| ORF Name | NTID | AAID | NT Length | AA Length | Score | Probability |
|---|---|---|---|---|---|---|
| 970625_c1_145 | 693 | 2613 | 68 | 207 | 197 | 1.1e-14 |

| Protein name | | | | Locus Name | | Acc# |
|---|---|---|---|---|---|---|
| | | | | sp:ILVI_ECOLI | | |

Description

III) (ACETOHYDROXY-ACID SYNTHASE III LARGE SUBUNIT) (ALS-III)

| ORF Name | NTID | AAID | NT Length | AA Length | Score | Probability |
|---|---|---|---|---|---|---|
| 9957828_f2_88 | 694 | 2614 | 149 | 450 | 85 | 0.00086 |

| Protein name | | | | Locus Name | | Acc# |
|---|---|---|---|---|---|---|
| transposase | | | | gp:CETC2 | | |

Description

Caenorhabditis elegans transposon Tc2.

| ORF Name | NTID | AAID | NT Length | AA Length | Score | Probability |
|---|---|---|---|---|---|---|
| 21736625_c2_11 | 695 | 2615 | 290 | 870 | 508 | 1.3e-48 |

| Protein name | | | | Locus Name | | Acc# |
|---|---|---|---|---|---|---|
| | | | | sp:APAH_HAEIN | | P44751 |

Description (DIADENOSINE TETRAPHOSPHATASE)

| ORF Name | NTID | AAID | NT Length | AA Length | Score | Probability |
|---|---|---|---|---|---|---|
| 26053825_f1_4 | 696 | 2616 | 528 | 1587 | 1002 | 5.8e-101 |

| Protein name | | | | Locus Name | | Acc# |
|---|---|---|---|---|---|---|
| | | | | sp:DNAB_ECOLI | | P03005 |

Description

REPLICATIVE DNA HELICASE,

| ORF Name | NTID | AAID | NT Length | AA Length | Score | Probability |
|---|---|---|---|---|---|---|
| 33984677_f3_6 | 697 | 2617 | 382 | 1146 | 555 | 1.4e-53 |

| Protein name | Locus Name | Acc# |
|---|---|---|
| biosynthetic alanine racemase | gp:AF165882 | AF165882 |

Description

Pseudomonas aeruginosa biosynthetic alanine racemase (alr) gene, complete cds.

| ORF Name | NTID | AAID | NT Length | AA Length | Score | Probability |
|---|---|---|---|---|---|---|
| 5181430_c3_14 | 698 | 2618 | 327 | 984 | 617 | 3.6e-60 |

| Protein name | Locus Name | Acc# |
|---|---|---|
| | sp:PDXA_ECOLI | P19624 |

Description

PYRIDOXAL PHOSPHATE BIOSYNTHETIC PROTEIN PDXA

| ORF Name | NTID | AAID | NT Length | AA Length | Score | Probability |
|---|---|---|---|---|---|---|
| 7680_c3_15 | 699 | 2619 | 295 | 888 | 603 | 1.1e-58 |

| Protein name | Locus Name | Acc# |
|---|---|---|
| | sp:KSGA_ECOLI | P06992 |

Description

DIMETHYLTRANSFERASE)

| ORF Name | NTID | AAID | NT Length | AA Length | Score | Probability |
|---|---|---|---|---|---|---|
| 10547156_c1_79 | 700 | 2620 | 1096 | 3291 | 4176 | 0.0 |

| Protein name | Locus Name | Acc# |
|---|---|---|
| carbamoylphosphate synthetase large subunit | gp:PAU81259 | |

Description

Pseudomonas aeruginosa dihydrodipicolinate reductase (dapB) gene, partial cds, carbamoylphosphate synthetase small subunit (carA) and carbamoylphosphate synthetase large subunit (carB) genes, complete cds, and FtsJ homolog (ftsJ) gene, partial cds.

| ORF Name | NTID | AAID | NT Length | AA Length | Score | Probability |
|---|---|---|---|---|---|---|
| 11915953_c1_76 | 701 | 2621 | 138 | 417 | 312 | 7.6e-28 |

Protein name: probable oxidoreductase
Locus Name: pir:T35853
Acc#: T35853

Description

| ORF Name | NTID | AAID | NT Length | AA Length | Score | Probability |
|---|---|---|---|---|---|---|
| 13947152_f2_37 | 702 | 2622 | 126 | 381 | | |

Protein name:
Locus Name:
Acc#:

Description

NO-HIT

| ORF Name | NTID | AAID | NT Length | AA Length | Score | Probability |
|---|---|---|---|---|---|---|
| 14094052_f1_20 | 703 | 2623 | 111 | 336 | 160 | 9.7e-12 |

Protein name:
Locus Name: sp:YCCK_ECOLI
Acc#:

Description

HYPOTHETICAL 12.4 KD PROTEIN IN HELD-SERT INTERGENIC REGION

| ORF Name | NTID | AAID | NT Length | AA Length | Score | Probability |
|---|---|---|---|---|---|---|
| 16601077_f2_30 | 704 | 2624 | 93 | 282 | 103 | 1.1e-05 |

Protein name: hypothetical protein
Locus Name: gp:SSU18930
Acc#: Y18930

Description

Sulfolobus solfataricus 281 kb genomic DNA fragment, strain P2.

| ORF Name | NTID | AAID | NT Length | AA Length | Score | Probability |
|---|---|---|---|---|---|---|
| 19562686_f3_66 | 705 | 2625 | 309 | 930 | 530 | 6.0e-51 |

Protein name:
Locus Name: sp:CBL_ECOLI
Acc#:

Description

TRANSCRIPTIONAL REGULATOR CBL

| ORF_Name | NTID | AAID | NT Length | AA Length | Score | Probability |
|---|---|---|---|---|---|---|
| 19571925_c3_117 | 706 | 2626 | 70 | 213 | | |

Protein name | Locus Name | Acc#

Description

NO-HIT

| ORF_Name | NTID | AAID | NT Length | AA Length | Score | Probability |
|---|---|---|---|---|---|---|
| 20313326_f2_40 | 707 | 2627 | 65 | 198 | | |

Protein name | Locus Name | Acc#

Description

NO-HIT

| ORF_Name | NTID | AAID | NT Length | AA Length | Score | Probability |
|---|---|---|---|---|---|---|
| 20488827_f1_10 | 708 | 2628 | 558 | 1677 | 1638 | 2.3e-168 |

| Protein name | Locus Name | Acc# |
|---|---|---|
| sulfite reductase | gp:AF026066 | AF026066 |

Description

Pseudomonas aeruginosa sulfite reductase (cysI) gene, complete cds.

| ORF_Name | NTID | AAID | NT Length | AA Length | Score | Probability |
|---|---|---|---|---|---|---|
| 20953402_c2_103 | 709 | 2629 | 328 | 987 | 213 | 3.2e-15 |

| Protein name | Locus Name | Acc# |
|---|---|---|
| | sp:LPPB_HAEIN | P44833 |

Description

OUTER MEMBRANE ANTIGENIC LIPOPROTEIN B PRECURSOR

| ORF_Name | NTID | AAID | NT Length | AA Length | Score | Probability |
|---|---|---|---|---|---|---|
| 21907078_f3_55 | 710 | 2630 | 66 | 201 | | |

Protein name | Locus Name | Acc#

Description

NO-HIT

| ORF Name | NTID | AAID | NT Length | AA Length | Score | Probability |
|---|---|---|---|---|---|---|
| 22766067_f1_21 | 711 | 2631 | 478 | 1437 | 96 | 0.012 |

| Protein name | Locus Name | Acc# |
|---|---|---|
| | sp:THDF_MYCGE | |

Description

POSSIBLE THIOPHENE AND FURAN OXIDATION PROTEIN THDF

| ORF Name | NTID | AAID | NT Length | AA Length | Score | Probability |
|---|---|---|---|---|---|---|
| 24251510_c2_88 | 712 | 2632 | 364 | 1095 | 746 | 7.8e-74 |

| Protein name | Locus Name | Acc# |
|---|---|---|
| hypothetical protein Rv3629c | pir:F70561 | F70561 |

Description

| ORF Name | NTID | AAID | NT Length | AA Length | Score | Probability |
|---|---|---|---|---|---|---|
| 24259555_f2_39 | 713 | 2633 | 219 | 660 | 375 | 1.6e-34 |

| Protein name | Locus Name | Acc# |
|---|---|---|
| similar to glutathione-s-transferase | gp:AF036940 | |

Description

Pseudomonas sp. U2 plasmid pWWU2, ferredoxin reductase (nagAa),salicylate-5-hydroxylase large oxygenase component (nagG),salicylate-5-hydroxylase small oxygenase component (nagH),ferredoxin (nagAb), naphthalene dioxygenase large oxygenasecomponent (nagAc), naphthalene dioxygenase small oxygenasecomponent (nagAd), cis-naphthalene dihydrodiol dehydrogenase(nagB), salicylaldehyde dehydrogenase

| ORF Name | NTID | AAID | NT Length | AA Length | Score | Probability |
|---|---|---|---|---|---|---|
| 24801562_c2_82 | 714 | 2634 | 554 | 1665 | 506 | 8.0e-73 |

| Protein name | Locus Name | Acc# |
|---|---|---|
| permease for AmpC beta-lactamase expression | gp:AF082985 | AF082985 |

Description

Pseudomonas aeruginosa permease for AmpC beta-lactamase expressionAmpG (ampG) gene, complete cds; and unknown gene.

| ORF Name | NTID | AAID | NT Length | AA Length | Score | Probability |
|---|---|---|---|---|---|---|
| 25448412_c2_95 | 715 | 2635 | 98 | 297 | 186 | 1.7e-14 |

| Protein name | Locus Name | Acc# |
|---|---|---|
| unknown | gp:AF033858 | AF033858 |

Description

Pediococcus pentosaceus strain ATCC43200 plasmid pMD136, completeplasmid sequence.

| ORF Name | NTID | AAID | NT Length | AA Length | Score | Probability |
|---|---|---|---|---|---|---|
| 29429590_f2_44 | 716 | 2636 | 162 | 489 | 241 | 2.5e-20 |

| Protein name | Locus Name | Acc# |
|---|---|---|
|  | sp:VDLD_HELPY | O05729 |

Description

PROTEIN VDLD

| ORF Name | NTID | AAID | NT Length | AA Length | Score | Probability |
|---|---|---|---|---|---|---|
| 30181587_f1_9 | 717 | 2637 | 76 | 231 | 43 | 0.037 |

| Protein name | Locus Name | Acc# |
|---|---|---|
| bone morphogenetic protein 2 | pir:A61387 | A61387 |

Description

| ORF Name | NTID | AAID | NT Length | AA Length | Score | Probability |
|---|---|---|---|---|---|---|
| 3129637_c2_94 | 718 | 2638 | 323 | 972 | 577 | 6.3e-56 |

| Protein name | Locus Name | Acc# |
|---|---|---|
| mrr restriction system protein | pir:F75508 | F75508 |

Description

| ORF Name | NTID | AAID | NT Length | AA Length | Score | Probability |
|---|---|---|---|---|---|---|
| 31375212_f3_54 | 719 | 2639 | 615 | 1848 | 1278 | 3.3e-130 |

| Protein name | Locus Name | Acc# |
|---|---|---|
|  | sp:YFBQ_ECOLI | P77727 |

Description

PROBABLE AMINOTRANSFERASE YFBQ,

| ORF_Name | NTID | AAID | NT Length | AA Length | Score | Probability |
|---|---|---|---|---|---|---|
| 32878_f2_25 | 720 | 2640 | 349 | 1050 | 176 | 1.2e-10 |

| Protein name | | | | Locus Name | Acc# |
|---|---|---|---|---|---|
| | | | | gp:ECO110K | |

Description

E.coli K12 genome, 0-2.4min. region.

| ORF_Name | NTID | AAID | NT Length | AA Length | Score | Probability |
|---|---|---|---|---|---|---|
| 33788387_c3_108 | 721 | 2641 | 66 | 201 | 87 | 0.00053 |

| Protein name | | | | Locus Name | Acc# |
|---|---|---|---|---|---|
| hypothetical protein SPCP31B10.02 | | | | pir:T41692 | T41692 |

Description

| ORF_Name | NTID | AAID | NT Length | AA Length | Score | Probability |
|---|---|---|---|---|---|---|
| 3915688_c1_78 | 722 | 2642 | 200 | 603 | 482 | 7.4e-46 |

| Protein name | | | | Locus Name | Acc# |
|---|---|---|---|---|---|
| | | | | sp:Y318_HAEIN | P43984 |

Description

HYPOTHETICAL PROTEIN HI0318

| ORF_Name | NTID | AAID | NT Length | AA Length | Score | Probability |
|---|---|---|---|---|---|---|
| 40875_f1_18 | 723 | 2643 | 126 | 381 | 189 | 8.2e-15 |

| Protein name | | | | Locus Name | Acc# |
|---|---|---|---|---|---|
| | | | | sp:YHEN_ECOLI | P45532 |

Description

HYPOTHETICAL 13.6 KD PROTEIN IN RPSL-FKPA INTERGENIC REGION

| ORF_Name | NTID | AAID | NT Length | AA Length | Score | Probability |
|---|---|---|---|---|---|---|
| 4490902_c2_101 | 724 | 2644 | 166 | 501 | 522 | 4.3e-50 |

| Protein name | | | | Locus Name | Acc# |
|---|---|---|---|---|---|
| | | | | sp:GREA_ECOLI | |

Description (GREA)

| ORF Name | NTID | AAID | NT Length | AA Length | Score | Probability |
|---|---|---|---|---|---|---|
| 4536668_c3_107 | 725 | 2645 | 940 | 2823 | 1554 | 1.9e-159 |

| Protein name | | | | Locus Name | | Acc# |
|---|---|---|---|---|---|---|
| | | | | sp:GLNE_ECOLI | | |

Description

SYNTHETASE ADENYLYLTRANSFERASE) (ATASE)

| ORF Name | NTID | AAID | NT Length | AA Length | Score | Probability |
|---|---|---|---|---|---|---|
| 4572125_c1_72 | 726 | 2646 | 311 | 936 | 820 | 1.1e-81 |

| Protein name | | | | Locus Name | | Acc# |
|---|---|---|---|---|---|---|
| unknown | | | | gp:PAU63816 | | U63816 |

Description

Pseudomonas aeruginosa glnE gene, partial cds; ilvE, ADP-heptose:LPS heptosyltransferase homolog (waaF), lipopolysaccharide heptosyltransferase I homolog (waaC), glucosyltransferase I homolog (waaG), RfaP protein (waaP), andunknown protein (waaX) genes, complete cds; and inaA gene, partialcds.

| ORF Name | NTID | AAID | NT Length | AA Length | Score | Probability |
|---|---|---|---|---|---|---|
| 5084827_f3_48 | 727 | 2647 | 163 | 492 | 193 | 1.5e-14 |

| Protein name | | | | Locus Name | | Acc# |
|---|---|---|---|---|---|---|
| | | | | sp:SURA_ECOLI | | |

Description (SURA), (PPIASE) (ROTAMASE C)

| ORF Name | NTID | AAID | NT Length | AA Length | Score | Probability |
|---|---|---|---|---|---|---|
| 5287555_c2_102 | 728 | 2648 | 125 | 378 | 125 | 5.0e-08 |

| Protein name | | | | Locus Name | | Acc# |
|---|---|---|---|---|---|---|
| | | | | sp:YC53_HAEIN | | P44139 |

Description

HYPOTHETICAL PROTEIN HI1253

| ORF Name | NTID | AAID | NT Length | AA Length | Score | Probability |
|---|---|---|---|---|---|---|
| 5322062_c1_69 | 729 | 2649 | 265 | 798 | 449 | 2.3e-42 |

| Protein name | Locus Name | Acc# |
|---|---|---|
| | sp:MOEB_ECOLI | P12282 |

Description

MOLYBDOPTERIN BIOSYNTHESIS MOEB PROTEIN

| ORF Name | NTID | AAID | NT Length | AA Length | Score | Probability |
|---|---|---|---|---|---|---|
| 6822208_c2_83 | 730 | 2650 | 296 | 891 | 502 | 5.6e-48 |

| Protein name | Locus Name | Acc# |
|---|---|---|
| | sp:HEMK_ECOLI | |

Description

HEMK PROTEIN

| ORF Name | NTID | AAID | NT Length | AA Length | Score | Probability |
|---|---|---|---|---|---|---|
| 6829637_f2_38 | 731 | 2651 | 455 | 1368 | 926 | 6.6e-93 |

| Protein name | Locus Name | Acc# |
|---|---|---|
| | sp:CYSG_ECOLI | |

Description

| ORF Name | NTID | AAID | NT Length | AA Length | Score | Probability |
|---|---|---|---|---|---|---|
| 7117182_c3_114 | 732 | 2652 | 115 | 348 | 200 | 5.6e-16 |

| Protein name | Locus Name | Acc# |
|---|---|---|
| unknown | gp:AF033858 | AF033858 |

Description

Pediococcus pentosaceus strain ATCC43200 plasmid pMD136, completeplasmid sequence.

| ORF Name | NTID | AAID | NT Length | AA Length | Score | Probability |
|---|---|---|---|---|---|---|
| 7281562_c1_77 | 733 | 2653 | 416 | 1251 | 739 | 6.4e-130 |

| Protein name | Locus Name | Acc# |
|---|---|---|
| | sp:CARA_PSEAE | P38098 |

Description

PHOSPHATE SYNTHETASE GLUTAMINE CHAIN)

| ORF Name | NTID | AAID | NT Length | AA Length | Score | Probability |
|---|---|---|---|---|---|---|
| 953181_c3_106 | 734 | 2654 | 450 | 1353 | 449 | 2.3e-42 |

| Protein name | | | | Locus Name | | Acc# |
|---|---|---|---|---|---|---|
| | | | | sp:Y16S_MYCTU | | P96936 |

Description

HYPOTHETICAL 54.8 KD PROTEIN CY20H10.28C

| ORF Name | NTID | AAID | NT Length | AA Length | Score | Probability |
|---|---|---|---|---|---|---|
| 978465_f1_19 | 735 | 2655 | 102 | 309 | | |

| Protein name | | | | Locus Name | | Acc# |
|---|---|---|---|---|---|---|

Description

NO-HIT

| ORF Name | NTID | AAID | NT Length | AA Length | Score | Probability |
|---|---|---|---|---|---|---|
| 16985642_c2_43 | 736 | 2656 | 69 | 210 | 127 | 9.7e-08 |

| Protein name | | | | Locus Name | | Acc# |
|---|---|---|---|---|---|---|
| | | | | sp:MURI_SYNY3 | | P73737 |

Description

GLUTAMATE RACEMASE,

| ORF Name | NTID | AAID | NT Length | AA Length | Score | Probability |
|---|---|---|---|---|---|---|
| 189186_c3_54 | 737 | 2657 | 233 | 702 | | |

| Protein name | | | | Locus Name | | Acc# |
|---|---|---|---|---|---|---|

Description

NO-HIT

| ORF Name | NTID | AAID | NT Length | AA Length | Score | Probability |
|---|---|---|---|---|---|---|
| 23628411_f1_6 | 738 | 2658 | 295 | 888 | 379 | 6.1e-35 |

| Protein name | | | | Locus Name | | Acc# |
|---|---|---|---|---|---|---|
| | | | | sp:YCHB_ECOLI | | P24209 |

Description

HYPOTHETICAL 30.9 KD PROTEIN IN HEMM-PRSA INTERGENIC REGION

| ORF Name | NTID | AAID | NT Length | AA Length | Score | Probability |
|---|---|---|---|---|---|---|
| 29494003_f2_13 | 739 | 2659 | 672 | 2019 | 241 | 6.6e-17 |

Protein name | Locus Name | Acc#
sp:YHE3_PSEAE | P42810

Description

HYPOTHETICAL 64.8 KD PROTEIN IN HEMM-HEMA INTERGENIC REGION (ORF3)

| ORF Name | NTID | AAID | NT Length | AA Length | Score | Probability |
|---|---|---|---|---|---|---|
| 29960761_c1_30 | 740 | 2660 | 468 | 1407 | 731 | 3.0e-72 |

Protein name | Locus Name | Acc#
sp:HEM1_PASMU | P95525

Description

GLUTAMYL-TRNA REDUCTASE, (GLUTR)

| ORF Name | NTID | AAID | NT Length | AA Length | Score | Probability |
|---|---|---|---|---|---|---|
| 31291251_f2_15 | 741 | 2661 | 265 | 798 | 924 | 1.1e-92 |

Protein name | Locus Name | Acc#
gp:ECOPRS | M13174

Description

E.coli prs gene encoding phosphoribosylpyrophosphate synthetase, complete cds.

| ORF Name | NTID | AAID | NT Length | AA Length | Score | Probability |
|---|---|---|---|---|---|---|
| 34641308_f3_23 | 742 | 2662 | 196 | 591 | 160 | 9.7e-12 |

Protein name | Locus Name | Acc#
sp:LOLB_PSEAE | P42812

Description

OUTER MEMBRANE LIPOPROTEIN LOLB PRECURSOR

| ORF Name | NTID | AAID | NT Length | AA Length | Score | Probability |
|---|---|---|---|---|---|---|
| 4869025_f3_19 | 743 | 2663 | 554 | 1665 | 1876 | 1.4e-193 |

| Protein name | | | | Locus Name | | Acc# |
|---|---|---|---|---|---|---|
| | | | | sp:ETFD_ACICA | | P94132 |

Description

DEHYDROGENASE) (ELECTRON-TRANSFERRING-FLAVOPROTEIN DEHYDROGENASE)

| ORF Name | NTID | AAID | NT Length | AA Length | Score | Probability |
|---|---|---|---|---|---|---|
| 10552153_f1_31 | 744 | 2664 | 74 | 225 | 168 | 7.1e-12 |

| Protein name | | | | Locus Name | | Acc# |
|---|---|---|---|---|---|---|
| | | | | gp:AB028868 | | AB028868 |

Description

Mus musculus P4(21)n mRNA, partial cds.

| ORF Name | NTID | AAID | NT Length | AA Length | Score | Probability |
|---|---|---|---|---|---|---|
| 10722125_f2_65 | 745 | 2665 | 161 | 486 | 165 | 2.9e-12 |

| Protein name | | | | Locus Name | | Acc# |
|---|---|---|---|---|---|---|
| | | | | sp:SMPA_ECOLI | | P23089 |

Description

SMALL PROTEIN A

| ORF Name | NTID | AAID | NT Length | AA Length | Score | Probability |
|---|---|---|---|---|---|---|
| 117037_f3_138 | 746 | 2666 | 218 | 657 | 375 | 1.6e-34 |

| Protein name | | | | Locus Name | | Acc# |
|---|---|---|---|---|---|---|
| | | | | sp:Y787_HAEIN | | P44052 |

Description

HYPOTHETICAL PROTEIN HI0787

| ORF Name | NTID | AAID | NT Length | AA Length | Score | Probability |
|---|---|---|---|---|---|---|
| 11885927_f1_51 | 747 | 2667 | 76 | 231 | | |

| Protein name | | | | Locus Name | | Acc# |
|---|---|---|---|---|---|---|

Description

NO-HIT

| ORF Name | NTID | AAID | NT Length | AA Length | Score | Probability |
|---|---|---|---|---|---|---|
| 12297203_c3_236 | 748 | 2668 | 78 | 237 | 138 | 2.1e-09 |

| Protein name | Locus Name | Acc# |
|---|---|---|
| hypothetical protein APE2061 | pir:G72510 | G72510 |

Description

| ORF Name | NTID | AAID | NT Length | AA Length | Score | Probability |
|---|---|---|---|---|---|---|
| 12506635_f2_83 | 749 | 2669 | 66 | 201 | | |

| Protein name | Locus Name | Acc# |
|---|---|---|
| | | |

Description

NO-HIT

| ORF Name | NTID | AAID | NT Length | AA Length | Score | Probability |
|---|---|---|---|---|---|---|
| 12697037_c2_201 | 750 | 2670 | 111 | 336 | 99 | 2.8e-05 |

| Protein name | Locus Name | Acc# |
|---|---|---|
| | gp:PADLDH | X70925 |

Description

P.acidilactici gene for d-lactate dehydrogenase.

| ORF Name | NTID | AAID | NT Length | AA Length | Score | Probability |
|---|---|---|---|---|---|---|
| 13078416_c3_233 | 751 | 2671 | 167 | 504 | 210 | 4.9e-17 |

| Protein name | Locus Name | Acc# |
|---|---|---|
| ribosomal-protein-serine N-acetyltransferase, rimL homolog ydaF | pir:F69768 | F69768 |

Description

| ORF Name | NTID | AAID | NT Length | AA Length | Score | Probability |
|---|---|---|---|---|---|---|
| 134635_c2_226 | 752 | 2672 | 147 | 444 | 539 | 6.7e-52 |

| Protein name | Locus Name | Acc# |
|---|---|---|
| ferric uptake regulator | gp:ABDNAFUR | Y14980 |

Description

Acinetobacter baumannii fur gene.

| ORF Name | NTID | AAID | NT Length | AA Length | Score | Probability |
|---|---|---|---|---|---|---|
| 13726003_c2_196 | 753 | 2673 | 349 | 1050 | 736 | 8.9e-73 |

| Protein name | Locus Name | Acc# |
|---|---|---|
| iron transport protein:protein slr1295:protein slr1295 | pir:S74691 | S74691 |

Description

---

| ORF Name | NTID | AAID | NT Length | AA Length | Score | Probability |
|---|---|---|---|---|---|---|
| 13870462_f3_144 | 754 | 2674 | 81 | 246 | 117 | 3.5e-07 |

| Protein name | Locus Name | Acc# |
|---|---|---|
| hypothetical protein jhp1163 | pir:B71840 | B71840 |

Description

---

| ORF Name | NTID | AAID | NT Length | AA Length | Score | Probability |
|---|---|---|---|---|---|---|
| 14553432_f2_67 | 755 | 2675 | 303 | 912 | 647 | 2.4e-63 |

| Protein name | Locus Name | Acc# |
|---|---|---|
|  | sp:METR_SALTY | P05984 |

Description

TRANSCRIPTIONAL ACTIVATOR PROTEIN METR

---

| ORF Name | NTID | AAID | NT Length | AA Length | Score | Probability |
|---|---|---|---|---|---|---|
| 15820312_c2_223 | 756 | 2676 | 867 | 2604 | 1893 | 2.2e-195 |

| Protein name | Locus Name | Acc# |
|---|---|---|
| UspA2 | gp:AF113611 | AF113611 |

Description

Moraxella catarrhalis strain V1171 UspA2 (uspA2) gene, completecds.

---

| ORF Name | NTID | AAID | NT Length | AA Length | Score | Probability |
|---|---|---|---|---|---|---|
| 16016926_f3_137 | 757 | 2677 | 237 | 714 | 197 | 3.1e-15 |

| Protein name | Locus Name | Acc# |
|---|---|---|
| growth factor-responsive protein, vascular smooth muscle:SM-20 | pir:A53770 | A53770 |

Description

| ORF Name | NTID | AAID | NT Length | AA Length | Score | Probability |
|---|---|---|---|---|---|---|
| 16064061_c2_187 | 758 | 2678 | 397 | 1194 | 738 | 5.5e-73 |

| Protein name | | | | Locus Name | | Acc# |
|---|---|---|---|---|---|---|
| | | | | sp:MURG_HAEIN | | P45065 |

Description (EC 2.4.1.-)

| ORF Name | NTID | AAID | NT Length | AA Length | Score | Probability |
|---|---|---|---|---|---|---|
| 16171905_c2_202 | 759 | 2679 | 74 | 225 | | |

| Protein name | | | | Locus Name | | Acc# |
|---|---|---|---|---|---|---|

Description

NO-HIT

| ORF Name | NTID | AAID | NT Length | AA Length | Score | Probability |
|---|---|---|---|---|---|---|
| 16585933_f1_11 | 760 | 2680 | 765 | 2298 | 2390 | 4.8e-248 |

| Protein name | | | | Locus Name | | Acc# |
|---|---|---|---|---|---|---|
| | | | | sp:IDH_AZOVI | | P16100 |

Description

DECARBOXYLASE) (IDH)

| ORF Name | NTID | AAID | NT Length | AA Length | Score | Probability |
|---|---|---|---|---|---|---|
| 16678186_c3_251 | 761 | 2681 | 488 | 1467 | 1057 | 8.6e-107 |

| Protein name | | | | Locus Name | | Acc# |
|---|---|---|---|---|---|---|
| hypothetical protein F32D8.4 | | | | pir:T21659 | | T21659 |

Description

| ORF Name | NTID | AAID | NT Length | AA Length | Score | Probability |
|---|---|---|---|---|---|---|
| 20080051_c1_171 | 762 | 2682 | 299 | 900 | 330 | 9.4e-30 |

| Protein name | | | | Locus Name | | Acc# |
|---|---|---|---|---|---|---|
| | | | | sp:YJJV_ECOLI | | |

Description

HYPOTHETICAL 28.9 KD PROTEIN IN OSMY-DEOC INTERGENIC REGION

| ORF_Name | NTID | AAID | NT Length | AA Length | Score | Probability |
|---|---|---|---|---|---|---|
| 20509628_c2_204 | 763 | 2683 | 378 | 1137 | 891 | 3.4e-89 |

Protein name | | | | Locus_Name | | Acc#
sp:FTSZ_ECOLI

Description
CELL DIVISION PROTEIN FTSZ

| ORF_Name | NTID | AAID | NT Length | AA Length | Score | Probability |
|---|---|---|---|---|---|---|
| 2132006_c2_218 | 764 | 2684 | 132 | 399 | 153 | 2.4e-10 |

Protein name | | | | Locus_Name | | Acc#
hypothetical protein sll1830 | | | | pir:S75232 | | S75232

Description

| ORF_Name | NTID | AAID | NT Length | AA Length | Score | Probability |
|---|---|---|---|---|---|---|
| 22048442_f2_95 | 765 | 2685 | 402 | 1209 | 1010 | 8.2e-102 |

Protein name | | | | Locus_Name | | Acc#
 | | | | sp:DAPE_HAEIN | | P44514

Description
SUCCINYL-DIAMINOPIMELATE DESUCCINYLASE, (SDAP)

| ORF_Name | NTID | AAID | NT Length | AA Length | Score | Probability |
|---|---|---|---|---|---|---|
| 22323956_f3_130 | 766 | 2686 | 61 | 186 | 109 | 6.5e-06 |

Protein name | | | | Locus_Name | | Acc#
hypothetical protein PH0221 | | | | pir:D71245 | | D71245

Description

| ORF_Name | NTID | AAID | NT Length | AA Length | Score | Probability |
|---|---|---|---|---|---|---|
| 22463311_f3_128 | 767 | 2687 | 103 | 312 | | |

Protein name | | | | Locus_Name | | Acc#

Description
NO-HIT

| ORF Name | NTID | AAID | NT Length | AA Length | Score | Probability |
|---|---|---|---|---|---|---|
| 22734807_f1_40 | 768 | 2688 | 97 | 294 | | |

Protein name | Locus Name | Acc#

Description

NO-HIT

| ORF Name | NTID | AAID | NT Length | AA Length | Score | Probability |
|---|---|---|---|---|---|---|
| 22930306_c1_170 | 769 | 2689 | 354 | 1065 | 427 | 5.0e-40 |

Protein name: 5'-nucleotidase | Locus Name: gp:CLI131243 | Acc#: AJ131243

Description

Columba livia mRNA for 5'-nucleotidase.

| ORF Name | NTID | AAID | NT Length | AA Length | Score | Probability |
|---|---|---|---|---|---|---|
| 23445136_f2_60 | 770 | 2690 | 583 | 1752 | 752 | 4.3e-120 |

Protein name: NH(3)-dependent NAD(+) synthetase | Locus Name: pir:G72277 | Acc#: G72277

Description

| ORF Name | NTID | AAID | NT Length | AA Length | Score | Probability |
|---|---|---|---|---|---|---|
| 23532300_c1_165 | 771 | 2691 | 78 | 237 | | |

Protein name | Locus Name | Acc#

Description

NO-HIT

| ORF Name | NTID | AAID | NT Length | AA Length | Score | Probability |
|---|---|---|---|---|---|---|
| 23556625_c3_245 | 772 | 2692 | 241 | 726 | 185 | 2.2e-14 |

Protein name | Locus Name: sp:FTSQ_ECOLI | Acc#: P06136

Description

CELL DIVISION PROTEIN FTSQ

| ORF Name | NTID | AAID | NT Length | AA Length | Score | Probability |
|---|---|---|---|---|---|---|
| 23615832_f1_16 | 773 | 2693 | 334 | 1005 | 125 | 9.1e-09 |

Protein name | Locus Name | Acc#
lysophospholipase homolog | pir:T02661 | T02661

Description

| ORF Name | NTID | AAID | NT Length | AA Length | Score | Probability |
|---|---|---|---|---|---|---|
| 24111015_c3_269 | 774 | 2694 | 154 | 465 | 274 | 8.1e-24 |

Protein name | Locus Name | Acc#
 | sp:RIBF_ECOLI |

Description

| ORF Name | NTID | AAID | NT Length | AA Length | Score | Probability |
|---|---|---|---|---|---|---|
| 24219056_c1_184 | 775 | 2695 | 246 | 741 | 512 | 4.9e-49 |

Protein name | Locus Name | Acc#
 | sp:YPT5_PSEAE | P24562

Description
HYPOTHETICAL 24.5 KD PROTEIN IN PILT 5'REGION (ORF5)

| ORF Name | NTID | AAID | NT Length | AA Length | Score | Probability |
|---|---|---|---|---|---|---|
| 24220786_f1_4 | 776 | 2696 | 370 | 1113 | 835 | 2.9e-83 |

Protein name | Locus Name | Acc#
 | sp:PILT_PSEAE | P24559

Description
TWITCHING MOBILITY PROTEIN

| ORF Name | NTID | AAID | NT Length | AA Length | Score | Probability |
|---|---|---|---|---|---|---|
| 24250928_c1_153 | 777 | 2697 | 78 | 237 | 207 | 1.0e-16 |

Protein name | Locus Name | Acc#
 | sp:YFHJ_ECOLI | P37096

Description
HYPOTHETICAL 7.7 KD PROTEIN IN PPEB-FDX INTERGENIC REGION

242

| ORF_Name | NTID | AAID | NT Length | AA Length | Score | Probability |
|---|---|---|---|---|---|---|
| 24255260_c2_229 | 778 | 2698 | 115 | 348 | | |// 
| Protein name | | | | | Locus Name | Acc# |

Description

NO-HIT

| ORF_Name | NTID | AAID | NT Length | AA Length | Score | Probability |
|---|---|---|---|---|---|---|
| 24412562_c2_189 | 779 | 2699 | 314 | 945 | 740 | 3.4e-73 |
| Protein name | | | | | Locus Name | Acc# |
| | | | | | sp:DDL_HAEIN | P44405 |

Description

D-ALANINE--D-ALANINE LIGASE, (D-ALANYLALANINE SYNTHETASE)

| ORF_Name | NTID | AAID | NT Length | AA Length | Score | Probability |
|---|---|---|---|---|---|---|
| 24415875_c1_174 | 780 | 2700 | 322 | 969 | 832 | 6.0e-83 |
| Protein name | | | | | Locus Name | Acc# |
| | | | | | sp:HEMZ_ECOLI | |

Description

SYNTHETASE)

| ORF_Name | NTID | AAID | NT Length | AA Length | Score | Probability |
|---|---|---|---|---|---|---|
| 24644577_f2_96 | 781 | 2701 | 535 | 1608 | 923 | 1.4e-92 |
| Protein name | | | | | Locus Name | Acc# |
| hypothetical protein | | | | | pir:S76051 | S76051 |

Description

| ORF_Name | NTID | AAID | NT Length | AA Length | Score | Probability |
|---|---|---|---|---|---|---|
| 24813161_f3_143 | 782 | 2702 | 344 | 1035 | 650 | 1.2e-63 |
| Protein name | | | | | Locus Name | Acc# |
| MsmX | | | | | gp:AB013374 | AB013374 |

Description

Bacillus halodurans C-125 mamX, yjdA, ykoK and yvfK genes, partial and complete cds.

| ORF Name | NTID | AAID | NT Length | AA Length | Score | Probability |
|---|---|---|---|---|---|---|
| 25579510_f3_109 | 783 | 2703 | 156 | 471 | 99 | 0.0018 |

| Protein name | Locus Name | Acc# |
|---|---|---|
| myosin alpha heavy chain, masticatory muscle | pir:S33732 | S33732 |

Description

| ORF Name | NTID | AAID | NT Length | AA Length | Score | Probability |
|---|---|---|---|---|---|---|
| 26212750_c2_205 | 784 | 2704 | 329 | 990 | 285 | 7.8e-25 |

| Protein name | Locus Name | Acc# |
|---|---|---|
| | gp:ATAC006436 | AC006436 |

Description

Arabidopsis thaliana chromosome II BAC F13J11 genomic sequence, complete sequence.

| ORF Name | NTID | AAID | NT Length | AA Length | Score | Probability |
|---|---|---|---|---|---|---|
| 26678567_c1_164 | 785 | 2705 | 63 | 192 | 88 | 0.00042 |

| Protein name | Locus Name | Acc# |
|---|---|---|
| hypothetical protein 29.1 | pir:S59084 | S59084 |

Description

| ORF Name | NTID | AAID | NT Length | AA Length | Score | Probability |
|---|---|---|---|---|---|---|
| 26813135_c2_192 | 786 | 2706 | 524 | 1575 | 1287 | 3.7e-131 |

| Protein name | Locus Name | Acc# |
|---|---|---|
| alkyl hydroperoxide reductase, F52A protein | pir:D64794 | D64794 |

Description

| ORF Name | NTID | AAID | NT Length | AA Length | Score | Probability |
|---|---|---|---|---|---|---|
| 273427_c3_263 | 787 | 2707 | 224 | 675 | 583 | 1.5e-56 |

| Protein name | Locus Name | Acc# |
|---|---|---|
| | sp:DEDA_ECOLI | P09548 |

Description

DEDA PROTEIN (DSG-1 PROTEIN)

| ORF_Name | NTID | AAID | NT Length | AA Length | Score | Probability |
|---|---|---|---|---|---|---|
| 29337825_f2_62 | 788 | 2708 | 67 | 204 | 131 | 1.2e-08 |

| Protein name | | Locus_Name | Acc# |
|---|---|---|---|
| | | sp:YPT1_PSEAE | P24560 |

Description

HYPOTHETICAL 17.0 KD PROTEIN IN PILT 5'REGION (ORF1)

| ORF_Name | NTID | AAID | NT Length | AA Length | Score | Probability |
|---|---|---|---|---|---|---|
| 31252614_c3_231 | 789 | 2709 | 68 | 207 | 85 | 0.0054 |

| Protein name | | Locus_Name | Acc# |
|---|---|---|---|
| glutathione synthetase | | gp:D88540 | D88540 |

Description

Synechococcus sp. DNA for glutathione synthetase, complete cds.

| ORF_Name | NTID | AAID | NT Length | AA Length | Score | Probability |
|---|---|---|---|---|---|---|
| 3236505_c2_217 | 790 | 2710 | 119 | 360 | 127 | 1.7e-07 |

| Protein name | | Locus_Name | Acc# |
|---|---|---|---|
| hypothetical protein sll1830 | | pir:S75232 | S75232 |

Description

| ORF_Name | NTID | AAID | NT Length | AA Length | Score | Probability |
|---|---|---|---|---|---|---|
| 32593750_f1_27 | 791 | 2711 | 366 | 1101 | 1382 | 3.1e-141 |

| Protein name | | Locus_Name | Acc# |
|---|---|---|---|
| | | sp:RECA_ACICA | P42438 |

Description

RECA PROTEIN

| ORF_Name | NTID | AAID | NT Length | AA Length | Score | Probability |
|---|---|---|---|---|---|---|
| 33788286_c2_188 | 792 | 2712 | 493 | 1482 | 1448 | 3.2e-148 |

| Protein name | | Locus_Name | Acc# |
|---|---|---|---|
| UDP-N-acetylmuramate:L-alanine ligase MurC | | gp:AF110740 | AF110740 |

Description

Pseudomonas aeruginosa UDP-N-acetylmuramate:L-alanine ligase MurC(murC) gene, complete cds.

| ORF Name | NTID | AAID | NT Length | AA Length | Score | Probability |
|---|---|---|---|---|---|---|
| 34040777_c1_169 | 793 | 2713 | 196 | 591 | 93 | 0.00011 |

| Protein name | | | | Locus Name | | Acc# |
|---|---|---|---|---|---|---|
| | | | | sp:PPDD_ECOLI | | P36647 |

Description

PREPILIN PEPTIDASE DEPENDENT PROTEIN D PRECURSOR

| ORF Name | NTID | AAID | NT Length | AA Length | Score | Probability |
|---|---|---|---|---|---|---|
| 34159412_f1_53 | 794 | 2714 | 330 | 993 | 497 | 1.9e-47 |

| Protein name | | | | Locus Name | | Acc# |
|---|---|---|---|---|---|---|
| oxidative stress transcriptional regulator | | | | gp:XCU94336 | | U94336 |

Description

Xanthomonas campestris alkyl hydroperoxide reductase subunits C(ahpC) and F (ahpF) and oxidative stress transcriptional regulator(oxyR) genes, complete cds.

| ORF Name | NTID | AAID | NT Length | AA Length | Score | Probability |
|---|---|---|---|---|---|---|
| 35276891_f3_132 | 795 | 2715 | 80 | 243 | 88 | 0.00042 |

| Protein name | | | | Locus Name | | Acc# |
|---|---|---|---|---|---|---|
| hypothetical protein | | | | pir:D75542 | | D75542 |

Description

| ORF Name | NTID | AAID | NT Length | AA Length | Score | Probability |
|---|---|---|---|---|---|---|
| 3907311_f3_110 | 796 | 2716 | 74 | 225 | | |

| Protein name | | | | Locus Name | | Acc# |
|---|---|---|---|---|---|---|

Description

NO-HIT

| ORF Name | NTID | AAID | NT Length | AA Length | Score | Probability |
|---|---|---|---|---|---|---|
| 3928750_c3_242 | 797 | 2717 | 298 | 897 | 412 | 1.9e-38 |

| Protein name | | | | Locus Name | | Acc# |
|---|---|---|---|---|---|---|
| | | | | sp:YHIR_HAEIN | | P31777 |

Description

HYPOTHETICAL PROTEIN HI0441 (ORFJ)

| ORF Name | NTID | AAID | NT Length | AA Length | Score | Probability |
|---|---|---|---|---|---|---|
| 3940943_f2_59 | 798 | 2718 | 118 | 357 | 93 | 0.00012 |
| Protein name | | | | Locus Name | | Acc# |
| | | | | sp:YGFE_ECOLI | | P45580 |

Description

HYPOTHETICAL 12.6 KD PROTEIN IN PEPP-SSR INTERGENIC REGION (O109)

| ORF Name | NTID | AAID | NT Length | AA Length | Score | Probability |
|---|---|---|---|---|---|---|
| 3947318_f3_116 | 799 | 2719 | 276 | 831 | 1038 | 8.9e-105 |
| Protein name | | | | Locus Name | | Acc# |
| | | | | sp:DAPD_MYCBO | | P56220 |

Description (THP SUCCINYLTRANSFERASE) (TETRAHYDROPICOLINATE SUCCINYLASE)

| ORF Name | NTID | AAID | NT Length | AA Length | Score | Probability |
|---|---|---|---|---|---|---|
| 4017832_f2_85 | 800 | 2720 | 211 | 636 | 525 | 2.0e-50 |
| Protein name | | | | Locus Name | | Acc# |
| DedA family protein | | | | pir:B75253 | | B75253 |

Description

| ORF Name | NTID | AAID | NT Length | AA Length | Score | Probability |
|---|---|---|---|---|---|---|
| 4023342_c1_186 | 801 | 2721 | 215 | 648 | 145 | 3.8e-10 |
| Protein name | | | | Locus Name | | Acc# |
| | | | | sp:YGFB_ECOLI | | P25533 |

Description (F194)

| ORF Name | NTID | AAID | NT Length | AA Length | Score | Probability |
|---|---|---|---|---|---|---|
| 402336_f2_89 | 802 | 2722 | 83 | 252 | | |
| Protein name | | | | Locus Name | | Acc# |

Description

NO-HIT

| ORF Name | NTID | AAID | NT Length | AA Length | Score | Probability |
|---|---|---|---|---|---|---|
| 4140943_f2_73 | 803 | 2723 | 157 | 474 | | |

| Protein name | | | | | Locus Name | Acc# |
|---|---|---|---|---|---|---|
| | | | | | | |

Description

NO-HIT

| ORF Name | NTID | AAID | NT Length | AA Length | Score | Probability |
|---|---|---|---|---|---|---|
| 4331430_f1_28 | 804 | 2724 | 313 | 942 | 124 | 2.4e-16 |

| Protein name | | | | | Locus Name | Acc# |
|---|---|---|---|---|---|---|
| | | | | | sp:RECX_VIBCH | Q56647 |

Description

REGULATORY PROTEIN RECX

| ORF Name | NTID | AAID | NT Length | AA Length | Score | Probability |
|---|---|---|---|---|---|---|
| 4332837_c3_256 | 805 | 2725 | 105 | 318 | 149 | 6.7e-10 |

| Protein name | | | | | Locus Name | Acc# |
|---|---|---|---|---|---|---|
| hypothetical protein sll1830 | | | | | pir:S75232 | S75232 |

Description

| ORF Name | NTID | AAID | NT Length | AA Length | Score | Probability |
|---|---|---|---|---|---|---|
| 4348813_c3_259 | 806 | 2726 | 350 | 1053 | 1035 | 1.8e-104 |

| Protein name | | | | | Locus Name | Acc# |
|---|---|---|---|---|---|---|
| | | | | | sp:GCP_HAEIN | P43764 |

Description (GLYCOPROTEASE)

| ORF Name | NTID | AAID | NT Length | AA Length | Score | Probability |
|---|---|---|---|---|---|---|
| 4694427_f3_114 | 807 | 2727 | 362 | 1089 | 884 | 1.9e-88 |

| Protein name | | | | | Locus Name | Acc# |
|---|---|---|---|---|---|---|
| | | | | | sp:LIPA_HAEIN | P44463 |

Description

LIPOIC ACID SYNTHETASE (LIP-SYN) (LIPOATE SYNTHASE)

| ORF Name | NTID | AAID | NT Length | AA Length | Score | Probability |
|---|---|---|---|---|---|---|
| 4773260_f2_79 | 808 | 2728 | 79 | 240 | | |

| Protein name | Locus Name | Acc# |
|---|---|---|
| | | |

Description

NO-HIT

| ORF Name | NTID | AAID | NT Length | AA Length | Score | Probability |
|---|---|---|---|---|---|---|
| 4798536_c2_191 | 809 | 2729 | 212 | 639 | 685 | 2.3e-67 |

| Protein name | Locus Name | Acc# |
|---|---|---|
| alkyl hydroperoxide reductase subunit C | gp:AF129406 | AF129406 |

Description

Bacteroides fragilis alkyl hydroperoxide reductase subunit C (ahpC)and alkyl hydroperoxide reductase subunit F (ahpF) genes, completecds.

| ORF Name | NTID | AAID | NT Length | AA Length | Score | Probability |
|---|---|---|---|---|---|---|
| 4824062_c2_200 | 810 | 2730 | 273 | 822 | 353 | 3.4e-32 |

| Protein name | Locus Name | Acc# |
|---|---|---|
| | sp:PSS_HELPY | |

Description (PHOSPHATIDYLSERINE SYNTHASE)

| ORF Name | NTID | AAID | NT Length | AA Length | Score | Probability |
|---|---|---|---|---|---|---|
| 6110943_c2_203 | 811 | 2731 | 435 | 1308 | 303 | 3.5e-26 |

| Protein name | Locus Name | Acc# |
|---|---|---|
| | sp:FTSA_BUCAP | O51928 |

Description

CELL DIVISION PROTEIN FTSA

| ORF Name | NTID | AAID | NT Length | AA Length | Score | Probability |
|---|---|---|---|---|---|---|
| 659686_c2_210 | 812 | 2732 | 278 | 837 | 485 | 3.5e-46 |

| Protein name | Locus Name | Acc# |
|---|---|---|
| | sp:YGDL_HAEIN | |

Description

HYPOTHETICAL PROTEIN HI0118

249

| ORF Name | NTID | AAID | NT Length | AA Length | Score | Probability |
|---|---|---|---|---|---|---|
| 6754081_c3_235 | 813 | 2733 | 254 | 765 | 169 | 1.1e-12 |
| Protein name | | | | Locus Name | | Acc# |
| hypothetical protein MTH939 | | | | pir:G69225 | | G69225 |

Description

| ORF Name | NTID | AAID | NT Length | AA Length | Score | Probability |
|---|---|---|---|---|---|---|
| 681453_f3_127 | 814 | 2734 | 84 | 255 | 76 | 0.038 |
| Protein name | | | | Locus Name | | Acc# |
| | | | | sp:YXEH_BACSU | | P54947 |

Description

HYPOTHETICAL 30.2 KD PROTEIN IN IDH-DEOR INTERGENIC REGION

| ORF Name | NTID | AAID | NT Length | AA Length | Score | Probability |
|---|---|---|---|---|---|---|
| 682641_f1_42 | 815 | 2735 | 86 | 261 | 100 | 2.2e-05 |
| Protein name | | | | Locus Name | | Acc# |
| hypothetical protein PH0217 | | | | pir:G71244 | | G71244 |

Description

| ORF Name | NTID | AAID | NT Length | AA Length | Score | Probability |
|---|---|---|---|---|---|---|
| 7222187_f1_35 | 816 | 2736 | 245 | 738 | 287 | 3.4e-25 |
| Protein name | | | | Locus Name | | Acc# |
| conserved hypothetical protein ykrA | | | | pir:C69862 | | C69862 |

Description

| ORF Name | NTID | AAID | NT Length | AA Length | Score | Probability |
|---|---|---|---|---|---|---|
| 781563_c2_227 | 817 | 2737 | 113 | 342 | 265 | 7.3e-23 |
| Protein name | | | | Locus Name | | Acc# |
| | | | | sp:YPT6_PSEAE | | P24564 |

Description

HYPOTHETICAL 19.5 KD PROTEIN IN PILT REGION (ORF6)

| ORF Name | NTID | AAID | NT Length | AA Length | Score | Probability |
|---|---|---|---|---|---|---|
| 812535_f1_43 | 818 | 2738 | 77 | 234 | | |

Protein name                                              Locus Name              Acc#

Description

NO-HIT

| ORF Name | NTID | AAID | NT Length | AA Length | Score | Probability |
|---|---|---|---|---|---|---|
| 10625252_f1_3 | 819 | 2739 | 581 | 1746 | 1790 | 1.8e-184 |

Protein name                                              Locus Name              Acc#
                                                          sp:SYP_HAEIN            P43830

Description

PROLYL-TRNA SYNTHETASE, (PROLINE--TRNA LIGASE) (PRORS)

| ORF Name | NTID | AAID | NT Length | AA Length | Score | Probability |
|---|---|---|---|---|---|---|
| 20496062_c2_30 | 820 | 2740 | 408 | 1227 | 1522 | 4.6e-156 |

Protein name                                              Locus Name              Acc#
                                                          sp:TRPB_ACICA           P16706

Description

TRYPTOPHAN SYNTHASE BETA CHAIN,

| ORF Name | NTID | AAID | NT Length | AA Length | Score | Probability |
|---|---|---|---|---|---|---|
| 22847180_c1_17 | 821 | 2741 | 213 | 642 | 568 | 5.7e-55 |

Protein name                                              Locus Name              Acc#
                                                          sp:YADG_ECOLI           P36879

Description

HYPOTHETICAL ABC TRANSPORTER ATP-BINDING PROTEIN YADG

| ORF Name | NTID | AAID | NT Length | AA Length | Score | Probability |
|---|---|---|---|---|---|---|
| 24642268_c3_37 | 822 | 2742 | 213 | 642 | 510 | 7.9e-49 |

Protein name                                              Locus Name              Acc#
                                                          sp:TRPF_ACICA           P16923

Description

N-(5'-PHOSPHORIBOSYL)ANTHRANILATE ISOMERASE, (PRAI)

| ORF Name | NTID | AAID | NT Length | AA Length | Score | Probability |
|---|---|---|---|---|---|---|
| 24814125_c2_31 | 823 | 2743 | 285 | 858 | 541 | 4.1e-52 |

| Protein name | | | | Locus Name | | Acc# |
|---|---|---|---|---|---|---|
| tryptophan synthase alpha chain | | | | gp:AF107094 | | AF107094 |

Description

Rhodobacter sphaeroides thiamine biosynthetic protein (thi) gene, partial cds; and tryptophan synthase alpha chain (trpA) gene, complete cds.

| ORF Name | NTID | AAID | NT Length | AA Length | Score | Probability |
|---|---|---|---|---|---|---|
| 30727194_c2_24 | 824 | 2744 | 62 | 189 | | |

| Protein name | | | | Locus Name | | Acc# |
|---|---|---|---|---|---|---|

Description

NO-HIT

| ORF Name | NTID | AAID | NT Length | AA Length | Score | Probability |
|---|---|---|---|---|---|---|
| 3941642_c2_25 | 825 | 2745 | 100 | 303 | 224 | 1.6e-18 |

| Protein name | | | | Locus Name | | Acc# |
|---|---|---|---|---|---|---|
| | | | | sp:YADG_ECOLI | | P36879 |

Description

HYPOTHETICAL ABC TRANSPORTER ATP-BINDING PROTEIN YADG

| ORF Name | NTID | AAID | NT Length | AA Length | Score | Probability |
|---|---|---|---|---|---|---|
| 4181557_c1_19 | 826 | 2746 | 281 | 846 | 553 | 2.2e-53 |

| Protein name | | | | Locus Name | | Acc# |
|---|---|---|---|---|---|---|
| | | | | sp:YQCD_ECOLI | | Q46920 |

Description

HYPOTHETICAL 32.6 KD PROTEIN IN SYD-SDAC INTERGENIC REGION

| ORF Name | NTID | AAID | NT Length | AA Length | Score | Probability |
|---|---|---|---|---|---|---|
| 4426338_c2_26 | 827 | 2747 | 260 | 783 | 744 | 1.3e-73 |

| Protein name | | | | Locus Name | | Acc# |
|---|---|---|---|---|---|---|
| | | | | sp:YADH_ECOLI | | |

Description

HYPOTHETICAL 28.5 KD PROTEIN IN HPT-PAND INTERGENIC REGION

| ORF Name | NTID | AAID | NT Length | AA Length | Score | Probability |
|---|---|---|---|---|---|---|
| 5120412_c3_32 | 828 | 2748 | 186 | 561 | 196 | 1.5e-15 |

| Protein name | Locus Name | Acc# |
|---|---|---|
| cytochrome c5 | gp:AVU94420 | U94420 |

Description

Azotobacter vinelandii aldehyde dehydrogenase (aldh) gene, partialcds, cytochrome c5 (cycB) gene, complete cds, and xanthinephosphoribosyltransferase-like protein (xrpt) gene, partial cds.

| ORF Name | NTID | AAID | NT Length | AA Length | Score | Probability |
|---|---|---|---|---|---|---|
| 7031312_c3_33 | 829 | 2749 | 66 | 201 | 129 | 7.5e-08 |

| Protein name | Locus Name | Acc# |
|---|---|---|
| | sp:YADG_ECOLI | P36879 |

Description

HYPOTHETICAL ABC TRANSPORTER ATP-BINDING PROTEIN YADG

| ORF Name | NTID | AAID | NT Length | AA Length | Score | Probability |
|---|---|---|---|---|---|---|
| 11198430_c3_60 | 830 | 2750 | 692 | 2079 | 3292 | 0.0 |

| Protein name | Locus Name | Acc# |
|---|---|---|
| lactoferrin binding protein B | gp:AF043131 | AF043131 |

Description

Moraxella catarrhalis strain 4223 lactoferrin binding protein B(lbpB) and lactoferrin binding protein A (lbpA) genes, completecds; and unknown genes.

| ORF Name | NTID | AAID | NT Length | AA Length | Score | Probability |
|---|---|---|---|---|---|---|
| 16128933_c2_53 | 831 | 2751 | 159 | 480 | 377 | 9.9e-35 |

| Protein name | Locus Name | Acc# |
|---|---|---|
| apolipoprotein N-acyltransferase | gp:AF038595 | AF038595 |

Description

Pseudomonas aeruginosa apolipoprotein N-acyltransferase (cutE)gene, complete cds.

| ORF Name | NTID | AAID | NT Length | AA Length | Score | Probability |
|---|---|---|---|---|---|---|
| 19704378_c3_64 | 832 | 2752 | 606 | 1821 | 1227 | 8.3e-125 |

| Protein name | Locus Name | Acc# |
|---|---|---|
| unknown | gp:AF043132 | AF043132 |

Description

Moraxella catarrhalis strain Q8 lactoferrin binding protein B(lbpB) and lactoferrin binding protein A (lbpA) genes, completecds; and unknown genes.

| ORF Name | NTID | AAID | NT Length | AA Length | Score | Probability |
|---|---|---|---|---|---|---|
| 24337826_c3_67 | 833 | 2753 | 718 | 2157 | 278 | 2.9e-21 |

| Protein name | Locus Name | Acc# |
|---|---|---|
| hypothetical protein K08H10.2a | pir:T23512 | |

Description

| ORF Name | NTID | AAID | NT Length | AA Length | Score | Probability |
|---|---|---|---|---|---|---|
| 34164812_c2_54 | 834 | 2754 | 198 | 597 | 712 | 1.6e-80 |

| Protein name | Locus Name | Acc# |
|---|---|---|
| lactoferrin binding protein B | gp:AF043133 | AF043133 |

Description

Moraxella catarrhalis strain VH19 lactoferrin binding protein B(lbpB) gene, complete cds.

| ORF Name | NTID | AAID | NT Length | AA Length | Score | Probability |
|---|---|---|---|---|---|---|
| 35837503_f2_26 | 835 | 2755 | 61 | 186 | | |

| Protein name | Locus Name | Acc# |
|---|---|---|
| | | |

Description

NO-HIT

| ORF Name | NTID | AAID | NT Length | AA Length | Score | Probability |
|---|---|---|---|---|---|---|
| 35945257_c1_46 | 836 | 2756 | 67 | 204 | | |

| Protein name | Locus Name | Acc# |
|---|---|---|
| | | |

Description

NO-HIT

| ORF Name | NTID | AAID | NT Length | AA Length | Score | Probability |
|---|---|---|---|---|---|---|
| 3906263_c2_55 | 837 | 2757 | 1003 | 3012 | 5252 | 0.0 |

| Protein name | Locus Name | Acc# |
|---|---|---|
| lactoferrin binding protein A | gp:AF043131 | AF043131 |

Description

Moraxella catarrhalis strain 4223 lactoferrin binding protein B(lbpB) and lactoferrin binding protein A (lbpA) genes, completecds; and unknown genes.

| ORF Name | NTID | AAID | NT Length | AA Length | Score | Probability |
|---|---|---|---|---|---|---|
| 3945388_f3_30 | 838 | 2758 | 413 | 1242 | 1219 | 5.9e-124 |

| Protein name | Locus Name | Acc# |
|---|---|---|
| beta-ketoacyl-ACP synthase I | gp:PAU70470 | U70470 |

Description

Pseudomonas aeruginosa lemA-type sensor kinase/response regulatorhomolog gene, partial cds, beta-hydroxy-ACP dehydrase (fabA) andbeta-ketoacyl-ACP synthase I (fabB) genes, complete cds.

| ORF Name | NTID | AAID | NT Length | AA Length | Score | Probability |
|---|---|---|---|---|---|---|
| 4005250_c3_68 | 839 | 2759 | 163 | 492 | 572 | 2.1e-55 |

| Protein name | Locus Name | Acc# |
|---|---|---|
| ribosomal protein S12:streptomycin resistance protein | pir:A42939 | |

Description

| ORF Name | NTID | AAID | NT Length | AA Length | Score | Probability |
|---|---|---|---|---|---|---|
| 4093767_c3_63 | 840 | 2760 | 544 | 1635 | 2854 | 3.2e-297 |

| Protein name | Locus Name | Acc# |
|---|---|---|
| unknown | gp:AF043131 | AF043131 |

Description

Moraxella catarrhalis strain 4223 lactoferrin binding protein B(lbpB) and lactoferrin binding protein A (lbpA) genes, completecds; and unknown genes.

| ORF Name | NTID | AAID | NT Length | AA Length | Score | Probability |
|---|---|---|---|---|---|---|
| 4804632_f2_17 | 841 | 2761 | 485 | 1458 | 572 | 2.1e-55 |

| Protein name | | | | Locus Name | | Acc# |
|---|---|---|---|---|---|---|
| | | | | sp:PABB_SALTY | | P12680 |

Description

PARA-AMINOBENZOATE SYNTHASE COMPONENT I, (ADC SYNTHASE)

| ORF Name | NTID | AAID | NT Length | AA Length | Score | Probability |
|---|---|---|---|---|---|---|
| 1018_c1_12 | 842 | 2762 | 229 | 690 | 163 | 4.7e-12 |

| Protein name | | | | Locus Name | | Acc# |
|---|---|---|---|---|---|---|
| | | | | gp:BPMB78P21 | | X87092 |

Description

Bacteriophage MB78 ORFs p21, p11.5, p26 & p28.

| ORF Name | NTID | AAID | NT Length | AA Length | Score | Probability |
|---|---|---|---|---|---|---|
| 12303577_c1_11 | 843 | 2763 | 105 | 318 | | |

| Protein name | | | | Locus Name | | Acc# |

Description

NO-HIT

| ORF Name | NTID | AAID | NT Length | AA Length | Score | Probability |
|---|---|---|---|---|---|---|
| 19557893_c2_17 | 844 | 2764 | 126 | 381 | | |

| Protein name | | | | Locus Name | | Acc# |

Description

NO-HIT

| ORF Name | NTID | AAID | NT Length | AA Length | Score | Probability |
|---|---|---|---|---|---|---|
| 20038305_c2_15 | 845 | 2765 | 75 | 228 | | |

| Protein name | | | | Locus Name | | Acc# |

Description

NO-HIT

| ORF Name | NTID | AAID | NT Length | AA Length | Score | Probability |
|---|---|---|---|---|---|---|
| 2134555_c1_13 | 846 | 2766 | 169 | 510 | | |

Protein name      Locus Name      Acc#

Description

NO-HIT

| ORF Name | NTID | AAID | NT Length | AA Length | Score | Probability |
|---|---|---|---|---|---|---|
| 23470625_c3_19 | 847 | 2767 | 189 | 570 | 287 | 5.9e-25 |

Protein name      Locus Name      Acc#
     gp:RP4TRANOKF      L10330

Description

Plasmid RP4 traN gene, complete cds; traO gene, complete cds; kfrAgene, complete cds.

| ORF Name | NTID | AAID | NT Length | AA Length | Score | Probability |
|---|---|---|---|---|---|---|
| 23632818_c3_25 | 848 | 2768 | 97 | 291 | | |

Protein name      Locus Name      Acc#

Description

NO-HIT

| ORF Name | NTID | AAID | NT Length | AA Length | Score | Probability |
|---|---|---|---|---|---|---|
| 31555_c3_20 | 849 | 2769 | 333 | 1002 | 225 | 2.0e-17 |

Protein name      Locus Name      Acc#
coat protein      pir:S58142

Description

| ORF Name | NTID | AAID | NT Length | AA Length | Score | Probability |
|---|---|---|---|---|---|---|
| 34381286_c3_21 | 850 | 2770 | 140 | 423 | | |

Protein name      Locus Name      Acc#

Description

NO-HIT

| ORF Name | NTID | AAID | NT Length | AA Length | Score | Probability |
|---|---|---|---|---|---|---|
| 34485637_c3_22 | 851 | 2771 | 137 | 414 | | |

Protein name | | | | | Locus Name | Acc#

Description

NO-HIT

| ORF Name | NTID | AAID | NT Length | AA Length | Score | Probability |
|---|---|---|---|---|---|---|
| 3907963_c3_23 | 852 | 2772 | 81 | 246 | | |

Protein name | | | | | Locus Name | Acc#

Description

NO-HIT

| ORF Name | NTID | AAID | NT Length | AA Length | Score | Probability |
|---|---|---|---|---|---|---|
| 4804763_c2_16 | 853 | 2773 | 122 | 369 | | |

Protein name | | | | | Locus Name | Acc#

Description

NO-HIT

| ORF Name | NTID | AAID | NT Length | AA Length | Score | Probability |
|---|---|---|---|---|---|---|
| 6928168_c2_18 | 854 | 2774 | 308 | 927 | | |

Protein name | | | | | Locus Name | Acc#

Description

NO-HIT

| ORF Name | NTID | AAID | NT Length | AA Length | Score | Probability |
|---|---|---|---|---|---|---|
| 12625177_f1_2 | 855 | 2775 | 148 | 447 | 435 | 7.0e-41 |

Protein name | | | | | Locus Name | Acc#
 | | | | | sp:DKSA_ECOLI | P18274

Description

DNAK SUPPRESSOR PROTEIN

| ORF Name | NTID | AAID | NT Length | AA Length | Score | Probability |
|---|---|---|---|---|---|---|
| 14241635_c2_80 | 856 | 2776 | 130 | 393 | | |

| Protein name | | | | | Locus Name | Acc# |
|---|---|---|---|---|---|---|
| | | | | | | |

Description

NO-HIT

| ORF Name | NTID | AAID | NT Length | AA Length | Score | Probability |
|---|---|---|---|---|---|---|
| 14876881_c2_82 | 857 | 2777 | 256 | 771 | 350 | 7.2e-32 |

| Protein name | | | | | Locus Name | Acc# |
|---|---|---|---|---|---|---|
| | | | | | sp:FMCH_BACNO | P17419 |

Description

POSSIBLE FIMBRIAL ASSEMBLY PROTEIN FIMC (SEROGROUP H1)

| ORF Name | NTID | AAID | NT Length | AA Length | Score | Probability |
|---|---|---|---|---|---|---|
| 16181301_f3_63 | 858 | 2778 | 203 | 612 | 126 | 2.6e-06 |

| Protein name | | | | | Locus Name | Acc# |
|---|---|---|---|---|---|---|
| | | | | | sp:YGGH_ECOLI | P32049 |

Description

HYPOTHETICAL 27.3 KD PROTEIN IN ANSB-MUTY INTERGENIC REGION (F239)

| ORF Name | NTID | AAID | NT Length | AA Length | Score | Probability |
|---|---|---|---|---|---|---|
| 16898413_c1_77 | 859 | 2779 | 100 | 303 | 286 | 9.1e-24 |

| Protein name | | | | | Locus Name | Acc# |
|---|---|---|---|---|---|---|
| | | | | | sp:Y712_HAEIN | P44836 |

Description

PROBABLE TONB-DEPENDENT RECEPTOR HI0712 PRECURSOR

| ORF Name | NTID | AAID | NT Length | AA Length | Score | Probability |
|---|---|---|---|---|---|---|
| 21517252_f1_3 | 860 | 2780 | 621 | 1866 | 1417 | 6.1e-145 |

| Protein name | | | | | Locus Name | Acc# |
|---|---|---|---|---|---|---|
| | | | | | sp:UVRC_PSEFL | P32966 |

Description

EXCINUCLEASE ABC SUBUNIT C

| ORF_Name | NTID | AAID | NT Length | AA Length | Score | Probability |
|---|---|---|---|---|---|---|
| 22004587_f2_24 | 861 | 2781 | 333 | 1002 | 436 | 5.5e-41 |

| Protein name | | | | Locus Name | Acc# |
|---|---|---|---|---|---|
| | | | | sp:YADB_ECOLI | |

Description

HYPOTHETICAL 34.9 KD PROTEIN IN PCNB-DKSA INTERGENIC REGION

| ORF_Name | NTID | AAID | NT Length | AA Length | Score | Probability |
|---|---|---|---|---|---|---|
| 23597187_f3_61 | 862 | 2782 | 769 | 2310 | 539 | 3.0e-100 |

| Protein name | | | | Locus Name | Acc# |
|---|---|---|---|---|---|
| | | | | sp:PRIA_RHORU | P05445 |

Description

PRIMOSOMAL PROTEIN N' (REPLICATION FACTOR Y)

| ORF_Name | NTID | AAID | NT Length | AA Length | Score | Probability |
|---|---|---|---|---|---|---|
| 23865681_f3_58 | 863 | 2783 | 739 | 2220 | 789 | 2.2e-78 |

| Protein name | | | | Locus Name | Acc# |
|---|---|---|---|---|---|
| | | | | sp:SPOT_HAEIN | P43811 |

Description ((PPGPP)ASE) (PENTA-PHOSPHATE GUANOSINE-3'-PYROPHOSPHOHYDROLASE)

| ORF_Name | NTID | AAID | NT Length | AA Length | Score | Probability |
|---|---|---|---|---|---|---|
| 24412817_c2_92 | 864 | 2784 | 84 | 255 | | |

| Protein name | | | | Locus Name | Acc# |
|---|---|---|---|---|---|

Description

NO-HIT

| ORF_Name | NTID | AAID | NT Length | AA Length | Score | Probability |
|---|---|---|---|---|---|---|
| 2510887_c1_76 | 865 | 2785 | 60 | 183 | | |

| Protein name | | | | Locus Name | Acc# |
|---|---|---|---|---|---|

Description

NO-HIT

| ORF Name | NTID | AAID | NT Length | AA Length | Score | Probability |
|---|---|---|---|---|---|---|
| 26594686_f1_14 | 866 | 2786 | 215 | 648 | 355 | 2.1e-32 |

Protein name | | | | Locus Name | | Acc# |
| | | | | sp:YICG_ECOLI | | |

Description

HYPOTHETICAL 22.0 KD PROTEIN IN RPH-GMK INTERGENIC REGION PRECURSOR

| ORF Name | NTID | AAID | NT Length | AA Length | Score | Probability |
|---|---|---|---|---|---|---|
| 29304827_c2_94 | 867 | 2787 | 63 | 192 | 286 | 9.1e-24 |

Protein name | | | | Locus Name | | Acc# |
| | | | | sp:Y712_HAEIN | | P44836 |

Description

PROBABLE TONB-DEPENDENT RECEPTOR HI0712 PRECURSOR

| ORF Name | NTID | AAID | NT Length | AA Length | Score | Probability |
|---|---|---|---|---|---|---|
| 29484418_c2_95 | 868 | 2788 | 566 | 1701 | 710 | 1.6e-118 |

Protein name | | | | Locus Name | | Acc# |
| methyltransferase | | | | gp:AF060119 | | AF060119 |

Description

Pasteurella haemolytica methyltransferase (mod) and restrictionendonuclease (res) genes, complete cds.

| ORF Name | NTID | AAID | NT Length | AA Length | Score | Probability |
|---|---|---|---|---|---|---|
| 30281911_c3_114 | 869 | 2789 | 79 | 240 | 286 | 9.1e-24 |

Protein name | | | | Locus Name | | Acc# |
| | | | | sp:Y712_HAEIN | | P44836 |

Description

PROBABLE TONB-DEPENDENT RECEPTOR HI0712 PRECURSOR

| ORF Name | NTID | AAID | NT Length | AA Length | Score | Probability |
|---|---|---|---|---|---|---|
| 34017010_f2_35 | 870 | 2790 | 307 | 924 | 708 | 8.3e-70 |

Protein name | | | | Locus Name | | Acc# |
| hypothetical protein b2431 | | | | pir:F65017 | | F65017 |

Description

| ORF Name | NTID | AAID | NT Length | AA Length | Score | Probability |
|---|---|---|---|---|---|---|
| 34407905_c2_93 | 871 | 2791 | 460 | 1383 | 1801 | 1.2e-185 |

| Protein name | Locus Name | Acc# |
|---|---|---|
| L-2,4-diaminobutyrate:2-ketoglutarate | gp:AB001599 | AB001599 |

Description

Acinetobacter baumannii DNA for L-2,4-diaminobutyrate:2-ketoglutarate 4-aminotransferase, complete cds.

| ORF Name | NTID | AAID | NT Length | AA Length | Score | Probability |
|---|---|---|---|---|---|---|
| 34641550_c3_119 | 872 | 2792 | 186 | 561 | 126 | 1.2e-07 |

| Protein name | Locus Name | Acc# |
|---|---|---|
| | sp:AIL_YEREN | P16454 |

Description

ATTACHMENT INVASION LOCUS PROTEIN PRECURSOR

| ORF Name | NTID | AAID | NT Length | AA Length | Score | Probability |
|---|---|---|---|---|---|---|
| 3923818_f2_34 | 873 | 2793 | 62 | 189 | | |

| Protein name | Locus Name | Acc# |
|---|---|---|
| | | |

Description

NO-HIT

| ORF Name | NTID | AAID | NT Length | AA Length | Score | Probability |
|---|---|---|---|---|---|---|
| 4306455_c1_65 | 874 | 2794 | 323 | 972 | 122 | 4.9e-07 |

| Protein name | Locus Name | Acc# |
|---|---|---|
| | sp:FMP1_PSEAE | P17838 |

Description

FIMBRIAL PROTEIN PRECURSOR (PILIN) (STRAIN P1)

| ORF Name | NTID | AAID | NT Length | AA Length | Score | Probability |
|---|---|---|---|---|---|---|
| 4329518_f3_56 | 875 | 2795 | 212 | 639 | 541 | 4.1e-52 |

| Protein name | Locus Name | Acc# |
|---|---|---|
| | sp:KGUA_ECOLI | P24234 |

Description

GUANYLATE KINASE, (GMP KINASE)

| ORF Name | NTID | AAID | NT Length | AA Length | Score | Probability |
|---|---|---|---|---|---|---|
| 4428413_c1_78 | 876 | 2796 | 517 | 1554 | 2128 | 2.8e-220 |

| Protein name | Locus Name | Acc# |
|---|---|---|
| L-2,4-diaminobutyrate decarboxylase | gp:ACCL24DD | D55724 |

Description

Acinetobacter baumannii gene for L-2,4-diaminobutyratedecarboxylase, complete cds.

| ORF Name | NTID | AAID | NT Length | AA Length | Score | Probability |
|---|---|---|---|---|---|---|
| 4538558_f3_51 | 877 | 2797 | 270 | 813 | 611 | 1.6e-59 |

| Protein name | Locus Name | Acc# |
|---|---|---|
| hypothetical protein | gp:PPPAL1 | X74218 |

Description

Pseudomonas putida ruvB, tolQ, tolR, tolA, tolB and oprL genes.

| ORF Name | NTID | AAID | NT Length | AA Length | Score | Probability |
|---|---|---|---|---|---|---|
| 4570318_f3_44 | 878 | 2798 | 228 | 687 | 448 | 3.0e-42 |

| Protein name | Locus Name | Acc# |
|---|---|---|
|  | sp:GPH_HAEIN | P44755 |

Description

PHOSPHOGLYCOLATE PHOSPHATASE, (PGP)

| ORF Name | NTID | AAID | NT Length | AA Length | Score | Probability |
|---|---|---|---|---|---|---|
| 4902305_c2_96 | 879 | 2799 | 869 | 2610 | 2182 | 5.3e-226 |

| Protein name | Locus Name | Acc# |
|---|---|---|
| restriction endonuclease | gp:AF060119 | AF060119 |

Description

Pasteurella haemolytica methyltransferase (mod) and restrictionendonuclease (res) genes, complete cds.

| ORF_Name | NTID | AAID | NT Length | AA Length | Score | Probability |
|---|---|---|---|---|---|---|
| 4964000_f3_57 | 880 | 2800 | 95 | 288 | 187 | 1.3e-14 |

Protein name | Locus Name | Acc#
sp:RPOZ_HAEIN | P43740

Description

OMEGA CHAIN) (RNA POLYMERASE OMEGA SUBUNIT)

| ORF_Name | NTID | AAID | NT Length | AA Length | Score | Probability |
|---|---|---|---|---|---|---|
| 5079408_f3_60 | 881 | 2801 | 151 | 456 | 367 | 1.1e-33 |

Protein name | Locus Name | Acc#
hypothetical protein 1 (vnfA 5' region) | pir:B44514 | B44514

Description

| ORF_Name | NTID | AAID | NT Length | AA Length | Score | Probability |
|---|---|---|---|---|---|---|
| 5080293_c2_89 | 882 | 2802 | 592 | 1779 | 1142 | 8.5e-116 |

Protein name | Locus Name | Acc#
 | sp:RECJ_HAEIN | P45112

Description

SINGLE-STRANDED-DNA-SPECIFIC EXONUCLEASE RECJ,

| ORF_Name | NTID | AAID | NT Length | AA Length | Score | Probability |
|---|---|---|---|---|---|---|
| 5339762_c3_109 | 883 | 2803 | 325 | 978 | 1184 | 3.0e-120 |

Protein name | Locus Name | Acc#
LytB | gp:AF027189 | AF027189

Description

Acinetobacter sp. BD413 lytB, comB, comC, comE, and comF genes, complete cds; and unknown genes.

| ORF_Name | NTID | AAID | NT Length | AA Length | Score | Probability |
|---|---|---|---|---|---|---|
| 97582_f3_42 | 884 | 2804 | 289 | 870 | 291 | 1.3e-25 |

Protein name | Locus Name | Acc#
 | sp:ICC_ECOLI | P36650

Description

ICC PROTEIN

| ORF Name | NTID | AAID | NT Length | AA Length | Score | Probability |
|---|---|---|---|---|---|---|
| 13673437_c2_39 | 885 | 2805 | 597 | 1791 | 150 | 3.5e-13 |

| Protein name | | | | Locus Name | | Acc# |
|---|---|---|---|---|---|---|
| putative terminase | | | | gp:AF147978 | | AF147978 |

Description

Bacteriophage D3 putative terminase, putative portal protein, putative ClpP protease, and major head protein genes, complete cds; and unknown genes.

| ORF Name | NTID | AAID | NT Length | AA Length | Score | Probability |
|---|---|---|---|---|---|---|
| 14181292_c3_43 | 886 | 2806 | 101 | 306 | | |

| Protein name | | | | Locus Name | | Acc# |
|---|---|---|---|---|---|---|

Description

NO-HIT

| ORF Name | NTID | AAID | NT Length | AA Length | Score | Probability |
|---|---|---|---|---|---|---|
| 19953125_c2_36 | 887 | 2807 | 215 | 648 | | |

| Protein name | | | | Locus Name | | Acc# |
|---|---|---|---|---|---|---|

Description

NO-HIT

| ORF Name | NTID | AAID | NT Length | AA Length | Score | Probability |
|---|---|---|---|---|---|---|
| 25665952_c1_33 | 888 | 2808 | 128 | 387 | 88 | 0.0036 |

| Protein name | | | | Locus Name | | Acc# |
|---|---|---|---|---|---|---|
| 1.7 protein | | | | gp:BPH251805 | | AJ251805 |

Description

Bacteriophage phi-YeO3-12 complete genome.

| ORF Name | NTID | AAID | NT Length | AA Length | Score | Probability |
|---|---|---|---|---|---|---|
| 26675311_c2_37 | 889 | 2809 | 107 | 324 | 145 | 3.8e-10 |

| Protein name | | | | Locus Name | | Acc# |
|---|---|---|---|---|---|---|
| hypothetical protein | | | | gp:XNE133022 | | AJ133022 |

Description

Xenorhabdus nematophilus proviral ORF1 to ORF8.

| ORF Name | NTID | AAID | NT Length | AA Length | Score | Probability |
|---|---|---|---|---|---|---|
| 32657262_c2_35 | 890 | 2810 | 150 | 453 | 209 | 6.7e-18 |

| Protein name | | | | Locus Name | | Acc# |
|---|---|---|---|---|---|---|
| DNA primase | | | | pir:C41830 | | C41830 |

Description

| ORF Name | NTID | AAID | NT Length | AA Length | Score | Probability |
|---|---|---|---|---|---|---|
| 3941887_c1_32 | 891 | 2811 | 185 | 558 | 88 | 0.019 |

| Protein name | | | | Locus Name | | Acc# |
|---|---|---|---|---|---|---|
| | | | | gp:PFA53C6 | | X17490 |

Description

Plasmodium falciparum mRNA for asparagine-rich antigen (clone53C6).

| ORF Name | NTID | AAID | NT Length | AA Length | Score | Probability |
|---|---|---|---|---|---|---|
| 5916253_c1_28 | 892 | 2812 | 257 | 774 | 259 | 3.1e-22 |

| Protein name | | | | Locus Name | | Acc# |
|---|---|---|---|---|---|---|
| | | | | sp:YE22_HAEIN | | P44193 |

Description

HYPOTHETICAL PROTEIN HI1422

| ORF Name | NTID | AAID | NT Length | AA Length | Score | Probability |
|---|---|---|---|---|---|---|
| 900215_c3_41 | 893 | 2813 | 797 | 2394 | 330 | 4.7e-27 |

| Protein name | | | | Locus Name | | Acc# |
|---|---|---|---|---|---|---|
| putative DNA primase | | | | gp:AF139719 | | AF139719 |

Description

Klebsiella oxytoca plasmid pACM1 putative DNA primase (pri) gene, complete cds; and unknown genes.

| ORF Name | NTID | AAID | NT Length | AA Length | Score | Probability |
|---|---|---|---|---|---|---|
| 10959627_f2_14 | 894 | 2814 | 294 | 885 | 513 | 3.8e-49 |

| Protein name | | | | Locus Name | | Acc# |
|---|---|---|---|---|---|---|
| | | | | sp:YBEX_ECOLI | | P77392 |

Description

HYPOTHETICAL 33.3 KD PROTEIN IN CUTE-ASNB INTERGENIC REGION

| ORF Name | NTID | AAID | NT Length | AA Length | Score | Probability |
|---|---|---|---|---|---|---|
| 1178127_f3_20 | 895 | 2815 | 963 | 2892 | 2605 | 1.9e-281 |

| Protein name | Locus Name | Acc# |
|---|---|---|
| SecA | gp:AB012226 | AB012226 |

Description

Vibrio alginolyticus gene for SecA, complete cds.

| ORF Name | NTID | AAID | NT Length | AA Length | Score | Probability |
|---|---|---|---|---|---|---|
| 12298468_f1_13 | 896 | 2816 | 102 | 309 | 82 | 0.017 |

| Protein name | Locus Name | Acc# |
|---|---|---|
| probable membrane protein L549.12 | pir:T02800 | T02800 |

Description

| ORF Name | NTID | AAID | NT Length | AA Length | Score | Probability |
|---|---|---|---|---|---|---|
| 12985393_f3_16 | 897 | 2817 | 270 | 813 | 537 | 1.1e-51 |

| Protein name | Locus Name | Acc# |
|---|---|---|
|  | sp:PEPD_HAEIN | P44817 |

Description (PEPTIDASE D)

| ORF Name | NTID | AAID | NT Length | AA Length | Score | Probability |
|---|---|---|---|---|---|---|
| 14538262_c2_40 | 898 | 2818 | 69 | 210 | 109 | 2.5e-06 |

| Protein name | Locus Name | Acc# |
|---|---|---|
| hypothetical protein APE0458 | pir:A72741 | A72741 |

Description

| ORF Name | NTID | AAID | NT Length | AA Length | Score | Probability |
|---|---|---|---|---|---|---|
| 14548260_c1_34 | 899 | 2819 | 244 | 735 | 265 | 7.3e-23 |

| Protein name | Locus Name | Acc# |
|---|---|---|
| hypothetical protein D1022.4 | pir:T34190 | T34190 |

Description

| ORF_Name | NTID | AAID | NT Length | AA Length | Score | Probability |
|---|---|---|---|---|---|---|
| 21640900_f1_8 | 900 | 2820 | 442 | 1329 | 1361 | 5.3e-139 |

| Protein name | | | | Locus Name | | Acc# |
|---|---|---|---|---|---|---|
| | | | | sp:GSA_PSEAE | | P48247 |

Description (GLUTAMATE-1-SEMIALDEHYDE AMINOTRANSFERASE) (GSA-AT)

| ORF_Name | NTID | AAID | NT Length | AA Length | Score | Probability |
|---|---|---|---|---|---|---|
| 24609561_c3_56 | 901 | 2821 | 241 | 726 | 147 | 2.4e-19 |

| Protein name | | | | Locus Name | | Acc# |
|---|---|---|---|---|---|---|
| | | | | sp:UP14_ECOLI | | |

Description

UNKNOWN PROTEIN FROM 2D-PAGE (SPOT PR51)

| ORF_Name | NTID | AAID | NT Length | AA Length | Score | Probability |
|---|---|---|---|---|---|---|
| 36329806_f1_2 | 902 | 2822 | 80 | 243 | 60 | 0.019 |

| Protein name | | | | Locus Name | | Acc# |
|---|---|---|---|---|---|---|
| thyroid hormone sulfotransferase, B2 | | | | pir:JC5885 | | JC5885 |

Description

| ORF_Name | NTID | AAID | NT Length | AA Length | Score | Probability |
|---|---|---|---|---|---|---|
| 4188811_f1_6 | 903 | 2823 | 159 | 480 | 310 | 1.2e-27 |

| Protein name | | | | Locus Name | | Acc# |
|---|---|---|---|---|---|---|
| conserved hypothetical protein | | | | pir:T03501 | | T03501 |

Description

| ORF_Name | NTID | AAID | NT Length | AA Length | Score | Probability |
|---|---|---|---|---|---|---|
| 4336018_f1_7 | 904 | 2824 | 115 | 348 | 349 | 9.1e-32 |

| Protein name | | | | Locus Name | | Acc# |
|---|---|---|---|---|---|---|
| | | | | sp:PHNA_ECOLI | | P16680 |

Description

PHNA PROTEIN

| ORF_Name | NTID | AAID | NT Length | AA Length | Score | Probability |
|---|---|---|---|---|---|---|
| 4689143_f2_15 | 905 | 2825 | 175 | 528 | 132 | 9.0e-08 |

| Protein name | Locus Name | Acc# |
|---|---|---|
| apolipoprotein N-acyltransferase | gp:AF038595 | AF038595 |

Description

Pseudomonas aeruginosa apolipoprotein N-acyltransferase (cutE)gene, complete cds.

| ORF_Name | NTID | AAID | NT Length | AA Length | Score | Probability |
|---|---|---|---|---|---|---|
| 5205312_f3_21 | 906 | 2826 | 69 | 210 | | |

Protein name

Locus Name    Acc#

Description

NO-HIT

| ORF_Name | NTID | AAID | NT Length | AA Length | Score | Probability |
|---|---|---|---|---|---|---|
| 22382752_c1_11 | 907 | 2827 | 117 | 354 | 100 | 2.2e-05 |

| Protein name | Locus Name | Acc# |
|---|---|---|
| hypothetical protein | pir:T10511 | T10511 |

Description

| ORF_Name | NTID | AAID | NT Length | AA Length | Score | Probability |
|---|---|---|---|---|---|---|
| 26251376_c1_8 | 908 | 2828 | 82 | 249 | | |

Protein name    Locus Name    Acc#

Description

NO-HIT

| ORF_Name | NTID | AAID | NT Length | AA Length | Score | Probability |
|---|---|---|---|---|---|---|
| 35188942_c3_14 | 909 | 2829 | 255 | 768 | 248 | 4.6e-21 |

| Protein name | Locus Name | Acc# |
|---|---|---|
| hypothetical protein slr1971 | pir:S75639 | S75639 |

Description

| ORF Name | NTID | AAID | NT Length | AA Length | Score | Probability |
|---|---|---|---|---|---|---|
| 35337805_c1_10 | 910 | 2830 | 185 | 558 | 152 | 5.9e-12 |

| Protein name | Locus Name | Acc# |
|---|---|---|
| sulfate transporter | gp:D89631 | D89631 |

Description

Arabidopsis thaliana mRNA for sulfate transporter, complete cds.

| ORF Name | NTID | AAID | NT Length | AA Length | Score | Probability |
|---|---|---|---|---|---|---|
| 35801416_f1_1 | 911 | 2831 | 255 | 768 | 379 | 6.1e-35 |

| Protein name | Locus Name | Acc# |
|---|---|---|
| | sp:RLUA_ECOLI | P39219 |

Description (PSEUDOURIDYLATE SYNTHASE) (URACIL HYDROLYASE)

| ORF Name | NTID | AAID | NT Length | AA Length | Score | Probability |
|---|---|---|---|---|---|---|
| 4328403_c2_13 | 912 | 2832 | 109 | 330 | 191 | 5.1e-15 |

| Protein name | Locus Name | Acc# |
|---|---|---|
| BolA protein | gp:PFL243174 | AJ243174 |

Description

Pseudomonas fluorescens partial Fumarase C gene, bolA gene and ORF1.

| ORF Name | NTID | AAID | NT Length | AA Length | Score | Probability |
|---|---|---|---|---|---|---|
| 4572206_c1_9 | 913 | 2833 | 380 | 1143 | 391 | 1.5e-35 |

| Protein name | Locus Name | Acc# |
|---|---|---|
| sulfate transporter | gp:AB008782 | AB008782 |

Description

Arabidopsis thaliana mRNA for sulfate transporter, complete cds.

| ORF Name | NTID | AAID | NT Length | AA Length | Score | Probability |
|---|---|---|---|---|---|---|
| 16990667_f1_7 | 914 | 2834 | 61 | 186 | 109 | 8.8e-06 |

| Protein name | Locus Name | Acc# |
|---|---|---|
| hemV protein | pir:S54440 | S54440 |

Description

| ORF Name | NTID | AAID | NT Length | AA Length | Score | Probability |
|---|---|---|---|---|---|---|
| 19534511_c3_45 | 915 | 2835 | 70 | 213 | | |

| Protein name | | Locus Name | Acc# |
|---|---|---|---|
| | | | |

Description

NO-HIT

| ORF Name | NTID | AAID | NT Length | AA Length | Score | Probability |
|---|---|---|---|---|---|---|
| 19573425_c1_31 | 916 | 2836 | 150 | 453 | | |

| Protein name | | Locus Name | Acc# |
|---|---|---|---|
| | | | |

Description

NO-HIT

| ORF Name | NTID | AAID | NT Length | AA Length | Score | Probability |
|---|---|---|---|---|---|---|
| 20408375_c2_34 | 917 | 2837 | 60 | 183 | | |

| Protein name | | Locus Name | Acc# |
|---|---|---|---|
| | | | |

Description

NO-HIT

| ORF Name | NTID | AAID | NT Length | AA Length | Score | Probability |
|---|---|---|---|---|---|---|
| 20930_c3_42 | 918 | 2838 | 144 | 435 | 87 | 0.0070 |

| Protein name | | Locus Name | Acc# |
|---|---|---|---|
| | | sp:ATPZ_PSEPU | P25760 |

Description

ATP SYNTHASE PROTEIN I

| ORF Name | NTID | AAID | NT Length | AA Length | Score | Probability |
|---|---|---|---|---|---|---|
| 20991307_c2_35 | 919 | 2839 | 302 | 909 | 128 | 8.0e-14 |

| Protein name | | Locus Name | Acc# |
|---|---|---|---|
| periplasmic zinc transporter ZnuA | | gp:AF141971 | AF141971 |

Description

Haemophilus ducreyi HI0318 homolog gene, partial cds;oxidoreductase homolog and periplasmic zinc transporter ZnuA (znuA)genes, complete cds; and ribose-5-phosphate isomerase A homologgene, partial cds.

271

| ORF Name | NTID | AAID | NT Length | AA Length | Score | Probability |
|---|---|---|---|---|---|---|
| 22129692_c2_37 | 920 | 2840 | 496 | 1491 | 1866 | 1.6e-192 |

Protein name: H+-transporting ATP synthase, beta chain
Locus Name: pir:D64071
Acc#: D64071

Description:

| ORF Name | NTID | AAID | NT Length | AA Length | Score | Probability |
|---|---|---|---|---|---|---|
| 24507777_c3_43 | 921 | 2841 | 520 | 1563 | 1979 | 1.7e-204 |

Protein name:
Locus Name: sp:ATPA_ECOLI
Acc#: P00822

Description: ATP SYNTHASE ALPHA CHAIN,

| ORF Name | NTID | AAID | NT Length | AA Length | Score | Probability |
|---|---|---|---|---|---|---|
| 25680186_c1_28 | 922 | 2842 | 160 | 483 | 371 | 4.3e-34 |

Protein name:
Locus Name: sp:ATPF_VIBAL
Acc#: P12989

Description: ATP SYNTHASE B CHAIN,

| ORF Name | NTID | AAID | NT Length | AA Length | Score | Probability |
|---|---|---|---|---|---|---|
| 34023378_c1_26 | 923 | 2843 | 296 | 891 | 745 | 9.9e-74 |

Protein name:
Locus Name: sp:ATP6_ECOLI
Acc#:

Description: ATP SYNTHASE A CHAIN, (PROTEIN 6)

| ORF Name | NTID | AAID | NT Length | AA Length | Score | Probability |
|---|---|---|---|---|---|---|
| 35159406_c3_39 | 924 | 2844 | 65 | 198 | 65 | 0.0045 |

Protein name: extensin homolog F2401.18
Locus Name: pir:T01456
Acc#: T01456

Description:

| ORF Name | NTID | AAID | NT Length | AA Length | Score | Probability |
|---|---|---|---|---|---|---|
| 3953587_f3_23 | 925 | 2845 | 174 | 525 | 236 | 8.6e-20 |

| Protein name | | | | Locus Name | | Acc# |
|---|---|---|---|---|---|---|
| | | | | sp:ZUR_ECOLI | | |

Description

ZINC UPTAKE REGULATION PROTEIN (ZINC UPTAKE REGULATOR)

| ORF Name | NTID | AAID | NT Length | AA Length | Score | Probability |
|---|---|---|---|---|---|---|
| 4120425_c1_29 | 926 | 2846 | 202 | 609 | 268 | 3.5e-23 |

| Protein name | | | | Locus Name | | Acc# |
|---|---|---|---|---|---|---|
| | | | | sp:ATPD_VIBAL | | P12987 |

Description

ATP SYNTHASE DELTA CHAIN,

| ORF Name | NTID | AAID | NT Length | AA Length | Score | Probability |
|---|---|---|---|---|---|---|
| 4332943_c1_27 | 927 | 2847 | 84 | 255 | 261 | 1.9e-22 |

| Protein name | | | | Locus Name | | Acc# |
|---|---|---|---|---|---|---|
| | | | | sp:ATPL_HAEIN | | P43721 |

Description (DICYCLOHEXYLCARBODIIMIDE-BINDING PROTEIN)

| ORF Name | NTID | AAID | NT Length | AA Length | Score | Probability |
|---|---|---|---|---|---|---|
| 56333_c3_44 | 928 | 2848 | 309 | 930 | 894 | 1.6e-89 |

| Protein name | | | | Locus Name | | Acc# |
|---|---|---|---|---|---|---|
| | | | | sp:ATPG_ECOLI | | |

Description

ATP SYNTHASE GAMMA CHAIN,

| ORF Name | NTID | AAID | NT Length | AA Length | Score | Probability |
|---|---|---|---|---|---|---|
| 7056441_c2_38 | 929 | 2849 | 139 | 417 | 300 | 1.4e-26 |

Protein name | | | | Locus Name | | Acc#
sp:ATPE_HAEIN — P43718

Description

ATP SYNTHASE EPSILON CHAIN,

| ORF Name | NTID | AAID | NT Length | AA Length | Score | Probability |
|---|---|---|---|---|---|---|
| 9928433_f2_17 | 930 | 2850 | 71 | 216 | | |

Protein name | | | | Locus Name | | Acc#

Description

NO-HIT

| ORF Name | NTID | AAID | NT Length | AA Length | Score | Probability |
|---|---|---|---|---|---|---|
| 3235950_c2_28 | 931 | 2851 | 561 | 1686 | 2096 | 6.8e-217 |

Protein name: urocanase | | | | Locus Name: gp:PSEHUTUU | | Acc#

Description

Pseudomonas putida urocanase (hutU) gene, complete cds.

| ORF Name | NTID | AAID | NT Length | AA Length | Score | Probability |
|---|---|---|---|---|---|---|
| 3940938_c2_30 | 932 | 2852 | 357 | 1074 | 366 | 1.4e-33 |

Protein name | | | | Locus Name | | Acc#
sp:HUTG_KLEAE — P19452

Description (HISTIDINE UTILIZATION PROTEIN G) (FRAGMENT)

| ORF Name | NTID | AAID | NT Length | AA Length | Score | Probability |
|---|---|---|---|---|---|---|
| 3953181_c3_34 | 933 | 2853 | 434 | 1305 | 1007 | 1.7e-101 |

Protein name | | | | Locus Name | | Acc#
gp:YP102KB — AL031866

Description

Yersinia pestis 102 kbases unstable region: from 1 to 119443.

| ORF Name | NTID | AAID | NT Length | AA Length | Score | Probability |
|---|---|---|---|---|---|---|
| 4822181_f3_14 | 934 | 2854 | 78 | 237 | | |

| Protein name | Locus Name | Acc# |
|---|---|---|
| | | |

Description

NO-HIT

| ORF Name | NTID | AAID | NT Length | AA Length | Score | Probability |
|---|---|---|---|---|---|---|
| 789037_c3_33 | 935 | 2855 | 525 | 1578 | 1486 | 3.0e-152 |

| Protein name | Locus Name | Acc# |
|---|---|---|
| histidine ammonia-lyase,:histidase | pir:A35251 | |

Description

| ORF Name | NTID | AAID | NT Length | AA Length | Score | Probability |
|---|---|---|---|---|---|---|
| 828942_f1_1 | 936 | 2856 | 296 | 891 | 180 | 7.0e-12 |

| Protein name | Locus Name | Acc# |
|---|---|---|
| | sp:YYAM_BACSU | P37511 |

Description

HYPOTHETICAL 32.9 KD PROTEIN IN TETB-EXOA INTERGENIC REGION

| ORF Name | NTID | AAID | NT Length | AA Length | Score | Probability |
|---|---|---|---|---|---|---|
| 10978400_c3_163 | 937 | 2857 | 253 | 762 | 186 | 1.7e-14 |

| Protein name | Locus Name | Acc# |
|---|---|---|
| | sp:HEM4_PSEAE | P48246 |

Description

)

| ORF Name | NTID | AAID | NT Length | AA Length | Score | Probability |
|---|---|---|---|---|---|---|
| 1259626_c2_127 | 938 | 2858 | 614 | 1845 | 1756 | 7.3e-181 |

| Protein name | Locus Name | Acc# |
|---|---|---|
| | sp:YA51_HAEIN | |

Description

HYPOTHETICAL ABC TRANSPORTER ATP-BINDING PROTEIN HI1051

275

| ORF Name | NTID | AAID | NT Length | AA Length | Score | Probability |
|---|---|---|---|---|---|---|
| 12672305_c2_140 | 939 | 2859 | 110 | 333 | 144 | 4.8e-10 |

Protein name | Locus Name | Acc#
sp:YGGX_HAEIN | P44048

Description

HYPOTHETICAL PROTEIN HI0760

| ORF Name | NTID | AAID | NT Length | AA Length | Score | Probability |
|---|---|---|---|---|---|---|
| 13131890_f3_71 | 940 | 2860 | 169 | 510 | 147 | 2.7e-10 |

Protein name | Locus Name | Acc#
sp:DSBC_ERWCH | P39691

Description

THIOL:DISULFIDE INTERCHANGE PROTEIN DSBC PRECURSOR

| ORF Name | NTID | AAID | NT Length | AA Length | Score | Probability |
|---|---|---|---|---|---|---|
| 14847290_f3_89 | 941 | 2861 | 61 | 186 | | |

Protein name | Locus Name | Acc#

Description

NO-HIT

| ORF Name | NTID | AAID | NT Length | AA Length | Score | Probability |
|---|---|---|---|---|---|---|
| 15875832_f3_92 | 942 | 2862 | 75 | 228 | | |

Protein name | Locus Name | Acc#

Description

NO-HIT

| ORF Name | NTID | AAID | NT Length | AA Length | Score | Probability |
|---|---|---|---|---|---|---|
| 16493891_c3_165 | 943 | 2863 | 118 | 357 | | |

Protein name | Locus Name | Acc#

Description

NO-HIT

| ORF Name | NTID | AAID | NT Length | AA Length | Score | Probability |
|---|---|---|---|---|---|---|
| 16610052_c3_183 | 944 | 2864 | 93 | 282 | | |

Protein name | Locus Name | Acc#

Description

NO-HIT

| ORF Name | NTID | AAID | NT Length | AA Length | Score | Probability |
|---|---|---|---|---|---|---|
| 1957701_f1_30 | 945 | 2865 | 277 | 834 | 329 | 1.2e-29 |

Protein name | Locus Name | Acc#
| | sp:GRPE_HAEIN | P43732

Description

GRPE PROTEIN

| ORF Name | NTID | AAID | NT Length | AA Length | Score | Probability |
|---|---|---|---|---|---|---|
| 19720930_f3_74 | 946 | 2866 | 276 | 831 | 597 | 4.8e-58 |

Protein name | Locus Name | Acc#
| | sp:DAPB_ECOLI | P04036

Description

DIHYDRODIPICOLINATE REDUCTASE,

| ORF Name | NTID | AAID | NT Length | AA Length | Score | Probability |
|---|---|---|---|---|---|---|
| 21489390_f2_59 | 947 | 2867 | 67 | 204 | | |

Protein name | Locus Name | Acc#

Description

NO-HIT

| ORF Name | NTID | AAID | NT Length | AA Length | Score | Probability |
|---|---|---|---|---|---|---|
| 21689063_f1_10 | 948 | 2868 | 414 | 1245 | 328 | 1.5e-29 |

| Protein name | Locus Name | Acc# |
|---|---|---|
| SrpJ | gp:AF176824 | AF176824 |

Description

Synechococcus PCC7942 plasmid pANL O-acetylserine(thiol)-lyase SrpD(srpD), gamma-glutamyltranspeptidase SrpE (srpE), alpha-helical coiled-coil protein SrpF (srpF), SrpJ (srpJ), ATP-binding protein of ABC transporter SrpK (srpK), membrane lipoprotein SrpL (srpL), and cytoplasmic membrane protein SrpM (srpM) genes, complete cds.

| ORF Name | NTID | AAID | NT Length | AA Length | Score | Probability |
|---|---|---|---|---|---|---|
| 22042177_f2_65 | 949 | 2869 | 493 | 1482 | 1203 | 2.9e-122 |

| Protein name | Locus Name | Acc# |
|---|---|---|
| argininosuccinate lyase argH | pir:C69589 | C69589 |

Description

| ORF Name | NTID | AAID | NT Length | AA Length | Score | Probability |
|---|---|---|---|---|---|---|
| 22070191_f1_5 | 950 | 2870 | 409 | 1230 | 486 | 2.8e-46 |

| Protein name | Locus Name | Acc# |
|---|---|---|
| cystathionine-gamma-lyase | gp:AF180145 | AF180145 |

Description

Zymomonas mobilis GTP-binding protein CgpA (cgpA), 60KD inner-membrane protein yidC (yidC), hypothetical protein, glutamine-pyruvate aminotransferase gltB (gltB), glutamate synthase small subunit gltS (gltS), undecaprenol kinase udk (udk), hypothetical protein, NADH dehydrogenase, hypothetical protein; zm12orf5, hypothetical protein, aspartate aminotransferase A, beta-hydroxysteroid dehydrogenase, phosphomannomutase pmm

| ORF Name | NTID | AAID | NT Length | AA Length | Score | Probability |
|---|---|---|---|---|---|---|
| 22922082_c2_138 | 951 | 2871 | 319 | 960 | | |

| Protein name | Locus Name | Acc# |
|---|---|---|
| | | |

Description

NO-HIT

| ORF Name | NTID | AAID | NT Length | AA Length | Score | Probability |
|---|---|---|---|---|---|---|
| 234701_c3_187 | 952 | 2872 | 73 | 222 | 115 | 5.1e-07 |

| Protein name | Locus Name | Acc# |
|---|---|---|
| extensin | pir:S22697 | |

Description

| ORF Name | NTID | AAID | NT Length | AA Length | Score | Probability |
|---|---|---|---|---|---|---|
| 23572127_f1_31 | 953 | 2873 | 636 | 1911 | 2307 | 3.0e-239 |

| Protein name | Locus Name | Acc# |
|---|---|---|
| | sp:DNAK_FRATU | P48205 |

Description

DNAK PROTEIN (HEAT SHOCK PROTEIN 70) (HSP70)

| ORF Name | NTID | AAID | NT Length | AA Length | Score | Probability |
|---|---|---|---|---|---|---|
| 23909688_f3_77 | 954 | 2874 | 466 | 1401 | 456 | 4.2e-43 |

| Protein name | Locus Name | Acc# |
|---|---|---|
| rubredoxin--NAD+ reductase,:hypothetical protein hydA 3'-region | pir:C65051 | C65051 |

Description

| ORF Name | NTID | AAID | NT Length | AA Length | Score | Probability |
|---|---|---|---|---|---|---|
| 24073762_c3_158 | 955 | 2875 | 220 | 663 | 681 | 6.0e-67 |

| Protein name | Locus Name | Acc# |
|---|---|---|
| AvtA | gp:AF014804 | AF014804 |

Description

Neisseria meningitidis PglB (pglB), PglC (pglC), PglD (pglD), andAvtA (avtA) genes, complete cds.

| ORF Name | NTID | AAID | NT Length | AA Length | Score | Probability |
|---|---|---|---|---|---|---|
| 24100465_f2_46 | 956 | 2876 | 321 | 966 | 639 | 1.3e-64 |

| Protein name | Locus Name | Acc# |
|---|---|---|
| intrinsic membrane protein | gp:AB000100 | AB000100 |

Description

Synechococcus sp. DNA for intrinsic membrane protein, malK-likeprotein, cyanase, complete cds.

| ORF Name | NTID | AAID | NT Length | AA Length | Score | Probability |
|---|---|---|---|---|---|---|
| 24391877_c1_109 | 957 | 2877 | 329 | 990 | 927 | 5.1e-93 |

Protein name | | | | Locus Name | | Acc#
| | | | | sp:HEM3_ECOLI | | |

Description

SYNTHASE) (HMBS) (PRE-UROPORPHYRINOGEN SYNTHASE)

| ORF Name | NTID | AAID | NT Length | AA Length | Score | Probability |
|---|---|---|---|---|---|---|
| 24417807_f3_76 | 958 | 2878 | 185 | 558 | 263 | 1.2e-22 |

Protein name | | | | Locus Name | | Acc#
Mip | | | | gp:S71704 | | S71704

Description

| ORF Name | NTID | AAID | NT Length | AA Length | Score | Probability |
|---|---|---|---|---|---|---|
| 24619003_f3_79 | 959 | 2879 | 287 | 864 | 625 | 5.2e-61 |

Protein name | | | | Locus Name | | Acc#
| | | | | sp:NRTC_SYNY3 | | P73450

Description

NITRATE TRANSPORT ATP-BINDING PROTEIN NRTC

| ORF Name | NTID | AAID | NT Length | AA Length | Score | Probability |
|---|---|---|---|---|---|---|
| 26053250_c1_112 | 960 | 2880 | 268 | 807 | | |

Protein name | | | | Locus Name | | Acc#

Description

NO-HIT

| ORF Name | NTID | AAID | NT Length | AA Length | Score | Probability |
|---|---|---|---|---|---|---|
| 26053250_c2_134 | 961 | 2881 | 116 | 351 | | |

Protein name | | | | Locus Name | | Acc#

Description

NO-HIT

| ORF Name | NTID | AAID | NT Length | AA Length | Score | Probability |
|---|---|---|---|---|---|---|
| 26362680_c2_129 | 962 | 2882 | 296 | 891 | 480 | 1.2e-45 |

| Protein name | | | | Locus Name | | Acc# |
|---|---|---|---|---|---|---|
| | | | | sp:YJFH_HAEIN | | P44906 |

Description

HYPOTHETICAL TRNA/RRNA METHYLTRANSFERASE HI0860,

| ORF Name | NTID | AAID | NT Length | AA Length | Score | Probability |
|---|---|---|---|---|---|---|
| 2928382_f2_40 | 963 | 2883 | 323 | 972 | 895 | 1.3e-89 |

| Protein name | | | | Locus Name | | Acc# |
|---|---|---|---|---|---|---|
| sodium-dependent transporter homolog yocS | | | | pir:E69902 | | E69902 |

Description

| ORF Name | NTID | AAID | NT Length | AA Length | Score | Probability |
|---|---|---|---|---|---|---|
| 29339432_c3_166 | 964 | 2884 | 322 | 969 | 92 | 4.2e-06 |

| Protein name | | | | Locus Name | | Acc# |
|---|---|---|---|---|---|---|
| hypothetical protein b2755 | | | | pir:G65056 | | G65056 |

Description

| ORF Name | NTID | AAID | NT Length | AA Length | Score | Probability |
|---|---|---|---|---|---|---|
| 29962837_c3_181 | 965 | 2885 | 288 | 867 | 117 | 9.9e-13 |

| Protein name | | | | Locus Name | | Acc# |
|---|---|---|---|---|---|---|
| | | | | sp:DNAJ_SYNP7 | | P50026 |

Description

DNAJ PROTEIN

| ORF Name | NTID | AAID | NT Length | AA Length | Score | Probability |
|---|---|---|---|---|---|---|
| 32629186_c2_139 | 966 | 2886 | 223 | 672 | | |

| Protein name | | | | Locus Name | | Acc# |
|---|---|---|---|---|---|---|

Description

NO-HIT

| ORF_Name | NTID | AAID | NT Length | AA Length | Score | Probability |
|---|---|---|---|---|---|---|
| 3307_f2_47 | 967 | 2887 | 119 | 360 | 349 | 9.1e-32 |

| Protein name | | | | Locus_Name | | Acc# |
|---|---|---|---|---|---|---|
| | | | | sp:YADR_HAEIN | | P45344 |

Description

HYPOTHETICAL PROTEIN HI1723

| ORF_Name | NTID | AAID | NT Length | AA Length | Score | Probability |
|---|---|---|---|---|---|---|
| 34492161_c3_168 | 968 | 2888 | 353 | 1062 | | |

| Protein name | | | | Locus_Name | | Acc# |
|---|---|---|---|---|---|---|

Description

NO-HIT

| ORF_Name | NTID | AAID | NT Length | AA Length | Score | Probability |
|---|---|---|---|---|---|---|
| 3940925_c3_182 | 969 | 2889 | 341 | 1026 | 466 | 3.7e-44 |

| Protein name | | | | Locus_Name | | Acc# |
|---|---|---|---|---|---|---|
| | | | | sp:YHET_ECOLI | | P45524 |

Description

HYPOTHETICAL 38.5 KD PROTEIN IN KIFB-PRKB INTERGENIC REGION

| ORF_Name | NTID | AAID | NT Length | AA Length | Score | Probability |
|---|---|---|---|---|---|---|
| 4095443_c3_170 | 970 | 2890 | 161 | 486 | 147 | 2.3e-10 |

| Protein name | | | | Locus_Name | | Acc# |
|---|---|---|---|---|---|---|
| hypothetical protein Rv0163 | | | | pir:G70903 | | G70903 |

Description

| ORF_Name | NTID | AAID | NT Length | AA Length | Score | Probability |
|---|---|---|---|---|---|---|
| 4187538_f2_50 | 971 | 2891 | 473 | 1422 | 1141 | 1.1e-115 |

| Protein name | | | | Locus_Name | | Acc# |
|---|---|---|---|---|---|---|
| | | | | sp:MPL_HAEIN | | P43948 |

Description

LIGASE,

| ORF Name | NTID | AAID | NT Length | AA Length | Score | Probability |
|---|---|---|---|---|---|---|
| 4328135_f1_13 | 972 | 2892 | 474 | 1425 | 812 | 7.9e-81 |

| Protein name | Locus Name | Acc# |
|---|---|---|
| periplasmic substrate binding protein | gp:AF001333 | AF001333 |

Description

Synechococcus PCC7942 periplasmic substrate binding protein (cynA), integral membrane protein (cynB) and ATP-binding protein (cynD) genes, complete cds.

| ORF Name | NTID | AAID | NT Length | AA Length | Score | Probability |
|---|---|---|---|---|---|---|
| 4328965_f3_99 | 973 | 2893 | 132 | 399 | 282 | 1.2e-24 |

| Protein name | Locus Name | Acc# |
|---|---|---|
| | sp:Y117_HAEDU | O30825 |

Description

HYPOTHETICAL PROTEIN HYP0117

| ORF Name | NTID | AAID | NT Length | AA Length | Score | Probability |
|---|---|---|---|---|---|---|
| 4423318_c3_160 | 974 | 2894 | 626 | 1881 | 2307 | 3.0e-239 |

| Protein name | Locus Name | Acc# |
|---|---|---|
| 93% identity over 631 amino acids with E. coli | gp:STYSTMF1 | AF170176 |

Description

Salmonella typhimurium fragment STMF1.

| ORF Name | NTID | AAID | NT Length | AA Length | Score | Probability |
|---|---|---|---|---|---|---|
| 4454512_f1_32 | 975 | 2895 | 111 | 336 | 113 | 9.3e-07 |

| Protein name | Locus Name | Acc# |
|---|---|---|
| | sp:Y173_HAEIN | P43960 |

Description

HYPOTHETICAL PROTEIN HI0173

| ORF Name | NTID | AAID | NT Length | AA Length | Score | Probability |
|---|---|---|---|---|---|---|
| 4548188_f1_38 | 976 | 2896 | 421 | 1266 | 1342 | 5.4e-137 |

| Protein name | | | | Locus Name | | Acc# |
|---|---|---|---|---|---|---|
| | | | | sp:DADA_ECOLI | | P29011 |

Description

D-AMINO ACID DEHYDROGENASE SMALL SUBUNIT,

| ORF Name | NTID | AAID | NT Length | AA Length | Score | Probability |
|---|---|---|---|---|---|---|
| 5119127_c2_153 | 977 | 2897 | 651 | 1956 | 1464 | 6.4e-150 |

| Protein name | | | | Locus Name | | Acc# |
|---|---|---|---|---|---|---|
| | | | | sp:YHES_ECOLI | | P45535 |

Description

HYPOTHETICAL ABC TRANSPORTER ATP-BINDING PROTEIN YHES

| ORF Name | NTID | AAID | NT Length | AA Length | Score | Probability |
|---|---|---|---|---|---|---|
| 6727086_f1_17 | 978 | 2898 | 563 | 1692 | 879 | 6.3e-88 |

| Protein name | | | Locus Name | | Acc# |
|---|---|---|---|---|---|
| putative gamma-glutamylcysteine synthetase | | | gp:PSP243941 | | AJ243941 |

Description

Pseudomonas sp. strain HR199 partial vanB, fdh, gcs, ehyA and ehyBgenes.

| ORF Name | NTID | AAID | NT Length | AA Length | Score | Probability |
|---|---|---|---|---|---|---|
| 673253_f3_72 | 979 | 2899 | 407 | 1224 | 1146 | 3.2e-116 |

| Protein name | | | | Locus Name | | Acc# |
|---|---|---|---|---|---|---|
| | | | | sp:DNAJ_SALTY | | Q60004 |

Description

DNAJ PROTEIN

| ORF Name | NTID | AAID | NT Length | AA Length | Score | Probability |
|---|---|---|---|---|---|---|
| 6854677_c3_167 | 980 | 2900 | 462 | 1389 | | |

| Protein name | | | | Locus Name | | Acc# |
|---|---|---|---|---|---|---|

Description

NO-HIT

| ORF_Name | NTID | AAID | NT Length | AA Length | Score | Probability |
|---|---|---|---|---|---|---|
| 801452_f2_60 | 981 | 2901 | 76 | 231 | | |

Protein name | | | | Locus Name | Acc#

Description

NO-HIT

| ORF_Name | NTID | AAID | NT Length | AA Length | Score | Probability |
|---|---|---|---|---|---|---|
| 884712_c1_113 | 982 | 2902 | 1191 | 3576 | 79 | 0.0031 |

Protein name: hypothetical protein PH1246 | Locus Name: pir:A71069 | Acc#: A71069

Description

| ORF_Name | NTID | AAID | NT Length | AA Length | Score | Probability |
|---|---|---|---|---|---|---|
| 915633_c1_115 | 983 | 2903 | 74 | 225 | | |

Protein name | | | | Locus Name | Acc#

Description

NO-HIT

| ORF_Name | NTID | AAID | NT Length | AA Length | Score | Probability |
|---|---|---|---|---|---|---|
| 9766888_f1_18 | 984 | 2904 | 182 | 549 | 229 | 4.8e-19 |

Protein name | | | | Locus Name: sp:YA21_PSEAE | Acc#: P21482

Description

HYPOTHETICAL 17.8 KD PROTEIN IN ALGR2 5'REGION

| ORF_Name | NTID | AAID | NT Length | AA Length | Score | Probability |
|---|---|---|---|---|---|---|
| 10329680_f1_3 | 985 | 2905 | 544 | 1635 | 587 | 5.5e-57 |

Protein name | | | | Locus Name: gp:PSEOPRC | Acc#: D28119

Description

Pseudomonas aeruginosa oprC gene for outer membrane protein C, complete cds.

| ORF Name | NTID | AAID | NT Length | AA Length | Score | Probability |
|---|---|---|---|---|---|---|
| 10626550_c3_128 | 986 | 2906 | 65 | 198 | | |

Protein name | Locus Name | Acc#

Description

NO-HIT

| ORF Name | NTID | AAID | NT Length | AA Length | Score | Probability |
|---|---|---|---|---|---|---|
| 11017010_c3_139 | 987 | 2907 | 247 | 744 | | |

Protein name | Locus Name | Acc#

Description

NO-HIT

| ORF Name | NTID | AAID | NT Length | AA Length | Score | Probability |
|---|---|---|---|---|---|---|
| 12894752_f1_13 | 988 | 2908 | 69 | 210 | 84 | 0.016 |

Protein name | Locus Name | Acc#
conserved hypothetical protein | pir:A72221 | A72221

Description

| ORF Name | NTID | AAID | NT Length | AA Length | Score | Probability |
|---|---|---|---|---|---|---|
| 13759627_c3_138 | 989 | 2909 | 88 | 267 | | |

Protein name | Locus Name | Acc#

Description

NO-HIT

| ORF Name | NTID | AAID | NT Length | AA Length | Score | Probability |
|---|---|---|---|---|---|---|
| 14633433_f3_55 | 990 | 2910 | 122 | 369 | | |

Protein name | Locus Name | Acc#

Description

NO-HIT

| ORF Name | NTID | AAID | NT Length | AA Length | Score | Probability |
|---|---|---|---|---|---|---|
| 16023402_c3_125 | 991 | 2911 | 887 | 2664 | 1410 | 6.3e-160 |

| Protein name | Locus Name | Acc# |
|---|---|---|
| | sp:FTSK_COXBU | P39920 |

Description

CELL DIVISION PROTEIN FTSK HOMOLOG

| ORF Name | NTID | AAID | NT Length | AA Length | Score | Probability |
|---|---|---|---|---|---|---|
| 19537930_f1_1 | 992 | 2912 | 97 | 294 | 116 | 4.5e-07 |

| Protein name | Locus Name | Acc# |
|---|---|---|
| hypothetical protein APE0900 | pir:D72685 | D72685 |

Description

| ORF Name | NTID | AAID | NT Length | AA Length | Score | Probability |
|---|---|---|---|---|---|---|
| 19812500_f1_14 | 993 | 2913 | 974 | 2925 | 2125 | 5.8e-220 |

| Protein name | Locus Name | Acc# |
|---|---|---|
| | sp:DPO1_HAEIN | P43741 |

Description

DNA POLYMERASE I, (POL I)

| ORF Name | NTID | AAID | NT Length | AA Length | Score | Probability |
|---|---|---|---|---|---|---|
| 2008433_c1_102 | 994 | 2914 | 287 | 864 | | |

| Protein name | Locus Name | Acc# |
|---|---|---|

Description

NO-HIT

| ORF Name | NTID | AAID | NT Length | AA Length | Score | Probability |
|---|---|---|---|---|---|---|
| 20506502_c2_105 | 995 | 2915 | 62 | 189 | | |

| Protein name | Locus Name | Acc# |
|---|---|---|

Description

NO-HIT

| ORF Name | NTID | AAID | NT Length | AA Length | Score | Probability |
|---|---|---|---|---|---|---|
| 20581377_c3_127 | 996 | 2916 | 888 | 2667 | 2717 | 1.1e-282 |

| Protein name | Locus Name | Acc# |
|---|---|---|
| DNA topoisomerase, | pir:G64119 | G64119 |

Description

---

| ORF Name | NTID | AAID | NT Length | AA Length | Score | Probability |
|---|---|---|---|---|---|---|
| 2131550_f1_9 | 997 | 2917 | 115 | 348 | 153 | 5.4e-11 |

| Protein name | Locus Name | Acc# |
|---|---|---|
| pterin-4-alpha-carbinolamine dehydratase:protein ssl2296:protein ssl2296 | pir:S74881 | S74881 |

Description

---

| ORF Name | NTID | AAID | NT Length | AA Length | Score | Probability |
|---|---|---|---|---|---|---|
| 22119402_f3_77 | 998 | 2918 | 262 | 789 | 491 | 8.2e-47 |

| Protein name | Locus Name | Acc# |
|---|---|---|
|  | sp:OCCM_AGRT1 | P35115 |

Description

OCTOPINE TRANSPORT SYSTEM PERMEASE PROTEIN OCCM

---

| ORF Name | NTID | AAID | NT Length | AA Length | Score | Probability |
|---|---|---|---|---|---|---|
| 234408_c2_111 | 999 | 2919 | 129 | 390 | 275 | 6.3e-24 |

| Protein name | Locus Name | Acc# |
|---|---|---|
|  | sp:RRMA_ECOLI | P36999 |

Description

METHYLTRANSFERASE)

---

| ORF Name | NTID | AAID | NT Length | AA Length | Score | Probability |
|---|---|---|---|---|---|---|
| 23928130_f3_66 | 1000 | 2920 | 63 | 192 |  |  |

| Protein name | Locus Name | Acc# |
|---|---|---|

Description

NO-HIT

| ORF Name | NTID | AAID | NT Length | AA Length | Score | Probability |
|---|---|---|---|---|---|---|
| 24256553_f2_31 | 1001 | 2921 | 751 | 2256 | 2080 | 3.4e-215 |

| Protein name | | | | Locus Name | | Acc# |
|---|---|---|---|---|---|---|
| DNA topoisomerase IV | | | | gp:AB023570 | | AB023570 |

Description

Vibrio parahaemolyticus parC gene for DNA topoisomerase IV, complete cds.

| ORF Name | NTID | AAID | NT Length | AA Length | Score | Probability |
|---|---|---|---|---|---|---|
| 24645763_c1_91 | 1002 | 2922 | 296 | 891 | 255 | 8.4e-22 |

| Protein name | | | | Locus Name | | Acc# |
|---|---|---|---|---|---|---|
| hypothetical protein jhp1155 | | | | pir:G71841 | | G71841 |

Description

| ORF Name | NTID | AAID | NT Length | AA Length | Score | Probability |
|---|---|---|---|---|---|---|
| 24881313_f2_32 | 1003 | 2923 | 70 | 213 | | |

| Protein name | | | | Locus Name | | Acc# |
|---|---|---|---|---|---|---|

Description

NO-HIT

| ORF Name | NTID | AAID | NT Length | AA Length | Score | Probability |
|---|---|---|---|---|---|---|
| 25417950_c3_134 | 1004 | 2924 | 162 | 489 | 214 | 1.8e-17 |

| Protein name | | | | Locus Name | | Acc# |
|---|---|---|---|---|---|---|
| | | | | sp:RRMA_ECOLI | | P36999 |

Description

METHYLTRANSFERASE)

| ORF Name | NTID | AAID | NT Length | AA Length | Score | Probability |
|---|---|---|---|---|---|---|
| 31406308_c2_113 | 1005 | 2925 | 114 | 345 | | |

| Protein name | | | | Locus Name | | Acc# |
|---|---|---|---|---|---|---|

Description

NO-HIT

| ORF Name | NTID | AAID | NT Length | AA Length | Score | Probability |
|---|---|---|---|---|---|---|
| 31485625_f3_72 | 1006 | 2926 | 275 | 828 | 427 | 5.0e-40 |

| Protein name | | | | Locus Name | | Acc# |
|---|---|---|---|---|---|---|
| | | | | gp:AB032934 | | AB032934 |

Description

Vibrio alginolyticus pfsA, orfC, orfD genes for PF60 and hypothetical proteins, complete cds.

| ORF Name | NTID | AAID | NT Length | AA Length | Score | Probability |
|---|---|---|---|---|---|---|
| 34025462_c1_104 | 1007 | 2927 | 69 | 210 | | |

| Protein name | | | | Locus Name | | Acc# |

Description

NO-HIT

| ORF Name | NTID | AAID | NT Length | AA Length | Score | Probability |
|---|---|---|---|---|---|---|
| 34086012_c1_97 | 1008 | 2928 | 138 | 417 | | |

| Protein name | | | | Locus Name | | Acc# |

Description

NO-HIT

| ORF Name | NTID | AAID | NT Length | AA Length | Score | Probability |
|---|---|---|---|---|---|---|
| 35360075_f1_2 | 1009 | 2929 | 166 | 501 | 73 | 0.032 |

| Protein name | | | | Locus Name | | Acc# |
|---|---|---|---|---|---|---|
| nef protein | | | | gp:AF169778 | | AF169778 |

Description

HIV-1 isolate G221 from India nef protein (nef) gene, partial cds; and 3' long terminal repeat, partial sequence.

| ORF Name | NTID | AAID | NT Length | AA Length | Score | Probability |
|---|---|---|---|---|---|---|
| 36110253_f2_36 | 1010 | 2930 | 108 | 327 | 76 | 0.0077 |

| Protein name | | | | Locus Name | | Acc# |
|---|---|---|---|---|---|---|
| outer surface protein A | | | | gp:BBPWUDII | | X68539 |

Description

B.burgdorferi (PWudII) plasmid OspA gene for outer surface proteinA.

290

| ORF Name | NTID | AAID | NT Length | AA Length | Score | Probability |
|---|---|---|---|---|---|---|
| 3945893_f3_71 | 1011 | 2931 | 286 | 861 | 825 | 3.3e-82 |

| Protein name | | | | Locus Name | | Acc# |
|---|---|---|---|---|---|---|
| | | | | gp:AB032934 | | AB032934 |

Description

Vibrio alginolyticus pfsA, orfC, orfD genes for PF60 and hypothetical proteins, complete cds.

| ORF Name | NTID | AAID | NT Length | AA Length | Score | Probability |
|---|---|---|---|---|---|---|
| 4337963_f2_51 | 1012 | 2932 | 268 | 807 | 434 | 9.0e-41 |

| Protein name | | | | Locus Name | | Acc# |
|---|---|---|---|---|---|---|
| | | | | gp:AB032934 | | AB032934 |

Description

Vibrio alginolyticus pfsA, orfC, orfD genes for PF60 and hypothetical proteins, complete cds.

| ORF Name | NTID | AAID | NT Length | AA Length | Score | Probability |
|---|---|---|---|---|---|---|
| 4691525_f1_7 | 1013 | 2933 | 78 | 237 | | |

| Protein name | | | | Locus Name | | Acc# |
|---|---|---|---|---|---|---|

Description

NO-HIT

| ORF Name | NTID | AAID | NT Length | AA Length | Score | Probability |
|---|---|---|---|---|---|---|
| 4735333_c2_110 | 1014 | 2934 | 570 | 1713 | 1749 | 4.0e-180 |

| Protein name | | | | Locus Name | | Acc# |
|---|---|---|---|---|---|---|
| | | | | sp:RF3_HAEIN | | P43928 |

Description

PEPTIDE CHAIN RELEASE FACTOR 3 (RF-3)

| ORF Name | NTID | AAID | NT Length | AA Length | Score | Probability |
|---|---|---|---|---|---|---|
| 5102193_f2_54 | 1015 | 2935 | 372 | 1119 | 897 | 7.8e-90 |

| Protein name | | | | | Locus Name | Acc# |
|---|---|---|---|---|---|---|
| | | | | | sp:GLMU_HAEIN | P43889 |

Description

ACETYLGLUCOSAMINE-1-PHOSPHATE URIDYLTRANSFERASE)

| ORF Name | NTID | AAID | NT Length | AA Length | Score | Probability |
|---|---|---|---|---|---|---|
| 5111013_c3_126 | 1016 | 2936 | 201 | 606 | | |

| Protein name | | | | | Locus Name | Acc# |
|---|---|---|---|---|---|---|

Description

NO-HIT

| ORF Name | NTID | AAID | NT Length | AA Length | Score | Probability |
|---|---|---|---|---|---|---|
| 6516518_f1_25 | 1017 | 2937 | 243 | 732 | 499 | 1.2e-47 |

| Protein name | | | | | Locus Name | Acc# |
|---|---|---|---|---|---|---|
| | | | | | sp:NOCQ_AGRT5 | P35118 |

Description

NOPALINE TRANSPORT SYSTEM PERMEASE PROTEIN NOCQ

| ORF Name | NTID | AAID | NT Length | AA Length | Score | Probability |
|---|---|---|---|---|---|---|
| 6820875_c1_100 | 1018 | 2938 | 345 | 1038 | 159 | 8.8e-09 |

| Protein name | | | | | Locus Name | Acc# |
|---|---|---|---|---|---|---|
| apolipoprotein A-IV precursor | | | | | pir:C40892 | C40892 |

Description

| ORF Name | NTID | AAID | NT Length | AA Length | Score | Probability |
|---|---|---|---|---|---|---|
| 807692_c3_137 | 1019 | 2939 | 563 | 1692 | 171 | 1.2e-08 |

| Protein name | | | | | Locus Name | Acc# |
|---|---|---|---|---|---|---|
| Trip230 | | | | | gp:AF007217 | AF007217 |

Description

Homo sapiens Trip230 mRNA, complete cds.

| ORF Name | NTID | AAID | NT Length | AA Length | Score | Probability |
|---|---|---|---|---|---|---|
| 978502_f2_52 | 1020 | 2940 | 266 | 801 | 430 | 2.4e-40 |

| Protein name | | | | Locus Name | | Acc# |
|---|---|---|---|---|---|---|
| | | | | gp:AB032934 | | AB032934 |

Description

Vibrio alginolyticus pfsA, orfC, orfD genes for PF60 and hypothetical proteins, complete cds.

| ORF Name | NTID | AAID | NT Length | AA Length | Score | Probability |
|---|---|---|---|---|---|---|
| 10056500_f1_3 | 1021 | 2941 | 78 | 237 | 163 | 4.7e-12 |

| Protein name | | | | Locus Name | | Acc# |
|---|---|---|---|---|---|---|
| hypothetical protein HI0187 | | | | pir:B64145 | | B64145 |

Description

| ORF Name | NTID | AAID | NT Length | AA Length | Score | Probability |
|---|---|---|---|---|---|---|
| 10656456_c3_200 | 1022 | 2942 | 463 | 1392 | 831 | 7.7e-83 |

| Protein name | | | | Locus Name | | Acc# |
|---|---|---|---|---|---|---|
| | | | | sp:YWBN_BACSU | | P39597 |

Description

HYPOTHETICAL 45.7 KD PROTEIN IN EPR-GALK INTERGENIC REGION PRECURSOR

| ORF Name | NTID | AAID | NT Length | AA Length | Score | Probability |
|---|---|---|---|---|---|---|
| 12603450_f1_20 | 1023 | 2943 | 558 | 1677 | 1262 | 1.6e-128 |

| Protein name | | | | Locus Name | | Acc# |
|---|---|---|---|---|---|---|
| | | | | sp:PILB_PSEAE | | P22608 |

Description

FIMBRIAL ASSEMBLY PROTEIN PILB

| ORF Name | NTID | AAID | NT Length | AA Length | Score | Probability |
|---|---|---|---|---|---|---|
| 12978955_f2_43 | 1024 | 2944 | 274 | 825 | 609 | 2.6e-59 |

| Protein name | | | | Locus Name | | Acc# |
|---|---|---|---|---|---|---|
| | | | | sp:YH25_AZOCH | | P54085 |

Description (ORF5)

| ORF Name | NTID | AAID | NT Length | AA Length | Score | Probability |
|---|---|---|---|---|---|---|
| 13679786_f3_112 | 1025 | 2945 | 110 | 333 | 105 | 1.2e-05 |

| Protein name | Locus Name | Acc# |
|---|---|---|
| hypothetical protein | gp:BSZ75208 | Z75208 |

Description

B.subtilis genomic sequence 89009bp.

| ORF Name | NTID | AAID | NT Length | AA Length | Score | Probability |
|---|---|---|---|---|---|---|
| 13712643_c3_187 | 1026 | 2946 | 215 | 648 | 113 | 0.00040 |

| Protein name | Locus Name | Acc# |
|---|---|---|
| conserved hypothetical protein | pir:B75483 | B75483 |

Description

| ORF Name | NTID | AAID | NT Length | AA Length | Score | Probability |
|---|---|---|---|---|---|---|
| 14191915_f2_69 | 1027 | 2947 | 365 | 1098 | 329 | 2.5e-34 |

| Protein name | Locus Name | Acc# |
|---|---|---|
| conserved hypothetical protein ylbK | pir:H69874 | H69874 |

Description

| ORF Name | NTID | AAID | NT Length | AA Length | Score | Probability |
|---|---|---|---|---|---|---|
| 14251568_f2_72 | 1028 | 2948 | 118 | 357 | 207 | 1.0e-16 |

| Protein name | Locus Name | Acc# |
|---|---|---|
| hypothetical protein APE1486 | pir:F72628 | F72628 |

Description

| ORF Name | NTID | AAID | NT Length | AA Length | Score | Probability |
|---|---|---|---|---|---|---|
| 14492180_c2_149 | 1029 | 2949 | 67 | 204 | | |

| Protein name | Locus Name | Acc# |
|---|---|---|
| | | |

Description

NO-HIT

| ORF Name | NTID | AAID | NT Length | AA Length | Score | Probability |
|---|---|---|---|---|---|---|
| 14511561_c3_197 | 1030 | 2950 | 1319 | 3960 | 3473 | 0.0 |

Protein name: phosphoribosylformylglycinamidine synthase,:formylglycinamide ribonucleotide synthetase:phosphoribosylformylglycinamidine Locus Name: pir:SYECPG    Acc#:

Description

| ORF Name | NTID | AAID | NT Length | AA Length | Score | Probability |
|---|---|---|---|---|---|---|
| 14878927_f2_42 | 1031 | 2951 | 271 | 816 | 294 | 4.8e-39 |

Protein name

Locus Name: sp:HIS2_AQUAE    Acc#: O67780

Description

| ORF Name | NTID | AAID | NT Length | AA Length | Score | Probability |
|---|---|---|---|---|---|---|
| 14882750_c2_164 | 1032 | 2952 | 409 | 1230 | 585 | 9.0e-57 |

Protein name: putative membrane transport protein.

Locus Name: gp:SCC75A    Acc#: AL133220

Description: Streptomyces coelicolor cosmid C75A.

| ORF Name | NTID | AAID | NT Length | AA Length | Score | Probability |
|---|---|---|---|---|---|---|
| 14970637_c3_176 | 1033 | 2953 | 237 | 714 | 791 | 1.3e-78 |

Protein name

Locus Name: sp:CLPP_ECOLI    Acc#: P19245

Description: PROTEIN F21.5)

| ORF Name | NTID | AAID | NT Length | AA Length | Score | Probability |
|---|---|---|---|---|---|---|
| 15831636_c2_158 | 1034 | 2954 | 127 | 384 | 236 | 1.5e-19 |

Protein name: Acriflavin resistance protein D.

Locus Name: gp:D90846    Acc#:

Description: E.coli genomic DNA, Kohara clone #357(46.5-46.8 min.).

295

| ORF_Name | NTID | AAID | NT Length | AA Length | Score | Probability |
|---|---|---|---|---|---|---|
| 165842_c2_157 | 1035 | 2955 | 205 | 618 | 332 | 5.8e-30 |

Protein name | Locus Name | Acc#
sp:NOLH_RHIME | P25198

Description
NODULATION PROTEIN NOLH PRECURSOR

| ORF_Name | NTID | AAID | NT Length | AA Length | Score | Probability |
|---|---|---|---|---|---|---|
| 16687526_f1_10 | 1036 | 2956 | 448 | 1347 | 1082 | 1.9e-109 |

Protein name | Locus Name | Acc#
sp:ARGA_ECOLI

Description
SYNTHASE) (AGS)

| ORF_Name | NTID | AAID | NT Length | AA Length | Score | Probability |
|---|---|---|---|---|---|---|
| 191675_c2_150 | 1037 | 2957 | 251 | 756 | 698 | 9.5e-69 |

Protein name | Locus Name | Acc#
5' adenylylsulfate APS reductase | gp:AF170343 | AF170343

Description
Burkholderia cepacia 5' adenylylsulfate APS reductase (cysH) gene, complete cds; and ATP sulfurylase small subunit (cysD) gene, partial cds.

| ORF_Name | NTID | AAID | NT Length | AA Length | Score | Probability |
|---|---|---|---|---|---|---|
| 19821942_c3_205 | 1038 | 2958 | 64 | 195 | | |

Protein name | Locus Name | Acc#

Description
NO-HIT

| ORF_Name | NTID | AAID | NT Length | AA Length | Score | Probability |
|---|---|---|---|---|---|---|
| 20203302_c3_185 | 1039 | 2959 | 226 | 681 | 141 | 4.0e-08 |

Protein name | Locus Name | Acc#
DnrE protein | gp:PST131716 | AJ131716

Description
Pseudomonas stutzeri dnrE gene and ORF235 (partial).

| ORF Name | NTID | AAID | NT Length | AA Length | Score | Probability |
|---|---|---|---|---|---|---|
| 20570385_c2_159 | 1040 | 2960 | 193 | 582 | | |

Protein name | Locus Name | Acc#

Description

NO-HIT

| ORF Name | NTID | AAID | NT Length | AA Length | Score | Probability |
|---|---|---|---|---|---|---|
| 21494010_c2_174 | 1041 | 2961 | 455 | 1368 | 1377 | 1.1e-140 |

Protein name: nitric oxide reductase | Locus Name: gp:AF002217 | Acc#: AF002217

Description

Ralstonia eutropha megaplasmid pHG1 nitric oxide reductase (norB) gene, complete cds.

| ORF Name | NTID | AAID | NT Length | AA Length | Score | Probability |
|---|---|---|---|---|---|---|
| 21676712_c1_120 | 1042 | 2962 | 130 | 393 | 395 | 1.2e-36 |

Protein name: sulfate adenylyltransferase subunit CysN | Locus Name: gp:AF130466 | Acc#: AF130466

Description

Campylobacter jejuni peptide chain release factor 2 (prfB) gene, partial cds; alpha-2,3-sialyltransferase (cst-I) and sulfateadenylyltransferase subunit CysD (cysD) genes, complete cds; andsulfate adenylyltransferase subunit CysN (cysN) gene, partial cds.

| ORF Name | NTID | AAID | NT Length | AA Length | Score | Probability |
|---|---|---|---|---|---|---|
| 22078812_c2_154 | 1043 | 2963 | 727 | 2184 | 1636 | 3.8e-168 |

Protein name | Locus Name: sp:RECG_ECOLI | Acc#

Description

ATP-DEPENDENT DNA HELICASE RECG,

| ORF_Name | NTID | AAID | NT Length | AA Length | Score | Probability |
|---|---|---|---|---|---|---|
| 22350926_c1_115 | 1044 | 2964 | 724 | 2175 | 2193 | 3.6e-227 |

Protein name | Locus Name | Acc#
| | sp:FAOB_PSEFR | P28793 |

Description

| ORF_Name | NTID | AAID | NT Length | AA Length | Score | Probability |
|---|---|---|---|---|---|---|
| 23556252_c3_203 | 1045 | 2965 | 600 | 1803 | 709 | 6.0e-85 |

Protein name: glutamate synthase (ferredoxin) homolog yerD | Locus Name: pir:C69794 | Acc#: C69794

Description

| ORF_Name | NTID | AAID | NT Length | AA Length | Score | Probability |
|---|---|---|---|---|---|---|
| 23593830_c3_199 | 1046 | 2966 | 340 | 1023 | 462 | 9.7e-44 |

Protein name | Locus Name: sp:YWBM_BACSU | Acc#: P39596

Description: HYPOTHETICAL 42.8 KD PROTEIN IN EPR-GALK INTERGENIC REGION

| ORF_Name | NTID | AAID | NT Length | AA Length | Score | Probability |
|---|---|---|---|---|---|---|
| 23651900_f2_48 | 1047 | 2967 | 328 | 987 | 634 | 5.8e-62 |

Protein name | Locus Name: sp:YOHI_HAEIN | Acc#: P44606

Description: HYPOTHETICAL PROTEIN HI0270

| ORF_Name | NTID | AAID | NT Length | AA Length | Score | Probability |
|---|---|---|---|---|---|---|
| 23862576_c1_124 | 1048 | 2968 | 153 | 462 | 182 | 4.5e-14 |

Protein name: probable antibiotic resistance protein mtrC | Locus Name: pir:S42418 | Acc#

Description

| ORF Name | NTID | AAID | NT Length | AA Length | Score | Probability |
|---|---|---|---|---|---|---|
| 24042500_c3_183 | 1049 | 2969 | 313 | 942 | 608 | 3.3e-59 |

| Protein name | | | | Locus Name | | Acc# |
|---|---|---|---|---|---|---|
| | | | | sp:CYSN_MYCTU | | Q10600 |

Description

SULFURYLASE)

| ORF Name | NTID | AAID | NT Length | AA Length | Score | Probability |
|---|---|---|---|---|---|---|
| 24302260_c3_179 | 1050 | 2970 | 410 | 1233 | 1331 | 8.0e-136 |

| Protein name | | | | Locus Name | | Acc# |
|---|---|---|---|---|---|---|
| 3-oxoacyl-CoA thiolase | | | | gp:AF150672 | | AF150672 |

Description

Pseudomonas putida 3-oxoacyl-CoA thiolase (fadA) gene, completecds.

| ORF Name | NTID | AAID | NT Length | AA Length | Score | Probability |
|---|---|---|---|---|---|---|
| 25584438_c3_189 | 1051 | 2971 | 143 | 432 | 174 | 7.6e-12 |

| Protein name | | | | Locus Name | | Acc# |
|---|---|---|---|---|---|---|
| CeoB | | | | gp:BCU97042 | | U97042 |

Description

Burkholderia cepacia CeoA (ceoA) and CeoB (ceoB) genes, completecds.

| ORF Name | NTID | AAID | NT Length | AA Length | Score | Probability |
|---|---|---|---|---|---|---|
| 25984558_c3_188 | 1052 | 2972 | 134 | 405 | 133 | 1.8e-07 |

| Protein name | | | | Locus Name | | Acc# |
|---|---|---|---|---|---|---|
| acriflavin resistance protein D (acrD) RP170 | | | | pir:F71727 | | F71727 |

Description

| ORF Name | NTID | AAID | NT Length | AA Length | Score | Probability |
|---|---|---|---|---|---|---|
| 26741556_c1_135 | 1053 | 2973 | 198 | 597 | 101 | 0.0011 |

| Protein name | | | | Locus Name | | Acc# |
|---|---|---|---|---|---|---|
| | | | | sp:HA34_BRELC | | Q99074 |

Description

HAM34 PROTEIN

| ORF Name | NTID | AAID | NT Length | AA Length | Score | Probability |
|---|---|---|---|---|---|---|
| 3245640_c3_190 | 1054 | 2974 | 425 | 1278 | 265 | 9.4e-20 |

Protein name: probable cation efflux system protein
Locus Name: pir:E71874
Acc#: E71874

Description:

| ORF Name | NTID | AAID | NT Length | AA Length | Score | Probability |
|---|---|---|---|---|---|---|
| 3375052_c1_125 | 1055 | 2975 | 144 | 435 | 177 | 3.6e-12 |

Protein name: probable efflux transporter
Locus Name: pir:H71918
Acc#: H71918

Description:

| ORF Name | NTID | AAID | NT Length | AA Length | Score | Probability |
|---|---|---|---|---|---|---|
| 34027092_c2_175 | 1056 | 2976 | 74 | 222 | 60 | 0.025 |

Protein name: tonoplast intrinsic protein
Locus Name: gp:AF037061
Acc#: AF037061

Description: Zea mays tonoplast intrinsic protein (ZmTIP1) mRNA, complete cds.

| ORF Name | NTID | AAID | NT Length | AA Length | Score | Probability |
|---|---|---|---|---|---|---|
| 35197126_f3_79 | 1057 | 2977 | 179 | 540 | 155 | 3.3e-11 |

Protein name: TatB protein
Locus Name: gp:ECO5830
Acc#: AJ005830

Description: Escherichia coli tatABCD operon.

| ORF Name | NTID | AAID | NT Length | AA Length | Score | Probability |
|---|---|---|---|---|---|---|
| 35339135_f2_61 | 1058 | 2978 | 264 | 795 | 308 | 2.9e-35 |

Protein name:
Locus Name: sp:LEP3_AERHY
Acc#: P45794

Description: TYPE 4 PREPILIN-LIKE PROTEIN SPECIFIC LEADER PEPTIDASE,

| ORF_Name | NTID | AAID | NT Length | AA Length | Score | Probability |
|---|---|---|---|---|---|---|
| 35395926_f1_6 | 1059 | 2979 | 511 | 1536 | 325 | 2.2e-35 |

| Protein name | | | | Locus_Name | | Acc# |
|---|---|---|---|---|---|---|
| probable helicase | | | | pir:T40239 | | T40239 |

Description

| ORF_Name | NTID | AAID | NT Length | AA Length | Score | Probability |
|---|---|---|---|---|---|---|
| 36047308_f2_50 | 1060 | 2980 | 105 | 318 | | |

| Protein name | | | | Locus_Name | | Acc# |
|---|---|---|---|---|---|---|

Description

NO-HIT

| ORF_Name | NTID | AAID | NT Length | AA Length | Score | Probability |
|---|---|---|---|---|---|---|
| 3939838_c2_173 | 1061 | 2981 | 66 | 201 | 189 | 8.2e-15 |

| Protein name | | | | Locus_Name | | Acc# |
|---|---|---|---|---|---|---|
| | | | | sp:RL35_PSESY | | P52830 |

Description

50S RIBOSOMAL PROTEIN L35

| ORF_Name | NTID | AAID | NT Length | AA Length | Score | Probability |
|---|---|---|---|---|---|---|
| 3947675_f2_46 | 1062 | 2982 | 250 | 753 | 375 | 1.6e-34 |

| Protein name | | | | Locus_Name | | Acc# |
|---|---|---|---|---|---|---|
| | | | | sp:HUTC_KLEAE | | P12380 |

Description

HISTIDINE UTILIZATION REPRESSOR

| ORF_Name | NTID | AAID | NT Length | AA Length | Score | Probability |
|---|---|---|---|---|---|---|
| 3954218_c3_177 | 1063 | 2983 | 441 | 1326 | 1252 | 7.6e-140 |

| Protein name | | | | Locus_Name | | Acc# |
|---|---|---|---|---|---|---|
| | | | | sp:CLPX_HAEIN | | P44838 |

Description

ATP-DEPENDENT CLP PROTEASE ATP-BINDING SUBUNIT CLPX

| ORF Name | NTID | AAID | NT Length | AA Length | Score | Probability |
|---|---|---|---|---|---|---|
| 4328428_c1_119 | 1064 | 2984 | 310 | 933 | 911 | 2.6e-91 |

Protein name: 
Locus Name: sp:CYSD_MYCTU
Acc#: Q10599

Description: SULFURYLASE)

| ORF Name | NTID | AAID | NT Length | AA Length | Score | Probability |
|---|---|---|---|---|---|---|
| 4485963_c3_206 | 1065 | 2985 | 121 | 366 | 469 | 1.8e-44 |

Protein name: ribosomal protein L20
Locus Name: pir:R5EC20
Acc#:

Description:

| ORF Name | NTID | AAID | NT Length | AA Length | Score | Probability |
|---|---|---|---|---|---|---|
| 5120443_f3_94 | 1066 | 2986 | 214 | 645 | 363 | 3.0e-33 |

Protein name: 
Locus Name: sp:YACE_VIBVU
Acc#: Q56741

Description: HYPOTHETICAL 22.5 KD PROTEIN IN VVPD 3'REGION (ORFX)

| ORF Name | NTID | AAID | NT Length | AA Length | Score | Probability |
|---|---|---|---|---|---|---|
| 5890643_f2_73 | 1067 | 2987 | 380 | 1143 | 131 | 7.7e-07 |

Protein name: dnaJ protein homolog
Locus Name: pir:S34632
Acc#: S34632

Description:

| ORF Name | NTID | AAID | NT Length | AA Length | Score | Probability |
|---|---|---|---|---|---|---|
| 7277_f3_93 | 1068 | 2988 | 423 | 1272 | 664 | 3.8e-65 |

Protein name: pilus assembly protein PilC
Locus Name: gp:AF038655
Acc#: AF038655

Description: Legionella pneumophila pilus assembly protein PilB (pilB), pilusassembly protein PilC (pilC), and type IV prepilin-like proteinspecific leader peptidase PilD (pilD) genes, complete cds.

| ORF_Name | NTID | AAID | NT Length | AA Length | Score | Probability |
|---|---|---|---|---|---|---|
| 978517_c2_166 | 1069 | 2989 | 433 | 1302 | 615 | 5.8e-112 |

Protein name | Locus Name | Acc#
sp:GLTS_HAEIN | P45240

Description
SODIUM/GLUTAMATE SYMPORT CARRIER PROTEIN (GLUTAMATE PERMEASE)

| ORF_Name | NTID | AAID | NT Length | AA Length | Score | Probability |
|---|---|---|---|---|---|---|
| 10547711_c2_8 | 1070 | 2990 | 275 | 828 | 933 | 1.2e-93 |

Protein name | Locus Name | Acc#
sp:ABC_HAEIN | P44785

Description
ATP-BINDING PROTEIN ABC

| ORF_Name | NTID | AAID | NT Length | AA Length | Score | Probability |
|---|---|---|---|---|---|---|
| 188807_c2_10 | 1071 | 2991 | 118 | 354 | 320 | 1.1e-28 |

Protein name | Locus Name | Acc#
sp:PLPA_PASHA |

Description
OUTER MEMBRANE LIPOPROTEIN 1 PRECURSOR (PLP1)

| ORF_Name | NTID | AAID | NT Length | AA Length | Score | Probability |
|---|---|---|---|---|---|---|
| 19589635_c1_7 | 1072 | 2992 | 99 | 300 | 190 | 6.5e-15 |

Protein name | Locus Name | Acc#
ORF120 | gp:ECORRNHK12 | D15061

Description
E.coli genomic DNA, 5'flanking region of rrnH gene.

| ORF_Name | NTID | AAID | NT Length | AA Length | Score | Probability |
|---|---|---|---|---|---|---|
| 24353193_f1_1 | 1073 | 2993 | 95 | 288 | 113 | 9.3e-07 |

Protein name | Locus Name | Acc#
hypothetical protein PH0133 | pir:C71234 | C71234

Description

| ORF_Name | NTID | AAID | NT Length | AA Length | Score | Probability |
|---|---|---|---|---|---|---|
| 35582056_c3_11 | 1074 | 2994 | 240 | 723 | 631 | 1.2e-61 |

| Protein name | Locus Name | Acc# |
|---|---|---|
| | sp:YAEE_HAEIN | P46492 |

Description

HYPOTHETICAL ABC TRANSPORTER PERMEASE PROTEIN HI0620.1

| ORF_Name | NTID | AAID | NT Length | AA Length | Score | Probability |
|---|---|---|---|---|---|---|
| 4144442_f2_6 | 1075 | 2995 | 131 | 396 | | |

| Protein name | Locus Name | Acc# |
|---|---|---|

Description

NO-HIT

| ORF_Name | NTID | AAID | NT Length | AA Length | Score | Probability |
|---|---|---|---|---|---|---|
| 16924127_f1_1 | 1076 | 2996 | 367 | 1104 | 137 | 7.2e-06 |

| Protein name | Locus Name | Acc# |
|---|---|---|
| | gp:PSENOSA | M60717 |

Description

P.stutzeri NosA protein (nosA) gene, complete cds.

| ORF_Name | NTID | AAID | NT Length | AA Length | Score | Probability |
|---|---|---|---|---|---|---|
| 5109792_f2_3 | 1077 | 2997 | 122 | 369 | | |

| Protein name | Locus Name | Acc# |
|---|---|---|

Description

NO-HIT

| ORF_Name | NTID | AAID | NT Length | AA Length | Score | Probability |
|---|---|---|---|---|---|---|
| 16681688_c1_3 | 1078 | 2998 | 60 | 183 | 55 | 0.044 |

| Protein name | Locus Name | Acc# |
|---|---|---|
| | sp:RNH_HELPY | P56120 |

Description

RIBONUCLEASE H, (RNASE H)

| ORF Name | NTID | AAID | NT Length | AA Length | Score | Probability |
|---|---|---|---|---|---|---|
| 24039143_f1_1 | 1079 | 2999 | 345 | 1038 | 637 | 2.8e-62 |

Protein name: ornithine decarboxylase
Locus Name: pir:D72200
Acc#: D72200

Description

| ORF Name | NTID | AAID | NT Length | AA Length | Score | Probability |
|---|---|---|---|---|---|---|
| 29337840_f2_2 | 1080 | 3000 | 150 | 450 | 95 | 0.014 |

Protein name: AvtA
Locus Name: gp:AF014804
Acc#: AF014804

Description: Neisseria meningitidis PglB (pglB), PglC (pglC), PglD (pglD), and AvtA (avtA) genes, complete cds.

| ORF Name | NTID | AAID | NT Length | AA Length | Score | Probability |
|---|---|---|---|---|---|---|
| 11900461_f2_7 | 1081 | 3001 | 69 | 210 | | |

Protein name
Locus Name
Acc#

Description: NO-HIT

| ORF Name | NTID | AAID | NT Length | AA Length | Score | Probability |
|---|---|---|---|---|---|---|
| 14573562_f1_2 | 1082 | 3002 | 341 | 1026 | 1075 | 1.1e-108 |

Protein name
Locus Name: sp:TRMU_ECOLI
Acc#

Description: (EC 2.1.1.61)

| ORF Name | NTID | AAID | NT Length | AA Length | Score | Probability |
|---|---|---|---|---|---|---|
| 30270465_f1_3 | 1083 | 3003 | 249 | 750 | 185 | 5.7e-14 |

Protein name
Locus Name: sp:YYAD_BACSU
Acc#: P37520

Description: HYPOTHETICAL 37.7 KD PROTEIN IN RPSF-SPO0J INTERGENIC REGION

| ORF Name | NTID | AAID | NT Length | AA Length | Score | Probability |
|---|---|---|---|---|---|---|
| 6365936_f2_6 | 1084 | 3004 | 108 | 327 | 170 | 8.5e-13 |
| Protein name | | | | Locus Name | | Acc# |
| | | | | gp:ECPURB | | X59307 |

Description

E.coli ORF-15, ORF-23, purB and phoP (5'end) genes.

| ORF Name | NTID | AAID | NT Length | AA Length | Score | Probability |
|---|---|---|---|---|---|---|
| 6537957_c1_11 | 1085 | 3005 | 200 | 603 | 454 | 6.8e-43 |
| Protein name | | | | Locus Name | | Acc# |
| | | | | sp:YGBB_ECOLI | | P36663 |

Description

HYPOTHETICAL 16.9 KD PROTEIN IN SURE-CYSC INTERGENIC REGION (ORF0)

| ORF Name | NTID | AAID | NT Length | AA Length | Score | Probability |
|---|---|---|---|---|---|---|
| 173187_f3_5 | 1086 | 3006 | 66 | 201 | | |
| Protein name | | | | Locus Name | | Acc# |

Description

NO-HIT

| ORF Name | NTID | AAID | NT Length | AA Length | Score | Probability |
|---|---|---|---|---|---|---|
| 34407827_f2_2 | 1087 | 3007 | 366 | 1101 | 786 | 4.5e-78 |
| Protein name | | | | Locus Name | | Acc# |
| | | | | sp:LCFA_ECOLI | | P29212 |

Description

SYNTHETASE)

| ORF Name | NTID | AAID | NT Length | AA Length | Score | Probability |
|---|---|---|---|---|---|---|
| 7285152_f1_1 | 1088 | 3008 | 69 | 207 | | |
| Protein name | | | | Locus Name | | Acc# |

Description

NO-HIT

| ORF Name | NTID | AAID | NT Length | AA Length | Score | Probability |
|---|---|---|---|---|---|---|
| 16056563_c2_63 | 1089 | 3009 | 141 | 426 | 90 | 0.020 |

| Protein name | Locus Name | Acc# |
|---|---|---|
| hypothetical wtfw protein | pir:T41252 | T41252 |

Description

---

| ORF Name | NTID | AAID | NT Length | AA Length | Score | Probability |
|---|---|---|---|---|---|---|
| 1986087_f3_30 | 1090 | 3010 | 412 | 1239 | 1316 | 3.1e-134 |

| Protein name | Locus Name | Acc# |
|---|---|---|
| | sp:SERA_HAEIN | P43885 |

Description

D-3-PHOSPHOGLYCERATE DEHYDROGENASE, (PGDH)

---

| ORF Name | NTID | AAID | NT Length | AA Length | Score | Probability |
|---|---|---|---|---|---|---|
| 2072762_f1_10 | 1091 | 3011 | 1220 | 3663 | 524 | 4.4e-93 |

| Protein name | Locus Name | Acc# |
|---|---|---|
| chromosome segregation SMC protein:minichromosome stabilizing protein SMC | pir:G69708 | |

Description

---

| ORF Name | NTID | AAID | NT Length | AA Length | Score | Probability |
|---|---|---|---|---|---|---|
| 21531252_f3_36 | 1092 | 3012 | 303 | 912 | 722 | 2.7e-71 |

| Protein name | Locus Name | Acc# |
|---|---|---|
| translation elongation factor EF-Ts | pir:EFECS | |

Description

---

| ORF Name | NTID | AAID | NT Length | AA Length | Score | Probability |
|---|---|---|---|---|---|---|
| 23406_f1_11 | 1093 | 3013 | 278 | 837 | 898 | 6.1e-90 |

| Protein name | Locus Name | Acc# |
|---|---|---|
| | sp:RS2_SPIPL | P34831 |

Description

30S RIBOSOMAL PROTEIN S2

| ORF Name | NTID | AAID | NT Length | AA Length | Score | Probability |
|---|---|---|---|---|---|---|
| 23437562_f1_7 | 1094 | 3014 | 253 | 762 | 186 | 3.2e-18 |

| Protein name | | Locus Name | Acc# |
|---|---|---|---|
| hypothetical protein HP0862 | | pir:F64627 | F64627 |

Description

---

| ORF Name | NTID | AAID | NT Length | AA Length | Score | Probability |
|---|---|---|---|---|---|---|
| 23613510_c2_70 | 1095 | 3015 | 374 | 1125 | 700 | 5.8e-69 |

| Protein name | | Locus Name | Acc# |
|---|---|---|---|
| | | sp:YCFO_ECOLI | P75949 |

Description

HYPOTHETICAL 37.6 KD PROTEIN IN FHUE-NDH INTERGENIC REGION

---

| ORF Name | NTID | AAID | NT Length | AA Length | Score | Probability |
|---|---|---|---|---|---|---|
| 23861686_f3_35 | 1096 | 3016 | 180 | 543 | 526 | 1.6e-50 |

| Protein name | | Locus Name | Acc# |
|---|---|---|---|
| invasion protein homolog | | gp:AF116285 | AF116285 |

Description

Pseudomonas aeruginosa invasion protein homolog andphosphoenolpyruvate-protein phosphotransferase PtsP (ptsP) genes,complete cds.

---

| ORF Name | NTID | AAID | NT Length | AA Length | Score | Probability |
|---|---|---|---|---|---|---|
| 2460181_f1_1 | 1097 | 3017 | 987 | 2964 | 3662 | 0.0 |

| Protein name | | Locus Name | Acc# |
|---|---|---|---|
| | | sp:RPOB_PSEPU | P19175 |

Description

BETA CHAIN) (RNA POLYMERASE BETA SUBUNIT)

| ORF Name | NTID | AAID | NT Length | AA Length | Score | Probability |
|---|---|---|---|---|---|---|
| 25401687_c3_88 | 1098 | 3018 | 141 | 426 | 372 | 3.3e-34 |

Protein name | Locus Name | Acc#
gp:PAU89892 | U89892

Description

Pseudomonas aeruginosa virulence factor regulator (vfr) gene, partial cds.

| ORF Name | NTID | AAID | NT Length | AA Length | Score | Probability |
|---|---|---|---|---|---|---|
| 26064760_c3_93 | 1099 | 3019 | 66 | 201 | | |

Protein name | Locus Name | Acc#

Description

NO-HIT

| ORF Name | NTID | AAID | NT Length | AA Length | Score | Probability |
|---|---|---|---|---|---|---|
| 29890701_f3_31 | 1100 | 3020 | 469 | 1410 | 1678 | 1.3e-172 |

Protein name | Locus Name | Acc#
sp:GSHR_HAEIN | P43783

Description

GLUTATHIONE REDUCTASE, (GR) (GRASE)

| ORF Name | NTID | AAID | NT Length | AA Length | Score | Probability |
|---|---|---|---|---|---|---|
| 32287567_f2_16 | 1101 | 3021 | 1422 | 4269 | 4932 | 0.0 |

Protein name: 99% identity over 1407 amino acids with E. coli | Locus Name: gp:STYSTMF1 | Acc#: AF170176

Description

Salmonella typhimurium fragment STMF1.

| ORF Name | NTID | AAID | NT Length | AA Length | Score | Probability |
|---|---|---|---|---|---|---|
| 3907166_f1_6 | 1102 | 3022 | 309 | 930 | 117 | 1.6e-06 |

Protein name: putative biotin protein ligase
Locus Name: gp:AF016461
Acc#: AF016461

Description: Bordetella pertussis putative biotin protein ligase (birA) gene, complete cds and Bvg accessory factor (baf) gene, partial cds.

| ORF Name | NTID | AAID | NT Length | AA Length | Score | Probability |
|---|---|---|---|---|---|---|
| 4507138_f1_5 | 1103 | 3023 | 727 | 2184 | 736 | 2.5e-88 |

Protein name:
Locus Name: sp:PRC_ECOLI
Acc#: P23865

Description: PROTEIN)

| ORF Name | NTID | AAID | NT Length | AA Length | Score | Probability |
|---|---|---|---|---|---|---|
| 4959501_c1_46 | 1104 | 3024 | 83 | 252 | | |

Protein name:
Locus Name:
Acc#:

Description: NO-HIT

| ORF Name | NTID | AAID | NT Length | AA Length | Score | Probability |
|---|---|---|---|---|---|---|
| 5119452_c3_92 | 1105 | 3025 | 267 | 804 | 398 | 5.9e-37 |

Protein name:
Locus Name: sp:Y902_HAEIN
Acc#: P44070

Description: HYPOTHETICAL PROTEIN HI0902

| ORF Name | NTID | AAID | NT Length | AA Length | Score | Probability |
|---|---|---|---|---|---|---|
| 11955251_c2_26 | 1106 | 3026 | 915 | 2748 | 2735 | 1.3e-284 |

Protein name:
Locus Name: sp:SYA_ECOLI
Acc#:

Description: ALANYL-TRNA SYNTHETASE, (ALANINE--TRNA LIGASE) (ALARS)

| ORF Name | NTID | AAID | NT Length | AA Length | Score | Probability |
|---|---|---|---|---|---|---|
| 16523292_c2_25 | 1107 | 3027 | 488 | 1467 | 1534 | 2.4e-157 |

Protein name | Locus Name | Acc#
sp:PUR8_HAEIN | P44797

Description
ADENYLOSUCCINATE LYASE, (ADENYLOSUCCINASE) (ASL)

| ORF Name | NTID | AAID | NT Length | AA Length | Score | Probability |
|---|---|---|---|---|---|---|
| 23475417_f3_18 | 1108 | 3028 | 73 | 222 | | |

Protein name | Locus Name | Acc#

Description
NO-HIT

| ORF Name | NTID | AAID | NT Length | AA Length | Score | Probability |
|---|---|---|---|---|---|---|
| 24308500_c1_22 | 1109 | 3029 | 155 | 468 | 282 | 1.2e-24 |

Protein name | Locus Name | Acc#
erythroid differentiation-related factor 2 | gp:AF040248 | AF040248

Description
Homo sapiens erythroid differentiation-related factor 2 mRNA, partial cds.

| ORF Name | NTID | AAID | NT Length | AA Length | Score | Probability |
|---|---|---|---|---|---|---|
| 31444625_c3_34 | 1110 | 3030 | 452 | 1359 | 646 | 3.1e-63 |

Protein name | Locus Name | Acc#
 | sp:YCLF_BACSU | P94408

Description
HYPOTHETICAL 53.3 KD PROTEIN IN SFP-GERKA INTERGENIC REGION

| ORF Name | NTID | AAID | NT Length | AA Length | Score | Probability |
|---|---|---|---|---|---|---|
| 33632752_c2_27 | 1111 | 3031 | 285 | 855 | 679 | 9.8e-67 |

Protein name | Locus Name | Acc#
aspartate kinase, II precursor:lysine-sensitive aspartokinase II | pir:A48946 |

Description

| ORF Name | NTID | AAID | NT Length | AA Length | Score | Probability |
|---|---|---|---|---|---|---|
| 33829043_c3_33 | 1112 | 3032 | 106 | 321 | | |

Protein name — Locus Name — Acc#

Description

NO-HIT

| ORF Name | NTID | AAID | NT Length | AA Length | Score | Probability |
|---|---|---|---|---|---|---|
| 4400283_c1_23 | 1113 | 3033 | 95 | 288 | | |

Protein name — Locus Name — Acc#

Description

NO-HIT

| ORF Name | NTID | AAID | NT Length | AA Length | Score | Probability |
|---|---|---|---|---|---|---|
| 6852262_c1_21 | 1114 | 3034 | 61 | 186 | | |

Protein name — Locus Name — Acc#

Description

NO-HIT

| ORF Name | NTID | AAID | NT Length | AA Length | Score | Probability |
|---|---|---|---|---|---|---|
| 9933552_f1_3 | 1115 | 3035 | 82 | 249 | | |

Protein name — Locus Name — Acc#

Description

NO-HIT

| ORF Name | NTID | AAID | NT Length | AA Length | Score | Probability |
|---|---|---|---|---|---|---|
| 9975052_c2_24 | 1116 | 3036 | 132 | 399 | | |

Protein name — Locus Name — Acc#

Description

NO-HIT

| ORF Name | NTID | AAID | NT Length | AA Length | Score | Probability |
|---|---|---|---|---|---|---|
| 1036637_c3_276 | 1117 | 3037 | 61 | 186 | | |

Protein name | Locus Name | Acc#

Description

NO-HIT

| ORF Name | NTID | AAID | NT Length | AA Length | Score | Probability |
|---|---|---|---|---|---|---|
| 1038885_f1_26 | 1118 | 3038 | 416 | 1251 | 1526 | 1.7e-156 |

Protein name: lactate dehydrogenase
Locus Name: gp:NMU58911
Acc#: U58911

Description

Neisseria meningitidis lactate dehydrogenase (lldA), HI0379 homologgenes, complete cds, HI1054 homolog gene, partial cds.

| ORF Name | NTID | AAID | NT Length | AA Length | Score | Probability |
|---|---|---|---|---|---|---|
| 10547558_c1_180 | 1119 | 3039 | 176 | 531 | 123 | 8.1e-08 |

Protein name: hypothetical protein APE1165
Locus Name: pir:H72586
Acc#: H72586

Description

| ORF Name | NTID | AAID | NT Length | AA Length | Score | Probability |
|---|---|---|---|---|---|---|
| 11711_c3_265 | 1120 | 3040 | 434 | 1305 | 489 | 1.3e-46 |

Protein name: HisX
Locus Name: gp:AF010189
Acc#: AF010189

Description

Pseudomonas stutzeri HflC (hflC) gene, partial cds; HisX (hisX)gene, complete cds; and PurA (purA) gene, partial cds.

| ORF Name | NTID | AAID | NT Length | AA Length | Score | Probability |
|---|---|---|---|---|---|---|
| 11991552_f3_108 | 1121 | 3041 | 286 | 861 | 614 | 7.6e-60 |

Protein name:
Locus Name: sp:TRPC_PSEPU
Acc#: P20578

Description

INDOLE-3-GLYCEROL PHOSPHATE SYNTHASE, (IGPS)

| ORF_Name | NTID | AAID | NT Length | AA Length | Score | Probability |
|---|---|---|---|---|---|---|
| 12222077_f2_53 | 1122 | 3042 | 198 | 597 | 469 | 1.8e-44 |

| Protein name | | | | Locus Name | Acc# |
|---|---|---|---|---|---|
| | | | | sp:RECR_HAEIN | P44712 |

Description

RECOMBINATION PROTEIN RECR

| ORF_Name | NTID | AAID | NT Length | AA Length | Score | Probability |
|---|---|---|---|---|---|---|
| 136302_c1_167 | 1123 | 3043 | 154 | 465 | 95 | 0.0012 |

| Protein name | | | | Locus Name | Acc# |
|---|---|---|---|---|---|
| hypothetical protein sll1675 | | | | pir:S74649 | S74649 |

Description

| ORF_Name | NTID | AAID | NT Length | AA Length | Score | Probability |
|---|---|---|---|---|---|---|
| 13678763_c1_182 | 1124 | 3044 | 223 | 672 | 194 | 2.4e-15 |

| Protein name | | | | Locus Name | Acc# |
|---|---|---|---|---|---|
| hypothetical protein RP471 | | | | pir:D71706 | D71706 |

Description

| ORF_Name | NTID | AAID | NT Length | AA Length | Score | Probability |
|---|---|---|---|---|---|---|
| 14094452_c3_267 | 1125 | 3045 | 60 | 183 | | |

| Protein name | | | | Locus Name | Acc# |
|---|---|---|---|---|---|

Description

NO-HIT

| ORF_Name | NTID | AAID | NT Length | AA Length | Score | Probability |
|---|---|---|---|---|---|---|
| 14103402_f1_7 | 1126 | 3046 | 286 | 861 | 265 | 7.3e-23 |

| Protein name | | | | Locus Name | Acc# |
|---|---|---|---|---|---|
| | | | | sp:YPUG_BACSU | P35154 |

Description

HYPOTHETICAL 29.6 KD PROTEIN IN RIBT-DACB INTERGENIC REGION (ORFX7)

| ORF Name | NTID | AAID | NT Length | AA Length | Score | Probability |
|---|---|---|---|---|---|---|
| 14273586_f2_57 | 1127 | 3047 | 451 | 1356 | 1508 | 1.4e-154 |

| Protein name | Locus Name | Acc# |
|---|---|---|
| | sp:ACCC_PSEAE | P37798 |

Description

CARBOXYLASE,) (ACC)

| ORF Name | NTID | AAID | NT Length | AA Length | Score | Probability |
|---|---|---|---|---|---|---|
| 14572132_f3_135 | 1128 | 3048 | 238 | 717 | 736 | 8.9e-73 |

| Protein name | Locus Name | Acc# |
|---|---|---|
| | sp:END3_HAEIN | P44319 |

Description

LYASE)

| ORF Name | NTID | AAID | NT Length | AA Length | Score | Probability |
|---|---|---|---|---|---|---|
| 14875305_f3_113 | 1129 | 3049 | 139 | 420 | 141 | 1.2e-09 |

| Protein name | Locus Name | Acc# |
|---|---|---|
| Ribonuclease D (EC 3.1.13.-) | gp:D90825 | |

Description

E.coli genomic DNA, Kohara clone #334(40.6-41.0 min.).

| ORF Name | NTID | AAID | NT Length | AA Length | Score | Probability |
|---|---|---|---|---|---|---|
| 16507827_c3_256 | 1130 | 3050 | 519 | 1560 | 1030 | 6.3e-104 |

| Protein name | Locus Name | Acc# |
|---|---|---|
| | sp:NADB_PSEAE | |

Description

L-ASPARTATE OXIDASE, (QUINOLINATE SYNTHETASE B)

| ORF Name | NTID | AAID | NT Length | AA Length | Score | Probability |
|---|---|---|---|---|---|---|
| 16510254_c1_154 | 1131 | 3051 | 308 | 927 | 1063 | 2.0e-107 |

| Protein name | | | | Locus Name | | Acc# |
|---|---|---|---|---|---|---|
| | | | | sp:RF1_ECOLI | | |

Description

PEPTIDE CHAIN RELEASE FACTOR 1 (RF-1)

| ORF Name | NTID | AAID | NT Length | AA Length | Score | Probability |
|---|---|---|---|---|---|---|
| 16829177_c1_172 | 1132 | 3052 | 95 | 288 | 83 | 0.041 |

| Protein name | | | | Locus Name | | Acc# |
|---|---|---|---|---|---|---|
| F1N21.17 | | | | gp:AC002130 | | AC002130 |

Description

The sequence of BAC F1N21 from Arabidopsis thaliana chromosome 1, complete sequence.

| ORF Name | NTID | AAID | NT Length | AA Length | Score | Probability |
|---|---|---|---|---|---|---|
| 19562800_f2_52 | 1133 | 3053 | 120 | 363 | 273 | 1.0e-23 |

| Protein name | | | | Locus Name | | Acc# |
|---|---|---|---|---|---|---|
| | | | | sp:YBAB_HAEIN | | P44711 |

Description

HYPOTHETICAL PROTEIN HI0442

| ORF Name | NTID | AAID | NT Length | AA Length | Score | Probability |
|---|---|---|---|---|---|---|
| 20312551_f1_8 | 1134 | 3054 | 202 | 609 | 243 | 1.6e-20 |

| Protein name | | | | Locus Name | | Acc# |
|---|---|---|---|---|---|---|
| | | | | sp:YPUH_BACSU | | P35155 |

Description

HYPOTHETICAL 22.0 KD PROTEIN IN RIBT-DACB INTERGENIC REGION (ORFX8)

| ORF_Name | NTID | AAID | NT Length | AA Length | Score | Probability |
|---|---|---|---|---|---|---|
| 20573252_c2_229 | 1135 | 3055 | 205 | 618 | 309 | 1.6e-27 |

| Protein name | | | | Locus Name | Acc# |
|---|---|---|---|---|---|
| | | | | sp:YDJA_ECOLI | P24250 |

Description

HYPOTHETICAL 20.1 KD PROTEIN IN SELD-SPPA INTERGENIC REGION (ORF183)

| ORF_Name | NTID | AAID | NT Length | AA Length | Score | Probability |
|---|---|---|---|---|---|---|
| 21667027_f2_89 | 1136 | 3056 | 832 | 2499 | 2093 | 1.4e-216 |

| Protein name | | | | Locus Name | Acc# |
|---|---|---|---|---|---|
| | | | | sp:LON_ERWAM | P46067 |

Description

ATP-DEPENDENT PROTEASE LA,

| ORF_Name | NTID | AAID | NT Length | AA Length | Score | Probability |
|---|---|---|---|---|---|---|
| 21681503_f1_9 | 1137 | 3057 | 329 | 990 | 758 | 4.2e-75 |

| Protein name | | | | Locus Name | Acc# |
|---|---|---|---|---|---|
| | | | | sp:YCIL_HAEIN | P45104 |

Description

HYPOTHETICAL PROTEIN HI1199

| ORF_Name | NTID | AAID | NT Length | AA Length | Score | Probability |
|---|---|---|---|---|---|---|
| 21754681_f3_119 | 1138 | 3058 | 197 | 594 | 284 | 7.1e-25 |

| Protein name | | | | Locus Name | Acc# |
|---|---|---|---|---|---|
| | | | | sp:YBEY_ECOLI | P77385 |

Description

HYPOTHETICAL 17.5 KD PROTEIN IN CUTE-ASNB INTERGENIC REGION

| ORF_Name | NTID | AAID | NT Length | AA Length | Score | Probability |
|---|---|---|---|---|---|---|
| 22128380_f1_41 | 1139 | 3059 | 87 | 264 | | |

| Protein name | | | | Locus Name | Acc# |
|---|---|---|---|---|---|
| | | | | | |

Description

NO-HIT

| ORF Name | NTID | AAID | NT Length | AA Length | Score | Probability |
|---|---|---|---|---|---|---|
| 22384635_f1_31 | 1140 | 3060 | 190 | 573 | 604 | 8.7e-59 |

Protein name: HemO
Locus Name: gp:AF133695
Acc#: AF133695

Description: Neisseria meningitidis HemO (hemO) gene, complete cds; and HmbR(hmbR) gene, partial cds.

| ORF Name | NTID | AAID | NT Length | AA Length | Score | Probability |
|---|---|---|---|---|---|---|
| 23444377_c1_199 | 1141 | 3061 | 492 | 1479 | 2364 | 2.7e-245 |

Protein name: outer membrane protein E
Locus Name: gp:MBOOMPE
Acc#: L31788

Description: Moraxella catarrhalis outer membrane protein E gene, complete cds.

| ORF Name | NTID | AAID | NT Length | AA Length | Score | Probability |
|---|---|---|---|---|---|---|
| 234700_c3_268 | 1142 | 3062 | 344 | 1035 | 1002 | 5.8e-101 |

Protein name: unknown
Locus Name: gp:AF109131
Acc#: AF109131

Description: Sinorhizobium meliloti homogentisate dioxygenase (hmgA) andmaleylacetoacetate isomerase (maiA) genes, complete cds; andunknown gene.

| ORF Name | NTID | AAID | NT Length | AA Length | Score | Probability |
|---|---|---|---|---|---|---|
| 23620263_c3_271 | 1143 | 3063 | 267 | 804 | 534 | 2.3e-51 |

Protein name:
Locus Name: sp:KDSB_ECOLI
Acc#: P04951

Description: SYNTHETASE) (CMP-2-KETO-3-DEOXYOCTULOSONIC ACID SYNTHETASE) (CKS)

| ORF Name | NTID | AAID | NT Length | AA Length | Score | Probability |
|---|---|---|---|---|---|---|
| 23651513_f1_43 | 1144 | 3064 | 259 | 780 | 589 | 3.4e-57 |
| Protein name | | | | Locus Name | | Acc# |
| | | | | sp:NADC_RHORU | | P77938 |

Description (QAPRTASE)

| ORF Name | NTID | AAID | NT Length | AA Length | Score | Probability |
|---|---|---|---|---|---|---|
| 24031586_f1_5 | 1145 | 3065 | 383 | 1152 | 976 | 3.3e-98 |
| Protein name | | | | Locus Name | | Acc# |
| | | | | sp:TRPD_ACICA | | P00500 |

Description

ANTHRANILATE PHOSPHORIBOSYLTRANSFERASE,

| ORF Name | NTID | AAID | NT Length | AA Length | Score | Probability |
|---|---|---|---|---|---|---|
| 24397555_f3_140 | 1146 | 3066 | 219 | 660 | 165 | 1.2e-11 |
| Protein name | | | | Locus Name | | Acc# |
| probable corA protein | | | | pir:F70952 | | F70952 |

Description

| ORF Name | NTID | AAID | NT Length | AA Length | Score | Probability |
|---|---|---|---|---|---|---|
| 24415782_f3_106 | 1147 | 3067 | 61 | 186 | 87 | 0.0079 |
| Protein name | | | | Locus Name | | Acc# |
| UUP protein | | | | gp:ECUUP | | Y09439 |

Description

E.coli uup gene, partial.

| ORF Name | NTID | AAID | NT Length | AA Length | Score | Probability |
|---|---|---|---|---|---|---|
| 24721962_c3_282 | 1148 | 3068 | 77 | 234 | | |
| Protein name | | | | Locus Name | | Acc# |

Description

NO-HIT

| ORF Name | NTID | AAID | NT Length | AA Length | Score | Probability |
|---|---|---|---|---|---|---|
| 24801937_c2_236 | 1149 | 3069 | 63 | 192 | | |

| Protein name | | | | | Locus Name | Acc# |
|---|---|---|---|---|---|---|
| | | | | | | |

Description

NO-HIT

| ORF Name | NTID | AAID | NT Length | AA Length | Score | Probability |
|---|---|---|---|---|---|---|
| 26756325_f1_1 | 1150 | 3070 | 314 | 945 | 1021 | 5.6e-103 |

| Protein name | | | | | Locus Name | Acc# |
|---|---|---|---|---|---|---|
| | | | | | sp:OTCA_PSESH | Q02047 |

Description (EC 2.1.3.3) (OTCASE)

| ORF Name | NTID | AAID | NT Length | AA Length | Score | Probability |
|---|---|---|---|---|---|---|
| 26757790_c3_255 | 1151 | 3071 | 376 | 1131 | 1065 | 1.2e-107 |

| Protein name | | | | | Locus Name | Acc# |
|---|---|---|---|---|---|---|
| | | | | | sp:NADA_ECOLI | |

Description

QUINOLINATE SYNTHETASE A

| ORF Name | NTID | AAID | NT Length | AA Length | Score | Probability |
|---|---|---|---|---|---|---|
| 2742036_f1_3 | 1152 | 3072 | 144 | 435 | 426 | 6.3e-40 |

| Protein name | | | | | Locus Name | Acc# |
|---|---|---|---|---|---|---|
| | | | | | sp:PAND_BACSU | P52999 |

Description (DECARBOXYLASE)

| ORF Name | NTID | AAID | NT Length | AA Length | Score | Probability |
|---|---|---|---|---|---|---|
| 29301691_f1_14 | 1153 | 3073 | 248 | 747 | 140 | 4.7e-07 |

| Protein name | | | | | Locus Name | Acc# |
|---|---|---|---|---|---|---|
| | | | | | sp:RND_HAEIN | P44442 |

Description

RIBONUCLEASE D, (RNASE D)

| ORF Name | NTID | AAID | NT Length | AA Length | Score | Probability |
|---|---|---|---|---|---|---|
| 29355287_f2_99 | 1154 | 3074 | 74 | 225 | 79 | 0.013 |

| Protein name | | | | Locus Name | | Acc# |
|---|---|---|---|---|---|---|
| MutT/nudix family protein | | | | pir:A75550 | | A75550 |

Description

---

| ORF Name | NTID | AAID | NT Length | AA Length | Score | Probability |
|---|---|---|---|---|---|---|
| 29484626_c1_173 | 1155 | 3075 | 356 | 1071 | 555 | 2.4e-57 |

| Protein name | | | | Locus Name | | Acc# |
|---|---|---|---|---|---|---|
| | | | | sp:YGI2_PSEPU | | P31857 |

Description

HYPOTHETICAL 32.4 KD PROTEIN IN GIDB-UNCI INTERGENIC REGION

---

| ORF Name | NTID | AAID | NT Length | AA Length | Score | Probability |
|---|---|---|---|---|---|---|
| 29531392_f1_40 | 1156 | 3076 | 124 | 375 | 173 | 1.5e-11 |

| Protein name | | | | Locus Name | | Acc# |
|---|---|---|---|---|---|---|
| Iustrin A | | | | pir:T08852 | | T08852 |

Description

---

| ORF Name | NTID | AAID | NT Length | AA Length | Score | Probability |
|---|---|---|---|---|---|---|
| 29572155_f2_49 | 1157 | 3077 | 343 | 1032 | 406 | 8.3e-38 |

| Protein name | | | | Locus Name | | Acc# |
|---|---|---|---|---|---|---|
| | | | | sp:HTRB_HAEIN | | |

Description

PROTEIN B)

---

| ORF Name | NTID | AAID | NT Length | AA Length | Score | Probability |
|---|---|---|---|---|---|---|
| 29890631_f2_56 | 1158 | 3078 | 157 | 474 | 259 | 3.1e-22 |

| Protein name | | | | Locus Name | | Acc# |
|---|---|---|---|---|---|---|
| | | | | sp:BCCP_HAEIN | | P43874 |

Description

BIOTIN CARBOXYL CARRIER PROTEIN OF ACETYL-COA CARBOXYLASE (BCCP)

| ORF Name | NTID | AAID | NT Length | AA Length | Score | Probability |
|---|---|---|---|---|---|---|
| 30204837_c2_230 | 1159 | 3079 | 447 | 1344 | 628 | 2.5e-61 |

| Protein name | Locus Name | Acc# |
|---|---|---|
| | sp:GPDA_ECOLI | P37606 |

Description

| ORF Name | NTID | AAID | NT Length | AA Length | Score | Probability |
|---|---|---|---|---|---|---|
| 30330056_f2_48 | 1160 | 3080 | 233 | 702 | 506 | 2.1e-48 |

| Protein name | Locus Name | Acc# |
|---|---|---|
| putative ATP-binding protein | gp:NME242841 | AJ242841 |

Description

Neisseria meningitidis DNA for opcA region, strain Z2491.

| ORF Name | NTID | AAID | NT Length | AA Length | Score | Probability |
|---|---|---|---|---|---|---|
| 32878_c2_250 | 1161 | 3081 | 80 | 243 | 89 | 0.00033 |

| Protein name | Locus Name | Acc# |
|---|---|---|
| | sp:SLYX_ECOLI | P30857 |

Description

SLYX PROTEIN

| ORF Name | NTID | AAID | NT Length | AA Length | Score | Probability |
|---|---|---|---|---|---|---|
| 34180317_f1_22 | 1162 | 3082 | 115 | 348 | 420 | 2.7e-39 |

| Protein name | Locus Name | Acc# |
|---|---|---|
| | sp:YCHF_HAEIN | P44681 |

Description

PROBABLE GTP-BINDING PROTEIN HI0393

| ORF Name | NTID | AAID | NT Length | AA Length | Score | Probability |
|---|---|---|---|---|---|---|
| 34417090_f3_151 | 1163 | 3083 | 76 | 231 | | |

| Protein name | Locus Name | Acc# |
|---|---|---|
| | | |

Description

NO-HIT

| ORF Name | NTID | AAID | NT Length | AA Length | Score | Probability |
|---|---|---|---|---|---|---|
| 35196902_f3_129 | 1164 | 3084 | 616 | 1851 | 631 | 1.2e-61 |

| Protein name | | | | Locus Name | | Acc# |
|---|---|---|---|---|---|---|
| L-lactate permease (lctP) homolog | | | | pir:F69350 | | F69350 |

Description

| ORF Name | NTID | AAID | NT Length | AA Length | Score | Probability |
|---|---|---|---|---|---|---|
| 35335137_c1_175 | 1165 | 3085 | 330 | 993 | 302 | 8.7e-27 |

| Protein name | | | | Locus Name | | Acc# |
|---|---|---|---|---|---|---|
|  | | | | sp:HOLB_PSEAE | | P52024 |

Description

DNA POLYMERASE III, DELTA' SUBUNIT,

| ORF Name | NTID | AAID | NT Length | AA Length | Score | Probability |
|---|---|---|---|---|---|---|
| 35353443_c2_215 | 1166 | 3086 | 347 | 1044 | 1128 | 2.6e-114 |

| Protein name | | | | Locus Name | | Acc# |
|---|---|---|---|---|---|---|
|  | | | | sp:PURA_VIBPA | | P40607 |

Description

ADENYLOSUCCINATE SYNTHETASE, (IMP--ASPARTATE LIGASE)

| ORF Name | NTID | AAID | NT Length | AA Length | Score | Probability |
|---|---|---|---|---|---|---|
| 35603128_f3_150 | 1167 | 3087 | 80 | 243 | | |

| Protein name | | | | Locus Name | | Acc# |
|---|---|---|---|---|---|---|

Description

NO-HIT

| ORF Name | NTID | AAID | NT Length | AA Length | Score | Probability |
|---|---|---|---|---|---|---|
| 3914143_c2_209 | 1168 | 3088 | 185 | 558 | 256 | 2.1e-29 |

| Protein name | | | | Locus Name | | Acc# |
|---|---|---|---|---|---|---|
| ExbB protein | | | | gp:BPE132741 | | AJ132741 |

Description

Bordetella pertussis hupB, tonB, exbB, exbD and basR genes and ORF1(partial).

| ORF Name | NTID | AAID | NT Length | AA Length | Score | Probability |
|---|---|---|---|---|---|---|
| 3914811_c3_280 | 1169 | 3089 | 370 | 1113 | 873 | 2.7e-87 |

| Protein name | Locus Name | Acc# |
|---|---|---|
| | sp:YHCM_ECOLI | P46442 |

Description

HYPOTHETICAL 43.1 KD PROTEIN IN RPLM-HHOA INTERGENIC REGION (F375)

| ORF Name | NTID | AAID | NT Length | AA Length | Score | Probability |
|---|---|---|---|---|---|---|
| 3937518_c1_171 | 1170 | 3090 | 264 | 795 | 618 | 2.9e-60 |

| Protein name | Locus Name | Acc# |
|---|---|---|
| | sp:YGI1_PSEPU | P31856 |

Description

HYPOTHETICAL 28.9 KD PROTEIN IN GIDB-UNCI INTERGENIC REGION

| ORF Name | NTID | AAID | NT Length | AA Length | Score | Probability |
|---|---|---|---|---|---|---|
| 3938818_c1_166 | 1171 | 3091 | 65 | 198 | 228 | 6.1e-19 |

| Protein name | Locus Name | Acc# |
|---|---|---|
| PurA | gp:AF010189 | AF010189 |

Description

Pseudomonas stutzeri HflC (hflC) gene, partial cds; HisX (hisX) gene, complete cds; and PurA (purA) gene, partial cds.

| ORF Name | NTID | AAID | NT Length | AA Length | Score | Probability |
|---|---|---|---|---|---|---|
| 3946931_f3_114 | 1172 | 3092 | 216 | 651 | 560 | 4.0e-54 |

| Protein name | Locus Name | Acc# |
|---|---|---|
| | gp:ECU89166 | U89166 |

Description

Eikenella corrodens lysine decarboxylase (ECORLD) gene, complete cds.

| ORF Name | NTID | AAID | NT Length | AA Length | Score | Probability |
|---|---|---|---|---|---|---|
| 3960260_f1_23 | 1173 | 3093 | 253 | 762 | 282 | 1.2e-24 |

| Protein name | Locus Name | Acc# |
|---|---|---|
| probable transcription regulator | pir:T34763 | T34763 |

Description

| ORF Name | NTID | AAID | NT Length | AA Length | Score | Probability |
|---|---|---|---|---|---|---|
| 4022217_f2_68 | 1174 | 3094 | 160 | 483 | 86 | 0.00087 |

Protein name: hypothetical protein F53A9.8
Locus Name: pir:T16439
Acc#: T16439

Description:

| ORF Name | NTID | AAID | NT Length | AA Length | Score | Probability |
|---|---|---|---|---|---|---|
| 4023443_c3_278 | 1175 | 3095 | 146 | 441 | 498 | 1.5e-47 |

Protein name:
Locus Name: sp:NDK_PSEAE
Acc#: Q59636

Description: NUCLEOSIDE DIPHOSPHATE KINASE, (NDK) (NDP KINASE)

| ORF Name | NTID | AAID | NT Length | AA Length | Score | Probability |
|---|---|---|---|---|---|---|
| 4101387_f1_4 | 1176 | 3096 | 219 | 660 | 710 | 5.1e-70 |

Protein name:
Locus Name: sp:TRPG_PSEAE
Acc#: P20576

Description: TRANSFERASE

| ORF Name | NTID | AAID | NT Length | AA Length | Score | Probability |
|---|---|---|---|---|---|---|
| 4145000_f2_47 | 1177 | 3097 | 415 | 1248 | 962 | 1.0e-96 |

Protein name:
Locus Name: sp:UUP1_HAEIN
Acc#:

Description: ABC TRANSPORTER ATP-BINDING PROTEIN UUP-1

| ORF Name | NTID | AAID | NT Length | AA Length | Score | Probability |
|---|---|---|---|---|---|---|
| 4181502_f3_149 | 1178 | 3098 | 130 | 393 | | |

Protein name:
Locus Name:
Acc#:

Description: NO-HIT

| ORF Name | NTID | AAID | NT Length | AA Length | Score | Probability |
|---|---|---|---|---|---|---|
| 4182762_f2_51 | 1179 | 3099 | 358 | 1077 | 374 | 1.9e-49 |

| Protein name | Locus Name | Acc# |
|---|---|---|
| tryptophan--tRNA ligase, | pir:H70385 | H70385 |

Description

---

| ORF Name | NTID | AAID | NT Length | AA Length | Score | Probability |
|---|---|---|---|---|---|---|
| 424203_f1_24 | 1180 | 3100 | 350 | 1053 | 542 | 3.2e-52 |

| Protein name | Locus Name | Acc# |
|---|---|---|
| putative exodeoxyribonuclease (EC 3.1.11.2). | gp:SCE87 | AL132674 |

Description

Streptomyces coelicolor cosmid E87.

---

| ORF Name | NTID | AAID | NT Length | AA Length | Score | Probability |
|---|---|---|---|---|---|---|
| 4331262_f3_141 | 1181 | 3101 | 222 | 669 | 402 | 2.2e-37 |

| Protein name | Locus Name | Acc# |
|---|---|---|
| probable corA protein | pir:F70952 | F70952 |

Description

---

| ORF Name | NTID | AAID | NT Length | AA Length | Score | Probability |
|---|---|---|---|---|---|---|
| 4506930_c1_174 | 1182 | 3102 | 356 | 1071 | 504 | 3.4e-48 |

| Protein name | Locus Name | Acc# |
|---|---|---|
|  | sp:LPXK_HAEIN | P44491 |

Description

TETRAACYLDISACCHARIDE 4'-KINASE, (LIPID A 4'-KINASE)

---

| ORF Name | NTID | AAID | NT Length | AA Length | Score | Probability |
|---|---|---|---|---|---|---|
| 4537837_f3_145 | 1183 | 3103 | 216 | 651 | 477 | 2.5e-45 |

| Protein name | Locus Name | Acc# |
|---|---|---|
| YciB homolog | gp:AF114793 | AF114793 |

Description

Vitreoscilla sp. YciB homolog, putative transcriptional activator, putative outer membrane protein, BioA homolog, and glutaminesynthetase homolog genes, complete cds; and unknown genes.

| ORF Name | NTID | AAID | NT Length | AA Length | Score | Probability |
|---|---|---|---|---|---|---|
| 4571880_f1_16 | 1184 | 3104 | 216 | 651 | 437 | 4.3e-41 |

| Protein name | Locus Name | Acc# |
|---|---|---|
| YbeZ protein | gp:STY249116 | AJ249116 |

Description

Salmonella typhimurium yleB (partial), miaB, ybeZ and ybeY(partial) genes.

| ORF Name | NTID | AAID | NT Length | AA Length | Score | Probability |
|---|---|---|---|---|---|---|
| 4722125_c2_211 | 1185 | 3105 | 465 | 1398 | 1197 | 1.3e-121 |

| Protein name | Locus Name | Acc# |
|---|---|---|
| | sp:Y325_HAEIN | P44640 |

Description

HYPOTHETICAL PROTEIN HI0325

| ORF Name | NTID | AAID | NT Length | AA Length | Score | Probability |
|---|---|---|---|---|---|---|
| 4798763_c1_155 | 1186 | 3106 | 141 | 426 | 274 | 8.1e-24 |

| Protein name | Locus Name | Acc# |
|---|---|---|
| ExbD protein | gp:BPE132741 | AJ132741 |

Description

Bordetella pertussis hupB, tonB, exbB, exbD and basR genes and ORF1(partial).

| ORF Name | NTID | AAID | NT Length | AA Length | Score | Probability |
|---|---|---|---|---|---|---|
| 4876005_f1_30 | 1187 | 3107 | 828 | 2487 | 1231 | 3.1e-125 |

| Protein name | Locus Name | Acc# |
|---|---|---|
| hypothetical protein TM1869 | pir:F72202 | F72202 |

Description

| ORF Name | NTID | AAID | NT Length | AA Length | Score | Probability |
|---|---|---|---|---|---|---|
| 4978375_c3_293 | 1188 | 3108 | 382 | 1149 | 261 | 7.7e-26 |

| Protein name | Locus Name | Acc# |
|---|---|---|
| beta-ketoacyl-acyl carrier protein synthase III | pir:B64545 | B64545 |

Description

| ORF_Name | NTID | AAID | NT Length | AA Length | Score | Probability |
|---|---|---|---|---|---|---|
| 5194068_f1_35 | 1189 | 3109 | 620 | 1863 | 1268 | 3.8e-129 |

| Protein name | | | | Locus Name | | Acc# |
|---|---|---|---|---|---|---|
| | | | | sp:KEFX_HAEIN | | P44933 |

Description (ANTIPORTER)

| ORF_Name | NTID | AAID | NT Length | AA Length | Score | Probability |
|---|---|---|---|---|---|---|
| 5976555_f3_111 | 1190 | 3110 | 769 | 2310 | 3096 | 0.0 |

| Protein name | | | | Locus Name | | Acc# |
|---|---|---|---|---|---|---|
| | | | | sp:RIR1_ECOLI | | |

Description (RIBONUCLEOTIDE REDUCTASE 1) (B1 PROTEIN) (R1 PROTEIN)

| ORF_Name | NTID | AAID | NT Length | AA Length | Score | Probability |
|---|---|---|---|---|---|---|
| 636513_f3_126 | 1191 | 3111 | 81 | 246 | | |

| Protein name | | | | Locus Name | | Acc# |
|---|---|---|---|---|---|---|

Description

NO-HIT

| ORF_Name | NTID | AAID | NT Length | AA Length | Score | Probability |
|---|---|---|---|---|---|---|
| 6516_f2_45 | 1192 | 3112 | 361 | 1086 | 176 | 7.2e-13 |

| Protein name | | | | Locus Name | | Acc# |
|---|---|---|---|---|---|---|
| hypothetical protein | | | | pir:S76259 | | S76259 |

Description

| ORF_Name | NTID | AAID | NT Length | AA Length | Score | Probability |
|---|---|---|---|---|---|---|
| 6828128_c2_223 | 1193 | 3113 | 201 | 606 | 105 | 0.00066 |

| Protein name | | | | Locus Name | | Acc# |
|---|---|---|---|---|---|---|
| phosphoglycerate mutase | | | | pir:G72260 | | G72260 |

Description

| ORF Name | NTID | AAID | NT Length | AA Length | Score | Probability |
|---|---|---|---|---|---|---|
| 6837827_c1_183 | 1194 | 3114 | 165 | 498 | 145 | 3.8e-10 |

| Protein name | Locus Name | Acc# |
|---|---|---|
| | sp:Y400_SYNY3 | Q55129 |

Description

HYPOTHETICAL 18.3 KD PROTEIN SLL0400

| ORF Name | NTID | AAID | NT Length | AA Length | Score | Probability |
|---|---|---|---|---|---|---|
| 786578_c3_259 | 1195 | 3115 | 86 | 261 | 99 | 2.8e-05 |

| Protein name | Locus Name | Acc# |
|---|---|---|
| unknown | gp:AF114793 | AF114793 |

Description

Vitreoscilla sp. YciB homolog, putative transcriptional activator, putative outer membrane protein, BioA homolog, and glutaminesynthetase homolog genes, complete cds; and unknown genes.

| ORF Name | NTID | AAID | NT Length | AA Length | Score | Probability |
|---|---|---|---|---|---|---|
| 969200_c3_270 | 1196 | 3116 | 234 | 705 | 360 | 6.2e-33 |

| Protein name | Locus Name | Acc# |
|---|---|---|
| | sp:GIDB_ECOLI | P17113 |

Description

GLUCOSE INHIBITED DIVISION PROTEIN B

| ORF Name | NTID | AAID | NT Length | AA Length | Score | Probability |
|---|---|---|---|---|---|---|
| 970375_f2_67 | 1197 | 3117 | 279 | 840 | 921 | 2.2e-92 |

| Protein name | Locus Name | Acc# |
|---|---|---|
| probable GTP-binding protein HI0393 | pir:I64150 | I64150 |

Description

| ORF Name | NTID | AAID | NT Length | AA Length | Score | Probability |
|---|---|---|---|---|---|---|
| 976531_f2_59 | 1198 | 3118 | 171 | 516 | 437 | 4.3e-41 |

| Protein name | Locus Name | Acc# |
|---|---|---|
| YbeZ protein | gp:STY249116 | AJ249116 |

Description

Salmonella typhimurium yleB (partial), miaB, ybeZ and ybeY(partial) genes.

| ORF Name | NTID | AAID | NT Length | AA Length | Score | Probability |
|---|---|---|---|---|---|---|
| 985925_f3_124 | 1199 | 3119 | 128 | 387 | | |

| Protein name | Locus Name | Acc# |
|---|---|---|
| | | |

Description

NO-HIT

| ORF Name | NTID | AAID | NT Length | AA Length | Score | Probability |
|---|---|---|---|---|---|---|
| 9954828_c2_208 | 1200 | 3120 | 322 | 969 | 170 | 3.9e-14 |

| Protein name | Locus Name | Acc# |
|---|---|---|
| TonB2 | gp:AF190125 | AF190125 |

Description

Pseudomonas aeruginosa TonB2 (tonB2), ExbB (exbB), and ExbD (exbD)genes, complete cds.

| ORF Name | NTID | AAID | NT Length | AA Length | Score | Probability |
|---|---|---|---|---|---|---|
| 10975667_c2_74 | 1201 | 3121 | 376 | 1131 | 524 | 2.6e-50 |

| Protein name | Locus Name | Acc# |
|---|---|---|
| thiamine-monophosphate kinase | gp:D17333 | D17333 |

Description

E. Coli thiL gene, complete cds.

| ORF Name | NTID | AAID | NT Length | AA Length | Score | Probability |
|---|---|---|---|---|---|---|
| 12500081_c3_90 | 1202 | 3122 | 270 | 813 | 855 | 2.2e-85 |

| Protein name | Locus Name | Acc# |
|---|---|---|
| | sp:HIS6_AZOBR | P26721 |

Description

HISF PROTEIN (CYCLASE)

| ORF Name | NTID | AAID | NT Length | AA Length | Score | Probability |
|---|---|---|---|---|---|---|
| 14572127_c1_50 | 1203 | 3123 | 165 | 498 | 433 | 1.1e-40 |

| Protein name | | | | | Locus Name | Acc# |
|---|---|---|---|---|---|---|
| | | | | | sp:RISB_ECOLI | |

Description (LUMAZINE SYNTHASE) (RIBOFLAVIN SYNTHASE BETA CHAIN)

| ORF Name | NTID | AAID | NT Length | AA Length | Score | Probability |
|---|---|---|---|---|---|---|
| 197212_c1_54 | 1204 | 3124 | 284 | 852 | | |

| Protein name | | | | | Locus Name | Acc# |
|---|---|---|---|---|---|---|

Description

NO-HIT

| ORF Name | NTID | AAID | NT Length | AA Length | Score | Probability |
|---|---|---|---|---|---|---|
| 21767011_f3_32 | 1205 | 3125 | 317 | 954 | 736 | 8.9e-73 |

| Protein name | | | | | Locus Name | Acc# |
|---|---|---|---|---|---|---|
| YafJ | | | | | gp:NGAJ2783 | AJ002783 |

Description

Neisseria gonorrhoeae aroK, aroB, yafJ genes and open readingframe.

| ORF Name | NTID | AAID | NT Length | AA Length | Score | Probability |
|---|---|---|---|---|---|---|
| 23645263_c3_93 | 1206 | 3126 | 201 | 606 | 190 | 2.4e-30 |

| Protein name | | | | | Locus Name | Acc# |
|---|---|---|---|---|---|---|
| | | | | | sp:PGPA_HAEIN | P44157 |

Description

PHOSPHATIDYLGLYCEROPHOSPHATASE A,

| ORF Name | NTID | AAID | NT Length | AA Length | Score | Probability |
|---|---|---|---|---|---|---|
| 23916007_c3_94 | 1207 | 3127 | 196 | 591 | 273 | 1.0e-23 |

| Protein name | | | | | Locus Name | Acc# |
|---|---|---|---|---|---|---|
| methylase | | | | | gp:LLCPJW565 | Y12736 |

Description

Lactococcus lactis cremoris plasmid pJW565 DNA, abiIM, abiIR genesand orfX.

| ORF Name | NTID | AAID | NT Length | AA Length | Score | Probability |
|---|---|---|---|---|---|---|
| 23947167_f3_37 | 1208 | 3128 | 653 | 1962 | 756 | 6.0e-87 |

| Protein name | Locus Name | Acc# |
|---|---|---|
| penicillin-binding protein 3 | pir:S54872 | S54872 |

Description

| ORF Name | NTID | AAID | NT Length | AA Length | Score | Probability |
|---|---|---|---|---|---|---|
| 24256687_f2_23 | 1209 | 3129 | 501 | 1506 | 537 | 1.8e-79 |

| Protein name | Locus Name | Acc# |
|---|---|---|
|  | sp:MURF_ECOLI |  |

Description (D-ALANYL-D-ALANINE-ADDING ENZYME)

| ORF Name | NTID | AAID | NT Length | AA Length | Score | Probability |
|---|---|---|---|---|---|---|
| 24353377_c1_45 | 1210 | 3130 | 225 | 678 | 155 | 3.3e-11 |

| Protein name | Locus Name | Acc# |
|---|---|---|
| hypothetical protein PAB0131 | pir:D75209 | D75209 |

Description

| ORF Name | NTID | AAID | NT Length | AA Length | Score | Probability |
|---|---|---|---|---|---|---|
| 26369016_f2_18 | 1211 | 3131 | 299 | 900 |  |  |

| Protein name | Locus Name | Acc# |
|---|---|---|

Description

NO-HIT

| ORF Name | NTID | AAID | NT Length | AA Length | Score | Probability |
|---|---|---|---|---|---|---|
| 3397336_c1_49 | 1212 | 3132 | 65 | 198 | 50 | 0.037 |

| Protein name | Locus Name | Acc# |
|---|---|---|
|  | sp:DHSD_PORPU | P80479 |

Description

DEHYDROGENASE, SUBUNIT IV)

| ORF Name | NTID | AAID | NT Length | AA Length | Score | Probability |
|---|---|---|---|---|---|---|
| 35968792_f2_24 | 1213 | 3133 | 201 | 606 | 346 | 1.9e-31 |

| Protein name | | | | Locus Name | | Acc# |
|---|---|---|---|---|---|---|
| | | | | sp:TPIS_MORSP | | Q01893 |

Description

TRIOSEPHOSPHATE ISOMERASE, (TIM)

| ORF Name | NTID | AAID | NT Length | AA Length | Score | Probability |
|---|---|---|---|---|---|---|
| 3907500_f1_5 | 1214 | 3134 | 341 | 1026 | 227 | 9.2e-18 |

| Protein name | | | | Locus Name | | Acc# |
|---|---|---|---|---|---|---|
| homoserine kinase homolog | | | | pir:T33726 | | T33726 |

Description

| ORF Name | NTID | AAID | NT Length | AA Length | Score | Probability |
|---|---|---|---|---|---|---|
| 3939665_c1_51 | 1215 | 3135 | 183 | 552 | 204 | 2.1e-16 |

| Protein name | | | | Locus Name | | Acc# |
|---|---|---|---|---|---|---|
| | | | | sp:NUSB_HAEIN | | P45150 |

Description

N UTILIZATION SUBSTANCE PROTEIN B HOMOLOG (NUSB PROTEIN)

| ORF Name | NTID | AAID | NT Length | AA Length | Score | Probability |
|---|---|---|---|---|---|---|
| 3953191_c1_44 | 1216 | 3136 | 502 | 1509 | 1501 | 7.7e-154 |

| Protein name | | | | Locus Name | | Acc# |
|---|---|---|---|---|---|---|
| glutamyl-tRNA synthetase | | | | gp:AF139107 | | AF139107 |

Description

Pseudomonas aeruginosa hypothetical multidrug resistance protein(mdr) gene, partial cds; hypothetical transcriptional activator(act) and glutamyl-tRNA synthetase (gltX) genes, complete cds; andtRNA-Ala and tRNA-Glu genes, complete sequence.

| ORF_Name | NTID | AAID | NT Length | AA Length | Score | Probability |
|---|---|---|---|---|---|---|
| 41703_f3_36 | 1217 | 3137 | 120 | 363 | | |

| Protein name | | | | | Locus Name | Acc# |
|---|---|---|---|---|---|---|
| | | | | | | |

Description

NO-HIT

| ORF_Name | NTID | AAID | NT Length | AA Length | Score | Probability |
|---|---|---|---|---|---|---|
| 4301943_f1_13 | 1218 | 3138 | 368 | 1107 | 1018 | 1.2e-102 |

| Protein name | | | | | Locus Name | Acc# |
|---|---|---|---|---|---|---|
| | | | | | sp:MRAY_HAEIN | P45062 |

Description (UDP-MURNAC-PENTAPEPTIDE PHOSPHOTRANSFERASE)

| ORF_Name | NTID | AAID | NT Length | AA Length | Score | Probability |
|---|---|---|---|---|---|---|
| 5111318_f2_22 | 1219 | 3139 | 523 | 1572 | 756 | 6.8e-75 |

| Protein name | | | | | Locus Name | Acc# |
|---|---|---|---|---|---|---|
| probable | | | | | gp:AF141867 | AF141867 |

Description

Vibrio cholerae probableUDP-N-acetylmuramoylalanyl-D-glutamate--2,6-diaminopimelate ligase(murE) gene, complete cds.

| ORF_Name | NTID | AAID | NT Length | AA Length | Score | Probability |
|---|---|---|---|---|---|---|
| 6754052_f3_35 | 1220 | 3140 | 336 | 1011 | 695 | 2.0e-68 |

| Protein name | | | | | Locus Name | Acc# |
|---|---|---|---|---|---|---|
| | | | | | sp:YABC_ECOLI | P18595 |

Description

HYPOTHETICAL 34.9 KD PROTEIN IN FRUR-FTSL INTERGENIC REGION (ORFB)

| ORF_Name | NTID | AAID | NT Length | AA Length | Score | Probability |
|---|---|---|---|---|---|---|
| 111552_f1_10 | 1221 | 3141 | 73 | 222 | | |

| Protein name | | | | | Locus Name | Acc# |
|---|---|---|---|---|---|---|
| | | | | | | |

Description

NO-HIT

| ORF Name | NTID | AAID | NT Length | AA Length | Score | Probability |
|---|---|---|---|---|---|---|
| 1189035_c3_48 | 1222 | 3142 | 179 | 540 | 616 | 4.7e-60 |

| Protein name | Locus Name | Acc# |
|---|---|---|
| adenylate kinase | gp:AB024426 | AB024426 |

Description

Pseudomonas putida adk gene for adenylate kinase, complete cds.

| ORF Name | NTID | AAID | NT Length | AA Length | Score | Probability |
|---|---|---|---|---|---|---|
| 12578208_f2_15 | 1223 | 3143 | 386 | 1161 | 1244 | 1.3e-126 |

| Protein name | Locus Name | Acc# |
|---|---|---|
| | sp:DHAS_PSEAE | Q51344 |

Description (DEHYDROGENASE)

| ORF Name | NTID | AAID | NT Length | AA Length | Score | Probability |
|---|---|---|---|---|---|---|
| 23444507_c3_45 | 1224 | 3144 | 452 | 1359 | | |

| Protein name | Locus Name | Acc# |
|---|---|---|
| | | |

Description

NO-HIT

| ORF Name | NTID | AAID | NT Length | AA Length | Score | Probability |
|---|---|---|---|---|---|---|
| 23536511_f2_16 | 1225 | 3145 | 338 | 1017 | 210 | 4.1e-15 |

| Protein name | Locus Name | Acc# |
|---|---|---|
| | sp:ASG1_ECOLI | P18840 |

Description (L-ASNASE I)

| ORF Name | NTID | AAID | NT Length | AA Length | Score | Probability |
|---|---|---|---|---|---|---|
| 245682_f1_8 | 1226 | 3146 | 303 | 912 | 689 | 8.5e-68 |

| Protein name | Locus Name | Acc# |
|---|---|---|
| | sp:TRUA_ECOLI | P07649 |

Description

I) (PSEUDOURIDINE SYNTHASE I) (URACIL HYDROLYASE) (PSU-I)

| ORF Name | NTID | AAID | NT Length | AA Length | Score | Probability |
|---|---|---|---|---|---|---|
| 34157662_c2_41 | 1227 | 3147 | 203 | 612 | 321 | 8.5e-29 |

| Protein name | | | | Locus Name | Acc# |
|---|---|---|---|---|---|
| | | | | sp:TIPB_PSEFL | P52237 |

Description

BIOGENESIS PROTEIN TIPB)

| ORF Name | NTID | AAID | NT Length | AA Length | Score | Probability |
|---|---|---|---|---|---|---|
| 4042131_c1_33 | 1228 | 3148 | 70 | 213 | | |

| Protein name | | | | Locus Name | Acc# |

Description

NO-HIT

| ORF Name | NTID | AAID | NT Length | AA Length | Score | Probability |
|---|---|---|---|---|---|---|
| 4112793_c1_37 | 1229 | 3149 | 423 | 1272 | 175 | 3.1e-10 |

| Protein name | | | | Locus Name | Acc# |
|---|---|---|---|---|---|
| | | | | sp:CCMH_HAEIN | P46458 |

Description

CYTOCHROME C-TYPE BIOGENESIS PROTEIN CCMH PRECURSOR

| ORF Name | NTID | AAID | NT Length | AA Length | Score | Probability |
|---|---|---|---|---|---|---|
| 4484436_c2_40 | 1230 | 3150 | 692 | 2079 | 1743 | 1.7e-179 |

| Protein name | | | | Locus Name | Acc# |
|---|---|---|---|---|---|
| | | | | sp:CCMF_PSEFL | P52225 |

Description

CYTOCHROME C-TYPE BIOGENESIS PROTEIN CYCK

| ORF Name | NTID | AAID | NT Length | AA Length | Score | Probability |
|---|---|---|---|---|---|---|
| 5265800_f1_9 | 1231 | 3151 | 77 | 234 | 274 | 8.1e-24 |

| Protein name | | | | Locus Name | Acc# |
|---|---|---|---|---|---|
| | | | | sp:IF1_BACSU | P20458 |

Description

TRANSLATION INITIATION FACTOR IF-1

| ORF Name | NTID | AAID | NT Length | AA Length | Score | Probability |
|---|---|---|---|---|---|---|
| 587775_c1_36 | 1232 | 3152 | 172 | 519 | 299 | 1.8e-26 |

Protein name | Locus Name | Acc#
| | sp:CCMH_ECOLI | P33925 |

Description

CYTOCHROME C-TYPE BIOGENESIS PROTEIN CCMH PRECURSOR

| ORF Name | NTID | AAID | NT Length | AA Length | Score | Probability |
|---|---|---|---|---|---|---|
| 5894082_f1_7 | 1233 | 3153 | 206 | 621 | 309 | 1.6e-27 |

Protein name | Locus Name | Acc#
| | sp:YHHF_ECOLI | P10120 |

Description 21.7 KD PROTEIN IN FTSY-NIKA INTERGENIC REGION

| ORF Name | NTID | AAID | NT Length | AA Length | Score | Probability |
|---|---|---|---|---|---|---|
| 1058462_c3_105 | 1234 | 3154 | 283 | 852 | 77 | 0.032 |

Protein name | Locus Name | Acc#
| 15 kDa vesicular-like antigen | gp:PFAVLAP | M94732 |

Description

Plasmodium falciparum 15 kDa vesicular-like antigen gene, exons 1 through 4.

| ORF Name | NTID | AAID | NT Length | AA Length | Score | Probability |
|---|---|---|---|---|---|---|
| 13688802_c2_101 | 1235 | 3155 | 76 | 231 | | |

Protein name | Locus Name | Acc#

Description

NO-HIT

| ORF Name | NTID | AAID | NT Length | AA Length | Score | Probability |
|---|---|---|---|---|---|---|
| 14644586_f2_28 | 1236 | 3156 | 391 | 1176 | 465 | 4.7e-44 |

Protein name | Locus Name | Acc#
| 36 kDa protein | gp:HPU86610 | U86610 |

Description

Helicobacter pylori 36 kDa protein gene, complete cds.

| ORF Name | NTID | AAID | NT Length | AA Length | Score | Probability |
|---|---|---|---|---|---|---|
| 16132787_f3_50 | 1237 | 3157 | 105 | 318 | 197 | 1.2e-15 |

| Protein name | Locus Name | Acc# |
|---|---|---|
| | sp:YDCQ_ECOLI | P76107 |

Description

HYPOTHETICAL 16.1 KD PROTEIN IN TEHB-ANSP INTERGENIC REGION

| ORF Name | NTID | AAID | NT Length | AA Length | Score | Probability |
|---|---|---|---|---|---|---|
| 19532661_f2_33 | 1238 | 3158 | 77 | 234 | | |

| Protein name | Locus Name | Acc# |
|---|---|---|

Description

NO-HIT

| ORF Name | NTID | AAID | NT Length | AA Length | Score | Probability |
|---|---|---|---|---|---|---|
| 20335427_c2_78 | 1239 | 3159 | 657 | 1974 | 239 | 2.0e-17 |

| Protein name | Locus Name | Acc# |
|---|---|---|
| minor tail protein gp26-related protein | pir:F75605 | F75605 |

Description

| ORF Name | NTID | AAID | NT Length | AA Length | Score | Probability |
|---|---|---|---|---|---|---|
| 21642510_c2_77 | 1240 | 3160 | 69 | 210 | | |

| Protein name | Locus Name | Acc# |
|---|---|---|

Description

NO-HIT

| ORF Name | NTID | AAID | NT Length | AA Length | Score | Probability |
|---|---|---|---|---|---|---|
| 21909377_f2_29 | 1241 | 3161 | 401 | 1206 | 261 | 3.0e-21 |

| Protein name | Locus Name | Acc# |
|---|---|---|
| hypothetical protein jhp1380 | pir:G71815 | G71815 |

Description

| ORF Name | NTID | AAID | NT Length | AA Length | Score | Probability |
|---|---|---|---|---|---|---|
| 22266577_f2_21 | 1242 | 3162 | 220 | 663 | 233 | 1.8e-19 |

| Protein name | Locus Name | Acc# |
|---|---|---|
| thiamine-phosphate pyrophosphorylase | gp:AF180145 | AF180145 |

Description

Zymomonas mobilis GTP-binding protein CgpA (cgpA), 60KDinner-membrane protein yidC (yidC), hypothetical protein,glutamine-pyruvate aminotransferase gltB (gltB), glutamate synthasesmall subunit gltS (gltS), undecaprenol kinase udk (udk),hypothetical protein, NADH dehydrogenase, hypothetical protein;zm12orf5, hypothetical protein, aspartate aminotransferase A,beta-hydroxysteroid dehydrogenase, phosphomannomutase pmm

| ORF Name | NTID | AAID | NT Length | AA Length | Score | Probability |
|---|---|---|---|---|---|---|
| 22894061_c3_119 | 1243 | 3163 | 165 | 498 | 222 | 2.6e-18 |

| Protein name | Locus Name | Acc# |
|---|---|---|
|  | sp:TOLR_PSEAE | P50599 |

Description

TOLR PROTEIN

| ORF Name | NTID | AAID | NT Length | AA Length | Score | Probability |
|---|---|---|---|---|---|---|
| 23444426_f3_45 | 1244 | 3164 | 419 | 1260 | 642 | 8.3e-94 |

| Protein name | Locus Name | Acc# |
|---|---|---|
| ATP-dependent helicase HrpA homolog. | gp:D90779 |  |

Description

E.coli genomic DNA, Kohara clone #268(31.6-32.0 min.).

| ORF Name | NTID | AAID | NT Length | AA Length | Score | Probability |
|---|---|---|---|---|---|---|
| 24021016_f3_43 | 1245 | 3165 | 1195 | 3588 | 2225 | 1.6e-266 |

| Protein name | Locus Name | Acc# |
|---|---|---|
|  | sp:MFD_HAEIN | P45128 |

Description

TRANSCRIPTION-REPAIR COUPLING FACTOR (TRCF)

| ORF Name | NTID | AAID | NT Length | AA Length | Score | Probability |
|---|---|---|---|---|---|---|
| 24401887_c1_62 | 1246 | 3166 | 114 | 345 | 165 | 2.9e-12 |

| Protein name | | | | Locus Name | | Acc# |
|---|---|---|---|---|---|---|
| | | | | gp:AB030825 | | AB030825 |

Description

Pseudomonas aeruginosa genomic DNA, partial sequence, strain:PAO1.

| ORF Name | NTID | AAID | NT Length | AA Length | Score | Probability |
|---|---|---|---|---|---|---|
| 25554561_f2_20 | 1247 | 3167 | 151 | 456 | 94 | 0.0015 |

| Protein name | | | | Locus Name | | Acc# |
|---|---|---|---|---|---|---|
| hypothetical protein PH1001 | | | | pir:D71092 | | D71092 |

Description

| ORF Name | NTID | AAID | NT Length | AA Length | Score | Probability |
|---|---|---|---|---|---|---|
| 2994032_c2_82 | 1248 | 3168 | 264 | 795 | 307 | 9.6e-35 |

| Protein name | | | | Locus Name | | Acc# |
|---|---|---|---|---|---|---|
| minor tail protein gp19 | | | | pir:T13105 | | T13105 |

Description

| ORF Name | NTID | AAID | NT Length | AA Length | Score | Probability |
|---|---|---|---|---|---|---|
| 31916632_f1_8 | 1249 | 3169 | 62 | 189 | | |

| Protein name | | | | Locus Name | | Acc# |
|---|---|---|---|---|---|---|

Description

NO-HIT

| ORF Name | NTID | AAID | NT Length | AA Length | Score | Probability |
|---|---|---|---|---|---|---|
| 3320327_c2_76 | 1250 | 3170 | 94 | 285 | | |

| Protein name | | | | Locus Name | | Acc# |
|---|---|---|---|---|---|---|

Description

NO-HIT

| ORF Name | NTID | AAID | NT Length | AA Length | Score | Probability |
|---|---|---|---|---|---|---|
| 34188892_c1_61 | 1251 | 3171 | 673 | 2022 | 227 | 4.5e-15 |

| Protein name | Locus Name | Acc# |
|---|---|---|
| | sp:VG26_BPMD2 | O64220 |

Description

MINOR TAIL PROTEIN GP26

| ORF Name | NTID | AAID | NT Length | AA Length | Score | Probability |
|---|---|---|---|---|---|---|
| 34415711_f1_10 | 1252 | 3172 | 368 | 1107 | 288 | 2.7e-25 |

| Protein name | Locus Name | Acc# |
|---|---|---|
| conserved hypothetical integral membrane protein HP1486 | pir:F64705 | F64705 |

Description

| ORF Name | NTID | AAID | NT Length | AA Length | Score | Probability |
|---|---|---|---|---|---|---|
| 35367058_f3_51 | 1253 | 3173 | 76 | 231 | 151 | 8.8e-11 |

| Protein name | Locus Name | Acc# |
|---|---|---|
| | sp:YDCQ_ECOLI | P76107 |

Description

HYPOTHETICAL 16.1 KD PROTEIN IN TEHB-ANSP INTERGENIC REGION

| ORF Name | NTID | AAID | NT Length | AA Length | Score | Probability |
|---|---|---|---|---|---|---|
| 35942905_f2_19 | 1254 | 3174 | 156 | 471 | 278 | 3.1e-24 |

| Protein name | Locus Name | Acc# |
|---|---|---|
| | sp:YIBK_ECOLI | P33899 |

Description

HYPOTHETICAL TRNA/RRNA METHYLTRANSFERASE YIBK,

| ORF Name | NTID | AAID | NT Length | AA Length | Score | Probability |
|---|---|---|---|---|---|---|
| 36118750_c2_104 | 1255 | 3175 | 77 | 234 | | |

| Protein name | Locus Name | Acc# |
|---|---|---|
| | | |

Description

NO-HIT

| ORF Name | NTID | AAID | NT Length | AA Length | Score | Probability |
|---|---|---|---|---|---|---|
| 36328956_f2_23 | 1256 | 3176 | 108 | 327 | | |

| Protein name | | Locus Name | Acc# |
|---|---|---|---|
| | | | |

Description

NO-HIT

| ORF Name | NTID | AAID | NT Length | AA Length | Score | Probability |
|---|---|---|---|---|---|---|
| 3944450_c2_93 | 1257 | 3177 | 232 | 699 | 422 | 1.7e-39 |

| Protein name | | Locus Name | Acc# |
|---|---|---|---|
| TolQ protein | | gp:PPPAL1 | X74218 |

Description

Pseudomonas putida ruvB, tolQ, tolR, tolA, tolB and oprL genes.

| ORF Name | NTID | AAID | NT Length | AA Length | Score | Probability |
|---|---|---|---|---|---|---|
| 4460387_f1_9 | 1258 | 3178 | 514 | 1545 | 240 | 3.4e-17 |

| Protein name | | Locus Name | Acc# |
|---|---|---|---|
| hypothetical protein jhp1382 | | pir:A71816 | A71816 |

Description

| ORF Name | NTID | AAID | NT Length | AA Length | Score | Probability |
|---|---|---|---|---|---|---|
| 4507703_c2_103 | 1259 | 3179 | 102 | 309 | 157 | 2.0e-11 |

| Protein name | | Locus Name | Acc# |
|---|---|---|---|
| | | sp:YO14_BPHP1 | P51716 |

Description

HYPOTHETICAL 14.9 KD PROTEIN IN REP-HOL INTERGENIC REGION (ORF14)

| ORF Name | NTID | AAID | NT Length | AA Length | Score | Probability |
|---|---|---|---|---|---|---|
| 4728415_c3_120 | 1260 | 3180 | 276 | 831 | 103 | 0.030 |

| Protein name | | Locus Name | Acc# |
|---|---|---|---|
| ras interacting protein RIPA | | gp:AF159241 | AF159241 |

Description

Dictyostelium discoideum ras interacting protein RIPA (ripA) mRNA, complete cds.

| ORF_Name | NTID | AAID | NT Length | AA Length | Score | Probability |
|---|---|---|---|---|---|---|
| 4730050_c1_73 | 1261 | 3181 | 439 | 1320 | 375 | 1.6e-34 |

| Protein name | Locus Name | Acc# |
|---|---|---|
| TolB | gp:HIU32470 | U32470 |

Description

Haemophilus influenzae tolQRAB gene cluster, inner membrane protein(tolQ) gene, partial cds, inner membrane protein (tolR), outermembrane integrity protein (tolA) and colicin tolerance protein(tolB) genes, complete cds.

| ORF_Name | NTID | AAID | NT Length | AA Length | Score | Probability |
|---|---|---|---|---|---|---|
| 5282805_c1_63 | 1262 | 3182 | 227 | 684 | 329 | 1.2e-29 |

| Protein name | Locus Name | Acc# |
|---|---|---|
| minor tail protein L homolog:protein gp18 | pir:T13104 | T13104 |

Description

| ORF_Name | NTID | AAID | NT Length | AA Length | Score | Probability |
|---|---|---|---|---|---|---|
| 5348393_c2_83 | 1263 | 3183 | 79 | 240 | | |

| Protein name | Locus Name | Acc# |
|---|---|---|
| | | |

Description

NO-HIT

| ORF_Name | NTID | AAID | NT Length | AA Length | Score | Probability |
|---|---|---|---|---|---|---|
| 682777_c2_79 | 1264 | 3184 | 139 | 420 | | |

| Protein name | Locus Name | Acc# |
|---|---|---|
| | | |

Description

NO-HIT

| ORF_Name | NTID | AAID | NT Length | AA Length | Score | Probability |
|---|---|---|---|---|---|---|
| 7265950_f1_7 | 1265 | 3185 | 1014 | 3045 | 726 | 3.1e-134 |

| Protein name | Locus Name | Acc# |
|---|---|---|
| | sp:HRPA_ECOLI | |

Description

ATP-DEPENDENT HELICASE HRPA

| ORF Name | NTID | AAID | NT Length | AA Length | Score | Probability |
|---|---|---|---|---|---|---|
| 24113927_f2_1 | 1266 | 3186 | 334 | 1005 | 116 | 0.0012 |

Protein name: STARP antigen
Locus Name: gp:PRSTARPA
Acc#: Z30339

Description: P.reichenowi STARP gene for STARP antigen.

| ORF Name | NTID | AAID | NT Length | AA Length | Score | Probability |
|---|---|---|---|---|---|---|
| 25673906_f1_1 | 1267 | 3187 | 206 | 621 | 435 | 7.0e-41 |

Protein name:
Locus Name: sp:YYCF_BACSU
Acc#: P37478

Description: INTERGENIC REGION

| ORF Name | NTID | AAID | NT Length | AA Length | Score | Probability |
|---|---|---|---|---|---|---|
| 29927207_f3_4 | 1268 | 3188 | 230 | 693 | 88 | 2.4e-05 |

Protein name: probable two component sensor protein
Locus Name: pir:C70624
Acc#: C70624

Description:

| ORF Name | NTID | AAID | NT Length | AA Length | Score | Probability |
|---|---|---|---|---|---|---|
| 35210305_f1_2 | 1269 | 3189 | 300 | 903 | 155 | 2.3e-08 |

Protein name: SmeS
Locus Name: gp:AF173226
Acc#: AF173226

Description: Stenotrophomonas maltophilia multidrug efflux system SmeR (smeR), SmeS (smeS), SmeA (smeA), SmeB (smeB), and SmeC (smeC) genes, complete cds.

| ORF Name | NTID | AAID | NT Length | AA Length | Score | Probability |
|---|---|---|---|---|---|---|
| 12938586_c3_89 | 1270 | 3190 | 152 | 459 | 296 | 3.8e-26 |

Protein name:
Locus Name: sp:PAL_PSEPU
Acc#: P43036

Description: PEPTIDOGLYCAN-ASSOCIATED LIPOPROTEIN PRECURSOR

344

| ORF Name | NTID | AAID | NT Length | AA Length | Score | Probability |
|---|---|---|---|---|---|---|
| 14237656_c1_39 | 1271 | 3191 | 85 | 258 | | |

| Protein name | Locus Name | Acc# |
|---|---|---|

Description

NO-HIT

| ORF Name | NTID | AAID | NT Length | AA Length | Score | Probability |
|---|---|---|---|---|---|---|
| 14492157_f3_31 | 1272 | 3192 | 276 | 831 | | |

| Protein name | Locus Name | Acc# |
|---|---|---|

Description

NO-HIT

| ORF Name | NTID | AAID | NT Length | AA Length | Score | Probability |
|---|---|---|---|---|---|---|
| 14875327_f2_18 | 1273 | 3193 | 867 | 2604 | 1592 | 1.7e-163 |

| Protein name | Locus Name | Acc# |
|---|---|---|
| membrane alanyl aminopeptidase | gp:AF157493 | AF157493 |

Description

Zymomonas mobilis ZM4 fosmid clone 42D7, complete sequence.

| ORF Name | NTID | AAID | NT Length | AA Length | Score | Probability |
|---|---|---|---|---|---|---|
| 156258_c3_90 | 1274 | 3194 | 199 | 600 | 126 | 2.6e-06 |

| Protein name | Locus Name | Acc# |
|---|---|---|
| NrpG | gp:PMU46488 | U46488 |

Description

Proteus mirabilis NrpS (nrpS) gene, partial cds, NrpU (nrpU), NrpT(nrpT), NrpA (nrpA), NrpB (nrpB), NrpG (nrpG) and IrpP (irpP)genes, complete cds.

| ORF Name | NTID | AAID | NT Length | AA Length | Score | Probability |
|---|---|---|---|---|---|---|
| 16180387_f3_36 | 1275 | 3195 | 384 | 1155 | 143 | 3.8e-07 |

| Protein name | Locus Name | Acc# |
|---|---|---|
| hypothetical protein RP367 | pir:H71693 | H71693 |

Description

| ORF Name | NTID | AAID | NT Length | AA Length | Score | Probability |
|---|---|---|---|---|---|---|
| 16507676_c2_64 | 1276 | 3196 | 338 | 1017 | 445 | 6.1e-42 |

Protein name | Locus Name | Acc#
| | sp:SMTA_ECOLI | |

Description

SMTA PROTEIN

| ORF Name | NTID | AAID | NT Length | AA Length | Score | Probability |
|---|---|---|---|---|---|---|
| 22116326_f2_14 | 1277 | 3197 | 109 | 330 | 205 | 1.7e-16 |

Protein name | Locus Name | Acc#
| | sp:PA1_KLEPN | P37446 |

Description (ACYLHYDROLASE) (OUTER MEMBRANE PHOSPHOLIPASE A) (OM PLA)

| ORF Name | NTID | AAID | NT Length | AA Length | Score | Probability |
|---|---|---|---|---|---|---|
| 22694056_f1_11 | 1278 | 3198 | 637 | 1914 | 1865 | 2.1e-192 |

Protein name | Locus Name | Acc#
| | sp:CLPB_HAEIN | P44403 |

Description

CLPB PROTEIN

| ORF Name | NTID | AAID | NT Length | AA Length | Score | Probability |
|---|---|---|---|---|---|---|
| 23495633_f2_15 | 1279 | 3199 | 349 | 1050 | 105 | 0.0072 |

Protein name | Locus Name | Acc#
| ComB | gp:AF027189 | AF027189 |

Description

Acinetobacter sp. BD413 lytB, comB, comC, comE, and comF genes, complete cds; and unknown genes.

| ORF Name | NTID | AAID | NT Length | AA Length | Score | Probability |
|---|---|---|---|---|---|---|
| 2376890_c2_56 | 1280 | 3200 | 90 | 273 | | |

Protein name | Locus Name | Acc#

Description

NO-HIT

| ORF Name | NTID | AAID | NT Length | AA Length | Score | Probability |
|---|---|---|---|---|---|---|
| 24395640_f3_38 | 1281 | 3201 | 282 | 849 | 291 | 1.3e-25 |

| Protein name | Locus Name | Acc# |
|---|---|---|
| ABC transporter potG | pir:B71694 | B71694 |

Description

---

| ORF Name | NTID | AAID | NT Length | AA Length | Score | Probability |
|---|---|---|---|---|---|---|
| 24643831_f1_3 | 1282 | 3202 | 346 | 1041 | 213 | 3.2e-16 |

| Protein name | Locus Name | Acc# |
|---|---|---|
| phospholipase A | gp:CCPLDA | Y11031 |

Description

C.coli pldA gene.

| ORF Name | NTID | AAID | NT Length | AA Length | Score | Probability |
|---|---|---|---|---|---|---|
| 24783453_f2_25 | 1283 | 3203 | 224 | 675 | 738 | 5.5e-73 |

| Protein name | Locus Name | Acc# |
|---|---|---|
|  | sp:CLPB_BACNO | P17422 |

Description

CLPB PROTEIN

| ORF Name | NTID | AAID | NT Length | AA Length | Score | Probability |
|---|---|---|---|---|---|---|
| 25817157_f3_34 | 1284 | 3204 | 250 | 753 | 319 | 1.4e-28 |

| Protein name | Locus Name | Acc# |
|---|---|---|
| hypothetical protein | gp:AHWAAA179 | Z96927 |

Description

Acinetobacter haemolyticus waaA gene, strain ATCC 17906.

| ORF Name | NTID | AAID | NT Length | AA Length | Score | Probability |
|---|---|---|---|---|---|---|
| 2995252_f3_37 | 1285 | 3205 | 342 | 1029 | 198 | 1.4e-13 |

| Protein name | Locus Name | Acc# |
|---|---|---|
| ct391 hypothetical protein | pir:G72072 | G72072 |

Description

| ORF Name | NTID | AAID | NT Length | AA Length | Score | Probability |
|---|---|---|---|---|---|---|
| 32703126_f2_22 | 1286 | 3206 | 304 | 915 | 369 | 6.9e-34 |

| Protein name | Locus Name | Acc# |
|---|---|---|
| hypothetical protein RP368 | pir:A71694 | A71694 |

Description

---

| ORF Name | NTID | AAID | NT Length | AA Length | Score | Probability |
|---|---|---|---|---|---|---|
| 35368941_f1_4 | 1287 | 3207 | 285 | 858 | 152 | 4.5e-09 |

| Protein name | Locus Name | Acc# |
|---|---|---|
| competence protein ComF | gp:PST249742 | AJ249742 |

Description

Pseudomonas stutzeri JM300 bioB (partial), comF and dof (partial) genes.

---

| ORF Name | NTID | AAID | NT Length | AA Length | Score | Probability |
|---|---|---|---|---|---|---|
| 35943885_c2_66 | 1288 | 3208 | 413 | 1242 | | |

| Protein name | Locus Name | Acc# |
|---|---|---|
| | | |

Description

NO-HIT

---

| ORF Name | NTID | AAID | NT Length | AA Length | Score | Probability |
|---|---|---|---|---|---|---|
| 4111633_f2_13 | 1289 | 3209 | 154 | 465 | | |

| Protein name | Locus Name | Acc# |
|---|---|---|
| | | |

Description

NO-HIT

---

| ORF Name | NTID | AAID | NT Length | AA Length | Score | Probability |
|---|---|---|---|---|---|---|
| 4142186_f1_2 | 1290 | 3210 | 246 | 741 | 777 | 4.0e-77 |

| Protein name | Locus Name | Acc# |
|---|---|---|
| | sp:RNPH_PSEAE | P50597 |

Description

NUCLEOTIDYLTRANSFERASE)

| ORF Name | NTID | AAID | NT Length | AA Length | Score | Probability |
|---|---|---|---|---|---|---|
| 4572203_f1_9 | 1291 | 3211 | 329 | 990 | 117 | 5.7e-05 |

| Protein name | | | | Locus Name | Acc# |
|---|---|---|---|---|---|
| merozoite surface antigen 2 | | | | gp:U91655 | U91655 |

Description

Plasmodium falciparum isolate V310, merozoite surface antigen 2(MSP-2) gene, partial cds.

| ORF Name | NTID | AAID | NT Length | AA Length | Score | Probability |
|---|---|---|---|---|---|---|
| 4797282_c2_74 | 1292 | 3212 | 67 | 204 | | |

| Protein name | | | | Locus Name | Acc# |
|---|---|---|---|---|---|

Description

NO-HIT

| ORF Name | NTID | AAID | NT Length | AA Length | Score | Probability |
|---|---|---|---|---|---|---|
| 5082637_f3_33 | 1293 | 3213 | 440 | 1323 | 635 | 4.5e-62 |

| Protein name | | | | Locus Name | Acc# |
|---|---|---|---|---|---|
| WaaA | | | | gp:AF026386 | AF026386 |

Description

Salmonella typhimurium strain LT2 LPS core oligosaccharidebiosynthesis region, WaaY (waaY) gene, partial cds; WaaJ (waaJ),WaaI (waaI), WaaB (waaB), WaaP (waaP), WaaG (waaG), and WaaQ (waaQ)genes, complete cds; and WaaA (waaA) gene, partial cds.

| ORF Name | NTID | AAID | NT Length | AA Length | Score | Probability |
|---|---|---|---|---|---|---|
| 5132838_f1_5 | 1294 | 3214 | 255 | 768 | | |

| Protein name | | | | Locus Name | Acc# |
|---|---|---|---|---|---|

Description

NO-HIT

| ORF Name | NTID | AAID | NT Length | AA Length | Score | Probability |
|---|---|---|---|---|---|---|
| 5867075_f3_29 | 1295 | 3215 | 202 | 609 | 105 | 0.00049 |

| Protein name | Locus Name | Acc# |
|---|---|---|
| pilV protein | pir:S77594 | S77594 |

Description

| ORF Name | NTID | AAID | NT Length | AA Length | Score | Probability |
|---|---|---|---|---|---|---|
| 790700_c2_65 | 1296 | 3216 | 379 | 1140 | 151 | 9.2e-08 |

| Protein name | Locus Name | Acc# |
|---|---|---|
| hypothetical protein TP0565 | pir:C71308 | C71308 |

Description

| ORF Name | NTID | AAID | NT Length | AA Length | Score | Probability |
|---|---|---|---|---|---|---|
| 9775283_c1_46 | 1297 | 3217 | 499 | 1500 | 469 | 1.8e-44 |

| Protein name | Locus Name | Acc# |
|---|---|---|
| probable alginate O-acetylation protein (algI) | pir:D71308 | D71308 |

Description

| ORF Name | NTID | AAID | NT Length | AA Length | Score | Probability |
|---|---|---|---|---|---|---|
| 115827_c1_7 | 1298 | 3218 | 330 | 993 | 877 | 1.0e-87 |

| Protein name | Locus Name | Acc# |
|---|---|---|
|  | sp:GLMU_HAEIN | P43889 |

Description

ACETYLGLUCOSAMINE-1-PHOSPHATE URIDYLTRANSFERASE)

| ORF Name | NTID | AAID | NT Length | AA Length | Score | Probability |
|---|---|---|---|---|---|---|
| 16828178_f1_2 | 1299 | 3219 | 616 | 1851 | 2166 | 2.6e-224 |

| Protein name | Locus Name | Acc# |
|---|---|---|
|  | sp:TYPA_HAEIN | P44910 |

Description

GTP-BINDING PROTEIN TYPA/BIPA HOMOLOG

350

| ORF Name | NTID | AAID | NT Length | AA Length | Score | Probability |
|---|---|---|---|---|---|---|
| 32656465_c2_10 | 1300 | 3220 | 78 | 237 | | |

| Protein name | | Locus Name | Acc# |
|---|---|---|---|
| | | | |

Description

NO-HIT

| ORF Name | NTID | AAID | NT Length | AA Length | Score | Probability |
|---|---|---|---|---|---|---|
| 3336053_f1_1 | 1301 | 3221 | 133 | 402 | 618 | 2.9e-60 |

| Protein name | | Locus Name | Acc# |
|---|---|---|---|
| outer membrane protein CD precursor | | pir:S39866 | S39866 |

Description

| ORF Name | NTID | AAID | NT Length | AA Length | Score | Probability |
|---|---|---|---|---|---|---|
| 10975831_c3_12 | 1302 | 3222 | 92 | 279 | | |

| Protein name | | Locus Name | Acc# |
|---|---|---|---|
| | | | |

Description

NO-HIT

| ORF Name | NTID | AAID | NT Length | AA Length | Score | Probability |
|---|---|---|---|---|---|---|
| 15912757_c1_8 | 1303 | 3223 | 123 | 372 | 86 | 0.048 |

| Protein name | | Locus Name | Acc# |
|---|---|---|---|
| FIP2 | | gp:AF061034 | AF061034 |

Description

Homo sapiens FIP2 alternatively translated mRNA, complete cds.

| ORF Name | NTID | AAID | NT Length | AA Length | Score | Probability |
|---|---|---|---|---|---|---|
| 22457187_f3_5 | 1304 | 3224 | 250 | 753 | 888 | 7.0e-89 |

| Protein name | | Locus Name | Acc# |
|---|---|---|---|
| | | sp:Y882_HAEIN | P44068 |

Description

HYPOTHETICAL PROTEIN HI0882

| ORF Name | NTID | AAID | NT Length | AA Length | Score | Probability |
|---|---|---|---|---|---|---|
| 35271883_f1_4 | 1305 | 3225 | 60 | 183 | | |

Protein name              Locus_Name      Acc#

Description

NO-HIT

| ORF Name | NTID | AAID | NT Length | AA Length | Score | Probability |
|---|---|---|---|---|---|---|
| 22848457_f2_3 | 1306 | 3226 | 134 | 405 | | |

Protein name              Locus_Name      Acc#

Description

NO-HIT

| ORF Name | NTID | AAID | NT Length | AA Length | Score | Probability |
|---|---|---|---|---|---|---|
| 22853376_f3_5 | 1307 | 3227 | 239 | 720 | | |

Protein name              Locus_Name      Acc#

Description

NO-HIT

| ORF Name | NTID | AAID | NT Length | AA Length | Score | Probability |
|---|---|---|---|---|---|---|
| 29296968_c3_9 | 1308 | 3228 | 77 | 234 | | |

Protein name              Locus_Name      Acc#

Description

NO-HIT

| ORF Name | NTID | AAID | NT Length | AA Length | Score | Probability |
|---|---|---|---|---|---|---|
| 976678_c3_10 | 1309 | 3229 | 190 | 570 | 265 | 7.3e-23 |

Protein name              Locus_Name      Acc#
                                         sp:PRTR_PSEAE     Q06553

Description

TRANSCRIPTION REGULATORY PROTEIN PRTR (PYOSIN REPRESSOR PROTEIN)

| ORF Name | NTID | AAID | NT Length | AA Length | Score | Probability |
|---|---|---|---|---|---|---|
| 989077_f1_1 | 1310 | 3230 | 122 | 369 | | |

| Protein name | Locus Name | Acc# |
|---|---|---|

Description

NO-HIT

| ORF Name | NTID | AAID | NT Length | AA Length | Score | Probability |
|---|---|---|---|---|---|---|
| 1062575_c3_34 | 1311 | 3231 | 109 | 330 | | |

| Protein name | Locus Name | Acc# |
|---|---|---|

Description

NO-HIT

| ORF Name | NTID | AAID | NT Length | AA Length | Score | Probability |
|---|---|---|---|---|---|---|
| 11125280_f3_13 | 1312 | 3232 | 146 | 441 | 538 | 8.6e-52 |

| Protein name | Locus Name | Acc# |
|---|---|---|
| nifU protein homolog HI0377 | pir:C64064 | C64064 |

Description

| ORF Name | NTID | AAID | NT Length | AA Length | Score | Probability |
|---|---|---|---|---|---|---|
| 1297092_c1_20 | 1313 | 3233 | 111 | 336 | 174 | 3.9e-12 |

| Protein name | Locus Name | Acc# |
|---|---|---|
| probable gamma-glutamyltranspeptidase precursor | pir:E70682 | E70682 |

Description

| ORF Name | NTID | AAID | NT Length | AA Length | Score | Probability |
|---|---|---|---|---|---|---|
| 15892918_c3_35 | 1314 | 3234 | 110 | 333 | 222 | 2.4e-17 |

| Protein name | Locus Name | Acc# |
|---|---|---|
| probable gamma-glutamyltranspeptidase | pir:T34901 | T34901 |

Description

| ORF Name | NTID | AAID | NT Length | AA Length | Score | Probability |
|---|---|---|---|---|---|---|
| 20727194_c2_24 | 1315 | 3235 | 91 | 276 | 318 | 1.8e-28 |

| Protein name | Locus Name | Acc# |
|---|---|---|
| | gp:AF017750 | AF017750 |

Description

Haemophilus ducreyi cytochrome C-type biogenesis protein (ccmH), recombinational DNA repair protein (recR), manganese superoxidedismutase (sodA), and CitG protein homolog (citG) genes, completecds.

| ORF Name | NTID | AAID | NT Length | AA Length | Score | Probability |
|---|---|---|---|---|---|---|
| 21679025_f1_1 | 1316 | 3236 | 420 | 1263 | 1516 | 2.0e-155 |

| Protein name | Locus Name | Acc# |
|---|---|---|
| | sp:NIFS_ECOLI | |

Description

NIFS PROTEIN HOMOLOG

| ORF Name | NTID | AAID | NT Length | AA Length | Score | Probability |
|---|---|---|---|---|---|---|
| 31797152_f3_14 | 1317 | 3237 | 186 | 561 | 224 | 1.6e-18 |

| Protein name | Locus Name | Acc# |
|---|---|---|
| | sp:HSCB_ECOLI | P36540 |

Description

CHAPERONE PROTEIN HSCB (HSC20)

| ORF Name | NTID | AAID | NT Length | AA Length | Score | Probability |
|---|---|---|---|---|---|---|
| 32244203_c2_26 | 1318 | 3238 | 72 | 219 | 125 | 5.0e-08 |

| Protein name | Locus Name | Acc# |
|---|---|---|
| | gp:VCH231122 | AJ231122 |

Description

Vibrio cholerae z61f gene.

| ORF_Name | NTID | AAID | NT Length | AA Length | Score | Probability |
|---|---|---|---|---|---|---|
| 33398287_f2_5 | 1319 | 3239 | 178 | 537 | 396 | 9.6e-37 |

Protein name | Locus_Name | Acc#
sp:YFHP_HAEIN | P44675

Description

HYPOTHETICAL PROTEIN HI0379

| ORF_Name | NTID | AAID | NT Length | AA Length | Score | Probability |
|---|---|---|---|---|---|---|
| 36129678_f1_2 | 1320 | 3240 | 112 | 339 | 384 | 1.8e-35 |

Protein name | Locus_Name | Acc#
sp:YFHF_HAEIN | P44672

Description

HYPOTHETICAL PROTEIN HI0376

| ORF_Name | NTID | AAID | NT Length | AA Length | Score | Probability |
|---|---|---|---|---|---|---|
| 36220382_c2_25 | 1321 | 3241 | 120 | 363 | 174 | 3.2e-12 |

Protein name | Locus_Name | Acc#
sp:GGT_PIG | P20735

Description

GLUTAMYLTRANSFERASE) (GGT)

| ORF_Name | NTID | AAID | NT Length | AA Length | Score | Probability |
|---|---|---|---|---|---|---|
| 4331938_f2_9 | 1322 | 3242 | 622 | 1869 | 1435 | 7.6e-147 |

Protein name | Locus_Name | Acc#
sp:HSCA_HAEIN | P44669

Description

CHAPERONE PROTEIN HSCA (HSC66)

| ORF Name | NTID | AAID | NT Length | AA Length | Score | Probability |
|---|---|---|---|---|---|---|
| 4332838_f2_10 | 1323 | 3243 | 115 | 348 | 397 | 7.5e-37 |

| Protein name | Locus Name | Acc# |
|---|---|---|
| ferredoxin | gp:AF096864 | AF096864 |

Description

Pseudomonas aeruginosa heat shock protein (hscB), heat shockprotein 66-KDa (hscA), ferredoxin (fdx), and nucleoside diphosphatekinase (ndk) genes, complete cds.

| ORF Name | NTID | AAID | NT Length | AA Length | Score | Probability |
|---|---|---|---|---|---|---|
| 5898593_c2_28 | 1324 | 3244 | 119 | 360 | | |

| Protein name | Locus Name | Acc# |
|---|---|---|
| | | |

Description

NO-HIT

| ORF Name | NTID | AAID | NT Length | AA Length | Score | Probability |
|---|---|---|---|---|---|---|
| 7070215_c2_27 | 1325 | 3245 | 161 | 486 | 351 | 5.6e-32 |

| Protein name | Locus Name | Acc# |
|---|---|---|
| putative gamma-glutamyltranspeptidase precursor | gp:PST249741 | AJ249741 |

Description

Pseudomonas stutzeri JM300 gacS (partial) and ggtB (partial) genes.

| ORF Name | NTID | AAID | NT Length | AA Length | Score | Probability |
|---|---|---|---|---|---|---|
| 12915808_f3_10 | 1326 | 3246 | 200 | 603 | | |

| Protein name | Locus Name | Acc# |
|---|---|---|
| | | |

Description

NO-HIT

| ORF Name | NTID | AAID | NT Length | AA Length | Score | Probability |
|---|---|---|---|---|---|---|
| 20737503_f3_8 | 1327 | 3247 | 371 | 1116 | 418 | 4.5e-39 |

| Protein name | Locus Name | Acc# |
|---|---|---|
| probable permease perM homolog (perM) RP630 | pir:E71668 | E71668 |

Description

| ORF Name | NTID | AAID | NT Length | AA Length | Score | Probability |
|---|---|---|---|---|---|---|
| 22000293_c2_13 | 1328 | 3248 | 97 | 294 | 348 | 1.2e-31 |

| Protein name | Locus Name | Acc# |
|---|---|---|
| 50S ribosomal protein homolog | gp:AF153712 | AF153712 |

Description

Pseudomonas sp. BG33R strain BG33R 50S ribosomal protein homologgene, complete cds.

| ORF Name | NTID | AAID | NT Length | AA Length | Score | Probability |
|---|---|---|---|---|---|---|
| 23863307_f3_9 | 1329 | 3249 | 261 | 786 | 194 | 2.4e-15 |

| Protein name | Locus Name | Acc# |
|---|---|---|
|  | sp:YFGE_HAEIN | O86235 |

Description

HYPOTHETICAL PROTEIN HI1225.1

| ORF Name | NTID | AAID | NT Length | AA Length | Score | Probability |
|---|---|---|---|---|---|---|
| 24308561_c3_17 | 1330 | 3250 | 182 | 549 | 710 | 5.1e-70 |

| Protein name | Locus Name | Acc# |
|---|---|---|
| phosphoribosylformylglycinamidine cyclo-ligase,:5'-phosphoribosyl-5-aminoimidazole synthetase | pir:AJECPC |  |

Description

| ORF Name | NTID | AAID | NT Length | AA Length | Score | Probability |
|---|---|---|---|---|---|---|
| 26277251_c3_18 | 1331 | 3251 | 131 | 396 | 352 | 4.4e-32 |

| Protein name | Locus Name | Acc# |
|---|---|---|
|  | sp:PUR5_ECOLI | P08178 |

Description (PHOSPHORIBOSYL-AMINOIMIDAZOLE SYNTHETASE) (AIR SYNTHASE)

357

| ORF Name | NTID | AAID | NT Length | AA Length | Score | Probability |
|---|---|---|---|---|---|---|
| 6142915_c2_14 | 1332 | 3252 | 228 | 687 | 382 | 2.9e-35 |

| Protein name | Locus Name | Acc# |
|---|---|---|
| 5'-phosphoribosylglycinamide transformylase | gp:STU68765 | U68765 |

Description

Salmonella typhimurium 5'-phosphoribosylglycinamide transformylase(purN) and 5'-phosphoribosyl-5-aminoimidazole synthetase (purI)genes, complete cds.

| ORF Name | NTID | AAID | NT Length | AA Length | Score | Probability |
|---|---|---|---|---|---|---|
| 10744000_c3_102 | 1333 | 3253 | 309 | 930 | 1094 | 1.0e-110 |

| Protein name | Locus Name | Acc# |
|---|---|---|
| probable Mn transport protein | pir:G64063 | |

Description

| ORF Name | NTID | AAID | NT Length | AA Length | Score | Probability |
|---|---|---|---|---|---|---|
| 1181631_f1_2 | 1334 | 3254 | 558 | 1677 | 1333 | 4.9e-136 |

| Protein name | Locus Name | Acc# |
|---|---|---|
| | sp:60IM_PSEPU | P25754 |

Description

60 KD INNER-MEMBRANE PROTEIN

| ORF Name | NTID | AAID | NT Length | AA Length | Score | Probability |
|---|---|---|---|---|---|---|
| 13703378_c3_117 | 1335 | 3255 | 95 | 288 | 163 | 4.7e-12 |

| Protein name | Locus Name | Acc# |
|---|---|---|
| | sp:YEAQ_ECOLI | P76246 |

Description

HYPOTHETICAL 8.7 KD PROTEIN IN GAPA-RND INTERGENIC REGION

| ORF Name | NTID | AAID | NT Length | AA Length | Score | Probability |
|---|---|---|---|---|---|---|
| 15031513_f3_43 | 1336 | 3256 | 479 | 1440 | 1390 | 4.5e-142 |

| Protein name | Locus Name | Acc# |
|---|---|---|
| | sp:THRC_METGL | P37145 |

Description

THREONINE SYNTHASE,

| ORF Name | NTID | AAID | NT Length | AA Length | Score | Probability |
|---|---|---|---|---|---|---|
| 15039077_cl_64 | 1337 | 3257 | 266 | 801 | 196 | 1.5e-15 |

Protein name | Locus Name | Acc#
gp:DNINTREG | X98546

Description

D.nodosus intB, regA, gepA, gepB, and gepC genes.

| ORF Name | NTID | AAID | NT Length | AA Length | Score | Probability |
|---|---|---|---|---|---|---|
| 15665903_cl_59 | 1338 | 3258 | 281 | 846 | 1074 | 1.4e-108 |

Protein name | Locus Name | Acc#
sp:Y360_HAEIN | P44661

Description

HYPOTHETICAL PROTEIN HI0360

| ORF Name | NTID | AAID | NT Length | AA Length | Score | Probability |
|---|---|---|---|---|---|---|
| 15798825_cl_65 | 1339 | 3259 | 165 | 498 | | |

Protein name | Locus Name | Acc#

Description

NO-HIT

| ORF Name | NTID | AAID | NT Length | AA Length | Score | Probability |
|---|---|---|---|---|---|---|
| 19538327_cl_72 | 1340 | 3260 | 213 | 642 | 218 | 7.0e-18 |

Protein name | Locus Name | Acc#
sp:Y882_METJA | Q58292

Description

HYPOTHETICAL PROTEIN MJ0882

| ORF Name | NTID | AAID | NT Length | AA Length | Score | Probability |
|---|---|---|---|---|---|---|
| 197188_f3_42 | 1341 | 3261 | 345 | 1038 | 659 | 1.3e-64 |

Protein name | Locus Name | Acc#
sp:FMT_PSEAE | O85732

Description

METHIONYL-TRNA FORMYLTRANSFERASE,

359

| ORF Name | NTID | AAID | NT Length | AA Length | Score | Probability |
|---|---|---|---|---|---|---|
| 20197175_f3_44 | 1342 | 3262 | 415 | 1248 | 453 | 5.0e-47 |

Protein name | Locus Name | Acc#
sp:SMF_HAEIN | P43862

Description

SMF PROTEIN (DNA PROCESSING CHAIN A)

| ORF Name | NTID | AAID | NT Length | AA Length | Score | Probability |
|---|---|---|---|---|---|---|
| 23440886_f2_27 | 1343 | 3263 | 602 | 1809 | 241 | 2.1e-19 |

Protein name | Locus Name | Acc#
sp:Y678_METJA | Q58091

Description

HYPOTHETICAL PROTEIN MJ0678

| ORF Name | NTID | AAID | NT Length | AA Length | Score | Probability |
|---|---|---|---|---|---|---|
| 241290_f2_31 | 1344 | 3264 | 65 | 198 | | |

Protein name | Locus Name | Acc#

Description

NO-HIT

| ORF Name | NTID | AAID | NT Length | AA Length | Score | Probability |
|---|---|---|---|---|---|---|
| 24244010_c3_106 | 1345 | 3265 | 83 | 252 | 69 | 0.042 |

Protein name | Locus Name | Acc#
hypothetical protein Y105C5B.x | pir:T26400 | T26400

Description

| ORF Name | NTID | AAID | NT Length | AA Length | Score | Probability |
|---|---|---|---|---|---|---|
| 24253187_c3_107 | 1346 | 3266 | 66 | 201 | | |

Protein name | Locus Name | Acc#

Description

NO-HIT

| ORF Name | NTID | AAID | NT Length | AA Length | Score | Probability |
|---|---|---|---|---|---|---|
| 24255262_c2_96 | 1347 | 3267 | 430 | 1293 | 873 | 2.7e-87 |

| Protein name | Locus Name | Acc# |
|---|---|---|
| conserved hypothetical protein | pir:C75339 | C75339 |

Description

---

| ORF Name | NTID | AAID | NT Length | AA Length | Score | Probability |
|---|---|---|---|---|---|---|
| 24256550_f3_40 | 1348 | 3268 | 165 | 498 | 465 | 4.7e-44 |

| Protein name | Locus Name | Acc# |
|---|---|---|
| | sp:YBAD_ECOLI | P25538 |

Description

HYPOTHETICAL 17.2 KD PROTEIN IN TSX-RIBG INTERGENIC REGION (ORF1)

---

| ORF Name | NTID | AAID | NT Length | AA Length | Score | Probability |
|---|---|---|---|---|---|---|
| 24337786_f3_48 | 1349 | 3269 | 311 | 936 | 657 | 2.1e-64 |

| Protein name | Locus Name | Acc# |
|---|---|---|
| | sp:ARGI_BRUAB | Q59174 |

Description

ARGINASE,

---

| ORF Name | NTID | AAID | NT Length | AA Length | Score | Probability |
|---|---|---|---|---|---|---|
| 24417762_f1_18 | 1350 | 3270 | 62 | 189 | 74 | 0.030 |

| Protein name | Locus Name | Acc# |
|---|---|---|
| | sp:FM1A_SERMA | P22595 |

Description

TYPE-1 FIMBRIAL PROTEIN SUBUNIT PRECURSOR

---

| ORF Name | NTID | AAID | NT Length | AA Length | Score | Probability |
|---|---|---|---|---|---|---|
| 24489626_f2_21 | 1351 | 3271 | 474 | 1425 | 1058 | 6.8e-107 |

| Protein name | Locus Name | Acc# |
|---|---|---|
| | sp:THDF_PSEPU | P25755 |

Description

POSSIBLE THIOPHENE AND FURAN OXIDATION PROTEIN THDF

| ORF_Name | NTID | AAID | NT Length | AA Length | Score | Probability |
|---|---|---|---|---|---|---|
| 24643777_f2_22 | 1352 | 3272 | 352 | 1059 | 682 | 4.3e-78 |

Protein name     Locus_Name     Acc#
    sp:RIBD_ECOLI     P25539

Description

RIBOFLAVIN-SPECIFIC DEAMINASE,

| ORF_Name | NTID | AAID | NT Length | AA Length | Score | Probability |
|---|---|---|---|---|---|---|
| 24643937_f1_4 | 1353 | 3273 | 450 | 1353 | 695 | 2.0e-68 |

Protein name     Locus_Name     Acc#
    sp:SUN_HAEIN     P44788

Description

SUN PROTEIN (FMU PROTEIN)

| ORF_Name | NTID | AAID | NT Length | AA Length | Score | Probability |
|---|---|---|---|---|---|---|
| 26603562_c2_86 | 1354 | 3274 | 303 | 912 | 1047 | 9.9e-106 |

Protein name     Locus_Name     Acc#
    sp:FECE_HAEIN     P44662

Description

IRON(III) DICITRATE TRANSPORT ATP-BINDING PROTEIN FECE HOMOLOG

| ORF_Name | NTID | AAID | NT Length | AA Length | Score | Probability |
|---|---|---|---|---|---|---|
| 2738783_f2_37 | 1355 | 3275 | 60 | 183 | | |

Protein name     Locus_Name     Acc#

Description

NO-HIT

| ORF_Name | NTID | AAID | NT Length | AA Length | Score | Probability |
|---|---|---|---|---|---|---|
| 2750262_f1_1 | 1356 | 3276 | 103 | 312 | 193 | 3.1e-15 |

Protein name     Locus_Name     Acc#
hypothetical protein SCH24.04     pir:T36569     T36569

Description

| ORF Name | NTID | AAID | NT Length | AA Length | Score | Probability |
|---|---|---|---|---|---|---|
| 29539015_c1_62 | 1357 | 3277 | 417 | 1254 | 666 | 2.3e-65 |

| Protein name | | | | Locus Name | | Acc# |
|---|---|---|---|---|---|---|
| | | | | sp:YDHH_ECOLI | | P77570 |

Description

HYPOTHETICAL 39.5 KD PROTEIN IN PDXH-SLYB INTERGENIC REGION

| ORF Name | NTID | AAID | NT Length | AA Length | Score | Probability |
|---|---|---|---|---|---|---|
| 30739700_f1_7 | 1358 | 3278 | 211 | 636 | 244 | 1.2e-20 |

| Protein name | | | | Locus Name | | Acc# |
|---|---|---|---|---|---|---|
| | | | | sp:YRDC_ECOLI | | P45748 |

Description

HYPOTHETICAL 20.8 KD PROTEIN IN AROE-SMG INTERGENIC REGION

| ORF Name | NTID | AAID | NT Length | AA Length | Score | Probability |
|---|---|---|---|---|---|---|
| 34088143_f3_55 | 1359 | 3279 | 106 | 321 | | |

| Protein name | | | | Locus Name | | Acc# |

Description

NO-HIT

| ORF Name | NTID | AAID | NT Length | AA Length | Score | Probability |
|---|---|---|---|---|---|---|
| 3913215_f2_26 | 1360 | 3280 | 165 | 498 | | |

| Protein name | | | | Locus Name | | Acc# |

Description

NO-HIT

| ORF Name | NTID | AAID | NT Length | AA Length | Score | Probability |
|---|---|---|---|---|---|---|
| 3939063_f2_23 | 1361 | 3281 | 225 | 678 | 519 | 8.8e-50 |

| Protein name | | | | Locus Name | | Acc# |
|---|---|---|---|---|---|---|
| | | | | sp:RISA_PHOPO | | P51961 |

Description

RIBOFLAVIN SYNTHASE ALPHA CHAIN,

| ORF Name | NTID | AAID | NT Length | AA Length | Score | Probability |
|---|---|---|---|---|---|---|
| 3942213_c2_97 | 1362 | 3282 | 367 | 1104 | 930 | 2.5e-93 |

| Protein name | | | | Locus Name | | Acc# |
|---|---|---|---|---|---|---|
| | | | | sp:GCH2_PHOLE | | Q02008 |

Description

| ORF Name | NTID | AAID | NT Length | AA Length | Score | Probability |
|---|---|---|---|---|---|---|
| 4785911_f2_29 | 1363 | 3283 | 435 | 1308 | 1321 | 9.1e-135 |

| Protein name | | | | Locus Name | | Acc# |
|---|---|---|---|---|---|---|
| | | | | sp:OAT_DROAN | | P49724 |

Description

ACID AMINOTRANSFERASE)

| ORF Name | NTID | AAID | NT Length | AA Length | Score | Probability |
|---|---|---|---|---|---|---|
| 5214052_f3_53 | 1364 | 3284 | 411 | 1236 | 1096 | 6.4e-111 |

| Protein name | | | | Locus Name | | Acc# |
|---|---|---|---|---|---|---|
| | | | | sp:SYY_HAEIN | | P43836 |

Description

TYROSYL-TRNA SYNTHETASE, (TYROSINE--TRNA LIGASE) (TYRRS)

| ORF Name | NTID | AAID | NT Length | AA Length | Score | Probability |
|---|---|---|---|---|---|---|
| 5282562_c1_63 | 1365 | 3285 | 265 | 798 | 693 | 3.2e-68 |

| Protein name | | | | Locus Name | | Acc# |
|---|---|---|---|---|---|---|
| hypothetical protein jhp0330 | | | | pir:B71947 | | B71947 |

Description

| ORF Name | NTID | AAID | NT Length | AA Length | Score | Probability |
|---|---|---|---|---|---|---|
| 6070166_f2_20 | 1366 | 3286 | 71 | 216 | | |

| Protein name | | | | Locus Name | | Acc# |
|---|---|---|---|---|---|---|

Description

NO-HIT

| ORF_Name | NTID | AAID | NT Length | AA Length | Score | Probability |
|---|---|---|---|---|---|---|
| 6147028_c1_60 | 1367 | 3287 | 292 | 879 | 870 | 5.6e-87 |

| Protein name | Locus Name | Acc# |
|---|---|---|
| | sp:YFED_YERPE | Q56955 |

Description

CHELATED IRON TRANSPORT SYSTEM MEMBRANE PROTEIN YFED

| ORF_Name | NTID | AAID | NT Length | AA Length | Score | Probability |
|---|---|---|---|---|---|---|
| 839752_f1_19 | 1368 | 3288 | 60 | 183 | | |

| Protein name | Locus Name | Acc# |
|---|---|---|

Description

NO-HIT

| ORF_Name | NTID | AAID | NT Length | AA Length | Score | Probability |
|---|---|---|---|---|---|---|
| 867183_c1_68 | 1369 | 3289 | 128 | 387 | 107 | 2.7e-05 |

| Protein name | Locus Name | Acc# |
|---|---|---|
| | sp:YRAM_BACSU | O07931 |

Description

HYPOTHETICAL 39.5 KD PROTEIN IN SIGZ-CSN INTERGENIC REGION

| ORF_Name | NTID | AAID | NT Length | AA Length | Score | Probability |
|---|---|---|---|---|---|---|
| 1197077_f3_44 | 1370 | 3290 | 375 | 1128 | 178 | 8.2e-11 |

| Protein name | Locus Name | Acc# |
|---|---|---|
| hypothetical protein TM0342 | pir:D72388 | D72388 |

Description

| ORF_Name | NTID | AAID | NT Length | AA Length | Score | Probability |
|---|---|---|---|---|---|---|
| 14641008_f3_46 | 1371 | 3291 | 271 | 816 | 360 | 6.2e-33 |

| Protein name | Locus Name | Acc# |
|---|---|---|
| putative thiol:disulfide interchange protein | gp:AF057031 | AF057031 |

Description

Pseudomonas aeruginosa putative thiol:disulfide interchange proteinprecursor (dsbC) gene, complete cds.

| ORF Name | NTID | AAID | NT Length | AA Length | Score | Probability |
|---|---|---|---|---|---|---|
| 15058126_f1_9 | 1372 | 3292 | 204 | 615 | 183 | 3.6e-14 |

| Protein name | Locus Name | Acc# |
|---|---|---|
| hypothetical protein | gp:AF088857 | AF088857 |

Description

Vogesella indigofera indigoidine biosynthesis regulatory locus, complete sequence.

| ORF Name | NTID | AAID | NT Length | AA Length | Score | Probability |
|---|---|---|---|---|---|---|
| 158638_c3_82 | 1373 | 3293 | 89 | 270 | 350 | 7.2e-32 |

| Protein name | Locus Name | Acc# |
|---|---|---|
| | sp:IMDH_ACICA | P31002 |

Description

DEHYDROGENASE) (IMPDH) (IMPD)

| ORF Name | NTID | AAID | NT Length | AA Length | Score | Probability |
|---|---|---|---|---|---|---|
| 16992775_f2_22 | 1374 | 3294 | 61 | 186 | 85 | 0.00086 |

| Protein name | Locus Name | Acc# |
|---|---|---|
| gamma-carboxymuconolactone decarboxylase | pir:B69129 | B69129 |

Description

| ORF Name | NTID | AAID | NT Length | AA Length | Score | Probability |
|---|---|---|---|---|---|---|
| 20353465_f2_21 | 1375 | 3295 | 167 | 504 | | |

| Protein name | Locus Name | Acc# |
|---|---|---|
| | | |

Description

NO-HIT

| ORF Name | NTID | AAID | NT Length | AA Length | Score | Probability |
|---|---|---|---|---|---|---|
| 20734687_c2_78 | 1376 | 3296 | 297 | 894 | 642 | 8.2e-63 |

| Protein name | Locus Name | Acc# |
|---|---|---|
| | sp:YAAJ_HAEIN | P44555 |

Description

HYPOTHETICAL PROTEIN HI0183

| ORF Name | NTID | AAID | NT Length | AA Length | Score | Probability |
|---|---|---|---|---|---|---|
| 21672011_c1_54 | 1377 | 3297 | 61 | 186 | 55 | 0.0095 |

| Protein name | | | | Locus Name | | Acc# |
|---|---|---|---|---|---|---|
| | | | | sp:YY10_METJA | | Q60309 |

Description

HYPOTHETICAL PROTEIN MJECS10

| ORF Name | NTID | AAID | NT Length | AA Length | Score | Probability |
|---|---|---|---|---|---|---|
| 23439077_f1_5 | 1378 | 3298 | 177 | 534 | 103 | 0.0035 |

| Protein name | | | | Locus Name | | Acc# |
|---|---|---|---|---|---|---|
| ORF MSV035 hypothetical protein | | | | gp:AF063866 | | AF063866 |

Description

Melanoplus sanguinipes entomopoxvirus, complete genome.

| ORF Name | NTID | AAID | NT Length | AA Length | Score | Probability |
|---|---|---|---|---|---|---|
| 2347156_f1_8 | 1379 | 3299 | 1105 | 3318 | 1839 | 2.0e-286 |

| Protein name | | | | Locus Name | | Acc# |
|---|---|---|---|---|---|---|
| isoleucine--tRNA ligase,:isoleucyl-tRNA synthetase | | | | pir:SYECIT | | |

Description

| ORF Name | NTID | AAID | NT Length | AA Length | Score | Probability |
|---|---|---|---|---|---|---|
| 23652183_c1_56 | 1380 | 3300 | 777 | 2334 | 3955 | 0.0 |

| Protein name | | | | Locus Name | | Acc# |
|---|---|---|---|---|---|---|
| outer membrane protein CopB | | | | gp:U69981 | | U69981 |

Description

Moraxella catarrhalis strain O12E outer membrane protein CopB gene, complete cds.

| ORF Name | NTID | AAID | NT Length | AA Length | Score | Probability |
|---|---|---|---|---|---|---|
| 23865660_c2_77 | 1381 | 3301 | 87 | 264 | | |

| Protein name | | | | Locus Name | | Acc# |
|---|---|---|---|---|---|---|

Description

NO-HIT

| ORF Name | NTID | AAID | NT Length | AA Length | Score | Probability |
|---|---|---|---|---|---|---|
| 25506316_f1_14 | 1382 | 3302 | 228 | 687 | 554 | 1.7e-53 |

| Protein name | Locus Name | Acc# |
|---|---|---|
| | sp:YIHA_ECOLI | |

Description

HYPOTHETICAL GTP-BINDING PROTEIN IN POLA-HEMN INTERGENIC REGION

| ORF Name | NTID | AAID | NT Length | AA Length | Score | Probability |
|---|---|---|---|---|---|---|
| 2584717_f3_43 | 1383 | 3303 | 87 | 264 | 127 | 3.1e-08 |

| Protein name | Locus Name | Acc# |
|---|---|---|
| gamma-carboxymuconolactone decarboxylase | pir:B69129 | B69129 |

Description

| ORF Name | NTID | AAID | NT Length | AA Length | Score | Probability |
|---|---|---|---|---|---|---|
| 25942137_f2_29 | 1384 | 3304 | 185 | 558 | 296 | 3.8e-26 |

| Protein name | Locus Name | Acc# |
|---|---|---|
| | sp:FKBX_PSEFL | P21863 |

Description (EC 5.2.1.8) (PPIASE) (ROTAMASE)

| ORF Name | NTID | AAID | NT Length | AA Length | Score | Probability |
|---|---|---|---|---|---|---|
| 26364431_c1_49 | 1385 | 3305 | 117 | 354 | 300 | 1.4e-26 |

| Protein name | Locus Name | Acc# |
|---|---|---|
| | pir:FEKRV | |

Description

| ORF Name | NTID | AAID | NT Length | AA Length | Score | Probability |
|---|---|---|---|---|---|---|
| 32056506_c3_81 | 1386 | 3306 | 401 | 1206 | 1486 | 3.0e-152 |

| Protein name | Locus Name | Acc# |
|---|---|---|
| | sp:IMDH_ACICA | P31002 |

Description

DEHYDROGENASE) (IMPDH) (IMPD)

| ORF Name | NTID | AAID | NT Length | AA Length | Score | Probability |
|---|---|---|---|---|---|---|
| 32477250_c1_65 | 1387 | 3307 | 443 | 1332 | 1422 | 1.8e-145 |

| Protein name | | | | Locus Name | | Acc# |
|---|---|---|---|---|---|---|
| | | | | sp:YCDG_ECOLI | | P75892 |

Description

HYPOTHETICAL 48.1 KD PROTEIN IN WRBA-PUTA INTERGENIC REGION

| ORF Name | NTID | AAID | NT Length | AA Length | Score | Probability |
|---|---|---|---|---|---|---|
| 34665952_f2_28 | 1388 | 3308 | 177 | 534 | 371 | 4.3e-34 |

| Protein name | | | | Locus Name | | Acc# |
|---|---|---|---|---|---|---|
| | | | | sp:LSPA_PSEFL | | P17942 |

Description

PEPTIDASE) (SIGNAL PEPTIDASE II) (SPASE II)

| ORF Name | NTID | AAID | NT Length | AA Length | Score | Probability |
|---|---|---|---|---|---|---|
| 4775762_f1_15 | 1389 | 3309 | 252 | 759 | 593 | 1.3e-57 |

| Protein name | | | | Locus Name | | Acc# |
|---|---|---|---|---|---|---|
| | | | | sp:YRAL_ECOLI | | P45528 |

Description

HYPOTHETICAL 31.3 KD PROTEIN IN AGAI-MTR INTERGENIC REGION (F286)

| ORF Name | NTID | AAID | NT Length | AA Length | Score | Probability |
|---|---|---|---|---|---|---|
| 5910313_f2_30 | 1390 | 3310 | 392 | 1179 | 895 | 1.3e-89 |

| Protein name | | | | Locus Name | | Acc# |
|---|---|---|---|---|---|---|
| homoserine O-acetyltransferase | | | | gp:LMMETYX | | Y10744 |

Description

L.meyeri metY and metX genes.

| ORF_Name | NTID | AAID | NT Length | AA Length | Score | Probability |
|---|---|---|---|---|---|---|
| 5976592_f2_41 | 1391 | 3311 | 152 | 459 | 276 | 5.0e-24 |

| Protein name | Locus Name | Acc# |
|---|---|---|
| LporfX | gp:LPU63641 | U63641 |

Description

Legionella pneumophila rpoD operon LporfX, LpdnaG, and LprpoDgenes, complete cds.

| ORF_Name | NTID | AAID | NT Length | AA Length | Score | Probability |
|---|---|---|---|---|---|---|
| 818765_f1_7 | 1392 | 3312 | 98 | 297 | | |

| Protein name | Locus Name | Acc# |
|---|---|---|

Description

NO-HIT

| ORF_Name | NTID | AAID | NT Length | AA Length | Score | Probability |
|---|---|---|---|---|---|---|
| 9765832_f2_38 | 1393 | 3313 | 458 | 1377 | 1102 | 1.5e-111 |

| Protein name | Locus Name | Acc# |
|---|---|---|
| homoserine dehydrogenase | gp:L78665 | L78665 |

Description

Methylobacillus flagellatum aspartate aminotransferase (aat),membrane protein (orf-1), homoserine dehydrogenase (hom), andthreonine synthase (thrC) thymidylate sythase (thyA) genes,complete cds.

| ORF_Name | NTID | AAID | NT Length | AA Length | Score | Probability |
|---|---|---|---|---|---|---|
| 9773436_f2_31 | 1394 | 3314 | 215 | 648 | 117 | 0.00011 |

| Protein name | Locus Name | Acc# |
|---|---|---|
| probable 24-sterol C-methyltransferase, | pir:T03845 | T03845 |

Description

| ORF_Name | NTID | AAID | NT Length | AA Length | Score | Probability |
|---|---|---|---|---|---|---|
| 10423125_c2_44 | 1395 | 3315 | 124 | 375 | | |

| Protein name | Locus Name | Acc# |
|---|---|---|

Description

NO-HIT

| ORF Name | NTID | AAID | NT Length | AA Length | Score | Probability |
|---|---|---|---|---|---|---|
| 1069202_f2_13 | 1396 | 3316 | 65 | 198 | | |

Protein name | Locus Name | Acc#

Description

NO-HIT

| ORF Name | NTID | AAID | NT Length | AA Length | Score | Probability |
|---|---|---|---|---|---|---|
| 12933427_f2_5 | 1397 | 3317 | 131 | 396 | 239 | 4.1e-20 |

Protein name | Locus Name | Acc#
 | sp:DHSC_ECOLI | P10446

Description

SUCCINATE DEHYDROGENASE CYTOCHROME B-556 SUBUNIT

| ORF Name | NTID | AAID | NT Length | AA Length | Score | Probability |
|---|---|---|---|---|---|---|
| 20330461_f3_19 | 1398 | 3318 | 229 | 690 | 714 | 1.9e-70 |

Protein name | Locus Name | Acc#
fumarate reductase flavoprotein subunit | gp:AB015757 | AB015757

Description

Rhodoferax fermentans genes for fumarate reductase subunits,complete cds.

| ORF Name | NTID | AAID | NT Length | AA Length | Score | Probability |
|---|---|---|---|---|---|---|
| 214128_f2_9 | 1399 | 3319 | 763 | 2292 | 2566 | 1.1e-266 |

Protein name | Locus Name | Acc#
 | sp:ODO1_AZOVI | P20707

Description (KETOGLUTARATE DEHYDROGENASE)

| ORF Name | NTID | AAID | NT Length | AA Length | Score | Probability |
|---|---|---|---|---|---|---|
| 21501557_f3_27 | 1400 | 3320 | 80 | 243 | | |

Protein name | Locus Name | Acc#

Description

NO-HIT

| ORF Name | NTID | AAID | NT Length | AA Length | Score | Probability |
|---|---|---|---|---|---|---|
| 21510931_f2_6 | 1401 | 3321 | 381 | 1146 | 1445 | 6.6e-148 |

Protein name: fumarate reductase flavoprotein subunit
Locus Name: gp:AB015757
Acc#: AB015757

Description: Rhodoferax fermentans genes for fumarate reductase subunits, complete cds.

| ORF Name | NTID | AAID | NT Length | AA Length | Score | Probability |
|---|---|---|---|---|---|---|
| 23469010_f3_25 | 1402 | 3322 | 62 | 189 | | |

Protein name:
Locus Name:
Acc#:

Description: NO-HIT

| ORF Name | NTID | AAID | NT Length | AA Length | Score | Probability |
|---|---|---|---|---|---|---|
| 23855067_c3_53 | 1403 | 3323 | 183 | 552 | 76 | 0.018 |

Protein name: putative adhesin MAA1
Locus Name: gp:AF154922
Acc#: AF154922

Description: Mycoplasma arthritidis strain 158 putative adhesin MAA1 (maa1) gene, complete cds.

| ORF Name | NTID | AAID | NT Length | AA Length | Score | Probability |
|---|---|---|---|---|---|---|
| 24241463_f2_10 | 1404 | 3324 | 68 | 207 | 131 | 2.6e-07 |

Protein name:
Locus Name: sp:ODO1_HAEIN
Acc#: P45303

Description: KETOGLUTARATE DEHYDROGENASE)

| ORF Name | NTID | AAID | NT Length | AA Length | Score | Probability |
|---|---|---|---|---|---|---|
| 24251441_f1_4 | 1405 | 3325 | 375 | 1128 | 129 | 5.8e-05 |

Protein name: heme receptor
Locus Name: gp:VIBHUTA
Acc#: L27149

Description: Vibrio cholerae heme receptor (hutA) gene, complete cds.

| ORF Name | NTID | AAID | NT Length | AA Length | Score | Probability |
|---|---|---|---|---|---|---|
| 24427262_f2_8 | 1406 | 3326 | 123 | 372 | 234 | 2.6e-18 |

| Protein name | Locus Name | Acc# |
|---|---|---|
| alpha-ketoglutarate dehydrogenase | gp:AF068740 | AF068740 |

Description

Pseudomonas putida dihydrolipoamide succinyltransferase (kgdB) andalpha-ketoglutarate dehydrogenase (kgdA) genes, complete cds.

| ORF Name | NTID | AAID | NT Length | AA Length | Score | Probability |
|---|---|---|---|---|---|---|
| 26367192_f1_2 | 1407 | 3327 | 488 | 1467 | 1401 | 3.0e-143 |

| Protein name | Locus Name | Acc# |
|---|---|---|
| dihydrolipoamide dehydrogenase | gp:PSELPDA | M28356 |

Description

P.fluorescens dihydrolipoamide dehydrogenase (lpd) gene, completecds.

| ORF Name | NTID | AAID | NT Length | AA Length | Score | Probability |
|---|---|---|---|---|---|---|
| 26377042_f2_7 | 1408 | 3328 | 192 | 579 | 790 | 1.7e-78 |

| Protein name | Locus Name | Acc# |
|---|---|---|
| succinate dehydrogenase putative iron sulphur | gp:SPSDH | Y13760 |

Description

Shewanella frigidimarina NCIMB400 sdhA, sdhB, sdhC, sdhD and sucAgenes.

| ORF Name | NTID | AAID | NT Length | AA Length | Score | Probability |
|---|---|---|---|---|---|---|
| 31439375_f1_1 | 1409 | 3329 | 135 | 408 | 275 | 6.3e-24 |

| Protein name | Locus Name | Acc# |
|---|---|---|
|  | sp:DHSD_ECOLI | P10445 |

Description

SUCCINATE DEHYDROGENASE HYDROPHOBIC MEMBRANE ANCHOR PROTEIN

| ORF Name | NTID | AAID | NT Length | AA Length | Score | Probability |
|---|---|---|---|---|---|---|
| 4064425_f3_26 | 1410 | 3330 | 599 | 1800 | 123 | 8.1e-05 |

| Protein name | Locus Name | Acc# |
|---|---|---|
|  | sp:FOXA_SALTY | Q56145 |

Description

FERRIOXAMINE B RECEPTOR PRECURSOR (FRAGMENT)

| ORF Name | NTID | AAID | NT Length | AA Length | Score | Probability |
|---|---|---|---|---|---|---|
| 584625_f2_11 | 1411 | 3331 | 420 | 1263 | 1194 | 2.6e-121 |

| Protein name | Locus Name | Acc# |
|---|---|---|
| dihydrolipoamide S-succinyltransferase,:2-oxogluturate dehydrogenase complex chain E2:succinyl | pir:S07779 |  |

Description

| ORF Name | NTID | AAID | NT Length | AA Length | Score | Probability |
|---|---|---|---|---|---|---|
| 9928130_c1_34 | 1412 | 3332 | 141 | 426 | 116 | 8.6e-07 |

| Protein name | Locus Name | Acc# |
|---|---|---|
| microfilarial sheath protein SHP3 precursor | gp:AF030944 |  |

Description

Brugia malayi microfilarial sheath protein SHP3a (Bmshp3a) andmicrofilarial sheath protein SHP3 precursor (Bmshp3) genes,complete cds.

| ORF Name | NTID | AAID | NT Length | AA Length | Score | Probability |
|---|---|---|---|---|---|---|
| 12619081_c3_114 | 1413 | 3333 | 147 | 444 | 205 | 1.7e-16 |

| Protein name | Locus Name | Acc# |
|---|---|---|
|  | sp:YBAN_ECOLI |  |

Description

HYPOTHETICAL 14.8 KD PROTEIN IN PRIC-APT INTERGENIC REGION

| ORF Name | NTID | AAID | NT Length | AA Length | Score | Probability |
|---|---|---|---|---|---|---|
| 12897562_c1_73 | 1414 | 3334 | 78 | 237 |  |  |

| Protein name | Locus Name | Acc# |
|---|---|---|

Description

NO-HIT

| ORF Name | NTID | AAID | NT Length | AA Length | Score | Probability |
|---|---|---|---|---|---|---|
| 1359776_c2_91 | 1415 | 3335 | 67 | 204 | | |

| Protein name | | | | | Locus Name | Acc# |
|---|---|---|---|---|---|---|
| | | | | | | |

Description

NO-HIT

| ORF Name | NTID | AAID | NT Length | AA Length | Score | Probability |
|---|---|---|---|---|---|---|
| 14064028_c2_105 | 1416 | 3336 | 269 | 810 | 182 | 4.5e-14 |

| Protein name | | | | | Locus Name | Acc# |
|---|---|---|---|---|---|---|
| | | | | | sp:YEAB_ECOLI | P43337 |

Description

HYPOTHETICAL 21.4 KD PROTEIN IN PABB-SDAA INTERGENIC REGION

| ORF Name | NTID | AAID | NT Length | AA Length | Score | Probability |
|---|---|---|---|---|---|---|
| 14657782_c2_104 | 1417 | 3337 | 173 | 522 | 333 | 4.5e-30 |

| Protein name | | | | | Locus Name | Acc# |
|---|---|---|---|---|---|---|
| | | | | | sp:BID2_HAEIN | P45248 |

Description 2) (DTB SYNTHETASE 2) (DTBS 2)

| ORF Name | NTID | AAID | NT Length | AA Length | Score | Probability |
|---|---|---|---|---|---|---|
| 14719437_f1_22 | 1418 | 3338 | 63 | 192 | | |

| Protein name | | | | | Locus Name | Acc# |
|---|---|---|---|---|---|---|
| | | | | | | |

Description

NO-HIT

| ORF Name | NTID | AAID | NT Length | AA Length | Score | Probability |
|---|---|---|---|---|---|---|
| 14882713_c3_116 | 1419 | 3339 | 287 | 864 | 289 | 8.1e-30 |

| Protein name | | | | | Locus Name | Acc# |
|---|---|---|---|---|---|---|
| | | | | | sp:BIOC_HAEIN | P45249 |

Description

PUTATIVE BIOTIN SYNTHESIS PROTEIN BIOC

| ORF Name | NTID | AAID | NT Length | AA Length | Score | Probability |
|---|---|---|---|---|---|---|
| 16464750_c2_86 | 1420 | 3340 | 326 | 981 | 123 | 6.0e-05 |

| Protein name | | | | Locus Name | | Acc# |
|---|---|---|---|---|---|---|
| | | | | sp:ZIPA_ECOLI | | P77173 |

Description

CELL DIVISION PROTEIN ZIPA

| ORF Name | NTID | AAID | NT Length | AA Length | Score | Probability |
|---|---|---|---|---|---|---|
| 16532256_f1_1 | 1421 | 3341 | 80 | 243 | 95 | 0.0015 |

| Protein name | | | | Locus Name | | Acc# |
|---|---|---|---|---|---|---|
| ubiquitin protein ligase | | | | pir:T39585 | | T39585 |

Description

| ORF Name | NTID | AAID | NT Length | AA Length | Score | Probability |
|---|---|---|---|---|---|---|
| 19572130_f3_58 | 1422 | 3342 | 310 | 933 | 1010 | 8.2e-102 |

| Protein name | | | | Locus Name | | Acc# |
|---|---|---|---|---|---|---|
| | | | | sp:CYSM_ECOLI | | P16703 |

Description (O-ACETYLSERINE (THIOL)-LYASE B) (CSASE B)

| ORF Name | NTID | AAID | NT Length | AA Length | Score | Probability |
|---|---|---|---|---|---|---|
| 19734630_f2_40 | 1423 | 3343 | 533 | 1602 | 400 | 3.1e-57 |

| Protein name | | | | Locus Name | | Acc# |
|---|---|---|---|---|---|---|
| | | | | sp:YGCA_HAEIN | | P44643 |

Description

HYPOTHETICAL RNA METHYLTRANSFERASE HI0333,

| ORF Name | NTID | AAID | NT Length | AA Length | Score | Probability |
|---|---|---|---|---|---|---|
| 20507762_f1_13 | 1424 | 3344 | 290 | 873 | 548 | 7.5e-53 |

| Protein name | | | | Locus Name | | Acc# |
|---|---|---|---|---|---|---|
| | | | | sp:DPSD_ECOLI | | P10740 |

Description

PHOSPHATIDYLSERINE DECARBOXYLASE PROENZYME,

| ORF Name | NTID | AAID | NT Length | AA Length | Score | Probability |
|---|---|---|---|---|---|---|
| 20839062_c2_92 | 1425 | 3345 | 444 | 1335 | 482 | 1.3e-48 |

| Protein name | | | | Locus Name | | Acc# |
|---|---|---|---|---|---|---|
| | | | | sp:DEAD_HAEIN | | P44586 |

Description

ATP-DEPENDENT RNA HELICASE DEAD HOMOLOG

| ORF Name | NTID | AAID | NT Length | AA Length | Score | Probability |
|---|---|---|---|---|---|---|
| 22144026_f1_26 | 1426 | 3346 | 284 | 855 | 443 | 4.3e-41 |

| Protein name | | | | Locus Name | | Acc# |
|---|---|---|---|---|---|---|
| | | | | sp:RELA_HAEIN | | P44644 |

Description (PPGPP SYNTHETASE I)

| ORF Name | NTID | AAID | NT Length | AA Length | Score | Probability |
|---|---|---|---|---|---|---|
| 22147806_f3_47 | 1427 | 3347 | 421 | 1266 | 866 | 1.5e-86 |

| Protein name | | | | Locus Name | | Acc# |
|---|---|---|---|---|---|---|
| | | | | sp:YGIC_ECOLI | | P24196 |

Description (O386)

| ORF Name | NTID | AAID | NT Length | AA Length | Score | Probability |
|---|---|---|---|---|---|---|
| 22691300_c2_99 | 1428 | 3348 | 612 | 1839 | 688 | 7.1e-72 |

| Protein name | | | | Locus Name | | Acc# |
|---|---|---|---|---|---|---|
| sensor kinase rtpA | | | | gp:AB002529 | | AB002529 |

Description

Pseudomonas tolaasii gene for sensor kinase rtpA, complete cds.

| ORF Name | NTID | AAID | NT Length | AA Length | Score | Probability |
|---|---|---|---|---|---|---|
| 22890917_f2_33 | 1429 | 3349 | 258 | 777 | 196 | 1.5e-15 |

Protein name | Locus Name | Acc#
| | sp:YBEN_ECOLI | P52085 |

Description

HYPOTHETICAL 24.5 KD PROTEIN IN PHPB-HOLA INTERGENIC REGION (ORFUU)

| ORF Name | NTID | AAID | NT Length | AA Length | Score | Probability |
|---|---|---|---|---|---|---|
| 23478458_c2_103 | 1430 | 3350 | 441 | 1326 | 1328 | 1.7e-135 |

Protein name | Locus Name | Acc#
BioA | gp:AF191556 | AF191556

Description

Xenorhabdus nematophilus YbhE (ybhE) gene, partial cds; Var1 (var1)and BioA (bioA) genes, complete cds; and unknown gene.

| ORF Name | NTID | AAID | NT Length | AA Length | Score | Probability |
|---|---|---|---|---|---|---|
| 24097812_c1_83 | 1431 | 3351 | 208 | 627 | 462 | 9.7e-44 |

Protein name | Locus Name | Acc#
| | sp:SSB_HAEIN | P44409 |

Description

SINGLE-STRAND BINDING PROTEIN (SSB) (HELIX-DESTABILIZING PROTEIN)

| ORF Name | NTID | AAID | NT Length | AA Length | Score | Probability |
|---|---|---|---|---|---|---|
| 24225088_f2_39 | 1432 | 3352 | 61 | 186 | | |

Protein name | Locus Name | Acc#

Description

NO-HIT

| ORF Name | NTID | AAID | NT Length | AA Length | Score | Probability |
|---|---|---|---|---|---|---|
| 25587827_c1_79 | 1433 | 3353 | 400 | 1203 | 888 | 7.0e-89 |

Protein name | Locus Name | Acc#
| | sp:BIOF_HAEIN | P44422 |

Description (LIGASE)

| ORF Name | NTID | AAID | NT Length | AA Length | Score | Probability |
|---|---|---|---|---|---|---|
| 26192160_f3_64 | 1434 | 3354 | 532 | 1599 | 894 | 1.6e-89 |

| Protein name | Locus Name | Acc# |
|---|---|---|
| | sp:RELA_ECOLI | P11585 |

Description (PPGPP SYNTHETASE I)

| ORF Name | NTID | AAID | NT Length | AA Length | Score | Probability |
|---|---|---|---|---|---|---|
| 29298385_f1_8 | 1435 | 3355 | 211 | 636 | 380 | 4.7e-35 |

| Protein name | Locus Name | Acc# |
|---|---|---|
| | gp:U90439 | |

Description

Arabidopsis thaliana chromosome II section 227 of 255 of thecomplete sequence.

| ORF Name | NTID | AAID | NT Length | AA Length | Score | Probability |
|---|---|---|---|---|---|---|
| 33708181_c1_75 | 1436 | 3356 | 411 | 1236 | 391 | 3.2e-36 |

| Protein name | Locus Name | Acc# |
|---|---|---|
| putative histidine kinase | gp:PST249741 | AJ249741 |

Description

Pseudomonas stutzeri JM300 gacS (partial) and ggtB (partial) genes.

| ORF Name | NTID | AAID | NT Length | AA Length | Score | Probability |
|---|---|---|---|---|---|---|
| 33728258_c3_117 | 1437 | 3357 | 78 | 237 | 85 | 0.0019 |

| Protein name | Locus Name | Acc# |
|---|---|---|
| | sp:BID2_HAEIN | P45248 |

Description 2) (DTB SYNTHETASE 2) (DTBS 2)

| ORF Name | NTID | AAID | NT Length | AA Length | Score | Probability |
|---|---|---|---|---|---|---|
| 35173953_f1_7 | 1438 | 3358 | 152 | 459 | 237 | 6.8e-20 |

| Protein name | Locus Name | Acc# |
|---|---|---|
|  | sp:YBEB_ECOLI |  |

Description

HYPOTHETICAL 11.6 KD PROTEIN IN MRDA-PHPB INTERGENIC REGION

| ORF Name | NTID | AAID | NT Length | AA Length | Score | Probability |
|---|---|---|---|---|---|---|
| 35183451_f2_38 | 1439 | 3359 | 261 | 786 | 259 | 3.1e-22 |

| Protein name | Locus Name | Acc# |
|---|---|---|
| hypothetical protein jhp0628 | pir:B71907 | B71907 |

Description

| ORF Name | NTID | AAID | NT Length | AA Length | Score | Probability |
|---|---|---|---|---|---|---|
| 4147637_c3_120 | 1440 | 3360 | 990 | 2973 | 3281 | 0.0 |

| Protein name | Locus Name | Acc# |
|---|---|---|
|  | sp:UVRA_ECOLI |  |

Description

EXCINUCLEASE ABC SUBUNIT A

| ORF Name | NTID | AAID | NT Length | AA Length | Score | Probability |
|---|---|---|---|---|---|---|
| 4199006_f3_56 | 1441 | 3361 | 69 | 210 | 52 | 0.022 |

| Protein name | Locus Name | Acc# |
|---|---|---|
| NADH dehydrogenase subunit 4 | gp:AF026170 | AF026170 |

Description

Teius teyou NADH dehydrogenase subunit 4 (ND4) gene, partial cds;and tRNA-His, tRNA-Ser, and tRNA-Leu genes, complete sequence,mitochondrial genes for mitochondrial products.

| ORF Name | NTID | AAID | NT Length | AA Length | Score | Probability |
|---|---|---|---|---|---|---|
| 4328431_f3_65 | 1442 | 3362 | 305 | 918 | 542 | 3.2e-52 |

| Protein name | Locus Name | Acc# |
|---|---|---|
| | sp:FPG_NEIME | P55044 |

Description

GLYCOSYLASE)

| ORF Name | NTID | AAID | NT Length | AA Length | Score | Probability |
|---|---|---|---|---|---|---|
| 4867812_c3_118 | 1443 | 3363 | 154 | 465 | 318 | 1.8e-28 |

| Protein name | Locus Name | Acc# |
|---|---|---|
| | sp:YIHZ_ECOLI | P32147 |

Description

HYPOTHETICAL 15.9 KD PROTEIN IN RBN-FDHE INTERGENIC REGION (O145)

| ORF Name | NTID | AAID | NT Length | AA Length | Score | Probability |
|---|---|---|---|---|---|---|
| 892177_c1_70 | 1444 | 3364 | 169 | 510 | 331 | 7.4e-30 |

| Protein name | Locus Name | Acc# |
|---|---|---|
| | gp:D83386 | D83386 |

Description

Shewanella violacea rhlE, cydD, cydC and putA genes, partial and complete cds.

| ORF Name | NTID | AAID | NT Length | AA Length | Score | Probability |
|---|---|---|---|---|---|---|
| 16847336_f3_5 | 1445 | 3365 | 177 | 534 | 633 | 7.3e-62 |

| Protein name | Locus Name | Acc# |
|---|---|---|
| DNA-directed RNA polymerase alpha chain | gp:AF047025 | AF047025 |

Description

Pseudomonas aeruginosa ribosomal protein S4 (rpsD) gene, partial cds; DNA-directed RNA polymerase alpha chain (rpoA), ribosomal large subunit protein L17 (rplQ), and catalase isozyme A (katA) genes, complete cds; and bacterioferritin (bfr) gene, partial cds.

| ORF_Name | NTID | AAID | NT Length | AA Length | Score | Probability |
|---|---|---|---|---|---|---|
| 16976442_c3_13 | 1446 | 3366 | 239 | 720 | 359 | 8.0e-33 |

Protein name | Locus Name | Acc#
--- | --- | ---
 | sp:YFCM_ECOLI |

Description

HYPOTHETICAL 21.1 KD PROTEIN IN FABB-MEPA INTERGENIC REGION

| ORF_Name | NTID | AAID | NT Length | AA Length | Score | Probability |
|---|---|---|---|---|---|---|
| 24226655_f2_3 | 1447 | 3367 | 165 | 498 | 499 | 1.2e-47 |

Protein name | Locus Name | Acc#
--- | --- | ---
DNA-directed RNA polymerase alpha chain | gp:AF047025 | AF047025

Description

Pseudomonas aeruginosa ribosomal protein S4 (rpsD) gene, partial cds; DNA-directed RNA polymerase alpha chain (rpoA), ribosomal large subunit protein L17 (rplQ), and catalase isozyme A (katA) genes, complete cds; and bacterioferritin (bfr) gene, partial cds.

| ORF_Name | NTID | AAID | NT Length | AA Length | Score | Probability |
|---|---|---|---|---|---|---|
| 24317501_f2_4 | 1448 | 3368 | 83 | 252 | 354 | 2.7e-32 |

Protein name | Locus Name | Acc#
--- | --- | ---
 | sp:RL17_PSEAE | O52761

Description

50S RIBOSOMAL PROTEIN L17

| ORF_Name | NTID | AAID | NT Length | AA Length | Score | Probability |
|---|---|---|---|---|---|---|
| 3001693_f2_2 | 1449 | 3369 | 217 | 654 | 683 | 3.7e-67 |

Protein name | Locus Name | Acc#
--- | --- | ---
ribosomal protein S4 | pir:A64095 | A64095

Description

| ORF Name | NTID | AAID | NT Length | AA Length | Score | Probability |
|---|---|---|---|---|---|---|
| 4867143_c1_9 | 1450 | 3370 | 191 | 576 | 314 | 4.7e-28 |

| Protein name | Locus Name | Acc# |
|---|---|---|
| probable translation factor yciO | pir:F64874 | F64874 |

Description

---

| ORF Name | NTID | AAID | NT Length | AA Length | Score | Probability |
|---|---|---|---|---|---|---|
| 6033377_c3_14 | 1451 | 3371 | 94 | 285 | 84 | 0.035 |

| Protein name | Locus Name | Acc# |
|---|---|---|
| hypothetical protein C34F6.9 | pir:T19736 | T19736 |

Description

---

| ORF Name | NTID | AAID | NT Length | AA Length | Score | Probability |
|---|---|---|---|---|---|---|
| 10437517_c1_70 | 1452 | 3372 | 62 | 189 | | |

| Protein name | Locus Name | Acc# |
|---|---|---|

Description

NO-HIT

| ORF Name | NTID | AAID | NT Length | AA Length | Score | Probability |
|---|---|---|---|---|---|---|
| 11808576_c2_83 | 1453 | 3373 | 72 | 219 | | |

| Protein name | Locus Name | Acc# |
|---|---|---|

Description

NO-HIT

| ORF Name | NTID | AAID | NT Length | AA Length | Score | Probability |
|---|---|---|---|---|---|---|
| 1359677_f2_17 | 1454 | 3374 | 373 | 1122 | 969 | 1.8e-97 |

| Protein name | Locus Name | Acc# |
|---|---|---|
| uroporphyrinogen decarboxylase | gp:ECOUW89 | U00006 |

Description

E. coli chromosomal region from 89.2 to 92.8 minutes.

| ORF Name | NTID | AAID | NT Length | AA Length | Score | Probability |
|---|---|---|---|---|---|---|
| 14898317_c3_94 | 1455 | 3375 | 591 | 1776 | 1769 | 3.1e-182 |

| Protein name | Locus Name | Acc# |
|---|---|---|
| | sp:SYD_ECOLI | P21889 |

Description (ASPRS)

| ORF Name | NTID | AAID | NT Length | AA Length | Score | Probability |
|---|---|---|---|---|---|---|
| 16522206_c1_56 | 1456 | 3376 | 207 | 624 | | |

| Protein name | Locus Name | Acc# |
|---|---|---|

Description

NO-HIT

| ORF Name | NTID | AAID | NT Length | AA Length | Score | Probability |
|---|---|---|---|---|---|---|
| 16614042_c3_107 | 1457 | 3377 | 125 | 378 | 142 | 7.9e-10 |

| Protein name | Locus Name | Acc# |
|---|---|---|
| hypothetical protein slr1903 | pir:S77514 | S77514 |

Description

| ORF Name | NTID | AAID | NT Length | AA Length | Score | Probability |
|---|---|---|---|---|---|---|
| 175817_f3_32 | 1458 | 3378 | 442 | 1329 | 1020 | 7.2e-103 |

| Protein name | Locus Name | Acc# |
|---|---|---|
| glyceraldehyde-3-phosphate dehydrogenase | gp:AF058302 | AF058302 |

Description

Streptomyces roseofulvus frenolicin biosynthetic gene cluster, complete sequence.

| ORF Name | NTID | AAID | NT Length | AA Length | Score | Probability |
|---|---|---|---|---|---|---|
| 20984532_c1_68 | 1459 | 3379 | 60 | 183 | | |

| Protein name | Locus Name | Acc# |
|---|---|---|

Description

NO-HIT

| ORF Name | NTID | AAID | NT Length | AA Length | Score | Probability |
|---|---|---|---|---|---|---|
| 2142151_f3_38 | 1460 | 3380 | 252 | 759 | 421 | 2.1e-39 |

| Protein name | Locus Name | Acc# |
|---|---|---|
| anion transport ABC transporter (ATP-bindi) homolog ytlC | pir:C69995 | C69995 |

Description

| ORF Name | NTID | AAID | NT Length | AA Length | Score | Probability |
|---|---|---|---|---|---|---|
| 23437558_f2_24 | 1461 | 3381 | 348 | 1047 | 946 | 5.0e-95 |

| Protein name | Locus Name | Acc# |
|---|---|---|
| 3-phosphoserine aminotransferase | gp:AF038578 | |

Description

Pseudomonas stutzeri gyrase A subunit (gyrA) gene, partial cds;3-phosphoserine aminotransferase (serC), chorismatemutase/prephenate dehydratase (aroQp/pheA), imidazole acetolphosphate aminotransferase (hisHb), and cyclohexadienyldehydrogenase (tyrAc) genes, complete cds; and5-enolpyruvylshikmate 3-P synthase (aroF) gene, partial cds.

| ORF Name | NTID | AAID | NT Length | AA Length | Score | Probability |
|---|---|---|---|---|---|---|
| 23526888_f1_7 | 1462 | 3382 | 65 | 198 | | |

| Protein name | Locus Name | Acc# |
|---|---|---|
| | | |

Description

NO-HIT

| ORF Name | NTID | AAID | NT Length | AA Length | Score | Probability |
|---|---|---|---|---|---|---|
| 23642875_f3_39 | 1463 | 3383 | 255 | 768 | | |

| Protein name | Locus Name | Acc# |
|---|---|---|
| | | |

Description

NO-HIT

| ORF Name | NTID | AAID | NT Length | AA Length | Score | Probability |
|---|---|---|---|---|---|---|
| 24103137_f2_16 | 1464 | 3384 | 409 | 1230 | 1079 | 4.0e-109 |

| Protein name | | | | Locus Name | | Acc# |
|---|---|---|---|---|---|---|
| | | | | sp:YHBZ_HAEIN | | P44915 |

Description

HYPOTHETICAL 43.4 KD GTP-BINDING PROTEIN HI0877

| ORF Name | NTID | AAID | NT Length | AA Length | Score | Probability |
|---|---|---|---|---|---|---|
| 24272135_c3_103 | 1465 | 3385 | 174 | 525 | 295 | 4.8e-26 |

| Protein name | | | | Locus Name | | Acc# |
|---|---|---|---|---|---|---|
| Lrp-family transcriptional regulators | | | | gp:D89015 | | D89015 |

Description

Pseudomonas putida genes for MdeR,MdeA and MdeB,complete cds.

| ORF Name | NTID | AAID | NT Length | AA Length | Score | Probability |
|---|---|---|---|---|---|---|
| 24410038_f2_19 | 1466 | 3386 | 443 | 1332 | 743 | 1.6e-73 |

| Protein name | | | | Locus Name | | Acc# |
|---|---|---|---|---|---|---|
| proteinase DO | | | | pir:H71936 | | H71936 |

Description

| ORF Name | NTID | AAID | NT Length | AA Length | Score | Probability |
|---|---|---|---|---|---|---|
| 25662512_c3_98 | 1467 | 3387 | 304 | 915 | 532 | 3.7e-51 |

| Protein name | | | | Locus Name | | Acc# |
|---|---|---|---|---|---|---|
| | | | | sp:YJJP_ECOLI | | P39402 |

Description

HYPOTHETICAL 30.5 KD PROTEIN IN DNAT-BGLJ INTERGENIC REGION (F277)

| ORF Name | NTID | AAID | NT Length | AA Length | Score | Probability |
|---|---|---|---|---|---|---|
| 25665963_f1_5 | 1468 | 3388 | 264 | 795 | 444 | 7.8e-42 |

| Protein name | | | | Locus Name | | Acc# |
|---|---|---|---|---|---|---|
| | | | | sp:GLO2_ECOLI | | Q47677 |

Description

II) (GLX II)

| ORF Name | NTID | AAID | NT Length | AA Length | Score | Probability |
|---|---|---|---|---|---|---|
| 2757750_f3_47 | 1469 | 3389 | 72 | 219 | 73 | 0.016 |

| Protein name | | | | Locus Name | | Acc# |
|---|---|---|---|---|---|---|
| | | | | gp:AB021078 | | AB021078 |

Description plasmid ColIb-P9 DNA, complete sequence.

| ORF Name | NTID | AAID | NT Length | AA Length | Score | Probability |
|---|---|---|---|---|---|---|
| 31412958_f2_23 | 1470 | 3390 | 250 | 753 | | |

| Protein name | | | | Locus Name | | Acc# |
|---|---|---|---|---|---|---|

Description

NO-HIT

| ORF Name | NTID | AAID | NT Length | AA Length | Score | Probability |
|---|---|---|---|---|---|---|
| 33394002_f2_30 | 1471 | 3391 | 507 | 1524 | 79 | 0.036 |

| Protein name | | | | Locus Name | | Acc# |
|---|---|---|---|---|---|---|
| cytochrome-c oxidase, chain I RP405 | | | | pir:D71698 | | D71698 |

Description

| ORF Name | NTID | AAID | NT Length | AA Length | Score | Probability |
|---|---|---|---|---|---|---|
| 35181680_c3_95 | 1472 | 3392 | 356 | 1071 | 267 | 4.5e-23 |

| Protein name | | | | Locus Name | | Acc# |
|---|---|---|---|---|---|---|
| | | | | gp:PFY14568 | | Y14568 |

Description

Pseudomonas fluorescens tag gene and partial glyQ, htrB genes.

| ORF Name | NTID | AAID | NT Length | AA Length | Score | Probability |
|---|---|---|---|---|---|---|
| 4009750_c1_69 | 1473 | 3393 | 221 | 666 | 279 | 2.4e-24 |

| Protein name | | | | Locus Name | | Acc# |
|---|---|---|---|---|---|---|
| hypothetical protein | | | | pir:S76551 | | S76551 |

Description

| ORF Name | NTID | AAID | NT Length | AA Length | Score | Probability |
|---|---|---|---|---|---|---|
| 4165952_f3_34 | 1474 | 3394 | 82 | 249 | | |

| Protein name | Locus Name | Acc# |
|---|---|---|
| | | |

Description

NO-HIT

| ORF Name | NTID | AAID | NT Length | AA Length | Score | Probability |
|---|---|---|---|---|---|---|
| 4328443_c1_74 | 1475 | 3395 | 176 | 531 | 193 | 3.1e-15 |

| Protein name | Locus Name | Acc# |
|---|---|---|
| hypothetical protein | pir:G75479 | G75479 |

Description

| ORF Name | NTID | AAID | NT Length | AA Length | Score | Probability |
|---|---|---|---|---|---|---|
| 4423193_c2_79 | 1476 | 3396 | 85 | 258 | 87 | 4.6e-07 |

| Protein name | Locus Name | Acc# |
|---|---|---|
| | sp:ARGD_ARCFU | O30156 |

Description

ACETYLORNITHINE AMINOTRANSFERASE, (ACOAT)

| ORF Name | NTID | AAID | NT Length | AA Length | Score | Probability |
|---|---|---|---|---|---|---|
| 4864077_c2_78 | 1477 | 3397 | 63 | 192 | 149 | 1.4e-10 |

| Protein name | Locus Name | Acc# |
|---|---|---|
| unknown | gp:AF062531 | AF062531 |

Description

Pseudomonas putida GB-1 signal peptidase (pilD) gene, partial cds;and unknown genes.

| ORF Name | NTID | AAID | NT Length | AA Length | Score | Probability |
|---|---|---|---|---|---|---|
| 4878407_f1_6 | 1478 | 3398 | 589 | 1770 | 1355 | 2.3e-138 |

| Protein name | Locus Name | Acc# |
|---|---|---|
| | sp:LEU1_YEAST | P06208 |

Description

SYNTHASE) (ALPHA-IPM SYNTHETASE)

| ORF_Name | NTID | AAID | NT Length | AA Length | Score | Probability |
|---|---|---|---|---|---|---|
| 5085963_f1_11 | 1479 | 3399 | 243 | 732 | 124 | 3.2e-13 |

Protein name: (blank) — Locus Name: sp:YDFN_BACSU — Acc#: P96692

Description: PUTATIVE NAD(P)H NITROREDUCTASE YDFN,

| ORF_Name | NTID | AAID | NT Length | AA Length | Score | Probability |
|---|---|---|---|---|---|---|
| 5115943_f2_21 | 1480 | 3400 | 330 | 993 | 585 | 9.0e-57 |

Protein name: hypothetical protein TM0484 — Locus Name: pir:C72369 — Acc#: C72369

Description:

| ORF_Name | NTID | AAID | NT Length | AA Length | Score | Probability |
|---|---|---|---|---|---|---|
| 5266588_f2_29 | 1481 | 3401 | 878 | 2637 | 2754 | 1.3e-286 |

Protein name: UspA1 — Locus Name: gp:AF113606 — Acc#: AF113606

Description: Moraxella catarrhalis strain ATCC25238 UspA1 (uspA1) gene, completecds.

| ORF_Name | NTID | AAID | NT Length | AA Length | Score | Probability |
|---|---|---|---|---|---|---|
| 802137_f3_37 | 1482 | 3402 | 261 | 786 | 459 | 2.0e-43 |

Protein name: ABC transporter, permease protein, cysTW family — Locus Name: pir:D72369 — Acc#: D72369

Description:

| ORF_Name | NTID | AAID | NT Length | AA Length | Score | Probability |
|---|---|---|---|---|---|---|
| 894387_c2_80 | 1483 | 3403 | 160 | 483 | 313 | 6.0e-28 |

Protein name: (blank) — Locus Name: sp:YJJP_HAEIN — Acc#: P44520

Description: HYPOTHETICAL PROTEIN HI0108

| ORF Name | NTID | AAID | NT Length | AA Length | Score | Probability |
|---|---|---|---|---|---|---|
| 976558_f2_18 | 1484 | 3404 | 61 | 186 | | |

Protein name | Locus Name | Acc#

Description

NO-HIT

| ORF Name | NTID | AAID | NT Length | AA Length | Score | Probability |
|---|---|---|---|---|---|---|
| 10740682_c2_12 | 1485 | 3405 | 297 | 894 | 678 | 1.3e-66 |

Protein name: probable acyl-CoA dehydrogenase | Locus Name: pir:B75282 | Acc#: B75282

Description

| ORF Name | NTID | AAID | NT Length | AA Length | Score | Probability |
|---|---|---|---|---|---|---|
| 16829202_f3_8 | 1486 | 3406 | 251 | 753 | 185 | 2.2e-14 |

Protein name | Locus Name: sp:PABC_ECOLI | Acc#: P28305

Description

4-AMINO-4-DEOXYCHORISMATE LYASE, (ADC LYASE)

| ORF Name | NTID | AAID | NT Length | AA Length | Score | Probability |
|---|---|---|---|---|---|---|
| 25421887_f1_2 | 1487 | 3407 | 188 | 567 | | |

Protein name | Locus Name | Acc#

Description

NO-HIT

| ORF Name | NTID | AAID | NT Length | AA Length | Score | Probability |
|---|---|---|---|---|---|---|
| 34160918_f3_7 | 1488 | 3408 | 64 | 195 | | |

Protein name | Locus Name | Acc#

Description

NO-HIT

| ORF Name | NTID | AAID | NT Length | AA Length | Score | Probability |
|---|---|---|---|---|---|---|
| 6365631_c3_13 | 1489 | 3409 | 275 | 828 | 475 | 4.1e-45 |

Protein name: shikimate dehydrogenase
Locus Name: gp:NPU82846
Acc#: U82846

Description: Neisseria pharyngis var. flava shikimate dehydrogenase (aroE) gene, complete cds.

| ORF Name | NTID | AAID | NT Length | AA Length | Score | Probability |
|---|---|---|---|---|---|---|
| 12156514_c1_16 | 1490 | 3410 | 162 | 489 | 336 | 2.2e-30 |

Protein name
Locus Name: sp:RSTA_ECOLI
Acc#: P52108

Description: TRANSCRIPTIONAL REGULATORY PROTEIN RSTA

| ORF Name | NTID | AAID | NT Length | AA Length | Score | Probability |
|---|---|---|---|---|---|---|
| 15625078_c1_19 | 1491 | 3411 | 179 | 537 | 444 | 7.8e-42 |

Protein name
Locus Name: sp:TRMD_SERMA
Acc#: P36244

Description: METHYLTRANSFERASE)

| ORF Name | NTID | AAID | NT Length | AA Length | Score | Probability |
|---|---|---|---|---|---|---|
| 23468928_c1_18 | 1492 | 3412 | 191 | 576 | 295 | 4.8e-26 |

Protein name
Locus Name: sp:RIMM_HAEIN
Acc#: P44568

Description: 16S RRNA PROCESSING PROTEIN RIMM

| ORF Name | NTID | AAID | NT Length | AA Length | Score | Probability |
|---|---|---|---|---|---|---|
| 23859377_f1_4 | 1493 | 3413 | 502 | 1509 | 525 | 2.0e-50 |

| Protein name | Locus Name | Acc# |
|---|---|---|
| EnvZ protein | gp:YEOMPR | Y08950 |

Description

Y.enterocolitica ompR and envZ genes.

| ORF Name | NTID | AAID | NT Length | AA Length | Score | Probability |
|---|---|---|---|---|---|---|
| 3961587_c2_21 | 1494 | 3414 | 86 | 261 | 279 | 2.4e-24 |

| Protein name | Locus Name | Acc# |
|---|---|---|
|  | sp:RS16_HAEIN | P44382 |

Description

30S RIBOSOMAL PROTEIN S16

| ORF Name | NTID | AAID | NT Length | AA Length | Score | Probability |
|---|---|---|---|---|---|---|
| 964692_c3_22 | 1495 | 3415 | 598 | 1797 | 442 | 1.3e-41 |

| Protein name | Locus Name | Acc# |
|---|---|---|
|  | sp:RSTB_ECOLI | P18392 |

Description

SENSOR PROTEIN RSTB,

| ORF Name | NTID | AAID | NT Length | AA Length | Score | Probability |
|---|---|---|---|---|---|---|
| 10676257_f2_68 | 1496 | 3416 | 393 | 1182 | 1212 | 3.2e-123 |

| Protein name | Locus Name | Acc# |
|---|---|---|
|  | sp:PUR9_HAEIN | P43852 |

Description

| ORF Name | NTID | AAID | NT Length | AA Length | Score | Probability |
|---|---|---|---|---|---|---|
| 10736257_f3_80 | 1497 | 3417 | 65 | 198 |  |  |

| Protein name | Locus Name | Acc# |
|---|---|---|

Description

NO-HIT

| ORF_Name | NTID | AAID | NT Length | AA Length | Score | Probability |
|---|---|---|---|---|---|---|
| 12556337_f1_31 | 1498 | 3418 | 128 | 387 | 477 | 2.5e-45 |

| Protein name | Locus Name | Acc# |
|---|---|---|
| | sp:PUR9_ECOLI | P15639 |

Description

| ORF_Name | NTID | AAID | NT Length | AA Length | Score | Probability |
|---|---|---|---|---|---|---|
| 1272283_f2_60 | 1499 | 3419 | 183 | 552 | 244 | 7.9e-20 |

| Protein name | Locus Name | Acc# |
|---|---|---|
| | sp:AARF_ECOLI | |

Description

UBIQUINONE BIOSYNTHESIS PROTEIN AARF

| ORF_Name | NTID | AAID | NT Length | AA Length | Score | Probability |
|---|---|---|---|---|---|---|
| 131700_c1_108 | 1500 | 3420 | 255 | 768 | 215 | 1.4e-16 |

| Protein name | Locus Name | Acc# |
|---|---|---|
| putative peptidyl-prolyl cis-trans isomerase | gp:ASAJ2316 | AJ002316 |

Description

Acinetobacter sp. ADP1 alkR & alkM genes, ORF1 & ORF4.

| ORF_Name | NTID | AAID | NT Length | AA Length | Score | Probability |
|---|---|---|---|---|---|---|
| 13876562_c1_128 | 1501 | 3421 | 75 | 228 | 73 | 0.016 |

| Protein name | Locus Name | Acc# |
|---|---|---|
| immunoglobulin kappa light chain variable | gp:AF131156 | AF131156 |

Description

Mus musculus immunoglobulin kappa light chain variable region gene, partial cds.

| ORF_Name | NTID | AAID | NT Length | AA Length | Score | Probability |
|---|---|---|---|---|---|---|
| 13947127_c3_217 | 1502 | 3422 | 584 | 1755 | 1216 | 1.6e-163 |

| Protein name | Locus Name | Acc# |
|---|---|---|
| | sp:SYQ_HAEIN | P43831 |

Description (GLNRS)

| ORF Name | NTID | AAID | NT Length | AA Length | Score | Probability |
|---|---|---|---|---|---|---|
| 14852035_c1_129 | 1503 | 3423 | 85 | 258 | 70 | 0.033 |

| Protein name | Locus Name | Acc# |
|---|---|---|
| tat protein | gp:HIVU86775 | U86775 |

Description

HIV-1 clone ZAM184-5.2 from Zambia, tat protein (tat) gene, partialcds, rev protein (rev), vpu protein (vpu), and envelopeglycoprotein (env) genes, complete cds and nef protein (nef)pseudogene.

| ORF Name | NTID | AAID | NT Length | AA Length | Score | Probability |
|---|---|---|---|---|---|---|
| 15663417_f2_42 | 1504 | 3424 | 79 | 240 | | |

| Protein name | Locus Name | Acc# |
|---|---|---|
| | | |

Description

NO-HIT

| ORF Name | NTID | AAID | NT Length | AA Length | Score | Probability |
|---|---|---|---|---|---|---|
| 16583425_c1_131 | 1505 | 3425 | 326 | 981 | 535 | 1.8e-51 |

| Protein name | Locus Name | Acc# |
|---|---|---|
| yfjB protein | pir:B65040 | B65040 |

Description

| ORF Name | NTID | AAID | NT Length | AA Length | Score | Probability |
|---|---|---|---|---|---|---|
| 19632665_c2_160 | 1506 | 3426 | 696 | 2091 | 633 | 2.3e-79 |

| Protein name | Locus Name | Acc# |
|---|---|---|
| | sp:COPA_ENTHR | |

Description

COPPER/POTASSIUM-TRANSPORTING ATPASE A,

| ORF Name | NTID | AAID | NT Length | AA Length | Score | Probability |
|---|---|---|---|---|---|---|
| 19706557_c3_193 | 1507 | 3427 | 216 | 651 | 148 | 4.8e-08 |

| Protein name | Locus Name | Acc# |
|---|---|---|
| probable component of cation transport for cbb3-type oxidase | pir:E71813 | E71813 |

Description

| ORF_Name | NTID | AAID | NT Length | AA Length | Score | Probability |
|---|---|---|---|---|---|---|
| 21753552_c3_220 | 1508 | 3428 | 168 | 507 | | |

| Protein name | | Locus Name | Acc# |
|---|---|---|---|
| | | | |

Description

NO-HIT

| ORF_Name | NTID | AAID | NT Length | AA Length | Score | Probability |
|---|---|---|---|---|---|---|
| 2197962_f1_11 | 1509 | 3429 | 122 | 369 | | |

| Protein name | | Locus Name | Acc# |
|---|---|---|---|
| | | | |

Description

NO-HIT

| ORF_Name | NTID | AAID | NT Length | AA Length | Score | Probability |
|---|---|---|---|---|---|---|
| 22145253_c2_177 | 1510 | 3430 | 210 | 633 | 592 | 1.6e-57 |

| Protein name | | Locus Name | Acc# |
|---|---|---|---|
| | | sp:ORN_HAEIN | P45340 |

Description

OLIGORIBONUCLEASE,

| ORF_Name | NTID | AAID | NT Length | AA Length | Score | Probability |
|---|---|---|---|---|---|---|
| 22272900_f1_5 | 1511 | 3431 | 227 | 684 | 263 | 1.2e-22 |

| Protein name | | Locus Name | Acc# |
|---|---|---|---|
| hypothetical protein | | gp:PST243354 | AJ243354 |

Description

Pseudomonas stutzeri hyp1 and comA genes and putative tolQ, exbB, tolR and exbD genes.

| ORF_Name | NTID | AAID | NT Length | AA Length | Score | Probability |
|---|---|---|---|---|---|---|
| 22285902_c3_212 | 1512 | 3432 | 229 | 690 | 299 | 1.8e-26 |

| Protein name | | Locus Name | Acc# |
|---|---|---|---|
| transposase slr2062:protein slr2062:protein slr2062 | | pir:S74909 | S74909 |

Description

| ORF Name | NTID | AAID | NT Length | AA Length | Score | Probability |
|---|---|---|---|---|---|---|
| 22710402_c2_154 | 1513 | 3433 | 78 | 237 | | |

Protein name | | | | Locus Name | | Acc# |

Description

NO-HIT

| ORF Name | NTID | AAID | NT Length | AA Length | Score | Probability |
|---|---|---|---|---|---|---|
| 23457632_f3_90 | 1514 | 3434 | 295 | 888 | 885 | 1.5e-88 |

Protein name | | | | Locus Name | | Acc# |
| | | | | sp:UBIE_ECOLI | | P27851 |

Description (EC 2.1.1.-)

| ORF Name | NTID | AAID | NT Length | AA Length | Score | Probability |
|---|---|---|---|---|---|---|
| 23475002_f1_9 | 1515 | 3435 | 182 | 549 | 121 | 4.8e-06 |

Protein name | | | | Locus Name | | Acc# |
| | | | | sp:CUTF_ECOLI | | P40710 |

Description

COPPER HOMEOSTASIS PROTEIN CUTF PRECURSOR (LIPOPROTEIN NLPE)

| ORF Name | NTID | AAID | NT Length | AA Length | Score | Probability |
|---|---|---|---|---|---|---|
| 23554676_f1_16 | 1516 | 3436 | 384 | 1155 | 692 | 4.1e-68 |

Protein name | | | | Locus Name | | Acc# |
| | | | | sp:AARF_ECOLI | | |

Description

UBIQUINONE BIOSYNTHESIS PROTEIN AARF

| ORF Name | NTID | AAID | NT Length | AA Length | Score | Probability |
|---|---|---|---|---|---|---|
| 23634656_c3_200 | 1517 | 3437 | 97 | 294 | 147 | 2.3e-10 |

Protein name | | | | Locus Name | | Acc# |
| | | | | sp:YEAC_ECOLI | | P76231 |

Description

HYPOTHETICAL 10.3 KD PROTEIN IN ANSA-GAPA INTERGENIC REGION

| ORF Name | NTID | AAID | NT Length | AA Length | Score | Probability |
|---|---|---|---|---|---|---|
| 24015950_c1_147 | 1518 | 3438 | 201 | 606 | 207 | 1.0e-16 |

| Protein name | Locus Name | Acc# |
|---|---|---|
| hypothetical protein | gp:AF157493 | AF157493 |

Description

Zymomonas mobilis ZM4 fosmid clone 42D7, complete sequence.

| ORF Name | NTID | AAID | NT Length | AA Length | Score | Probability |
|---|---|---|---|---|---|---|
| 24259702_f1_10 | 1519 | 3439 | 500 | 1503 | 275 | 2.4e-23 |

| Protein name | Locus Name | Acc# |
|---|---|---|
| | sp:YF46_ARCFU | O28726 |

Description

HYPOTHETICAL PROTEIN AF1546

| ORF Name | NTID | AAID | NT Length | AA Length | Score | Probability |
|---|---|---|---|---|---|---|
| 24303583_f1_30 | 1520 | 3440 | 93 | 282 | 169 | 1.1e-12 |

| Protein name | Locus Name | Acc# |
|---|---|---|
| small DNA binding protein Fis | gp:AF040379 | AF040379 |

Description

Proteus vulgaris ribosomal protein L11 methyltransferase (prmA)gene, partial cds; yhdG homolog gene, complete cds; and small DNAbinding protein Fis (fis) gene, partial cds.

| ORF Name | NTID | AAID | NT Length | AA Length | Score | Probability |
|---|---|---|---|---|---|---|
| 24306510_c3_209 | 1521 | 3441 | 224 | 675 | 443 | 1.0e-41 |

| Protein name | Locus Name | Acc# |
|---|---|---|
| | sp:EST2_PSEFL | Q53547 |

Description

CARBOXYLESTERASE 2, (ESTERASE II)

| ORF_Name | NTID | AAID | NT Length | AA Length | Score | Probability |
|---|---|---|---|---|---|---|
| 24613752_c2_168 | 1522 | 3442 | 241 | 726 | 813 | 6.2e-81 |

| Protein name | Locus Name | Acc# |
|---|---|---|
| superoxide dismutase, (Mn):SodA protein | pir:JC6542 | JC6542 |

Description

| ORF_Name | NTID | AAID | NT Length | AA Length | Score | Probability |
|---|---|---|---|---|---|---|
| 24614125_f2_65 | 1523 | 3443 | 816 | 2451 | 1566 | 1.0e-160 |

| Protein name | Locus Name | Acc# |
|---|---|---|
| penicillin-binding protein 1B | gp:AF147449 | AF147449 |

Description

Pseudomonas aeruginosa strain PAO1 penicillin-binding protein 1B(ponB) gene, complete cds.

| ORF_Name | NTID | AAID | NT Length | AA Length | Score | Probability |
|---|---|---|---|---|---|---|
| 24640762_f3_79 | 1524 | 3444 | 388 | 1167 | 1412 | 2.1e-144 |

| Protein name | Locus Name | Acc# |
|---|---|---|
|  | sp:METK_ECOLI |  |

Description

ADENOSYLTRANSFERASE) (ADOMET SYNTHETASE)

| ORF_Name | NTID | AAID | NT Length | AA Length | Score | Probability |
|---|---|---|---|---|---|---|
| 25551385_f1_17 | 1525 | 3445 | 175 | 528 | 298 | 2.3e-26 |

| Protein name | Locus Name | Acc# |
|---|---|---|
| adenine phosphoribosyltransferase,:protein sll1430:protein sll1430 | pir:S75440 | S75440 |

Description

| ORF_Name | NTID | AAID | NT Length | AA Length | Score | Probability |
|---|---|---|---|---|---|---|
| 25665962_f1_8 | 1526 | 3446 | 115 | 348 | 75 | 0.0099 |

| Protein name | Locus Name | Acc# |
|---|---|---|
| glutamyl-tRNA (Gln) amidotransferase subunit C | pir:D70484 | D70484 |

Description

| ORF Name | NTID | AAID | NT Length | AA Length | Score | Probability |
|---|---|---|---|---|---|---|
| 29687660_f3_88 | 1527 | 3447 | 310 | 933 | 441 | 1.6e-41 |

| Protein name | Locus Name | Acc# |
|---|---|---|
| hypothetical protein | pir:S76006 | S76006 |

Description

---

| ORF Name | NTID | AAID | NT Length | AA Length | Score | Probability |
|---|---|---|---|---|---|---|
| 30650250_f1_12 | 1528 | 3448 | 298 | 897 | 664 | 3.8e-65 |

| Protein name | Locus Name | Acc# |
|---|---|---|
| conserved hypothetical protein | pir:A75256 | A75256 |

Description

---

| ORF Name | NTID | AAID | NT Length | AA Length | Score | Probability |
|---|---|---|---|---|---|---|
| 31541442_c3_183 | 1529 | 3449 | 317 | 954 | 338 | 6.5e-30 |

| Protein name | Locus Name | Acc# |
|---|---|---|
| putative peptidyl-prolyl cis-trans isomerase | gp:ASAJ2316 | AJ002316 |

Description

Acinetobacter sp. ADP1 alkR & alkM genes, ORF1 & ORF4.

---

| ORF Name | NTID | AAID | NT Length | AA Length | Score | Probability |
|---|---|---|---|---|---|---|
| 32694687_c2_181 | 1530 | 3450 | 140 | 423 | 117 | 2.0e-06 |

| Protein name | Locus Name | Acc# |
|---|---|---|
|  | sp:YPBB_BACSU | P50728 |

Description

HYPOTHETICAL 40.7 KD PROTEIN IN FER-RECQ INTERGENIC REGION

---

| ORF Name | NTID | AAID | NT Length | AA Length | Score | Probability |
|---|---|---|---|---|---|---|
| 33213555_c3_216 | 1531 | 3451 | 60 | 183 | 106 | 1.3e-05 |

| Protein name | Locus Name | Acc# |
|---|---|---|
|  | gp:ECU82664 | U82664 |

Description

Escherichia coli minutes 9 to 11 genomic sequence.

399

| ORF Name | NTID | AAID | NT Length | AA Length | Score | Probability |
|---|---|---|---|---|---|---|
| 33245927_c3_213 | 1532 | 3452 | 229 | 690 | 606 | 5.3e-59 |

| Protein name | | | | Locus Name | | Acc# |
|---|---|---|---|---|---|---|
| | | | | sp:YCFV_ECOLI | | P75957 |

Description

HYPOTHETICAL ABC TRANSPORTER ATP-BINDING PROTEIN YCFV

| ORF Name | NTID | AAID | NT Length | AA Length | Score | Probability |
|---|---|---|---|---|---|---|
| 33394050_f3_76 | 1533 | 3453 | 269 | 810 | 340 | 8.2e-31 |

| Protein name | | | | Locus Name | | Acc# |
|---|---|---|---|---|---|---|
| | | | | sp:YBBF_ECOLI | | |

Description

HYPOTHETICAL 26.9 KD PROTEIN IN PURE-PPIB INTERGENIC REGION

| ORF Name | NTID | AAID | NT Length | AA Length | Score | Probability |
|---|---|---|---|---|---|---|
| 3465_f3_89 | 1534 | 3454 | 71 | 216 | | |

| Protein name | | | | Locus Name | | Acc# |
|---|---|---|---|---|---|---|

Description

NO-HIT

| ORF Name | NTID | AAID | NT Length | AA Length | Score | Probability |
|---|---|---|---|---|---|---|
| 3906561_f1_18 | 1535 | 3455 | 248 | 747 | 311 | 9.7e-28 |

| Protein name | | | | Locus Name | | Acc# |
|---|---|---|---|---|---|---|
| | | | | gp:STMBLDA | | M80628 |

Description

Streptomyces griseus transfer RNA-Leu (bldA) gene and ORF, completecds.

| ORF Name | NTID | AAID | NT Length | AA Length | Score | Probability |
|---|---|---|---|---|---|---|
| 3910693_f2_39 | 1536 | 3456 | 172 | 519 | 526 | 1.6e-50 |

| Protein name | | | | Locus Name | | Acc# |
|---|---|---|---|---|---|---|
| | | | | sp:CYPB_ECOLI | | |

Description (ROTAMASE B)

| ORF Name | NTID | AAID | NT Length | AA Length | Score | Probability |
|---|---|---|---|---|---|---|
| 3944178_f2_52 | 1537 | 3457 | 328 | 987 | | |

| Protein name | Locus Name | Acc# |
|---|---|---|

Description

NO-HIT

| ORF Name | NTID | AAID | NT Length | AA Length | Score | Probability |
|---|---|---|---|---|---|---|
| 3953218_c1_125 | 1538 | 3458 | 943 | 2832 | 156 | 1.1e-10 |

| Protein name | Locus Name | Acc# |
|---|---|---|
| PhoC protein | gp:KPN250377 | AJ250377 |

Description

Klebsiella pneumoniae partial selD gene for SelD protein and phoC gene for PhoC protein.

| ORF Name | NTID | AAID | NT Length | AA Length | Score | Probability |
|---|---|---|---|---|---|---|
| 3991527_f2_67 | 1539 | 3459 | 2142 | 6429 | 577 | 4.0e-51 |

| Protein name | Locus Name | Acc# |
|---|---|---|
| | gp:U41852 | U41852 |

Description

Haemophilus influenzae hsf gene, complete cds.

| ORF Name | NTID | AAID | NT Length | AA Length | Score | Probability |
|---|---|---|---|---|---|---|
| 4322793_f2_57 | 1540 | 3460 | 217 | 654 | | |

| Protein name | Locus Name | Acc# |
|---|---|---|

Description

NO-HIT

| ORF Name | NTID | AAID | NT Length | AA Length | Score | Probability |
|---|---|---|---|---|---|---|
| 4410943_c3_219 | 1541 | 3461 | 91 | 276 | 103 | 1.1e-05 |

| Protein name | Locus Name | Acc# |
|---|---|---|
| | sp:YGFY_ECOLI | Q46825 |

Description

HYPOTHETICAL 10.5 KD PROTEIN IN FLDB-BGLA INTERGENIC REGION

| ORF Name | NTID | AAID | NT Length | AA Length | Score | Probability |
|---|---|---|---|---|---|---|
| 4688887_c3_211 | 1542 | 3462 | 452 | 1359 | 142 | 7.9e-07 |

| Protein name | | | | Locus Name | | Acc# |
|---|---|---|---|---|---|---|
| metal transporter Nramp4 | | | | gp:AF202540 | | AF202540 |

Description

Arabidopsis thaliana metal transporter Nramp4 mRNA, complete cds.

| ORF Name | NTID | AAID | NT Length | AA Length | Score | Probability |
|---|---|---|---|---|---|---|
| 4782812_c1_141 | 1543 | 3463 | 147 | 444 | 95 | 0.011 |

| Protein name | | | | Locus Name | | Acc# |
|---|---|---|---|---|---|---|
| hypothetical protein TM1026 | | | | pir:A72303 | | A72303 |

Description

| ORF Name | NTID | AAID | NT Length | AA Length | Score | Probability |
|---|---|---|---|---|---|---|
| 4798430_c1_151 | 1544 | 3464 | 453 | 1362 | 447 | 7.2e-62 |

| Protein name | | | | Locus Name | | Acc# |
|---|---|---|---|---|---|---|
| | | | | gp:SC9745 | | |

Description

S.cerevisiae chromosome XIII cosmid 9745.

| ORF Name | NTID | AAID | NT Length | AA Length | Score | Probability |
|---|---|---|---|---|---|---|
| 5125318_c3_206 | 1545 | 3465 | 356 | 1071 | 184 | 5.0e-21 |

| Protein name | | | | Locus Name | | Acc# |
|---|---|---|---|---|---|---|
| | | | | gp:ATAC007168 | | AC007168 |

Description

Arabidopsis thaliana chromosome II BAC T26C19 genomic sequence,complete sequence.

| ORF Name | NTID | AAID | NT Length | AA Length | Score | Probability |
|---|---|---|---|---|---|---|
| 5192757_c1_144 | 1546 | 3466 | 425 | 1278 | 734 | 1.5e-72 |

| Protein name | | | | Locus Name | | Acc# |
|---|---|---|---|---|---|---|
| | | | | sp:YCFW_ECOLI | | P75958 |

Description

HYPOTHETICAL 45.3 KD PROTEIN IN MFD-COBB INTERGENIC REGION

| ORF Name | NTID | AAID | NT Length | AA Length | Score | Probability |
|---|---|---|---|---|---|---|
| 5343752_f3_101 | 1547 | 3467 | 316 | 951 | 630 | 1.5e-61 |

| Protein name | Locus Name | Acc# |
|---|---|---|
| | sp:PRMA_ECOLI | |

Description

RIBOSOMAL PROTEIN L11 METHYLTRANSFERASE,

| ORF Name | NTID | AAID | NT Length | AA Length | Score | Probability |
|---|---|---|---|---|---|---|
| 7042580_c1_142 | 1548 | 3468 | 75 | 228 | | |

| Protein name | Locus Name | Acc# |
|---|---|---|

Description

NO-HIT

| ORF Name | NTID | AAID | NT Length | AA Length | Score | Probability |
|---|---|---|---|---|---|---|
| 7312717_f3_77 | 1549 | 3469 | 75 | 228 | 77 | 0.028 |

| Protein name | Locus Name | Acc# |
|---|---|---|
| conserved hypothetical protein 262 | pir:S59078 | S59078 |

Description

| ORF Name | NTID | AAID | NT Length | AA Length | Score | Probability |
|---|---|---|---|---|---|---|
| 822680_c3_218 | 1550 | 3470 | 417 | 1254 | 675 | 8.8e-82 |

| Protein name | Locus Name | Acc# |
|---|---|---|
| glyceraldehyde-3-phosphate dehydrogenase | gp:BACPGKTIMG | M87647 |

Description

Bacillus megaterium glyceraldehyde-3-phosphate dehydrogenase (gap),phosphoglycerate kinase (pgk), and triose phosphate isomerase (tpi)genes, complete cds.

| ORF Name | NTID | AAID | NT Length | AA Length | Score | Probability |
|---|---|---|---|---|---|---|
| 9767325_f3_82 | 1551 | 3471 | 147 | 444 | 476 | 3.2e-45 |

| Protein name | Locus Name | Acc# |
|---|---|---|
| transposase homolog A | gp:HPU95957 | U95957 |

Description

Helicobacter pylori insertion sequence IS606 transposase homologs A(tnpA) and B (tnpB) genes, complete cds.

| ORF Name | NTID | AAID | NT Length | AA Length | Score | Probability |
|---|---|---|---|---|---|---|
| 12635413_f3_5 | 1552 | 3472 | 813 | 2442 | 1030 | 4.2e-129 |

| Protein name | Locus Name | Acc# |
|---|---|---|
| | sp:UP05_ECOLI | |

Description

UNKNOWN PROTEIN FROM 2D-PAGE SPOTS M62/M63/O3/O9/T35 PRECURSOR

| ORF Name | NTID | AAID | NT Length | AA Length | Score | Probability |
|---|---|---|---|---|---|---|
| 31671880_f1_2 | 1553 | 3473 | 185 | 558 | 360 | 6.2e-33 |

| Protein name | Locus Name | Acc# |
|---|---|---|
| FabZ | gp:NMU79481 | U79481 |

Description

Neisseria meningitidis UDP-3-O-(R-3-hydroxymyristoyl)-glucosamineN-acyltransferase (lpxD) gene, partial cds, and3(R)-hydroxymyristoyl acyl carrier protein dehydrase (fabZ) andUDP-N-acetylglucosamine acyltransferase (lpxA) genes, complete cds.

| ORF Name | NTID | AAID | NT Length | AA Length | Score | Probability |
|---|---|---|---|---|---|---|
| 36148427_f3_8 | 1554 | 3474 | 67 | 201 | | |

| Protein name | Locus Name | Acc# |
|---|---|---|
| | | |

Description

NO-HIT

| ORF Name | NTID | AAID | NT Length | AA Length | Score | Probability |
|---|---|---|---|---|---|---|
| 4412963_f2_4 | 1555 | 3475 | 185 | 558 | 470 | 1.4e-44 |

| Protein name | Locus Name | Acc# |
|---|---|---|
| | sp:LPXA_ECOLI | |

Description

| (EC 2.3.1.129) (UDP-N-ACETYLGLUCOSAMINE ACYLTRANSFERASE) |
|---|

| ORF Name | NTID | AAID | NT Length | AA Length | Score | Probability |
|---|---|---|---|---|---|---|
| 4687640_f2_3 | 1556 | 3476 | 340 | 1023 | 667 | 1.8e-65 |

| Protein name | Locus Name | Acc# |
|---|---|---|
| | sp:LPXD_HAEIN | P43888 |

Description

| (EC 2.3.1.-) |
|---|

| ORF Name | NTID | AAID | NT Length | AA Length | Score | Probability |
|---|---|---|---|---|---|---|
| 11978127_f1_2 | 1557 | 3477 | 379 | 1140 | 811 | 1.0e-80 |

| Protein name | Locus Name | Acc# |
|---|---|---|
| | sp:YECP_ECOLI | |

Description

| HYPOTHETICAL 37.0 KD PROTEIN IN ASPS-BISZ INTERGENIC REGION |
|---|

| ORF Name | NTID | AAID | NT Length | AA Length | Score | Probability |
|---|---|---|---|---|---|---|
| 14658562_f3_6 | 1558 | 3478 | 309 | 930 | 835 | 2.9e-83 |

| Protein name | Locus Name | Acc# |
|---|---|---|
| | sp:YEDI_ECOLI | |

Description

| HYPOTHETICAL 32.2 KD PROTEIN IN DSRB-VSR INTERGENIC REGION |
|---|

| ORF Name | NTID | AAID | NT Length | AA Length | Score | Probability |
|---|---|---|---|---|---|---|
| 23714375_f3_8 | 1559 | 3479 | 100 | 303 | 70 | 0.033 |

| Protein name | Locus Name | Acc# |
|---|---|---|
| outer membrane protein H.8 precursor | pir:S04157 | S04157 |

Description

| ORF_Name | NTID | AAID | NT Length | AA Length | Score | Probability |
|---|---|---|---|---|---|---|
| 24253427_f3_7 | 1560 | 3480 | 85 | 258 | | |

Protein name | Locus Name | Acc#

Description

NO-HIT

| ORF_Name | NTID | AAID | NT Length | AA Length | Score | Probability |
|---|---|---|---|---|---|---|
| 24322153_f3_5 | 1561 | 3481 | 257 | 774 | 475 | 4.1e-45 |

Protein name | Locus Name | Acc#
 | sp:YECO_HAEIN |

Description

HYPOTHETICAL PROTEIN HI0319/320

| ORF_Name | NTID | AAID | NT Length | AA Length | Score | Probability |
|---|---|---|---|---|---|---|
| 24804651_c2_16 | 1562 | 3482 | 62 | 189 | 171 | 3.1e-12 |

Protein name | Locus Name | Acc#
 | sp:SSP2_PLAYO | Q01443

Description

SPOROZOITE SURFACE PROTEIN 2 PRECURSOR

| ORF_Name | NTID | AAID | NT Length | AA Length | Score | Probability |
|---|---|---|---|---|---|---|
| 35181956_c1_11 | 1563 | 3483 | 251 | 756 | | |

Protein name | Locus Name | Acc#

Description

NO-HIT

| ORF_Name | NTID | AAID | NT Length | AA Length | Score | Probability |
|---|---|---|---|---|---|---|
| 3955437_c2_19 | 1564 | 3484 | 73 | 219 | 138 | 2.1e-09 |

Protein name | Locus Name | Acc#
peptide methionine sulfoxide reductase | pir:E75345 | E75345

Description

| ORF Name | NTID | AAID | NT Length | AA Length | Score | Probability |
|---|---|---|---|---|---|---|
| 5117337_f3_9 | 1565 | 3485 | 379 | 1140 | 1148 | 2.0e-116 |

| Protein name | | Locus Name | Acc# |
|---|---|---|---|
| serine-pyruvate aminotransferase | | pir:F75269 | F75269 |

Description

| ORF Name | NTID | AAID | NT Length | AA Length | Score | Probability |
|---|---|---|---|---|---|---|
| 1063441_c3_193 | 1566 | 3486 | 442 | 1329 | 272 | 1.4e-21 |

| Protein name | | Locus Name | Acc# |
|---|---|---|---|
| hypothetical protein 25 | | pir:T13514 | T13514 |

Description

| ORF Name | NTID | AAID | NT Length | AA Length | Score | Probability |
|---|---|---|---|---|---|---|
| 10650681_c3_218 | 1567 | 3487 | 102 | 309 | 72 | 1.0e-05 |

| Protein name | | Locus Name | Acc# |
|---|---|---|---|
| unknown | | gp:AF050676 | AF050676 |

Description

Pseudomonas aeruginosa lipoprotein (oprX) and ferric uptakeregulator (fur) genes, complete cds; and unknown genes.

| ORF Name | NTID | AAID | NT Length | AA Length | Score | Probability |
|---|---|---|---|---|---|---|
| 119027_c2_166 | 1568 | 3488 | 95 | 288 | | |

| Protein name | | Locus Name | Acc# |
|---|---|---|---|
| | | | |

Description

NO-HIT

| ORF Name | NTID | AAID | NT Length | AA Length | Score | Probability |
|---|---|---|---|---|---|---|
| 1227302_c3_221 | 1569 | 3489 | 90 | 273 | 85 | 0.012 |

| Protein name | | Locus Name | Acc# |
|---|---|---|---|
| probable fatty-acid--CoA ligase, fadD7 | | pir:C69471 | C69471 |

Description

| ORF Name | NTID | AAID | NT Length | AA Length | Score | Probability |
|---|---|---|---|---|---|---|
| 12773910_c2_171 | 1570 | 3490 | 116 | 351 | | |

Protein name                                                  Locus Name         Acc#

Description

NO-HIT

| ORF Name | NTID | AAID | NT Length | AA Length | Score | Probability |
|---|---|---|---|---|---|---|
| 12973332_f1_18 | 1571 | 3491 | 63 | 192 | | |

Protein name                                                  Locus Name         Acc#

Description

NO-HIT

| ORF Name | NTID | AAID | NT Length | AA Length | Score | Probability |
|---|---|---|---|---|---|---|
| 12992125_c2_170 | 1572 | 3492 | 152 | 459 | | |

Protein name                                                  Locus Name         Acc#

Description

NO-HIT

| ORF Name | NTID | AAID | NT Length | AA Length | Score | Probability |
|---|---|---|---|---|---|---|
| 13085160_c3_196 | 1573 | 3493 | 236 | 711 | | |

Protein name                                                  Locus Name         Acc#

Description

NO-HIT

| ORF Name | NTID | AAID | NT Length | AA Length | Score | Probability |
|---|---|---|---|---|---|---|
| 1371003_f3_87 | 1574 | 3494 | 413 | 1242 | 1088 | 4.5e-110 |

| Protein name | Locus Name | Acc# |
|---|---|---|
| Na+/H+-exchanging protein:Na+/H+ antiporter | pir:JX0360 | JX0360 |

Description

| ORF Name | NTID | AAID | NT Length | AA Length | Score | Probability |
|---|---|---|---|---|---|---|
| 14647033_c3_209 | 1575 | 3495 | 192 | 579 | 128 | 1.8e-07 |

| Protein name | Locus Name | Acc# |
|---|---|---|
| muramoyl-pentapeptide carboxypeptidase | pir:T34747 | T34747 |

Description

| ORF Name | NTID | AAID | NT Length | AA Length | Score | Probability |
|---|---|---|---|---|---|---|
| 14745253_c3_214 | 1576 | 3496 | 468 | 1407 | 596 | 6.1e-58 |

| Protein name | Locus Name | Acc# |
|---|---|---|
| hypothetical protein Rv3734c | pir:G70797 | G70797 |

Description

| ORF Name | NTID | AAID | NT Length | AA Length | Score | Probability |
|---|---|---|---|---|---|---|
| 15633253_c1_149 | 1577 | 3497 | 150 | 453 | | |

Protein name                                           Locus Name         Acc#

Description

NO-HIT

| ORF Name | NTID | AAID | NT Length | AA Length | Score | Probability |
|---|---|---|---|---|---|---|
| 16485906_c3_192 | 1578 | 3498 | 484 | 1455 | 207 | 2.3e-14 |

| Protein name | Locus Name | Acc# |
|---|---|---|
| | sp:VG17_BPMD2 | O64210 |

Description

MAJOR HEAD PROTEIN GP17

| ORF Name | NTID | AAID | NT Length | AA Length | Score | Probability |
|---|---|---|---|---|---|---|
| 16595716_f2_69 | 1579 | 3499 | 60 | 183 | | |

Protein name                                           Locus Name         Acc#

Description

NO-HIT

| ORF Name | NTID | AAID | NT Length | AA Length | Score | Probability |
|---|---|---|---|---|---|---|
| 16597827_c1_133 | 1580 | 3500 | 205 | 618 | 92 | 0.022 |

| Protein name | Locus Name | Acc# |
|---|---|---|
| putative prohead protease | gp:AF181080 | AF181080 |

Description

Rhodobacter capsulatus putative large terminase, putative portalprotein, and putative prohead protease genes, complete cds; andputative capsid protein gene, partial cds.

| ORF Name | NTID | AAID | NT Length | AA Length | Score | Probability |
|---|---|---|---|---|---|---|
| 19547875_c1_157 | 1581 | 3501 | 124 | 375 | 189 | 8.2e-15 |

| Protein name | Locus Name | Acc# |
|---|---|---|
| mono-heme c-type cytochrome ScyA | gp:AF044582 | AF044582 |

Description

Shewanella putrefaciens NrfG homolog gene, partial cds; andmono-heme c-type cytochrome ScyA (scyA), cytochrome c maturationprotein A (ccmA), cytochrome c maturation protein B (ccmB),cytochrome c maturation protein C (ccmC), cytochrome c maturationprotein D (ccmD), and cytochrome c maturation protein E (ccmE)genes, complete cds.

| ORF Name | NTID | AAID | NT Length | AA Length | Score | Probability |
|---|---|---|---|---|---|---|
| 19697265_c2_179 | 1582 | 3502 | 65 | 198 | 75 | 0.020 |

| Protein name | Locus Name | Acc# |
|---|---|---|
|  | sp:YC67_ASTLO | P34778 |

Description

HYPOTHETICAL 20.1 KD PROTEIN YCF67 (ORF170)

| ORF Name | NTID | AAID | NT Length | AA Length | Score | Probability |
|---|---|---|---|---|---|---|
| 20917082_f3_105 | 1583 | 3503 | 71 | 216 |  |  |

| Protein name | Locus Name | Acc# |
|---|---|---|
|  |  |  |

Description

NO-HIT

| ORF Name | NTID | AAID | NT Length | AA Length | Score | Probability |
|---|---|---|---|---|---|---|
| 21663410_f1_17 | 1584 | 3504 | 170 | 513 | | |

| Protein name | | Locus Name | Acc# |
|---|---|---|---|

Description

NO-HIT

| ORF Name | NTID | AAID | NT Length | AA Length | Score | Probability |
|---|---|---|---|---|---|---|
| 22351557_c3_191 | 1585 | 3505 | 89 | 270 | 70 | 0.0039 |

| Protein name | Locus Name | Acc# |
|---|---|---|
| hypothetical protein F26B6.23 | pir:T01147 | T01147 |

Description

| ORF Name | NTID | AAID | NT Length | AA Length | Score | Probability |
|---|---|---|---|---|---|---|
| 22381542_c3_199 | 1586 | 3506 | 257 | 774 | 457 | 3.3e-43 |

| Protein name | Locus Name | Acc# |
|---|---|---|
| minor tail protein L homolog:protein gp18 | pir:T13104 | T13104 |

Description

| ORF Name | NTID | AAID | NT Length | AA Length | Score | Probability |
|---|---|---|---|---|---|---|
| 23437561_f2_52 | 1587 | 3507 | 690 | 2073 | 1985 | 4.0e-205 |

| Protein name | Locus Name | Acc# |
|---|---|---|
| | sp:SYM_HAEIN | P43828 |

Description (METRS)

| ORF Name | NTID | AAID | NT Length | AA Length | Score | Probability |
|---|---|---|---|---|---|---|
| 23549217_c1_144 | 1588 | 3508 | 192 | 579 | 113 | 5.4e-05 |

| Protein name | Locus Name | Acc# |
|---|---|---|
| hypothetical protein | pir:T14651 | T14651 |

Description

| ORF Name | NTID | AAID | NT Length | AA Length | Score | Probability |
|---|---|---|---|---|---|---|
| 23847257_c2_167 | 1589 | 3509 | 125 | 378 | | |

| Protein name | | | | | Locus Name | Acc# |
|---|---|---|---|---|---|---|
| | | | | | | |

Description

NO-HIT

| ORF Name | NTID | AAID | NT Length | AA Length | Score | Probability |
|---|---|---|---|---|---|---|
| 24316886_f3_115 | 1590 | 3510 | 151 | 456 | 356 | 1.7e-32 |

| Protein name | | | | | Locus Name | Acc# |
|---|---|---|---|---|---|---|
| | | | | | sp:YDCQ_ECOLI | P76107 |

Description

HYPOTHETICAL 16.1 KD PROTEIN IN TEHB-ANSP INTERGENIC REGION

| ORF Name | NTID | AAID | NT Length | AA Length | Score | Probability |
|---|---|---|---|---|---|---|
| 24415876_f2_48 | 1591 | 3511 | 154 | 465 | | |

| Protein name | | | | | Locus Name | Acc# |
|---|---|---|---|---|---|---|
| | | | | | | |

Description

NO-HIT

| ORF Name | NTID | AAID | NT Length | AA Length | Score | Probability |
|---|---|---|---|---|---|---|
| 24417540_c2_187 | 1592 | 3512 | 209 | 630 | 600 | 2.3e-58 |

| Protein name | | | | | Locus Name | Acc# |
|---|---|---|---|---|---|---|
| | | | | | gp:XCRPFB | Y09700 |

Description

X.campestris rpfB gene.

| ORF Name | NTID | AAID | NT Length | AA Length | Score | Probability |
|---|---|---|---|---|---|---|
| 24431265_c2_182 | 1593 | 3513 | 486 | 1461 | 1261 | 2.1e-128 |

| Protein name | | | | | Locus Name | Acc# |
|---|---|---|---|---|---|---|
| | | | | | sp:SYC_ECOLI | P21888 |

Description (CYSRS)

| ORF Name | NTID | AAID | NT Length | AA Length | Score | Probability |
|---|---|---|---|---|---|---|
| 24614431_c2_173 | 1594 | 3514 | 169 | 510 | | |

| Protein name | | Locus Name | Acc# |
|---|---|---|---|
| | | | |

Description

NO-HIT

| ORF Name | NTID | AAID | NT Length | AA Length | Score | Probability |
|---|---|---|---|---|---|---|
| 24631552_c2_181 | 1595 | 3515 | 271 | 816 | 723 | 2.1e-71 |

| Protein name | Locus Name | Acc# |
|---|---|---|
| thiamin biosynthesis protein thiG | pir:B70487 | B70487 |

Description

| ORF Name | NTID | AAID | NT Length | AA Length | Score | Probability |
|---|---|---|---|---|---|---|
| 24882676_c2_163 | 1596 | 3516 | 198 | 597 | 261 | 1.9e-22 |

| Protein name | Locus Name | Acc# |
|---|---|---|
| | sp:YE18_HAEIN | P44189 |

Description

HYPOTHETICAL PROTEIN HI1418

| ORF Name | NTID | AAID | NT Length | AA Length | Score | Probability |
|---|---|---|---|---|---|---|
| 25397700_c1_148 | 1597 | 3517 | 221 | 666 | 388 | 6.7e-36 |

| Protein name | Locus Name | Acc# |
|---|---|---|
| minor tail protein gp20 | pir:T13106 | T13106 |

Description

| ORF Name | NTID | AAID | NT Length | AA Length | Score | Probability |
|---|---|---|---|---|---|---|
| 25493762_c1_161 | 1598 | 3518 | 60 | 183 | | |

| Protein name | Locus Name | Acc# |
|---|---|---|
| | | |

Description

NO-HIT

| ORF_Name | NTID | AAID | NT Length | AA Length | Score | Probability |
|---|---|---|---|---|---|---|
| 25584627_c3_216 | 1599 | 3519 | 60 | 183 | | |

| Protein name | | Locus Name | Acc# |
|---|---|---|---|
| | | | |

Description

NO-HIT

| ORF_Name | NTID | AAID | NT Length | AA Length | Score | Probability |
|---|---|---|---|---|---|---|
| 2581542_c3_213 | 1600 | 3520 | 72 | 219 | | |

| Protein name | | Locus Name | Acc# |
|---|---|---|---|
| | | | |

Description

NO-HIT

| ORF_Name | NTID | AAID | NT Length | AA Length | Score | Probability |
|---|---|---|---|---|---|---|
| 26819002_c1_141 | 1601 | 3521 | 90 | 273 | 72 | 0.020 |

| Protein name | | Locus Name | Acc# |
|---|---|---|---|
| hypothetical protein yorB | | pir:T12887 | |

Description

| ORF_Name | NTID | AAID | NT Length | AA Length | Score | Probability |
|---|---|---|---|---|---|---|
| 276927_f2_58 | 1602 | 3522 | 330 | 993 | 111 | 0.0016 |

| Protein name | | Locus Name | Acc# |
|---|---|---|---|
| | | sp:FINQ_ECOLI | P18809 |

Description

FINQ PROTEIN

| ORF_Name | NTID | AAID | NT Length | AA Length | Score | Probability |
|---|---|---|---|---|---|---|
| 2792176_c2_180 | 1603 | 3523 | 112 | 339 | 112 | 1.2e-06 |

| Protein name | | Locus Name | Acc# |
|---|---|---|---|
| | | sp:YRKF_BACSU | P54433 |

Description

HYPOTHETICAL 20.7 KD PROTEIN IN BLTR-SPOIIIC INTERGENIC REGION

| ORF Name | NTID | AAID | NT Length | AA Length | Score | Probability |
|---|---|---|---|---|---|---|
| 29337908_f1_37 | 1604 | 3524 | 82 | 249 | | |

| Protein name | Locus Name | Acc# |
|---|---|---|
| | | |

Description

NO-HIT

| ORF Name | NTID | AAID | NT Length | AA Length | Score | Probability |
|---|---|---|---|---|---|---|
| 31678827_c3_222 | 1605 | 3525 | 244 | 735 | 527 | 1.3e-50 |

| Protein name | Locus Name | Acc# |
|---|---|---|
| long-chain-fatty-acid-CoA ligase | gp:AF150669 | AF150669 |

Description

Pseudomonas putida long-chain-fatty-acid-CoA ligase (fadD) gene, complete cds.

| ORF Name | NTID | AAID | NT Length | AA Length | Score | Probability |
|---|---|---|---|---|---|---|
| 32062552_f3_102 | 1606 | 3526 | 61 | 186 | 54 | 0.0065 |

| Protein name | Locus Name | Acc# |
|---|---|---|
| | sp:Y683_METJA | Q58096 |

Description

HYPOTHETICAL PROTEIN MJ0683

| ORF Name | NTID | AAID | NT Length | AA Length | Score | Probability |
|---|---|---|---|---|---|---|
| 3207751_f3_103 | 1607 | 3527 | 126 | 381 | | |

| Protein name | Locus Name | Acc# |
|---|---|---|
| | | |

Description

NO-HIT

| ORF Name | NTID | AAID | NT Length | AA Length | Score | Probability |
|---|---|---|---|---|---|---|
| 35187543_c3_217 | 1608 | 3528 | 378 | 1137 | 105 | 0.0058 |

| Protein name | Locus Name | Acc# |
|---|---|---|
| AdcB protein | gp:SPADCA | Z71552 |

Description

Streptococcus pneumoniae adcRCBA operon.

| ORF Name | NTID | AAID | NT Length | AA Length | Score | Probability |
|---|---|---|---|---|---|---|
| 3937813_c1_158 | 1609 | 3529 | 233 | 702 | 368 | 8.9e-34 |

Protein name | | | | Locus Name | | Acc#
| | | | | sp:CYC4_PSEST | | Q52369

Description

CYTOCHROME C4 PRECURSOR

| ORF Name | NTID | AAID | NT Length | AA Length | Score | Probability |
|---|---|---|---|---|---|---|
| 402217_c3_194 | 1610 | 3530 | 161 | 486 | | |

Protein name | | | | Locus Name | | Acc#

Description

NO-HIT

| ORF Name | NTID | AAID | NT Length | AA Length | Score | Probability |
|---|---|---|---|---|---|---|
| 4069212_c3_195 | 1611 | 3531 | 118 | 357 | 83 | 0.017 |

Protein name | | | | Locus Name | | Acc#
| | | | | sp:Y182_METJA | | Q57641

Description

HYPOTHETICAL PROTEIN MJ0182

| ORF Name | NTID | AAID | NT Length | AA Length | Score | Probability |
|---|---|---|---|---|---|---|
| 4331563_c2_172 | 1612 | 3532 | 1179 | 3540 | 181 | 1.2e-09 |

Protein name | | | | Locus Name | | Acc#
unknown | | | | gp:AF011378 | | AF011378

Description

Bacteriophage sk1 complete genome.

| ORF Name | NTID | AAID | NT Length | AA Length | Score | Probability |
|---|---|---|---|---|---|---|
| 4415938_c2_177 | 1613 | 3533 | 1627 | 4884 | 1863 | 3.4e-198 |

Protein name | | | | Locus Name | | Acc#
tail tip fiber protein gp21 | | | | pir:T13107 | | T13107

Description

| ORF Name | NTID | AAID | NT Length | AA Length | Score | Probability |
|---|---|---|---|---|---|---|
| 4861263_c2_169 | 1614 | 3534 | 121 | 366 | | |

| Protein name | Locus Name | Acc# |
|---|---|---|
| | | |

Description

NO-HIT

| ORF Name | NTID | AAID | NT Length | AA Length | Score | Probability |
|---|---|---|---|---|---|---|
| 4867819_c2_162 | 1615 | 3535 | 196 | 591 | 404 | 1.4e-37 |

| Protein name | Locus Name | Acc# |
|---|---|---|
| hypothetical protein HP1334 | pir:F64686 | F64686 |

Description

| ORF Name | NTID | AAID | NT Length | AA Length | Score | Probability |
|---|---|---|---|---|---|---|
| 5130075_c2_186 | 1616 | 3536 | 431 | 1296 | 858 | 1.1e-85 |

| Protein name | Locus Name | Acc# |
|---|---|---|
| | sp:DFP_HAEIN | P44953 |

Description

DNA/PANTOTHENATE METABOLISM FLAVOPROTEIN HOMOLOG

| ORF Name | NTID | AAID | NT Length | AA Length | Score | Probability |
|---|---|---|---|---|---|---|
| 553437_f1_28 | 1617 | 3537 | 91 | 276 | | |

| Protein name | Locus Name | Acc# |
|---|---|---|
| | | |

Description

NO-HIT

| ORF Name | NTID | AAID | NT Length | AA Length | Score | Probability |
|---|---|---|---|---|---|---|
| 6375032_c2_175 | 1618 | 3538 | 282 | 849 | 301 | 1.1e-33 |

| Protein name | Locus Name | Acc# |
|---|---|---|
| minor tail protein gp19 | pir:T13105 | T13105 |

Description

417

| ORF_Name | NTID | AAID | NT Length | AA Length | Score | Probability |
|---|---|---|---|---|---|---|
| 682777_c1_145 | 1619 | 3539 | 135 | 408 | | |

Protein name — Locus Name — Acc#

Description

NO-HIT

| ORF_Name | NTID | AAID | NT Length | AA Length | Score | Probability |
|---|---|---|---|---|---|---|
| 683187_c1_135 | 1620 | 3540 | 71 | 216 | | |

Protein name — Locus Name — Acc#

Description

NO-HIT

| ORF_Name | NTID | AAID | NT Length | AA Length | Score | Probability |
|---|---|---|---|---|---|---|
| 6925452_f3_100 | 1621 | 3541 | 68 | 207 | 69 | 0.042 |

Protein name: hypothetical protein APE0740 — Locus Name: pir:E72664 — Acc#: E72664

Description

| ORF_Name | NTID | AAID | NT Length | AA Length | Score | Probability |
|---|---|---|---|---|---|---|
| 790807_f1_16 | 1622 | 3542 | 101 | 306 | | |

Protein name — Locus Name — Acc#

Description

NO-HIT

| ORF_Name | NTID | AAID | NT Length | AA Length | Score | Probability |
|---|---|---|---|---|---|---|
| 830300_f1_21 | 1623 | 3543 | 65 | 198 | | |

Protein name — Locus Name — Acc#

Description

NO-HIT

| ORF Name | NTID | AAID | NT Length | AA Length | Score | Probability |
|---|---|---|---|---|---|---|
| 865782_c3_198 | 1624 | 3544 | 750 | 2253 | 173 | 6.3e-12 |

Protein name:

Locus Name: gp:AB030825

Acc#: AB030825

Description: Pseudomonas aeruginosa genomic DNA, partial sequence, strain:PAO1.

| ORF Name | NTID | AAID | NT Length | AA Length | Score | Probability |
|---|---|---|---|---|---|---|
| 14175056_f1_2 | 1625 | 3545 | 67 | 204 | 116 | 4.5e-07 |

Protein name:

Locus Name: gp:ABCARRA

Acc#: X70360

Description: A.brasilense carR gene.

| ORF Name | NTID | AAID | NT Length | AA Length | Score | Probability |
|---|---|---|---|---|---|---|
| 23831527_c3_33 | 1626 | 3546 | 674 | 2025 | 619 | 1.7e-74 |

Protein name: protein-disulfide reductase

Locus Name: gp:AF010322

Acc#: AF010322

Description: Pseudomonas aeruginosa protein-disulfide reductase (dipZ) and catabolic dehydroquinase (aroQ) genes, complete cds.

| ORF Name | NTID | AAID | NT Length | AA Length | Score | Probability |
|---|---|---|---|---|---|---|
| 26276961_c2_28 | 1627 | 3547 | 405 | 1218 | 1607 | 4.5e-165 |

Protein name: chloroacetaldehyde dehydrogenase

Locus Name: gp:AF029733

Acc#: AF029733

Description: Xanthobacter autotrophicus linear plasmid pXAU1 chloroacetaldehydedehydrogenase (aldA) gene, complete cds.

| ORF Name | NTID | AAID | NT Length | AA Length | Score | Probability |
|---|---|---|---|---|---|---|
| 33581289_c2_24 | 1628 | 3548 | 512 | 1539 | 1211 | 4.1e-123 |

| Protein name | | | | Locus Name | | Acc# |
|---|---|---|---|---|---|---|
| | | | | sp:Y736_HAEIN | | P44849 |

Description

HYPOTHETICAL SODIUM-DEPENDENT TRANSPORTER HI0736

| ORF Name | NTID | AAID | NT Length | AA Length | Score | Probability |
|---|---|---|---|---|---|---|
| 5312692_f3_15 | 1629 | 3549 | 411 | 1236 | 1075 | 1.1e-108 |

| Protein name | | | | Locus Name | | Acc# |
|---|---|---|---|---|---|---|
| sodium/proton-dependent alanine carrier pr homolog yrbD | | | | pir:C69972 | | C69972 |

Description

| ORF Name | NTID | AAID | NT Length | AA Length | Score | Probability |
|---|---|---|---|---|---|---|
| 6152307_c2_26 | 1630 | 3550 | 387 | 1164 | 1087 | 5.7e-110 |

| Protein name | | | | Locus Name | | Acc# |
|---|---|---|---|---|---|---|
| | | | | sp:CYDB_ECOLI | | P11027 |

Description

BD-I OXIDASE SUBUNIT II)

| ORF Name | NTID | AAID | NT Length | AA Length | Score | Probability |
|---|---|---|---|---|---|---|
| 781461_c2_25 | 1631 | 3551 | 480 | 1443 | 1563 | 2.1e-160 |

| Protein name | | | | Locus Name | | Acc# |
|---|---|---|---|---|---|---|
| | | | | sp:CYDA_AZOVI | | Q09049 |

Description

CYTOCHROME D UBIQUINOL OXIDASE SUBUNIT I,

| ORF Name | NTID | AAID | NT Length | AA Length | Score | Probability |
|---|---|---|---|---|---|---|
| 125143_c1_36 | 1632 | 3552 | 82 | 249 | 137 | 5.7e-09 |

| Protein name | | | | Locus Name | | Acc# |
|---|---|---|---|---|---|---|
| probable enoyl-CoA hydratase | | | | pir:G75557 | | G75557 |

Description

| ORF Name | NTID | AAID | NT Length | AA Length | Score | Probability |
|---|---|---|---|---|---|---|
| 12632255_c3_48 | 1633 | 3553 | 239 | 720 | 136 | 8.4e-06 |

| Protein name | Locus Name | Acc# |
|---|---|---|
| probable erythrocyte-binding protein MAEBL | pir:T09127 | T09127 |

Description

| ORF Name | NTID | AAID | NT Length | AA Length | Score | Probability |
|---|---|---|---|---|---|---|
| 13064425_f1_6 | 1634 | 3554 | 160 | 483 | 569 | 4.4e-55 |

| Protein name | Locus Name | Acc# |
|---|---|---|
| | sp:HEM6_ECOLI | P36553 |

Description (COPROPORPHYRINOGENASE) (COPROGEN OXIDASE)

| ORF Name | NTID | AAID | NT Length | AA Length | Score | Probability |
|---|---|---|---|---|---|---|
| 16692186_f2_20 | 1635 | 3555 | 158 | 477 | 166 | 2.3e-12 |

| Protein name | Locus Name | Acc# |
|---|---|---|
| | sp:CYCP_ALCSP | P00138 |

Description

CYTOCHROME C'

| ORF Name | NTID | AAID | NT Length | AA Length | Score | Probability |
|---|---|---|---|---|---|---|
| 195277_f1_11 | 1636 | 3556 | 405 | 1218 | 491 | 8.2e-47 |

| Protein name | Locus Name | Acc# |
|---|---|---|
| ORF396 protein | gp:PSDNGC | Z73914 |

Description

Pseudomonas stutzeri orf175 gene.

| ORF Name | NTID | AAID | NT Length | AA Length | Score | Probability |
|---|---|---|---|---|---|---|
| 197137_c2_46 | 1637 | 3557 | 710 | 2133 | 965 | 2.5e-156 |

| Protein name | Locus Name | Acc# |
|---|---|---|
| | sp:DXS_HAEIN | P45205 |

Description

1-DEOXYXYLULOSE-5-PHOSPHATE SYNTHASE (DXP SYNTHASE)

| ORF Name | NTID | AAID | NT Length | AA Length | Score | Probability |
|---|---|---|---|---|---|---|
| 22697263_c1_37 | 1638 | 3558 | 104 | 315 | 87 | 0.0022 |

| Protein name | Locus Name | Acc# |
|---|---|---|
| probable enoyl-coA hydratase | pir:E70868 | E70868 |

Description

| ORF Name | NTID | AAID | NT Length | AA Length | Score | Probability |
|---|---|---|---|---|---|---|
| 24323500_f1_5 | 1639 | 3559 | 171 | 516 | 435 | 7.0e-41 |

| Protein name | Locus Name | Acc# |
|---|---|---|
|  | sp:HEM6_ECOLI | P36553 |

Description (COPROPORPHYRINOGENASE) (COPROGEN OXIDASE)

| ORF Name | NTID | AAID | NT Length | AA Length | Score | Probability |
|---|---|---|---|---|---|---|
| 30120325_c1_32 | 1640 | 3560 | 103 | 312 |  |  |

| Protein name | Locus Name | Acc# |
|---|---|---|

Description

NO-HIT

| ORF Name | NTID | AAID | NT Length | AA Length | Score | Probability |
|---|---|---|---|---|---|---|
| 33449042_c3_54 | 1641 | 3561 | 126 | 378 | 294 | 6.2e-26 |

| Protein name | Locus Name | Acc# |
|---|---|---|
| SuhB | gp:AF010139 | AF010139 |

Description

Azotobacter vinelandii iron-sulfur cluster assembly gene cluster, suhB, cysE2, iscS, iscU, iscA, hscB, hscA and fdx genes complete cds; ndk gene, partial cds.

| ORF Name | NTID | AAID | NT Length | AA Length | Score | Probability |
|---|---|---|---|---|---|---|
| 33986312_f2_16 | 1642 | 3562 | 209 | 630 | 522 | 4.3e-50 |

| Protein name | Locus Name | Acc# |
|---|---|---|
|  | sp:GCH2_HAEIN | P44571 |

Description

GTP CYCLOHYDROLASE II,

| ORF Name | NTID | AAID | NT Length | AA Length | Score | Probability |
|---|---|---|---|---|---|---|
| 35441086_c2_43 | 1643 | 3563 | 149 | 450 | 96 | 0.011 |

| Protein name | Locus Name | Acc# |
|---|---|---|
| cell wall-binding protein homolog yvcE | pir:F70031 | F70031 |

Description

| ORF Name | NTID | AAID | NT Length | AA Length | Score | Probability |
|---|---|---|---|---|---|---|
| 5859703_c1_33 | 1644 | 3564 | 464 | 1395 | 705 | 1.7e-69 |

| Protein name | Locus Name | Acc# |
|---|---|---|
|  | gp:ECOFOLC | J02808 |

Description

E.coli folC gene encoding folylpolyglutamate-dihydrofolatesynthetase, and a protein required for its expression, completecds.

| ORF Name | NTID | AAID | NT Length | AA Length | Score | Probability |
|---|---|---|---|---|---|---|
| 1046926_c1_177 | 1645 | 3565 | 217 | 654 | 325 | 3.2e-29 |

| Protein name | Locus Name | Acc# |
|---|---|---|
| yrp protein:multiple regulator protein | pir:S70842 | S70842 |

Description

| ORF Name | NTID | AAID | NT Length | AA Length | Score | Probability |
|---|---|---|---|---|---|---|
| 10588311_c3_274 | 1646 | 3566 | 401 | 1206 | 1495 | 3.3e-153 |

| Protein name | Locus Name | Acc# |
|---|---|---|
| ribonucleoside-diphosphate reductase, beta chain | pir:C64135 | C64135 |

Description

| ORF Name | NTID | AAID | NT Length | AA Length | Score | Probability |
|---|---|---|---|---|---|---|
| 10602250_f2_95 | 1647 | 3567 | 132 | 399 | 251 | 2.2e-21 |

| Protein name | Locus Name | Acc# |
|---|---|---|
| aluminum tolerance protein | pir:PC4440 |  |

Description

| ORF Name | NTID | AAID | NT Length | AA Length | Score | Probability |
|---|---|---|---|---|---|---|
| 10751006_c1_182 | 1648 | 3568 | 153 | 462 | 125 | 5.0e-08 |

Protein name | Locus Name | Acc#
gp:ABCARRA | X70360

Description
A.brasilense carR gene.

| ORF Name | NTID | AAID | NT Length | AA Length | Score | Probability |
|---|---|---|---|---|---|---|
| 11912951_f1_20 | 1649 | 3569 | 107 | 324 | | |

Protein name | Locus Name | Acc#

Description
NO-HIT

| ORF Name | NTID | AAID | NT Length | AA Length | Score | Probability |
|---|---|---|---|---|---|---|
| 1297216_c3_289 | 1650 | 3570 | 185 | 558 | 125 | 5.0e-08 |

Protein name | Locus Name | Acc#
colicin V production protein homolog | pir:E70195 | E70195

Description

| ORF Name | NTID | AAID | NT Length | AA Length | Score | Probability |
|---|---|---|---|---|---|---|
| 14275330_f2_68 | 1651 | 3571 | 489 | 1470 | 377 | 9.9e-35 |

Protein name | Locus Name | Acc#
 | sp:Y4WB_RHISN | P55680

Description
HYPOTHETICAL ZINC PROTEASE-LIKE PROTEIN Y4WB

| ORF Name | NTID | AAID | NT Length | AA Length | Score | Probability |
|---|---|---|---|---|---|---|
| 14508500_c2_247 | 1652 | 3572 | 513 | 1542 | 1546 | 1.3e-158 |

Protein name | Locus Name | Acc#
amidophosphoribosyltransferase, | pir:XQEC |

Description

| ORF Name | NTID | AAID | NT Length | AA Length | Score | Probability |
|---|---|---|---|---|---|---|
| 14900187_f3_134 | 1653 | 3573 | 220 | 663 | 361 | 4.9e-33 |

Protein name: probable 2-hydroxyhepta-2,4-diene-1,7-dioate isomerase b1180

Locus Name: pir:A64864

Acc#: A64864

Description

---

| ORF Name | NTID | AAID | NT Length | AA Length | Score | Probability |
|---|---|---|---|---|---|---|
| 15908263_c1_143 | 1654 | 3574 | 108 | 327 | 307 | 2.6e-27 |

Protein name: RpsA

Locus Name: gp:AF035937

Acc#: AF035937

Description: Pseudomonas aeruginosa strain IATS 06 RpsA (rpsA) gene, partial cds; Ihf-Beta, Wzz (wzz), and Wzx (wzx) genes, complete cds; and wbp gene cluster for O-antigen biosynthesis, complete sequence.

| ORF Name | NTID | AAID | NT Length | AA Length | Score | Probability |
|---|---|---|---|---|---|---|
| 16194442_f3_135 | 1655 | 3575 | 458 | 1377 | 1285 | 6.0e-131 |

Protein name:

Locus Name: sp:PUR2_SALTY

Acc#: P26977

Description: RIBONUCLEOTIDE SYNTHETASE) (PHOSPHORIBOSYLGLYCINAMIDE SYNTHETASE)

| ORF Name | NTID | AAID | NT Length | AA Length | Score | Probability |
|---|---|---|---|---|---|---|
| 16828790_f1_43 | 1656 | 3576 | 292 | 879 | 398 | 5.9e-37 |

Protein name:

Locus Name: sp:YJAD_HAEIN

Acc#: P44710

Description: HYPOTHETICAL PROTEIN HI0432

| ORF Name | NTID | AAID | NT Length | AA Length | Score | Probability |
|---|---|---|---|---|---|---|
| 19698381_c1_189 | 1657 | 3577 | 60 | 183 | | |

| Protein name | Locus Name | Acc# |
|---|---|---|
| | | |

Description

NO-HIT

| ORF Name | NTID | AAID | NT Length | AA Length | Score | Probability |
|---|---|---|---|---|---|---|
| 1972931_f2_63 | 1658 | 3578 | 68 | 207 | 57 | 0.023 |

| Protein name | Locus Name | Acc# |
|---|---|---|
| unknown | gp:AF197128 | AF197128 |

Description

Rattus norvegicus unknown mRNA.

| ORF Name | NTID | AAID | NT Length | AA Length | Score | Probability |
|---|---|---|---|---|---|---|
| 20601558_c1_163 | 1659 | 3579 | 273 | 822 | 737 | 7.0e-73 |

| Protein name | Locus Name | Acc# |
|---|---|---|
| | sp:YGHU_ECOLI | Q46845 |

Description

HYPOTHETICAL 34.2 KD PROTEIN IN GSP-HYBG INTERGENIC REGION

| ORF Name | NTID | AAID | NT Length | AA Length | Score | Probability |
|---|---|---|---|---|---|---|
| 2111556_c1_164 | 1660 | 3580 | 1383 | 4152 | 161 | 1.3e-29 |

| Protein name | Locus Name | Acc# |
|---|---|---|
| | sp:EX5C_HAEIN | P44945 |

Description

EXODEOXYRIBONUCLEASE V GAMMA CHAIN,

| ORF Name | NTID | AAID | NT Length | AA Length | Score | Probability |
|---|---|---|---|---|---|---|
| 21642556_c3_272 | 1661 | 3581 | 87 | 264 | | |

| Protein name | Locus Name | Acc# |
|---|---|---|
| | | |

Description

NO-HIT

| ORF Name | NTID | AAID | NT Length | AA Length | Score | Probability |
|---|---|---|---|---|---|---|
| 22751387_c3_271 | 1662 | 3582 | 150 | 453 | | |

| Protein name | | | | | Locus Name | Acc# |
|---|---|---|---|---|---|---|
| | | | | | | |

Description

NO-HIT

| ORF Name | NTID | AAID | NT Length | AA Length | Score | Probability |
|---|---|---|---|---|---|---|
| 23611527_c3_275 | 1663 | 3583 | 114 | 345 | 140 | 1.3e-09 |

| Protein name | | | | | Locus Name | Acc# |
|---|---|---|---|---|---|---|
| | | | | | sp:YFAE_HAEIN | P45154 |

Description

HYPOTHETICAL PROTEIN HI1309

| ORF Name | NTID | AAID | NT Length | AA Length | Score | Probability |
|---|---|---|---|---|---|---|
| 23676035_c3_262 | 1664 | 3584 | 410 | 1233 | 177 | 1.3e-10 |

| Protein name | | | | | Locus Name | Acc# |
|---|---|---|---|---|---|---|
| YtfP | | | | | gp:AF008220 | AF008220 |

Description

Bacillus subtilis rrnB-dnaB genomic region.

| ORF Name | NTID | AAID | NT Length | AA Length | Score | Probability |
|---|---|---|---|---|---|---|
| 23725387_c2_244 | 1665 | 3585 | 318 | 957 | 1046 | 1.3e-105 |

| Protein name | | | | | Locus Name | Acc# |
|---|---|---|---|---|---|---|
| | | | | | sp:FTSY_HAEIN | P44870 |

Description

CELL DIVISION PROTEIN FTSY

| ORF Name | NTID | AAID | NT Length | AA Length | Score | Probability |
|---|---|---|---|---|---|---|
| 23728465_c1_161 | 1666 | 3586 | 925 | 2778 | 2856 | 2.0e-297 |

| Protein name | | | | | Locus Name | Acc# |
|---|---|---|---|---|---|---|
| pyruvate dehydrogenase (lipoamide) | | | | | gp:AZPDHE | Y15124 |

Description

Azotobacter vinelandii pdhE gene.

427

| ORF_Name | NTID | AAID | NT Length | AA Length | Score | Probability |
|---|---|---|---|---|---|---|
| 23989512_c3_268 | 1667 | 3587 | 393 | 1182 | 1066 | 9.6e-108 |

| Protein name | Locus Name | Acc# |
|---|---|---|
| | sp:PHEA_PSEST | P27603 |

Description

| ORF_Name | NTID | AAID | NT Length | AA Length | Score | Probability |
|---|---|---|---|---|---|---|
| 24303127_c1_171 | 1668 | 3588 | 407 | 1224 | 797 | 3.1e-79 |

| Protein name | Locus Name | Acc# |
|---|---|---|
| carboxynorspermidine decarboxylase | gp:VIBCANSDC | D31783 |

Description

Vibrio alginolyticus nspC gene for carboxynorspermidinedecarboxylase(CANSDC), complete cds.

| ORF_Name | NTID | AAID | NT Length | AA Length | Score | Probability |
|---|---|---|---|---|---|---|
| 24407750_c3_253 | 1669 | 3589 | 248 | 747 | 603 | 1.1e-58 |

| Protein name | Locus Name | Acc# |
|---|---|---|
| | sp:DCOP_HAEIN | P43812 |

Description

DECARBOXYLASE)

| ORF_Name | NTID | AAID | NT Length | AA Length | Score | Probability |
|---|---|---|---|---|---|---|
| 24642711_c2_216 | 1670 | 3590 | 773 | 2322 | 960 | 1.6e-96 |

| Protein name | Locus Name | Acc# |
|---|---|---|
| | sp:AROA_BACSU | P20691 |

Description (5-ENOLPYRUVYLSHIKIMATE-3-PHOSPHATE SYNTHASE) (EPSP SYNTHASE)

| ORF_Name | NTID | AAID | NT Length | AA Length | Score | Probability |
|---|---|---|---|---|---|---|
| 25025987_c2_232 | 1671 | 3591 | 207 | 624 | 484 | 4.5e-46 |

| Protein name | Locus Name | Acc# |
|---|---|---|
| | sp:YRBH_ECOLI | P45395 |

Description

HYPOTHETICAL 35.2 KD PROTEIN IN MURA-RPON INTERGENIC REGION (O328)

| ORF Name | NTID | AAID | NT Length | AA Length | Score | Probability |
|---|---|---|---|---|---|---|
| 25431625_c3_251 | 1672 | 3592 | 106 | 321 | 224 | 1.6e-18 |

| Protein name | | Locus Name | Acc# |
|---|---|---|---|
| | | sp:IHFB_ERWCH | P37983 |

Description

INTEGRATION HOST FACTOR BETA-SUBUNIT (IHF-BETA)

| ORF Name | NTID | AAID | NT Length | AA Length | Score | Probability |
|---|---|---|---|---|---|---|
| 25445452_c1_144 | 1673 | 3593 | 215 | 648 | 313 | 6.0e-28 |

| Protein name | | Locus Name | Acc# |
|---|---|---|---|
| conserved hypothetical protein | | pir:F75285 | F75285 |

Description

| ORF Name | NTID | AAID | NT Length | AA Length | Score | Probability |
|---|---|---|---|---|---|---|
| 25564402_c3_285 | 1674 | 3594 | 739 | 2220 | 82 | 9.2e-06 |

| Protein name | | Locus Name | Acc# |
|---|---|---|---|
| hypothetical protein SCI7.24c | | pir:T36920 | T36920 |

Description

| ORF Name | NTID | AAID | NT Length | AA Length | Score | Probability |
|---|---|---|---|---|---|---|
| 26359451_c2_249 | 1675 | 3595 | 713 | 2142 | 2272 | 1.5e-235 |

| Protein name | | Locus Name | Acc# |
|---|---|---|---|
| | | sp:UVRB_PSEAE | |

Description

EXCINUCLEASE ABC SUBUNIT B

| ORF Name | NTID | AAID | NT Length | AA Length | Score | Probability |
|---|---|---|---|---|---|---|
| 26750090_c2_245 | 1676 | 3596 | 347 | 1044 | 880 | 4.9e-88 |

| Protein name | | Locus Name | Acc# |
|---|---|---|---|
| | | sp:PYRD_SALTY | P25468 |

Description (DHODEHASE)

| ORF Name | NTID | AAID | NT Length | AA Length | Score | Probability |
|---|---|---|---|---|---|---|
| 2923562_c2_233 | 1677 | 3597 | 177 | 534 | 352 | 4.4e-32 |

| Protein name | | Locus Name | Acc# |
|---|---|---|---|
| | | sp:YRBI_ECOLI | |

Description

HYPOTHETICAL 20.0 KD PROTEIN IN MURA-RPON INTERGENIC REGION

| ORF Name | NTID | AAID | NT Length | AA Length | Score | Probability |
|---|---|---|---|---|---|---|
| 29336052_f1_41 | 1678 | 3598 | 474 | 1425 | 440 | 9.1e-46 |

| Protein name | Locus Name | Acc# |
|---|---|---|
| ABC1 protein homolog T15B16.14 | pir:T02007 | T02007 |

Description

| ORF Name | NTID | AAID | NT Length | AA Length | Score | Probability |
|---|---|---|---|---|---|---|
| 30173201_f2_94 | 1679 | 3599 | 66 | 201 | | |

| Protein name | Locus Name | Acc# |
|---|---|---|

Description

NO-HIT

| ORF Name | NTID | AAID | NT Length | AA Length | Score | Probability |
|---|---|---|---|---|---|---|
| 30469092_c1_151 | 1680 | 3600 | 250 | 753 | 152 | 6.4e-09 |

| Protein name | Locus Name | Acc# |
|---|---|---|
| unknown | gp:MLCL622 | Z95398 |

Description

Mycobacterium leprae cosmid L622.

| ORF Name | NTID | AAID | NT Length | AA Length | Score | Probability |
|---|---|---|---|---|---|---|
| 30600453_f3_139 | 1681 | 3601 | 697 | 2094 | 777 | 2.0e-86 |

| Protein name | Locus Name | Acc# |
|---|---|---|
| hypothetical protein b2324 | pir:B65005 | B65005 |

Description

| ORF Name | NTID | AAID | NT Length | AA Length | Score | Probability |
|---|---|---|---|---|---|---|
| 30720027_f3_141 | 1682 | 3602 | 154 | 465 | 382 | 2.9e-35 |

| Protein name | Locus Name | Acc# |
|---|---|---|
| hypothetical protein | gp:PPPAL1 | X74218 |

Description

Pseudomonas putida ruvB, tolQ, tolR, tolA, tolB and oprL genes.

| ORF Name | NTID | AAID | NT Length | AA Length | Score | Probability |
|---|---|---|---|---|---|---|
| 31800280_c1_158 | 1683 | 3603 | 305 | 918 | 649 | 1.5e-63 |

| Protein name | Locus Name | Acc# |
|---|---|---|
| hypothetical protein | gp:PFFC2 | Y11998 |

Description

P.fluorescens FC2.1, FC2.2, FC2.3c, FC2.4 and FC2.5c open readingframes.

| ORF Name | NTID | AAID | NT Length | AA Length | Score | Probability |
|---|---|---|---|---|---|---|
| 31828211_f2_69 | 1684 | 3604 | 1208 | 3627 | 2934 | 0.0 |

| Protein name | Locus Name | Acc# |
|---|---|---|
| proline dehydrogenase | gp:ATU39263 | U39263 |

Description

Agrobacterium tumefaciens plasmid pAtR10 proline dehydrogenase(putA) and Prp (prp) genes, complete cds.

| ORF Name | NTID | AAID | NT Length | AA Length | Score | Probability |
|---|---|---|---|---|---|---|
| 33229667_c3_270 | 1685 | 3605 | 72 | 219 | | |

| Protein name | Locus Name | Acc# |
|---|---|---|
| | | |

Description

NO-HIT

| ORF Name | NTID | AAID | NT Length | AA Length | Score | Probability |
|---|---|---|---|---|---|---|
| 33985930_f1_23 | 1686 | 3606 | 288 | 867 | | |

| Protein name | Locus Name | Acc# |
|---|---|---|
| | | |

Description

NO-HIT

| ORF Name | NTID | AAID | NT Length | AA Length | Score | Probability |
|---|---|---|---|---|---|---|
| 34062503_c1_178 | 1687 | 3607 | 181 | 546 | 224 | 1.6e-18 |

Protein name | Locus Name | Acc#
sp:YHBN_HAEIN | P45074

Description

HYPOTHETICAL PROTEIN HI1149 PRECURSOR

| ORF Name | NTID | AAID | NT Length | AA Length | Score | Probability |
|---|---|---|---|---|---|---|
| 34172883_c1_176 | 1688 | 3608 | 166 | 501 | 296 | 3.8e-26 |

Protein name | Locus Name | Acc#
sp:YJEE_HAEIN | P44492

Description

HYPOTHETICAL PROTEIN HI0065 PRECURSOR

| ORF Name | NTID | AAID | NT Length | AA Length | Score | Probability |
|---|---|---|---|---|---|---|
| 34409658_f2_84 | 1689 | 3609 | 360 | 1083 | 757 | 5.3e-75 |

Protein name | Locus Name | Acc#
carboxyl esterase | pir:S57530 | S57530

Description

| ORF Name | NTID | AAID | NT Length | AA Length | Score | Probability |
|---|---|---|---|---|---|---|
| 35157165_c1_191 | 1690 | 3610 | 204 | 615 | 303 | 2.7e-29 |

Protein name | Locus Name | Acc#
methylated-DNA--protein-cysteine S-methyltransferase, | pir:D64604 | D64604

Description

| ORF Name | NTID | AAID | NT Length | AA Length | Score | Probability |
|---|---|---|---|---|---|---|
| 36072135_c3_295 | 1691 | 3611 | 686 | 2061 | 564 | 1.5e-54 |

Protein name | Locus Name | Acc#
| sp:EX5A_ECOLI |

Description

ALPHA CHAIN)

| ORF Name | NTID | AAID | NT Length | AA Length | Score | Probability |
|---|---|---|---|---|---|---|
| 36112900_f2_91 | 1692 | 3612 | 103 | 312 | 253 | 1.4e-21 |

| Protein name | Locus Name | Acc# |
|---|---|---|
| | gp:ECU24202 | U24202 |

Description

Escherichia coli ECOR 50 (yciD) gene, partial cds, and (yciC),(yciB), (yciA), membrane protein (tonB), (yciI), putative potassiumchannel (kch), and cardiolipin synthase (cls) genes, complete cds.

| ORF Name | NTID | AAID | NT Length | AA Length | Score | Probability |
|---|---|---|---|---|---|---|
| 36129676_c3_252 | 1693 | 3613 | 139 | 420 | 85 | 0.00086 |

| Protein name | Locus Name | Acc# |
|---|---|---|
| hypothetical protein yrvD | pir:G69980 | G69980 |

Description

| ORF Name | NTID | AAID | NT Length | AA Length | Score | Probability |
|---|---|---|---|---|---|---|
| 3915943_c2_226 | 1694 | 3614 | 414 | 1245 | 1163 | 5.0e-118 |

| Protein name | Locus Name | Acc# |
|---|---|---|
| | sp:METZ_PSEAE | P55218 |

Description

O-SUCCINYLHOMOSERINE SULFHYDRYLASE, (OSH SULFHYDRYLASE)

| ORF Name | NTID | AAID | NT Length | AA Length | Score | Probability |
|---|---|---|---|---|---|---|
| 3922193_f2_50 | 1695 | 3615 | 381 | 1146 | 708 | 8.3e-70 |

| Protein name | Locus Name | Acc# |
|---|---|---|
| probable pvdS protein | pir:B70591 | B70591 |

Description

| ORF Name | NTID | AAID | NT Length | AA Length | Score | Probability |
|---|---|---|---|---|---|---|
| 3933437_c2_229 | 1696 | 3616 | 202 | 609 | 387 | 8.6e-36 |

| Protein name | Locus Name | Acc# |
|---|---|---|
| hypothetical protein jhp0867 | pir:B71879 | B71879 |

Description

| ORF Name | NTID | AAID | NT Length | AA Length | Score | Probability |
|---|---|---|---|---|---|---|
| 4016943_f2_67 | 1697 | 3617 | 473 | 1422 | 653 | 5.6e-64 |

| Protein name | | | | Locus Name | | Acc# |
|---|---|---|---|---|---|---|
| | | | | sp:Y4WA_RHISN | | P55679 |

Description

HYPOTHETICAL ZINC PROTEASE Y4WA,

| ORF Name | NTID | AAID | NT Length | AA Length | Score | Probability |
|---|---|---|---|---|---|---|
| 4103293_c1_179 | 1698 | 3618 | 245 | 738 | 822 | 6.9e-82 |

| Protein name | | | | Locus Name | | Acc# |
|---|---|---|---|---|---|---|
| putative ABC transporter ATP-binding protein | | | | gp:AF013987 | | AF013987 |

Description

Vibrio cholerae strain O395 putative ABC transporter ATP-bindingprotein, sigma54 (rpoN), putative sigma54 modulation protein andnitrogen regulatory IIA protein (ptsN) genes, complete cds.

| ORF Name | NTID | AAID | NT Length | AA Length | Score | Probability |
|---|---|---|---|---|---|---|
| 4114702_c1_159 | 1699 | 3619 | 119 | 360 | 194 | 2.4e-15 |

| Protein name | | | | Locus Name | | Acc# |
|---|---|---|---|---|---|---|
| probable dihydroneopterin aldolase, | | | | pir:H65093 | | H65093 |

Description

| ORF Name | NTID | AAID | NT Length | AA Length | Score | Probability |
|---|---|---|---|---|---|---|
| 4489463_f2_90 | 1700 | 3620 | 425 | 1278 | | |

| Protein name | | | | Locus Name | | Acc# |
|---|---|---|---|---|---|---|

Description

NO-HIT

| ORF Name | NTID | AAID | NT Length | AA Length | Score | Probability |
|---|---|---|---|---|---|---|
| 4689693_c3_278 | 1701 | 3621 | 372 | 1119 | 509 | 8.2e-55 |

| Protein name | | | | Locus Name | | Acc# |
|---|---|---|---|---|---|---|
| | | | | sp:MIAA_HAEIN | | P44495 |

Description (IPP TRANSFERASE)

| ORF Name | NTID | AAID | NT Length | AA Length | Score | Probability |
|---|---|---|---|---|---|---|
| 4772050_f2_86 | 1702 | 3622 | 441 | 1326 | 487 | 2.2e-46 |

| Protein name | | | | Locus Name | | Acc# |
|---|---|---|---|---|---|---|
| | | | | sp:DP3E_HAEIN | | P43745 |

Description

DNA POLYMERASE III, EPSILON CHAIN,

| ORF Name | NTID | AAID | NT Length | AA Length | Score | Probability |
|---|---|---|---|---|---|---|
| 4816513_c3_294 | 1703 | 3623 | 1318 | 3957 | 230 | 3.1e-41 |

| Protein name | | | | Locus Name | | Acc# |
|---|---|---|---|---|---|---|
| | | | | sp:EX5B_ECOLI | | P08394 |

Description

BETA CHAIN)

| ORF Name | NTID | AAID | NT Length | AA Length | Score | Probability |
|---|---|---|---|---|---|---|
| 4863458_c2_234 | 1704 | 3624 | 172 | 519 | | |

| Protein name | | | | Locus Name | | Acc# |
|---|---|---|---|---|---|---|

Description

NO-HIT

| ORF Name | NTID | AAID | NT Length | AA Length | Score | Probability |
|---|---|---|---|---|---|---|
| 4876525_c3_293 | 1705 | 3625 | 229 | 690 | | |

| Protein name | | | | Locus Name | | Acc# |
|---|---|---|---|---|---|---|

Description

NO-HIT

| ORF Name | NTID | AAID | NT Length | AA Length | Score | Probability |
|---|---|---|---|---|---|---|
| 4878135_c2_250 | 1706 | 3626 | 350 | 1053 | 810 | 1.3e-80 |

| Protein name | | | | Locus Name | | Acc# |
|---|---|---|---|---|---|---|
| yhdG homolog | | | | gp:AF040378 | | AF040378 |

Description

Serratia marcescens ribosomal protein L11 methyltransferase (prmA)gene, partial cds; and yhdG homolog and small DNA binding proteinFis (fis) genes, complete cds.

| ORF Name | NTID | AAID | NT Length | AA Length | Score | Probability |
|---|---|---|---|---|---|---|
| 4881700_c3_290 | 1707 | 3627 | 479 | 1440 | 381 | 3.7e-35 |

| Protein name | Locus Name | Acc# |
|---|---|---|
| hypothetical protein 5 | pir:T00101 | T00101 |

Description

| ORF Name | NTID | AAID | NT Length | AA Length | Score | Probability |
|---|---|---|---|---|---|---|
| 4884675_c3_283 | 1708 | 3628 | 253 | 762 | 138 | 1.5e-07 |

| Protein name | Locus Name | Acc# |
|---|---|---|
| hypothetical protein | gp:AF031940 | AF031940 |

Description

Sinorhizobium meliloti alcohol dehydrogenase (adhA) gene, completecds.

| ORF Name | NTID | AAID | NT Length | AA Length | Score | Probability |
|---|---|---|---|---|---|---|
| 5086693_c3_277 | 1709 | 3629 | 419 | 1260 | 793 | 8.2e-79 |

| Protein name | Locus Name | Acc# |
|---|---|---|
| hypothetical protein slr0049 | pir:S74347 | S74347 |

Description

| ORF Name | NTID | AAID | NT Length | AA Length | Score | Probability |
|---|---|---|---|---|---|---|
| 5098937_f2_51 | 1710 | 3630 | 543 | 1632 | 520 | 3.1e-53 |

| Protein name | Locus Name | Acc# |
|---|---|---|
| probable exodeoxyribonuclease VII large subunit | pir:C75549 | C75549 |

Description

| ORF Name | NTID | AAID | NT Length | AA Length | Score | Probability |
|---|---|---|---|---|---|---|
| 5110963_c1_162 | 1711 | 3631 | 559 | 1680 | 1056 | 1.1e-106 |

| Protein name | Locus Name | Acc# |
|---|---|---|
| | sp:ODP2_PSEAE | Q59638 |

Description

COMPLEX, (E2)

| ORF_Name | NTID | AAID | NT Length | AA Length | Score | Probability |
|---|---|---|---|---|---|---|
| 5112763_f2_89 | 1712 | 3632 | 277 | 834 | 364 | 2.4e-33 |

| Protein name | | | | Locus Name | | Acc# |
|---|---|---|---|---|---|---|
| | | | | sp:YDGM_HAEIN | | P71396 |

Description

PUTATIVE FERREDOXIN-LIKE PROTEIN HI1684

| ORF_Name | NTID | AAID | NT Length | AA Length | Score | Probability |
|---|---|---|---|---|---|---|
| 5323750_f3_108 | 1713 | 3633 | 104 | 315 | | |

| Protein name | | | | Locus Name | | Acc# |

Description

NO-HIT

| ORF_Name | NTID | AAID | NT Length | AA Length | Score | Probability |
|---|---|---|---|---|---|---|
| 6484691_f1_26 | 1714 | 3634 | 377 | 1134 | 738 | 5.5e-73 |

| Protein name | | | | Locus Name | | Acc# |
|---|---|---|---|---|---|---|
| | | | | sp:CYSP_ECOLI | | P16700 |

Description

THIOSULFATE-BINDING PROTEIN PRECURSOR

| ORF_Name | NTID | AAID | NT Length | AA Length | Score | Probability |
|---|---|---|---|---|---|---|
| 806512_c3_279 | 1715 | 3635 | 137 | 414 | 171 | 1.8e-12 |

| Protein name | | | | Locus Name | | Acc# |
|---|---|---|---|---|---|---|
| polysialic acid capsule expression protein | | | | pir:B70434 | | B70434 |

Description

| ORF_Name | NTID | AAID | NT Length | AA Length | Score | Probability |
|---|---|---|---|---|---|---|
| 11562_c3_7 | 1716 | 3636 | 78 | 237 | | |

| Protein name | | | | Locus Name | | Acc# |

Description

NO-HIT

| ORF Name | NTID | AAID | NT Length | AA Length | Score | Probability |
|---|---|---|---|---|---|---|
| 20395432_c2_6 | 1717 | 3637 | 70 | 213 | | |

| Protein name | | | | | Locus Name | Acc# |
|---|---|---|---|---|---|---|

Description

NO-HIT

| ORF Name | NTID | AAID | NT Length | AA Length | Score | Probability |
|---|---|---|---|---|---|---|
| 36117135_f1_1 | 1718 | 3638 | 335 | 1008 | 1334 | 3.8e-136 |

| Protein name | | | | | Locus Name | Acc# |
|---|---|---|---|---|---|---|
| malate dehydrogenase | | | | | gp:AF109682 | AF109682 |

Description

Aquaspirillum arcticum malate dehydrogenase (MDH) gene, completecds.

| ORF Name | NTID | AAID | NT Length | AA Length | Score | Probability |
|---|---|---|---|---|---|---|
| 6682962_f1_2 | 1719 | 3639 | 85 | 258 | | |

| Protein name | | | | | Locus Name | Acc# |
|---|---|---|---|---|---|---|

Description

NO-HIT

| ORF Name | NTID | AAID | NT Length | AA Length | Score | Probability |
|---|---|---|---|---|---|---|
| 13958403_f1_1 | 1720 | 3640 | 399 | 1200 | 1251 | 2.4e-127 |

| Protein name | | | | | Locus Name | Acc# |
|---|---|---|---|---|---|---|
| | | | | | sp:YLIG_ECOLI | P75802 |

Description

HYPOTHETICAL 49.6 KD PROTEIN IN MOEA-DACC INTERGENIC REGION

| ORF Name | NTID | AAID | NT Length | AA Length | Score | Probability |
|---|---|---|---|---|---|---|
| 16506250_f2_4 | 1721 | 3641 | 140 | 423 | 236 | 4.8e-19 |

| Protein name | | | | | Locus Name | Acc# |
|---|---|---|---|---|---|---|
| unknown | | | | | gp:AF026544 | AF026544 |

Description

Ralstonia eutropha phbF and beta-ketothiolase (bktB) genes, complete cds; and unknown genes.

| ORF Name | NTID | AAID | NT Length | AA Length | Score | Probability |
|---|---|---|---|---|---|---|
| 20782550_f3_16 | 1722 | 3642 | 242 | 729 | 933 | 1.2e-93 |

| Protein name | | | | | Locus Name | Acc# |
|---|---|---|---|---|---|---|
| | | | | | sp:MTNG_NEIGO | P08455 |

Description

METHYLTRANSFERASE NGOPII) (M.NGOPII)

| ORF Name | NTID | AAID | NT Length | AA Length | Score | Probability |
|---|---|---|---|---|---|---|
| 24328950_f2_8 | 1723 | 3643 | 153 | 462 | 336 | 2.2e-30 |

| Protein name | | | | | Locus Name | Acc# |
|---|---|---|---|---|---|---|
| | | | | | sp:YRFH_ECOLI | P45802 |

Description

HYPOTHETICAL 15.5 KD PROTEIN IN MRCA-PCKA INTERGENIC REGION (O133)

| ORF Name | NTID | AAID | NT Length | AA Length | Score | Probability |
|---|---|---|---|---|---|---|
| 29859790_c2_32 | 1724 | 3644 | 74 | 225 | | |

| Protein name | | | | | Locus Name | Acc# |
|---|---|---|---|---|---|---|

Description

NO-HIT

| ORF Name | NTID | AAID | NT Length | AA Length | Score | Probability |
|---|---|---|---|---|---|---|
| 3942592_f2_6 | 1725 | 3645 | 252 | 759 | 741 | 2.6e-73 |

| Protein name | | | | | Locus Name | Acc# |
|---|---|---|---|---|---|---|
| hypothetical protein, 26K | | | | | pir:JC5479 | JC5479 |

Description

| ORF Name | NTID | AAID | NT Length | AA Length | Score | Probability |
|---|---|---|---|---|---|---|
| 4103390_f3_15 | 1726 | 3646 | 85 | 258 | 323 | 5.2e-29 |

| Protein name | | | | | Locus Name | Acc# |
|---|---|---|---|---|---|---|
| | | | | | sp:MTNG_NEIGO | P08455 |

Description

METHYLTRANSFERASE NGOPII) (M.NGOPII)

| ORF Name | NTID | AAID | NT Length | AA Length | Score | Probability |
|---|---|---|---|---|---|---|
| 42837_f1_2 | 1727 | 3647 | 71 | 216 | 170 | 2.5e-12 |

Protein name | Locus Name | Acc#
sp:MTNG_NEIGO | P08455

Description
METHYLTRANSFERASE NGOPII) (M.NGOPII)

| ORF Name | NTID | AAID | NT Length | AA Length | Score | Probability |
|---|---|---|---|---|---|---|
| 4976512_f2_7 | 1728 | 3648 | 518 | 1557 | 1265 | 7.8e-129 |

Protein name: threonine dehydratase, biosynthetic | Locus Name: pir:E75502 | Acc#: E75502

Description

| ORF Name | NTID | AAID | NT Length | AA Length | Score | Probability |
|---|---|---|---|---|---|---|
| 7038307_f1_3 | 1729 | 3649 | 127 | 384 | 228 | 6.1e-19 |

Protein name | Locus Name | Acc#
sp:PA1F_HUMAN

Description
(EC 3.1.3.48) (ADIPOCYTE ACID PHOSPHATASE, ISOZYME ALPHA)

| ORF Name | NTID | AAID | NT Length | AA Length | Score | Probability |
|---|---|---|---|---|---|---|
| 30175950_f1_1 | 1730 | 3650 | 77 | 234 | 292 | 5.8e-25 |

Protein name | Locus Name | Acc#
sp:THIC_BACSU

Description
THIAMINE BIOSYNTHESIS PROTEIN THIC

| ORF Name | NTID | AAID | NT Length | AA Length | Score | Probability |
|---|---|---|---|---|---|---|
| 4470181_f3_5 | 1731 | 3651 | 156 | 471 | 635 | 4.5e-62 |

Protein name | Locus Name | Acc#
sp:THIC_ECOLI | P30136

Description
THIAMINE BIOSYNTHESIS PROTEIN THIC

| ORF_Name | NTID | AAID | NT Length | AA Length | Score | Probability |
|---|---|---|---|---|---|---|
| 7119001_f2_4 | 1732 | 3652 | 73 | 222 | 85 | 0.013 |

| Protein name | | | | Locus Name | | Acc# |
|---|---|---|---|---|---|---|
| | | | | sp:YA51_HAEIN | | |

Description

HYPOTHETICAL ABC TRANSPORTER ATP-BINDING PROTEIN HI1051

| ORF_Name | NTID | AAID | NT Length | AA Length | Score | Probability |
|---|---|---|---|---|---|---|
| 24254702_f3_3 | 1733 | 3653 | 252 | 759 | 253 | 1.4e-21 |

| Protein name | | | | Locus Name | | Acc# |
|---|---|---|---|---|---|---|
| | | | | sp:YIAT_ECOLI | | P37681 |

Description

HYPOTHETICAL 27.4 KD PROTEIN IN AVTA-SELB INTERGENIC REGION PRECURSOR

| ORF_Name | NTID | AAID | NT Length | AA Length | Score | Probability |
|---|---|---|---|---|---|---|
| 25787500_c3_6 | 1734 | 3654 | 278 | 837 | 503 | 4.4e-48 |

| Protein name | | | | Locus Name | | Acc# |
|---|---|---|---|---|---|---|
| | | | | sp:BFRA_NEIGO | | P72080 |

Description

BACTERIOFERRITIN A

| ORF_Name | NTID | AAID | NT Length | AA Length | Score | Probability |
|---|---|---|---|---|---|---|
| 5133575_c3_7 | 1735 | 3655 | 162 | 489 | 489 | 1.3e-46 |

| Protein name | | | | Locus Name | | Acc# |
|---|---|---|---|---|---|---|
| | | | | sp:BFRB_NEIGO | | P77914 |

Description

BACTERIOFERRITIN B (BFR A) (BFR B)

| ORF_Name | NTID | AAID | NT Length | AA Length | Score | Probability |
|---|---|---|---|---|---|---|
| 21984375_c1_10 | 1736 | 3656 | 473 | 1422 | 708 | 8.3e-70 |

Protein name: (blank) Locus Name: sp:AIP2_YEAST Acc#: P46681

Description: ACTIN INTERACTING PROTEIN 2

| ORF_Name | NTID | AAID | NT Length | AA Length | Score | Probability |
|---|---|---|---|---|---|---|
| 23535910_f1_2 | 1737 | 3657 | 492 | 1479 | 1489 | 1.4e-152 |

Protein name: (blank) Locus Name: sp:YEGQ_ECOLI Acc#: (blank)

Description: PUTATIVE PROTEASE YEGQ,

| ORF_Name | NTID | AAID | NT Length | AA Length | Score | Probability |
|---|---|---|---|---|---|---|
| 25677176_f3_6 | 1738 | 3658 | 205 | 615 | 516 | 1.8e-49 |

Protein name: site-specific DNA-methyltransferase (cytosine-specific), HP1121   Locus Name: pir:A64660   Acc#: A64660

Description:

| ORF_Name | NTID | AAID | NT Length | AA Length | Score | Probability |
|---|---|---|---|---|---|---|
| 3926262_c2_13 | 1739 | 3659 | 225 | 678 | 134 | 8.6e-08 |

Protein name: TerZ   Locus Name: gp:AF168355   Acc#: AF168355

Description: Proteus mirabilis tellurite resistance locus, complete sequence; and unknown gene.

| ORF Name | NTID | AAID | NT Length | AA Length | Score | Probability |
|---|---|---|---|---|---|---|
| 3946943_f1_1 | 1740 | 3660 | 510 | 1533 | 808 | 2.1e-80 |

| Protein name | Locus Name | Acc# |
|---|---|---|
| OprM | gp:AB011381 | AB011381 |

Description

Pseudomonas aeruginosa gene for OprM, complete cds.

| ORF Name | NTID | AAID | NT Length | AA Length | Score | Probability |
|---|---|---|---|---|---|---|
| 2110657_c2_3 | 1741 | 3661 | 221 | 663 | 570 | 3.5e-55 |

| Protein name | Locus Name | Acc# |
|---|---|---|
|  | sp:Y926_SYNY3 | P72872 |

Description

HYPOTHETICAL 37.9 KD PROTEIN SLL0926

| ORF Name | NTID | AAID | NT Length | AA Length | Score | Probability |
|---|---|---|---|---|---|---|
| 16040887_f3_11 | 1742 | 3662 | 504 | 1512 | 2557 | 9.6e-266 |

| Protein name | Locus Name | Acc# |
|---|---|---|
| unknown | gp:AF039312 | AF039312 |

Description

Moraxella catarrhalis strain 4223 transferrin binding protein A(tbpA) and transferrin binding protein B (tbpB) genes, completecds; and unknown gene.

| ORF Name | NTID | AAID | NT Length | AA Length | Score | Probability |
|---|---|---|---|---|---|---|
| 4016563_c1_13 | 1743 | 3663 | 108 | 327 | 92 | 0.00021 |

| Protein name | Locus Name | Acc# |
|---|---|---|
| conserved hypothetical protein ykoJ | pir:F69859 | F69859 |

Description

| ORF Name | NTID | AAID | NT Length | AA Length | Score | Probability |
|---|---|---|---|---|---|---|
| 4484567_f1_1 | 1744 | 3664 | 899 | 2700 | 4565 | 0.0 |

| Protein name | Locus Name | Acc# |
|---|---|---|
| transferrin binding protein A | gp:AF039312 | AF039312 |

Description

Moraxella catarrhalis strain 4223 transferrin binding protein A(tbpA) and transferrin binding protein B (tbpB) genes, completecds; and unknown gene.

| ORF Name | NTID | AAID | NT Length | AA Length | Score | Probability |
|---|---|---|---|---|---|---|
| 4775207_f2_9 | 1745 | 3665 | 173 | 522 | 728 | 1.6e-71 |

| Protein name | Locus Name | Acc# |
|---|---|---|
| transferrin binding protein A | gp:AF039315 | AF039315 |

Description

Moraxella catarrhalis strain Q8 transferrin binding protein A(tbpA) and transferrin binding protein B (tbpB) genes, completecds; and unknown gene.

| ORF Name | NTID | AAID | NT Length | AA Length | Score | Probability |
|---|---|---|---|---|---|---|
| 33380275_f1_2 | 1746 | 3666 | 65 | 198 | | |

| Protein name | Locus Name | Acc# |
|---|---|---|
| | | |

Description

NO-HIT

| ORF Name | NTID | AAID | NT Length | AA Length | Score | Probability |
|---|---|---|---|---|---|---|
| 35361043_c1_7 | 1747 | 3667 | 62 | 189 | 93 | 0.00048 |

| Protein name | Locus Name | Acc# |
|---|---|---|
| phosphate-binding protein, phosphate-repressible | pir:I64120 | I64120 |

Description

| ORF Name | NTID | AAID | NT Length | AA Length | Score | Probability |
|---|---|---|---|---|---|---|
| 36501561_c3_9 | 1748 | 3668 | 301 | 903 | 842 | 5.2e-84 |

| Protein name | | | | Locus Name | | Acc# |
|---|---|---|---|---|---|---|
| | | | | sp:PSTC_HAEIN | | P45191 |

Description

PHOSPHATE TRANSPORT SYSTEM PERMEASE PROTEIN PSTC

| ORF Name | NTID | AAID | NT Length | AA Length | Score | Probability |
|---|---|---|---|---|---|---|
| 5960433_c1_8 | 1749 | 3669 | 60 | 183 | | |

| Protein name | | | | Locus Name | | Acc# |

Description

NO-HIT

| ORF Name | NTID | AAID | NT Length | AA Length | Score | Probability |
|---|---|---|---|---|---|---|
| 4429510_f1_1 | 1750 | 3670 | 477 | 1434 | 1328 | 1.7e-135 |

| Protein name | | | | Locus Name | | Acc# |
|---|---|---|---|---|---|---|
| | | | | sp:MANB_SALMO | | Q01411 |

Description

PHOSPHOMANNOMUTASE, (PMM)

| ORF Name | NTID | AAID | NT Length | AA Length | Score | Probability |
|---|---|---|---|---|---|---|
| 4459376_c2_15 | 1751 | 3671 | 294 | 885 | 575 | 1.0e-55 |

| Protein name | | | | Locus Name | | Acc# |
|---|---|---|---|---|---|---|
| conserved hypothetical protein | | | | pir:D75311 | | D75311 |

Description

| ORF Name | NTID | AAID | NT Length | AA Length | Score | Probability |
|---|---|---|---|---|---|---|
| 10429517_c1_34 | 1752 | 3672 | 413 | 1242 | 573 | 1.7e-55 |

| Protein name | | | | Locus Name | | Acc# |
|---|---|---|---|---|---|---|
| conserved hypothetical protein | | | | pir:A75525 | | A75525 |

Description

| ORF Name | NTID | AAID | NT Length | AA Length | Score | Probability |
|---|---|---|---|---|---|---|
| 12384625_c3_48 | 1753 | 3673 | 362 | 1089 | 386 | 1.1e-35 |

| Protein name | | | | Locus Name | | Acc# |
|---|---|---|---|---|---|---|
| | | | | sp:YGBO_ECOLI | | Q57261 |

Description

HYPOTHETICAL 39.1 KD PROTEIN IN SURE-CYSC INTERGENIC REGION

| ORF Name | NTID | AAID | NT Length | AA Length | Score | Probability |
|---|---|---|---|---|---|---|
| 15915625_f2_13 | 1754 | 3674 | 170 | 513 | | |

| Protein name | Locus Name | Acc# |
|---|---|---|

Description

NO-HIT

| ORF Name | NTID | AAID | NT Length | AA Length | Score | Probability |
|---|---|---|---|---|---|---|
| 21673425_f2_12 | 1755 | 3675 | 447 | 1344 | 507 | 1.7e-48 |

| Protein name | | | | Locus Name | | Acc# |
|---|---|---|---|---|---|---|
| | | | | sp:UBIH_ECOLI | | P25534 |

Description

UBIH PROTEIN,

| ORF Name | NTID | AAID | NT Length | AA Length | Score | Probability |
|---|---|---|---|---|---|---|
| 2195931_c1_29 | 1756 | 3676 | 69 | 210 | 93 | 0.0018 |

| Protein name | | Locus Name | | Acc# |
|---|---|---|---|---|
| conserved hypothetical protein aq_2107 | | pir:F70480 | | F70480 |

Description

| ORF Name | NTID | AAID | NT Length | AA Length | Score | Probability |
|---|---|---|---|---|---|---|
| 22355001_f3_23 | 1757 | 3677 | 73 | 222 | | |

| Protein name | Locus Name | Acc# |
|---|---|---|

Description

NO-HIT

| ORF Name | NTID | AAID | NT Length | AA Length | Score | Probability |
|---|---|---|---|---|---|---|
| 23954035_c3_50 | 1758 | 3678 | 175 | 528 | 119 | 3.8e-05 |

| Protein name | Locus Name | Acc# |
|---|---|---|
| conserved hypothetical protein aq_2107 | pir:F70480 | F70480 |

Description

| ORF Name | NTID | AAID | NT Length | AA Length | Score | Probability |
|---|---|---|---|---|---|---|
| 25665885_c2_36 | 1759 | 3679 | 241 | 726 | 389 | 6.3e-45 |

| Protein name | Locus Name | Acc# |
|---|---|---|
|  | sp:MIAE_SALTY | Q08015 |

Description

TRNA-(MS[2

| ORF Name | NTID | AAID | NT Length | AA Length | Score | Probability |
|---|---|---|---|---|---|---|
| 30100880_c3_51 | 1760 | 3680 | 201 | 606 | 186 | 1.7e-14 |

| Protein name | Locus Name | Acc# |
|---|---|---|
| hypothetical protein aq_2108 | pir:G70480 | G70480 |

Description

| ORF Name | NTID | AAID | NT Length | AA Length | Score | Probability |
|---|---|---|---|---|---|---|
| 3994052_f1_3 | 1761 | 3681 | 192 | 579 | 682 | 4.7e-67 |

| Protein name | Locus Name | Acc# |
|---|---|---|
| probable dctp deaminase | pir:B71565 | B71565 |

Description

| ORF Name | NTID | AAID | NT Length | AA Length | Score | Probability |
|---|---|---|---|---|---|---|
| 4109790_c1_28 | 1762 | 3682 | 155 | 468 | 176 | 2.2e-12 |

| Protein name | Locus Name | Acc# |
|---|---|---|
| conserved hypothetical protein aq_2107 | pir:F70480 | F70480 |

Description

| ORF Name | NTID | AAID | NT Length | AA Length | Score | Probability |
|---|---|---|---|---|---|---|
| 4319837_c2_37 | 1763 | 3683 | 493 | 1482 | 466 | 3.7e-44 |

| Protein name | Locus Name | Acc# |
|---|---|---|
| | sp:YJEF_ECOLI | P31806 |

Description

HYPOTHETICAL 54.7 KD PROTEIN IN PSD-AMIB INTERGENIC REGION (URF1)

| ORF Name | NTID | AAID | NT Length | AA Length | Score | Probability |
|---|---|---|---|---|---|---|
| 4345068_f3_21 | 1764 | 3684 | 128 | 387 | 177 | 1.5e-13 |

| Protein name | Locus Name | Acc# |
|---|---|---|
| | sp:YOHJ_ECOLI | P33372 |

Description

HYPOTHETICAL 14.6 KD PROTEIN IN PBPG-CDD INTERGENIC REGION

| ORF Name | NTID | AAID | NT Length | AA Length | Score | Probability |
|---|---|---|---|---|---|---|
| 4790637_f3_22 | 1765 | 3685 | 183 | 552 | 295 | 4.8e-26 |

| Protein name | Locus Name | Acc# |
|---|---|---|
| | sp:YOHK_HAEIN | P45146 |

Description

HYPOTHETICAL PROTEIN HI1298

| ORF Name | NTID | AAID | NT Length | AA Length | Score | Probability |
|---|---|---|---|---|---|---|
| 5900203_f1_1 | 1766 | 3686 | 689 | 2070 | 1609 | 2.8e-165 |

| Protein name | Locus Name | Acc# |
|---|---|---|
| | sp:REP_ECOLI | P09980 |

Description

ATP-DEPENDENT DNA HELICASE REP,

| ORF Name | NTID | AAID | NT Length | AA Length | Score | Probability |
|---|---|---|---|---|---|---|
| 6658527_c2_39 | 1767 | 3687 | 184 | 555 | 228 | 5.6e-18 |

| Protein name | Locus Name | Acc# |
|---|---|---|
| conserved hypothetical protein aq_2107 | pir:F70480 | F70480 |

Description

| ORF Name | NTID | AAID | NT Length | AA Length | Score | Probability |
|---|---|---|---|---|---|---|
| 7226518_f2_17 | 1768 | 3688 | 102 | 309 | 112 | 1.2e-06 |

| Protein name | Locus Name | Acc# |
|---|---|---|
| hypothetical protein | gp:POL010393 | AJ010393 |

Description

Pseudomonas oleovorans phaI and phaF genes, and ORF1, ORF2(partial) and ORF3.

| ORF Name | NTID | AAID | NT Length | AA Length | Score | Probability |
|---|---|---|---|---|---|---|
| 22897332_c2_15 | 1769 | 3689 | 153 | 462 | 338 | 1.3e-30 |

| Protein name | Locus Name | Acc# |
|---|---|---|
| | sp:FMAH_BACNO | P04953 |

Description (SUBUNITS PILIN)

| ORF Name | NTID | AAID | NT Length | AA Length | Score | Probability |
|---|---|---|---|---|---|---|
| 36210875_f2_3 | 1770 | 3690 | 883 | 2652 | 3272 | 0.0 |

| Protein name | Locus Name | Acc# |
|---|---|---|
| | sp:ACO2_ECOLI | |

Description (ACONITASE 2)

| ORF Name | NTID | AAID | NT Length | AA Length | Score | Probability |
|---|---|---|---|---|---|---|
| 14853143_c1_9 | 1771 | 3691 | 703 | 2112 | 1460 | 1.7e-149 |

| Protein name | Locus Name | Acc# |
|---|---|---|
| | sp:YHGF_NEIME | Q51152 |

Description

HYPOTHETICAL 83.1 KD PROTEIN IN REGION E

| ORF Name | NTID | AAID | NT Length | AA Length | Score | Probability |
|---|---|---|---|---|---|---|
| 16050817_f1_1 | 1772 | 3692 | 225 | 678 | 203 | 2.7e-16 |

| Protein name | Locus Name | Acc# |
|---|---|---|
| hypothetical protein sll0788 | pir:S77018 | S77018 |

Description

| ORF Name | NTID | AAID | NT Length | AA Length | Score | Probability |
|---|---|---|---|---|---|---|
| 10175877_f3_73 | 1773 | 3693 | 264 | 795 | 124 | 2.2e-11 |

| Protein name | Locus Name | Acc# |
|---|---|---|
| DnrD protein | gp:PST131715 | AJ131715 |

Description

Pseudomonas stutzeri dnrD gene and ORF194 (partial) and ORF63(partial).

| ORF Name | NTID | AAID | NT Length | AA Length | Score | Probability |
|---|---|---|---|---|---|---|
| 10195250_f2_49 | 1774 | 3694 | 81 | 246 | | |

| Protein name | Locus Name | Acc# |
|---|---|---|
| | | |

Description

NO-HIT

| ORF Name | NTID | AAID | NT Length | AA Length | Score | Probability |
|---|---|---|---|---|---|---|
| 10546930_f1_18 | 1775 | 3695 | 239 | 720 | 576 | 8.1e-56 |

| Protein name | Locus Name | Acc# |
|---|---|---|
| | sp:MODB_HAEIN | P45322 |

Description

MOLYBDENUM TRANSPORT SYSTEM PERMEASE PROTEIN MODB

| ORF Name | NTID | AAID | NT Length | AA Length | Score | Probability |
|---|---|---|---|---|---|---|
| 11113152_f3_70 | 1776 | 3696 | 142 | 429 | 205 | 1.7e-16 |

| Protein name | Locus Name | Acc# |
|---|---|---|
| hypothetical protein APE1291 | pir:D72603 | D72603 |

Description

| ORF Name | NTID | AAID | NT Length | AA Length | Score | Probability |
|---|---|---|---|---|---|---|
| 12367711_f3_63 | 1777 | 3697 | 259 | 780 | 438 | 3.4e-41 |

| Protein name | Locus Name | Acc# |
|---|---|---|
| | sp:MODD_AZOVI | P37732 |

Description

MOLYBDENUM TRANSPORT ATP-BINDING PROTEIN MODD

450

| ORF Name | NTID | AAID | NT Length | AA Length | Score | Probability |
|---|---|---|---|---|---|---|
| 15710327_c1_84 | 1778 | 3698 | 266 | 801 | 427 | 5.0e-40 |

| Protein name | Locus Name | Acc# |
|---|---|---|
| putative chaperone | gp:PSNARXL | Y15252 |

Description

Pseudomonas aeruginosa narX, narL, narK1, narK2, narG, narH, narJ, narI, nifM, moaA genes.

| ORF Name | NTID | AAID | NT Length | AA Length | Score | Probability |
|---|---|---|---|---|---|---|
| 15781576_c2_103 | 1779 | 3699 | 223 | 672 | 594 | 1.0e-57 |

| Protein name | Locus Name | Acc# |
|---|---|---|
|  | sp:YADF_ECOLI |  |

Description

HYPOTHETICAL 25.1 KD PROTEIN IN HPT-PAND INTERGENIC REGION

| ORF Name | NTID | AAID | NT Length | AA Length | Score | Probability |
|---|---|---|---|---|---|---|
| 19735188_f3_58 | 1780 | 3700 | 677 | 2034 | 484 | 3.8e-70 |

| Protein name | Locus Name | Acc# |
|---|---|---|
| nitrate/nitrite sensory protein | gp:PSNARXL | Y15252 |

Description

Pseudomonas aeruginosa narX, narL, narK1, narK2, narG, narH, narJ, narI, nifM, moaA genes.

| ORF Name | NTID | AAID | NT Length | AA Length | Score | Probability |
|---|---|---|---|---|---|---|
| 19806552_f2_31 | 1781 | 3701 | 187 | 564 | 134 | 5.5e-08 |

| Protein name | Locus Name | Acc# |
|---|---|---|
| Notch homolog | gp:AF033013 | AF033013 |

Description

Bombyx mori Notch homolog mRNA, partial cds.

| ORF Name | NTID | AAID | NT Length | AA Length | Score | Probability |
|---|---|---|---|---|---|---|
| 19806552_f3_51 | 1782 | 3702 | 180 | 543 | 142 | 1.3e-09 |

| Protein name | | | | Locus Name | | Acc# |
|---|---|---|---|---|---|---|
| Notch homolog | | | | gp:AF033013 | | AF033013 |

Description

Bombyx mori Notch homolog mRNA, partial cds.

| ORF Name | NTID | AAID | NT Length | AA Length | Score | Probability |
|---|---|---|---|---|---|---|
| 20423500_f2_33 | 1783 | 3703 | 269 | 810 | 420 | 2.7e-39 |

| Protein name | | | | Locus Name | | Acc# |
|---|---|---|---|---|---|---|
| | | | | sp:MOEB_SALTY | | Q56067 |

Description

MOLYBDOPTERIN BIOSYNTHESIS MOEB PROTEIN

| ORF Name | NTID | AAID | NT Length | AA Length | Score | Probability |
|---|---|---|---|---|---|---|
| 20587686_f1_8 | 1784 | 3704 | 139 | 420 | | |

| Protein name | | | | Locus Name | | Acc# |
|---|---|---|---|---|---|---|

Description

NO-HIT

| ORF Name | NTID | AAID | NT Length | AA Length | Score | Probability |
|---|---|---|---|---|---|---|
| 20876387_f1_13 | 1785 | 3705 | 234 | 705 | 247 | 5.9e-21 |

| Protein name | | | | Locus Name | | Acc# |
|---|---|---|---|---|---|---|
| | | | | sp:YIIM_ECOLI | | P32157 |

Description

HYPOTHETICAL 26.6 KD PROTEIN IN KDGT-CPXA INTERGENIC REGION (O234)

| ORF Name | NTID | AAID | NT Length | AA Length | Score | Probability |
|---|---|---|---|---|---|---|
| 21485962_c2_129 | 1786 | 3706 | 63 | 189 | | |

| Protein name | | | | Locus Name | | Acc# |
|---|---|---|---|---|---|---|

Description

NO-HIT

| ORF Name | NTID | AAID | NT Length | AA Length | Score | Probability |
|---|---|---|---|---|---|---|
| 21673452_c3_141 | 1787 | 3707 | 448 | 1347 | 1455 | 5.8e-149 |

| Protein name | Locus Name | Acc# |
|---|---|---|
| nitrate extrusion protein | gp:PSNARXL | Y15252 |

Description

Pseudomonas aeruginosa narX, narL, narK1, narK2, narG, narH, narJ, narI, nifM, moaA genes.

| ORF Name | NTID | AAID | NT Length | AA Length | Score | Probability |
|---|---|---|---|---|---|---|
| 21688888_c1_76 | 1788 | 3708 | 332 | 999 | 1035 | 1.8e-104 |

| Protein name | Locus Name | Acc# |
|---|---|---|
|  | sp:THII_SALTY |  |

Description

THIAMINE BIOSYNTHESIS PROTEIN THII

| ORF Name | NTID | AAID | NT Length | AA Length | Score | Probability |
|---|---|---|---|---|---|---|
| 22000717_f1_19 | 1789 | 3709 | 145 | 438 |  |  |

| Protein name | Locus Name | Acc# |
|---|---|---|

Description

NO-HIT

| ORF Name | NTID | AAID | NT Length | AA Length | Score | Probability |
|---|---|---|---|---|---|---|
| 22378418_f1_17 | 1790 | 3710 | 283 | 852 | 502 | 5.6e-48 |

| Protein name | Locus Name | Acc# |
|---|---|---|
|  | sp:MODA_HAEIN | P45323 |

Description

MOLYBDATE-BINDING PERIPLASMIC PROTEIN PRECURSOR

| ORF Name | NTID | AAID | NT Length | AA Length | Score | Probability |
|---|---|---|---|---|---|---|
| 22554031_f3_60 | 1791 | 3711 | 194 | 585 | 499 | 1.2e-47 |

| Protein name | Locus Name | Acc# |
|---|---|---|
|  | sp:MOAB_ECOLI | P30746 |

Description

MOLYBDENUM COFACTOR BIOSYNTHESIS PROTEIN B

453

| ORF Name | NTID | AAID | NT Length | AA Length | Score | Probability |
|---|---|---|---|---|---|---|
| 24068812_f1_12 | 1792 | 3712 | 258 | 777 | 561 | 3.1e-54 |

| Protein name | Locus Name | Acc# |
|---|---|---|
| nitrate/nitrite regulatory protein | gp:PSNARXL | Y15252 |

Description

Pseudomonas aeruginosa narX, narL, narK1, narK2, narG, narH, narJ, narI, nifM, moaA genes.

| ORF Name | NTID | AAID | NT Length | AA Length | Score | Probability |
|---|---|---|---|---|---|---|
| 24423375_f1_5 | 1793 | 3713 | 71 | 216 | | |

| Protein name | Locus Name | Acc# |
|---|---|---|
| | | |

Description

NO-HIT

| ORF Name | NTID | AAID | NT Length | AA Length | Score | Probability |
|---|---|---|---|---|---|---|
| 24423375_f2_32 | 1794 | 3714 | 66 | 201 | | |

| Protein name | Locus Name | Acc# |
|---|---|---|
| | | |

Description

NO-HIT

| ORF Name | NTID | AAID | NT Length | AA Length | Score | Probability |
|---|---|---|---|---|---|---|
| 24651536_f1_16 | 1795 | 3715 | 200 | 603 | 310 | 1.2e-27 |

| Protein name | Locus Name | Acc# |
|---|---|---|
| | sp:Y903_SYNY3 | Q55371 |

Description

HYPOTHETICAL 16.5 KD PROTEIN SLR0903

| ORF Name | NTID | AAID | NT Length | AA Length | Score | Probability |
|---|---|---|---|---|---|---|
| 25507260_f1_9 | 1796 | 3716 | 338 | 1017 | 82 | 0.048 |

| Protein name | Locus Name | Acc# |
|---|---|---|
| MHC class I antigen | pir:I57454 | I57454 |

Description

| ORF_Name | NTID | AAID | NT Length | AA Length | Score | Probability |
|---|---|---|---|---|---|---|
| 275283_f1_15 | 1797 | 3717 | 196 | 591 | 142 | 7.9e-10 |

| Protein name | Locus Name | Acc# |
|---|---|---|
| hypothetical protein Rv2453c | pir:D70864 | D70864 |

Description

| ORF_Name | NTID | AAID | NT Length | AA Length | Score | Probability |
|---|---|---|---|---|---|---|
| 2853437_f1_11 | 1798 | 3718 | 66 | 201 | | |

| Protein name | Locus Name | Acc# |
|---|---|---|

Description

NO-HIT

| ORF_Name | NTID | AAID | NT Length | AA Length | Score | Probability |
|---|---|---|---|---|---|---|
| 29432768_c2_123 | 1799 | 3719 | 91 | 276 | | |

| Protein name | Locus Name | Acc# |
|---|---|---|

Description

NO-HIT

| ORF_Name | NTID | AAID | NT Length | AA Length | Score | Probability |
|---|---|---|---|---|---|---|
| 30509827_f1_7 | 1800 | 3720 | 134 | 405 | | |

| Protein name | Locus Name | Acc# |
|---|---|---|

Description

NO-HIT

| ORF_Name | NTID | AAID | NT Length | AA Length | Score | Probability |
|---|---|---|---|---|---|---|
| 31453162_c2_128 | 1801 | 3721 | 77 | 234 | 197 | 1.2e-15 |

| Protein name | Locus Name | Acc# |
|---|---|---|
| hypothetical protein | gp:AF213822 | AF213822 |

Description

Zymomonas mobilis strain ZM4 fosmid clone 42B3, complete sequence.

| ORF Name | NTID | AAID | NT Length | AA Length | Score | Probability |
|---|---|---|---|---|---|---|
| 33331633_c1_83 | 1802 | 3722 | 521 | 1566 | 2362 | 4.4e-245 |

| Protein name | Locus Name | Acc# |
|---|---|---|
| respiratory nitrate reductase beta subunit | gp:PSNARXL | Y15252 |

Description

Pseudomonas aeruginosa narX, narL, narK1, narK2, narG, narH, narJ, narI, nifM, moaA genes.

| ORF Name | NTID | AAID | NT Length | AA Length | Score | Probability |
|---|---|---|---|---|---|---|
| 33758515_f1_6 | 1803 | 3723 | 174 | 525 | | |

| Protein name | Locus Name | Acc# |
|---|---|---|

Description

NO-HIT

| ORF Name | NTID | AAID | NT Length | AA Length | Score | Probability |
|---|---|---|---|---|---|---|
| 36351552_f3_61 | 1804 | 3724 | 91 | 276 | 145 | 3.8e-10 |

| Protein name | Locus Name | Acc# |
|---|---|---|
| hypothetical protein ssr1527 | pir:S75710 | |

Description

| ORF Name | NTID | AAID | NT Length | AA Length | Score | Probability |
|---|---|---|---|---|---|---|
| 36371012_c2_102 | 1805 | 3725 | 60 | 183 | | |

| Protein name | Locus Name | Acc# |
|---|---|---|

Description

NO-HIT

| ORF Name | NTID | AAID | NT Length | AA Length | Score | Probability |
|---|---|---|---|---|---|---|
| 3906555_f2_36 | 1806 | 3726 | 172 | 519 | 296 | 3.8e-26 |

| Protein name | Locus Name | Acc# |
|---|---|---|
| probable molybdenum-pterin-binding-protein | pir:S57954 | S57954 |

Description

| ORF Name | NTID | AAID | NT Length | AA Length | Score | Probability |
|---|---|---|---|---|---|---|
| 4011062_c1_91 | 1807 | 3727 | 427 | 1284 | 1152 | 7.4e-117 |

Protein name: nitrate extrusion protein
Locus Name: gp:PSNARXL
Acc#: Y15252

Description: Pseudomonas aeruginosa narX, narL, narK1, narK2, narG, narH, narJ, narI, nifM, moaA genes.

| ORF Name | NTID | AAID | NT Length | AA Length | Score | Probability |
|---|---|---|---|---|---|---|
| 4070308_c3_134 | 1808 | 3728 | 442 | 1329 | 676 | 2.0e-66 |

Protein name:
Locus Name: sp:MOEA_HAEIN
Acc#: P45210

Description: MOLYBDOPTERIN BIOSYNTHESIS MOEA PROTEIN

| ORF Name | NTID | AAID | NT Length | AA Length | Score | Probability |
|---|---|---|---|---|---|---|
| 4344003_f3_59 | 1809 | 3729 | 364 | 1095 | 737 | 7.0e-73 |

Protein name:
Locus Name: sp:MOAA_HAEIN
Acc#: P45311

Description: MOLYBDENUM COFACTOR BIOSYNTHESIS PROTEIN A

| ORF Name | NTID | AAID | NT Length | AA Length | Score | Probability |
|---|---|---|---|---|---|---|
| 4788876_c3_133 | 1810 | 3730 | 248 | 747 | 704 | 2.2e-69 |

Protein name: respiratory nitrate reductase gamma subunit
Locus Name: gp:PSNARXL
Acc#: Y15252

Description: Pseudomonas aeruginosa narX, narL, narK1, narK2, narG, narH, narJ, narI, nifM, moaA genes.

| ORF Name | NTID | AAID | NT Length | AA Length | Score | Probability |
|---|---|---|---|---|---|---|
| 4797093_f3_52 | 1811 | 3731 | 157 | 474 | | |

| Protein name | Locus Name | Acc# |
|---|---|---|
| | | |

Description

NO-HIT

| ORF Name | NTID | AAID | NT Length | AA Length | Score | Probability |
|---|---|---|---|---|---|---|
| 4806502_c2_127 | 1812 | 3732 | 102 | 309 | 117 | 3.5e-07 |

| Protein name | Locus Name | Acc# |
|---|---|---|
| negative regulator of translation | gp:AF213822 | AF213822 |

Description

Zymomonas mobilis strain ZM4 fosmid clone 42B3, complete sequence.

| ORF Name | NTID | AAID | NT Length | AA Length | Score | Probability |
|---|---|---|---|---|---|---|
| 4886251_f2_35 | 1813 | 3733 | 168 | 507 | 354 | 2.7e-32 |

| Protein name | Locus Name | Acc# |
|---|---|---|
| molybdenum cofactor biosynthesis protein C | gp:AF108766 | AF108766 |

Description

Rhodobacter sphaeroides AsmA (asmA) gene, partial cds; YbaU (ybaU), anthranilate synthase component I (trpE), YibQ (yibQ), anthranilatesynthase component II (trpG), anthranilatephosphoribosyltransferase (trpD), indole-3-glycerol phosphatesynthase (trpC), molybdenum cofactor biosynthesis protein C (moaC), molybdenum cofactor biosynthesis protein A (moeA), LexA

| ORF Name | NTID | AAID | NT Length | AA Length | Score | Probability |
|---|---|---|---|---|---|---|
| 4897576_c3_147 | 1814 | 3734 | 69 | 210 | | |

| Protein name | Locus Name | Acc# |
|---|---|---|
| | | |

Description

NO-HIT

| ORF Name | NTID | AAID | NT Length | AA Length | Score | Probability |
|---|---|---|---|---|---|---|
| 5282812_f3_56 | 1815 | 3735 | 65 | 198 | 52 | 0.032 |

| Protein name | | Locus Name | Acc# |
|---|---|---|---|
| MDP1 | | gp:AB013441 | AB013441 |

Description

Mycobacterium bovis gene for MDP1, complete cds.

| ORF Name | NTID | AAID | NT Length | AA Length | Score | Probability |
|---|---|---|---|---|---|---|
| 630053_f2_47 | 1816 | 3736 | 385 | 1158 | 320 | 1.1e-28 |

| Protein name | | Locus Name | Acc# |
|---|---|---|---|
| ORF396 protein | | gp:PSDNGC | Z73914 |

Description

Pseudomonas stutzeri orf175 gene.

| ORF Name | NTID | AAID | NT Length | AA Length | Score | Probability |
|---|---|---|---|---|---|---|
| 635903_f1_10 | 1817 | 3737 | 75 | 228 | | |

| Protein name | | Locus Name | Acc# |
|---|---|---|---|

Description

NO-HIT

| ORF Name | NTID | AAID | NT Length | AA Length | Score | Probability |
|---|---|---|---|---|---|---|
| 7064692_c1_86 | 1818 | 3738 | 369 | 1110 | 415 | 9.3e-39 |

| Protein name | | Locus Name | Acc# |
|---|---|---|---|
| NifM protein | | gp:PSNARXL | Y15252 |

Description

Pseudomonas aeruginosa narX, narL, narK1, narK2, narG, narH, narJ, narI, nifM, moaA genes.

| ORF Name | NTID | AAID | NT Length | AA Length | Score | Probability |
|---|---|---|---|---|---|---|
| 7225637_f3_50 | 1819 | 3739 | 1739 | 5220 | 540 | 6.2e-50 |

| Protein name | | Locus Name | Acc# |
|---|---|---|---|
| filamentous hemagglutinin-like protein PspA:probable secreted protein | | pir:T09083 | T09083 |

Description

459

| ORF_Name | NTID | AAID | NT Length | AA Length | Score | Probability |
|---|---|---|---|---|---|---|
| 9814751_c3_131 | 1820 | 3740 | 1271 | 3816 | 5075 | 0.0 |

| Protein name | Locus_Name | Acc# |
|---|---|---|
| alpha-subunit of nitrate reductase | gp:PFU71398 | U71398 |

Description

Pseudomonas fluorescens nitrate reductase alpha-subunit (narG) andbeta-subunit (narH) genes, partial cds.

| ORF_Name | NTID | AAID | NT Length | AA Length | Score | Probability |
|---|---|---|---|---|---|---|
| 1176576_f3_28 | 1821 | 3741 | 157 | 474 | 314 | 4.7e-28 |

| Protein name | Locus_Name | Acc# |
|---|---|---|
|  | sp:YAII_ECOLI |  |

Description

HYPOTHETICAL 17.0 KD PROTEIN IN PROC-AROL INTERGENIC REGION

| ORF_Name | NTID | AAID | NT Length | AA Length | Score | Probability |
|---|---|---|---|---|---|---|
| 14647507_f2_20 | 1822 | 3742 | 405 | 1218 | 386 | 1.1e-35 |

| Protein name | Locus_Name | Acc# |
|---|---|---|
| conserved hypothetical protein aq_740 | pir:A70365 | A70365 |

Description

| ORF_Name | NTID | AAID | NT Length | AA Length | Score | Probability |
|---|---|---|---|---|---|---|
| 23443752_f3_23 | 1823 | 3743 | 661 | 1986 | 298 | 3.4e-23 |

| Protein name | Locus_Name | Acc# |
|---|---|---|
|  | sp:YTRP_PSEPU | P40604 |

Description

HYPOTHETICAL 62.7 KD PROTEIN IN TRPE-TRPG INTERGENIC REGION PRECURSOR

| ORF_Name | NTID | AAID | NT Length | AA Length | Score | Probability |
|---|---|---|---|---|---|---|
| 23610636_c3_58 | 1824 | 3744 | 274 | 825 | 755 | 8.7e-75 |

| Protein name | Locus_Name | Acc# |
|---|---|---|
|  | sp:YQCB_HAEIN | P44197 |

Description

HYPOTHETICAL PROTEIN HI1435

460

| ORF Name | NTID | AAID | NT Length | AA Length | Score | Probability |
|---|---|---|---|---|---|---|
| 24644035_c2_45 | 1825 | 3745 | 219 | 660 | 255 | 8.4e-22 |

| Protein name | Locus Name | Acc# |
|---|---|---|
| probable citrate lyase beta chain | pir:T35062 | T35062 |

Description

---

| ORF Name | NTID | AAID | NT Length | AA Length | Score | Probability |
|---|---|---|---|---|---|---|
| 250251_f2_18 | 1826 | 3746 | 192 | 579 | 525 | 2.0e-50 |

| Protein name | Locus Name | Acc# |
|---|---|---|
| | sp:PUR6_HAEIN | P43849 |

Description (EC 4.1.1.21) (AIR CARBOXYLASE) (AIRC)

---

| ORF Name | NTID | AAID | NT Length | AA Length | Score | Probability |
|---|---|---|---|---|---|---|
| 25485763_f1_1 | 1827 | 3747 | 89 | 270 | | |

| Protein name | Locus Name | Acc# |
|---|---|---|
| | | |

Description

NO-HIT

---

| ORF Name | NTID | AAID | NT Length | AA Length | Score | Probability |
|---|---|---|---|---|---|---|
| 25510974_c1_34 | 1828 | 3748 | 185 | 558 | 331 | 7.4e-30 |

| Protein name | Locus Name | Acc# |
|---|---|---|
| | sp:YBEQ_ECOLI | P77234 |

Description

HYPOTHETICAL 37.3 KD PROTEIN IN LEUS-GLTL INTERGENIC REGION

---

| ORF Name | NTID | AAID | NT Length | AA Length | Score | Probability |
|---|---|---|---|---|---|---|
| 29304668_f3_30 | 1829 | 3749 | 302 | 909 | 556 | 1.1e-53 |

| Protein name | Locus Name | Acc# |
|---|---|---|
| | sp:SYK3_ECOLI | |

Description

HYPOTHETICAL LYSYL-TRNA SYNTHETASE HOMOLOG, (GX)

| ORF_Name | NTID | AAID | NT Length | AA Length | Score | Probability |
|---|---|---|---|---|---|---|
| 31275301_f1_11 | 1830 | 3750 | 352 | 1059 | 516 | 1.8e-49 |

Protein name | | | | Locus_Name | | Acc# |
| | | | | sp:PDXB_ECOLI | | P05459 |

Description

ERYTHRONATE-4-PHOSPHATE DEHYDROGENASE,

| ORF_Name | NTID | AAID | NT Length | AA Length | Score | Probability |
|---|---|---|---|---|---|---|
| 34179211_f3_24 | 1831 | 3751 | 330 | 993 | 158 | 1.2e-08 |

Protein name: probable protein serine-threonine phosphatase | Locus_Name: pir:C75297 | Acc# C75297

Description

| ORF_Name | NTID | AAID | NT Length | AA Length | Score | Probability |
|---|---|---|---|---|---|---|
| 36365625_f2_17 | 1832 | 3752 | 147 | 444 | 348 | 1.2e-31 |

Protein name: hypothetical protein jhp1377 | Locus_Name: pir:D71815 | Acc# D71815

Description

| ORF_Name | NTID | AAID | NT Length | AA Length | Score | Probability |
|---|---|---|---|---|---|---|
| 5118952_c1_35 | 1833 | 3753 | 403 | 1212 | 703 | 2.8e-69 |

Protein name | | | | Locus_Name: sp:PYR2_PSEAE | | Acc# Q51551

Description

CATALYTIC CHAIN)

| ORF_Name | NTID | AAID | NT Length | AA Length | Score | Probability |
|---|---|---|---|---|---|---|
| 5275300_f3_22 | 1834 | 3754 | 347 | 1044 | 954 | 7.1e-96 |

Protein name | | | | Locus_Name: sp:BIOB_ECOLI | | Acc# P12996

Description

BIOTIN SYNTHASE, (BIOTIN SYNTHETASE)

| ORF_Name | NTID | AAID | NT Length | AA Length | Score | Probability |
|---|---|---|---|---|---|---|
| 5948342_f3_27 | 1835 | 3755 | 259 | 780 | 530 | 6.0e-51 |

| Protein name | Locus_Name | Acc# |
|---|---|---|
| | sp:PURK_PSEAE | P72158 |

Description (AIR CARBOXYLASE) (AIRC)

| ORF_Name | NTID | AAID | NT Length | AA Length | Score | Probability |
|---|---|---|---|---|---|---|
| 7041_f1_8 | 1836 | 3756 | 132 | 399 | 155 | 1.5e-10 |

| Protein name | Locus_Name | Acc# |
|---|---|---|
| | sp:PURK_AQUAE | O66608 |

Description (AIR CARBOXYLASE) (AIRC)

| ORF_Name | NTID | AAID | NT Length | AA Length | Score | Probability |
|---|---|---|---|---|---|---|
| 12991392_f2_18 | 1837 | 3757 | 101 | 306 | 160 | 9.7e-12 |

| Protein name | Locus_Name | Acc# |
|---|---|---|
| unknown | gp:PDU08856 | U08856 |

Description

Paracoccus denitrificans insertion sequence IS1248b, completesequence.

| ORF_Name | NTID | AAID | NT Length | AA Length | Score | Probability |
|---|---|---|---|---|---|---|
| 15110912_c3_69 | 1838 | 3758 | 358 | 1077 | 690 | 6.7e-68 |

| Protein name | Locus_Name | Acc# |
|---|---|---|
| | sp:YQJM_BACSU | P54550 |

Description

PROBABLE NADH-DEPENDENT FLAVIN OXIDOREDUCTASE YQJM,

| ORF_Name | NTID | AAID | NT Length | AA Length | Score | Probability |
|---|---|---|---|---|---|---|
| 15632781_c2_61 | 1839 | 3759 | 79 | 240 | | |

| Protein name | Locus_Name | Acc# |
|---|---|---|
| | | |

Description

NO-HIT

| ORF Name | NTID | AAID | NT Length | AA Length | Score | Probability |
|---|---|---|---|---|---|---|
| 15673816_f3_31 | 1840 | 3760 | 472 | 1419 | 1772 | 1.5e-182 |

| Protein name | Locus Name | Acc# |
|---|---|---|
| type I site-specific deoxyribonuclease, Hsd chain R:type I restriction enzyme, Hsd, chain R:type I restriction-modification system, | pir:JC5216 | JC5216 |

Description

| ORF Name | NTID | AAID | NT Length | AA Length | Score | Probability |
|---|---|---|---|---|---|---|
| 19823578_f3_29 | 1841 | 3761 | 405 | 1218 | 130 | 1.0e-07 |

| Protein name | Locus Name | Acc# |
|---|---|---|
| hypothetical protein | pir:A75592 | A75592 |

Description

| ORF Name | NTID | AAID | NT Length | AA Length | Score | Probability |
|---|---|---|---|---|---|---|
| 21642052_c3_70 | 1842 | 3762 | 232 | 699 | 686 | 1.8e-67 |

| Protein name | Locus Name | Acc# |
|---|---|---|
|  | sp:YC78_HAEIN |  |

Description

PUTATIVE NAD(P)H NITROREDUCTASE,

| ORF Name | NTID | AAID | NT Length | AA Length | Score | Probability |
|---|---|---|---|---|---|---|
| 21673201_f3_25 | 1843 | 3763 | 220 | 663 | 364 | 2.4e-33 |

| Protein name | Locus Name | Acc# |
|---|---|---|
| protein Tp70 | pir:A71309 |  |

Description

| ORF Name | NTID | AAID | NT Length | AA Length | Score | Probability |
|---|---|---|---|---|---|---|
| 2189075_c2_66 | 1844 | 3764 | 126 | 381 | 195 | 1.9e-15 |

| Protein name | Locus Name | Acc# |
|---|---|---|
|  | sp:YPRO_OWEFU |  |

Description

HYPOTHETICAL PROLINE-RICH PROTEIN (FRAGMENT)

| ORF Name | NTID | AAID | NT Length | AA Length | Score | Probability |
|---|---|---|---|---|---|---|
| 22143752_f1_9 | 1845 | 3765 | 636 | 1911 | 2756 | 7.9e-287 |

| Protein name | Locus Name | Acc# |
|---|---|---|
| type I site-specific deoxyribonuclease, Hsd chain R:type I restriction enzyme, Hsd, chain R:type I restriction-modification system, | pir:JC5216 | JC5216 |

Description

---

| ORF Name | NTID | AAID | NT Length | AA Length | Score | Probability |
|---|---|---|---|---|---|---|
| 23437551_f1_4 | 1846 | 3766 | 83 | 252 | | |

| Protein name | Locus Name | Acc# |
|---|---|---|
| | | |

Description

NO-HIT

---

| ORF Name | NTID | AAID | NT Length | AA Length | Score | Probability |
|---|---|---|---|---|---|---|
| 23490937_c3_81 | 1847 | 3767 | 93 | 282 | 73 | 0.037 |

| Protein name | Locus Name | Acc# |
|---|---|---|
| nicotinamide adenine dinucleotide dehydrogenase | gp:AF025836 | AF025836 |

Description

Echinostoma sp.I. Africa nicotinamide adenine dinucleotidedehydrogenase subunit 1 (ND1) gene, mitochondrial gene encodingmitochondrial protein, partial cds.

---

| ORF Name | NTID | AAID | NT Length | AA Length | Score | Probability |
|---|---|---|---|---|---|---|
| 24704462_c2_51 | 1848 | 3768 | 206 | 621 | 296 | 3.8e-26 |

| Protein name | Locus Name | Acc# |
|---|---|---|
| cinnamyl-alcohol dehydrogenase | gp:AF083333 | AF083333 |

Description

Medicago sativa cinnamyl-alcohol dehydrogenase (MsaCad1) mRNA, complete cds.

| ORF Name | NTID | AAID | NT Length | AA Length | Score | Probability |
|---|---|---|---|---|---|---|
| 32667715_f3_26 | 1849 | 3769 | 188 | 567 | 106 | 0.00093 |

| Protein name | Locus Name | Acc# |
|---|---|---|
| hypothetical protein TP0570 | pir:H71308 | H71308 |

Description

| ORF Name | NTID | AAID | NT Length | AA Length | Score | Probability |
|---|---|---|---|---|---|---|
| 35350802_f1_5 | 1850 | 3770 | 167 | 504 | 345 | 2.4e-31 |

| Protein name | Locus Name | Acc# |
|---|---|---|
| putative transposase | gp:AF007429 | AF007429 |

Description

Haemophilus paragallinarum IS-like putative transposase gene, complete cds.

| ORF Name | NTID | AAID | NT Length | AA Length | Score | Probability |
|---|---|---|---|---|---|---|
| 36564842_f2_19 | 1851 | 3771 | 460 | 1383 | 573 | 1.7e-55 |

| Protein name | Locus Name | Acc# |
|---|---|---|
| type I site-specific deoxyribonuclease, Hsd chain S:type I restriction enzyme, Hsd, chain S:type I restriction-modification system, | pir:JC5218 | JC5218 |

Description

| ORF Name | NTID | AAID | NT Length | AA Length | Score | Probability |
|---|---|---|---|---|---|---|
| 4032715_f3_27 | 1852 | 3772 | 116 | 351 | 214 | 1.8e-17 |

| Protein name | Locus Name | Acc# |
|---|---|---|
|  | sp:Y4SN_RHISN | P50358 |

Description

HYPOTHETICAL 14.4 KD PROTEIN Y4SN

| ORF Name | NTID | AAID | NT Length | AA Length | Score | Probability |
|---|---|---|---|---|---|---|
| 4111333_f3_33 | 1853 | 3773 | 201 | 603 | 238 | 5.3e-20 |

| Protein name | Locus Name | Acc# |
|---|---|---|
|  | sp:NAHR_PSEPU | P10183 |

Description

TRANSCRIPTIONAL ACTIVATOR PROTEIN NAHR

| ORF Name | NTID | AAID | NT Length | AA Length | Score | Probability |
|---|---|---|---|---|---|---|
| 4895127_cl_36 | 1854 | 3774 | 116 | 351 | 334 | 3.6e-30 |

| Protein name | Locus Name | Acc# |
|---|---|---|
| Orf8 | gp:AB011413 | AB011413 |

Description

Streptomyces griseus genes for Orf2, Orf3, Orf4, Orf5, AfsA, Orf8, partial and complete cds.

| ORF Name | NTID | AAID | NT Length | AA Length | Score | Probability |
|---|---|---|---|---|---|---|
| 7034808_cl_49 | 1855 | 3775 | 70 | 213 | 51 | 0.033 |

| Protein name | Locus Name | Acc# |
|---|---|---|
| hypothetical protein ZK856.5 | pir:T28044 | T28044 |

Description

| ORF Name | NTID | AAID | NT Length | AA Length | Score | Probability |
|---|---|---|---|---|---|---|
| 7080001_f1_2 | 1856 | 3776 | 371 | 1116 | 298 | 2.3e-26 |

| Protein name | Locus Name | Acc# |
|---|---|---|
|  | sp:YGCG_ECOLI | P55140 |

Description

HYPOTHETICAL 34.9 KD PROTEIN IN CYSJ-ENO INTERGENIC REGION (O313)

| ORF Name | NTID | AAID | NT Length | AA Length | Score | Probability |
|---|---|---|---|---|---|---|
| 7083578_cl_37 | 1857 | 3777 | 60 | 183 | 162 | 2.4e-11 |

| Protein name | Locus Name | Acc# |
|---|---|---|
| NADP-dependent alcohol hydrogenase | gp:LMFL1063 | AL121862 |

Description

Leishmania major Friedlin chromosome 23 cosmid L1063, complete cds.

| ORF Name | NTID | AAID | NT Length | AA Length | Score | Probability |
|---|---|---|---|---|---|---|
| 9782666_f1_7 | 1858 | 3778 | 554 | 1665 | 2520 | 8.0e-262 |

| Protein name | | Locus Name | Acc# |
|---|---|---|---|
| ALXA and HSDM | | gp:PHU46781 | U46781 |

Description

Pasteurella haemolytica putative coproporphyrinogen III oxidase(hemN') gene, partial cds, leukotoxin transcriptional activator and restriction modification methylase subunit (alxA-hsdM), (hsdS) and (hsdR) genes, complete cds.

| ORF Name | NTID | AAID | NT Length | AA Length | Score | Probability |
|---|---|---|---|---|---|---|
| 14257160_f1_2 | 1859 | 3779 | 294 | 885 | | |

| Protein name | | Locus Name | Acc# |
|---|---|---|---|

Description

NO-HIT

| ORF Name | NTID | AAID | NT Length | AA Length | Score | Probability |
|---|---|---|---|---|---|---|
| 16180437_f3_18 | 1860 | 3780 | 502 | 1509 | 1460 | 1.7e-149 |

| Protein name | | Locus Name | Acc# |
|---|---|---|---|
| | | sp:GABD_ECOLI | P25526 |

Description

, (SSDH)

| ORF Name | NTID | AAID | NT Length | AA Length | Score | Probability |
|---|---|---|---|---|---|---|
| 19806552_f1_1 | 1861 | 3781 | 174 | 525 | 131 | 2.6e-07 |

| Protein name | | Locus Name | Acc# |
|---|---|---|---|
| probable ankyrin | | pir:H71274 | H71274 |

Description

| ORF Name | NTID | AAID | NT Length | AA Length | Score | Probability |
|---|---|---|---|---|---|---|
| 24407502_f3_17 | 1862 | 3782 | 224 | 675 | 392 | 2.5e-36 |

| Protein name | | Locus Name | Acc# |
|---|---|---|---|
| glycine betaine/carnitine/choline ABC transporter (membrane p) opuCD | | pir:F69670 | F69670 |

Description

| ORF Name | NTID | AAID | NT Length | AA Length | Score | Probability |
|---|---|---|---|---|---|---|
| 25900252_c2_30 | 1863 | 3783 | 417 | 1254 | 138 | 1.3e-05 |

| Protein name | Locus Name | Acc# |
|---|---|---|
| putative natural resistance-associated | gp:CCA133735 | AJ133735 |

Description

Cyprinus carpio mRNA for putative natural resistance-associatedmacrophage protein (NRAMP).

| ORF Name | NTID | AAID | NT Length | AA Length | Score | Probability |
|---|---|---|---|---|---|---|
| 34094385_c1_23 | 1864 | 3784 | 107 | 324 | 155 | 6.3e-11 |

| Protein name | Locus Name | Acc# |
|---|---|---|
| AttJ | gp:U59485 | |

Description

Agrobacterium tumefaciens AtrC (atrC) gene, partial cds; AtrB(atrB), AtrA (atrA), AttA1 (attA1), AttA2 (attA2), AttB (attB),AttC (attC), AttD (attD), AttE (attE), and AttF (attF) genes,complete cds; AttG (attG) gene, alternative splice products,complete cds; AttH (attH), AttI (attI), AttJ (attJ), AttK (attK),AttL (attL), AttM (attM), AttO (attO), AttP (attP), AttR (attR),AttS (attS), AttT (attT), AttU (attU), attV (attV), AttW (attW),AttX

| ORF Name | NTID | AAID | NT Length | AA Length | Score | Probability |
|---|---|---|---|---|---|---|
| 4770887_f1_3 | 1865 | 3785 | 176 | 531 | 130 | 2.7e-14 |

| Protein name | Locus Name | Acc# |
|---|---|---|
| hypothetical protein | gp:SSU18930 | Y18930 |

Description

Sulfolobus solfataricus 281 kb genomic DNA fragment, strain P2.

| ORF Name | NTID | AAID | NT Length | AA Length | Score | Probability |
|---|---|---|---|---|---|---|
| 4875260_c2_33 | 1866 | 3786 | 72 | 219 | | |

| Protein name | Locus Name | Acc# |
|---|---|---|
| | | |

Description

NO-HIT

| ORF Name | NTID | AAID | NT Length | AA Length | Score | Probability |
|---|---|---|---|---|---|---|
| 4884702_c1_27 | 1867 | 3787 | 226 | 681 | 404 | 1.4e-37 |

| Protein name | Locus Name | Acc# |
|---|---|---|
| NonF | gp:AF074603 | AF074603 |

Description

Streptomyces griseus subsp. griseus nonactin biosynthesis genecluster, partial sequence.

| ORF Name | NTID | AAID | NT Length | AA Length | Score | Probability |
|---|---|---|---|---|---|---|
| 6740692_f2_10 | 1868 | 3788 | 165 | 498 | | |

| Protein name | Locus Name | Acc# |
|---|---|---|
| | | |

Description

NO-HIT

| ORF Name | NTID | AAID | NT Length | AA Length | Score | Probability |
|---|---|---|---|---|---|---|
| 7218752_f3_15 | 1869 | 3789 | 129 | 390 | 88 | 0.030 |

| Protein name | Locus Name | Acc# |
|---|---|---|
| putative polysaccharide polymerase | gp:SPCPS14E | X85787 |

Description

S.pneumoniae cps14 locus.

| ORF Name | NTID | AAID | NT Length | AA Length | Score | Probability |
|---|---|---|---|---|---|---|
| 786305_f1_5 | 1870 | 3790 | 317 | 954 | 632 | 9.4e-62 |

| Protein name | Locus Name | Acc# |
|---|---|---|
| probable osmoprotection binding protein | pir:G71892 | G71892 |

Description

| ORF Name | NTID | AAID | NT Length | AA Length | Score | Probability |
|---|---|---|---|---|---|---|
| 792090_f2_12 | 1871 | 3791 | 148 | 447 | | |

| Protein name | Locus Name | Acc# |
|---|---|---|
| | | |

Description

NO-HIT

| ORF Name | NTID | AAID | NT Length | AA Length | Score | Probability |
|---|---|---|---|---|---|---|
| 12273437_f3_58 | 1872 | 3792 | 337 | 1014 | 1680 | 8.3e-173 |

| Protein name | Locus Name | Acc# |
|---|---|---|
| | sp:SYGA_MORCA | P77892 |

Description

ALPHA CHAIN) (GLYRS)

| ORF Name | NTID | AAID | NT Length | AA Length | Score | Probability |
|---|---|---|---|---|---|---|
| 14181500_f2_36 | 1873 | 3793 | 693 | 2082 | 1593 | 1.4e-163 |

| Protein name | Locus Name | Acc# |
|---|---|---|
| | sp:SYGB_HAEIN | P43822 |

Description

BETA CHAIN) (GLYRS)

| ORF Name | NTID | AAID | NT Length | AA Length | Score | Probability |
|---|---|---|---|---|---|---|
| 19650062_c1_101 | 1874 | 3794 | 279 | 840 | 581 | 2.4e-56 |

| Protein name | Locus Name | Acc# |
|---|---|---|
| | sp:BUDC_KLEPN | Q48436 |

Description

ACETOIN(DIACETYL) REDUCTASE, (ACETOIN DEHYDROGENASE) (AR)

| ORF Name | NTID | AAID | NT Length | AA Length | Score | Probability |
|---|---|---|---|---|---|---|
| 21648382_f1_22 | 1875 | 3795 | 279 | 840 | 813 | 6.2e-81 |

| Protein name | Locus Name | Acc# |
|---|---|---|
| | sp:ACCA_ECOLI | P30867 |

Description (EC 6.4.1.2)

| ORF Name | NTID | AAID | NT Length | AA Length | Score | Probability |
|---|---|---|---|---|---|---|
| 21650017_c2_112 | 1876 | 3796 | 254 | 765 | 437 | 4.3e-41 |

| Protein name | Locus Name | Acc# |
|---|---|---|
| | sp:LPTP_ECOLI | P23885 |

Description

LEUCYL/PHENYLALANYL-TRNA--PROTEIN TRANSFERASE,

| ORF Name | NTID | AAID | NT Length | AA Length | Score | Probability |
|---|---|---|---|---|---|---|
| 21657752_c3_147 | 1877 | 3797 | 345 | 1038 | 580 | 3.0e-56 |

| Protein name | Locus Name | Acc# |
|---|---|---|
| | sp:YZ37_SYNY3 | Q55480 |

Description

HYPOTHETICAL SUGAR KINASE SLR0537

| ORF Name | NTID | AAID | NT Length | AA Length | Score | Probability |
|---|---|---|---|---|---|---|
| 21987811_f2_34 | 1878 | 3798 | 237 | 714 | 384 | 6.2e-41 |

| Protein name | Locus Name | Acc# |
|---|---|---|
| | sp:PGSA_HAEIN | P44528 |

Description (EC 2.7.8.5) (PHOSPHATIDYLGLYCEROPHOSPHATE SYNTHASE) (PGP SYNTHASE)

| ORF Name | NTID | AAID | NT Length | AA Length | Score | Probability |
|---|---|---|---|---|---|---|
| 22038132_f3_67 | 1879 | 3799 | 76 | 231 | | |

| Protein name | Locus Name | Acc# |
|---|---|---|

Description

NO-HIT

| ORF Name | NTID | AAID | NT Length | AA Length | Score | Probability |
|---|---|---|---|---|---|---|
| 22384628_f1_5 | 1880 | 3800 | 448 | 1347 | 1005 | 2.8e-101 |

| Protein name | Locus Name | Acc# |
|---|---|---|
| | sp:YKGC_ECOLI | P77212 |

Description

INTERGENIC REGION

| ORF Name | NTID | AAID | NT Length | AA Length | Score | Probability |
|---|---|---|---|---|---|---|
| 23493812_f2_33 | 1881 | 3801 | 998 | 2997 | 972 | 6.2e-119 |

| Protein name | | Locus Name | Acc# |
|---|---|---|---|
| metalloprotease 1 | | gp:AF061243 | AF061243 |

Description

Homo sapiens metalloprotease 1 (MP1) mRNA, complete cds.

| ORF Name | NTID | AAID | NT Length | AA Length | Score | Probability |
|---|---|---|---|---|---|---|
| 23875027_f2_50 | 1882 | 3802 | 396 | 1191 | 621 | 1.4e-60 |

| Protein name | | Locus Name | Acc# |
|---|---|---|---|
| | | sp:RLUC_HAEIN | P44433 |

Description (PSEUDOURIDYLATE SYNTHASE) (URACIL HYDROLYASE)

| ORF Name | NTID | AAID | NT Length | AA Length | Score | Probability |
|---|---|---|---|---|---|---|
| 24118802_c3_138 | 1883 | 3803 | 441 | 1326 | 1742 | 2.2e-179 |

| Protein name | | Locus Name | Acc# |
|---|---|---|---|
| serine hydroxymethyltransferase | | gp:AF073769 | AF073769 |

Description

Acinetobacter radioresistens serine hydroxymethyltransferase (glyA) gene, complete cds.

| ORF Name | NTID | AAID | NT Length | AA Length | Score | Probability |
|---|---|---|---|---|---|---|
| 24268777_c3_134 | 1884 | 3804 | 1181 | 3546 | 1542 | 1.5e-160 |

| Protein name | | Locus Name | Acc# |
|---|---|---|---|
| ribonuclease E,:cell shape-determining protein:message stability-altering protein:RNase E | | pir:S27311 | |

Description

| ORF Name | NTID | AAID | NT Length | AA Length | Score | Probability |
|---|---|---|---|---|---|---|
| 24900257_f1_11 | 1885 | 3805 | 86 | 261 | 145 | 3.8e-10 |

| Protein name | | Locus Name | Acc# |
|---|---|---|---|
| conserved hypothetical protein | | pir:B72287 | B72287 |

Description

| ORF Name | NTID | AAID | NT Length | AA Length | Score | Probability |
|---|---|---|---|---|---|---|
| 25657776_c1_102 | 1886 | 3806 | 149 | 450 | 180 | 7.4e-14 |

| Protein name | Locus Name | Acc# |
|---|---|---|
| | sp:PSPE_ECOLI | P23857 |

Description

PHAGE SHOCK PROTEIN E PRECURSOR

| ORF Name | NTID | AAID | NT Length | AA Length | Score | Probability |
|---|---|---|---|---|---|---|
| 26565686_c3_149 | 1887 | 3807 | 348 | 1047 | 691 | 5.2e-68 |

| Protein name | Locus Name | Acc# |
|---|---|---|
| hypothetical protein slr0787 | pir:S77001 | S77001 |

Description

| ORF Name | NTID | AAID | NT Length | AA Length | Score | Probability |
|---|---|---|---|---|---|---|
| 26754011_c1_86 | 1888 | 3808 | 357 | 1074 | 1765 | 8.1e-182 |

| Protein name | Locus Name | Acc# |
|---|---|---|
| NAD repressor/NMN transporter NadRp | gp:MCU73324 | U73324 |

Description

Moraxella catarrhalis glycyl-tRNA synthetase beta subunit (GlyRS) and NAD repressor/NMN transporter NadRp (NadR) genes, partial cds, and glycyl-tRNA synthetase alpha subunit (GlyRS) gene, complete cds.

| ORF Name | NTID | AAID | NT Length | AA Length | Score | Probability |
|---|---|---|---|---|---|---|
| 2845637_c3_137 | 1889 | 3809 | 172 | 519 | 168 | 1.4e-12 |

| Protein name | Locus Name | Acc# |
|---|---|---|
| | sp:UBIC_ECOLI | |

Description

CHORISMATE--PYRUVATE LYASE,

| ORF Name | NTID | AAID | NT Length | AA Length | Score | Probability |
|---|---|---|---|---|---|---|
| 30332811_f2_51 | 1890 | 3810 | 541 | 1626 | 1087 | 5.7e-110 |

| Protein name | Locus Name | Acc# |
|---|---|---|
| exopolyphosphatase | gp:AF053463 | AF053463 |

Description

Pseudomonas aeruginosa thioredoxin (trx) and exopolyphosphatase(ppx) genes, complete cds.

| ORF Name | NTID | AAID | NT Length | AA Length | Score | Probability |
|---|---|---|---|---|---|---|
| 30726562_f3_62 | 1891 | 3811 | 768 | 2307 | 2256 | 7.6e-234 |

| Protein name | Locus Name | Acc# |
|---|---|---|
| hypothetical protein | gp:PFFC2 | Y11998 |

Description

P.fluorescens FC2.1, FC2.2, FC2.3c, FC2.4 and FC2.5c open readingframes.

| ORF Name | NTID | AAID | NT Length | AA Length | Score | Probability |
|---|---|---|---|---|---|---|
| 33240686_c3_140 | 1892 | 3812 | 260 | 783 | 155 | 1.4e-09 |

| Protein name | Locus Name | Acc# |
|---|---|---|
|  | sp:PNUC_ECOLI |  |

Description

PNUC PROTEIN

| ORF Name | NTID | AAID | NT Length | AA Length | Score | Probability |
|---|---|---|---|---|---|---|
| 34421878_c2_120 | 1893 | 3813 | 408 | 1227 | 991 | 8.5e-100 |

| Protein name | Locus Name | Acc# |
|---|---|---|
|  | sp:YHIN_ECOLI |  |

Description

HYPOTHETICAL 43.8 KD PROTEIN IN RHSB-PIT INTERGENIC REGION

| ORF Name | NTID | AAID | NT Length | AA Length | Score | Probability |
|---|---|---|---|---|---|---|
| 34578126_f3_54 | 1894 | 3814 | 355 | 1068 | 91 | 0.023 |

| Protein name | Locus Name | Acc# |
|---|---|---|
| translation elongation factor eEF-1 alpha chain PIK-A49:phosphatidylinositol 4-kinase activator PIK-A49 | pir:A45325 | |

Description

| ORF Name | NTID | AAID | NT Length | AA Length | Score | Probability |
|---|---|---|---|---|---|---|
| 4695252_f2_29 | 1895 | 3815 | 213 | 642 | 497 | 1.9e-47 |

| Protein name | Locus Name | Acc# |
|---|---|---|
| | sp:YHGI_ECOLI | P46847 |

Description

HYPOTHETICAL 21.0 KD PROTEIN IN BIOH-GNTT INTERGENIC REGION (O191)

| ORF Name | NTID | AAID | NT Length | AA Length | Score | Probability |
|---|---|---|---|---|---|---|
| 4875885_c2_126 | 1896 | 3816 | 164 | 495 | 120 | 1.7e-07 |

| Protein name | Locus Name | Acc# |
|---|---|---|
| | sp:YFMU_COXBU | P45680 |

Description

HYPOTHETICAL 15.8 KD PROTEIN IN FMU-RPMH INTERGENIC REGION

| ORF Name | NTID | AAID | NT Length | AA Length | Score | Probability |
|---|---|---|---|---|---|---|
| 6651712_f1_15 | 1897 | 3817 | 536 | 1611 | 1545 | 1.7e-158 |

| Protein name | Locus Name | Acc# |
|---|---|---|
| isocitrate lyase | gp:AB004651 | AB004651 |

Description

Hyphomicrobium methylovorum gene for isocitrate lyase,inorganicphosphate transporter,methionine synthase,complete and partial cds.

| ORF Name | NTID | AAID | NT Length | AA Length | Score | Probability |
|---|---|---|---|---|---|---|
| 6759625_c3_150 | 1898 | 3818 | 187 | 564 | 248 | 4.6e-21 |

| Protein name | Locus Name | Acc# |
|---|---|---|
| hypothetical protein TP0895 | pir:D71266 | D71266 |

Description

| ORF Name | NTID | AAID | NT Length | AA Length | Score | Probability |
|---|---|---|---|---|---|---|
| 14642925_f3_23 | 1899 | 3819 | 351 | 1056 | | |

| Protein name | Locus Name | Acc# |
|---|---|---|
| | | |

Description

NO-HIT

| ORF Name | NTID | AAID | NT Length | AA Length | Score | Probability |
|---|---|---|---|---|---|---|
| 16693750_f3_17 | 1900 | 3820 | 100 | 303 | 137 | 2.7e-09 |

| Protein name | Locus Name | Acc# |
|---|---|---|
| conserved hypothetical protein yerL | pir:A69795 | A69795 |

Description

| ORF Name | NTID | AAID | NT Length | AA Length | Score | Probability |
|---|---|---|---|---|---|---|
| 183437_f3_18 | 1901 | 3821 | 496 | 1491 | 2443 | 1.2e-253 |

| Protein name | Locus Name | Acc# |
|---|---|---|
| | sp:AMID_MORCA | Q49091 |

Description

PUTATIVE AMIDASE,

| ORF Name | NTID | AAID | NT Length | AA Length | Score | Probability |
|---|---|---|---|---|---|---|
| 1987793_f2_16 | 1902 | 3822 | 264 | 795 | 189 | 8.2e-15 |

| Protein name | Locus Name | Acc# |
|---|---|---|
| | sp:MINC_ECOLI | P18196 |

Description

CELL DIVISION INHIBITOR MINC

| ORF Name | NTID | AAID | NT Length | AA Length | Score | Probability |
|---|---|---|---|---|---|---|
| 22078181_c3_52 | 1903 | 3823 | 137 | 411 | 161 | 7.6e-12 |

| Protein name | Locus Name | Acc# |
|---|---|---|
| maf-type protein | pir:D72129 | D72129 |

Description

| ORF Name | NTID | AAID | NT Length | AA Length | Score | Probability |
|---|---|---|---|---|---|---|
| 22942053_f1_9 | 1904 | 3824 | 70 | 210 | | |

| Protein name | | | | Locus Name | | Acc# |
|---|---|---|---|---|---|---|
| | | | | | | |

Description

NO-HIT

| ORF Name | NTID | AAID | NT Length | AA Length | Score | Probability |
|---|---|---|---|---|---|---|
| 23492792_c2_37 | 1905 | 3825 | 203 | 612 | 141 | 1.0e-09 |

| Protein name | | | | Locus Name | | Acc# |
|---|---|---|---|---|---|---|
| | | | | sp:CYC5_AZOVI | | P11732 |

Description

CYTOCHROME C5

| ORF Name | NTID | AAID | NT Length | AA Length | Score | Probability |
|---|---|---|---|---|---|---|
| 24259651_f2_14 | 1906 | 3826 | 319 | 960 | 462 | 9.7e-44 |

| Protein name | | | | Locus Name | | Acc# |
|---|---|---|---|---|---|---|
| | | | | sp:YIHG_ECOLI | | P32129 |

Description

HYPOTHETICAL 36.3 KD PROTEIN IN DSBA-POLA INTERGENIC REGION

| ORF Name | NTID | AAID | NT Length | AA Length | Score | Probability |
|---|---|---|---|---|---|---|
| 24351556_c1_28 | 1907 | 3827 | 231 | 696 | 389 | 5.3e-36 |

| Protein name | | | | Locus Name | | Acc# |
|---|---|---|---|---|---|---|
| outer membrane protein homolog | | | | gp:AF067083 | | AF067083 |

Description

Vitreoscilla sp. outer membrane protein homolog gene, complete cds;Trp repressor binding protein gene, partial cds; and unknown genes.

| ORF Name | NTID | AAID | NT Length | AA Length | Score | Probability |
|---|---|---|---|---|---|---|
| 30203430_c2_35 | 1908 | 3828 | 86 | 261 | | |

| Protein name | | | | Locus Name | | Acc# |
|---|---|---|---|---|---|---|
| | | | | | | |

Description

NO-HIT

| ORF Name | NTID | AAID | NT Length | AA Length | Score | Probability |
|---|---|---|---|---|---|---|
| 31423200_f3_25 | 1909 | 3829 | 181 | 546 | 622 | 1.1e-60 |

Protein name: cell division inhibitor minD:septum site-determining protein minD
Locus Name: pir:CCECID
Acc#:

Description

| ORF Name | NTID | AAID | NT Length | AA Length | Score | Probability |
|---|---|---|---|---|---|---|
| 4729837_f3_19 | 1910 | 3830 | 317 | 954 | 1626 | 4.4e-167 |

Protein name: BRO-1
Locus Name: gp:MCBLABRO1
Acc#: Z54180

Description: M.catarrhalis bla gene.

| ORF Name | NTID | AAID | NT Length | AA Length | Score | Probability |
|---|---|---|---|---|---|---|
| 4791053_c1_31 | 1911 | 3831 | 72 | 219 | 54 | 0.0063 |

Protein name: gag protein
Locus Name: gp:MUSERVGG2
Acc#: M26006

Description: Mouse endogenous retrovirus truncated gag gene, complete cds, clonedel env-2 15.3.

| ORF Name | NTID | AAID | NT Length | AA Length | Score | Probability |
|---|---|---|---|---|---|---|
| 976677_f3_20 | 1912 | 3832 | 494 | 1485 | 2124 | 7.4e-220 |

Protein name:
Locus Name: sp:YBL3_MORCA
Acc#: Q49092

Description: HYPOTHETICAL 46.4 KD PROTEIN IN BLOR-1 3'REGION (ORF3)

| ORF Name | NTID | AAID | NT Length | AA Length | Score | Probability |
|---|---|---|---|---|---|---|
| 14469635_f2_5 | 1913 | 3833 | 716 | 2151 | 1425 | 8.7e-146 |

| Protein name | | | | Locus Name | | Acc# |
|---|---|---|---|---|---|---|
| | | | | sp:OPDA_HAEIN | | P44573 |

Description

OLIGOPEPTIDASE A,

| ORF Name | NTID | AAID | NT Length | AA Length | Score | Probability |
|---|---|---|---|---|---|---|
| 19569430_c3_39 | 1914 | 3834 | 275 | 828 | 454 | 6.8e-43 |

| Protein name | | | | Locus Name | | Acc# |
|---|---|---|---|---|---|---|
| | | | | sp:YBHP_ECOLI | | P75772 |

Description

HYPOTHETICAL 28.8 KD PROTEIN IN MOAE-RHLE INTERGENIC REGION

| ORF Name | NTID | AAID | NT Length | AA Length | Score | Probability |
|---|---|---|---|---|---|---|
| 21718878_c1_20 | 1915 | 3835 | 269 | 810 | | |

| Protein name | | | | Locus Name | | Acc# |

Description

NO-HIT

| ORF Name | NTID | AAID | NT Length | AA Length | Score | Probability |
|---|---|---|---|---|---|---|
| 22847175_f3_15 | 1916 | 3836 | 83 | 252 | 81 | 0.0023 |

| Protein name | | | | Locus Name | | Acc# |
|---|---|---|---|---|---|---|
| | | | | sp:YHEV_ECOLI | | P56622 |

Description

HYPOTHETICAL 7.6 KD PROTEIN IN SLYD-KEFB INTERGENIC REGION

| ORF Name | NTID | AAID | NT Length | AA Length | Score | Probability |
|---|---|---|---|---|---|---|
| 23445300_c3_37 | 1917 | 3837 | 923 | 2772 | 778 | 2.2e-100 |

| Protein name | | | | Locus Name | | Acc# |
|---|---|---|---|---|---|---|
| prolyl oligopeptidase, precursor | | | | pir:A38086 | | A38086 |

Description

| ORF Name | NTID | AAID | NT Length | AA Length | Score | Probability |
|---|---|---|---|---|---|---|
| 3907568_c2_28 | 1918 | 3838 | 124 | 375 | 70 | 0.033 |

| Protein name | Locus Name | Acc# |
|---|---|---|
| ORF102 | gp:AF162221 | AF162221 |

Description

Xestia c-nigrum granulovirus genome, complete sequence.

| ORF Name | NTID | AAID | NT Length | AA Length | Score | Probability |
|---|---|---|---|---|---|---|
| 4773287_c1_26 | 1919 | 3839 | 212 | 639 | 503 | 4.4e-48 |

| Protein name | Locus Name | Acc# |
|---|---|---|
| | sp:YGGV_ECOLI | P52061 |

Description

HYPOTHETICAL 21.0 KD PROTEIN IN GSHB-ANSB INTERGENIC REGION (O197)

| ORF Name | NTID | AAID | NT Length | AA Length | Score | Probability |
|---|---|---|---|---|---|---|
| 964212_c3_35 | 1920 | 3840 | 410 | 1233 | 104 | 0.0091 |

| Protein name | Locus Name | Acc# |
|---|---|---|
| voltage-dependent anion channel protein 1b | gp:AF178951 | AF178951 |

Description

Zea mays voltage-dependent anion channel protein 1b (vdac1b) mRNA, complete cds; nuclear gene for mitochondrial product.

SEQUENCE LISTING

The patent contains a lengthy "Sequence Listing" section. A copy of the "Sequence Listing" is available in electronic form from the USPTO web site (http://seqdata.uspto.gov/sequence.html?DocID=6673910B1). An electronic copy of the "Sequence Listing" will also be available from the USPTO upon request and payment of the fee set forth in 37 CFR 1.19(b)(3).

What is claimed is:

1. An isolated nucleic acid molecule encoding an *M. catarrhalis* polypeptide of SEQ ID NO: 2139.

2. A recombinant expression vector comprising the nucleic acid of claim 1 operably linked to a transcription regulatory element.

3. A cell comprising a recombinant expression vector of claim 2.

4. An isolated nucleic acid molecule selected from the group consisting of:
   (a) SEQ ID NO: 219;
   (b) an RNA of (a), wherein U is substituted for T.

5. A recombinant expression vector comprising the nucleic acid of claim 4 operably linked to a transcription regulatory element.

6. A cell comprising a recombinant expression vector of claim 5.

7. An isolated nucleic acid molecule of at least about 40 consecutive nucleotides in length, wherein the isolated nucleic acid molecule is selected from the group consisting of:
   (a) an isolated nucleic acid molecule fragment of SEQ ID NO: 219;
   (b) an RNA of (a), wherein U is substituted for T.

8. An isolated nucleic acid molecule of at least about 40 consecutive nucleotides in length, wherein the isolated nucleic acid molecule hybridizes under conditions of high stringency to an isolated nucleic acid having a nucleotide sequence selected from the group consisting of:
   (a) SEQ ID NO: 219;
   (b) an RNA of (a), wherein U is substituted for T.

9. An isolated nucleic acid comprising the sequence of SEQ ID NO: 219.

10. A recombinant expression vector comprising SEQ ID NO: 219 operably linked to a transcription regulatory element.

11. A cell comprising a recombinant expression vector, wherein the recombinant expression vector includes SEQ ID NO: 219 operably linked to a transcription regulatory element.

12. An isolated nucleic acid molecule that hybridizes under conditions of high stringency to SEQ ID NO: 219, wherein the isolated nucleic acid molecule is at least about 40 consecutive nucleotides in length.

13. A recombinant expression vector comprising an isolated nucleic acid operably linked to a transcription regulatory element, wherein the isolated nucleic acid hybridizes under conditions of high stringency to SEQ ID NO: 219 and is at least about 40 consecutive nucleotides in length.

14. A cell comprising a recombinant expression vector, wherein the recombinant expression vector includes an isolated nucleic acid operably linked to a transcription regulatory element, wherein the isolated nucleic acid hybridizes under conditions of high stringency to SEQ ID NO: 219 and is at least about 40 consecutive nucleotides in length.

* * * * *